(12) United States Patent
Hatanaka et al.

(10) Patent No.: US 11,298,326 B2
(45) Date of Patent: Apr. 12, 2022

(54) NUCLEIC ACID-CONTAINING LIPID NANOPARTICLES

(71) Applicant: Kyowa Kirin Co., Ltd., Tokyo (JP)

(72) Inventors: Kentaro Hatanaka, Tokyo (JP); Nobuhiro Yagi, Tokyo (JP); Takeshi Kuboyama, Tokyo (JP); Kaori Yagi, Tokyo (JP); Shintaro Hosoe, Tokyo (JP)

(73) Assignee: KYOWA KIRIN CO., LTD., Tokyo (JP)

( * ) Notice: Subject to any disclaimer, the term of this patent is extended or adjusted under 35 U.S.C. 154(b) by 0 days.

(21) Appl. No.: 15/560,854

(22) PCT Filed: Mar. 24, 2016

(86) PCT No.: PCT/JP2016/059511
§ 371 (c)(1),
(2) Date: Sep. 22, 2017

(87) PCT Pub. No.: WO2016/153012
PCT Pub. Date: Sep. 29, 2016

(65) Prior Publication Data
US 2018/0353434 A1 Dec. 13, 2018

(30) Foreign Application Priority Data

Mar. 24, 2015 (JP) .............................. JP2015-060819

(51) Int. Cl.
*A61K 9/51* (2006.01)
*C07C 217/28* (2006.01)
(Continued)

(52) U.S. Cl.
CPC .......... *A61K 9/5123* (2013.01); *A61K 9/0019* (2013.01); *A61K 9/1272* (2013.01);
(Continued)

(58) Field of Classification Search
CPC .. A61K 9/127; A61K 9/5123; A61K 31/7088; A61K 31/713; A61K 9/1272;
(Continued)

(56) References Cited

U.S. PATENT DOCUMENTS 4,948,520 A 8/1990 Sasaki
5,994,317 A 11/1999 Wheeler
(Continued)

FOREIGN PATENT DOCUMENTS

DE 274 332 12/1989
EP 2 319 519 5/2011
(Continued)

OTHER PUBLICATIONS

Kunitake, T., et al in J. Am. Chem. Soc., vol. 106, pp. 1978-1983, 1984.*
(Continued)

*Primary Examiner* — Gollamudi S Kishore
(74) *Attorney, Agent, or Firm* — Wenderoth, Lind & Ponack, L.L.P.

(57) ABSTRACT

The present invention provides nucleic acid-containing lipid nanoparticles containing a lipid (lipid A) which has a hydrophilic unit having a single quaternary ammonium group, and three independent, optionally substituted hydrocarbon groups, a lipid derivative or fatty acid derivative of a water-soluble polymer, and a nucleic acid.

3 Claims, 6 Drawing Sheets

Specification includes a Sequence Listing.

(51) Int. Cl.

| | | |
|---|---|---|
| A61K 9/127 | (2006.01) | |
| C07D 223/04 | (2006.01) | |
| C07C 229/12 | (2006.01) | |
| A61K 31/713 | (2006.01) | |
| A61P 29/00 | (2006.01) | |
| C07C 237/22 | (2006.01) | |
| C07D 401/04 | (2006.01) | |
| A61K 9/00 | (2006.01) | |
| C07D 295/088 | (2006.01) | |
| C07D 207/12 | (2006.01) | |
| A61P 35/00 | (2006.01) | |
| C07D 317/28 | (2006.01) | |
| C07D 211/22 | (2006.01) | |
| C07D 207/08 | (2006.01) | |
| C12N 15/11 | (2006.01) | |
| A61K 31/7088 | (2006.01) | |
| C07C 211/63 | (2006.01) | |
| C07C 215/08 | (2006.01) | |
| C07C 219/08 | (2006.01) | |
| C07C 229/06 | (2006.01) | |
| C07C 233/20 | (2006.01) | |
| C07C 237/08 | (2006.01) | |
| C07C 271/16 | (2006.01) | |
| C07D 451/14 | (2006.01) | |
| C12N 15/113 | (2010.01) | |

(52) U.S. Cl.
CPC ........ *A61K 31/7088* (2013.01); *A61K 31/713* (2013.01); *A61P 29/00* (2018.01); *A61P 35/00* (2018.01); *C07C 211/63* (2013.01); *C07C 215/08* (2013.01); *C07C 217/28* (2013.01); *C07C 219/08* (2013.01); *C07C 229/06* (2013.01); *C07C 229/12* (2013.01); *C07C 233/20* (2013.01); *C07C 237/08* (2013.01); *C07C 237/22* (2013.01); *C07C 271/16* (2013.01); *C07D 207/08* (2013.01); *C07D 207/12* (2013.01); *C07D 211/22* (2013.01); *C07D 223/04* (2013.01); *C07D 295/088* (2013.01); *C07D 317/28* (2013.01); *C07D 401/04* (2013.01); *C07D 451/14* (2013.01); *C12N 15/111* (2013.01); *C12N 15/113* (2013.01); *C12N 2310/14* (2013.01); *C12N 2320/32* (2013.01); *C12N 2320/51* (2013.01)

(58) Field of Classification Search
CPC .. A61K 9/0019; C12N 15/111; C12N 15/113; C12N 2310/14; C12N 2320/32; C12N 2320/51; C07C 237/22; C07C 229/12; C07C 229/06; C07C 211/63; C07C 215/08; C07C 219/08; C07C 233/20; C07C 237/08; C07C 271/16; C07C 217/28; C07D 451/14; C07D 401/04; C07D 223/04; C07D 317/28; C07D 295/088; C07D 211/22; C07D 207/12; C07D 207/08; A61P 35/00; A61P 29/00
See application file for complete search history.

(56) References Cited

U.S. PATENT DOCUMENTS

| | | | | |
|---|---|---|---|---|
| 6,124,270 | A * | 9/2000 | Haensler | ............... A61K 31/14 424/812 |
| 8,999,351 | B2 | 4/2015 | Manoharan et al. | |
| 9,061,063 | B2 | 6/2015 | Maier et al. | |
| 9,139,554 | B2 | 9/2015 | Hope et al. | |
| 9,175,245 | B2 | 11/2015 | Allen et al. | |
| 9,175,246 | B2 | 11/2015 | Allen et al. | |
| 9,186,325 | B2 | 11/2015 | Manoharan et al. | |
| 9,187,711 | B2 | 11/2015 | Allen et al. | |
| 9,220,683 | B2 | 12/2015 | Manoharan et al. | |
| 9,408,914 | B2 | 8/2016 | Kuboyama et al. | |
| 9,682,139 | B2 | 6/2017 | Manoharan et al. | |
| 9,707,292 | B2 | 7/2017 | Manoharan et al. | |
| 9,764,036 | B2 | 9/2017 | Manoharan et al. | |
| 9,796,662 | B2 | 10/2017 | Allen et al. | |
| 9,839,616 | B2 | 12/2017 | Kuboyama et al. | |
| 9,845,306 | B2 | 12/2017 | Kuboyama et al. | |
| 9,920,028 | B2 | 3/2018 | Kuboyama et al. | |
| 10,117,941 | B2 | 11/2018 | Manoharan et al. | |
| 10,342,758 | B2 | 7/2019 | Kuboyama et al. | |
| 10,369,226 | B2 | 8/2019 | Maier et al. | |
| 2003/0129221 | A1 | 7/2003 | Semple et al. | |
| 2004/0033267 | A1 | 2/2004 | Merisko-Liversidge et al. | |
| 2005/0170508 | A1* | 8/2005 | Huang | ............... A61K 9/1272 435/458 |
| 2008/0050461 | A1 | 2/2008 | Merisko-Liversidge et al. | |
| 2008/0107741 | A1 | 5/2008 | Merisko-Liversidge et al. | |
| 2008/0220075 | A1 | 9/2008 | Merisko-Liversidge et al. | |
| 2008/0226732 | A1 | 9/2008 | Merisko-Liversidge et al. | |
| 2008/0279949 | A1 | 11/2008 | Merisko-Liversidge et al. | |
| 2009/0148491 | A1* | 6/2009 | Hossainy | ............ A61K 9/0024 424/423 |
| 2010/0041152 | A1 | 2/2010 | Wheeler et al. | |
| 2010/0322852 | A1 | 12/2010 | Merisko-Liversidge et al. | |
| 2010/0322853 | A1 | 12/2010 | Merisko-Liversidge et al. | |
| 2010/0329976 | A1 | 12/2010 | Merisko-Liversidge et al. | |
| 2011/0117026 | A1* | 5/2011 | Tseng | ................... A61K 9/1271 424/9.6 |
| 2011/0256175 | A1 | 10/2011 | Hope et al. | |
| 2011/0262527 | A1* | 10/2011 | Heyes | .................... C12N 15/88 424/450 |
| 2011/0311582 | A1 | 12/2011 | Manoharan et al. | |
| 2011/0311583 | A1 | 12/2011 | Manoharan et al. | |
| 2012/0027796 | A1 | 2/2012 | Manoharan et al. | |
| 2012/0058144 | A1 | 3/2012 | Manoharan et al. | |
| 2012/0095075 | A1 | 4/2012 | Manoharan et al. | |
| 2012/0116064 | A1 | 5/2012 | Dai et al. | |
| 2012/0172411 | A1 | 7/2012 | Heyes et al. | |
| 2012/0192856 | A1 | 8/2012 | Xu | |
| 2013/0108685 | A1 | 5/2013 | Kuboyama et al. | |
| 2013/0129811 | A1 | 5/2013 | Kuboyama et al. | |
| 2013/0149374 | A1 | 6/2013 | Lee et al. | |
| 2013/0156845 | A1* | 6/2013 | Manoharan | ........... C12N 15/111 424/450 |
| 2013/0195920 | A1 | 8/2013 | Maier et al. | |
| 2013/0225409 | A1 | 8/2013 | Allen et al. | |
| 2013/0225469 | A1 | 8/2013 | Allen et al. | |
| 2013/0225473 | A1 | 8/2013 | Allen et al. | |
| 2013/0225859 | A1 | 8/2013 | Allen et al. | |
| 2013/0237421 | A1 | 9/2013 | Allen et al. | |
| 2013/0243848 | A1 | 9/2013 | Lobovkina et al. | |
| 2013/0288946 | A1 | 10/2013 | Allen et al. | |
| 2014/0005423 | A1 | 1/2014 | Allen et al. | |
| 2014/0039032 | A1 | 2/2014 | Kuboyama et al. | |
| 2014/0045913 | A1* | 2/2014 | Kuboyama | .......... A61K 9/5123 514/44 A |
| 2014/0294978 | A1 | 10/2014 | Kuboyama et al. | |
| 2015/0174261 | A1* | 6/2015 | Kuboyama | .......... C07D 211/06 424/451 |
| 2015/0265708 | A1 | 9/2015 | Manoharan et al. | |
| 2015/0273068 | A1 | 10/2015 | Maier et al. | |
| 2015/0343062 | A1 | 12/2015 | Kuboyama et al. | |
| 2015/0376118 | A1 | 12/2015 | Allen et al. | |
| 2016/0016897 | A1 | 1/2016 | Allen et al. | |
| 2016/0016898 | A1 | 1/2016 | Allen et al. | |
| 2016/0023989 | A1 | 1/2016 | Allen et al. | |
| 2016/0024003 | A1 | 1/2016 | Allen et al. | |
| 2016/0032218 | A1 | 2/2016 | Allen et al. | |
| 2016/0095924 | A1 | 4/2016 | Hope et al. | |
| 2016/0199485 | A1 | 7/2016 | Manoharan et al. | |
| 2016/0213785 | A1 | 7/2016 | Manoharan et al. | |
| 2016/0304487 | A1 | 10/2016 | Kuboyama et al. | |
| 2017/0042825 | A1 | 2/2017 | Kuboyama et al. | |
| 2018/0043009 | A1 | 2/2018 | Manoharan et al. | |
| 2018/0064807 | A1 | 3/2018 | Manoharan et al. | |

(56) References Cited

U.S. PATENT DOCUMENTS

| | | |
|---|---|---|
| 2018/0092971 A1 | 4/2018 | Manoharan et al. |
| 2018/0125985 A1 | 5/2018 | Manoharan et al. |
| 2019/0167800 A1 | 6/2019 | Manoharan et al. |

FOREIGN PATENT DOCUMENTS

| | | |
|---|---|---|
| EP | 2 567 951 | 3/2013 |
| EP | 2 774 912 | 9/2014 |
| EP | 3 178 807 | 6/2017 |
| JP | 2000-508642 | 7/2000 |
| JP | 2002-501511 | 1/2002 |
| JP | 2011-514360 | 5/2011 |
| JP | 2012-505250 | 3/2012 |
| JP | 2012-508261 | 4/2012 |
| JP | 2015-500835 | 1/2015 |
| WO | 96/40964 | 12/1996 |
| WO | 2004/002453 A | 1/2004 |
| WO | 2009/114695 | 9/2009 |
| WO | 2011/136368 | 11/2011 |
| WO | 2011/140627 | 11/2011 |
| WO | 2012/061093 | 5/2012 |
| WO | 2012/105958 | 8/2012 |
| WO | 2013/089151 | 6/2013 |
| WO | 2014/007398 | 1/2014 |

OTHER PUBLICATIONS

T. Kunitake et al., "Bilayer Membranes of Triple-Chain, Fluorocarbon Amphiphiles", Journal of American Chemical Society, 1985, vol. 107, pp. 692-696.

E. Kitatsuji et al., "Studies on the Components in NTU Shale Oil. III, The Hofmann Degradation of Alkylpiperidines", Journal of the Pharmaceutical Society of Japan, 1971, vol. 91, No. 7, pp. 713-720.

A. Mokhtarieh et al., "Asymmetric liposome particles with highly efficient encapsulation of siRNA and without nonspecific cell penetration suitable for target-specific delivery", Biochemica et Biophysica Acta, 2012, vol. 1818, pp. 1633-1641.

S. Semple et al., "Efficient encapsulation of antisense oligonucleotides in lipid vesicles using ionizable aminolipids: formation of novel small multilamellar vesicle suuctures", Biochimica et Biophysica Acta, 2001, vol. 1510, pp. 152-166.

C. Wong et al., "Multistage nanoparticle delivery system for deep penetration into tumor tissue", Proceedings of the National Academy of Sciences, 2011, vol. 108, No. 6, pp. 2426-2431.

A. Leung et al., "Lipid Nanoparticles Containing siRNA Synthesized by Microfluidic Mixing Exhibit an Electron-Dense Nanostructured Core", The Journal of Physical Chemistry, 2012, vol. 116, pp. 18440-18450.

N. Belliveau et al., "Microfluidic Synthesis of Highly Potent Limit-size Lipid Nanoparticles for In Vivo Delivery of siRNA", Molecular Therapy-Nucleic Acids, 2012, vol. 1, e37, pp. 1-9.

I. Zhigaltsev et al., "Bottom-Up Design and Synthesis of Limit Size Lipid Nanoparticle Systems with Aqueous and Triglyceride Cores Using Millisecond Microfluidic Mixing", Langmuir, 2012, vol. 28, pp. 3633-3640.

S. Chen et al., "Development of lipid nanoparticle formulations of siRNA for hepatocyte gene silencing following subcutaneous administration", Journal of Controlled Release, 2014, vol. 196, pp. 106-112.

W. Li et al., "Lipid-based Nanoparticles for Nucleic Acid Delivery", Pharmaceutical Research, vol. 24, No. 3, Mar. 2007, pp. 438-449.

T. Kunitake et al., "Bilayer Membranes of Triple-Chain Ammonium Amphiphiles", Journal of the American Chemical Society, 1984, vol. 106, pp. 1978-1983.

\* cited by examiner

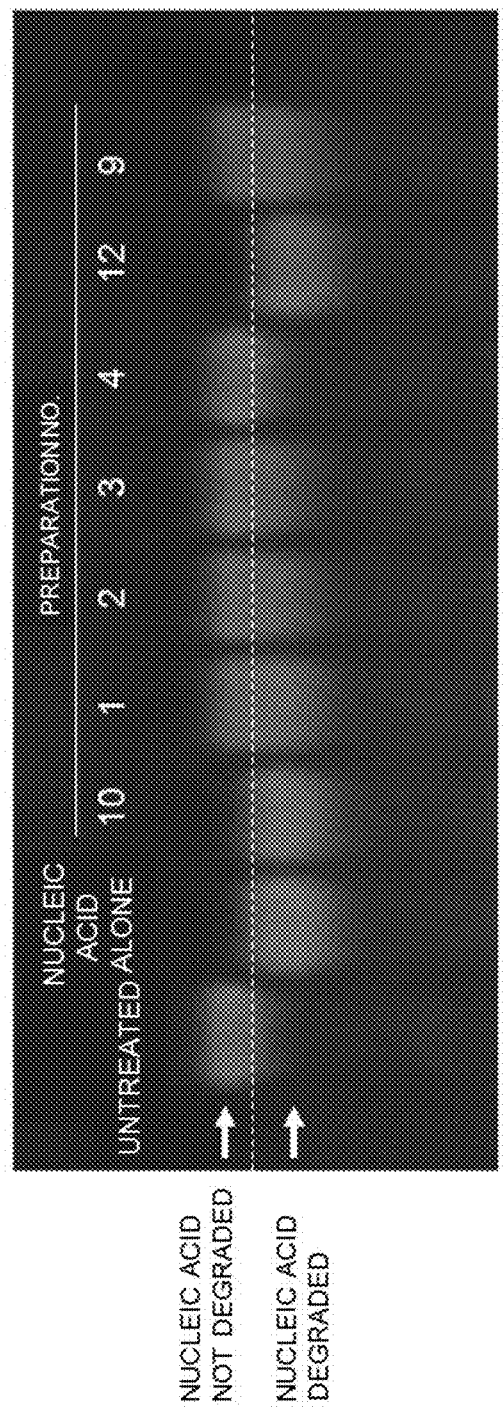
[Fig. 1]

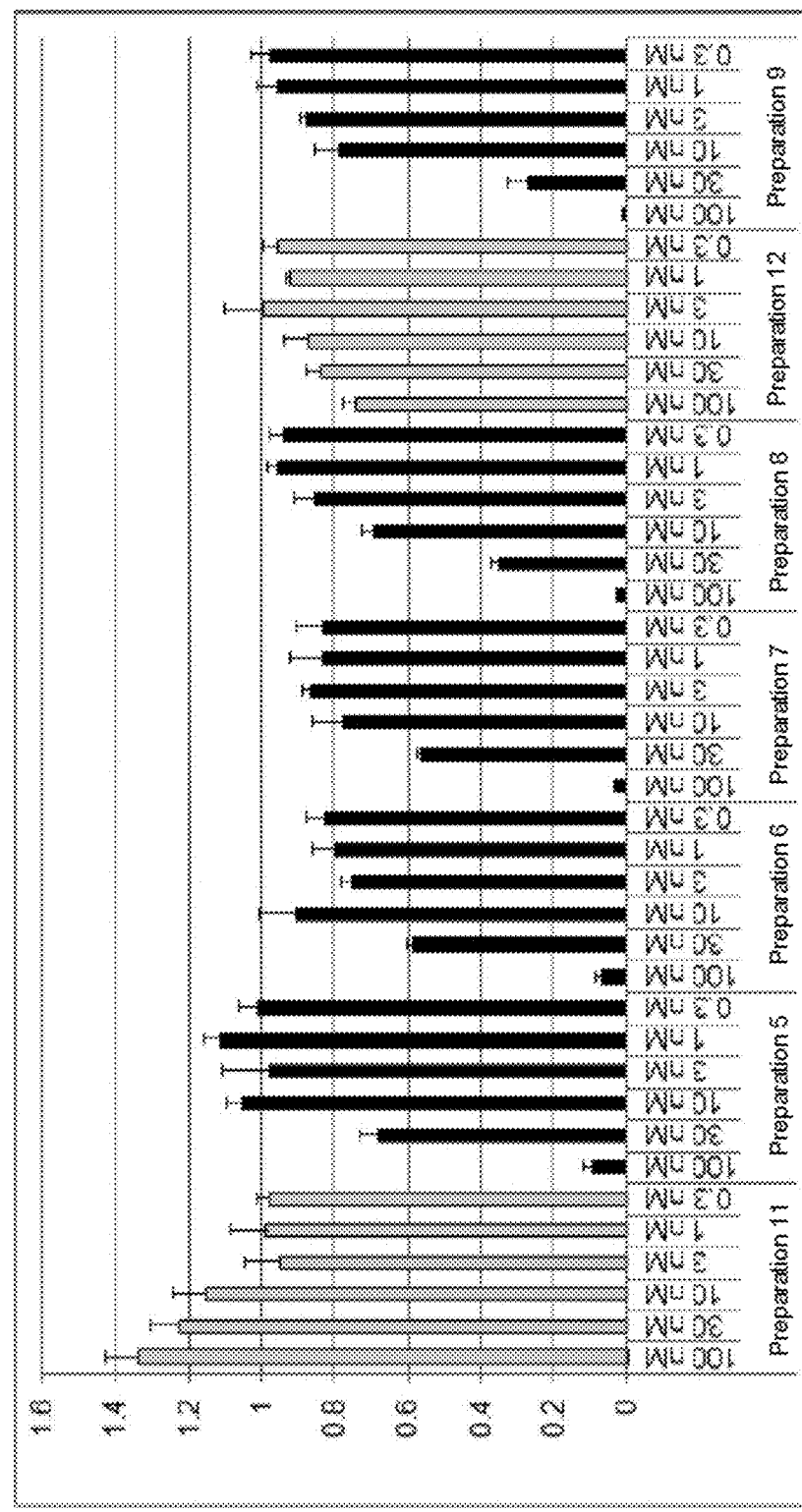
[Fig. 2]

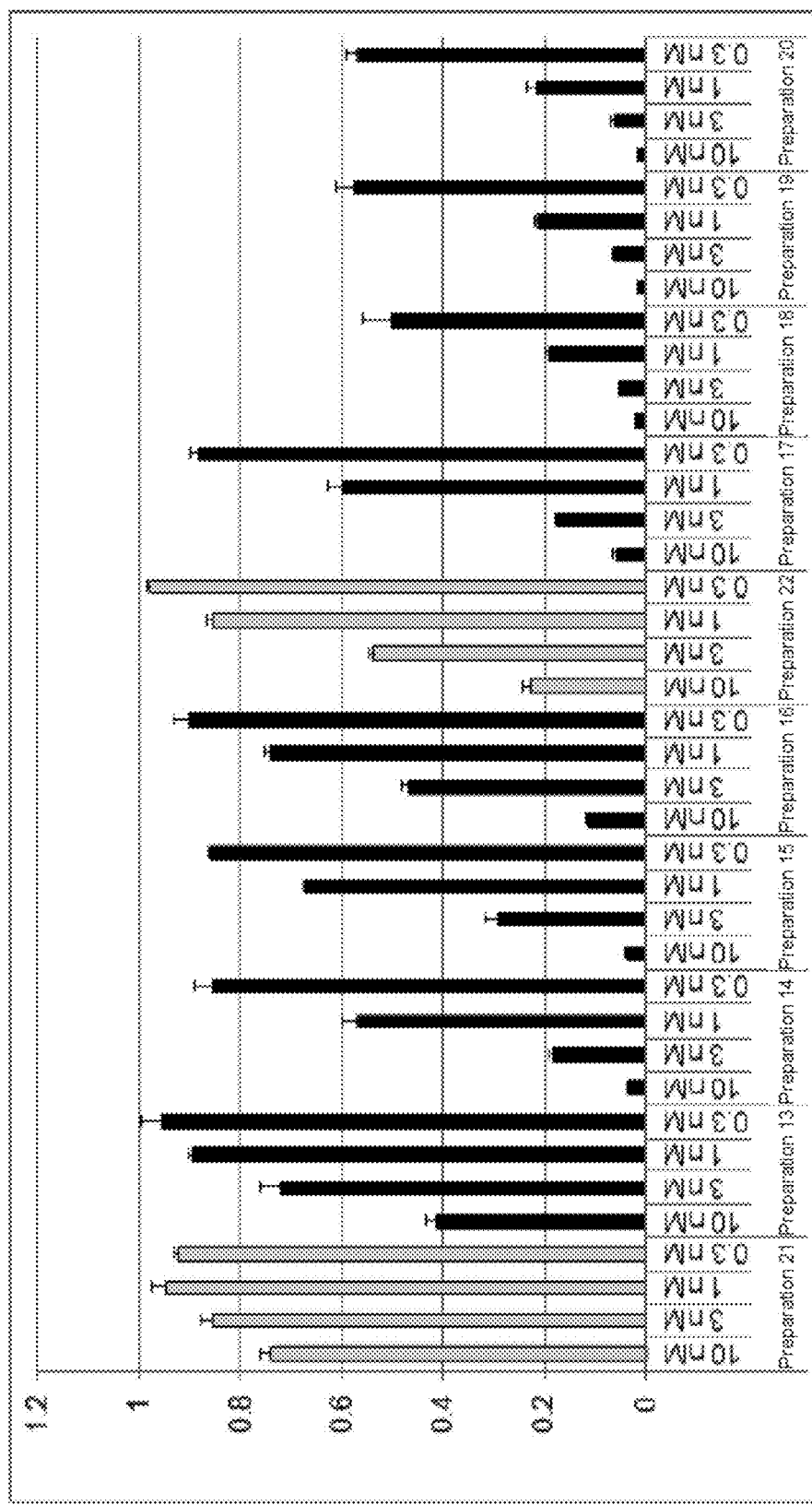
[Fig. 3]

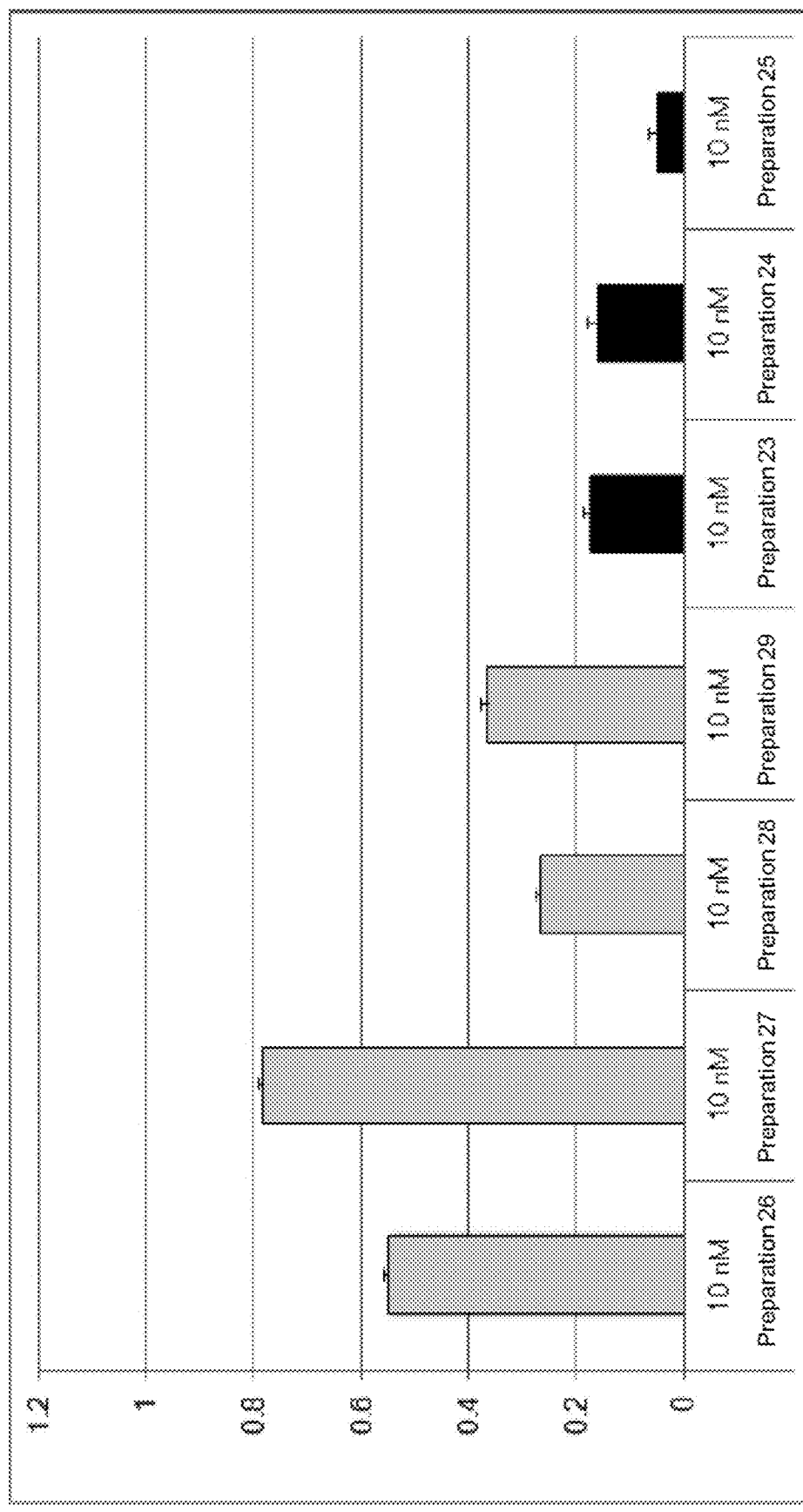
[Fig. 4]

[Fig. 5]
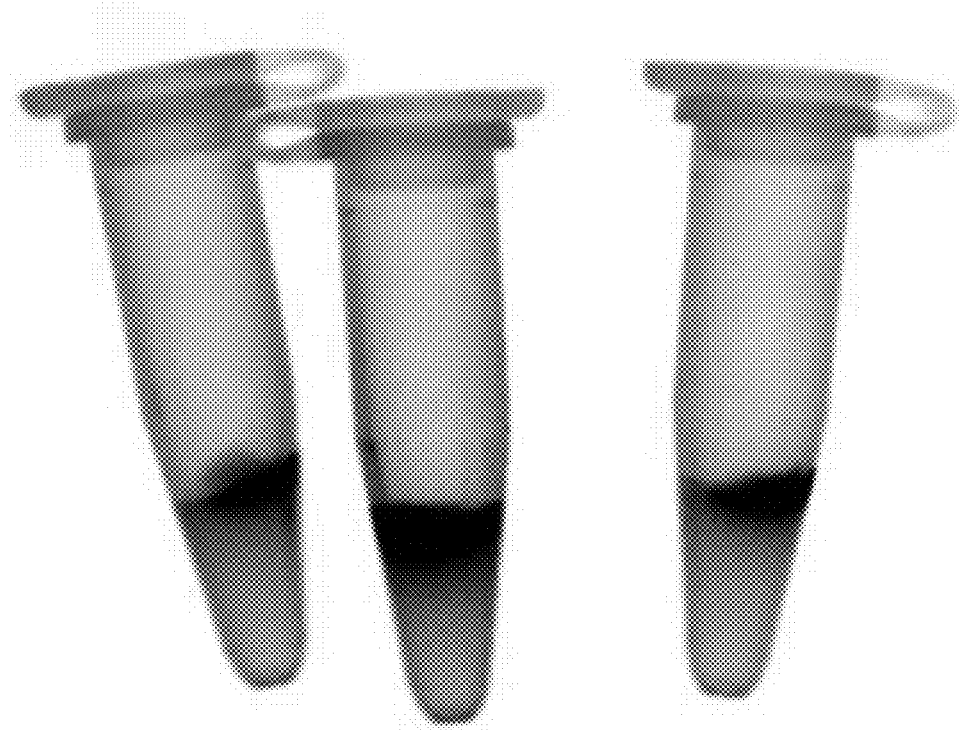
[Fig. 6]
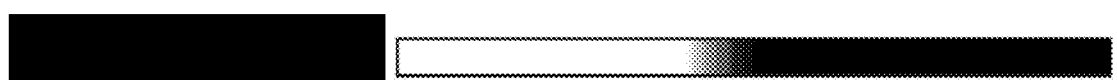

[Fig. 7]
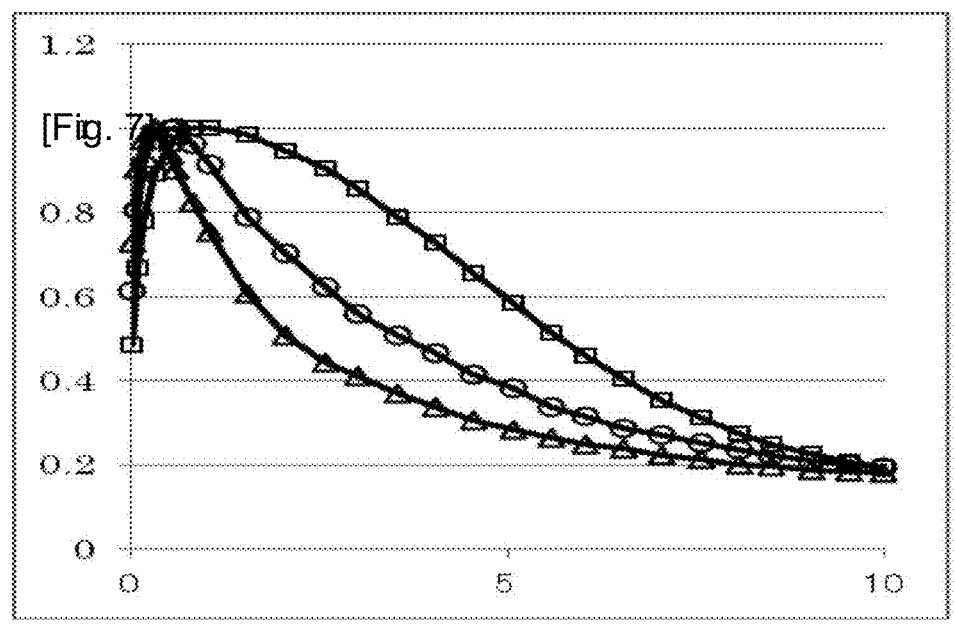

NUCLEIC ACID-CONTAINING LIPID NANOPARTICLES

TECHNICAL FIELD

The present invention relates to, for instance, nucleic acid-containing lipid nanoparticles that are useful for use as a pharmaceutical and to a method for producing the lipid nanoparticles. In addition, the present invention relates to, for instance, a lipid that is useful for producing the lipid nanoparticles.

BACKGROUND ART

A method consisting of forming a complex of a nucleic acid with a cationic lipid and other lipids followed by administering that complex is known as a means of efficiently delivering nucleic acids such as plasmid DNA (pDNA), antisense oligodeoxynucleic acids (ODN) and short interfering RNA (siRNA) to cells in vivo.

In Patent Document 1 and Non-Patent Document 1, a method for producing liposomes containing nucleic acid and the like is reported that consists of, for example, adding a dried cationic lipid, an aqueous sodium citrate solution of siRNA, and a solution obtained by dissolving a neutral lipid and a polyethylene glycol-modified phospholipid in HEPES ([N-(2-hydroxyethyl)piperazine-N'-(2-ethanesulfonic acid)]) buffered saline (hereinafter abbreviated as "HBS") and ethanol, to diethyl ether to form a water-in-oil (W/O) emulsion followed by mixing the solution and treating by antiphase evaporation to produce an siRNA-encapsulating liposome.

In Patent Document 2 and Non-Patent Document 2, a method is reported for producing an ODN-encapsulating liposome by dissolving the ODN in an aqueous citric acid solution having a pH of 3.8, adding an ethanol solution of a lipid, and lowering the ethanol concentration to 20 v/v % to prepare a liposome that encapsulates the ODN, and after having filtered with a sizing film and removed excess ethanol by dialysis, the sample is further dialyzed at pH 7.5 to remove ODN adhered to the surface of the liposome and produce an ODN-encapsulating liposome.

In addition, in Patent Document 3, a method is reported for producing a pDNA-encapsulating liposome by mixing a solution obtained by dissolving pDNA in a citric acid solution and a solution obtained by dissolving a lipid in ethanol with a T-shaped mixer to lower the concentration of the ethanol to 45 v/v %, followed by further adding citrate buffer solution to lower the ethanol concentration to 20 v/v % to prepare a liposome that encapsulates pDNA, and after removing excess pDNA with an anion exchange resin, excess ethanol is removed by ultrafiltration to produce a pDNA-encapsulating liposome.

Moreover, in Patent Document 4, a method is reported for producing a pDNA-encapsulating liposome by compounding pDNA with a cationic lipid in the form of a micelle in an organic solvent containing water, and after further adding lipid, removing the organic solvent by dialysis.

In Patent Document 5, a method is reported for producing a pDNA-encapsulating liposome by similarly compounding pDNA with a cationic lipid in the form of a micelle in an aqueous solution of a surfactant, and after further adding lipid, removing the surfactant by dialysis.

Although the cationic lipid used to form the above-mentioned complex is normally an amphiphilic molecule having a lipophilic unit containing one to a plurality of hydrocarbon groups, and a cationic hydrophilic unit containing at least one primary amine, secondary amine, tertiary amine or quaternary ammonium group, those having two hydrocarbon groups are used most commonly.

On the other hand, Patent Document 6 discloses that lipid particles having a particle size of 82 nm to 95 nm were obtained using the same method as that of Patent Document 3 by using a cationic lipid having three hydrocarbon groups instead of a cationic lipid having two hydrocarbon groups. This document specifically discloses a cationic lipid having three hydrocarbon groups in the form of 13-B2 represented by the formula indicated below.

[C1]

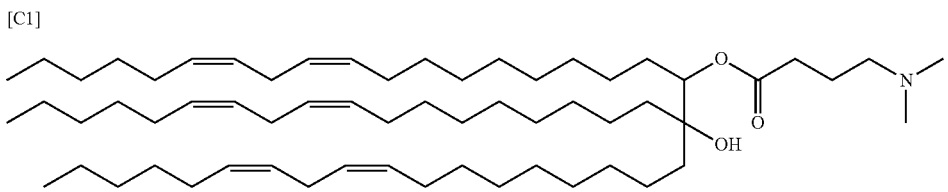

Nucleic acid-encapsulating liposomes produced using these methods have a size of about 50 nm to 100 nm.

On the other hand, Non-Patent Document 2 reports that, in a test using polymer micelles encapsulating dichloro(1, 2-diaminocyclohexane) platinum (II) having a particle size of 30 nm to 100 nm, the amount delivered to tumors increases and antitumor effects become stronger as the particle size of the polymer micelle decreases. In addition, Non-Patent Document 3 reports that 10 nm quantum dots are more widely distributed in tumors in comparison with 100 nm quantum dots based on the results of an experiment for evaluating permeability using quantum dots. Namely, although a smaller particle size is required for efficient delivery to tumors in the case of lipid particles as well, it was difficult for any of the previously described methods to efficiently prepare highly stable lipid particles having a small particle size.

Amidst these circumstances, Patent Document 7 and Non-Patent Documents 4 to 7 report that siRNA-containing lipid nanoparticles are obtained by mixing a solution prepared by dissolving a cationic lipid, neutral lipid and polyethylene glycol-modified lipid in ethanol with siRNA dissolved in acetate buffer by a herringbone structure in the form of a microfluidics device and removing the ethanol. In this method, as a result of going through a reverse micelle structure in which a cationic lipid in a polar organic solvent internalizes a nucleic acid by causing electrostatic interaction with the nucleic acid in parallel with reducing the proportion of the polar organic solvent, lipid nanoparticles are produced in which a reverse micelle structure having a nucleic acid is coated with a lipid membrane. Although the particle size of these lipid nanoparticles varies according to the rates, at which the polar organic solvent having the lipid dissolved therein and the aqueous solution having the nucleic acid dissolved therein pass through the microfluidics device, as well as the PEG content thereof, the lipid nanoparticles are reported to be extremely small. The siRNA-encapsulating liposomes obtained according to this method are reported to demonstrate pharmacological effects on the liver not only in the case of intravenous administration, but also in the case of subcutaneous administration.

CITATION LIST

Patent Document

Patent Document 1: U.S. Patent Application Publication No. 2013/0149374 (Specification)
Patent Document 2: Japanese Translation of PCT Application No. 2002-501511
Patent Document 3: WO 2004/002453
Patent Document 4: WO 96/40964
Patent Document 5: U.S. Patent Application Publication No. 2010/0041152 (Specification)
Patent Document 6: U.S. Patent Application Publication No. 2012/0172411 (Specification)
Patent Document 7: WO 2011/140627

Non-Patent Document

Non-Patent Document 1: Biochimica et Biophysica Acta, 2012, Vol. 1818, pp. 1633-1641
Non-Patent Document 2: Biochimica et Biophysica Acta, 2001, Vol. 1510, pp. 152-166
Non-Patent Document 3: Proceedings of the National Academy of Sciences, 2011, Vol. 108, No. 6, pp. 2426-2431
Non-Patent Document 4: The Journal of Physical Chemistry, 2012, Vol. 116, pp. 18440-18450
Non-Patent Document 5: Molecular Therapy—Nucleic Acids, 2012, Vol. 1, e37
Non-Patent Document 6: Langmuir, 2012, Vol. 28, pp. 3633-3640
Non-Patent Document 7: Journal of Controlled Release, 2014, Vol. 196, pp. 106-112

SUMMARY

Technical Problem

Objectives of the present invention are to provide nucleic acid-containing lipid nanoparticles that are useful as a pharmaceutical and are more stable and smaller than conventional particles, and a method for producing the lipid nanoparticles. In addition, an object of the present invention is to provide a lipid that is useful for producing the lipid nanoparticles.

Solution to Problem

The present invention relates to the following (1) to (91).
(1) Nucleic acid-containing lipid nanoparticles, comprising: a lipid (lipid A), which has a hydrophilic unit having a single quaternary ammonium group and three independent, optionally substituted hydrocarbon groups; a lipid derivative or fatty acid derivative of a water-soluble polymer; and a nucleic acid.
(2) The lipid nanoparticles described in (1), wherein the number of moles of the quaternary ammonium group in the lipid A is 0.01 times or more the number of moles of phosphorous atoms in the nucleic acid.

(3) The lipid nanoparticles described in (1) or (2), wherein the lipid A is a lipid represented by the following formulas or a combination thereof:

formula (I)
[C2]

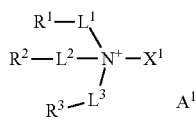

(I)

(wherein,
$R^1$ to $R^3$, the same or different, are a linear or branched, optionally substituted C8-C24 alkyl, C8-C24 alkenyl or C8-C24 alkynyl,
$L^1$ to $L^3$, the same or different, are absent or are —$Z^1$—$(CY^1Y^2)_{p1}$— or —$Z^2$—$(CY^3Y^4)_{p2}$—$Z^3$—$(CY^5Y^6)_{p3}$— (wherein, $Y^1$ to $Y^6$, the same or different, are a hydrogen atom or optionally substituted C1-C4 alkyl, $Z^1$ to $Z^3$, the same or different, are —O—, —$NY^{7A}$—, —CO—O—, —O—CO—, —CO—$NY^{7B}$—, —$NY^{7C}$—CO— or —$NY^{7D}$—CO—O— (wherein, $Y^{7A}$ to $Y^{7D}$, the same or different, are a hydrogen atom or optionally substituted C1-C4 alkyl), and $p^1$ to $p^3$, the same or different, are an integer of 1 to 5),
$X^1$ is an optionally substituted C1-C4 alkyl, and
$A^1$ is a pharmaceutically acceptable anion);

formula (II)
[C3]

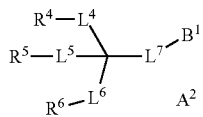

(II)

(wherein,
$R^4$ to $R^6$, the same or different, are a linear or branched, optionally substituted C8-C24 alkyl, C8-C24 alkenyl or C8-C24 alkynyl,
$L^4$ to $L^6$, the same or different, are absent or are —$Z^4$—$(CY^8Y^9)_{p4}$— or —$Z^5$—$(CY^{10}Y^{11})_{p5}$—$Z^6$—$(CY^{12}Y^{13})_{p6}$— (wherein, $Y^8$ to $Y^{13}$, the same or different, are a hydrogen atom or optionally substituted C1-C4 alkyl, $Z^4$ to $Z^6$, the same or different, are —O—, —$NY^{14A}$—, —CO—O—, —O—CO—, —CO—$NY^{14B}$—, —$NY^{14C}$—CO— or —$NY^{14D}$—CO—O— (wherein, $Y^{14A}$ to $Y^{14D}$, the same or different, are a hydrogen atom or optionally substituted C1-C4 alkyl), $p^4$ is an integer of 0 to 5, $p^5$ is an integer of 1 to 5, and $p^6$ is an integer of 0 to 5),
$L^7$ is absent or is —$(CY^{15}Y^{16})_{p7}$—, —$(CY^{17}Y^{18})_{p8}$—$Z^7$—$(C^{19}Y^{20})_{p9}$— or —$(CY^{21}Y^{22})_{p10}$—$Z^8$—$(CY^{23}Y^{24})_{p11}$—$Z^9$—$(CY^{25}Y^{26})_{p12}$— (wherein, $Y^{15}$ to $Y^{26}$, the same or different, are a hydrogen atom or optionally substituted C1-C4 alkyl, $Z^7$ to $Z^9$, the same or different, are —O—, —$NY^{27A}$—, —CO—O—, —O—CO—, —CO—$NY^{27B}$—, —$NY^{27C}$—CO— or —$NY^{27D}$—CO—O— (wherein, $Y^{27A}$ to $Y^{27D}$, the same or different, are a hydrogen atom or optionally substituted C1-C4 alkyl), $p^7$ is an integer of 1 to 5, $p^8$ is an integer of 0 to 5, $p^9$ is an integer of 1 to 5, $p^{10}$ is an integer of 0 to 5, $p^{11}$ is an integer of 1 to 5, and $p^{12}$ is an integer of 1 to 5), $B^1$ is

[C4]

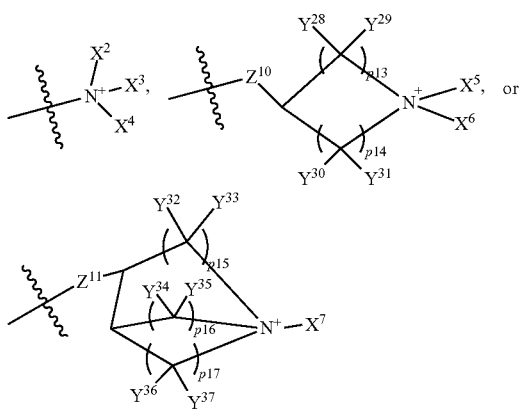

(wherein, $X^2$ and $X^3$, the same or different, are an optionally substituted C1-C4 alkyl or are combined together to form an optionally substituted C4-C6 heterocycle with an adjacent nitrogen atom, $X^4$ is an optionally substituted C1-C4 alkyl, $X^5$ and $X^6$, the same or different, are an optionally substituted C1-C4 alkyl or are combined together to form an optionally substituted C4-C6 heterocycle with an adjacent nitrogen atom, $X^7$ is an optionally substituted C1-C4 alkyl, $Y^{28}$ to $Y^{37}$, the same or different, are a hydrogen atom or optionally substituted C1-C4 alkyl, $Z^{10}$ and $Z^{11}$, the same or different, are —O—, —NY$^{38A}$—, —CO—O—, —O—CO—, —CO—NY$^{38B}$, —NY$^{38C}$—CO— or —NY$^{38D}$—CO—O— (wherein, $Y^{38A}$ to $Y^{38D}$, the same or different, are a hydrogen atom or optionally substituted C1-C4 alkyl), $p^{13}$ is an integer of 0 to 5, and $p^{14}$ to $p^{17}$, the same or different, are an integer of 1 to 5), and $A^2$ is a pharmaceutically acceptable anion);

formula (III)

[C5]

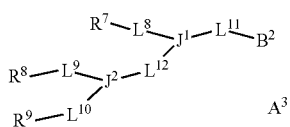

(wherein, $R^7$ to $R^9$, the same or different, are a linear or branched, optionally substituted C8-C24 alkyl, C8-C24 alkenyl or C8-C24 alkynyl, $L^8$ to $L^{10}$, the same or different, are absent or are —Z$^{12}$—(CY$^{39}$Y$^{40}$)$_{p18}$— or —Z$^{13}$—(CY$^{41}$Y$^{42}$)$_{p19}$—Z$^{14}$—(CY$^{43}$Y$^{44}$)$_{p20}$— (wherein, $Y^{39}$ to $Y^{44}$, the same or different, are a hydrogen atom or optionally substituted C1-C4 alkyl, $Z^{12}$ to $Z^{14}$, the same or different, are —O—, —NY$^{45A}$—, —CO—O—, —O—CO—, —CO—NY$^{45B}$, —NY$^{45C}$—CO—, —NY$^{45D}$—CO—O or —CO— (wherein, $Y^{45A}$ to $Y^{45D}$, the same or different, are a hydrogen atom or optionally substituted C1-C4 alkyl), $p^{18}$ is an integer of 0 to 5, $p^{19}$ is an integer of 1 to 5, and $p^{20}$ is an integer of 0 to 5), $L^{11}$ is absent or is —(CY$^{46}$Y$^{47}$)$_{p21}$—, —(CY$^{48}$Y$^{49}$)$_{p22}$—Z$^{15}$—(CY$^{50}$Y$^{51}$)$_{p23}$— or —(CY$^{52}$Y$^{53}$)$_{p24}$—Z$^{16}$—(CY$^{54}$Y$^{55}$)$_{p25}$—Z$^{17}$—(CY$^{56}$Y$^{57}$)$_{p26}$— (wherein, $Y^{46}$ to $Y^{57}$, the same or different, are a hydrogen atom or optionally substituted C1-C4 alkyl, $Z^{15}$ to $Z^{17}$, the same or different, are —O—, —NY$^{58A}$—, —CO—O—, —O—CO—, —CO—NY$^{58B}$—, —NY$^{58C}$—CO—, NY$^{58D}$—CO—O— or —CO— (wherein, $Y^{58A}$ to $Y^{58D}$, the same or different, are a hydrogen atom or optionally substituted C1-C4 alkyl), $p^{21}$ is an integer of 1 to 5, $p^{22}$ is an integer of 0 to 5, $p^{23}$ is an integer of 1 to 5, $p^{24}$ is an integer of 0 to 5, $p^{25}$ is an integer of 1 to 5, and $p^{26}$ is an integer of 1 to 5), $L^{12}$ is absent or is —(CY$^{59}$Y$^{60}$)$_{p27}$—, —(CY$^{61}$Y$^{62}$)$_{p28}$—Z$^{18}$—(CY$^{63}$Y$^{64}$)$_{p29}$— or —(CY$^{65}$Y$^{66}$)$_{p30}$—Z$^{19}$—(CY$^{67}$Y$^{68}$)$_{p31}$—Z$^{20}$—(CY$^{69}$Y$^{70}$)$_{p32}$— (wherein, $Y^{59}$ to $Y^{70}$, the same or different, are a hydrogen atom or optionally substituted C1-C4 alkyl, $Z^{18}$ to $Z^{20}$, the same or different, are —O—, —NY$^{71A}$—, —CO—O—, —O—CO—, —CO—NY$^{71B}$, —NY$^{71C}$—CO—, —NY$^{71D}$—CO—O— or —CO— (wherein, $Y^{71A}$ to $Y^{71D}$, the same or different, are a hydrogen atom or optionally substituted C1-C4 alkyl), $p^{27}$ is an integer of 1 to 5, $p^{28}$ is an integer of 0 to 5, $p^{29}$ is an integer of 0 to 5, $p^{30}$ is an integer of 0 to 5, $p^{31}$ is an integer of 1 to 5, and $p^{32}$ is an integer of 0 to 5), $J^1$ and $J^2$, the same or different, are $CY^{72}$ or N (wherein, $Y^{72}$ is a hydrogen atom, hydroxyl, optionally substituted C1-C4 alkyl, optionally substituted C1-C4 alkoxy or optionally substituted C1-C4 acyloxy group), $B^2$ is

[C6]

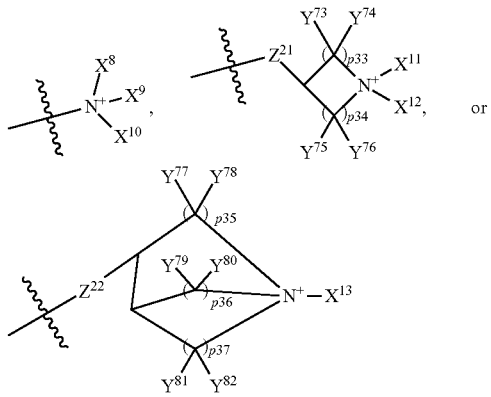

(wherein, $X^8$ and $X^9$, the same or different, are an optionally substituted C1-C4 alkyl or are combined together to form an optionally substituted C4-C6 heterocycle with an adjacent nitrogen atom, $X^{10}$ is an optionally substituted C1-C4 alkyl, $X^{11}$ and $X^{12}$, the same or different, are an optionally substituted C1-C4 alkyl or are combined together to form an optionally substituted C4-C6 heterocycle with an adjacent nitrogen atom, $X^{13}$ is an optionally substituted C1-C4 alkyl, $Y^{73}$ to $Y^{82}$, the same or different, are a hydrogen atom or optionally substituted C1-C4 alkyl, $Z^{21}$ and $Z^{22}$, the same or different, are —O—, —NY$^{83A}$—, —CO—O—, —O—CO—, —CO—NY$^{83B}$, —NY$^{83C}$—CO— or —NY$^{83D}$—CO—O— (wherein, $Y^{83A}$ to $Y^{83D}$, the same or different, are a hydrogen atom or optionally substituted C1-C4 alkyl), $p^{33}$ is an integer of 0 to 5, and $p^{34}$ to $p^{37}$, the same or different, are an integer of 1 to 5), and $A^3$ is a pharmaceutically acceptable anion);

formula (IV)

[C7]

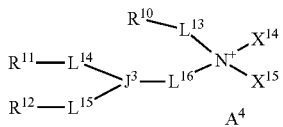

(wherein, $R^{10}$ to $R^{12}$, the same or different, are a linear or branched, optionally substituted C8-C24 alkyl, C8-C24 alkenyl or C8-C24 alkynyl, $L^{13}$ is absent or is $-Z^{23}-(CY^{83}Y^{84})_{p38}-$ or $-Z^{24}-(CY^{85}Y^{86})_{p39}-Z^{25}-(CY^{87}Y^{88})_{p40}-$ (wherein, $Y^{83}$ to $Y^{88}$, the same or different, are a hydrogen atom or optionally substituted C1-C4 alkyl, $Z^{23}$ to $Z^{25}$, the same or different, are $-O-$, $-NY^{89A}-$, $-CO-O-$, $-O-CO-$, $-CO-NY^{89B}-$, $-NY^{89C}-CO-$ or $-NY^{89D}-CO-O-$ (wherein, $Y^{89A}$ to $Y^{89D}$, the same or different, are a hydrogen atom or optionally substituted C1-C4 alkyl), and $p^{38}$ to $p^{40}$, the same or different, are an integer of 1 to 5), $L^{14}$ and $L^{15}$, the same or different, are absent or are $-Z^{26}-(CY^{90}Y^{91})_{p41}-$ or $-Z^{27}-(CY^{92}Y^{93})_{p42}-Z^{28}-(CY^{94}Y^{95})_{p43}-$ (wherein, $Y^{90}$ to $Y^{95}$, the same or different, are a hydrogen atom or optionally substituted C1-C4 alkyl, $Z^{26}$ to $Z^{28}$, the same or different, are $-O-$, $-NY^{96A}-$, $-CO-O-$, $-O-CO-$, $-CO-NY^{96B}-$, $-NY^{96C}-CO-$, $-NY^{96D}-CO-O-$ or $-CO-$ (wherein, $Y^{96A}$ to $Y^{96D}$, the same or different, are a hydrogen atom or optionally substituted C1-C4 alkyl), $p^{41}$ is an integer of 0 to 5, $p^{42}$ is an integer of 1 to 5, and $p^{43}$ is an integer of 0 to 5), $L^{16}$ is absent or is $-(CY^{97}Y^{98})_{p44}-$, $-(CY^{99}Y^{100})_{p45}-Z^{29}-(CY^{101}Y^{102})_{p46}-$ or $-(CY^{103}Y^{104})_{p47}-Z^{30}-(CY^{105}Y^{106})_{p48}-Z^{31}-(CY^{107}Y^{108})_{p49}-$ (wherein, $Y^{97}$ to $Y^{108}$, the same or different, are a hydrogen atom or optionally substituted C1-C4 alkyl, $Z^{29}$ to $Z^{31}$, the same or different, are $-O-$, $-NY^{109A}-$, $-CO-O-$, $-O-CO-$, $-CO-NY^{109B}-$, $-NY^{109C}-CO-$, $-NY^{109D}-CO-O-$ or $-CO-$ (wherein, $Y^{109A}$ to $Y^{109D}$, the same or different, are a hydrogen atom or optionally substituted C1-C4 alkyl), $p^{44}$ is an integer of 1 to 5, $p^{45}$ is an integer of 0 to 5, $p^{46}$ is an integer of 1 to 5, $p^{47}$ is an integer of 0 to 5, $p^{48}$ is an integer of 1 to 5, and $p^{49}$ is an integer of 1 to 5), $J^3$ is $CY^{110}$ or N (wherein, $Y^{110}$ is a hydrogen atom, hydroxyl, optionally substituted C1-C4 alkyl, optionally substituted C1-C4 alkoxy or optionally substituted C1-C4 acyloxy group), $X^{14}$ and $X^{15}$, the same or different, are an optionally substituted C1-C4 alkyl or are combined together to form an optionally substituted C4-C6 heterocycle with an adjacent nitrogen atom, and $A^4$ is a pharmaceutically acceptable anion); or formula (V') or formula (V'')
[C8]

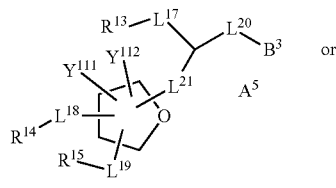
(V')

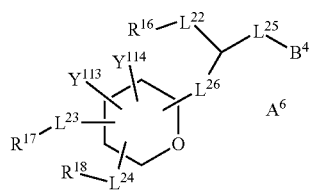
(V'')

(wherein, $R^{13}$ to $R^{18}$, the same or different, are a linear or branched, optionally substituted C8-C24 alkyl, C8-C24 alkenyl or C8-C24 alkynyl, $Y^{111}$ to $Y^{114}$, the same or different, are a hydrogen atom, hydroxyl or optionally substituted C1-C4 alkyl, $L^{17}$ to $L^{19}$ and $L^{22}$ to $L^{24}$, the same or different, are absent or are $Z^{32}-(CY^{115}Y^{116})_{p51}-$ or $-Z^{33}-(CY^{117}Y^{118})_{p52}-Z^{34}-(CY^{119}Y^{120})_{p53}-$ (wherein, $Y^{115}$ to $Y^{120}$, the same or different, are a hydrogen atom or optionally substituted C1-C4 alkyl, $Z^{32}$ to $Z^{34}$, the same or different, are $-O-$, $-NY^{121A}-$, $-CO-O-$, $-O-CO-$, $-CO-NY^{121B}-$, $-NY^{121C}-CO-$, $-NY^{121D}-CO-O-$ or $-CO-$ (wherein, $Y^{121A}$ to $Y^{121D}$, the same or different, are a hydrogen atom or optionally substituted C1-C4 alkyl), $p^{51}$ is an integer of 0 to 5, $p^{52}$ is an integer of 1 to 5, and $p^{53}$ is an integer of 0 to 5), $L^{20}$ and $L^{25}$, the same or different, are absent or are $-(CY^{122}Y^{123})_{p54}-$, $-(CY^{124}Y^{125})_{p55}-Z^{35}-(CY^{126}Y^{127})_{p56}-$ or $-(CY^{128}Y^{129})_{p57}-Z^{36}-(CY^{130}Y^{131})_{p58}-Z^{37}-(CY^{132}Y^{133})_{p59}-$ (wherein, $Y^{122}$ to $Y^{133}$, the same or different, are a hydrogen atom or optionally substituted C1-C4 alkyl, $Z^{35}$ to $Z^{37}$, the same or different, are $-O-$, $-NY^{134A}-$, $-CO-O-$, $-O-CO-$, $-CO-NY^{134B}-$, $-NY^{134C}-CO-$, $-NY^{134D}-CO-O-$ or $-CO-$ (wherein, $Y^{134A}$ to $Y^{134D}$, the same or different, are a hydrogen atom or optionally substituted C1-C4 alkyl), $p^{54}$ is an integer of 1 to 5, $p^{55}$ is an integer of 0 to 5, $p^{56}$ is an integer of 1 to 5, $p^{57}$ is an integer of 0 to 5, $p^{58}$ is an integer of 1 to 5 and $p^{59}$ is an integer of 1 to 5), $L^{21}$ and $L^{26}$, the same or different, are absent or are $-(CY^{135}Y^{136})_{p60}-$, $-(CY^{137}Y^{138})_{p61}-Z^{38}-(CY^{139}Y^{140})_{p62}-$ or $-(CY^{141}Y^{142})_{p63}-Z^{39}-(CY^{143}Y^{144})_{p64}-Z^{40}-(CY^{145}Y^{146})_{p65}-$ (wherein, $Y^{135}$ to $Y^{146}$, the same or different, are a hydrogen atom or optionally substituted C1-C4 alkyl, $Z^{38}$ to $Z^{40}$, the same or different, are $-O-$, $-NY^{147A}-$, $-CO-O-$, $-O-CO-$, $-CO-NY^{147B}-$, $-NY^{147C}-CO-$, $-NY^{147D}-CO-O-$ or $-CO-$ (wherein, $Y^{147A}$ to $Y^{147D}$, the same or different, are a hydrogen atom or optionally substituted C1-C4 alkyl), $p^{60}$ is an integer of 1 to 5, $p^{61}$ is an integer of 0 to 5, $p^{62}$ is an integer of 0 to 5, $p^{63}$ is an integer of 0 to 5, $p^{64}$ is an integer of 1 to 5, and $p^{65}$ is an integer of 0 to 5), $B^3$ and $B^4$, the same or different, are

[C9]

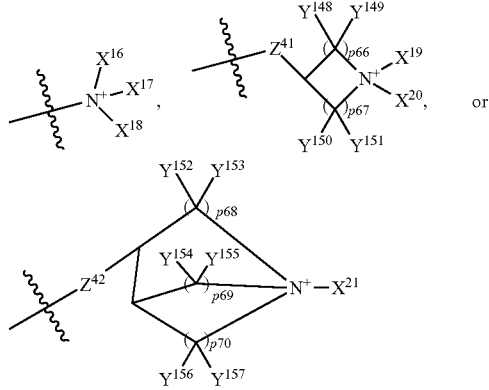

(wherein, $X^{16}$ and $X^{17}$, the same or different, are an optionally substituted C1-C4 alkyl or are combined together to form an optionally substituted C4-C6 heterocycle with an adjacent nitrogen atom, $X^{18}$ is an optionally substituted C1-C4 alkyl, $X^{19}$ and $X^{20}$, the same or different, are an optionally substituted C1-C4 alkyl or are combined together to form an optionally substituted C4-C6 heterocycle with an adjacent nitrogen atom, $X^{21}$ is an optionally substituted C1-C4 alkyl, $Y^{148}$ to $Y^{157}$, the same or different, are a hydrogen atom or optionally substituted C1-C4 alkyl, $Z^{41}$ and $Z^{42}$, the same or different, are —O—, —NY$^{158A}$—, —CO—O—, —O—CO—, —CO—NY$^{158B}$, —NY$^{158C}$—CO— or —NY$^{158D}$—CO—O— (wherein, $Y^{158A}$ to $Y^{158D}$, the same or different, are a hydrogen atom or optionally substituted C1-C4 alkyl), $p^{66}$ is an integer of 0 to 5, and $p^{67}$ to $p^{70}$, the same or different, are an integer of 1 to 5), and $A^5$ and $A^6$, the same or different, are a pharmaceutically acceptable anion).

(4) The lipid nanoparticles described in (3), wherein the lipid A is a lipid represented by formula (I), and in formula (I), one of $L^1$ to $L^3$ is —CO—O—$(Y^1Y^2)_{p1}$— or —O—CO—$(CY^1Y^2)_{p1}$— or two or more of $L^1$ to $L^3$, the same or different, are —CO—O—$(Y^1Y^2)_{p1}$— or —O—CO—$(CY^1Y^2)_{p1}$—, and $R^1$ to $R^3$ are linear or branched C15-C20 alkenyl or C9-C18 alkyl and are the same.

(5) The lipid nanoparticles described in (3), wherein the lipid A is represented by formula (II), and in formula (II), one of $L^4$ to $L^6$ is —CO—O—$(Y^8Y^9)_{p4}$—, —O—CO—$(CY^8Y^9)_{p4}$— or —O—CO—$(CY^{10}Y^{11})_{p5}$—O—$(CY^{12}Y^{13})_{p6}$— or two or more of $L^4$ to $L^6$, the same or different, are —CO—O—$(Y^8Y^9)_{p4}$—, —O—CO—$(CY^8Y^9)_{p4}$— or —O—CO—$(CY^{10}Y^{11})_{p5}$—O—$(CY^{12}Y^{13})_{p6}$—, and $R^4$ to $R^6$ are linear or branched C15-C20 alkenyl or C9-C18 alkyl and are the same.

(6) The lipid nanoparticles described in (3), wherein the lipid A is a lipid represented by formula (III), and in formula (III), one of $L^8$ to $L^{10}$ is —CO—O—$(CY^{39}Y^{40})_{p18}$— or —O—CO—$(CY^{39}Y^{40})_{p18}$— or two or more of $L^8$ to $L^{10}$, the same or different, are —CO—O—$(CY^{39}Y^{40})_{p18}$— or —O—CO—$(CY^{39}Y^{40})_{p18}$—, and $R^7$ to $R^9$ are a linear or branched C15-C20 alkenyl or C9-C18 alkyl.

(7) The lipid nanoparticles described in (3), wherein the lipid A is a lipid represented by formula (IV), and in formula (IV), $L^{13}$ is —CO—O—$(CY^{83}Y^{84})_{p38}$— or —O—CO—$(CY^{83}Y^{84})_{p38}$—, one of $L^{14}$ and $L^{15}$ is —CO—O—$(Y^{90}Y^{91})_{p41}$— or —O—CO—$(CY^{90}Y^{91})_{p41}$—, $L^{13}$ is —CO—O—$(CY^{83}Y^{84})_{p38}$— or —O—CO—$(CY^{83}Y^{84})_{p38}$— and one of $L^{14}$ and $L^{15}$ is —CO—O—$(Y^{90}Y^{91})_{p41}$— or —O—CO—$(CY^{90}Y^{91})_{p41}$—, $L^{14}$ and $L^{15}$, the same or different, are —CO—O—$(Y^{90}Y^{91})_{p41}$— or —O—CO—$(CY^{90}Y^{91})_{p41}$— or $L^{13}$ is —CO—O—$(CY^{83}Y^{84})_{p38}$— or —O—CO—$(CY^{83}Y^{84})_{p38}$— and $L^{14}$ and $L^{15}$, the same or different, are —CO—O—$(Y^{90}Y^{91})_{p41}$— or —O—CO—$(CY^{90}Y^{91})_{p41}$—, and $R^{10}$ to $R^{12}$ are a linear or branched C15-C20 alkenyl or C9-C18 alkyl.

(8) The lipid nanoparticles described in (3), wherein the lipid A is represented by formula (V'), and in formula (V'), one of $L^{17}$ to $L^{19}$ is —CO—O— or —O— or two or more of $L^{17}$ to $L^{19}$, the same or different, are —CO—O— or —O—, and $R^{13}$ to $R^{15}$ are a linear or branched C15-C20 alkenyl or C9-C18 alkyl.

(9) The lipid nanoparticles described in any one of (1) to (8), wherein the content of the lipid derivative or fatty acid derivative of the water-soluble polymer is 0.005 times or more the total number of moles of lipid.

(10) The lipid nanoparticles described in any one of (1) to (9), wherein the water-soluble polymer unit of the lipid derivative or fatty acid derivative of the water-soluble polymer is selected from the group consisting of polyethylene glycol, polyglycerin, polyethyleneimine, polyvinyl alcohol, polyacrylic acid and polyacrylamide.

(11) The lipid nanoparticles described in any one of (1) to (10), wherein the ratio of the total number of moles of lipid to the number of moles of nucleic acid (total number of moles of lipid/number of moles of nucleic acid) is 50 or more.

(12) The lipid nanoparticles described in any one of (1) to (11), wherein the nucleic acid is a nucleic acid having an expression inhibitory action on a target gene that uses RNA interference (RNAi).

(13) The lipid nanoparticles described in (12), wherein the target gene is a gene associated with tumors or inflammation.

(14) The lipid nanoparticles described in any one of (1) to (13), further containing a lipid (lipid B), which has a hydrophilic unit having one optionally substituted amino group or one quaternary ammonium group, and a hydrophobic unit having two independent, optionally substituted hydrocarbon groups.

(15) The lipid nanoparticles described in (14), wherein the content of the lipid B is 0.1 times or more the total number of moles of lipid.

(16) The lipid nanoparticles described in (14) or (15), wherein the number of moles of the amino group or quaternary ammonium group of the hydrophilic unit in the lipid B is 0.01 times or more the number of moles of phosphoric acid atoms in the nucleic acid.

(17) The lipid nanoparticles described in any one of (14) to (16), wherein the lipid B is:

formula (CL-I)
[C10]

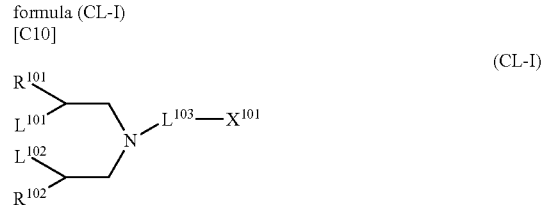

(CL-I)

(wherein, $R^{101}$ and $R^{102}$, the same or different, are a linear or branched C10-C24 alkyl, C10-C24 alkenyl or C10-C24 alkynyl, $L^{101}$ and $L^{102}$ are hydrogen atoms or are combined together to form a single bond or C1-C3 alkylene, $L^{103}$ is a single bond, —CO— or —CO—O—, and in the case where $L^{103}$ is a single bond, $X^{101}$ is a hydrogen atom, C1-C6 alkyl, C3-C6 alkenyl, pyrrolidin-3-yl, piperidin-3-yl or piperidin-4-yl, or a C1-C6 alkyl or C3-C6 alkenyl substituted with one to three of the same or different amino, monoalkylamino, dialkylamino, trialkylammonio, hydroxyl, alkoxy, carbamoyl, monoalkylcarbamoyl, dialkylcarbamoyl, pyrrolidinyl, piperidyl or morpholinyl, or in the case where $L^{103}$ is —CO— or —CO—O—, $X^{101}$ is a pyrrolidin-2-yl, pyrrolidin-3-yl, piperidin-2-yl, piperidin-3-yl, piperidin-4-yl, morpholin-2-yl or morpholin-3-yl, or a C1-C6 alkyl or C3-C6 alkenyl substituted with one to three of the same or different amino, monoalkylamino, dialkylamino, trialkylammonio, hydroxyl, alkoxy, carbamoyl, monoalkylcarbamoyl, dialkylcarbamoyl, pyrrolidinyl, piperidyl or morpholinyl, and at least one of the substituents is an amino, monoalkylamino, dialkylamino, trialkylammonio, pyrrolidinyl, piperidyl or morpholinyl);

formula (CL-II)
[C11]

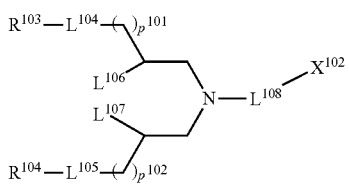
(CL-II)

(wherein,
$R^{103}$ and $R^{104}$, the same or different, are a linear or branched C12-C24 alkyl, C12-C24 alkenyl or C12-C24 alkynyl,
$p^{101}$ and $p^{102}$, the same or different, are an integer of 0 to 3,
$L^{106}$ and $L^{107}$ are hydrogen atoms or are combined together to form a single bond or C1-C3 alkylene,
$L^{104}$ and $L^{105}$, the same or different, are —O—, —CO—O— or —O—CO—,
$L^{108}$ is a single bond, —CO— or —CO—O—, and in the case where $L^{108}$ is a single bond,
$X^{102}$ is a hydrogen atom, C1-C6 alkyl, C3-C6 alkenyl, pyrrolidin-2-yl, pyrrolidin-3-yl, piperidin-3-yl or piperidin-4-yl, or a C1-C6 alkyl or C3-C6 alkenyl substituted with one to three of the same or different amino, monoalkylamino, dialkylamino, trialkylammonio, hydroxyl, alkoxy, carbamoyl, monoalkylcarbamoyl, dialkylcarbamoyl, pyrrolidinyl, piperidyl or morpholinyl,
or in the case where $L^{108}$ is —CO— or —CO—O—,
$X^{102}$ is a pyrrolidin-2-yl, pyrrolidin-3-yl, piperidin-2-yl, piperidin-3-yl, piperidin-4-yl, morpholin-2-yl or morpholin-3-yl, or a C1-C6 alkyl or C3-C6 alkenyl substituted with one to three of the same or different amino, monoalkylamino, dialkylamino, trialkylammonio, hydroxyl, alkoxy, carbamoyl, monoalkylcarbamoyl, dialkylcarbamoyl, pyrrolidinyl, piperidyl or morpholinyl, and at least one of the substituents is an amino, monoalkylamino, dialkylamino, trialkylammonio, pyrrolidinyl, piperidyl or morpholinyl);

formula (CL-III)
[C12]

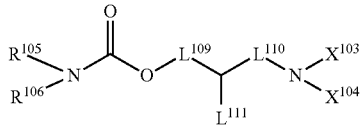
(CL-III)

(wherein,
$R^{105}$ is a linear or branched C8-C24 alkyl, C8-C24 alkenyl or C8-C24 alkynyl,
$R^{106}$ is a linear or branched C8-C24 alkyl, C8-C24 alkenyl, C8-C24 alkynyl, C8-C24 alkoxyethyl, C8-C24 alkoxypropyl, C8-C24 alkenyloxyethyl, C8-C24 alkenyloxypropyl, C8-C24 alkynyloxyethyl or C8-C24 alkynyloxypropyl,
$X^{103}$ and $X^{104}$, the same or different, are a C1-C3 alkyl or are combined together to form a C2-C8 alkylene, or $X^{103}$ forms a C2-C8 alkylene with $L^{111}$,
$L^{111}$ is a hydrogen atom, C1-C6 alkyl, C3-C6 alkenyl, amino, monoalkylamino, hydroxyl, alkoxy, carbamoyl, monoalkylcarbamoyl or dialkylcarbamoyl, or a C1-C6 alkyl or C3-C6 alkenyl substituted with one to three of the same or different amino, monoalkylamino, hydroxyl, alkoxy, carbamoyl, monoalkylcarbamoyl or dialkylcarbamoyl, or forms a C2-C8 alkylene with $X^{103}$,
$L^{109}$ is a C1-C6 alkylene, and
$L^{110}$ is a single bond or a C1-C6 alkylene, provided that, in the case where the sum of the number of carbon atoms of $L^{109}$ and $L^{110}$ is 7 or less and $L^{111}$ is a hydrogen atom, $L^{110}$ is a single bond, while in the case where $L^{111}$ forms a C2-C6 alkylene with
$X^{103}$, $L^{110}$ is a single bond, methylene or ethylene);

formula (CL-IV)
[C13]

(CL-IV)

(wherein,
$R^{107}$ is a linear or branched C8-C24 alkyl, C8-C24 alkenyl or C8-C24 alkynyl, and
$R^{108}$ is a linear or branched C8-C24 alkyl, C8-C24 alkenyl, C8-C24 alkynyl, C8-C24 alkoxyethyl, C8-C24 alkoxypropyl, C8-C24 alkenyloxyethyl, C8-C24 alkenyloxypropyl, C8-C24 alkynyloxyethyl or C8-C24 alkynyloxypropyl);

formula (CL-V)
[C14]

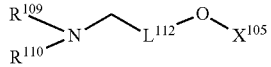
(CL-V)

(wherein,
$R^{109}$ is a linear or branched C8-C24 alkyl, C8-C24 alkenyl or C8-C24 alkynyl,
$R^{110}$ is a linear or branched C8-C24 alkyl, C8-C24 alkenyl, C8-C24 alkynyl, C8-C24 alkoxyethyl, C8-C24 alkoxypropyl, C8-C24 alkenyloxyethyl, C8-C24 alkenyloxypropyl, C8-C24 alkynyloxyethyl or C8-C24 alkynyloxypropyl),
$L^{112}$ is a C1-C3 alkylene, and
$X^{105}$ is a hydrogen atom or C1-C3 alkyl);

formula (CL-VI)
[C15]

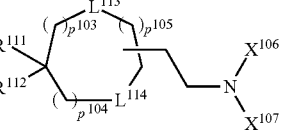
(CL-VI)

(wherein,
$R^{111}$ and $R^{112}$, the same or different, are a linear or branched, optionally substituted C8-C24 alkyl, C8-C24 alkenyl or C8-C24 alkynyl,
$X^{106}$ and $X^{107}$, the same or different, are a C1-C3 alkyl or are combined together to form a C2-C8 alkylene,
$p^{103}$ to $p^{105}$, the same or different, are 0 or 1, provided that $p^{103}$ to $p^{105}$ are not simultaneously 0, and
$L^{113}$ and $L^{114}$, the same or different, are O, S or NH); or formula (CL-VII)
[C16]

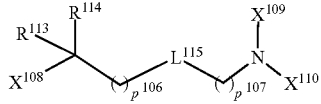
(CL-VII)

(wherein, $R^{113}$ and $R^{114}$, the same or different, are a linear or branched, optionally substituted C8-C24 alkyl, C8-C24 alkenyl or C8-C24 alkynyl, $X^{109}$ and $X^{110}$, the same or different, are a C1-C3 alkyl or are combined together to form a C2-C8 alkylene, $X^{108}$ is a hydrogen atom, hydroxyl, optionally substituted C1-C4 alkyl, optionally substituted C1-C4 alkoxy or optionally substituted C1-C4 acyloxy group, $L^{115}$ is —CO—O— or —O—CO—, and $p^{106}$ is an integer of 0 to 3 and $p^{107}$ is an integer of 1 to 4).

(18) The lipid nanoparticles described in any one of (1) to (17), further containing a neutral lipid.

(19) The lipid nanoparticles described in (18), wherein the content of the neutral lipid is 0.05 times or more the total number of moles of lipid.

(20) The lipid nanoparticles described in (18) or (19), wherein the neutral lipid is selected from the group consisting of phospholipids, sterols, glyceroglycolipids, sphingoglycolipids and sphingoids.

(21) The lipid nanoparticles described in any one of (1) to (20), wherein the average particle size is 20 nm to 65 nm.

(22) A method for producing nucleic acid-containing lipid nanoparticles, the method including:

(a) preparing a first lipid solution containing a lipid (lipid A) and a nucleic acid by mixing the lipid A, which has a hydrophilic unit having one quaternary ammonium group, and three independent, optionally substituted hydrocarbon groups, with a nucleic acid in a mixed solvent of a water-miscible organic solvent and water, (b) preparing a third lipid solution by adding a second lipid solution containing a lipid derivative or fatty acid derivative of a water-soluble polymer to the first lipid solution, and (c) adding water or an aqueous buffer solution to the third lipid solution.

(23) The production method described in (22), wherein, in step (a), one or more lipids (lipid B), which has a hydrophilic unit having a lipid derivative or fatty acid derivative of a water-soluble polymer, a neutral lipid and one optionally substituted amino group, and a hydrophobic unit having two independent, optionally substituted hydrocarbon groups, are mixed with the lipid A and the nucleic acid.

(24) The production method described in (22), wherein, in step (b), the second lipid solution further contains a neutral lipid and/or a lipid (lipid B), which has a hydrophilic unit having one optionally substituted amino group, and a hydrophobic unit having two independent, optionally substituted hydrocarbon groups.

(25) The production method described in any one of (22) to (24), wherein the water-miscible organic solvent is an alcohol, dimethylsulfoxide, tetrahydrofuran, acetone, acetonitrile or a mixture thereof.

(26) The production method described in any one of (22) to (24), wherein the water-miscible organic solvent is an alcohol.

(27) The production method described in (25) or (26), wherein the alcohol is methanol, ethanol, propanol, butanol or a mixture thereof.

(28) The production method described in any one of (22) to (27), wherein the content of the water-miscible organic solvent in the water of the third lipid solution obtained in step (b) is 50% (v/v) or more based on the solution.

(29) The production method described in any one of (22) to (28), wherein, in step (c), the concentration of the water-miscible organic solvent in the water of the third lipid solution obtained in step (b) is made to be 50% (v/v) or less by adding water or aqueous buffer solution.

(30) The production method described in (29), wherein the concentration of the water-miscible organic solvent in the water of the third lipid solution obtained in step (b) is made to be 50% (v/v) or less within one minute.

(31) The production method described in any one of (22) to (30), wherein the number of moles of the quaternary ammonium group in the lipid A is 0.01 times or more the number of moles of phosphorous atoms in the nucleic acid.

(32) The production method described in any one of (22) to (31), wherein the content of the water-miscible organic solvent in the water of the first lipid solution obtained in step (a) is 50% (v/v) or more based on the solution.

(33) The production method described in any one of (22) to (32), wherein the aqueous buffer solution is a phosphate buffer solution, citrate buffer solution or acetate buffer solution.

(34) The production method described in any one of (22) to (33), wherein the ratio of the total number of moles of lipid to the number of moles of nucleic acid in the solution obtained in step (c) (total number of moles of lipid/number of moles of nucleic acid) is 50 or more.

(35) The production method described in any one of (22) to (34), wherein the nucleic acid is a nucleic acid having an expression inhibitory action on a target gene that uses RNA interference (RNAi).

(36) The production method described in (35), wherein the target gene is associated with tumors or inflammation.

(37) The production method described in any one of (22) to (36), wherein the lipid A is a lipid represented by the following formulas or a combination thereof:

formula (I)
[C17]

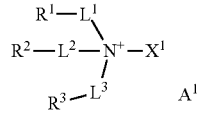

(I)

(wherein, $R^1$ to $R^3$, the same or different, are a linear or branched, optionally substituted C8-C24 alkyl, C8-C24 alkenyl or C8-C24 alkynyl, $L^1$ to $L^3$, the same or different, are absent or are —$Z^1$—$(CY^1Y^2)_{p1}$— or —$Z^2$—$(CY^3Y^4)_{p2}$—$Z^3$—$(CY^5Y^6)_{p3}$— (wherein, $Y^1$ to $Y^6$, the same or different, are a hydrogen atom or optionally substituted C1-C4 alkyl, $Z^1$ to $Z^3$, the same or different, are —O—, —$NY^{7A}$—, —CO—O—, —O—CO—, —CO—$NY^{7B}$—, —$NY^{7C}$—CO— or —$NY^{7D}$—CO—O— (wherein, $Y^{7A}$ to $Y^{7D}$ the same or different, are a hydrogen atom or optionally substituted C1-C4 alkyl), and $p^1$ to $p^3$, the same or different, are an integer of 1 to 5), $X^1$ is an optionally substituted C1-C4 alkyl, and $A^1$ is a pharmaceutically acceptable anion);

formula (II)
[C18]

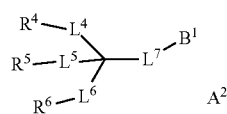

(II)

(wherein,

R$^4$ to R$^6$, the same or different, are a linear or branched, optionally substituted C8-C24 alkyl, C8-C24 alkenyl or C8-C24 alkynyl, L$^4$ to L$^6$, the same or different, are absent or are —Z$^4$—(CY$^8$Y$^9$)$_{p4}$— or —Z$^5$—(CY$^{10}$Y$^{11}$)$_{p5}$—Z$^6$—(CY$^{12}$Y$^{13}$)$_{p6}$— (wherein, Y$^8$ to Y$^{13}$, the same or different, are a hydrogen atom or optionally substituted C1-C4 alkyl, Z$^4$ to Z$^6$, the same or different, are —O—, —NY$^{14A}$—, —CO—O—, —O—CO—, —CO—NY$^{14B}$—, —NY$^{14C}$—CO— or —NY$^{14D}$—CO—O— (wherein, Y$^{14A}$ to Y$^{14D}$, the same or different, are a hydrogen atom or optionally substituted C1-C4 alkyl), p$^4$ is an integer of 0 to 5, p$^5$ is an integer of 1 to 5, and p$^6$ is an integer of 0 to 5), L$^7$ is absent or is —(CY$^{15}$Y$^{16}$)$_{p7}$—, —(CY$^{17}$Y$^{18}$)$_{p8}$—Z$^7$—(CY$^{19}$Y$^{20}$)$_{p9}$— or —(CY$^{21}$Y$^{22}$)$_{p10}$—Z$^8$—(CY$^{23}$Y$^{24}$)$_{p11}$—Z$^9$—(CY$^{25}$Y$^{26}$)$_{p12}$— (wherein, Y$^{15}$ to Y$^{26}$, the same or different, are a hydrogen atom or optionally substituted C1-C4 alkyl, Z$^7$ to Z$^9$, the same or different, are —O—, —NY$^{27A}$—, —CO—O—, —O—CO—, —CO—NY$^{27B}$—, —NY$^{27C}$—CO— or —NY$^{27D}$—CO—O— (wherein, Y$^{27A}$ to Y$^{27D}$, the same or different, are a hydrogen atom or optionally substituted C1-C4 alkyl), p$^7$ is an integer of 1 to 5, p$^8$ is an integer of 0 to 5, p$^9$ is an integer of 1 to 5, p$^{10}$ is an integer of 0 to 5, p$^{11}$ is an integer of 1 to 5, and p$^{12}$ is an integer of 1 to 5), B$^1$ is

[C19]

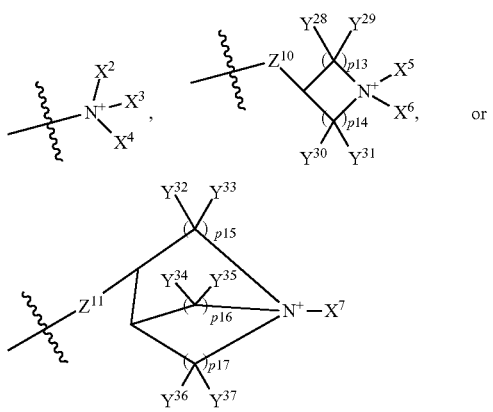

(wherein, X$^2$ and X$^3$, the same or different, are an optionally substituted C1-C4 alkyl or are combined together to form an optionally substituted C4-C6 heterocycle with an adjacent nitrogen atom, X$^4$ is an optionally substituted C1-C4 alkyl, X$^5$ and X$^6$, the same or different, are an optionally substituted C1-C4 alkyl or are combined together to form an optionally substituted C4-C6 heterocycle with an adjacent nitrogen atom, X$^7$ is an optionally substituted C1-C4 alkyl, Y$^{28}$ to Y$^{37}$, the same or different, are a hydrogen atom or optionally substituted C1-C4 alkyl, Z$^{10}$ and Z$^{11}$, the same or different, are —O—, —NY$^{38A}$—, —CO—O—, —O—CO—, —CO—NY$^{38B}$—, —NY$^{38C}$—CO— or —NY$^{38D}$—CO—O— (wherein, Y$^{38A}$ to Y$^{38D}$, the same or different, are a hydrogen atom or optionally substituted C1-C4 alkyl), p$^{13}$ is an integer of 0 to 5, and p$^{14}$ to p$^{17}$, the same or different, are an integer of 1 to 5), and A$^2$ is a pharmaceutically acceptable anion);

formula (III)

[C20]

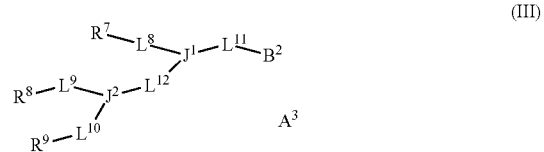

(wherein,

R$^7$ to R$^9$, the same or different, are a linear or branched, optionally substituted C8-C24 alkyl, C8-C24 alkenyl or C8-C24 alkynyl, L$^8$ to L$^{10}$, the same or different, are absent or are —Z$^{12}$—(CY$^{39}$Y$^{40}$)$_{p18}$— or —Z$^{13}$—(CY$^{41}$Y$^{42}$)$_{p19}$—Z$^{14}$—(CY$^{43}$Y$^{44}$)$_{p20}$— (wherein, Y$^{39}$ to Y$^{44}$, the same or different, are a hydrogen atom or optionally substituted C1-C4 alkyl, Z$^{12}$ to Z$^{14}$, the same or different, are —O—, —NY$^{45A}$—, —CO—O—, —O—CO—, —CO—NY$^{45B}$—, —NY$^{45C}$—CO—, —NY$^{45D}$—CO—O— or —CO— (wherein, Y$^{45A}$ to Y$^{45D}$, the same or different, are a hydrogen atom or optionally substituted C1-C4 alkyl), p$^{18}$ is an integer of 0 to 5, p$^{19}$ is an integer of 1 to 5, and p$^{20}$ is an integer of 0 to 5), L$^{11}$ is absent or is —(CY$^{46}$Y$^{47}$)$_{p21}$—, —(CY$^{48}$Y$^{49}$)$_{p22}$—Z$^{15}$—(CY$^{50}$Y$^{51}$)$_{p23}$— Or —(CY$^{52}$Y$^{53}$)$_{p24}$—Z$^{16}$—(CY$^{54}$Y$^{55}$)$_{p25}$—Z$^{17}$—(CY$^{56}$Y$^{57}$)$_{p26}$— (wherein, Y$^{46}$ to Y$^{57}$, the same or different, are a hydrogen atom or optionally substituted C1-C4 alkyl, Z$^{15}$ to Z$^{17}$, the same or different, are —O—, —NY$^{58A}$—, —CO—O—, —O—CO—, —CO—NY$^{58B}$—, —NY$^{58C}$—CO—, —NY$^{58D}$—CO—O— or —CO— (wherein, Y$^{58A}$ to Y$^{58D}$, the same or different, are a hydrogen atom or optionally substituted C1-C4 alkyl), p$^{21}$ is an integer of 1 to 5, p$^{22}$ is an integer of 0 to 5, p$^{23}$ is an integer of 1 to 5, p$^{24}$ is an integer of 0 to 5, p$^{25}$ is an integer of 1 to 5, and p$^{26}$ is an integer of 1 to 5), L$^{12}$ is absent or is —(CY$^{59}$Y$^{60}$)$_{p27}$—, —(CY$^{61}$Y$^{62}$)$_{p28}$—Z$^{18}$—(CY$^{63}$Y$^{64}$)$_{p29}$— or —(CY$^{65}$Y$^{66}$)$_{p30}$—Z$^{19}$—(CY$^{67}$Y$^{68}$)$_{p31}$—Z$^{20}$—(CY$^{69}$Y$^{70}$)$_{p32}$— (wherein, Y$^{59}$ to Y$^{70}$, the same or different, are a hydrogen atom or optionally substituted C1-C4 alkyl, Z$^{18}$ to Z$^{20}$, the same or different, are —O—, —NY$^{71A}$—, —CO—O—, —O—CO—, —CO—NY$^{71B}$—, —NY$^{71C}$—CO—, —NY$^{71D}$—CO—O— or —CO— (wherein, Y$^{71A}$ to Y$^{71D}$, the same or different, are a hydrogen atom or optionally substituted C1-C4 alkyl), p$^{27}$ is an integer of 1 to 5, p$^{28}$ is an integer of 0 to 5, p$^{29}$ is an integer of 0 to 5, p$^{30}$ is an integer of 0 to 5, p$^{31}$ is an integer of 1 to 5, and p$^{32}$ is an integer of 0 to 5), J$^1$ and J$^2$, the same or different, are CY$^{72}$ or N (wherein, Y$^{72}$ is a hydrogen atom, hydroxyl, optionally substituted C1-C4 alkyl, optionally substituted C1-C4 alkoxy or optionally substituted C1-C4 acyloxy group), B$^2$ is

[C21]

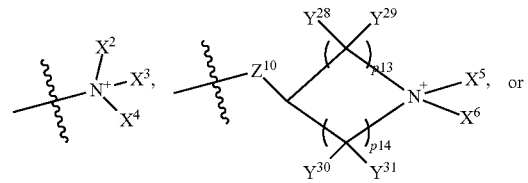

-continued

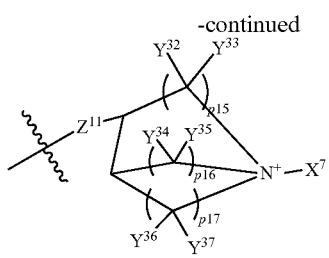

(wherein, $X^8$ and $X^9$, the same or different, are an optionally substituted C1-C4 alkyl or are combined together to form an optionally substituted C4-C6 heterocycle with an adjacent nitrogen atom, $X^{10}$ is an optionally substituted C1-C4 alkyl, $X^{11}$ and $X^{12}$, the same or different, are an optionally substituted C1-C4 alkyl or are combined together to form an optionally substituted C4-C6 heterocycle with an adjacent nitrogen atom, $X^{13}$ is an optionally substituted C1-C4 alkyl, $Y^{73}$ to $Y^{82}$, the same or different, are a hydrogen atom or optionally substituted C1-C4 alkyl, $Z^{21}$ and $Z^{22}$, the same or different, are —O—, —NY$^{83A}$—, —CO—O—, —O—CO—, —CO—NY$^{83B}$, —NY$^{83C}$—CO— or —NY$^{83D}$—CO—O— (wherein, Y$^{83A}$ to Y$^{83D}$, the same or different, are a hydrogen atom or optionally substituted C1-C4 alkyl), $p^{33}$ is an integer of 0 to 5, and $p^{34}$ to $p^{37}$, the same or different, are an integer of 1 to 5), and $A^3$ is a pharmaceutically acceptable anion);

formula (IV)
[C22]

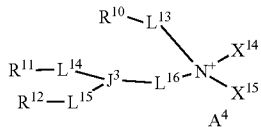

(wherein, $R^{10}$ to $R^{12}$, the same or different, are a linear or branched, optionally substituted C8-C24 alkyl, C8-C24 alkenyl or C8-C24 alkynyl, $L^{13}$ is absent or is —Z$^{23}$—(CY$^{83}$Y$^{84}$)$_{p38}$— or —Z$^{24}$—(CY$^{85}$Y$^{86}$)$_{p39}$—Z$^{25}$—(CY$^{87}$Y$^{88}$)$_{p40}$— (wherein, Y$^{83}$ to Y$^{88}$, the same or different, are a hydrogen atom or optionally substituted C1-C4 alkyl, Z$^{23}$ to Z$^{25}$, the same or different, are —O—, —NY$^{89A}$—, —CO—O—, —O—CO—, —CO—NY$^{89B}$—, —NY$^{89C}$—CO— or —NY$^{89D}$—CO—O— (wherein, Y$^{89A}$ to Y$^{89D}$, the same or different, are a hydrogen atom or optionally substituted C1-C4 alkyl), and $p^{38}$ to $p^{40}$, the same or different, are an integer of 1 to 5), $L^{14}$ and $L^{15}$, the same or different, are absent or are —Z$^{26}$—(CY$^{90}$Y$^{91}$)$_{p41}$— or —Z$^{27}$—(CY$^{92}$Y$^{93}$)$_{p42}$—Z$^{28}$—(CY$^{94}$Y$^{95}$)$_{p43}$— (wherein, Y$^{90}$ to Y$^{95}$, the same or different, are a hydrogen atom or optionally substituted C1-C4 alkyl, Z$^{26}$ to Z$^{28}$, the same or different, are —O—, —NY$^{96A}$—, —CO—O—, —O—CO—, —CO—NY$^{96B}$—, —NY$^{96C}$—CO—, —NY$^{96D}$—CO—O— or —CO— (wherein, Y$^{96A}$ to Y$^{96D}$, the same or different, are a hydrogen atom or optionally substituted C1-C4 alkyl), $p^{41}$ is an integer of 0 to 5, $p^{42}$ is an integer of 1 to 5, and $p^{43}$ is an integer of 0 to 5), $L^{16}$ is absent or is —(CY$^{97}$Y$^{98}$)$_{p44}$—, —(CY$^{99}$Y$^{100}$)$_{p45}$—Z$^{29}$—(CY$^{101}$Y$^{102}$)$_{p46}$— or —(CY$^{103}$Y$^{104}$)$_{p47}$—Z$^{30}$—(CY$^{105}$Y$^{106}$)$_{p48}$—Z$^{31}$—(CY$^{107}$Y$^{108}$)$_{p49}$— (wherein, Y$^{97}$ to Y$^{108}$, the same or different, are a hydrogen atom or optionally substituted C1-C4 alkyl, Z$^{29}$ to Z$^{31}$, the same or different, are —O—, —NY$^{109A}$—, —CO—O—, —O—CO—, —CO—NY$^{109B}$—, —NY$^{109C}$—CO—, —NY$^{109D}$—CO—O— or —CO— (wherein, Y$^{109A}$ to Y$^{109D}$, the same or different, are a hydrogen atom or optionally substituted C1-C4 alkyl), $p^{44}$ is an integer of 1 to 5, $p^{45}$ is an integer of 0 to 5, $p^{46}$ is an integer of 1 to 5, $p^{47}$ is an integer of 0 to 5, $p^{48}$ is an integer of 1 to 5, and $p^{49}$ is an integer of 1 to 5), $J^3$ is CY$^{110}$ or N (wherein, Y$^{110}$ is a hydrogen atom, hydroxyl, optionally substituted C1-C4 alkyl, optionally substituted C1-C4 alkoxy or optionally substituted C1-C4 acyloxy group), $X^{14}$ and $X^{15}$, the same or different, are an optionally substituted C1-C4 alkyl or are combined together to form an optionally substituted C4-C6 heterocycle with an adjacent nitrogen atom, and $A^4$ is a pharmaceutically acceptable anion); or formula (V') or formula (V'')
[C23]

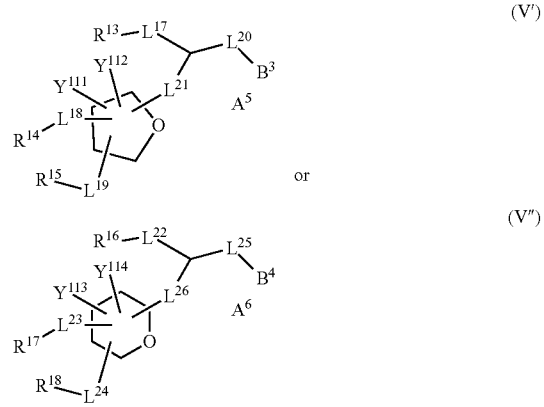

(wherein, $R^{13}$ to $R^{18}$, the same or different, are a linear or branched, optionally substituted C8-C24 alkyl, C8-C24 alkenyl or C8-C24 alkynyl, $Y^{111}$ to $Y^{114}$, the same or different, are a hydrogen atom, hydroxyl or optionally substituted C1-C4 alkyl, $L^{17}$ to $L^{19}$ and $L^{22}$ to $L^{24}$, the same or different, are absent or are —Z$^{32}$—(CY$^{115}$Y$^{116}$)$_{p51}$— or —Z$^{33}$—(CY$^{117}$Y$^{118}$)$_{p52}$—Z$^{34}$—(CY$^{119}$Y$^{120}$)$_{p53}$— (wherein, Y$^{115}$ to Y$^{120}$, the same or different, are a hydrogen atom or optionally substituted C1-C4 alkyl, Z$^{32}$ to Z$^{34}$, the same or different, are —O—, —NY$^{121A}$—, —CO—O—, —O—CO—, —CO—NY$^{121B}$, —NY$^{121C}$—CO—, —NY$^{121D}$—CO—O— or —CO— (wherein, Y$^{121A}$ to Y$^{121D}$, the same or different, are a hydrogen atom or optionally substituted C1-C4 alkyl), $p^{51}$ is an integer of 0 to 5, $p^{52}$ is an integer of 1 to 5, and $p^{53}$ is an integer of 0 to 5), $L^{20}$ and $L^{25}$, the same or different, are absent or are —(CY$^{122}$Y$^{123}$)$_{p54}$—, —(CY$^{124}$Y$^{125}$)$_{p55}$—Z$^{35}$—(CY$^{126}$Y$^{127}$)$_{p56}$— or —(CY$^{128}$Y$^{129}$)$_{p57}$—Z$^{36}$—(CY$^{130}$Y$^{131}$)$_{p58}$—Z$^{37}$—(CY$^{132}$Y$^{133}$)$_{p59}$— (wherein, Y$^{122}$ to Y$^{133}$, the same or different, are a hydrogen atom or optionally substituted C1-C4 alkyl, Z$^{35}$ to Z$^{37}$, the same or different, are —O—, —NY$^{134A}$—, —CO—O—, —O—CO—, —CO—NY$^{134B}$, —NY$^{134C}$—CO—, —NY$^{134D}$—CO—O— or —CO— (wherein, Y$^{134A}$ to Y$^{134D}$, the same or different, are a hydrogen atom or optionally substituted C1-C4 alkyl), $p^{54}$ is an integer of 1 to 5, $p^{55}$ is an integer of 0 to 5, $p^{56}$ is an integer of 1 to 5, $p^{57}$ is an integer of 0 to 5, $p^{58}$ is an integer of 1 to 5 and $p^{59}$ is an integer of 1 to 5), $L^{21}$ and $L^{26}$, the same or different, are absent or are $-(CY^{135}Y^{136})_{p60}-$, $-(CY^{137}Y^{138})_{p61}-Z^{38}-(CY^{139}Y^{140})_{p62}-$ or $-(CY^{141}Y^{142})_{p63}-Z^{39}-(CY^{143}Y^{144})_{p64}-Z^{40}-(CY^{145}Y^{146})_{p65}-$ (wherein, $Y^{135}$ to $Y^{146}$, the same or different, are a hydrogen atom or optionally substituted C1-C4 alkyl, $Z^{38}$ to $Z^{40}$, the same or different, are $-O-$, $-NY^{147A}-$, $-CO-O-$, $-O-CO-$, $-CO-NY^{147B}-$, $-NY^{147C}-CO-$, $-NY^{147D}-CO-O-$ or $-CO-$ (wherein, $Y^{147A}$ to $Y^{147D}$, the same or different, are a hydrogen atom or optionally substituted C1-C4 alkyl), $p^{60}$ is an integer of 1 to 5, $p^{61}$ is an integer of 0 to 5, $p^{62}$ is an integer of 0 to 5, $p^{63}$ is an integer of 0 to 5, $p^{64}$ is an integer of 1 to 5, and $p^{65}$ is an integer of 0 to 5), $B^3$ and $B^4$, the same or different, are

[C24]

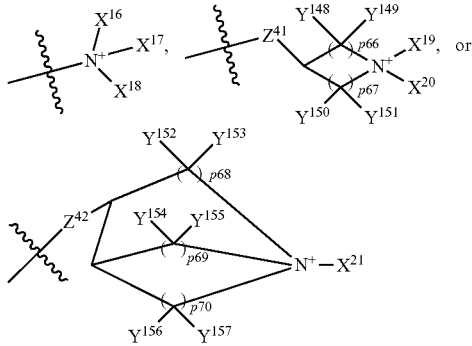

(wherein, $X^{16}$ and $X^{17}$, the same or different, are an optionally substituted C1-C4 alkyl or are combined together to form an optionally substituted C4-C6 heterocycle with an adjacent nitrogen atom, $X^{18}$ is an optionally substituted C1-C4 alkyl, $X^{19}$ and $X^{20}$, the same or different, are an optionally substituted C1-C4 alkyl or are combined together to form an optionally substituted C4-C6 heterocycle with an adjacent nitrogen atom, $X^{21}$ is an optionally substituted C1-C4 alkyl, $Y^{148}$ to $Y^{157}$, the same or different, are a hydrogen atom or optionally substituted C1-C4 alkyl, $Z^{41}$ and $Z^{42}$, the same or different, are $-O-$, $-NY^{158A}-$, $-CO-O-$, $-O-CO-$, $-CO-NY^{158B}-$, $-NY^{158C}-CO-$ or $-NY^{158D}-CO-O-$ (wherein, $Y^{158A}$ to $Y^{158D}$, the same or different, are a hydrogen atom or optionally substituted C1-C4 alkyl), $p^{66}$ is an integer of 0 to 5, and $p^{67}$ to $p^{70}$, the same or different, are an integer of 1 to 5), and $A^5$ and $A^6$, the same or different, are a pharmaceutically acceptable anion).

(38) The production method described in (37), wherein the lipid A is a lipid represented by formula (I), and in formula (I), one of $L^1$ to $L^3$ is $-CO-O-(Y^1Y^2)_{p1}-$ or $-O-CO-(CY^1Y^2)_{p1}-$ or two or more of $L^1$ to $L^3$, the same or different, are $-CO-O-(Y^1Y^2)_{p1}-$ or $-O-CO-(CY^1Y^2)_{p1}-$, and $R^1$ to $R^3$ are linear or branched C15-C20 alkenyl or C9-C18 alkyl and are the same.

(39) The production method described in (37), wherein the lipid A is a lipid represented by, and in formula (II), one of $L^4$ to $L^6$ is $-CO-O-(Y^8Y^9)_{p4}-$, $-O-CO-(CY^8Y^9)_{p4}-$ or $-O-CO-(CY^{10}Y^{11})_{p5}-O-(CY^{12}Y^{13})_{p6}-$ or two or more of $L^4$ to $L^6$, the same or different, are $-CO-O-(Y^8Y^9)_{p4}-$, $-O-CO-(CY^8Y^9)_{p4}-$ or $-O-CO-(CY^{10}Y^{11})_{p5}-O-(CY^{12}Y^{13})_{p6}-$, and $R^4$ to $R^6$ are linear or branched C15-C20 alkenyl or C9-C18 alkyl and are the same.

(40) The production method described in (37), wherein the lipid A is a lipid represented by formula (III), and in formula (III), one of $L^8$ to $L^{10}$ is $-CO-O-(CY^{39}Y^{40})_{p18}-$ or $-O-CO-(CY^{39}Y^{40})_{p18}-$ or two or more of $L^8$ to $L^{10}$, the same or different, are $-CO-O-(CY^{39}Y^{40})_{p18}-$ or $-O-CO-(CY^{39}Y^{40})_{p18}-$, and $R^7$ to $R^9$ are a linear or branched C15-C20 alkenyl or C9-C18 alkyl.

(41) The production method described in (37), wherein the lipid A is a lipid represented by formula (IV), and in formula (IV), $L^{13}$ is $-CO-O-(CY^{83}Y^{84})_{p38}-$ or $-O-CO-(CY^{83}Y^{84})_{p38}-$, one of $L^{14}$ and $L^{15}$ is $-CO-O-(Y^{90}Y^{91})_{p41}-$ or $-O-CO-(CY^{90}Y^{91})_{p41}-$, $L^{13}$ is $-CO-O-(Y^{83}Y^{84})_{p38}-$ or $-O-CO-(CY^{83}Y^{84})_{p38}-$ and one of $L^{14}$ and $L^{15}$ is $-CO-O-(Y^{90}Y^{91})_{p41}-$ or $-O-CO-(CY^{90}Y^{91})_{p41}-$, $L^{14}$ and $L^{15}$, the same or different, are $-CO-O-(Y^{90}Y^{91})_{p41}-$ or $-O-CO-(CY^{90}Y^{91})_{p41}-$ or $L^{13}$ is $-CO-O-(CY^{83}Y^{84})_{p38}-$ or $-O-CO-(CY^{83}Y^{84})_{p38}-$ and $L^{14}$ and $L^{15}$, the same or different, are $-CO-O-(Y^{90}Y^{91})_{p41}-$ or $-O-CO-(CY^{90}Y^{91})_{p41}-$, and $R^{10}$ to $R^{12}$ are a linear or branched C15-C20 alkenyl or C9-C18 alkyl.

(42) The production method described in (37), wherein the lipid A is a lipid represented by formula (V'), and in formula (V'), one of $L^{17}$ to $L^{19}$ is $-CO-O-$ or $-O-$ or two or more of $L^{17}$ to $L^{19}$, the same or different, are $-CO-O-$ or $-O-$, and $R^{13}$ to $R^{15}$ are a linear or branched C15-C20 alkenyl or C9-C18 alkyl.

(43) The production method described in any one of (22) to (42), wherein, in step (a), the lipid (lipid B), which has a hydrophilic unit having one optionally substituted amino group, and a hydrophobic unit having two independent, optionally substituted hydrocarbon groups, is mixed with the lipid A and the nucleic acid.

(44) The production method described in (43), wherein the lipid B is:

formula (CL-I)

[C25]

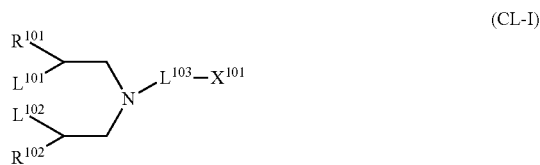

(CL-I)

(wherein, $R^{101}$ and $R^{102}$, the same or different, are a linear or branched C10-C24 alkyl, C10-C24 alkenyl or C10-C24 alkynyl, $L^{101}$ and $L^{102}$ are hydrogen atoms or are combined together to form a single bond or C1-C3 alkylene, $L^{103}$ is a single bond, $-CO-$ or $-CO-O-$, and in the case where $L^{103}$ is a single bond, $X^{101}$ is a hydrogen atom, C1-C6 alkyl, C3-C6 alkenyl, pyrrolidin-3-yl, piperidin-3-yl or piperidin-4-yl, or a C1-C6 alkyl or C3-C6 alkenyl substituted with one to three of the same or different amino, monoalkylamino, dialkylamino, trialkylammonio, hydroxyl, alkoxy, carbamoyl, monoalkylcarbamoyl, dialkylcarbamoyl, pyrrolidinyl, piperidyl or morpholinyl, or in the case where $L^{103}$ is —CO— or —CO—O—, $X^{101}$ is a pyrrolidin-2-yl, pyrrolidin-3-yl, piperidin-2-yl, piperidin-3-yl, piperidin-4-yl, morpholin-2-yl or morpholin-3-yl, or a C1-C6 alkyl or C3-C6 alkenyl substituted with one to three of the same or different amino, monoalkylamino, dialkylamino, trialkylammonio, hydroxyl, alkoxy, carbamoyl, monoalkylcarbamoyl, dialkylcarbamoyl, pyrrolidinyl, piperidyl or morpholinyl, and at least one of the substituents is an amino, monoalkylamino, dialkylamino, trialkylammonio, pyrrolidinyl, piperidyl or morpholinyl);

formula (CL-II)

[C26]

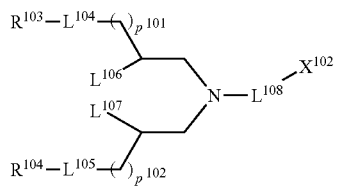

(CL-II)

(wherein, $R^{103}$ and $R^{104}$, the same or different, are a linear or branched C12-C24 alkyl, C12-C24 alkenyl or C12-C24 alkynyl, $p^{101}$ and $p^{102}$, the same or different, are an integer of 0 to 3, $L^{106}$ and $L^{107}$ are hydrogen atoms or are combined together to form a single bond or C2-C8 alkylene, $L^{104}$ and $L^{105}$, the same or different, are —O—, —CO—O— or —O—CO—, $L^{108}$ is a single bond, —CO— or —CO—O—, and in the case where $L^{108}$ is a single bond, $X^{102}$ is a hydrogen atom, C1-C6 alkyl, C3-C6 alkenyl, pyrrolidin-2-yl, pyrrolidin-3-yl, piperidin-3-yl or piperidin-4-yl, or a C1-C6 alkyl or C3-C6 alkenyl substituted with one to three of the same or different amino, monoalkylamino, dialkylamino, trialkylammonio, hydroxyl, alkoxy, carbamoyl, monoalkylcarbamoyl, dialkylcarbamoyl, pyrrolidinyl, piperidyl or morpholinyl, or in the case where $L^{108}$ is —CO— or —CO—O—, $X^{102}$ is a pyrrolidin-2-yl, pyrrolidin-3-yl, piperidin-2-yl, piperidin-3-yl, piperidin-4-yl, morpholin-2-yl or morpholin-3-yl, or a C1-C6 alkyl or C3-C6 alkenyl substituted with one to three of the same or different amino, monoalkylamino, dialkylamino, trialkylammonio, hydroxyl, alkoxy, carbamoyl, monoalkylcarbamoyl, dialkylcarbamoyl, pyrrolidinyl, piperidyl or morpholinyl, and at least one of the substituents is an amino, monoalkylamino, dialkylamino, trialkylammonio, pyrrolidinyl, piperidyl or morpholinyl);

formula (CL-III)

[C27]

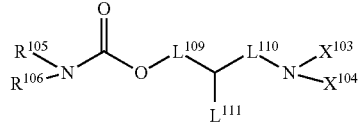

(CL-III)

(wherein, $R^{105}$ is a linear or branched C8-C24 alkyl, C8-C24 alkenyl or C8-C24 alkynyl, $R^{106}$ is a linear or branched C8-C24 alkyl, C8-C24 alkenyl, C8-C24 alkynyl, C8-C24 alkoxyethyl, C8-C24 alkoxypropyl, C8-C24 alkenyloxyethyl, C8-C24 alkenyloxypropyl, C8-C24 alkynyloxyethyl or C8-C24 alkynyloxypropyl, $X^{103}$ and $X^{104}$, the same or different, are a C1-C3 alkyl or are combined together to form a C2-C8 alkylene, or $X^{103}$ forms a C2-C8 alkylene with $L^{111}$, $L^{111}$ is a hydrogen atom, C1-C6 alkyl, C3-C6 alkenyl, amino, monoalkylamino, hydroxyl, alkoxy, carbamoyl, monoalkylcarbamoyl or dialkylcarbamoyl, or a C1-C6 alkyl or C3-C6 alkenyl substituted with one to three of the same or different amino, monoalkylamino, hydroxyl, alkoxy, carbamoyl, monoalkylcarbamoyl or dialkylcarbamoyl, or forms a C2-C8 alkylene with $X^{103}$, $L^{109}$ is a C1-C6 alkylene, and $L^{110}$ is a single bond or a C1-C6 alkylene, provided that, in the case where the sum of the number of carbon atoms of $L^{109}$ and $L^{110}$ is 7 or less and $L^{111}$ is a hydrogen atom, $L^{110}$ is a single bond, while in the case where $L^{111}$ forms a C2-C6 alkylene with $X^{103}$, $L^{110}$ is a single bond, methylene or ethylene);

formula (CL-IV)

[C28]

(CL-IV)

(wherein, $R^{107}$ is a linear or branched C8-C24 alkyl, C8-C24 alkenyl or C8-C24 alkynyl, and $R^{108}$ is a linear or branched C8-C24 alkyl, C8-C24 alkenyl, C8-C24 alkynyl, C8-C24 alkoxyethyl, C8-C24 alkoxypropyl, C8-C24 alkenyloxyethyl, C8-C24 alkenyloxypropyl, C8-C24 alkynyloxyethyl or C8-C24 alkynyloxypropyl);

formula (CL-V)

[C29]

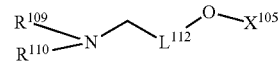

(CL-V)

(wherein, $R^{109}$ is a linear or branched C8-C24 alkyl, C8-C24 alkenyl or C8-C24 alkynyl, $R^{110}$ is a linear or branched C8-C24 alkyl, C8-C24 alkenyl, C8-C24 alkynyl, C8-C24 alkoxyethyl, C8-C24 alkoxypropyl, C8-C24 alkenyloxyethyl, C8-C24 alkenyloxypropyl, C8-C24 alkynyloxyethyl or C8-C24 alkynyloxypropyl), $L^{112}$ is a C1-C3 alkylene, and $X^{105}$ is a hydrogen atom or C1-C3 alkyl);

formula (CL-VI)

[C30]

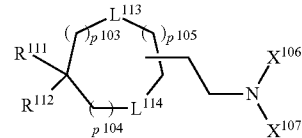

(CL-VI)

(wherein, $R^{111}$ and $R^{112}$, the same or different, are a linear or branched, optionally substituted C8-C24 alkyl, C8-C24 alkenyl or C8-C24 alkynyl, $X^{106}$ and $X^{107}$, the same or different, are a C1-C3 alkyl or are combined together to form a C2-C8 alkylene, $p^{103}$, $p^{104}$ and $p^{105}$, the same or different, are 0 or 1, provided that $p^{103}$, $p^{104}$ and $p^{105}$ are not simultaneously 0, and $L^{113}$ and $L^{114}$, the same or different, are O, S or NH); or formula (CL-VII)

[C31]

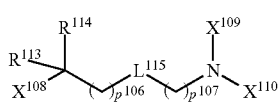
(CL-VII)

(wherein, $R^{113}$ and $R^{114}$, the same or different, are a linear or branched, optionally substituted C8-C24 alkyl, C8-C24 alkenyl or C8-C24 alkynyl, $X^{109}$ and $X^{110}$, the same or different, are a C1-C3 alkyl or are combined together to form a C2-C8 alkylene, $X^{108}$ is a hydrogen atom, hydroxyl, optionally substituted C1-C4 alkyl, optionally substituted C1-C4 alkoxy or optionally substituted C1-C4 acyloxy group, $L^{115}$ is —CO—O— or —O—CO—, and $p^{106}$ is an integer of 0 to 3 and $p^{107}$ is an integer of 1 to 4).

(45) A method for producing nucleic acid-containing lipid nanoparticles, the method including:

(a) preparing a first lipid solution containing a lipid (lipid A) and a nucleic acid by mixing the lipid A, having a hydrophilic unit having one quaternary ammonium group, and three independent, optionally substituted hydrocarbon groups, with a nucleic acid and a lipid derivative or fatty acid derivative of a water-soluble polymer in a mixed solvent of a water-miscible organic solvent and water, and (b) adding water or an aqueous buffer solution to the first lipid solution.

(46) The production method described in (45), including mixing a neutral lipid and/or a lipid (lipid B), which has a hydrophilic unit having one optionally substituted amino group, and a hydrophobic unit having two independent, optionally substituted hydrocarbon groups, in step (a).

(47) The production method described in (45) or (46), wherein the water-miscible organic solvent is an alcohol, dimethylsulfoxide, tetrahydrofuran, acetone, acetonitrile or a mixture thereof.

(48) The production method described in (45) or (46), wherein the water-miscible organic solvent is an alcohol.

(49) The production method described in (47) or (48), wherein the alcohol is methanol, ethanol, propanol, butanol or a mixture thereof.

(50) The production method described in any one of (45) to (49), wherein the content of the water-miscible organic solvent in the water of the first lipid solution obtained in step (a) is 50% (v/v) or more based on the solution.

(51) The production method described in any one of (45) to (50), wherein, in step (b), the concentration of the water-miscible organic solvent in the water of the first lipid solution obtained in step (a) is made to be 50% (v/v) or less by adding water or aqueous buffer solution.

(52) The production method described in (51), wherein the concentration of the water-miscible organic solvent in the water of the first lipid solution obtained in step (a) is made to be 50% (v/v) or less within one minute.

(53) The production method described in any one of (45) to (52), wherein the number of moles of the quaternary ammonium group in the lipid A is 0.01 times or more the number of moles of phosphorous atoms in the nucleic acid.

(54) The production method described in any one of (45) to (53), wherein the content of the water-miscible organic solvent in the water of the first lipid solution obtained in step (a) is 50% (v/v) or more based on the solution.

(55) The production method described in any one of (45) to (54), wherein the aqueous buffer solution is a phosphate buffer solution, citrate buffer solution or acetate buffer solution.

(56) The production method described in any one of (45) to (55), wherein the ratio of the total number of moles of lipid to the number of moles of nucleic acid used in step (a) (total number of moles of lipid/number of moles of nucleic acid) is 50 or more.

(57) The production method described in any one of (45) to (56), wherein the nucleic acid is a nucleic acid having an expression inhibitory action on a target gene that uses RNA interference (RNAi).

(58) The production method described in (57), wherein the target gene is associated with tumors or inflammation.

(59) The production method described in any one of (45) to (58), wherein the lipid A is a lipid represented by the following formulas or a combination thereof:

formula (I)

[C32]

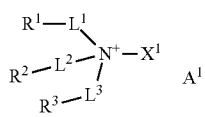
(I)

(wherein, $R^1$ to $R^3$, the same or different, are a linear or branched, optionally substituted C8-C24 alkyl, C8-C24 alkenyl or C8-C24 alkynyl, $L^1$ to $L^3$, the same or different, are absent or are —$Z^1$—$(CY^1Y^2)_{p1}$— or —$Z^2$—$(CY^3Y^4)_{p2}$—$Z^3$—$(CY^5Y^6)_{p3}$— (wherein, $Y^1$ to $Y^6$, the same or different, are a hydrogen atom or optionally substituted C1-C4 alkyl, $Z^1$ to $Z^3$, the same or different, are —O—, —$NY^{7A}$—, —CO—O—, —O—CO—, —CO—$NY^{7B}$—, —$NY^{7C}$—CO— or —$NY^{7D}$—CO—O— (wherein, $Y^{7A}$ to $Y^{7D}$, the same or different, are a hydrogen atom or optionally substituted C1-C4 alkyl), and $p^1$ to $p^3$, the same or different, are an integer of 1 to 5), $X^1$ is an optionally substituted C1-C4 alkyl, and $A^1$ is a pharmaceutically acceptable anion);

formula (II)

[C33]

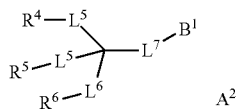
(II)

(wherein,

R⁴ to R⁶, the same or different, are a linear or branched, optionally substituted C8-C24 alkyl, C8-C24 alkenyl or C8-C24 alkynyl, L⁴ to L⁶, the same or different, are absent or are —Z⁴—(CY⁸Y⁹)$_{p4}$— or —Z⁵—(CY¹⁰Y¹¹)$_{p5}$—Z⁶—(CY¹²Y¹³)$_{p6}$— (wherein, Y⁸ to Y¹³, the same or different, are a hydrogen atom or optionally substituted C1-C4 alkyl, Z⁴ to Z⁶, the same or different, are —O—, —NY$^{14A}$—, —CO—O—, —O—CO—, —CO—NY$^{14B}$—, —NY$^{14C}$—CO— or —NY$^{14D}$—CO—O— (wherein, Y$^{14A}$ to Y$^{14D}$, the same or different, are a hydrogen atom or optionally substituted C1-C4 alkyl, p⁴ is an integer of 0 to 5, p⁵ is an integer of 1 to 5, and p⁶ is an integer of 0 to 5), L⁷ is absent or is —(CY¹⁵Y¹⁶)$_{p7}$—, —(CY¹⁷Y¹⁸)$_{p8}$—Z⁷—(CY¹⁹Y²⁰)$_{p9}$— or —(CY²¹Y²²)$_{p10}$—Z⁸—(CY²³Y²⁴)$_{p11}$—Z⁹—(CY²⁵Y²⁶)$_{p12}$— (wherein, Y¹⁵ to Y²⁶, the same or different, are a hydrogen atom or optionally substituted C1-C4 alkyl, Z⁷ to Z⁹, the same or different, are —O—, —NY$^{27A}$—, —CO—O—, —O—CO—, —CO—NY$^{27B}$—, —NY$^{27C}$—CO— or —NY$^{27D}$—CO—O— (wherein, Y$^{27A}$ to Y$^{27D}$, the same or different, are a hydrogen atom or optionally substituted C1-C4 alkyl), p⁷ is an integer of 1 to 5, p⁸ is an integer of 0 to 5, p⁹ is an integer of 1 to 5, p¹⁰ is an integer of 0 to 5, p¹¹ is an integer of 1 to 5, and p¹² is an integer of 1 to 5), B¹ is

[C34]

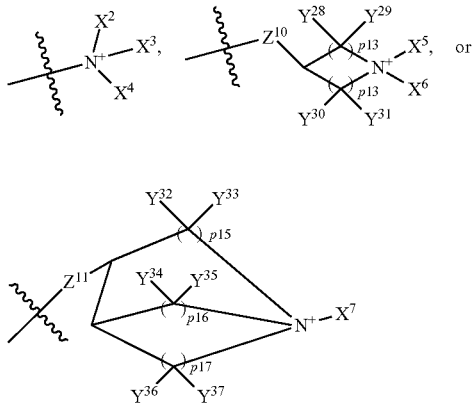

(wherein, X² and X³, the same or different, are an optionally substituted C1-C4 alkyl or are combined together to form an optionally substituted C4-C6 heterocycle with an adjacent nitrogen atom, X⁴ is an optionally substituted C1-C4 alkyl, X⁵ and X⁶, the same or different, are an optionally substituted C1-C4 alkyl or are combined together to form an optionally substituted C4-C6 heterocycle with an adjacent nitrogen atom, X⁷ is an optionally substituted C1-C4 alkyl, Y²⁸ to Y³⁷, the same or different, are a hydrogen atom or optionally substituted C1-C4 alkyl, Z¹⁰ and Z¹¹, the same or different, are —O—, —NY$^{38A}$—, —CO—O—, —O—CO—, —CO—NY$^{38B}$—, —NY$^{38C}$—CO— or —NY$^{38D}$—CO—O— (wherein, Y$^{38A}$ to Y$^{38D}$, the same or different, are a hydrogen atom or optionally substituted C1-C4 alkyl), p¹³ is an integer of 0 to 5, and p¹⁴ to p¹⁷, the same or different, are an integer of 1 to 5), and A² is a pharmaceutically acceptable anion);

formula (III)

[C35]

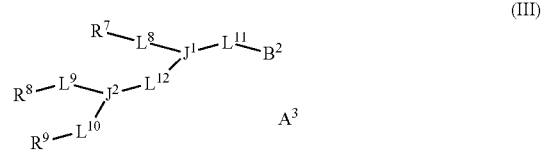

(wherein,

R⁷ to R⁹, the same or different, are a linear or branched, optionally substituted C8-C24 alkyl, C8-C24 alkenyl or C8-C24 alkynyl, L⁸ to L¹⁰, the same or different, are absent or are —Z¹²—(CY³⁹Y⁴⁰)$_{p18}$— or —Z¹³—(CY⁴¹Y⁴²)$_{p19}$—Z¹⁴—(CY⁴³Y⁴⁴)$_{p20}$— (wherein, Y³⁹ to Y⁴⁴, the same or different, are a hydrogen atom or optionally substituted C1-C4 alkyl, Z¹² to Z¹⁴, the same or different, are —O—, —NY$^{45A}$—, —CO—O—, —O—CO—, —CO—NY$^{45B}$—, —NY$^{45C}$—CO—, —NY$^{45D}$—CO—O— or —CO— (wherein, Y$^{45A}$ to Y$^{45D}$, the same or different, are a hydrogen atom or optionally substituted C1-C4 alkyl), p¹⁸ is an integer of 0 to 5, p¹⁹ is an integer of 1 to 5, and p²⁰ is an integer of 0 to 5), L¹¹ is absent or is —(CY⁴⁶Y⁴⁷)$_{p21}$—, —(CY⁴⁸Y⁴⁹)$_{p22}$—Z¹⁵—(CY⁵⁰Y⁵¹)$_{p23}$— or —(CY⁵²Y⁵³)$_{p24}$—Z¹⁶—(CY⁵⁴Y⁵⁵)$_{p25}$—Z¹⁷—(CY⁵⁶Y⁵⁷)$_{p26}$— (wherein, Y⁴⁶ to Y⁵⁷, the same or different, are a hydrogen atom or optionally substituted C1-C4 alkyl, Z¹⁵ to Z¹⁷, the same or different, are —O—, —NY$^{58A}$—, —CO—O—, —O—CO—, —CO—NY$^{58B}$—, —NY$^{58C}$—CO—, —NY$^{58D}$—CO—O— or —CO— (wherein, Y$^{58A}$ to Y$^{58D}$, the same or different, are a hydrogen atom or optionally substituted C1-C4 alkyl), p²¹ is an integer of 1 to 5, p²² is an integer of 0 to 5, p²³ is an integer of 1 to 5, p²⁴ is an integer of 0 to 5, p²⁵ is an integer of 1 to 5, and p²⁶ is an integer of 1 to 5), L¹² is absent or is —(CY⁵⁹Y⁶⁰)$_{p27}$—, —(CY⁶¹Y⁶²)$_{p28}$—Z¹⁸—(CY⁶³CY⁶⁴)$_{p29}$— or —(CY⁶⁵Y⁶⁶)$_{p30}$—Z¹⁹—(CY⁶⁷Y⁶⁸)$_{p31}$—Z²⁰—(CY⁶⁹Y⁷⁰)$_{p32}$— (wherein, Y⁵⁹ to Y⁷⁰, the same or different, are a hydrogen atom or optionally substituted C1-C4 alkyl, Z¹⁸ to Z²⁰, the same or different, are —O—, —NY$^{71A}$—, —CO—O—, —O—CO—, —CO—NY$^{71B}$—, —NY$^{71C}$—CO—, —NY$^{71D}$—CO—O— or —CO— (wherein, Y$^{71A}$ to Y$^{71D}$, the same or different, are a hydrogen atom or optionally substituted C1-C4 alkyl), p²⁷ is an integer of 1 to 5, p²⁸ is an integer of 0 to 5, p²⁹ is an integer of 0 to 5, p³⁰ is an integer of 0 to 5, p³¹ is an integer of 1 to 5, and p³² is an integer of 0 to 5), J¹ and J², the same or different, are CY⁷² or N (wherein, Y⁷² is a hydrogen atom, hydroxyl, optionally substituted C1-C4 alkyl, optionally substituted C1-C4 alkoxy or optionally substituted C1-C4 acyloxy group), B² is

[C36]

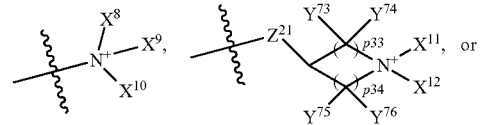

-continued

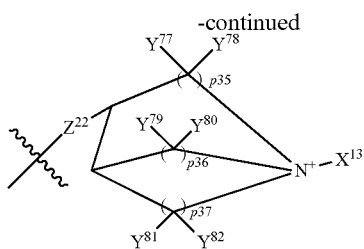

(wherein, $X^8$ and $X^9$, the same or different, are an optionally substituted C1-C4 alkyl or are combined together to form an optionally substituted C4-C6 heterocycle with an adjacent nitrogen atom, $X^{10}$ is an optionally substituted C1-C4 alkyl, $X^{11}$ and $X^{12}$, the same or different, are an optionally substituted C1-C4 alkyl or are combined together to form an optionally substituted C4-C6 heterocycle with an adjacent nitrogen atom, $X^{13}$ is an optionally substituted C1-C4 alkyl, $Y^{73}$ to $Y^{82}$, the same or different, are a hydrogen atom or optionally substituted C1-C4 alkyl, $Z^{21}$ and $Z^{22}$, the same or different, are —O—, —NY$^{83A}$—, —CO—O—, —O—CO—, —CO—NY$^{83B}$—, —NY$^{83C}$—CO— or —NY$^{83D}$—CO—O— (wherein, $Y^{83A}$ to $Y^{83D}$, the same or different, are a hydrogen atom or optionally substituted C1-C4 alkyl), $p^{33}$ is an integer of 0 to 5, and $p^{34}$ to $p^{37}$, the same or different, are an integer of 1 to 5), and $A^3$ is a pharmaceutically acceptable anion);

formula (IV)

[C37]

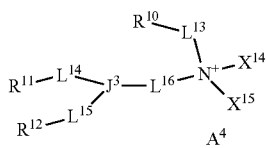

(wherein, $R^{10}$ to $R^{12}$, the same or different, are a linear or branched, optionally substituted C8-C24 alkyl, C8-C24 alkenyl or C8-C24 alkynyl, $L^{13}$ is absent or is —Z$^{23}$—(CY$^{83}$Y$^{84}$)$_{p38}$— or —Z$^{24}$—(CY$^{85}$Y$^{86}$)$_{p39}$—Z$^{25}$—(CY$^{87}$Y$^{88}$)$_{p40}$— (wherein, $Y^{83}$ to $Y^{88}$, the same or different, are a hydrogen atom or optionally substituted C1-C4 alkyl, $Z^{23}$ to $Z^{25}$, the same or different, are —O—, —NY$^{89A}$—, —CO—O—, —O—CO—, —CO—NY$^{89B}$—, —NY$^{89C}$—CO— or —NY$^{89D}$—CO—O— (wherein, $Y^{89A}$ to $Y^{89D}$, the same or different, are a hydrogen atom or optionally substituted C1-C4 alkyl), and $p^{38}$ to $p^{40}$, the same or different, are an integer of 1 to 5), $L^{14}$ and $L^{15}$, the same or different, are absent or are —Z$^{26}$—(CY$^{90}$Y$^{91}$)$_{p41}$— or —Z$^{27}$—(CY$^{92}$Y$^{93}$)$_{p42}$—Z$^{28}$—(CY$^{94}$Y$^{95}$)$_{p43}$— (wherein, $Y^{90}$ to $Y^{95}$, the same or different, are a hydrogen atom or optionally substituted C1-C4 alkyl, $Z^{26}$ to $Z^{28}$, the same or different, are —O—, —NY$^{96A}$—, —CO—O—, —O—CO—, —CO—NY$^{96B}$—, —NY$^{96C}$—CO—, —NY$^{96D}$—CO—O— or —CO— (wherein, $Y^{96A}$ to $Y^{96D}$, the same or different, are a hydrogen atom or optionally substituted C1-C4 alkyl), $p^{41}$ is an integer of 0 to 5, $p^{42}$ is an integer of 1 to 5, and $p^{43}$ is an integer of 0 to 5), $L^{16}$ is absent or is —(CY$^{97}$Y$^{98}$)$_{p44}$—, —(CY$^{99}$Y$^{100}$)$_{p45}$—Z$^{29}$—(CY$^{101}$Y$^{102}$)$_{p46}$— or —(CY$^{103}$Y$^{104}$)$_{p47}$—Z$^{30}$—(CY$^{105}$Y$^{106}$)$_{p48}$—Z$^{31}$—(CY$^{107}$Y$^{108}$)$_{p49}$— (wherein, $Y^{97}$ to $Y^{108}$, the same or different, are a hydrogen atom or optionally substituted C1-C4 alkyl, $Z^{29}$ to $Z^{31}$, the same or different, are —O—, —NY$^{109A}$—, —CO—O—, —O—CO—, —CO—NY$^{109B}$—, —NY$^{109C}$—CO— —NY$^{109D}$—CO—O— or —CO— (wherein, $Y^{109A}$ to $Y^{109D}$, the same or different, are a hydrogen atom or optionally substituted C1-C4 alkyl, $p^{44}$ is an integer of 1 to 5, $p^{45}$ is an integer of 0 to 5, $p^{46}$ is an integer of 1 to 5, $p^{47}$ is an integer of 0 to 5, $p^{48}$ is an integer of 1 to 5, and $p^{49}$ is an integer of 1 to 5), $J^3$ is CY$^{110}$ or N (wherein, $Y^{110}$ is a hydrogen atom, hydroxyl, optionally substituted C1-C4 alkyl, optionally substituted C1-C4 alkoxy or optionally substituted C1-C4 acyloxy group), $X^{14}$ and $X^{15}$, the same or different, are an optionally substituted C1-C4 alkyl or are combined together to form an optionally substituted C4-C6 heterocycle with an adjacent nitrogen atom, and $A^4$ is a pharmaceutically acceptable anion); or formula (V') or formula (V'')

[C38]

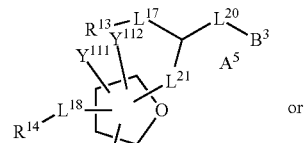

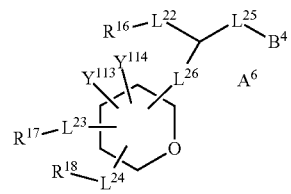

(wherein, $R^{13}$ to $R^{18}$, the same or different, are a linear or branched, optionally substituted C8-C24 alkyl, C8-C24 alkenyl or C8-C24 alkynyl, $Y^{111}$ to $Y^{114}$, the same or different, are a hydrogen atom, hydroxyl or optionally substituted C1-C4 alkyl, $L^{17}$ to $L^{19}$ and $L^{22}$ to $L^{24}$, the same or different, are absent or are —Z$^{32}$—(CY$^{115}$Y$^{116}$)$_{p51}$— or —Z$^{33}$—(CY$^{117}$Y$^{118}$)$_{p52}$—Z$^{34}$—(CY$^{119}$Y$^{120}$)$_{p53}$— (wherein, $Y^{115}$ to $Y^{120}$, the same or different, are a hydrogen atom or optionally substituted C1-C4 alkyl, $Z^{32}$ to $Z^{34}$, the same or different, are —O—, —NY$^{121A}$—, —CO—O—, —O—CO—, —CO—NY$^{121B}$—, —NY$^{121C}$—CO—, —NY$^{121D}$—CO—O— or —CO— (wherein, $Y^{121A}$ to $Y^{121D}$, the same or different, are a hydrogen atom or optionally substituted C1-C4 alkyl), $p^{51}$ is an integer of 0 to 5, $p^{52}$ is an integer of 1 to 5, and $p^{53}$ is an integer of 0 to 5), $L^{20}$ and $L^{25}$, the same or different, are absent or are —(CY$^{122}$Y$^{123}$)$_{p54}$—, —(CY$^{124}$Y$^{125}$)$_{p55}$—Z$^{35}$—(CY$^{126}$Y$^{127}$)$_{p56}$— or —(CY$^{128}$Y$^{129}$)$_{p57}$—Z$^{36}$—(CY$^{130}$Y$^{131}$)$_{p58}$—Z$^{37}$—(CY$^{132}$Y$^{133}$)$_{p59}$— (wherein, $Y^{122}$ to $Y^{133}$, the same or different, are a hydrogen atom or optionally substituted C1-C4 alkyl, $Z^{35}$ to $Z^{37}$, the same or different, are —O—, —NY$^{134A}$—, —CO—O—, —O—CO—, —CO—NY$^{134B}$—, —NY$^{134C}$—CO—, —NY$^{134D}$—CO—O— or —CO— (wherein, $Y^{134A}$ to $Y^{134D}$, the same or different, are a hydrogen atom or optionally substituted C1-C4 alkyl), $p^{54}$ is an integer of 1 to 5, $p^{55}$ is an integer of 0 to 5, $p^{56}$ is an integer of 1 to 5, $p^{57}$ is an integer of 0 to 5, $p^{58}$ is an integer of 1 to 5 and $p^{59}$ is an integer of 1 to 5), $L^{21}$ and $L^{26}$, the same or different, are absent or are $-(CY^{135}Y^{136})_{p60}-$, $-(CY^{137}Y^{138})_{p61}-Z^{38}-(CY^{139}Y^{140})_{p62}-$ or $-(CY^{141}Y^{142})_{p63}-Z^{39}-(CY^{143}Y^{144})_{p64}-Z^{40}-(CY^{145}Y^{146})_{p65}-$ (wherein, $Y^{135}$ to $Y^{146}$, the same or different, are a hydrogen atom or optionally substituted C1-C4 alkyl, $Z^{38}$ to $Z^{40}$, the same or different, are $-O-$, $-NY^{147A}-$, $-CO-O-$, $-O-CO-$, $-CO-NY^{147B}-$, $-NY^{147C}-CO-$, $-NY^{147D}-CO-O-$ or $-CO-$ (wherein, $Y^{147A}$ to $Y^{147D}$, the same or different, are a hydrogen atom or optionally substituted C1-C4 alkyl), $p^{60}$ is an integer of 1 to 5, $p^{61}$ is an integer of 0 to 5, $p^{62}$ is an integer of 0 to 5, $p^{63}$ is an integer of 0 to 5, $p^{64}$ is an integer of 1 to 5, and $p^{65}$ is an integer of 0 to 5), $B^3$ and $B^4$, the same or different, are

[C39]

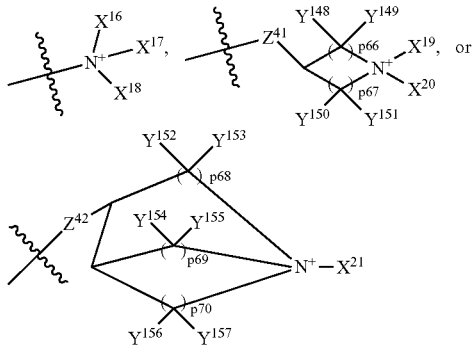

(wherein, $X^{16}$ and $X^{17}$, the same or different, are an optionally substituted C1-C4 alkyl or are combined together to form an optionally substituted C4-C6 heterocycle with an adjacent nitrogen atom, $X^{18}$ is an optionally substituted C1-C4 alkyl, $X^{19}$ and $X^{20}$, the same or different, are an optionally substituted C1-C4 alkyl or are combined together to form an optionally substituted C4-C6 heterocycle with an adjacent nitrogen atom, $X^{21}$ is an optionally substituted C1-C4 alkyl, $Y^{148}$ to $Y^{157}$, the same or different, are a hydrogen atom or optionally substituted C1-C4 alkyl, $Z^{41}$ and $Z^{42}$, the same or different, are $-O-$, $-NY^{158A}-$, $-CO-O-$, $-O-CO-$, $-CO-NY^{158B}-$, $-NY^{158C}-CO-$ or $-NY^{158D}-CO-O-$ (wherein, $Y^{158A}$ to $Y^{158D}$, the same or different, are a hydrogen atom or optionally substituted C1-C4 alkyl), $p^{66}$ is an integer of 0 to 5, and $p^{67}$ to $p^{70}$, the same or different, are an integer of 1 to 5), and $A^5$ and $A^6$, the same or different, are a pharmaceutically acceptable anion).

(60) The production method described in (59), wherein the lipid A is a lipid represented by formula (I), and in formula (I), one of $L^1$ to $L^3$ is $-CO-O-(Y^1Y^2)_{p1}-$ or $-O-CO-(CY^1Y^2)_{p1}-$ or two or more of $L^1$ to $L^3$, the same or different, are $-CO-O-(Y^1Y^2)_{p1}-$ or $-O-CO-(CY^1Y^2)_{p1}-$, and $R^1$ to $R^3$ are linear or branched C15-C20 alkenyl or C9-C18 alkyl and are the same.

(61) The production method described in (59), wherein the lipid A is represented by formula (II), and in formula (II), one of $L^4$ to $L^6$ is $-CO-O-(Y^8Y^9)_{p4}-$, $-O-CO-(CY^8Y^9)_{p4}-$ or $-O-CO-(CY^{10}Y^{11})_{p5}-O-(CY^{12}Y^{13})_{p6}-$ or two or more of $L^4$ to $L^6$ the same or different, are $-CO-O-(Y^8Y^9)_{p4}-$, $-O-CO-(CY^8Y^9)_{p4}-$ or $-O-CO-(CY^{10}Y^{11})_{p5}-O-(CY^{12}Y^{13})_{p6}-$, and $R^4$ to $R^6$ are linear or branched C15-C20 alkenyl or C9-C18 alkyl and are the same.

(62) The production method described in (59), wherein the lipid A is a lipid represented by formula (III), and in formula (III), one of $L^8$ to $L^{10}$ is $-CO-O-(Y^{39}Y^{40})_{p18}-$ or $-O-CO-(CY^{39}Y^{40})_{p18}-$ or two or more of $L^8$ to $L^{10}$, the same or different, are $-CO-O-(Y^{39}Y^{40})_{p18}-$ or $-O-CO-(CY^{39}Y^{40})_{p18}-$, and $R^7$ to $R^9$ are linear or branched C15-C20 alkenyl or C9-C18 alkyl.

(63) The production method described in (59), wherein the lipid A is a lipid represented by formula (IV), and in formula (IV), $L^{13}$ is $-CO-O-(Y^{83}Y^{84})_{p38}-$ or $-O-CO-(CY^{83}Y^{84})_{p38}-$, one of $L^{14}$ and $L^{15}$ is $-CO-O-(Y^{90}Y^{91})_{p41}-$ or $-O-CO-(CY^{90}Y^{91})_{p41}-L^{13}$ is $-CO-O-(Y^{83}Y^{84})_{p38}-$ or $-O-CO-(CY^{83}Y^{84})_{p38}-$ and one of $L^{14}$ and $L^{15}$ is $-CO-O-(Y^{90}Y^{91})_{p41}-$ or $-O-CO-(CY^{90}Y^{91})_{p41}-$, $L^{14}$ and $L^{15}$, the same or different, are $-CO-O-(Y^{90}Y^{91})_{p41}-$ or $-O-CO-(CY^{90}Y^{91})_{p41}-$ or $L^{13}$ is $-CO-O-(Y^{83}Y^{84})_{p38}-$ or $-O-CO-(CY^{83}Y^{84})_{p38}-$ and $L^{14}$ and $L^{15}$, the same or different, are $-CO-O-(Y^{90}Y^{91})_{p41}-$ or $-O-CO-(CY^{90}Y^{91})_{p41}-$, and $R^{10}$ to $R^{12}$ are linear or branched C15-C20 alkenyl or C9-C18 alkyl.

(64) The production method described in (59), wherein the lipid A is represented by formula (V'), and in formula (V'), one of $L^{17}$ to $L^{19}$ is $-CO-O-$ or $-O-$ or two or more of $L^{17}$ to $L^{19}$, the same or different, are $-CO-O-$ or $-O-$, and $R^{13}$ to $R^{15}$ are linear or branched C15-C20 alkenyl or C9-C18 alkyl.

(65) The production method described in any one of (45) to (64), wherein, in step (a), the lipid (lipid B), which has a hydrophilic unit having one optionally substituted amino group, and a hydrophobic unit having two independent, optionally substituted hydrocarbon groups, is mixed with the lipid A, the nucleic acid and a lipid derivative or fatty acid derivative of a water-soluble polymer.

(66) The production method described in (65), wherein the lipid B is:

formula (CL-I)

[C40]

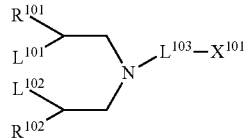

(CL-I)

(wherein, $R^{101}$ and $R^{102}$, the same or different, are a linear or branched C10-C24 alkyl, C10-C24 alkenyl or C10-C24 alkynyl, $L^{101}$ and $L^{102}$ are hydrogen atoms or are combined together to form a single bond or C1-C3 alkylene, $L^{103}$ is a single bond, $-CO-$ or $-CO-O-$, and in the case where $L^{103}$ is a single bond, $X^{101}$ is a hydrogen atom, C1-C6 alkyl, C3-C6 alkenyl, pyrrolidin-3-yl, piperidin-3-yl or piperidin-4-yl, or a C1-C6 alkyl or C3-C6 alkenyl substituted with one to three of the same or different amino, monoalkylamino, dialkylamino, trialkylammonio, hydroxyl, alkoxy, carbamoyl, monoalkylcarbamoyl, dialkylcarbamoyl, pyrrolidinyl, piperidyl or morpholinyl, or in the case where $L^{103}$ is —CO— or —CO—O—, $X^{101}$ is a pyrrolidin-2-yl, pyrrolidin-3-yl, piperidin-2-yl, piperidin-3-yl, piperidin-4-yl, morpholin-2-yl or morpholin-3-yl, or a C1-C6 alkyl or C3-C6 alkenyl substituted with one to three of the same or different amino, monoalkylamino, dialkylamino, trialkylammonio, hydroxyl, alkoxy, carbamoyl, monoalkylcarbamoyl, dialkylcarbamoyl, pyrrolidinyl, piperidyl or morpholinyl, and at least one of the substituents is an amino, monoalkylamino, dialkylamino, trialkylammonio, pyrrolidinyl, piperidyl or morpholinyl);

formula (CL-II)

[C41]

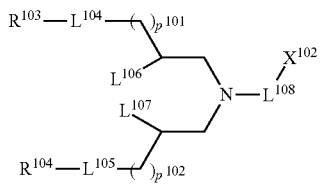

(CL-II)

(wherein, $R^{103}$ and $R^{104}$, the same or different, are a linear or branched C12-C24 alkyl, C12-C24 alkenyl or C12-C24 alkynyl, $p^{101}$ and $p^{102}$, the same or different, are an integer of 0 to 3, $L^{106}$ and $L^{107}$ are hydrogen atoms or are combined together to form a single bond or C2-C8 alkylene, $L^{104}$ and $L^{105}$, the same or different, are —O—, —CO—O— or —O—CO—, $L^{108}$ is a single bond, —CO— or —CO—O—, and in the case where $L^{108}$ is a single bond, $X^{102}$ is a hydrogen atom, C1-C6 alkyl, C3-C6 alkenyl, pyrrolidin-2-yl, pyrrolidin-3-yl, piperidin-3-yl or piperidin-4-yl, or a C1-C6 alkyl or C3-C6 alkenyl substituted with one to three of the same or different amino, monoalkylamino, dialkylamino, trialkylammonio, hydroxyl, alkoxy, carbamoyl, monoalkylcarbamoyl, dialkylcarbamoyl, pyrrolidinyl, piperidyl or morpholinyl, or in the case where $L^{108}$ is —CO— or —CO—O—, $X^{102}$ is a pyrrolidin-2-yl, pyrrolidin-3-yl, piperidin-2-yl, piperidin-3-yl, piperidin-4-yl, morpholin-2-yl or morpholin-3-yl, or a C1-C6 alkyl or C3-C6 alkenyl substituted with one to three of the same or different amino, monoalkylamino, dialkylamino, trialkylammonio, hydroxyl, alkoxy, carbamoyl, monoalkylcarbamoyl, dialkylcarbamoyl, pyrrolidinyl, piperidyl or morpholinyl, and at least one of the substituents is an amino, monoalkylamino, dialkylamino, trialkylammonio, pyrrolidinyl, piperidyl or morpholinyl);

formula (CL-III)

[C42]

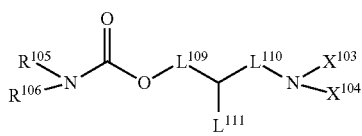

(CL-III)

(wherein, $R^{105}$ is a linear or branched C8-C24 alkyl, C8-C24 alkenyl or C8-C24 alkynyl, $R^{106}$ is a linear or branched C8-C24 alkyl, C8-C24 alkenyl, C8-C24 alkynyl, C8-C24 alkoxyethyl, C8-C24 alkoxypropyl, C8-C24 alkenyloxyethyl, C8-C24 alkenyloxypropyl, C8-C24 alkynyloxyethyl or C8-C24 alkynyloxypropyl, $X^{103}$ and $X^{104}$, the same or different, are a C1-C3 alkyl or are combined together to form a C2-C8 alkylene, or $X^{103}$ forms a C2-C8 alkylene with $L^{111}$, $L^{111}$ is a hydrogen atom, C1-C6 alkyl, C3-C6 alkenyl, amino, monoalkylamino, hydroxyl, alkoxy, carbamoyl, monoalkylcarbamoyl or dialkylcarbamoyl, or a C1-C6 alkyl or C3-C6 alkenyl substituted with one to three of the same or different amino, monoalkylamino, hydroxyl, alkoxy, carbamoyl, monoalkylcarbamoyl or dialkylcarbamoyl, or forms a C2-C8 alkylene with $X^{103}$, $L^{109}$ is a C1-C6 alkylene, and $L^{110}$ is a single bond or a C1-C6 alkylene, provided that, in the case where the sum of the number of carbon atoms of $L^{109}$ and $L^{110}$ is 7 or less and $L^{111}$ is a hydrogen atom, $L^{110}$ is a single bond, while in the case $L^{111}$ forms a C2-C6 alkylene with $X^{103}$, $L^{110}$ is a single bond, methylene or ethylene);

formula (CL-IV)

[C43]

(CL-IV)

(wherein, $R^{107}$ is a linear or branched C8-C24 alkyl, C8-C24 alkenyl or C8-C24 alkynyl, and $R^{108}$ is a linear or branched C8-C24 alkyl, C8-C24 alkenyl, C8-C24 alkynyl, C8-C24 alkoxyethyl, C8-C24 alkoxypropyl, C8-C24 alkenyloxyethyl, C8-C24 alkenyloxypropyl, C8-C24 alkynyloxyethyl or C8-C24 alkynyloxypropyl);

formula (CL-V)

[C44]

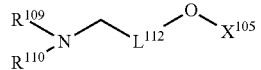

(CL-V)

(wherein, $R^{109}$ is a linear or branched C8-C24 alkyl, C8-C24 alkenyl or C8-C24 alkynyl, $R^{110}$ is a linear or branched C8-C24 alkyl, C8-C24 alkenyl, C8-C24 alkynyl, C8-C24 alkoxyethyl, C8-C24 alkoxypropyl, C8-C24 alkenyloxyethyl, C8-C24 alkenyloxypropyl, C8-C24 alkynyloxyethyl or C8-C24 alkynyloxypropyl), $L^{112}$ is a C1-C3 alkylene, and $X^{105}$ is a hydrogen atom or C1-C3 alkyl);

formula (CL-VI)

[C45]

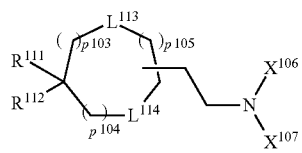

(CL-VI)

(wherein, $R^{111}$ and $R^{112}$, the same or different, are a linear or branched, optionally substituted C8-C24 alkyl, C8-C24 alkenyl or C8-C24 alkynyl, $X^{106}$ and $X^{107}$, the same or different, are a C1-C3 alkyl or are combined together to form a C2-C8 alkylene, $p^{103}$, $p^{104}$ and $p^{105}$, the same or different, are 0 or 1, provided that $p^{103}$, $p^{104}$ and $p^{105}$ are not simultaneously 0, and $L^{113}$ and $L^{114}$, the same or different, are O, S or NH); or formula (CL-VII)

[C46]

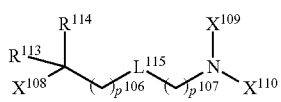

(CL-VII)

(wherein, $R^{113}$ and $R^{114}$, the same or different, are a linear or branched, optionally substituted C8-C24 alkyl, C8-C24 alkenyl or C8-C24 alkynyl, $X^{109}$ and $X^{110}$, the same or different, are a C1-C3 alkyl or are combined together to form a C2-C8 alkylene, $X^{108}$ is a hydrogen atom, hydroxyl, optionally substituted C1-C4 alkyl, optionally substituted C1-C4 alkoxy or optionally substituted C1-C4 acyloxy group, $L^{115}$ is —CO—O— or —O—CO—, and $p^{106}$ is an integer of 0 to 3, and $p^{107}$ is an integer of 1 to 4).

(67) Nucleic acid-containing lipid nanoparticles obtained by the production method described in any one of (22) to (66).

(68) A method for stabilizing nucleic acid-containing lipid nanoparticles, which uses a lipid (lipid A) which has a hydrophilic unit having a single quaternary ammonium group, and three independent, optionally substituted hydrocarbon groups, in a lipid membrane composing nucleic acid-containing lipid nanoparticles.

(69) The method described in (68), wherein the number of moles of the quaternary ammonium group in the lipid A is 0.01 times or more the number of moles of phosphorous atoms in the nucleic acid.

(70) The method described in (68) or (69), wherein the lipid A is a lipid represented by the following formulas or a combination thereof:

formula (I)

[C47]

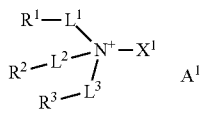

(I)

(wherein, $R^1$ to $R^3$, the same or different, are a linear or branched, optionally substituted C8-C24 alkyl, C8-C24 alkenyl or C8-C24 alkynyl, $L^1$ to $L^3$, the same or different, are absent or are —$Z^1$—$(CY^1Y^2)_{p1}$— or —$Z^2$—$(CY^3Y^4)_{p2}$—$Z^3$—$(CY^5Y^6)_{p3}$— (wherein, $Y^1$ to $Y^6$, the same or different, are a hydrogen atom or optionally substituted C1-C4 alkyl, $Z^1$ to $Z^3$, the same or different, are —O—, —$NY^{7A}$—, —CO—O—, —O—CO—, —CO—$NY^{7B}$—, —$NY^{7C}$—CO— or —$NY^{7D}$—CO—O— (wherein, $Y^{7A}$ to $Y^{7D}$ the same or different, are a hydrogen atom or optionally substituted C1-C4 alkyl), and $p^1$ to $p^3$, the same or different, are an integer of 1 to 5), $X^1$ is an optionally substituted C1-C4 alkyl, and $A^1$ is a pharmaceutically acceptable anion);

formula (II)

[C48]

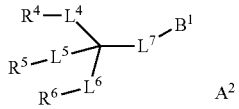

(II)

(wherein, $R^4$ to $R^6$, the same or different, are a linear or branched, optionally substituted C8-C24 alkyl, C8-C24 alkenyl or C8-C24 alkynyl, $L^4$ to $L^6$, the same or different, are absent or are —$Z^4$—$(CY^8Y^9)_{p4}$— or —$Z^5$—$(CY^{10}Y^{11})_{p5}$—$Z^6$—$(CY^{12}Y^{13})_{p6}$— (wherein, $Y^8$ to $Y^{13}$, the same or different, are a hydrogen atom or optionally substituted C1-C4 alkyl, $Z^4$ to $Z^6$, the same or different, are —O—, —$NY^{14A}$—, —CO—O—, —O—CO—, —CO—$NY^{14B}$—, —$NY^{14C}$—CO— or —$NY^{14D}$—CO—O— (wherein, $Y^{14A}$ to $Y^{14D}$, the same or different, are a hydrogen atom or optionally substituted C1-C4 alkyl), $p^4$ is an integer of 0 to 5, $p^5$ is an integer of 1 to 5, and $p^6$ is an integer of 0 to 5), $L^7$ is absent or is —$(CY^{15}Y^{16})_{p7}$—, —$(CY^{17}Y^{18})_{p8}$—$Z^7$—$(CY^{19}Y^{20})_{p9}$— or —$(CY^{21}Y^{22})_{p10}$—$Z^8$—$(CY^{23}Y^{24})_{p11}$—$Z^9$—$(CY^{25}Y^{26})_{p12}$— (wherein, $Y^{15}$ to $Y^{26}$, the same or different, are a hydrogen atom or optionally substituted C1-C4 alkyl, $Z^7$ to $Z^9$, the same or different, are —O—, —$NY^{27A}$—, —CO—O—, —O—CO—, —CO—$NY^{27B}$—, —$NY^{27C}$—CO— or —$NY^{27D}$—CO—O— (wherein, $Y^{27A}$ to $Y^{27D}$, the same or different, are a hydrogen atom or optionally substituted C1-C4 alkyl), $p^7$ is an integer of 1 to 5, $p^8$ is an integer of 0 to 5, $p^9$ is an integer of 1 to 5, $p^{10}$ is an integer of 0 to 5, $p^{11}$ is an integer of 1 to 5, and $p^{12}$ is an integer of 1 to 5), $B^1$ is

[C49]

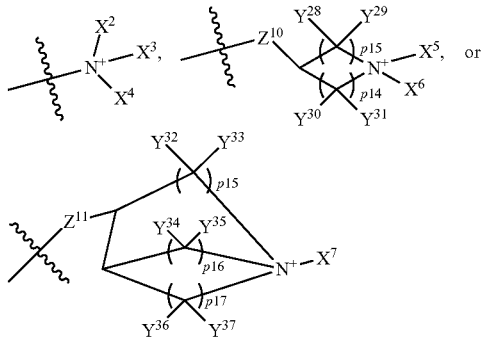

(wherein, $X^2$ and $X^3$, the same or different, are an optionally substituted C1-C4 alkyl or are combined together to form an optionally substituted C4-C6 heterocycle with an adjacent nitrogen atom, $X^4$ is an optionally substituted C1-C4 alkyl, $X^5$ and $X^6$, the same or different, are an optionally substituted C1-C4 alkyl or are combined together to form an optionally substituted C4-C6 heterocycle with an adjacent nitrogen atom, $X^7$ is an optionally substituted C1-C4 alkyl, $Y^{28}$ to $Y^{37}$, the same or different, are a hydrogen atom or optionally substituted C1-C4 alkyl, $Z^{10}$ and $Z^{11}$, the same or different, are —O—, —NY$^{38A}$—, —CO—O—, —O—CO—, —CO—NY$^{38B}$—, —NY$^{38C}$—CO— or —NY$^{38D}$—CO—O— (wherein, $Y^{38A}$ to $Y^{38D}$, the same or different, are a hydrogen atom or optionally substituted C1-C4 alkyl), $p^{13}$ is an integer of 0 to 5, and $p^{14}$ to $p^{17}$, the same or different, are an integer of 1 to 5), and $A^2$ is a pharmaceutically acceptable anion);

formula (III)

[C50]

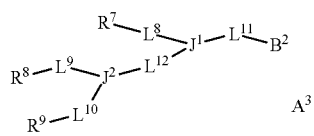

(III)

(wherein, $R^7$ to $R^9$, the same or different, are a linear or branched, optionally substituted C8-C24 alkyl, C8-C24 alkenyl or C8-C24 alkynyl, $L^8$ to $L^{10}$, the same or different, are absent or are —$Z^{12}$—(CY$^{39}$Y$^{40}$)$_{p18}$— or —$Z^{13}$—(CY$^{41}$Y$^{42}$)$_{p19}$—$Z^{14}$—(CY$^{43}$Y$^{44}$)$_{p20}$— (wherein, $Y^{39}$ to $Y^{44}$, the same or different, are a hydrogen atom or optionally substituted C1-C4 alkyl, $Z^{12}$ to $Z^{14}$, the same or different, are —O—, —NY$^{45A}$—, —CO—O—, —O—CO—, —CO—NY$^{45B}$—, —NY$^{45C}$—CO—, —NY$^{45D}$—CO—O— or —CO— (wherein, $Y^{45A}$ to $Y^{45D}$, the same or different, are a hydrogen atom or optionally substituted C1-C4 alkyl), $p^{18}$ is an integer of 0 to 5, $p^{19}$ is an integer of 1 to 5, and $p^{20}$ is an integer of 0 to 5), $L^{11}$ is absent or is —(CY$^{46}$Y$^{47}$)$_{p21}$—, —(CY$^{48}$Y$^{49}$)$_{p22}$—$Z^{15}$—(CY$^{50}$Y$^{51}$)$_{p23}$— or —(CY$^{52}$Y$^{53}$)$_{p24}$—$Z^{16}$—(CY$^{54}$Y$^{55}$)$_{p25}$—$Z^{17}$—(CY$^{56}$Y$^{57}$)$_{p26}$— (wherein, $Y^{46}$ to $Y^{57}$, the same or different, are a hydrogen atom or optionally substituted C1-C4 alkyl, $Z^{15}$ to $Z^{17}$, the same or different, are —O—, —NY$^{58A}$—, —CO—O—, —O—CO—, —CO—NY$^{58B}$—, —NY$^{58C}$—CO—, —NY$^{58D}$—CO—O— or —CO— (wherein, $Y^{58A}$ to $Y^{58D}$, the same or different, are a hydrogen atom or optionally substituted C1-C4 alkyl), $p^{21}$ is an integer of 1 to 5, $p^{22}$ is an integer of 0 to 5, $p^{23}$ is an integer of 1 to 5, $p^{24}$ is an integer of 0 to 5, $p^{25}$ is an integer of 1 to 5, and $p^{26}$ is an integer of 1 to 5), $L^{12}$ is absent or is —(CY$^{59}$Y$^{60}$)$_{p27}$—, —(CY$^{61}$Y$^{62}$)$_{p28}$—$Z^{18}$—(CY$^{63}$CY$^{64}$)$_{p29}$— or —(CY$^{65}$Y$^{66}$)$_{p30}$—$Z^{19}$—(CY$^{67}$Y$^{68}$)$_{p31}$—$Z^{20}$—(CY$^{69}$Y$^{70}$)$_{p32}$— (wherein, $Y^{59}$ to $Y^{70}$, the same or different, are a hydrogen atom or optionally substituted C1-C4 alkyl, $Z^{18}$ to $Z^{20}$, the same or different, are —O—, —NY$^{71A}$—, —CO—O—, —O—CO—, —CO—NY$^{71B}$—, —NY$^{71C}$—CO—, —NY$^{71D}$—CO—O— or —CO— (wherein, $Y^{71A}$ to $Y^{71D}$, the same or different, are a hydrogen atom or optionally substituted C1-C4 alkyl), $p^{27}$ is an integer of 1 to 5, $p^{28}$ is an integer of 0 to 5, $p^{29}$ is an integer of 0 to 5, $p^{30}$ is an integer of 0 to 5, $p^{31}$ is an integer of 1 to 5, and $p^{32}$ is an integer of 0 to 5), $J^1$ and $J^2$, the same or different, are CY$^{72}$ or N (wherein, $Y^{72}$ is a hydrogen atom, hydroxyl, optionally substituted C1-C4 alkyl, optionally substituted C1-C4 alkoxy or optionally substituted C1-C4 acyloxy group), $B^2$ is

[C51]

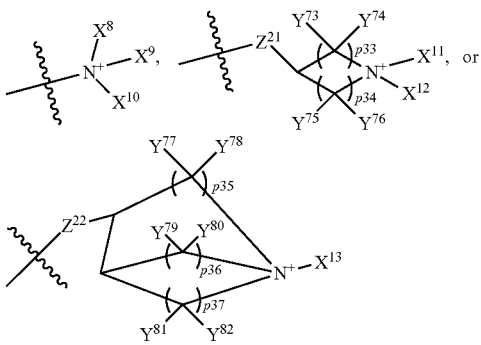

(wherein, $X^8$ and $X^9$, the same or different, are an optionally substituted C1-C4 alkyl or are combined together to form an optionally substituted C4-C6 heterocycle with an adjacent nitrogen atom, $X^{10}$ is an optionally substituted C1-C4 alkyl, $X^{11}$ and $X^{12}$, the same or different, are an optionally substituted C1-C4 alkyl or are combined together to form an optionally substituted C4-C6 heterocycle with an adjacent nitrogen atom, $X^{13}$ is an optionally substituted C1-C4 alkyl, $Y^{73}$ to $Y^{82}$, the same or different, are a hydrogen atom or optionally substituted C1-C4 alkyl, $Z^{21}$ and $Z^{22}$, the same or different, are —O—, —NY$^{83A}$—, —CO—O—, —O—CO—, —CO—NY$^{83B}$, —NY$^{83C}$—CO— or —NY$^{83D}$—CO—O— (wherein, $Y^{83A}$ to $Y^{83D}$, the same or different, are a hydrogen atom or optionally substituted C1-C4 alkyl), $p^{33}$ is an integer of 0 to 5, and $p^{34}$ to $p^{37}$, the same or different, are an integer of 1 to 5), and $A^3$ is a pharmaceutically acceptable anion);

formula (IV)

[C52]

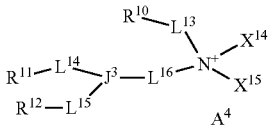

(IV)

(wherein, $R^{10}$ to $R^{12}$, the same or different, are a linear or branched, optionally substituted C8-C24 alkyl, C8-C24 alkenyl or C8-C24 alkynyl, $L^{13}$ is absent or is —$Z^{23}$—(CY$^{83}$Y$^{84}$)$_{p38}$— or —$Z^{24}$—(CY$^{85}$Y$^{86}$)$_{p39}$—$Z^{25}$—(CY$^{87}$Y$^{88}$)$_{p40}$— (wherein, $Y^{83}$ to $Y^{88}$, the same or different, are a hydrogen atom or optionally substituted C1-C4 alkyl, $Z^{23}$ to $Z^{25}$, the same or different, are —O—, —NY$^{89A}$—, —CO—O—, —O—CO—, —CO—NY$^{89B}$—, —NY$^{89C}$—CO— or —NY$^{89D}$—CO—O— (wherein, $Y^{89A}$ to $Y^{89D}$, the same or different, are a hydrogen atom or optionally substituted C1-C4 alkyl), and $p^{38}$ to $p^{40}$, the same or different, are an integer of 1 to 5), $L^{14}$ and $L^{15}$, the same or different, are absent or are —$Z^{26}$—(CY$^{90}$Y$^{91}$)$_{p41}$— or —$Z^{27}$—(CY$^{92}$Y$^{93}$)$_{p42}$—$Z^{28}$—(CY$^{94}$Y$^{95}$)$_{p43}$— (wherein, $Y^{90}$ to $Y^{95}$, the same or different, are a hydrogen atom or optionally substituted C1-C4 alkyl, $Z^{26}$ to $Z^{28}$, the same or different, are —O—, —NY$^{96A}$—, —CO—O—, —O—CO—, —CO—NY$^{96B}$—, —NY$^{96C}$—

CO—, —NY$^{96D}$—CO—O— or —CO— (wherein, Y$^{96A}$ to Y$^{96D}$, the same or different, are a hydrogen atom or optionally substituted C1-C4 alkyl), p$^{41}$ is an integer of 0 to 5, p$^{42}$ is an integer of 1 to 5, and p$^{43}$ is an integer of 0 to 5), L$^{16}$ is absent or is —(CY$^{97}$Y$^{98}$)$_{p44}$—, —(CY$^{99}$Y$^{100}$)$_{p45}$—Z$^{29}$—(CY$^{101}$Y$^{102}$)$_{p46}$— or —(CY$^{103}$Y$^{104}$)$_{p47}$—Z$^{30}$—(CY$^{105}$Y$^{106}$)$_{p48}$—Z$^{31}$—(CY$^{107}$Y$^{108}$)$_{p49}$— (wherein, Y$^{97}$ to Y$^{108}$, the same or different, are a hydrogen atom or optionally substituted C1-C4 alkyl, Z$^{29}$ to Z$^{31}$, the same or different, are —O—, —NY$^{109A}$—, —CO—O—, —O—CO—, —CO—NY$^{109B}$—, —NY$^{109C}$—CO—, —NY$^{109D}$—CO—O— or —CO— (wherein, Y$^{109A}$ to Y$^{109D}$, the same or different, are a hydrogen atom or optionally substituted C1-C4 alkyl), p$^{44}$ is an integer of 1 to 5, p$^{45}$ is an integer of 0 to 5, p$^{46}$ is an integer of 1 to 5, p$^{47}$ is an integer of 0 to 5, p$^{48}$ is an integer of 1 to 5, and p$^{49}$ is an integer of 1 to 5), J$^3$ is CY$^{110}$ or N (wherein, Y$^{110}$ is a hydrogen atom, hydroxyl, optionally substituted C1-C4 alkyl, optionally substituted C1-C4 alkoxy or optionally substituted C1-C4 acyloxy group), X$^{14}$ and X$^{15}$, the same or different, are an optionally substituted C1-C4 alkyl or are combined together to form an optionally substituted C4-C6 heterocycle with an adjacent nitrogen atom, and A$^4$ is a pharmaceutically acceptable anion); or formula (V') or formula (V'')

[C53]

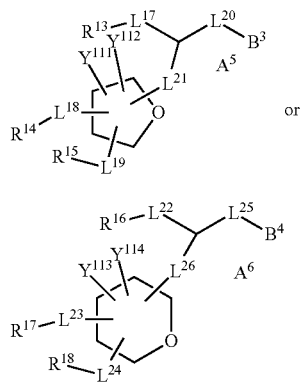

(wherein,

R$^{13}$ to R$^{18}$, the same or different, are a linear or branched, optionally substituted C8-C24 alkyl, C8-C24 alkenyl or C8-C24 alkynyl, Y$^{111}$ to Y$^{114}$, the same or different, are a hydrogen atom, hydroxyl or optionally substituted C1-C4 alkyl, L$^{17}$ to L$^{19}$ and L$^{22}$ to L$^{24}$, the same or different, are absent or are —Z$^{32}$—(CY$^{115}$Y$^{116}$)$_{p51}$— or —Z$^{33}$—(CY$^{117}$Y$^{118}$)$_{p52}$—Z$^{34}$—(CY$^{119}$Y$^{120}$)$_{p53}$— (wherein, Y$^{115}$ to Y$^{120}$, the same or different, are a hydrogen atom or optionally substituted C1-C4 alkyl, Z$^{32}$ to Z$^{34}$, the same or different, are —O—, —NY$^{121A}$—, —CO—O—, —O—CO—, —CO—NY$^{121B}$—, —NY$^{121C}$—CO—, —NY$^{121D}$—CO—O— or —CO— (wherein, Y$^{121A}$ to Y$^{121D}$, the same or different, are a hydrogen atom or optionally substituted C1-C4 alkyl), p$^{51}$ is an integer of 0 to 5, p$^{52}$ is an integer of 1 to 5, and p$^{53}$ is an integer of 0 to 5), L$^{20}$ and L$^{25}$, the same or different, are absent or are —(CY$^{122}$Y$^{123}$)$_{p54}$—, —(CY$^{124}$Y$^{125}$)$_{p55}$—Z$^{35}$—(CY$^{126}$Y$^{127}$)$_{p56}$— or —(CY$^{128}$Y$^{129}$)$_{p57}$—Z$^{36}$—(CY$^{130}$Y$^{131}$)$_{p58}$—Z$^{37}$—(CY$^{132}$Y$^{133}$)$_{p59}$— (wherein, Y$^{122}$ to Y$^{133}$, the same or different, are a hydrogen atom or optionally substituted C1-C4 alkyl, Z$^{35}$ to Z$^{37}$, the same or different, are —O—, —NY$^{134A}$—, —CO—O—, —O—CO—, —CO—NY$^{134B}$—, —NY$^{134C}$—CO—, —NY$^{134D}$—CO—O— or —CO— (wherein, Y$^{134A}$ to Y$^{134D}$, the same or different, are a hydrogen atom or optionally substituted C1-C4 alkyl), p$^{54}$ is an integer of 1 to 5, p$^{55}$ is an integer of 0 to 5, p$^{56}$ is an integer of 1 to 5, p$^{57}$ is an integer of 0 to 5, p$^{58}$ is an integer of 1 to 5 and p$^{59}$ is an integer of 1 to 5), L$^{21}$ and L$^{26}$, the same or different, are absent or are —(CY$^{135}$Y$^{136}$)$_{p60}$—, —(CY$^{137}$Y$^{138}$)$_{p61}$—Z$^{38}$—(CY$^{139}$Y$^{140}$)$_{p62}$— or —(CY$^{141}$Y$^{142}$)$_{p63}$—Z$^{39}$—(CY$^{143}$Y$^{144}$)$_{p64}$—Z$^{40}$—(CY$^{145}$Y$^{146}$)$_{p65}$— (wherein, Y$^{135}$ to Y$^{146}$, the same or different, are a hydrogen atom or optionally substituted C1-C4 alkyl, Z$^{38}$ to Z$^{40}$, the same or different, are —O—, —NY$^{147A}$—, —CO—O—, —O—CO—, —CO—NY$^{147B}$—, —NY$^{147C}$—CO—, —NY$^{147D}$—CO—O— or —CO— (wherein, Y$^{147A}$ to Y$^{147D}$, the same or different, are a hydrogen atom or optionally substituted C1-C4 alkyl), p$^{60}$ is an integer of 1 to 5, p$^{61}$ is an integer of 0 to 5, p$^{62}$ is an integer of 0 to 5, p$^{63}$ is an integer of 0 to 5, p$^{64}$ is an integer of 1 to 5, and p$^{65}$ is an integer of 0 to 5), B$^3$ and B$^4$, the same or different, are

[C54]

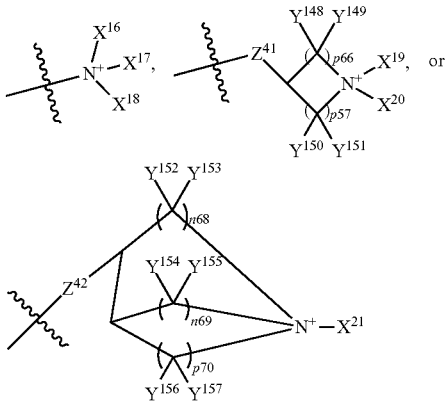

(wherein, X$^{16}$ and X$^{17}$, the same or different, are an optionally substituted C1-C4 alkyl or are combined together to form an optionally substituted C4-C6 heterocycle with an adjacent nitrogen atom, X$^{18}$ is an optionally substituted C1-C4 alkyl, X$^{19}$ and X$^{20}$, the same or different, are an optionally substituted C1-C4 alkyl or are combined together to form an optionally substituted C4-C6 heterocycle with an adjacent nitrogen atom, X$^{21}$ is an optionally substituted C1-C4 alkyl, Y$^{148}$ to Y$^{157}$, the same or different, are a hydrogen atom or optionally substituted C1-C4 alkyl, Z$^{41}$ and Z$^{42}$, the same or different, are —O—, —NY$^{158A}$—, —CO—O—, —O—CO—, —CO—NY$^{158B}$—, —NY$^{158C}$—CO— or —NY$^{158D}$—CO—O— (wherein, Y$^{158A}$ to Y$^{158D}$, the same or different, are a hydrogen atom or optionally substituted C1-C4 alkyl), p$^{66}$ is an integer of 0 to 5, and p$^{67}$ to p$^{70}$, the same or different, are an integer of 1 to 5), and A$^5$ and A$^6$, the same or different, are a pharmaceutically acceptable anion).

(71) The method described in (70), wherein the lipid A is a lipid represented by formula (I), and in formula (I), one of L$^1$ to L$^3$ is —CO—O—(Y$^1$Y$^2$)$_{p1}$— or —O—CO—(CY$^1$Y$^2$)$_{p1}$— or two or more of L$^1$ to L$^3$, the same or different, are —CO—O—(Y$^1$Y$^2$)$_{p1}$— or —O—CO—(CY$^1$Y$^2$)$_{p1}$— and R$^1$ to R$^3$ are linear or branched C15-C20 alkenyl or C9-C18 alkyl and are the same.

(72) The method described in (70), wherein the lipid A is represented by formula (II), and in formula (II), one of $L^4$ to $L^6$ is —CO—O—$(Y^8Y^9)_{p4}$—, —O—CO—$(CY^8Y^9)_{p4}$— or —O—CO—$(CY^{10}Y^{11})_{p5}$—O—$(CY^{12}Y^{13})_{p6}$— or two or more of $L^4$ to $L^6$, the same or different, are —CO—O—$(Y^8Y^9)_{p4}$—, —O—CO—$(CY^8Y^9)_{p4}$— or —O—CO—$(CY^{10}Y^{11})_{p5}$—O—$(CY^{12}Y^{13})_{p6}$—, and $R^4$ to $R^6$ are linear or branched C15-C20 alkenyl or C9-C18 alkyl and are the same.

(73) The method described in (70), wherein the lipid A is a lipid represented by formula (III), and in formula (III), one of $L^8$ to $L^{10}$ is —CO—O—$(Y^{39}Y^{40})_{p18}$— or —O—CO—$(CY^{39}Y^{40})_{p18}$— or two or more of $L^8$ to $L^{10}$, the same or different, are —CO—O—$(Y^{39}Y^{40})_{p18}$— or —O—CO—$(CY^{39}Y^{40})_{p18}$—, and $R^7$ to $R^9$ are a linear or branched C15-C20 alkenyl or C9-C18 alkyl.

(74) The method described in (70), wherein the lipid A is a lipid represented by formula (IV), and in formula (IV), $L^{13}$ is —CO—O—$(Y^{83}Y^{84})_{p38}$— or —O—CO—$(CY^{83}Y^{84})_{p38}$—, one of $L^{14}$ and $L^{15}$ is —CO—O—$(Y^{90}Y^{91})_{p41}$— or —O—CO—$(CY^{90}Y^{91})_{p41}$-$L^{13}$ is —CO—O—$(Y^{83}Y^{84})_{p38}$— or —O—CO—$(CY^{83}Y^{84})_{p38}$— and one of $L^{14}$ and $L^{15}$ is —CO—O—$(Y^{90}Y^{91})_{p41}$— or —O—CO—$(CY^{90}Y^{91})_{p41}$—, $L^{14}$ and $L^{15}$, the same or different, are —CO—O—$(Y^{90}Y^{91})_{p41}$— or —O—CO—$(CY^{90}Y^{91})_{p41}$— or $L^{13}$ is —CO—O—$(Y^{83}Y^{84})_{p38}$— or —O—CO—$(CY^{83}Y^{84})_{p38}$— and $L^{14}$ and $L^{15}$, the same or different, are —CO—O—$(Y^{90}Y^{91})_{p41}$— or —O—CO—$(CY^{90}Y^{91})_{p41}$—, and $R^{10}$ to $R^{12}$ are linear or branched C15-C20 alkenyl or C9-C18 alkyl.

(75) The method described in (70), wherein the lipid A is represented by formula (V'), wherein one of $L^{17}$ to $L^{19}$ is —CO—O— or —O— or two or more of $L^{17}$ to $L^{19}$, the same or different, are —CO—O— or —O—, and $R^{13}$ to $R^{15}$ are linear or branched C15-C20 alkenyl or C9-C18 alkyl.

(76) A lipid (lipid A) which has a hydrophilic unit having one quaternary ammonium group and three independent, optionally substituted hydrocarbon groups, and selected from the group consisting of lipids represented by:

formula (I)

[C55]

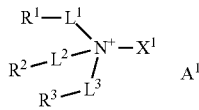

(I)

(wherein,
$R^1$ to $R^3$, the same or different, are a linear or branched, optionally substituted C8-C24 alkyl, C8-C24 alkenyl or C8-C24 alkynyl,
$L^1$ to $L^3$, the same or different, are absent or are —$Z^1$—$(CY^1Y^2)_{p1}$— or —$Z^2$—$(CY^3Y^4)_{p2}$—$Z^3$—$(CY^5Y^6)_{p3}$— (wherein, $Y^1$ to $Y^6$, the same or different, are a hydrogen atom or optionally substituted C1-C4 alkyl, $Z^1$ to $Z^3$, the same or different, are —O—, —$NY^{7A}$—, —CO—O—, —O—CO—, —CO—$NY^{7B}$—, —$NY^{7C}$—CO— or —$NY^{7D}$—CO—O— (wherein, $Y^{7A}$ to $Y^{7D}$ the same or different, are a hydrogen atom or optionally substituted C1-C4 alkyl), and $p^1$ to $p^3$, the same or different, are an integer of 1 to 5),
$X^1$ is an optionally substituted C1-C4 alkyl, and
$A^1$ is a pharmaceutically acceptable anion);

formula (II)

[C56]

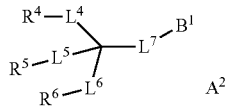

(II)

(wherein,
$R^4$ to $R^6$, the same or different, are a linear or branched, optionally substituted C8-C24 alkyl, C8-C24 alkenyl or C8-C24 alkynyl,
$L^4$ to $L^6$, the same or different, are absent or are —$Z^4$—$(CY^8Y^9)_{p4}$— or —$Z^5$—$(CY^{10}Y^{11})_{p5}$—$Z^6$—$(CY^{12}Y^{13})_{p6}$— (wherein, $Y^8$ to $Y^{13}$, the same or different, are a hydrogen atom or optionally substituted C1-C4 alkyl, $Z^4$ to $Z^6$, the same or different, are —O—, —$NY^{14A}$—, —CO—O—, —O—CO—, —CO—$NY^{14B}$—, —$NY^{14C}$—CO— or —$NY^{14D}$—CO—O— (wherein, $Y^{14A}$ to $Y^{14D}$, the same or different, are a hydrogen atom or optionally substituted C1-C4 alkyl), $p^4$ is an integer of 0 to 5, $p^5$ is an integer of 1 to 5, and $p^6$ is an integer of 0 to 5),
$L^7$ is absent or is —$(CY^{15}Y^{16})_{p7}$—, —$(CY^{17}Y^{18})_{p8}$—$Z^7$—$(CY^{19}Y^{20})_{p9}$— or —$(CY^{21}Y^{22})_{p10}$—$Z^8$—$(CY^{23}Y^{24})_{p11}$—$Z^9$—$(CY^{25}Y^{26})_{p12}$— (wherein, $Y^{15}$ to $Y^{26}$, the same or different, are a hydrogen atom or optionally substituted C1-C4 alkyl, $Z^7$ to $Z^9$, the same or different, are —O—, —$NY^{27A}$—, —CO—O—, —O—CO—, —CO—$NY^{27B}$—, —$NY^{27C}$—CO— or —$NY^{27D}$—CO—O— (wherein, $Y^{27A}$ to $Y^{27D}$, the same or different, are a hydrogen atom or optionally substituted C1-C4 alkyl), $p^7$ is an integer of 1 to 5, $p^8$ is an integer of 0 to 5, $p^9$ is an integer of 1 to 5, $p^{10}$ is an integer of 0 to 5, $p^{11}$ is an integer of 1 to 5, and $p^{12}$ is an integer of 1 to 5),
$B^1$ is

[C57]

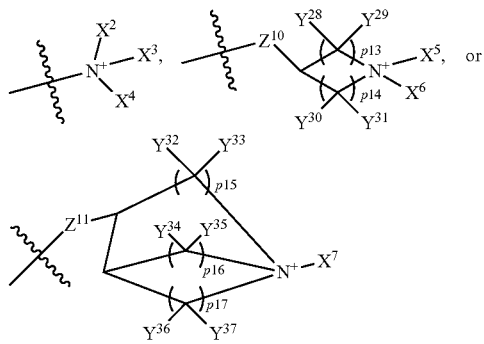

(wherein, $X^2$ and $X^3$, the same or different, are an optionally substituted C1-C4 alkyl or are combined together to form an optionally substituted C4-C6 heterocycle with an adjacent nitrogen atom, $X^4$ is an optionally substituted C1-C4 alkyl, $X^5$ and $X^6$, the same or different, are an optionally substituted C1-C4 alkyl or are combined together to form an optionally substituted C4-C6 heterocycle with an adjacent nitrogen atom, $X^7$ is an optionally substituted C1-C4 alkyl, $Y^{28}$ to $Y^{37}$, the same or different, are a hydrogen atom or optionally substituted C1-C4 alkyl, $Z^{10}$ and $Z^{11}$, the same or different, are —O—, —$NY^{38A}$—, —CO—O—, —O—CO—, —CO—$NY^{38B}$—, —$NY^{38C}$—CO— or —NY$^{38D}$—CO—O— (wherein, Y$^{38A}$ to Y$^{38D}$, the same or different, are a hydrogen atom or optionally substituted C1-C4 alkyl), p$^{13}$ is an integer of 0 to 5, and p$^{14}$ to p$^{17}$, the same or different, are an integer of 1 to 5), and A$^2$ is a pharmaceutically acceptable anion);

formula (III)

[C58]

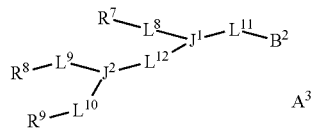

(III)

(wherein,

R$^7$ to R$^9$, the same or different, are a linear or branched, optionally substituted C8-C24 alkyl, C8-C24 alkenyl or C8-C24 alkynyl, L$^8$ to L$^{10}$, the same or different, are absent or are —Z$^{12}$—(CY$^{39}$Y$^{40}$)$_{p18}$— or —Z$^{13}$—(CY$^{41}$Y$^{42}$)$_{p19}$—Z$^{14}$—(CY$^{43}$Y$^{44}$)$_{p20}$— (wherein, Y$^{39}$ to Y$^{44}$, the same or different, are a hydrogen atom or optionally substituted C1-C4 alkyl, Z$^{12}$ to Z$^{14}$, the same or different, are —O—, —NY$^{45A}$—, —CO—O—, —O—CO—, —CO—NY$^{45B}$—, —NY$^{45C}$—CO—, —NY$^{45D}$—CO—O— or —CO— (wherein, Y$^{45A}$ to Y$^{45D}$, the same or different, are a hydrogen atom or optionally substituted C1-C4 alkyl), p$^{18}$ is an integer of 0 to 5, p$^{19}$ is an integer of 1 to 5, and p$^{20}$ is an integer of 0 to 5), L$^{11}$ is absent or is —(CY$^{46}$Y$^{47}$)$_{p21}$—, —(CY$^{48}$Y$^{49}$)$_{p22}$—Z$^{15}$—(CY$^{50}$Y$^{51}$)$_{p23}$— or —(CY$^{52}$Y$^{53}$)$_{p24}$—Z$^{16}$—(CY$^{54}$Y$^{55}$)$_{p25}$—Z$^{17}$—(CY$^{56}$Y$^{57}$)$_{p26}$— (wherein, Y$^{46}$ to Y$^{57}$, the same or different, are a hydrogen atom or optionally substituted C1-C4 alkyl, Z$^{15}$ to Z$^{17}$, the same or different, are —O—, —NY$^{58A}$—, —CO—O—, —O—CO—, —CO—NY$^{58B}$—, —NY$^{58C}$—CO—, —NY$^{58D}$—CO—O— or —CO— (wherein, Y$^{58A}$ to Y$^{58D}$, the same or different, are a hydrogen atom or optionally substituted C1-C4 alkyl), p$^{21}$ is an integer of 1 to 5, p$^{22}$ is an integer of 0 to 5, p$^{23}$ is an integer of 1 to 5, p$^{24}$ is an integer of 0 to 5, p$^{25}$ is an integer of 1 to 5, and p$^{26}$ is an integer of 1 to 5), L$^{12}$ is absent or is —(CY$^{59}$Y$^{60}$)$_{p27}$—, —(CY$^{61}$Y$^{62}$)$_{p28}$—Z$^{18}$—(CY$^{63}$CY$^{64}$)$_{p29}$— or —(CY$^{65}$Y$^{66}$)$_{p30}$—Z$^{19}$—(CY$^{67}$Y$^{68}$)$_{p31}$—Z$^{20}$—(CY$^{69}$Y$^{70}$)$_{p32}$— (wherein, Y$^{59}$ to Y$^{70}$, the same or different, are a hydrogen atom or optionally substituted C1-C4 alkyl, Z$^{18}$ to Z$^{20}$, the same or different, are —O—, —NY$^{71A}$—, —CO—O—, —O—CO—, —CO—NY$^{71B}$—, —NY$^{71C}$—CO—, —NY$^{71D}$—CO—O— or —CO— (wherein, Y$^{71A}$ to Y$^{71D}$, the same or different, are a hydrogen atom or optionally substituted C1-C4 alkyl), p$^{27}$ is an integer of 1 to 5, p$^{28}$ is an integer of 0 to 5, p$^{29}$ is an integer of 0 to 5, p$^{30}$ is an integer of 0 to 5, p$^{31}$ is an integer of 1 to 5, and p$^{32}$ is an integer of 0 to 5), J$^1$ and J$^2$, the same or different, are CY$^{72}$ or N (wherein, Y$^{72}$ is a hydrogen atom, hydroxyl, optionally substituted C1-C4 alkyl, optionally substituted C1-C4 alkoxy or optionally substituted C1-C4 acyloxy group), B$^2$ is

[C59]

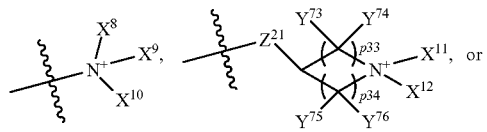

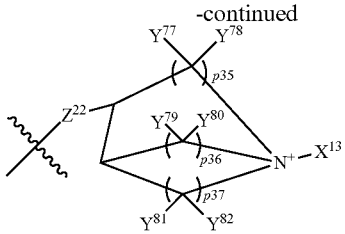

(wherein, X$^8$ and X$^9$, the same or different, are an optionally substituted C1-C4 alkyl or are combined together to form an optionally substituted C4-C6 heterocycle with an adjacent nitrogen atom, X$^{10}$ is an optionally substituted C1-C4 alkyl, X$^{11}$ and X$^{12}$, the same or different, are an optionally substituted C1-C4 alkyl or are combined together to form an optionally substituted C4-C6 heterocycle with an adjacent nitrogen atom, X$^{13}$ is an optionally substituted C1-C4 alkyl, Y$^{73}$ to Y$^{82}$, the same or different, are a hydrogen atom or optionally substituted C1-C4 alkyl, Z$^{21}$ and Z$^{22}$, the same or different, are —O—, —NY$^{83A}$—, —CO—O—, —O—CO—, —CO—NY$^{83B}$—, —NY$^{83C}$—CO— or —NY$^{83D}$—CO—O— (wherein, Y$^{83A}$ to Y$^{83D}$, the same or different, are a hydrogen atom or optionally substituted C1-C4 alkyl), p$^{33}$ is an integer of 0 to 5, and p$^{34}$ to p$^{37}$, the same or different, are an integer of 1 to 5), and A$^3$ is a pharmaceutically acceptable anion);

formula (IV)

[C60]

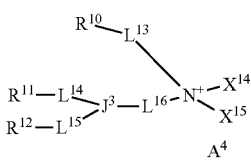

(IV)

(wherein,

R$^{10}$ to R$^{12}$, the same or different, are a linear or branched, optionally substituted C8-C24 alkyl, C8-C24 alkenyl or C8-C24 alkynyl, L$^{13}$ is absent or is —Z$^{23}$—(CY$^{83}$Y$^{84}$)$_{p38}$— or —Z$^{24}$—(CY$^{85}$Y$^{86}$)$_{p39}$—Z$^{25}$—(CY$^{87}$Y$^{88}$)$_{p40}$— (wherein, Y$^{83}$ to Y$^{88}$, the same or different, are a hydrogen atom or optionally substituted C1-C4 alkyl, Z$^{23}$ to Z$^{25}$, the same or different, are —O—, —NY$^{89A}$—, —CO—O—, —O—CO—, —CO—NY$^{89B}$—, —NY$^{89C}$—CO— or —NY$^{89D}$—CO—O— (wherein, Y$^{89A}$ to Y$^{89D}$, the same or different, are a hydrogen atom or optionally substituted C1-C4 alkyl), and p$^{38}$ to p$^{40}$, the same or different, are an integer of 1 to 5), L$^{14}$ and L$^{15}$, the same or different, are absent or are —Z$^{26}$—(CY$^{90}$Y$^{91}$)$_{p41}$— or —Z$^{27}$—(CY$^{92}$Y$^{93}$)$_{p42}$—Z$^{28}$—(CY$^{94}$Y$^{95}$)$_{p43}$— (wherein, Y$^{90}$ to Y$^{95}$, the same or different, are a hydrogen atom or optionally substituted C1-C4 alkyl, Z$^{26}$ to Z$^{28}$, the same or different, are —O—, —NY$^{96A}$—, —CO—O—, —O—CO—, —CO—NY$^{96B}$—, —NY$^{96C}$—CO—, —NY$^{96D}$—CO—O— or —CO— (wherein, Y$^{96A}$ to Y$^{96D}$, the same or different, are a hydrogen atom or optionally substituted C1-C4 alkyl), p$^{41}$ is an integer of 0 to 5, p$^{42}$ is an integer of 1 to 5, and p$^{43}$ is an integer of 0 to 5), L$^{16}$ is absent or is —(CY$^{97}$Y$^{98}$)$_{p44}$—, —(CY$^{99}$Y$^{100}$)$_{p45}$—Z$^{29}$—(CY$^{101}$Y$^{102}$)$_{p46}$— or —(CY$^{103}$Y$^{104}$)$_{p47}$—Z$^{30}$—(CY$^{105}$Y$^{106}$)$_{p48}$—Z$^{31}$—(CY$^{107}$Y$^{108}$)$_{p49}$— (wherein, Y$^{97}$ to Y$^{108}$, the same or different, are a hydrogen atom or optionally substituted C1-C4 alkyl, $Z^{29}$ to $Z^{31}$, the same or different, are —O—, —NY$^{109A}$—, —CO—O—, —O—CO—, —CO—NY$^{109B}$—, —NY$^{109C}$—CO—, —NY$^{109D}$—CO—O— or —CO— (wherein, $Y^{109A}$ to $Y^{109D}$, the same or different, are a hydrogen atom or optionally substituted C1-C4 alkyl), $p^{44}$ is an integer of 1 to 5, $p^{45}$ is an integer of 0 to 5, $p^{46}$ is an integer of 1 to 5, $p^{47}$ is an integer of 0 to 5, $p^{48}$ is an integer of 1 to 5, and $p^{49}$ is an integer of 1 to 5), $J^3$ is CY$^{110}$ or N (wherein, $Y^{110}$ is a hydrogen atom, hydroxyl, optionally substituted C1-C4 alkyl, optionally substituted C1-C4 alkoxy or optionally substituted C1-C4 acyloxy group), $X^{14}$ and $X^{15}$, the same or different, are an optionally substituted C1-C4 alkyl or are combined together to form an optionally substituted C4-C6 heterocycle with an adjacent nitrogen atom, and $A^4$ is a pharmaceutically acceptable anion); or formula (V') or formula (V")
[C61]

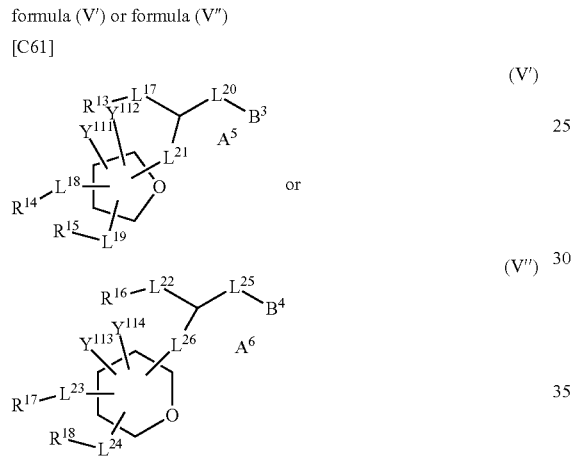

(wherein, $R^{13}$ to $R^{18}$, the same or different, are a linear or branched, optionally substituted C8-C24 alkyl, C8-C24 alkenyl or C8-C24 alkynyl, $Y^{111}$ to $Y^{114}$, the same or different, are a hydrogen atom, hydroxyl or optionally substituted C1-C4 alkyl, $L^{17}$ to $L^{19}$ and $L^{22}$ to $L^{24}$, the same or different, are absent or are —$Z^{32}$—(CY$^{115}$Y$^{116}$)$_{p51}$— or —$Z^{33}$—(CY$^{117}$Y$^{118}$)$_{p52}$—$Z^{34}$—(CY$^{119}$Y$^{120}$)$_{p53}$— (wherein, $Y^{115}$ to $Y^{120}$, the same or different, are a hydrogen atom or optionally substituted C1-C4 alkyl, $Z^{32}$ to $Z^{34}$, the same or different, are —O—, —NY$^{121A}$—, —CO—O—, —O—CO—, —CO—NY$^{121B}$—, —NY$^{121C}$—CO—, —NY$^{121D}$—CO—O— or —CO— (wherein, $Y^{121A}$ to $Y^{121D}$, the same or different, are a hydrogen atom or optionally substituted C1-C4 alkyl), $p^{51}$ is an integer of 0 to 5, $p^{52}$ is an integer of 1 to 5, and $p^{53}$ is an integer of 0 to 5), $L^{20}$ and $L^{25}$, the same or different, are absent or are —(CY$^{122}$Y$^{123}$)$_{p54}$—, —(CY$^{124}$Y$^{125}$)$_{p55}$—$Z^{35}$—(CY$^{126}$Y$^{127}$)$_{p56}$— or —(CY$^{128}$Y$^{129}$)$_{p57}$—$Z^{36}$—(CY$^{130}$Y$^{131}$)$_{p58}$—$Z^{37}$—(CY$^{132}$Y$^{133}$)$_{p59}$— (wherein, $Y^{122}$ to $Y^{133}$, the same or different, are a hydrogen atom or optionally substituted C1-C4 alkyl, $Z^{35}$ to $Z^{37}$, the same or different, are —O—, —NY$^{134A}$—, —CO—O—, —O—CO—, —CO—NY$^{134B}$—, —NY$^{134C}$—CO—, —NY$^{134D}$—CO—O— or —CO— (wherein, $Y^{134A}$ to $Y^{134D}$, the same or different, are a hydrogen atom or optionally substituted C1-C4 alkyl), $p^{54}$ is an integer of 1 to 5, $p^{55}$ is an integer of 0 to 5, $p^{56}$ is an integer of 1 to 5, $p^{57}$ is an integer of 0 to 5, $p^{58}$ is an integer of 1 to 5 and $p^{59}$ is an integer of 1 to 5), $L^{21}$ and $L^{26}$, the same or different, are absent or are —(CY$^{135}$Y$^{136}$)$_{p60}$—, —(CY$^{137}$Y$^{138}$)$_{p61}$—$Z^{38}$—(CY$^{139}$Y$^{140}$)$_{p62}$— or —(CY$^{141}$Y$^{142}$)$_{p63}$—$Z^{39}$—(CY$^{143}$Y$^{144}$)$_{p64}$—$Z^{40}$—(CY$^{145}$Y$^{146}$)$_{p65}$— (wherein, $Y^{135}$ to $Y^{146}$, the same or different, are a hydrogen atom or optionally substituted C1-C4 alkyl, $Z^{38}$ to $Z^{40}$, the same or different, are —O—, —NY$^{147A}$—, —CO—O—, —O—CO—, —CO—NY$^{147B}$—, —NY$^{147C}$—CO—, —NY$^{147D}$—CO—O— or —CO— (wherein, $Y^{147A}$ to $Y^{147D}$, the same or different, are a hydrogen atom or optionally substituted C1-C4 alkyl), $p^{60}$ is an integer of 1 to 5, $p^{61}$ is an integer of 0 to 5, $p^{62}$ is an integer of 0 to 5, $p^{63}$ is an integer of 0 to 5, $p^{64}$ is an integer of 1 to 5, and $p^{65}$ is an integer of 0 to 5), $B^3$ and $B^4$, the same or different, are

[C62]

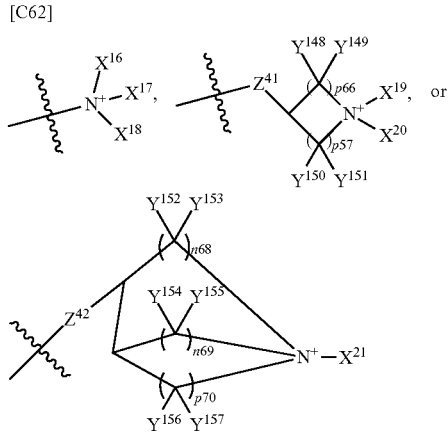

(wherein, $X^{16}$ and $X^{17}$, the same or different, are an optionally substituted C1-C4 alkyl or are combined together to form an optionally substituted C4-C6 heterocycle with an adjacent nitrogen atom, $X^{18}$ is an optionally substituted C1-C4 alkyl, $X^{19}$ and $X^{20}$, the same or different, are an optionally substituted C1-C4 alkyl or are combined together to form an optionally substituted C4-C6 heterocycle with an adjacent nitrogen atom, $X^{21}$ is an optionally substituted C1-C4 alkyl, $Y^{148}$ to $Y^{157}$, the same or different, are a hydrogen atom or optionally substituted C1-C4 alkyl, $Z^{41}$ and $Z^{42}$, the same or different, are —O—, —NY$^{158A}$—, —CO—O—, —O—CO—, —CO—NY$^{158B}$—, —NY$^{158C}$—CO— or —NY$^{158D}$—CO—O— (wherein, $Y^{158A}$ to $Y^{158D}$, the same or different, are a hydrogen atom or optionally substituted C1-C4 alkyl), $p^{66}$ is an integer of 0 to 5, and $p^{67}$ to $p^{70}$, the same or different, are an integer of 1 to 5), and $A^5$ and $A^6$, the same or different, are a pharmaceutically acceptable anion).

(77) The lipid described in (76), wherein the lipid A is a lipid represented by formula (I), and in formula (I), one of $L^1$ to $L^3$ is —CO—O—(Y$^1$Y$^2$)$_{p1}$— or —O—CO—(CY$^1$Y$^2$)$_{p1}$— or two or more of $L^1$ to $L^3$, the same or different, are —CO—O—(Y$^1$Y$^2$)$_{p1}$— or —O—CO—(CY$^1$Y$^2$)$_{p1}$—, and $R^1$ to $R^3$ are linear or branched C15-C20 alkenyl or C9-C18 alkyl and are the same.

(78) The lipid described in (76), wherein the lipid A is represented by formula (II), and in formula (II), one of $L^4$ to $L^6$ is —CO—O—(Y$^8$Y$^9$)$_{p4}$—, —O—CO—(CY$^8$Y$^9$)$_{p4}$— or —O—CO—(CY$^{10}$Y$^{11}$)$_{p5}$—O—(CY$^{12}$Y$^{13}$)$_{p6}$— or two or more of $L^4$ to $L^6$, the same or different, are —CO—O—

$(Y^8Y^9)_{p4}$—, —O—CO—$(CY^8Y^9)_{p4}$— or —O—CO—$(CY^{10}Y^{11})_{p5}$—O—$(CY^{12}Y^{13})_{p6}$—, and $R^4$ to $R^6$ are linear or branched C15-C20 alkenyl or C9-C18 alkyl and are the same.

(79) The lipid described in (76), wherein the lipid A is a lipid represented by formula (III), and in formula (III), one of $L^8$ to $L^{10}$ is —CO—O—$(Y^{39}Y^{40})_{p18}$— or —O—CO—$(CY^{39}Y^{40})_{p18}$— or two or more of $L^8$ to $L^{10}$, the same or different, are —CO—O—$(Y^{39}Y^{40})_{p18}$— or —O—CO—$(CY^{39}Y^{40})_{p18}$—, and $R^7$ to $R^9$ are linear or branched C15-C20 alkenyl or C9-C18 alkyl.

(80) The lipid described in (76), wherein the lipid A is a lipid represented by formula (IV), and formula (IV), $L^{13}$ is —CO—O—$(Y^{83}Y^{84})_{p38}$— or —O—CO—$(CY^{83}Y^{84})_{p38}$—, one of $L^{14}$ and $L^{15}$ is —CO—O—$(Y^{90}Y^{91})_{p41}$— or —O—CO—$(CY^{90}Y^{91})_{p41}$—, $L^{13}$ is —CO—O—$(Y^{83}Y^{84})_{p38}$— or —O—CO—$(CY^{83}Y^{84})_{p38}$— and one of $L^{14}$ and $L^{15}$ is —CO—O—$(Y^{90}Y^{91})_{p41}$— or —O—CO—$(CY^{90}Y^{91})_{p41}$—, $L^{14}$ and $L^{15}$, the same or different, are —CO—O—$(Y^{90}Y^{91})_{p41}$— or —O—CO—$(CY^{90}Y^{91})_{p41}$— or $L^{13}$ is —CO—O—$(Y^{83}Y^{84})_{p38}$— or —O—CO—$(CY^{83}Y^{84})_{p38}$— and $L^{14}$ and $L^{15}$, the same or different, are —CO—O—$(Y^{90}Y^{91})_{p41}$— or —O—CO—$(CY^{90}Y^{91})_{p41}$—, and $R^{10}$ to $R^{12}$ are linear or branched C15-C20 alkenyl or C9-C18 alkyl.

(81) The lipid described in (76), wherein the lipid A is represented by formula (V'), and in formula (V'), one of $L^{17}$ to $L^{19}$ is —CO—O— or —O— or two or more of $L^{17}$ to $L^{19}$, the same or different, are —CO—O— or —O—, and $R^{13}$ to $R^{15}$ are linear or branched C15-C20 alkenyl or C9-C18 alkyl.

(82) A method for introducing a nucleic acid into a cell by using the nucleic acid-containing lipid nanoparticles described in any one of (1) to (21) and (67).

(83) The method described in (82), wherein the cell is a mammalian cell at the site of tumors or inflammation.

(84) The method described in (83), wherein the cell is a cell present in the liver, stomach, lung, pancreas or spleen of a mammal.

(85) The method described in any one of (82) to (84), wherein the method for introducing into a cell is a method for introducing into a cell by intravenous administration or subcutaneous administration.

(86) A treatment method for cancer or inflammatory disease, the method including administration of the nucleic acid-containing lipid nanoparticles described in any one of (1) to (21) and (67) to a mammal.

(87) The method described in (86), wherein the administration method is intravenous administration or subcutaneous administration.

(88) A pharmaceutical containing the nucleic acid-containing lipid nanoparticles described in any one of (1) to (21) and (67).

(89) The pharmaceutical described in (88), which is for intravenous administration or subcutaneous administration.

(90) A therapeutic agent for cancer or inflammatory disease, which contains the nucleic acid-containing lipid nanoparticles described in any one of (1) to (21) and (67).

(91) The therapeutic agent described in (90), which is for intravenous administration or subcutaneous administration.

Advantageous Effects of Invention

According to the present invention, nucleic acid-containing lipid nanoparticles, which are useful as a pharmaceutical and are more stable and smaller in comparison with conventional particles, and a method for producing these lipid nanoparticles, can be provided. In addition, according to the present invention, a lipid can be provided that is useful for producing these lipid nanoparticles.

BRIEF DESCRIPTION OF DRAWINGS

FIG. 1 indicates the resistance of nucleic acid loaded into nucleic acid-containing lipid nanoparticles containing a lipid A to decomposition by serum nuclease; and the untreated nucleic acid, nucleic acid alone and preparation numbers of the nucleic acid-containing preparations are indicated on the horizontal axis, while the locations of untreated nucleic acids and nucleic acids decomposed by serum nuclease are indicated on the vertical axis.

FIG. 2 indicates the results of evaluating the gene suppression of nucleic acid-containing lipid nanoparticles containing a lipid A; and the preparation numbers and nucleic acid concentrations used are indicated on the horizontal axis, while gene suppression rates are indicated on the vertical axis.

FIG. 3 indicates the results of evaluating the gene suppression of nucleic acid-containing lipid nanoparticles containing a lipid A and a neutral lipid; and the preparation numbers and nucleic acid concentrations used are indicated on the horizontal axis, while gene suppression rates are indicated on the vertical axis.

FIG. 4 indicates the results of evaluating the gene suppression of nucleic acid-containing lipid nanoparticles containing a lipid A, a neutral lipid and various cationic lipids; and the preparation numbers and nucleic acid concentrations used are indicated on the horizontal axis, while gene suppression rates are indicated on the vertical axis.

FIG. 5 indicates the results of evaluating the permeability of nucleic acid-containing lipid nanoparticles with respect to collagen gel; and the preparation numbers used are indicated on the horizontal axis, and the width of the black color is the permeation width of the nucleic acid-containing lipid nanoparticles.

FIG. 6 indicates the results of evaluating the permeability of nucleic acid-containing lipid nanoparticles with respect to collagen gel; and the width of the white color is the permeation width of the nucleic acid-containing lipid nanoparticles.

FIG. 7 indicates the results of evaluating the permeation distance of the nucleic acid-containing lipid nanoparticles of FIG. 6 for collagen gel; the horizontal axis of the graph indicates the permeated distance (mm), while the vertical axis of the graph indicates normalized fluorescence intensity; and the markers are nucleic acid alone (□), Preparation 197 (o) and Preparation 199 (Δ).

DESCRIPTION OF EMBODIMENTS

The following provides a detailed explanation of embodiments of the present invention. The embodiments explained below do not limit the present invention.

The nucleic acid-containing lipid nanoparticles of the present invention contain a lipid that has a hydrophilic unit having one quaternary ammonium group and three independent, optionally substituted hydrocarbon groups (lipid A), a lipid derivative or fatty acid derivative of a water-soluble polymer, and a nucleic acid. In the present invention, as a result of obtaining nucleic acid-containing nanoparticles by using a lipid that has a hydrophilic unit having one quaternary ammonium group and three independent, optionally substituted hydrocarbon groups (lipid A), along with a lipid derivative or fatty acid derivative of a water-soluble polymer and a nucleic acid, nucleic acid-containing lipid nanoparticles can be obtained that are superior in terms of physicochemical stability and physiological activity.

In the present invention, there are no particular limitations on the lipid that has a hydrophilic unit having one quaternary ammonium group and three independent, optionally substituted hydrocarbon groups (lipid A) provided it is a molecule that has one quaternary ammonium group as a hydrophilic unit, and three independent, optionally substituted hydrocarbon groups, in a molecule thereof, and examples thereof include those lipids represented by the following structural formulas (A) to (C). In the following structural formulas (A) to (C), "hydrophilic unit" is a hydrophilic unit having one quaternary ammonium group, while the three "hydrophobic units" is three independent, optionally substituted hydrocarbon groups.

Zero to 3 of the 4 bonds of the quaternary ammonium group that composes the hydrophobic unit bond with 0 to 3 of any of the hydrocarbon groups that form the hydrophobic unit, while the remaining bond bonds with a linear and/or cyclic hydrocarbon group which may or may not have one or more substituents. Although the optionally substituted linear and/or cyclic hydrocarbon group that composes the hydrophilic unit may be any group composed of carbon atoms and hydrogen atoms, it preferably has 1 to 10 carbon atoms, more preferably 1 to 6 carbon atoms, and even more preferably 1 to 3 carbon atoms.

In addition, the hydrophilic unit may have one or more ether groups, ester groups or amide groups bonded through the carbon atoms in the optionally substituted linear and/or cyclic hydrocarbon group that composes the hydrophilic unit. Moreover, examples of substituents in the optionally substituted linear and/or cyclic hydrocarbon group include carbamate, amino, monoalkylamino, dialkylamino, pyrrolidin-2-yl, pyrrolidin-3-yl, piperidin-2-yl, piperidin-3-yl, piperidin-4-yl, morpholin-2-yl, morpholin-3-yl, hydroxyl, alkoxy, alkoxycarbonyl, hydroxycarbonyl, carbamoyl, monoalkylcarbamoyl, dialkylcarbamoyl, nitro, cyano, fluoro, chloro and bromo groups.

In addition, the hydrocarbon groups that form the hydrophobic unit may be any group composed of 8 to 24 carbon atoms and hydrogen atoms. Hydrocarbon groups can be categorized from the viewpoint of topology, and although examples thereof include linear hydrocarbon groups, branched hydrocarbon groups and cyclic hydrocarbon groups (such as a cholesteryl), linear or branched hydrocarbon groups are preferable. In addition, hydrocarbon groups can also be categorized based on the presence or absence of unsaturated bonds (double or triple bonds), and although hydrocarbon groups having unsaturated bonds can be categorized based on the presence or absence of aromatic properties, hydrocarbon groups composed only of saturated bonds (alkyl) or non-aromatic hydrocarbon groups having unsaturated bonds (such as alkenyl or alkynyl) are preferable. The hydrocarbon groups in lipid A are preferably linear or branched C8-C24 alkyl, C8-C24 alkenyl or C8-C24 alkynyl.

The hydrocarbon groups that form the hydrophobic unit may each be directly bonded to the quaternary ammonium group of the hydrophilic unit, or may be bonded to the quaternary ammonium group through an ether, ester or amide bond and optionally substituted linear and/or cyclic hydrocarbon group that composes the hydrophilic unit. In addition, as indicated in structural formulas (B) and (C), hydrocarbon groups that compose two or three hydrophobic units are bonded through carbon atoms, and those carbon atoms either bond directly with the quaternary ammonium group of the hydrophilic unit or bond with the quaternary ammonium group through an ether, ester or amide bond and optionally substituted linear and/or cyclic hydrocarbon group that composes the hydrophilic unit.

[C63]

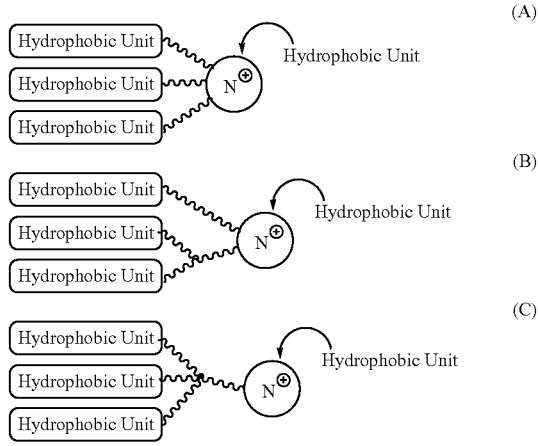

Examples of lipid A include compounds represented by:

formula (I)
[C64]

(wherein,
$R^1$ to $R^3$, the same or different, are a linear or branched, optionally substituted C8-C24 alkyl, C8-C24 alkenyl or C8-C24 alkynyl,
$L^1$ to $L^3$, the same or different, are absent or are $—Z^1—(CY^1Y^2)_{p1}—$ or $—Z^2—(CY^3Y^4)_{p2}—Z^3—(CY^5Y^6)_{p3}—$ (wherein, $Y^1$ to $Y^6$, the same or different, are a hydrogen atom or optionally substituted C1-C4 alkyl, $Z^1$ to $Z^3$, the same or different, are $—O—$, $—NY^{7A}—$, $—CO—O—$, $—O—CO—$, $—CO—NY^{7B}—$, $—NY^{7C}—CO—$ or $—NY^{7D}—CO—O—$ (wherein, $Y^{7A}$ to $Y^{7D}$, the same or different, are a hydrogen atom or optionally substituted C1-C4 alkyl), and $p^1$ to $p^3$, the same or different, are an integer of 1 to 5),
$X^1$ is an optionally substituted C1-C4 alkyl, and
$A^1$ is a pharmaceutically acceptable anion);

formula (II)
[C65]

(wherein,
$R^4$ to $R^6$, the same or different, are a linear or branched, optionally substituted C8-C24 alkyl, C8-C24 alkenyl or C8-C24 alkynyl, L⁴ to L⁶, the same or different, are absent or are —Z⁴—(CY⁸Y⁹)$_{p4}$— or —Z⁵—(CY¹⁰Y¹¹)$_{p5}$—Z⁶—(CY¹²Y¹³)$_{p6}$— (wherein, Y⁸ to Y¹³, the same or different, are a hydrogen atom or optionally substituted C1-C4 alkyl, Z⁴ to Z⁶, the same or different, are —O—, —NY¹⁴ᴬ—, —CO—O—, —O—CO—, —CO—NY¹⁴ᴮ—, —NY¹⁴ᶜ—CO— or —NY¹⁴ᴰ—CO—O— (wherein, Y¹⁴ᴬ to Y¹⁴ᴰ the same or different, are a hydrogen atom or optionally substituted C1-C4 alkyl), p⁴ is an integer of 0 to 5, p⁵ is an integer of 1 to 5, and p⁶ is an integer of 0 to 5), L⁷ is absent or is —(CY¹⁵Y¹⁶)$_{p7}$—, —(CY¹⁷Y¹⁸)$_{p8}$—Z⁷—(CY¹⁹Y²⁰)$_{p9}$— or —(CY²¹Y²²)$_{p10}$—Z⁸—(CY²³Y²⁴)$_{p11}$—Z⁹—(CY²⁵Y²⁶)$_{p12}$— (wherein, Y¹⁵ to Y²⁶, the same or different, are a hydrogen atom or optionally substituted C1-C4 alkyl, Z⁷ to Z⁹, the same or different, are —O—, —NY²⁷ᴬ—, —CO—O—, —O—CO—, —CO—NY²⁷ᴮ—, —NY²⁷ᶜ—CO— or —NY²⁷ᴰ—CO—O— (wherein, Y²⁷ᴬ to Y²⁷ᴰ, the same or different, are a hydrogen atom or optionally substituted C1-C4 alkyl), p⁷ is an integer of 1 to 5, p⁸ is an integer of 0 to 5, p⁹ is an integer of 1 to 5, p¹⁰ is an integer of 0 to 5, p¹¹ is an integer of 1 to 5, and p¹² is an integer of 1 to 5), B¹ is

[C66]

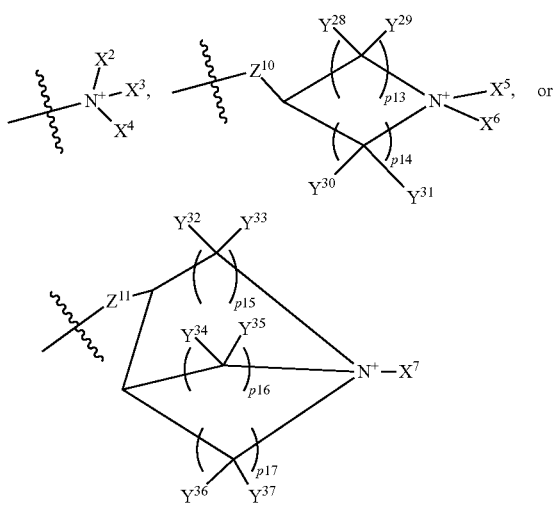

(wherein, X² and X³, the same or different, are an optionally substituted C1-C4 alkyl or are combined together to form an optionally substituted C4-C6 heterocycle with an adjacent nitrogen atom, X⁴ is an optionally substituted C1-C4 alkyl, X⁵ and X⁶, the same or different, are an optionally substituted C1-C4 alkyl or are combined together to form an optionally substituted C4-C6 heterocycle with an adjacent nitrogen atom, X⁷ is an optionally substituted C1-C4 alkyl, Y²⁸ to Y³⁷, the same or different, are a hydrogen atom or optionally substituted C1-C4 alkyl, Z¹⁰ and Z¹¹, the same or different, are —O—, —NY³⁸ᴬ—, —CO—O—, —O—CO—, —CO—NY³⁸ᴮ, —NY³⁸ᶜ—CO— or —NY³⁸ᴰ—CO—O— (wherein, Y³⁸ᴬ to Y³⁸ᴰ, the same or different, are a hydrogen atom or optionally substituted C1-C4 alkyl), p¹³ is an integer of 0 to 5, and p¹⁴ to p¹⁷, the same or different, are an integer of 1 to 5), and A² is a pharmaceutically acceptable anion);

formula (III)
[C67]

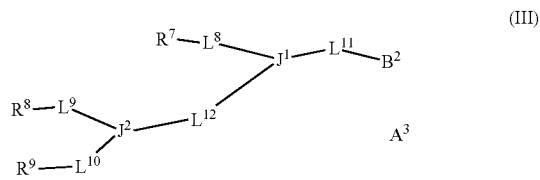

(wherein,
R⁷ to R⁹, the same or different, are a linear or branched, optionally substituted C8-C24 alkyl, C8-C24 alkenyl or C8-C24 alkynyl,
L⁸ to L¹⁰, the same or different, are absent or are —Z¹²—(CY³⁹Y⁴⁰)$_{p18}$— or —Z¹³—(CY⁴¹Y⁴²)$_{p19}$—Z¹⁴—(CY⁴³Y⁴⁴)$_{p20}$— (wherein, Y³⁹ to Y⁴⁴, the same or different, are a hydrogen atom or optionally substituted C1-C4 alkyl, Z¹² to Z¹⁴, the same or different, are —O—, —NY⁴⁵ᴬ—, —CO—O—, —O—CO—, —CO—NY⁴⁵ᴮ—, —NY⁴⁵ᶜ—CO—, NY⁴⁵ᴰ—CO—0 or —CO— (wherein, Y⁴⁵ᴬ to Y⁴⁵ᴰ, the same or different, are a hydrogen atom or optionally substituted C1-C4 alkyl), p¹⁸ is an integer of 0 to 5, p¹⁹ is an integer of 1 to 5, and p²⁰ is an integer of 0 to 5), L¹¹ is absent or is —(CY⁴⁶Y⁴⁷)$_{p21}$—, —(CY⁴⁸Y⁴⁹)$_{p22}$—Z¹⁵—(CY⁵⁰Y⁵¹)$_{p23}$— or —(CY⁵²Y⁵³)$_{p24}$—Z¹⁶—(CY⁵⁴Y⁵⁵)$_{p25}$—Z¹⁷—(CY⁵⁶Y⁵⁷)$_{p26}$— (wherein, Y⁴⁶ to Y⁵⁷, the same or different, are a hydrogen atom or optionally substituted C1-C4 alkyl, Z¹⁵ to Z¹⁷, the same or different, are —O—, —NY⁵⁸ᴬ—, —CO—O—, —O—CO—, —CO—NY⁵⁸ᴮ—, —NY⁵⁸ᶜ—CO—, NY⁵⁸ᴰ—CO—O— or —CO— (wherein, Y⁵⁸ᴬ to Y⁵⁸ᴰ, the same or different, are a hydrogen atom or optionally substituted C1-C4 alkyl), p²¹ is an integer of 1 to 5, p²² is an integer of 0 to 5, p²³ is an integer of 1 to 5, p²⁴ is an integer of 0 to 5, p²⁵ is an integer of 1 to 5, and p²⁶ is an integer of 1 to 5), L¹² is absent or is —(CY⁵⁹Y⁶⁰)$_{p27}$—, —(CY⁶¹Y⁶²)$_{p28}$—Z¹⁸—(CY⁶³CY⁶⁴)$_{p29}$— or —(CY⁶⁵Y⁶⁶)$_{p30}$—Z¹⁹—(CY⁶⁷Y⁶⁸)$_{p31}$—Z²⁰—(CY⁶⁹Y⁷⁰)$_{p32}$— (wherein, Y⁵⁹ to Y⁷⁰, the same or different, are a hydrogen atom or optionally substituted C1-C4 alkyl, Z¹⁸ to Z²⁰, the same or different, are —O—, —NY⁷¹ᴬ—, —CO—O—, —O—CO—, —CO—NY⁷¹ᴮ—, —NY⁷¹ᶜ—CO—, —NY⁷¹ᴰ—CO—O— or —CO— (wherein, Y⁷¹ᴬ to Y⁷¹ᴰ, the same or different, are a hydrogen atom or optionally substituted C1-C4 alkyl), p²⁷ is an integer of 1 to 5, p²⁸ is an integer of 0 to 5, p²⁹ is an integer of 0 to 5, p³⁰ is an integer of 0 to 5, p³¹ is an integer of 1 to 5, and p³² is an integer of 0 to 5), J¹ and J², the same or different, are CY⁷² or N (wherein, Y⁷² is a hydrogen atom, hydroxyl, optionally substituted C1-C4 alkyl, optionally substituted C1-C4 alkoxy or optionally substituted C1-C4 acyloxy group), B² is

[C68]

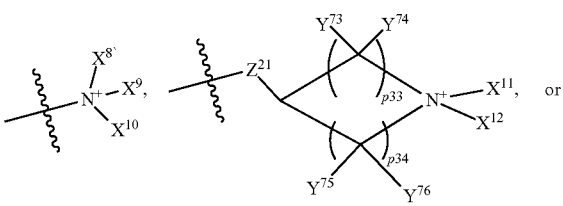

-continued

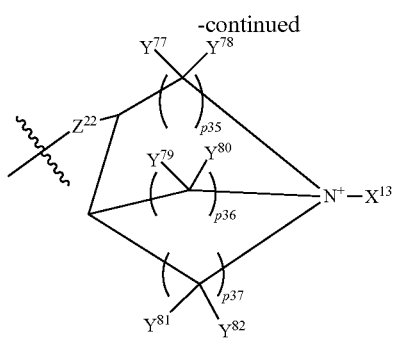

(wherein, $X^8$ and $X^9$, the same or different, are an optionally substituted C1-C4 alkyl or are combined together to form an optionally substituted C4-C6 heterocycle with an adjacent nitrogen atom, $X^{10}$ is an optionally substituted C1-C4 alkyl, $X^{11}$ and $X^{12}$, the same or different, are an optionally substituted C1-C4 alkyl or are combined together to form an optionally substituted C4-C6 heterocycle with an adjacent nitrogen atom, $X^{13}$ is an optionally substituted C1-C4 alkyl, $Y^{73}$ to $Y^{82}$, the same or different, are a hydrogen atom or optionally substituted C1-C4 alkyl, $Z^{21}$ and $Z^{22}$, the same or different, are —O—, —NY$^{83A}$—, —CO—O—, —O—CO—, —CO—NY$^{83B}$, —NY$^{83C}$—CO— or —NY$^{83D}$—CO—O— (wherein, $Y^{83A}$ to $Y^{83D}$, the same or different, are a hydrogen atom or optionally substituted C1-C4 alkyl), $p^{33}$ is an integer of 0 to 5, and $p^{34}$ to $p^{37}$, the same or different, are an integer of 1 to 5), and $A^3$ is a pharmaceutically acceptable anion);

formula (IV)

[C69]

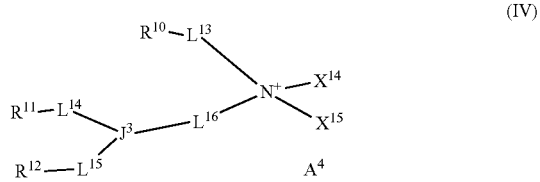

(IV)

(wherein, $R^{10}$ to $R^{12}$, the same or different, are a linear or branched, optionally substituted C8-C24 alkyl, C8-C24 alkenyl or C8-C24 alkynyl, $L^{13}$ is absent or is —Z$^{23}$—(CY$^{83}$Y$^{84}$)$_{p38}$— or —Z$^{24}$—(CY$^{85}$Y$^{86}$)$_{p39}$—Z$^{25}$—(CY$^{87}$Y$^{88}$)$_{p40}$— (wherein, $Y^{83}$ to $Y^{88}$, the same or different, are a hydrogen atom or optionally substituted C1-C4 alkyl, $Z^{23}$ to $Z^{25}$, the same or different, are —O—, —NY$^{89A}$—, —CO—O—, —O—CO—, —CO—NY$^{89B}$—, —NY$^{89C}$—CO— or —NY$^{89D}$—CO—O— (wherein, $Y^{89A}$ to $Y^{89D}$, the same or different, are a hydrogen atom or optionally substituted C1-C4 alkyl), and $p^{38}$ to $p^{40}$, the same or different, are an integer of 1 to 5), $L^{14}$ and $L^{15}$, the same or different, are absent or are —Z$^{26}$—(CY$^{90}$Y$^{91}$)$_{p41}$— or —Z$^{27}$—(CY$^{92}$Y$^{93}$)$_{p42}$—Z$^{28}$—(CY$^{94}$Y$^{95}$)$_{p43}$— (wherein, $Y^{90}$ to $Y^{95}$, the same or different, are a hydrogen atom or optionally substituted C1-C4 alkyl, $Z^{26}$ to $Z^{28}$, the same or different, are —O—, —NY$^{96A}$—, —CO—O—, —O—CO—, —CO—NY$^{96B}$—, —NY$^{96C}$—CO—, —NY$^{96D}$—CO—O— or —CO— (wherein, $Y^{96A}$ to $Y^{96D}$, the same or different, are a hydrogen atom or optionally substituted C1-C4 alkyl), $p^{41}$ is an integer of 0 to 5, $p^{42}$ is an integer of 1 to 5, and $p^{43}$ is an integer of 0 to 5), $L^{16}$ is absent or is —(CY$^{97}$Y$^{98}$)$_{p44}$—, —(CY$^{99}$Y$^{100}$)$_{p45}$—Z$^{29}$—(CY$^{101}$Y$^{102}$)$_{p46}$— or —(CY$^{103}$Y$^{104}$)$_{p47}$—Z$^{30}$—(CY$^{105}$Y$^{106}$)$_{p48}$—Z$^{31}$—(CY$^{107}$Y$^{108}$)$_{p49}$— (wherein, $Y^{97}$ to $Y^{108}$, the same or different, are a hydrogen atom or optionally substituted C1-C4 alkyl, $Z^{29}$ to $Z^{31}$, the same or different, are —O—, —NY$^{109A}$—, —CO—O—, —O—CO—, —CO—NY$^{109B}$—, —NY$^{109C}$—CO—, —NY$^{109D}$—CO—O— or —CO— (wherein, $Y^{109A}$ to $Y^{109D}$, the same or different, are a hydrogen atom or optionally substituted C1-C4 alkyl), $p^{44}$ is an integer of 1 to 5, $p^{45}$ is an integer of 0 to 5, $p^{46}$ is an integer of 1 to 5, $p^{47}$ is an integer of 0 to 5, $p^{48}$ is an integer of 1 to 5, and $p^{49}$ is an integer of 1 to 5), $J^3$ is CY$^{110}$ or N (wherein, $Y^{110}$ is a hydrogen atom, hydroxyl, optionally substituted C1-C4 alkyl, optionally substituted C1-C4 alkoxy or optionally substituted C1-C4 acyloxy group), $X^{14}$ and $X^{15}$, the same or different, are an optionally substituted C1-C4 alkyl or are combined together to form an optionally substituted C4-C6 heterocycle with an adjacent nitrogen atom, and $A^4$ is a pharmaceutically acceptable anion); or formula (V') or formula (V")

[C70]

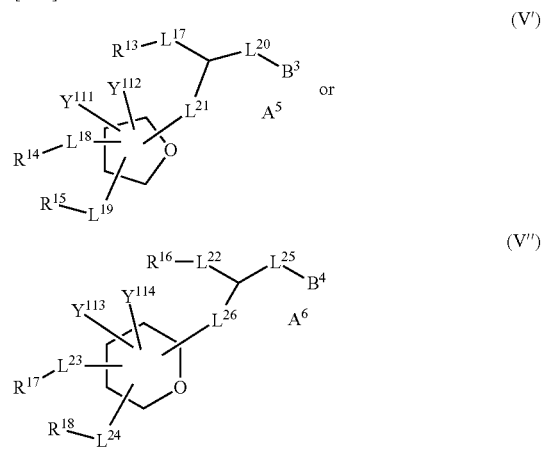

(wherein, $R^{13}$ to $R^{18}$, the same or different, are a linear or branched, optionally substituted C8-C24 alkyl, C8-C24 alkenyl or C8-C24 alkynyl, $Y^{111}$ to $Y^{114}$, the same or different, are a hydrogen atom, hydroxyl or optionally substituted C1-C4 alkyl, $L^{17}$ to $L^{19}$ and $L^{22}$ to $L^{24}$, the same or different, are absent or are —Z$^{32}$—(CY$^{115}$Y$^{116}$)$_{p51}$— or —Z$^{33}$—(CY$^{117}$Y$^{118}$)$_{p52}$—Z$^{34}$—(CY$^{119}$Y$^{120}$)$_{p53}$— (wherein, $Y^{115}$ to $Y^{120}$, the same or different, are a hydrogen atom or optionally substituted C1-C4 alkyl, $Z^{32}$ to $Z^{34}$, the same or different, are —O—, —NY$^{121A}$—, —CO—O—, —O—CO—, —CO—NY$^{121B}$—, —NY$^{121C}$—CO—, —NY$^{121D}$—CO—0 or —CO— (wherein, $Y^{121A}$ to $Y^{121D}$, the same or different, are a hydrogen atom or optionally substituted C1-C4 alkyl), $p^{51}$ is an integer of 0 to 5, $p^{52}$ is an integer of 1 to 5, and $p^{53}$ is an integer of 0 to 5), $L^{20}$ and $L^{25}$, the same or different, are absent or are —(CY$^{122}$Y$^{123}$)$_{p54}$—, —(CY$^{124}$Y$^{125}$)$_{p55}$—Z$^{35}$—(CY$^{126}$Y$^{127}$)$_{p56}$— or —(CY$^{128}$Y$^{129}$)$_{p57}$—Z$^{36}$—(CY$^{130}$Y$^{131}$)$_{p58}$—Z$^{37}$—(CY$^{132}$Y$^{133}$)$_{p59}$— (wherein, $Y^{122}$ to $Y^{133}$, the same or different, are a hydrogen atom or optionally substituted C1-C4 alkyl, $Z^{35}$ to $Z^{37}$, the same or different, are —O—, —NY$^{134A}$—, —CO—O—, —O—CO—, —CO—NY$^{134B}$—, —NY$^{134C}$—CO—, —NY$^{134D}$—CO—O— or —CO— (wherein, Y$^{134A}$ to Y$^{134D}$, the same or different, are a hydrogen atom or optionally substituted C1-C4 alkyl), $p^{54}$ is an integer of 1 to 5, $p^{55}$ is an integer of 0 to 5, $p^{56}$ is an integer of 1 to 5, $p^{57}$ is an integer of 0 to 5, $p^{58}$ is an integer of 1 to 5 and $p^{59}$ is an integer of 1 to 5), L$^{21}$ and L$^{26}$, the same or different, are absent or are —(CY$^{135}$Y$^{136}$)$_{p60}$—, —(CY$^{137}$Y$^{138}$)$_{p61}$—Z$^{38}$—(CY$^{139}$Y$^{140}$)$_{p62}$— or —(CY$^{141}$Y$^{142}$)$_{p63}$—Z$^{39}$—(CY$^{143}$Y$^{144}$)$_{p64}$—Z$^{40}$—(CY$^{145}$Y$^{146}$)$_{p65}$— (wherein, Y$^{135}$ to Y$^{146}$, the same or different, are a hydrogen atom or optionally substituted C1-C4 alkyl, Z$^{38}$ to Z$^{40}$, the same or different, are —O—, —NY$^{147A}$—, —CO—O—, —O—CO—, —CO—NY$^{147B}$—, —NY$^{147C}$—CO—, —NY$^{147D}$—CO—O— or —CO— (wherein, Y$^{147A}$ to Y$^{147D}$, the same or different, are a hydrogen atom or optionally substituted C1-C4 alkyl), $p^{60}$ is an integer of 1 to 5, $p^{61}$ is an integer of 0 to 5, $p^{62}$ is an integer of 0 to 5, $p^{63}$ is an integer of 0 to 5, $p^{64}$ is an integer of 1 to 5, and $p^{65}$ is an integer of 0 to 5), B$^3$ and B$^4$, the same or different, are

[C71]

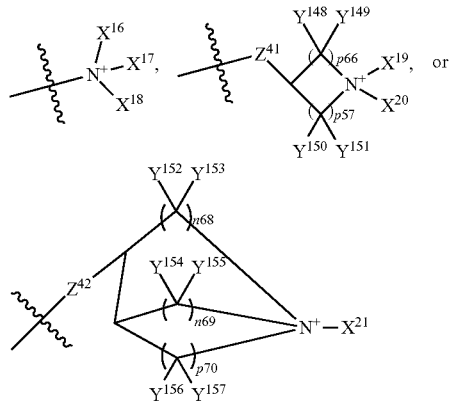

(wherein, X$^{16}$ and X$^{17}$, the same or different, are an optionally substituted C1-C4 alkyl or are combined together to form an optionally substituted C4-C6 heterocycle with an adjacent nitrogen atom, X$^{18}$ is an optionally substituted C1-C4 alkyl, X$^{19}$ and X$^{20}$, the same or different, are an optionally substituted C1-C4 alkyl or are combined together to form an optionally substituted C4-C6 heterocycle with an adjacent nitrogen atom, X$^{21}$ is an optionally substituted C1-C4 alkyl, Y$^{148}$ to Y$^{157}$, the same or different, are a hydrogen atom or optionally substituted C1-C4 alkyl, Z$^{41}$ and Z$^{42}$, the same or different, are —O—, —NY$^{158A}$—, —CO—O—, —O—CO—, —CO—NY$^{158B}$—, —NY$^{158C}$—CO— or —NY$^{158D}$—CO—O— (wherein, Y$^{158A}$ to Y$^{158D}$, the same or different, are a hydrogen atom or optionally substituted C1-C4 alkyl), $p^{66}$ is an integer of 0 to 5, and $p^{67}$ to $p^{70}$, the same or different, are an integer of 1 to 5), and A$^5$ and A$^6$, the same or different, are a pharmaceutically acceptable anion).

Compounds represented by formulas (I) to (IV), (V') and (V'') are hereinafter also referred to as Compounds (I) to (IV), (V') and (V''), respectively. This applies similarly to compounds of other formula numbers as well.

The following provides an explanation of the definitions of each of the groups in formulas (I) to (V'').

Examples of linear or branched C8-C24 alkyl include octyl, nonyl, decyl, undecyl, dodecyl, tridecyl, tetradecyl, 2,6,10-trimethylundecyl, pentadecyl, 3,7,11-trimethyldodecyl, hexadecyl, heptadecyl, octadecyl, 6,10,14-trimethylpentadcan-2-yl, nonadecyl, 2,6,10,14-tetramethylpentadecyl, icosyl, 3,7,11,15-tetramethylhexadecyl, henicosyl, docosyl, tricosyl and tetracosyl, preferably include nonyl, decyl, undecyl, dodecyl, tridecyl, tetradecyl, pentadecyl, hexadecyl, heptadecyl and octadecyl, and more preferably include undecyl, dodecyl, tridecyl, tetradecyl, pentadecyl and hexadecyl.

Examples of linear or branched C9-C18 alkyl include nonyl, decyl, undecyl, dodecyl, tridecyl, tetradecyl, 2,6,10-trimethylundecyl, pentadecyl, 3,7,11-trimethyldodecyl, hexadecyl, heptadecyl, octadecyl and 6,10,14-trimethylpentadcan-2-yl, preferably include nonyl, decyl, undecyl, dodecyl, tridecyl, tetradecyl, pentadecyl, hexadecyl, heptadecyl and octadecyl, and more preferably include undecyl, dodecyl, tridecyl, tetradecyl, pentadecyl and hexadecyl.

Linear or branched C8-C24 alkenyl refer to linear or branched C8-C24 alkenyl containing 1 to 3 double bonds, examples of which include (Z)-tridec-8-enyl, (Z)-tetradec-9-enyl, (Z)-pentadec-8-enyl, (Z)-hexadec-9-enyl, (Z)-heptadec-5-enyl, (Z)-octadec-6-enyl, (Z)-heptadec-8-enyl, (Z)-octadec-9-enyl, (E)-heptadec-8-enyl, (E)-octadec-9-enyl, (Z)-heptadec-10-enyl, (Z)-octadec-11-enyl, (8Z,11Z)-heptadeca-8,11-dienyl, (9Z,12Z)-octadeca-9,12-dienyl, (8Z,11Z,14Z)-octadeca-8,11,14-trienyl, (9Z,12Z,15Z)-octadeca-9,12,15-trienyl, (Z)-nonadec-10-enyl, (Z)-icos-11-enyl, (10Z,13Z)-nonadeca-10,13-dienyl, (11Z,14Z)-icosa-11,14-dienyl, 2,6,10-trimethylundeca-1,5,9-trienyl, 3,7,11-trimethyldodeca-2,6,10-trienyl, 2,6,10,14-tetramethylpentadec-1-enyl and 3,7,11,15-tetramethylhexadec-2-enyl, preferably include (Z)-pentadec-8-enyl, (Z)-hexadec-9-enyl, (Z)-heptadec-5-enyl, (Z)-octadec-6-enyl, (Z)-heptadec-8-enyl, (Z)-octadec-9-enyl, (8Z,11Z)-heptadeca-8,11-dienyl and (9Z,12Z)-octadeca-9,12-dienyl, and more preferably include (Z)-heptadec-8-enyl, (Z)-octadec-9-enyl, (8Z,11Z)-heptadeca-8,11-dienyl and (9Z,12Z)-octadeca-9,12-dienyl.

Examples of linear or branched C15-C20 alkenyl include (Z)-pentadec-8-enyl, (Z)-hexadec-9-enyl, (Z)-heptadec-5-enyl, (Z)-octadec-6-enyl, (Z)-heptadec-8-enyl, (Z)-octadec-9-enyl, (E)-heptadec-8-enyl, (E)-octadec-9-enyl, (Z)-heptadec-10-enyl, (Z)-octadec-11-enyl, (8Z,11Z)-heptadeca-8,11-dienyl, (9Z,12Z)-octadeca-9,12-dienyl, (8Z,11Z,14Z)-octadeca-8,11,14-trienyl, (9Z,12Z,15Z)-octadeca-9,12,15-trienyl, (Z)-nonadec-10-enyl, (Z)-icos-11-enyl, (10Z,13Z)-nonadeca-10,13-dienyl, (11Z,14Z)-icosa-11,14-dienyl and 3,7,11,15-tetramethylhexadec-2-enyl, preferably include (Z)-pentadec-8-enyl, (Z)-hexadec-9-enyl, (Z)-heptadec-5-enyl, (Z)-octadec-6-enyl, (Z)-heptadec-8-enyl, (Z)-octadec-9-enyl, (8Z,11Z)-heptadeca-8,11-dienyl and (9Z,12Z)-octadeca-9,12-dienyl, and more preferably include (Z)-heptadec-8-enyl, (Z)-octadec-9-enyl, (8Z,11Z)-heptadeca-8,11-dienyl and (9Z,12Z)-octadeca-9,12-dienyl.

In addition, in the present invention, groups having a cyclopropane ring formed by formally adding a methylene biradical to the double bond of a linear or branched, optionally substituted C8-C24 alkenyl are also included in C8-C24 alkenyl. Examples thereof include the following cyclopropane rings corresponding to (Z)-hexadec-9-enyl, (9Z,12Z)-octadeca-9,12-dienyl and (8Z,11Z)-heptadeca-8,11-dienyl.

[C72]

[C73]

[C74]

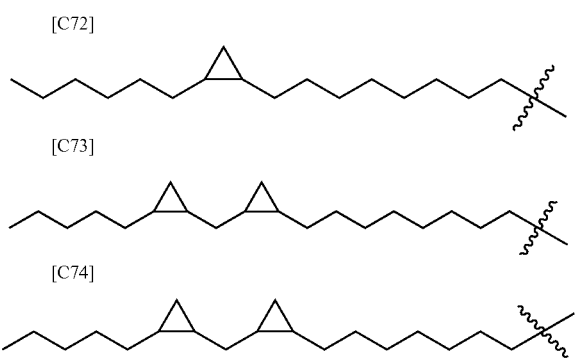

Linear or branched C8-C24 alkynyl refer to linear or branched C8-C24 alkynyl containing 1 to 3 triple bonds, and examples thereof include dodec-11-ynyl, tridec-12-ynyl, pentadec-6-ynyl, hexadec-7-ynyl, pentadeca-4,6-diynyl, hexadeca-5,7-diynyl, heptadec-8-ynyl and octadec-9-ynyl, preferably include pentadec-6-ynyl, hexadec-7-ynyl, pentadeca-4,6-diynyl, hexadeca-5,7-diynyl, heptadec-8-ynyl and octadec-9-ynyl, and more preferably include heptadec-8-ynyl and octadec-9-ynyl.

Examples of C1-C4 alkyl include methyl, ethyl, propyl, isopropyl, cyclopropyl, butyl, isobutyl, sec-butyl, tert-butyl, cyclobutyl and cyclopropylmethyl, preferably include methyl and ethyl, and more preferably include methyl.

The alkyl moiety of an optionally substituted C1-C4 alkoxy group has the same meaning as the above-mentioned C1-C4 alkyl.

Examples of substituents in linear or branched, optionally substituted C8-C24 alkyl, C8-C24 alkenyl and C8-C24 alkynyl include hydroxyl, alkoxy, alkoxycarbonyl, nitro, cyano, fluoro, chloro and bromo groups. In these substituents, the alkyl moiety in an alkoxy group or alkoxycarbonyl has the same meaning as the above-mentioned C1-C4 alkyl.

Examples of substituents in optionally substituted C1-C4 alkyl include amino, monoalkylamino, dialkylamino, pyrrolidin-2-yl, pyrrolidin-3-yl, piperidin-2-yl, piperidin-3-yl, piperidin-4-yl, morpholin-2-yl, morpholin-3-yl, hydroxyl, alkoxy, alkoxycarbonyl, hydroxycarbonyl, carbamoyl, monoalkylcarbamoyl, dialkylcarbamoyl, nitro, cyano, fluoro, chloro and bromo groups. In these substituents, the alkyl moiety in the monoalkylamino, dialkylamino, alkoxy, alkoxycarbonyl, monoalkylcarbamoyl and dialkylcarbamoyl has the same meaning as the above-mentioned C1-C4 alkyl. The two alkyl in dialkylamino or dialkylcarbamoyl may be the same or different.

In the present invention, pyrrolidin-2-yl, pyrrolidin-3-yl, piperidin-2-yl, piperidin-3-yl, piperidin-4-yl, morpholin-2-yl and morpholin-3-yl respectively include those in which a C1-C3 alkyl such as a methyl or ethyl is bonded to a nitrogen atom in the ring.

Examples of C1-C3 alkyl include methyl, ethyl, propyl, isopropyl and cyclopropyl, preferably include methyl and ethyl, and more preferably include a methyl.

Examples of C4-C6 heterocycle formed by $X^2$ and $X^3$ with an adjacent nitrogen atom include pyrrolidine, piperidine, morpholine and azepane, and preferably include pyrrolidine and piperidine. Examples of substituents in optionally substituted C4-C6 heterocycle formed by $X^2$ and $X^3$ with an adjacent nitrogen atom include optionally substituted C1-C4 alkyl (same as previously defined), amino, monoalkylamino, dialkylamino, pyrrolidin-2-yl, pyrrolidin-3-yl, piperidin-2-yl, piperidin-3-yl, piperidin-4-yl, morpholin-2-yl, morpholin-3-yl, hydroxyl, alkoxy, alkoxycarbonyl, hydroxycarbonyl, carbamoyl, monoalkylcarbamoyl, dialkylcarbamoyl, nitro, cyano, fluoro, chloro and bromo groups. In these substituents, the alkyl moiety in the monoalkylamino, dialkylamino, alkoxy, alkoxycarbonyl, monoalkylcarbamoyl and dialkylcarbamoyl has the same meaning as the above-mentioned C1-C4 alkyl. The two alkyl in dialkylamino groups or dialkylcarbamoyl may be the same or different.

The heterocyclic moiety and substituents of optionally substituted C4-C6 heterocycle formed by $X^5$ and $X^6$ with an adjacent nitrogen atom are each the same as previously defined.

The heterocyclic moiety and substituents of optionally substituted C4-C6 heterocycle formed by $X^8$ and $X^9$ with an adjacent nitrogen atom are each the same as previously defined.

The heterocyclic moiety and substituents of optionally substituted C4-C6 heterocycle formed by $X^{11}$ and $X^{12}$ with an adjacent nitrogen atom are each the same as previously defined.

The heterocyclic moiety and substituents of optionally substituted C4-C6 heterocycle formed by $X^{14}$ and $X^{15}$ with an adjacent nitrogen atom are each the same as previously defined.

The heterocyclic moiety and substituents of optionally substituted C4-C6 heterocycle formed by $X^{16}$ and $X^{17}$ with an adjacent nitrogen atom are each the same as previously defined.

The heterocyclic moiety and substituents of optionally substituted C4-C6 heterocycle formed by $X^{19}$ and $X^{20}$ with an adjacent nitrogen atom are each the same as previously defined.

Examples of the acyl in C1-C4 acyloxy include formyl, acetyl, propanoyl, 2-methylpropanoyl, cyclopropanoyl and butanoyls, and preferably include acetyl.

Examples of substituents in optionally substituted C1-C4 acyloxy include amino, monoalkylamino, dialkylamino, pyrrolidin-2-yl, pyrrolidin-3-yl, piperidin-2-yl, piperidin-3-yl, piperidin-4-yl, morpholin-2-yl, morpholin-3-yl, hydroxyl, alkoxy, alkoxycarbonyl, hydroxycarbonyl, carbamoyl, monoalkylcarbamoyl, dialkylcarbamoyl, nitro, cyano, fluoro, chloro and bromo groups. In these substituents, the alkyl moiety in the monoalkylamino, dialkylamino, alkoxy, alkoxycarbonyl, monoalkylcarbamoyl and dialkylcarbamoyl has the same meaning as the above-mentioned C1-C4 alkyl. The two alkyl in dialkylamino groups and dialkylcarbamoyl may be the same or different.

A quaternary ammonium group refers to a group that has a nitrogen atom having four covalent bonds with four carbon atoms. A quaternary ammonium group differs from a group in which hydrogen atoms have been added to primary to tertiary amines in that it has a permanent positive charge regardless of the surrounding pH.

Examples of pharmaceutically acceptable anions include, but are not limited to, inorganic ions such as chloride ions, bromide ions, iodide ions, nitrate ions, sulfate ions or phosphate ions, and organic acid ions such as acetate ions, oxalate ions, maleate ions, fumarate ions, citrate ions, benzoate ions or methanesulfonate ions.

In formula (I), $R^1$ to $R^3$ are preferably the same and are linear or branched C8-C24 alkyl, C8-C24 alkenyl or C8-C24 alkynyl, are more preferably the same and are linear or branched C8-C24 alkyl or C8-C24 alkenyl, are even more preferably the same and are linear or branched C15-C20 alkenyl or are the same and are linear or branched C9-C18 alkyl, and are most preferably the same and are linear C15-C20 alkenyl or are the same and are linear C9-C18 alkyl.

$L^1$ to $L^3$ are preferably the same or different and are absent or are —$Z^1$—$(CY^1Y^2)_{p1}$— or —$Z^2$—$(CY^3Y^4)_{p2}$—$Z^3$—$(CY^5Y^6)_{p3}$—, and preferably are —$Z^1$—$(CY^1Y^2)_{p1}$—. $Y^1$ to $Y^6$ are preferably the same or different and are a hydrogen atom or optionally substituted C1-C4 alkyl, and $Y^1$ to $Y^6$ preferably are hydrogen atoms. $Z^1$ to $Z^3$, the same or different, are —O—, —$NY^{7A}$—, —CO—O—, —O—CO—, —CO—$NY^{7B}$—, —$NY^{7C}$—CO— or —$NY^{7D}$—CO—O—, and preferably are —O—, —CO—O—, —O—CO—, —CO—$NY^{7B}$— or —$NY^{7C}$—CO—. $Y^{7A}$ to $Y^{7D}$, the same or different, are a hydrogen atom or optionally substituted C1-C4 alkyl, and preferably are a hydrogen atom or methyl, $p^1$ to $p^3$, the same or different, are an integer of 1 to 5, and preferably are 1 or 2.

$L^1$ to $L^3$ are preferably the same or different and are —O—$(CY^1Y^2)_{p1}$—, —CO—O—$(CY^1Y^2)_{p1}$—, —O—CO—$(CY^1Y^2)_{p1}$—, —CO—$NY^{7B}$—$(CY^1Y^2)_{p1}$— or —$NY^{7C}$—CO—$(CY^1Y^2)_{p1}$—, more preferably the same or different and are —CO—O—$(CY^1Y^2)_{p1}$— or —O—CO—$(CY^1Y^2)_{p1}$—, and even more preferably the same and are —CO—O—$(CH_2)_2$—.

In formula (I), at least one of $L^1$ to $L^3$ is preferably the same or different and is —CO—O—$(CY^1Y^2)_{p1}$— or —O—CO—$(CY^1Y^2)_{p1}$—, and $R^1$ to $R^3$ are preferably the same and are linear C15-C20 alkenyl or are preferably the same and are linear C9 to C18 alkyl.

In the case at least one of $L^1$ to $L^3$ is —O—$(CY^1Y^2)_{p1}$—, —O—CO—$(CY^1Y^2)_{p1}$— or —$NY^{7C}$—CO—$(CY^1Y^2)_{p1}$—, $R^1$ to $R^3$ bound to a nitrogen atom ($N^+$) having a positive charge, —O—$(CY^1Y^2)_{p1}$—, —O—CO—$(CY^1Y^2)_{p1}$— or —$NR^6$—CO—$(CY^1Y^2)_{p1}$— are more preferably the same and are an octyl, decyl, dodecyl, tetradecyl, hexadecyl, octadecyl, icosyl, docosyl, tetracosyl, (Z)-tetradec-9-enyl, (Z)-hexadec-9-enyl, (Z)-octadec-6-enyl, (Z)-octadec-9-enyl, (E) octadec-9-enyl, (Z)-octadec-11-enyl, (9Z,12Z)-octadeca-9,12-dienyl, (9Z,12Z,15Z)-octadeca-9,12,15-trienyl, (Z)-icos-11-enyl, (11Z,14Z)-icosa-11,14-dienyl, 3,7,11-trimethyldodeca-2,6,10-trienyl or 3,7,11,15-tetramethylhexadec-2-enyl, and even more preferably are a dodecyl, tetradecyl, hexadecyl, (Z)-hexadec-9-enyl, (Z)-octadec-6-enyl, (Z)-octadec-9-enyl or (9Z,12Z)-octadeca-9,12-dienyl.

In the case of at least one of $L^1$ to $L^3$ is —CO—O—$(CY^1Y^2)_{p1}$— or —CO—$NY^{7B}$—CO—$(CY^1Y^2)_{p1}$—, $R^1$ to $R^3$ bound to —CO—O—$(CY^1Y^2)_{p1}$— or —CO—$NY^{7B}$—$(CY^1Y^2)_{p1}$— are more preferably the same or different and are a nonyl, undecyl, tridecyl, pentadecyl, heptadecyl, nonadecyl, henicosyl, tricosyl, (Z)-tridec-8-enyl, (Z)-pentadec-8-enyl, (Z)-heptadec-5-enyl, (Z)-heptadec-8-enyl, (E)-heptadec-8-enyl, (Z)-heptadec-10-enyl, (8Z,11Z)-heptadeca-8,11-dienyl, (8Z,11Z,14Z)-octadeca-8,11,14-trienyl, (Z)-nonadec-10-enyl, (10Z,13Z)-nonadeca-10,13-dienyl, (11Z,14Z)-icosa-11,14-dienyl, 2,6,10-trimethylundeca-1,5,9-trienyl or 2,6,10,14-tetramethylpentadec-1-enyl, and even more preferably are an undecyl, tridecyl, pentadecyl, (Z)-pentadec-8-enyl, (Z)-heptadec-5-enyl, (Z)-heptadec-8-enyl or (8Z,11Z)-heptadeca-8,11-dienyl.

$X^1$ preferably is a methyl, hydroxypropyl or hydroxyethyl, and more preferably is a methyl.

In formula (II), $R^4$ to $R^6$ are preferably the same and are linear or branched C8-C24 alkyl, C8-C24 alkenyl or C8-C24 alkynyl, are more preferably the same and are linear or branched C8-C24 alkyl or C8-C24 alkenyl, are even more preferably the same and are linear or branched C15-C20 alkenyl or C9-C18 alkyl, and are most preferably the same and are linear C15-C20 alkenyl or are the same and are linear C9-C18 alkyl.

$L^4$ to $L^6$, the same or different, are absent or are —$Z^4$—$(CY^8Y^9)_{p4}$— or —$Z^5$—$(CY^{10}Y^{11})_{p5}$—$Z^6$—$(CY^{12}Y^{13})_{p6}$—, preferably are —$Z^4$—$(CY^8Y^9)_{p4}$— or —$Z^5$—$(CY^{10}Y^{11})_{p5}$—$Z^6$—$(CY^{12}Y^{13})_{p6}$—, and more preferably are —$Z^4$—$(CY^8Y^9)_{p4}$—. $Y^8$ to $Y^{13}$, the same or different, are a hydrogen atom or optionally substituted C1-C4 alkyl, and $Y^8$ to $Y^{13}$ preferably are a hydrogen atom. $Z^4$ to $Z^6$, the same or different, are —O—, —$NY^{14A}$—, —CO—O—, —O—CO—, —CO—$NY^{14B}$—, —$NY^{14C}$—CO— or —$NY^{14D}$—CO—O—, and preferably are —O—, —CO—O—, —O—CO—, —CO—$NY^{14B}$— or —$NY^{14C}$—CO—. $Y^{27A}$ to $Y^{27D}$, the same or different, are a hydrogen atom or optionally substituted C1-C4 alkyl, and preferably are a hydrogen atom or methyl, $p^4$ is an integer of 0 to 5, $p^5$ is an integer of 1 to 5, and $p^6$ is an integer of 0 to 5, and each of these preferably is 1 or 2.

$L^4$ to $L^6$ are preferably the same or different and are —O—$(CY^8Y^9)_{p4}$—, —CO—O—$(CY^8Y^9)_{p4}$—, —O—CO—$(CY^8Y^9)_{p4}$—, —CO—$NY^{14B}$—$(CY^8Y^9)_{p4}$—, —$NY^{14C}$—CO—$(CY^8Y^9)_{p4}$—, —$NY^{14D}$—CO—O—$(CY^8Y^9)_{p4}$— or —O—CO—$(CY^{10}Y^{11})_{p5}$—$Z^6$—$(CY^{12}Y^{13})_{p6}$—, are more preferably the same or different and are —CO—O—$(CY^8Y^9)_{p4}$—, —O—CO—$(CY^8Y^9)_{p4}$—, or —O—CO—$(CY^{10}Y^{11})_{p5}$—O—$(CY^{12}Y^{13})_{p6}$—, and are even more preferably the same and are —CO—O—$CH_2$—.

In formula (II), preferably at least one of $L^4$ to $L^6$, the same or different, are —CO—O—$(CY^8Y^9)_{p4}$—, —O—CO—$(CY^8Y^9)_{p4}$— or —O—CO—$(CY^{10}Y^{11})_{p5}$—O—$(CY^{12}Y^{13})_{p6}$—, and $R^4$ to $R^6$, preferably the same or different, are a linear C15-C20 alkenyl or are the same and are C9-C18 alkyl.

In the case at least one of $L^4$ to $L^6$ is absent or is —O—$(CY^8Y^9)_{p4}$—, —O—CO—$(CY^8Y^9)_{p4}$—, —$NY^{14C}$—CO—$(CY^8Y^9)_{p4}$—, —$NY^{14D}$—CO—O— or —O—CO—$(CY^{10}Y^{11})_{p5}$—O—$(CY^{12}Y^{13})_{p6}$—, $R^7$ to $R^9$ bound to a carbon atom adjacent to $L^7$, —O—$(CY^8Y^9)_{p4}$—, —O—CO—$(CY^8Y^9)_{p4}$—, —$NY^{14C}$—CO—$(CY^8Y^9)_{p4}$—, —$NY^{14D}$—CO—O— or —O—CO—$(CY^{10}Y^{11})_{p5}$—$Z^6$—$(CY^{12}Y^{13})_{p6}$— are preferably the same or different and respectively are an octyl, decyl, dodecyl, tetradecyl, hexadecyl, octadecyl, icosyl, docosyl, tetracosyl, (Z)-tetradec-9-enyl, (Z)-hexadec-9-enyl, (Z)-octadec-6-enyl, (Z)-octadec-9-enyl, (E)-octadec-9-enyl, (Z)-octadec-11-enyl, (9Z,12Z)-octadeca-9,12-dienyl, (9Z,12Z,15Z)-octadeca-9,12,15-trienyl, (Z)-icos-11-enyl, (11Z,14Z)-icosa-11,14-dienyl, 3,7,11-trimethyldodeca-2,6,10-trienyl or 3,7,11,15-tetramethylhexadec-2-enyl, and more preferably are a dodecyl, tetradecyl, hexadecyl, (Z)-hexadec-9-enyl, (Z)-octadec-6-enyl, (Z)-octadec-9-enyl or (9Z,12Z)-octadeca-9,12-dienyl.

In the case at least one of $L^4$ to $L^6$ is —CO—O—$(CY^8Y^9)_{p4}$— or —CO—$NY^{14B}$—$(CY^8Y^9)_{p4}$—, $R^4$ to $R^6$ bound to —CO—O—$(CY^8Y^9)_{p4}$— or —CO—$NY^{14B}$—$(CY^8Y^9)_{p4}$— are preferably the same or different and respectively are a nonyl, undecyl, tridecyl, pentadecyl, heptadecyl, nonadecyl, henicosyl, tricosyl, (Z)-tridec-8-enyl, (Z)-pentadec-8-enyl, (Z)-heptadec-5-enyl, (Z)-heptadec-8-enyl, (E)-hepadec-8-enyl, (Z)-heptadec-10-enyl, (8Z,11Z)-heptadeca-8,11-dienyl, (8Z,11Z,14Z)-octadeca-8,11,14-trienyl, (Z)-nonadec-10-enyl, (10Z,13Z)-nonadeca-10,13-dienyl, (11Z,14Z)-icosa-11,14-dienyl, 2,6,10-trimethylundeca-1,5,9-trienyl or 2,6,10,14-tetramethylpentadec-1-enyl, and more preferably are an undecyl, tridecyl, pentadecyl, (Z)-pentadec-8-enyl, (Z)-heptadec-5-enyl, (Z)-heptadec-8-enyl or (8Z,11Z)-heptadeca-8,11-dienyl.

$L^7$ is preferably absent or is —$(CY^{15}Y^{16})_{p7}$—, —$(CY^{17}Y^{18})_{p8}$—O—CO—$(CY^{19}Y^{20})_{p9}$— or —$(CY^{17}Y^{18})_{p8}$—$NY^{27C}$—CO—$(CY^{19}Y^{20})_{p9}$—, and is more preferably absent or is —$(CY^{15}Y^{16})_{p7}$—. In this case, $B^1$ preferably is:

[C75]

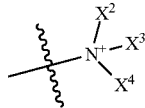

and more preferably is —$N^+(CH_3)_3$.

In the case $L^7$ is —$(CY^{15}Y^{16})_{p7}$—, $p^7$ is preferably 1 to 3, more preferably 1 to 2 and even more preferably 1, and $Y^{15}$ to $Y^{16}$ preferably respectively are a hydrogen atom. $B^1$ preferably is —$N^+(CH_3)_3$.

In the case $L^7$ is —$(CY^{17}Y^{18})_{p8}$—O—CO—$(CY^{19}Y^{20})_{p9}$— or —$(CY^{17}Y^{18})_{p8}$—$N^{27C}$—CO—$(CY^{19}Y^{20})_{p9}$—, $p^8$ is preferably 0 to 3 and $p^9$ is preferably 1 to 3, and $p^8$ is more preferably 0 to 1 and $p^9$ is more preferably 1 to 3, while $Y^{17}$ to $Y^{20}$ respectively preferably are a hydrogen atom and $Y^{27C}$ preferably is a hydrogen atom or methyl. $B^1$ preferably is —$N^+(CH_3)_3$.

$X^2$ and $X^3$ are preferably the same or different and are a methyl or ethyl, or are combined together to form an optionally substituted C4-C6 heterocyclic group with an adjacent nitrogen atom, are more preferably the same and are methyl or are combined together to form pyrrolidine or piperidine with an adjacent nitrogen atom, and even more preferably are the same and are methyl.

$X^4$ preferably is a methyl, ethyl, hydroxypropyl or hydroxyethyl, and more preferably is a methyl.

$X^2$ and $X^3$ are preferably the same or different and are a methyl or ethyl, $X^4$ preferably is a methyl, ethyl, hydroxypropyl or hydroxyethyl, and $X^2$ to $X^4$ more preferably are methyl.

$B^1$ representing

[C76]

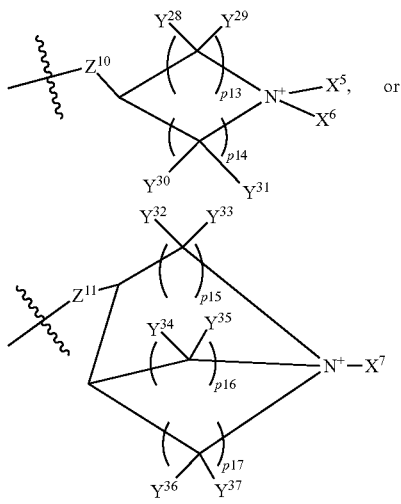

and $L^7$ representing absent or representing $(CY^{15}Y^{16})_{p7}$—, —$(CY^{17}Y^{18})_{p8}$—O—CO—$(CY^{19}Y^{20})_{p9}$— or —$(CY^{17}Y^{18})_{p8}$—$NY^{27C}$—CO—$(CY^{19}Y^{20})_{p9}$— is also a preferred embodiment of the present invention. In this case, $B^1$ more preferably is

[C77]

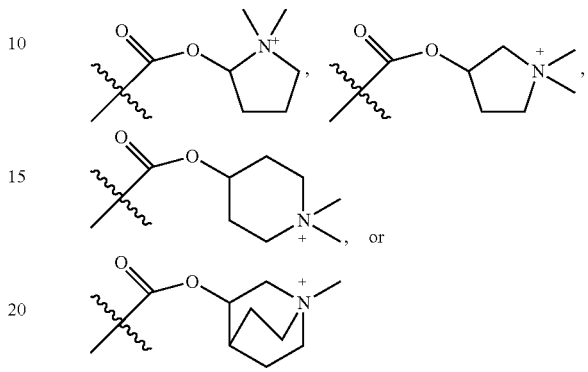

and $L^7$ is more preferably absent or is —NH—CO—$(CH_2)_{p9}$—, —O—CO—$(CH_2)_{p9}$—, —$CH_2$—NH—CO—$(CH_2)_{p9}$— or —$CH_2$—O—CO—$(CH_2)_{p9}$—.

In formula (III), $R^7$ preferably is a linear or branched C8-C24 alkyl or C8-C24 alkenyl, more preferably is a linear or branched C15-C20 alkenyl or linear or branched C9-C18 alkyl, and are most preferably the same and are linear C15-C20 alkenyl or are the same and are linear C9-C18 alkyl. $R^8$ and $R^9$ preferably are linear or branched C8-C24 alkyl, C8-C24 alkenyl or C8-C24 alkynyl and are the same, more preferably are linear or branched C15-C20 alkenyl or linear or branched C9-C18 alkyl and are the same, and most preferably are linear C15-C20 alkenyl or linear C9-C18 alkyl and are the same.

$L^8$ is absent or is —$Z^{12}$—$(CY^{39}Y^{40})_{p18}$— or —$Z^{13}$—$(CY^{41}Y^{42})_{p19}$—$Z^{14}$—$(CY^{43}Y^{44})_{p20}$—, and is preferably absent or is —$Z^{12}$—$(CY^{39}Y^{40})_{p18}$—. $L^9$ and $L^{10}$ are the same or different and are absent or are —$Z^{12}$—$(CY^{39}Y^{40})_{p18}$— or —$Z^{13}$—$(CY^{41}Y^{42})_{p19}$—$Z^{14}$—$(CY^{43}Y^{44})_{p20}$—, or are preferably the same or different and absent or are —$Z^{12}$—$(CY^{39}Y^{40})_{p18}$—. $Y^{39}$ to $Y^{44}$, the same or different, are a hydrogen atom or optionally substituted C1-C4 alkyl, and $Y^{39}$ to $Y^{44}$ preferably are a hydrogen atom. $Z^{12}$ to $Z^{14}$ are the same or different and are —O—, —$NY^{45A}$—, —CO—O—, —O—CO—, —CO—$NY^{45B}$—, —$NY^{45C}$—CO—, $NY^{45D}$—CO—0 or —CO—, and preferably are —CO—O—, —O—CO—, —CO—$NY^{45B}$—, —$NY^{45C}$—CO— or —CO—. $Y^{45A}$ to $Y^{45D}$, the same or different, are a hydrogen atom or optionally substituted C1-C4 alkyl, and preferably are a hydrogen atom or methyl, $p^{18}$ is an integer of 0 to 5 and is preferably 0 or 1, $p^{19}$ is an integer of 1 to 5 and is preferably 1 or 2. $p^{20}$ is an integer of 0 to 5 and is preferably 0 or 1.

One of $L^8$ to $L^{10}$ preferably is —CO—O—$(CY^{39}Y^{40})_{p18}$— or —O—CO—$(CY^{39}Y^{40})_{p18}$— or two or more of $L^8$ to $L^{10}$ are preferably the same or different and are —CO—O—$(CY^{39}Y^{40})_{p18}$— or —O—CO—$(CY^{39}Y^{40})_{p18}$—, and $R^7$ to $R^9$ preferably are C15-C20 alkenyl or C9-C18 alkyl, and $R^8$ to $R^9$ are preferably the same.

$L^8$ is preferably absent or is —CO—O—$(CY^{39}Y^{40})_{p18}$—, —O—CO—$(CY^{39}Y^{40})_{p18}$—, —CO—$NY^{45B}$—$(CY^{39}Y^{40})_{p18}$— or —$NY^{45C}$—CO—$(CY^{39}Y^{40})_{p18}$—, is more preferably absent or is —CO—O—$(CY^{39}Y^{40})_{p18}$—, —O—CO—$(CY^{39}Y^{40})_{p18}$— or —CO—$NY^{45B}$—$(CY^{39}Y^{40})_{p18}$—, and is even more preferably absent or is —CO—O—(CH$_2$)$_{p18}$—, —O—CO—(CH$_2$)$_{p18}$— or —CO—NH—(CH$_2$)$_{p18}$—.

L$^9$ and L$^{10}$ are preferably the same or different and are —CO—O—(CY$^{39}$Y$^{40}$)$_{p18}$—, —O—CO—(CY$^{39}$Y$^{40}$)$_{p18}$—, —CO—NY$^{45B}$—(CY$^{39}$Y$^{40}$)$_{p18}$— or —NY$^{45C}$—CO—(CY$^{39}$Y$^{40}$)$_{p18}$—, are more preferably the same or different and are —CO—O—(CY$^{39}$Y$^{40}$)$_{p18}$— or —O—CO—(CY$^{39}$Y$^{40}$)$_{p18}$—, are even more preferably the same or different and are —CO—O—(CH$_2$)$_{p18}$—, and are most preferably absent or are —CO—O—(CH$_2$)$_{p18}$—.

In formula (III), one of L$^8$ to L$^{10}$ is preferably absent or is —CO—O—(CY$^{39}$Y$^{40}$)$_{p18}$—, —O—CO—(CY$^{39}$Y$^{40}$)$_{p18}$—, —CO—NY$^{45B}$—(CY$^{39}$Y$^{40}$)$_{p18}$— or —NY$^{45C}$—CO—(CY$^{39}$Y$^{40}$)$_{p18}$— or two or more of L$^8$ to L$^{10}$ are preferably the same or different and are absent or are —CO—O—(CY$^{39}$Y$^{40}$)$_{p18}$—, —O—CO—(CY$^{39}$Y$^{40}$)$_{p18}$—, —CO—NY$^{45B}$—(CY$^{39}$Y$^{40}$)$_{p18}$— or —NY$^{45C}$—CO—(CY$^{39}$Y$^{40}$)$_{p18}$—, and R$^7$ to R$^9$ preferably are a linear C15-C20 alkenyl or C9-C18 alkyl, and R$^8$ to R$^9$ are preferably the same.

In the case at least one of L$^8$ to L$^{10}$ is absent or is —O—(CY$^{39}$Y$^{40}$)$_{p18}$—, —O—CO—(CY$^{39}$Y$^{40}$)$_{p18}$—, —NY$^{45C}$—CO—(CY$^{39}$Y$^{40}$)$_{p18}$— or —NY$^{45D}$—CO—O—(CY$^{39}$Y$^{40}$)$_{p18}$— R$^7$ to R$^9$ bound to J$^1$, J$^2$, —O—(CY$^{39}$Y$^{40}$)$_{p18}$—, —O—CO—(CY$^{39}$Y$^{40}$)$_{p18}$—, —NY$^{45C}$—CO—(CY$^{39}$Y$^{40}$)$_{p18}$— or —NY$^{45D}$—CO—O—(CY$^{39}$Y$^{40}$)$_{p18}$— are preferably the same or different and respectively are an octyl, decyl, dodecyl, tetradecyl, hexadecyl, octadecyl, icosyl, docosyl, tetracosyl, (Z)-tetradec-9-enyl, (Z)-hexadec-9-enyl, (Z)-octadec-6-enyl, (Z)-octadec-9-enyl, (E) octadec-9-enyl, (Z)-octadec-11-enyl, (9Z,12Z)-octadeca-9,12-dienyl, (9Z,12Z,15Z)-octadeca-9,12,15-trienyl, (Z)-icos-11-enyl, (11Z,14Z)-icosa-11,14-dienyl, 3,7,11-trimethyldodeca-2,6,10-trienyl or 3,7,11,15-tetramethylhexadec-2-enyl, and more preferably are a dodecyl, tetradecyl, hexadecyl, (Z)-hexadec-9-enyl, (Z)-octadec-6-enyl, (Z)-octadec-9-enyl or (9Z,12Z)-octadeca-9,12-dienyl.

In the case at least one of L$^8$ to L$^{10}$ is —CO—O—(CY$^{39}$Y$^{40}$)$_{p18}$—, —CO—NY$^{45B}$—(CY$^{39}$Y$^{40}$)$_{p18}$— or —CO—(CY$^{39}$Y$^{40}$)$_{p18}$—, R$^7$ to R$^9$ bound to —CO—O—(CY$^{39}$Y$^{40}$)$_{p18}$—, —CO—NY$^{45B}$—(CY$^{39}$Y$^{40}$)$_{p18}$— or —CO—(CY$^{39}$Y$^{40}$)$_{p18}$— are preferably the same or different and respectively are a nonyl, undecyl, tridecyl, pentadecyl, heptadecyl, nonadecyl, henicosyl, tricosyl, (Z)-tridec-8-enyl, (Z)-pentadec-8-enyl, (Z)-heptadec-5-enyl, (Z)-heptadec-8-enyl, (E)-heptadec-8-enyl, (Z)-heptadec-10-enyl, (8Z,11Z)-heptadeca-8,11-dienyl, (8Z,11Z,14Z)-octadeca-8,11,14-trienyl, (Z)-nonadec-10-enyl, (10Z,13Z)-nonadeca-10,13-dienyl, (11Z,14Z)-icosa-11,14-dienyl, 2,6,10-trimethylundeca-1,5,9-trienyl or 2,6,10,14-tetramethylpentadec-1-enyl, and more preferably are an undecyl, tridecyl, pentadecyl, (Z)-pentadec-8-enyl, (Z)-heptadec-5-enyl, (Z)-heptadec-8-enyl or (8Z,11Z)-heptadeca-8,11-dienyl.

L$^{11}$ is absent or is —(CY$^{46}$Y$^{47}$)$_{p21}$—, —(CY$^{48}$Y$^{49}$)$_{p22}$—Z$^{15}$—(CY$^{50}$Y$^{51}$)$_{p23}$— or —(CY$^{52}$Y$^{53}$)$_{p24}$—Z$^{16}$—(CY$^{54}$Y$^{55}$)$_{p25}$—Z$^{17}$—(CY$^{56}$Y$^{57}$)$_{p26}$—, or preferably is absent or is —(CY$^{46}$Y$^{47}$)$_{p21}$— or —(CY$^{48}$Y$^{49}$)$_{p22}$—Z$^{15}$—(CY$^{50}$Y$^{51}$)$_{p23}$—. Y$^{46}$ to Y$^{57}$, the same or different, are a hydrogen atom or optionally substituted C1-C4 alkyl, and Y$^{46}$ to Y$^{57}$ preferably are a hydrogen atom. Z$^{15}$ to Z$^{17}$, the same or different, are —O—, —NY$^{58A}$—, —CO—O—, —O—CO—, —CO—NY$^{58B}$—, —NY$^{58C}$—, NY$^{58D}$—CO—O— or —CO—, preferably are —CO—O—, —O—CO—, —CO—NY$^{58B}$—, —NY$^{58C}$—CO— or —CO—, and more preferably are —O—CO— or —NY$^{58C}$—CO— p$^{21}$ is an integer of 1 to 5 and is preferably 1 to 3, and p$^{22}$ is an integer of 0 to 5 and is preferably 0 to 3. p$^{23}$ is an integer of 1 to 5 and is preferably 1 or 2.

L$^{11}$ is preferably absent or is —(CY$^{46}$Y$^{47}$)$_{p21}$—, —(CY$^{48}$Y$^{49}$)$_{p22}$—O—CO—(CY$^{50}$Y$^{51}$)$_{p23}$— or —(CY$^{48}$Y$^{49}$)$_{p22}$—NY$^{58C}$—CO—(CY$^{50}$Y$^{51}$)$_{p23}$—, is more preferably absent or is —(CY$^{46}$Y$^{47}$)$_{p21}$—, and is even more preferably absent or is —(CH$_2$)$_{p2}$—.

L$^{12}$ is preferably absent or is —(CY$^{59}$Y$^{60}$)$_{p27}$—, is more preferably absent or is —(CH$_2$)$_{p27}$—, and is even more preferably absent or is —CH$_2$— or —(CH$_2$)$_2$—.

J$^1$ and J$^2$, the same or different, are CY$^{72}$ or N, and J$^1$ and J$^2$ are preferably the same or different and are CH, C(OH) or N.

J$^1$ preferably is CH when L$^{11}$ is absent.

L$^9$ and L$^{10}$ representing absent, L$^{12}$ representing —CO—(CH$_2$)$_{p29}$—, J$^1$ representing CH and J$^2$ representing N is also a preferred embodiment of the present invention. At this time, L$^8$ preferably is —CO—NY$^{45B}$—(CH$_2$)$_{p18}$— and L$^{11}$ is preferably absent or is —(CH$_2$)$_{p21}$—.

L$^9$ and L$^{10}$ representing absent, L$^{12}$ representing —O—CO—(CH$_2$)$_{p29}$— and J$^1$ and J$^2$ representing CH is also a preferred embodiment of the present invention. At this time, L$^8$ preferably is —O—CO—(CH$_2$)$_{p18}$— and L$^{11}$ is preferably absent.

B$^2$ preferably is

[C78]

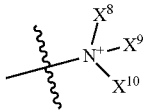

and more preferably is —N$^+$(CH$_3$)$_3$.

X$^8$ to X$^{10}$ respectively have the same meanings as the above-mentioned X$^2$ to X$^4$.

In formula (IV), R$^{10}$ preferably is a linear or branched C8-C24 alkyl or C8-C24 alkenyl, more preferably is a linear or branched C15-C20 alkenyl or linear or branched C9 to C18 alkyl, and most preferably is a linear C15-C20 alkenyl or linear C9-C18 alkyl. R$^{11}$ and R$^{12}$ preferably are a linear or branched C8-C24 alkyl, C8-C24 alkenyl or C8-C24 alkynyl and are the same, more preferably are a linear or branched C15-C20 alkenyl or linear or branched C9-C18 alkyl and are the same, and most preferably are a linear C15-C20 alkenyl or linear C9-C18 alkyl and are the same.

L$^{13}$ is preferably present or is —Z$^{23}$—(CY$^{83}$Y$^{84}$)$_{p38}$— or —Z$^{24}$—(CY$^{85}$Y$^{86}$)$_{p39}$—Z$^{25}$—(CY$^{87}$Y$^{88}$)$_{p40}$— and is preferably absent or is —Z$^{23}$—(CY$^{83}$Y$^{84}$)$_{p38}$—. Y$^{83}$ to Y$^{88}$, the same or different, are a hydrogen atom or optionally substituted C1-C4 alkyl, and Y$^{83}$ to Y$^{88}$ preferably are a hydrogen atom. Z$^{23}$ to Z$^{25}$, the same or different, are —O—, —NY$^{89A}$—, —CO—O—, —O—CO—, —CO—NY$^{89B}$—, —NY$^{89C}$—CO— or —NY$^{89D}$—CO—O—, preferably are —CO—O—, —O—CO—, —CO—NY$^{89B}$— or —NY$^{89C}$—CO—, and more preferably are —CO—NY$^{89B}$—. Y$^{89A}$ to Y$^{89D}$, the same or different, are a hydrogen atom or optionally substituted C1-C4 alkyl, and preferably are a hydrogen atom or methyl, p$^{38}$ to p$^{40}$, the same or different, are an integer of 1 to 5 and preferably are 1 or 2.

L$^{13}$ is preferably absent or is —CO—O—(CY$^{83}$Y$^{84}$)$_{p38}$—, —O—CO—(CY$^{83}$Y$^{84}$)$_{p38}$—, —CO—NY$^{89B}$—(CY$^{83}$Y$^{84}$)$_{p38}$— or —NY$^{89C}$—CO—(CY$^{83}$Y$^{84}$)$_{p38}$— is more preferably absent or is —CO—O—(CH$_2$)$_{p38}$—, —O—CO—($CH_2$)$_{p38}$— or —CO—$NCH_3$—($CH_2$)$_{p38}$— and is even more preferably absent or is —CO—$NCH_3$—($CH_2$)$_{p38}$—.

$L^{14}$ and $L^{15}$, the same or different, are absent or are —$Z^{26}$—($CY^{90}Y^{91}$)$_{p41}$— or —$Z^{27}$—($CY^{92}Y^{93}$)$_{p42}$—$Z^{28}$—($CY^{94}Y^{95}$)$_{p43}$— and are preferably absent or are —$Z^{26}$—($CY^{90}Y^{91}$)$_{p41}$—. $Y^{90}$ to $Y^{95}$, the same or different, are a hydrogen atom or optionally substituted C1-C4 alkyl, and $Y^{90}$ to $Y^{95}$ preferably are a hydrogen atom. $Z^{26}$ to $Z^{28}$, the same or different, are —O—, —$NY^{96A}$—, —CO—O—, —O—CO—, —CO—$NY^{96B}$—, —$NY^{96C}$—CO—, —$NY^{96D}$—CO—O— or —CO—, and preferably are —CO—O—, —O—CO—, —CO—$NY^{96B}$—, —$NY^{96C}$—CO— or —CO—. $Y^{96A}$ to $Y^{96D}$, the same or different, are a hydrogen atom or optionally substituted C1-C4 alkyl, and preferably are a hydrogen atom or methyl, $p^{41}$ is an integer of 0 to 5 and is preferably 1 or 2. $p^{42}$ is an integer of 1 to 5 and is preferably 1 or 2. $p^{43}$ is an integer of 0 to 5 and is preferably 0 to 2.

$L^{14}$ and $L^{15}$ are preferably the same or different and are absent or are —CO—O—($CY^{90}Y^{91}$)$_{p41}$—, —O—CO—($CY^{90}Y^{91}$)$_{p41}$—, —CO—$NY^{96B}$—($CY^{90}Y^{91}$)$_{p41}$—, —$NY^{96C}$—CO—($CY^{90}Y^{91}$)$_{p41}$— or —CO—($CY^{90}Y^{91}$)$_{p41}$—, are more preferably the same or different and absent or are —CO—O—($CY^{90}Y^{91}$)$_{p41}$—, —O—CO—($CY^{90}Y^{91}$)$_{p41}$— or —CO—($CY^{90}Y^{91}$)$_{p41}$—, and are even more preferably the same or different and absent or are —CO—O—($CH_2$)$_{p41}$—, —O—CO—($CH_2$)$_{p41}$— or —CO—.

In formula (IV), $L^{13}$ preferably is —CO—O—($CY^{83}Y^{84}$)$_{p38}$—, —O—CO—($CY^{83}Y^{84}$)$_{p38}$— or —CO—$NY^{89B}$—($CY^{83}Y^{84}$)$_{p38}$— and one of $L^{14}$ and $L^{15}$ preferably is —CO—O—($CY^{90}Y^{91}$)$_{p41}$— or —O—CO—($CY^{90}Y^{91}$)$_{p41}$— or $L^{13}$ preferably is —CO—O—($CY^{83}Y^{84}$)$_{p38}$—, —O—CO—($CY^{83}Y^{84}$)$_{p38}$— or —CO—$NY^{89B}$—($CY^{83}Y^{84}$)$_{p38}$— and one of $L^{14}$ and $L^{15}$ preferably is —CO—O—($CY^{90}Y^{91}$)$_{p41}$— or —O—CO—($CY^{90}Y^{91}$)$_{p41}$— $L^{14}$ and $L^{15}$ are preferably the same or different and are —CO—O—($CY^{90}Y^{91}$)$_{p41}$— or —O—CO—($CY^{90}Y^{91}$)$_{p41}$— $L^{13}$ preferably is —CO—O—($CY^{83}Y^{84}$)$_{p38}$—, —O—CO—($CY^{83}Y^{84}$)$_{p38}$— or —CO—$NY^{89B}$—($CY^{83}Y^{84}$)$_{p38}$— and $L^{14}$ and $L^{15}$ are preferably the same or different and is —CO—O—($CY^{90}Y^{91}$)$_{p41}$— or —O—CO—($CY^{90}Y^{91}$)$_{p41}$— and $R^{10}$ to $R^{12}$ preferably are a linear or branched C15-C20 alkenyl or C9-C18 alkyl. $R^{11}$ and $R^{12}$ are preferably the same.

In the case $L^{13}$ is absent or is —O—($CY^{83}Y^{84}$)$_{p38}$—, —$NY^{89A}$—($CY^{83}Y^{84}$)$_{p38}$—, —O—CO—($CY^{83}Y^{84}$)$_{p38}$—, —$NY^{89C}$—CO—($CY^{83}Y^{84}$)$_{p38}$— or —$NY^{89D}$—CO—O—($CY^{83}Y^{84}$)$_{p38}$— $R^{10}$ preferably is an octyl, decyl, dodecyl, tetradecyl, hexadecyl, octadecyl, icosyl, docosyl, tetracosyl, (Z)-tetradec-9-enyl, (Z)-hexadec-9-enyl, (Z)-octadec-6-enyl, (Z)-octadec-9-enyl, (E)-octadec-9-enyl, (Z)-octadec-11-enyl, (9Z,12Z)-octadeca-9,12-dienyl, (9Z,12Z,15Z)-octadeca-9,12,15-trienyl, (Z)-icos-11-enyl, (11Z,14Z)-icosa-11,14-dienyl, 3,7,11-trimethyldodeca-2,6,10-trienyl or 3,7,11,15-tetramethylhexadec-2-enyl, and more preferably is a dodecyl, tetradecyl, hexadecyl, (Z)-hexadec-9-enyl, (Z)-octadec-6-enyl, (Z)-octadec-9-enyl or (9Z,12Z)-octadeca-9,12-dienyl.

In the case $L^{13}$ is —CO—O—($CY^{83}Y^{84}$)$_{p38}$— or CO—$NY^{89B}$—($CY^{83}Y^{84}$)$_{p38}$—, $R^{10}$ preferably is a nonyl, undecyl, tridecyl, pentadecyl, heptadecyl, nonadecyl, henicosyl, tricosyl, (Z)-tridec-8-enyl, (Z)-pentadec-8-enyl, (Z)-heptadec-5-enyl, (Z)-heptadec-8-enyl, (E)-heptadec-8-enyl, (Z)-heptadec-10-enyl, (8Z,11Z)-heptadeca-8,11-dienyl, (8Z,11Z,14Z)-octadeca-8,11,14-trienyl, (Z)-nonadec-10-enyl, (10Z,13Z)-nonadeca-10,13-dienyl, (11Z,14Z)-icosa-11,14-dienyl, 2,6,10-trimethylundeca-1,5,9-trienyl or 2,6,10,14-tetramethylpentadeca-1-enyl, and more preferably is an undecyl, tridecyl, pentadecyl, (Z)-pentadec-8-enyl, (Z)-heptadec-5-enyl, (Z)-heptadec-8-enyl or (8Z,11Z)-heptadeca-8,11-dienyl.

In addition, in the case at least one of $L^{14}$ and $L^{15}$ is absent or is —O—($CY^{90}Y^{91}$)$_{p41}$—, —$NY^{96A}$—($CY^{90}Y^{91}$)$_{p41}$— or —O—CO—($CY^{90}Y^{91}$)$_{p41}$—, —$NY^{96C}$—CO—($CY^{90}Y^{91}$)$_{p41}$— or —$NY^{96D}$—CO—O—($CY^{90}Y^{91}$)$_{p41}$—, $R^{11}$ and $R^{12}$ bound to $J^3$, —O—($CY^{90}Y^{91}$)$_{p41}$—, —$NY^{96A}$—($CY^{90}Y^{91}$)$_{p41}$—, —O—CO—($CY^{90}Y^{91}$)$_{p41}$—, —$NY^{96C}$—CO—($CY^{90}Y^{91}$)$_{p41}$— or —$NY^{96D}$—CO—O—($CY^{90}Y^{91}$)$_{p41}$— are preferably the same or different and respectively are an octyl, decyl, dodecyl, tetradecyl, hexadecyl, octadecyl, icosyl, docosyl, tetracosyl, (Z)-tetradec-9-enyl, (Z)-hexadec-9-enyl, (Z)-octadec-6-enyl, (Z)-octadec-9-enyl, (E) octadec-9-enyl, (Z)-octadec-11-enyl, (9Z,12Z)-octadeca-9,12-dienyl, (9Z,12Z,15Z)-octadeca-9,12,15-trienyl, (Z)-icos-11-enyl, (11Z,14Z)-icosa-11,14-dienyl, 3,7,11-trimethyldodeca-2,6,10-trienyl or 3,7,11,15-tetramethylhexadec-2-enyl, and more preferably are a dodecyl, tetradecyl, hexadecyl, (Z)-hexadec-9-enyl, (Z)-octadec-6-enyl, (Z)-octadec-9-enyl or (9Z,12Z)-octadeca-9,12-dienyl.

In the case at least one of $L^{14}$ to $L^{15}$ is —CO—O—($CY^{90}Y^{91}$)$_{p41}$— or —CO—$NY^{96B}$—($CY^{90}Y^{91}$)$_{p41}$—, $R^{11}$ and $R^{12}$ bound to —CO—O—($CY^{90}Y^{91}$)$_{p41}$— or —CO—$NY^{96B}$—($CY^{90}Y^{91}$)$_{p41}$— are preferably the same or different and respectively are a nonyl, undecyl, tridecyl, pentadecyl, heptadecyl, nonadecyl, henicosyl, tricosyl, (Z)-tridec-8-enyl, (Z)-pentadec-8-enyl, (Z)-heptadec-5-enyl, (Z)-heptadec-8-enyl, (E)-heptadec-8-enyl, (Z)-heptadec-10-enyl, (8Z,11Z)-heptadeca-8,11-dienyl, (8Z,11Z,14Z)-octadeca-8,11,14-trienyl, (Z)-nonadec-10-enyl, (10Z,13Z)-nonadeca-10,13-dienyl, (11Z,14Z)-icosa-11,14-dienyl, 2,6,10-trimethylundeca-1,5,9-trienyl or 2,6,10,14-tetramethylpentadec-1-enyl, and more preferably are an undecyl, tridecyl, pentadecyl, (Z)-pentadec-8-enyl, (Z)-heptadec-5-enyl, (Z)-heptadec-8-enyl or (8Z,11Z)-heptadeca-8,11-dienyl.

$L^{16}$ is absent or is —($CY^{97}Y^{98}$)$_{p44}$—, —($CY^{99}Y^{100}$)$_{p45}$—$Z^{29}$—($CY^{101}Y^{102}$)$_{p46}$— or —($CY^{103}Y^{104}$)$_{p47}$—$Z^{30}$—($CY^{105}Y^{106}$)$_{p48}$—$Z^{31}$—($CY^{107}Y^{108}$)$_{p49}$—, is preferably absent or is —($CY^{97}Y^{98}$)$_{p44}$— or —($CY^{99}Y^{100}$)$_{p45}$—$Z^{29}$—($CY^{101}Y^{102}$)$_{p46}$—, is more preferably absent or is —($CY^{97}Y^{98}$)$_{p44}$—, —($CY^{99}Y^{100}$)$_{p45}$—O—CO—($CY^{101}Y^{102}$)$_{p46}$—, —($CY^{99}Y^{100}$)$_{p45}$—$NY^{109C}$—CO—($CY^{101}Y^{102}$)$_{p46}$— or —CO—($CY^{101}Y^{102}$)$_{p46}$—, and is even more preferably absent or is —($CH_2$)$_{p44}$— or —CO—($CH_2$)$_{p46}$—.

$J^3$ is $CY^{110}$ or N, and preferably is CH or N. In addition, when $J^3$ is N, preferably $L^{14}$ is absent, $L^{15}$ is —CO—, and $L^{16}$ is absent or is —($CY^{97}Y^{98}$)$_{p44}$—, and more preferably $L^{14}$ is absent, $L^{15}$ is absent and $L^{16}$ is —CO—($CY^{101}Y^{102}$)$_{p46}$—.

$X^{14}$ and $X^{15}$ respectively have the same meanings as the above-mentioned $X^2$ and $X^3$.

In formula (V'), $R^{13}$ preferably is a linear or branched C8-C24 alkyl or C8-C24 alkenyl, more preferably is a linear or branched C15-C20 alkenyl or linear or branched C9 to C18 alkyl, and most preferably is a linear C15-C20 alkenyl or linear C9-C18 alkyl. $R^{14}$ and $R^{15}$ preferably are a linear or branched C8-C24 alkyl, C8-C24 alkenyl or C8-C24 alkynyl and are the same, more preferably are linear or branched C15-C20 alkenyl or linear or branched C9-C18 alkyl and are the same, and most preferably are linear C15-C20 alkenyl or linear C9-C18 alkyl and are the same.

$L^{17}$ to $L^{19}$, the same or different, are —$Z^{32}$—$(CY^{115}Y^{116})_{p51}$— or —$Z^{33}$—$(CY^{117}Y^{118})_{p52}$—$Z^{34}$—$(CY^{119}Y^{120})_{p53}$—, preferably are —$Z^{32}$—$(CY^{115}Y^{116})_{p51}$—, more preferably are —O—$(CY^{115}Y^{116})_{p51}$— or —CO—O—$(CY^{115}Y^{116})_{p51}$—, and even more preferably are —O— or —CO—O—.

In formula (V'), $L^{17}$ to $L^{19}$ are preferably the same or different and are —O— or —CO—O—, and $R^{13}$ to $R^{15}$ preferably are a linear C15-C20 alkenyl or C9-C18 alkyl. At this time, $L^{17}$ to $L^{19}$ are preferably the same and are —O— or —CO—O— and $R^{13}$ to $R^{15}$ preferably are the same and are a linear C15-C20 alkenyl or C9-C18 alkyl.

In the case at least one of $L^{17}$ to $L^{19}$ is absent or is —O—$(CY^{115}Y^{116})_{p51}$—, —O—CO—$(CY^{115}Y^{116})_{p51}$—, —$NY^{121C}$—CO—$(CY^{115}Y^{116})_{p518}$— or —$NY^{121D}$—CO—O—$(CY^{115}Y^{116})_{p51}$—, $R^{13}$ to $R^{15}$ bound to a carbon atom, —O—$(CY^{115}Y^{116})_{p51}$—, —O—CO—$(CY^{115}Y^{116})_{p51}$—, —$NY^{121C}$—CO—$(CY^{115}Y^{116})_{p518}$— or —$NY^{121D}$—CO—O—$(CY^{115}Y^{116})_{p51}$— adjacent to a furanose ring or $L^{20}$ are preferably the same or different and respectively are an octyl, decyl, dodecyl, tetradecyl, hexadecyl, octadecyl, icosyl, docosyl, tetracosyl, (Z)-tetradec-9-enyl, (Z)-hexadec-9-enyl, (Z)-octadec-6-enyl, (Z)-octadec-9-enyl, (E)-octadec-9-enyl, (Z)-octadec-11-enyl, (9Z,12Z)-octadeca-9,12-dienyl, (9Z,12Z,15Z)-octadeca-9,12,15-trienyl, (Z)-icos-11-enyl, (11Z,14Z)-icosa-11,14-dienyl, 3,7,11-trimethyldodeca-2,6,10-trienyl or 3,7,11,15-tetramethylhexadec-2-enyl, and more preferably are a dodecyl, tetradecyl, hexadecyl, (Z)-hexadec-9-enyl, (Z)-octadec-6-enyl, (Z)-octadec-9-enyl or (9Z,12Z)-octadeca-9,12-dienyl.

In the case at least one of $L^{17}$ to $L^{19}$ is —CO—O—$(CY^{115}Y^{116})_{p51}$—, —CO—$NY^{121B}$—$(CY^{115}Y^{116})_{p51}$— or —CO—$(CY^{115}Y^{116})_{p51}$—, $R^{13}$ to $R^{15}$ bound to —CO—O—$(CY^{115}Y^{116})_{p51}$—, —CO—$NY^{121B}$—$(CY^{115}Y^{116})_{p51}$— or —CO—$(CY^{115}Y^{116})_{p51}$— are preferably the same or different and respectively are a nonyl, undecyl, tridecyl, pentadecyl, heptadecyl, nonadecyl, henicosyl, tricosyl, (Z)-tridec-8-enyl, (Z)-pentadec-8-enyl, (Z)-heptadec-5-enyl, (Z)-heptadec-8-enyl, (E)-heptadec-8-enyl, (Z)-heptadec-10-enyl, (8Z,11Z)-heptadeca-8,11-dienyl, (8Z,11Z,14Z)-octadeca-8,11,14-trienyl, (Z)-nonadec-10-enyl, (10Z,13Z)-nonadeca-10,13-dienyl, (11Z,14Z)-icosa-11,14-dienyl, 2,6,10-trimethylundeca-1,5,9-trienyl or 2,6,10,14-tetramethylpentadec-1-enyl, and more preferably are an undecyl, tridecyl, pentadecyl, (Z)-pentadec-8-enyl, (Z)-heptadec-5-enyl, (Z)-heptadec-8-enyl or (8Z,11Z)-heptadeca-8,11-dienyl.

$L^{20}$ is absent or is —$(CY^{122}Y^{123})_{p54}$—, —$(CY^{124}Y^{125})_{p55}$—$Z^{35}$—$(CY^{126}Y^{127})_{p56}$— or —$(CY^{128}Y^{129})_{p57}$—$Z^{36}$—$(CY^{130}Y^{131})_{p58}$—$Z^{37}$—$(CY^{132}Y^{133})_{p59}$—, preferably is —$(CY^{122}Y^{123})_{p54}$—, more preferably is —$(CH_2)_{p54}$— and even more preferably is —$CH_2$—.

$L^{21}$ is absent or is —$(CY^{135}Y^{136})_{p60}$—, —$(CY^{137}Y^{138})_{p61}$—$Z^{38}$—$(CY^{139}Y^{140})_{p62}$— or —$(CY^{141}Y^{142})_{p63}$—$Z^{39}$—$(CY^{143}Y^{144})_{p64}$—$Z^{40}$—$(CY^{145}Y^{146})_{p65}$—, is preferably absent or is —$(CY^{135}Y^{136})_{p60}$—, is more preferably absent or is —$(CH_2)_{p60}$—, and even more preferably is absent.

$B^3$ preferably is

[C79]

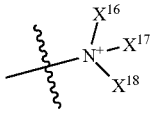

and more preferably is —$N^+(CH_3)_3$.

$Y^{111}$ and $Y^{112}$, the same or different, are a hydrogen atom, hydroxyl or optionally substituted C1-C4 alkyl, are preferably the same or different and are a hydrogen atom or hydroxyl, and are more preferably the same and are hydrogen atoms.

In formula (V"), $R^{16}$ to $R^{18}$, $L^{22}$ to $L^{26}$, $B^4$, $Y^{113}$ to $Y^{114}$ and $A^6$ respectively have the same meanings as $R^{13}$ to $R^{15}$, $L^{17}$ to $L^{21}$, $B^3$, $Y^{111}$ to $Y^{112}$ and $A^5$.

In formula (V'), when $Y^{111}$ is a hydrogen atom, the four substituents on the pyran ring are preferably respectively substituted at four different carbon atoms on the pyran ring. Formula (V') is more preferably the formula indicated below.

[C80]

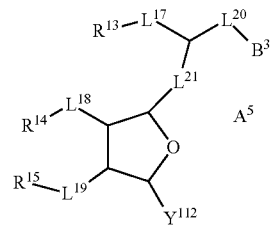

At this time, even more preferably $L^{17}$ to $L^{19}$ are the same or different and are —O— or —CO—O— while $R^{13}$ to $R^{15}$ are a linear C15-C20 alkenyl or C9-C18 alkyl, and most preferably, $L^{17}$ to $L^{19}$ are the same or different and are —O— or —CO—O—, $R^{13}$ to $R^{15}$ are a linear C15-C20 alkenyl or C9-C18 alkyl, $L^{17}$ and $L^{21}$ are absent, and $Y^{112}$ is a hydrogen atom or hydroxyl.

In formula (V"), the four substituents on the furan ring are preferably respectively substituted at four different carbon atoms on the furan ring. Formula (V") is more preferably the formula indicated below.

[C81]

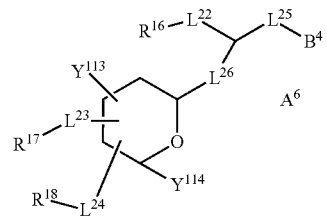

At this time, even more preferably $L^{22}$ to $L^{24}$ are the same or different and are —O— or —CO—O— while $R^{16}$ to $R^{18}$ are a linear C15-C20 alkenyl or C9-C18 alkyl, and most preferably, $L^{22}$ to $L^{24}$ are the same or different and are —O— or —CO—O—, $R^{16}$ to $R^{18}$ are a linear C15-C20 alkenyl or C9-C18 alkyl, $L^{22}$ and $L^{26}$ are absent, and $Y^{114}$ is a hydrogen atom or hydroxyl.

Furthermore, in the definitions of each of the following formulas in the definitions of formulas $B^1$, $B^2$, $B^3$ and $B^4$,

[C82]

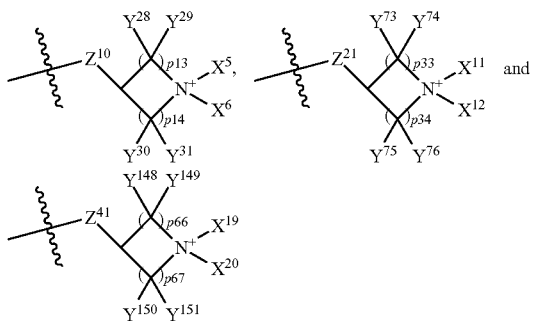

in the case $p^{13}$, $p^{33}$ and $p^{66}$ are zero, $N^+$ respectively bonds to carbon atoms adjacent to $Z^{10}$, $Z^{21}$ and $Z^{41}$.

The nucleic acid-containing lipid nanoparticles of the present invention may also contain a cationic lipid in addition to the lipid (lipid A) having a hydrophilic unit having one quaternary ammonium group and three independent, optionally substituted hydrocarbon groups. There are no particular limitations on the cationic lipid other than lipid A used in the present invention provided it is an amphiphilic molecule (other than lipid A) having a lipophilic unit containing one or more optionally substituted hydrocarbon groups and a cationic hydrophilic unit containing at least one primary amine, secondary amine, tertiary amine or quaternary ammonium group, and is preferably a lipid (lipid B) having a hydrophilic unit having one optionally substituted amino group or one quaternary ammonium group and a hydrophobic unit having two independent, optionally substituted hydrocarbon groups.

Examples of the cationic lipid other than lipid A used in the present invention include the cationic lipids described in WO 2013/089151, WO 2011/136368, WO 2014/007398, WO 2010/042877 or WO 2010/054401.

The lipid B used in the present invention is, for example, a lipid represented by formula (CL-I)

[C83]

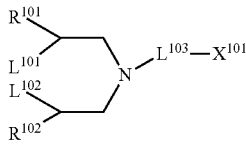

(wherein, $R^{101}$ and $R^{102}$, the same or different, are a linear or branched C10-C24 alkyl, C10-C24 alkenyl or C10-C24 alkynyl, $L^{101}$ and $L^{102}$ are hydrogen atoms or are combined together to form a single bond or C2-C8 alkylene, $L^{103}$ is a single bond, —CO— or —CO—O—, and in the case $L^{103}$ is a single bond, $X^{101}$ is a hydrogen atom, C1-C6 alkyl, C3-C6 alkenyl, pyrrolidin-3-yl, piperidin-3-yl or piperidin-4-yl, or a C1-C6 alkyl or C3-C6 alkenyl substituted with one to three of the same or different amino, monoalkylamino, dialkylamino, trialkylammonio, hydroxyl, alkoxy, carbamoyl, monoalkylcarbamoyl, dialkylcarbamoyl, pyrrolidinyl, piperidyl or morpholinyl, or in the case $L^{103}$ is —CO— or —CO—O—, $X^{101}$ is a pyrrolidin-2-yl, pyrrolidin-3-yl, piperidin-2-yl, piperidin-3-yl, piperidin-4-yl, morpholin-2-yl or morpholin-3-yl, or a C1-C6 alkyl or C3-C6 alkenyl substituted with one to three of the same or different amino, monoalkylamino, dialkylamino, trialkylammonio, hydroxyl, alkoxy, carbamoyl, monoalkylcarbamoyl, dialkylcarbamoyl, pyrrolidinyl, piperidyl or morpholinyl, and at least one of the substituents is an amino, monoalkylamino, dialkylamino, trialkylammonio, pyrrolidinyl, piperidyl or morpholinyl);

formula (CL-II)

[C84]

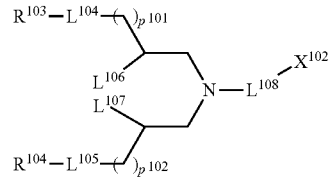

(wherein, $R^{103}$ and $R^{104}$, the same or different, are a linear or branched C12-C24 alkyl, C12-C24 alkenyl or C12-C24 alkynyl, $p^{101}$ and $p^{102}$, the same or different, are an integer of 0 to 3, $L^{106}$ and $L^{107}$ are hydrogen atoms or are combined together to form a single bond or C2-C8 alkylene, $L^{104}$ and $L^{105}$, the same or different, are —O—, —CO—O— or —O—CO—, $L^{108}$ is a single bond, —CO— or —CO—O—, and in the case $L^{108}$ is a single bond, $X^{102}$ is a hydrogen atom, C1-C6 alkyl, C3-C6 alkenyl, pyrrolidin-2-yl, pyrrolidin-3-yl, piperidin-3-yl or piperidin-4-yl, or a C1-C6 alkyl or C3-C6 alkenyl substituted with one to three of the same or different amino, monoalkylamino, dialkylamino, trialkylammonio, hydroxyl, alkoxy, carbamoyl, monoalkylcarbamoyl, dialkylcarbamoyl, pyrrolidinyl, piperidyl or morpholinyl, or in the case $L^{108}$ is —CO— or —CO—O—, $X^{102}$ is a pyrrolidin-2-yl, pyrrolidin-3-yl, piperidin-2-yl, piperidin-3-yl, piperidin-4-yl, morpholin-2-yl or morpholin-3-yl, or a C1-C6 alkyl or C3-C6 alkenyl substituted with one to three of the same or different amino, monoalkylamino, dialkylamino, trialkylammonio, hydroxyl, alkoxy, carbamoyl, monoalkylcarbamoyl, dialkylcarbamoyl, pyrrolidinyl, piperidyl or morpholinyl, and at least one of the substituents is an amino, monoalkylamino, dialkylamino, trialkylammonio, pyrrolidinyl, piperidyl or morpholinyl);

formula (CL-III)

[C85]

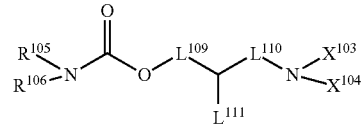

(wherein, $R^{105}$ is a linear or branched C8-C24 alkyl, C8-C24 alkenyl or C8-C24 alkynyl, $R^{106}$ is a linear or branched C8-C24 alkyl, C8-C24 alkenyl, C8-C24 alkynyl, C8-C24 alkoxyethyl, C8-C24 alkoxypropyl, C8-C24 alkenyloxyethyl, C8-C24 alkenyloxypropyl, C8-C24 alkynyloxyethyl or C8-C24 alkynyloxypropyl, $X^{103}$ and $X^{104}$, the same or different, are a C1-C3 alkyl or are combined together to form a C2-C8 alkylene, or $X^{103}$ forms a C2-C8 alkylene with $L^{111}$, $L^{111}$ is a hydrogen atom, C1-C6 alkyl, C3-C6 alkenyl, amino, monoalkylamino, hydroxyl, alkoxy, carbamoyl, monoalkylcarbamoyl or dialkylcarbamoyl, or a C1-C6 alkyl or C3-C6 alkenyl substituted with one to three of the same or different amino, monoalkylamino, hydroxyl, alkoxy, carbamoyl, monoalkylcarbamoyl or dialkylcarbamoyl, or forms a C2-C8 alkylene with $X^{103}$, $L^{109}$ is a C1-C6 alkylene, and $L^{110}$ is a single bond or a C1-C6 alkylene, provided that, in the case the sum of the number of carbon atoms of $L^{109}$ and $L^{110}$ is 7 or less and $L^{111}$ is a hydrogen atom, $L^{110}$ is a single bond, while in the case $L^{111}$ forms a C2-C6 alkylene with $X^{103}$, $L^{110}$ is a single bond, methylene or ethylene);

formula (CL-IV)

[C86]

(CL-IV)

(wherein, $R^{107}$ is a linear or branched C8-C24 alkyl, C8-C24 alkenyl or C8-C24 alkynyl, and $R^{108}$ is a linear or branched C8-C24 alkyl, C8-C24 alkenyl, C8-C24 alkynyl, C8-C24 alkoxyethyl, C8-C24 alkoxypropyl, C8-C24 alkenyloxyethyl, C8-C24 alkenyloxypropyl, C8-C24 alkynyloxyethyl or C8-C24 alkynyloxypropyl);

formula (CL-V)

[C87]

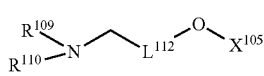

(CL-V)

(wherein, $R^{109}$ is a linear or branched C8-C24 alkyl, C8-C24 alkenyl or C8-C24 alkynyl, $R^{110}$ is a linear or branched C8-C24 alkyl, C8-C24 alkenyl, C8-C24 alkynyl, C8-C24 alkoxyethyl, C8-C24 alkoxypropyl, C8-C24 alkenyloxyethyl, C8-C24 alkenyloxypropyl, C8-C24 alkynyloxyethyl or C8-C24 alkynyloxypropyl, $L^{112}$ is a C1-C3 alkylene, and $X^{105}$ is a hydrogen atom or C1-C3 alkyl);

formula (CL-VI)

[C88]

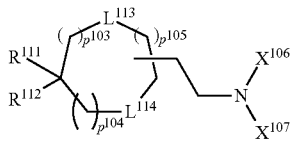

(CL-VI)

(wherein, $R^{111}$ and $R^{112}$, the same or different, are a linear or branched, optionally substituted C8-C24 alkyl, C8-C24 alkenyl or C8-C24 alkynyl, $X^{106}$ and $X^{107}$, the same or different, are a C1-C3 alkyl or are combined together to form a C2-C8 alkylene, $p^{103}$, $p^{104}$ and $p^{105}$, the same or different, are 0 or 1, provided that $p^{103}$, $p^{104}$ and $p^{105}$ are not simultaneously 0, and $L^{113}$ and $L^{114}$, the same or different, are 0, S or NH); or formula (CL-VII)

[C89]

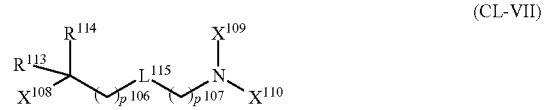

(CL-VII)

(wherein, $R^{113}$ and $R^{114}$, the same or different, are a linear or branched, optionally substituted C8-C24 alkyl, C8-C24 alkenyl or C8-C24 alkynyl, $X^{109}$ and $X^{110}$, the same or different, are a C1-C3 alkyl or are combined together to form a C2-C8 alkylene, $X^{108}$ is a hydrogen atom, hydroxyl, optionally substituted C1-C4 alkyl, optionally substituted C1-C4 alkoxy or optionally substituted C1-C4 acyloxy group, $L^{115}$ is —CO—O— or —O—CO—, $p^{106}$ is an integer of 0 to 3, and $p^{107}$ is an integer of 1 to 4).

In the definitions of each group in formula (CL-I), examples of linear or branched C10-C24 alkyl include decyl, undecyl, dodecyl, tridecyl, 6,10-dimethylundec-2-yl, tetradecyl, pentadecyl, hexadecyl, heptadecyl, octadecyl, 6,10,14-trimethylpentadcan-2-yl, nonadecyl, icosyl, henicosyl, docosyl, tricosyl and tetracosyl, preferably include decyl, undecyl, dodecyl, tridecyl, tetradecyl, pentadecyl, hexadecyl, heptadecyl and octadecyl, and more preferably include tridecyl, tetradecyl, pentadecyl, hexadecyl, heptadecyl and octadecyl.

Linear or branched C10-C24 alkenyl refer to linear or branched C10-C24 alkenyl containing 1 to 3 double bonds, examples of which include (Z)-dodec-7-enyl, (Z)-tetradec-7-enyl, (Z)-tetradec-9-enyl, (Z)-hexadec-4-enyl, (Z)-hexadec-7-enyl, (E)-hexadec-7-enyl, (Z)-hexadec-9-enyl, (7Z,10Z)-hexadeca-7,10-dienyl, (7Z,10Z,13Z)-hexadeca-7,10,13-trienyl, (Z)-octadec-6-enyl, (Z)-octadec-9-enyl, (E)-octadec-9-enyl, (9Z,12Z)-octadeca-9,12-dienyl, (Z)-octadec-11-enyl, (9Z,12Z,15Z)-octadeca-9,12,15-trienyl, (Z)-isoc-11-enyl and (11Z,14Z)-icosa-11,14-dienyl, preferably include (Z)-dodec-7-enyl, (Z)-tetradec-7-enyl, (Z)-hexadec-4-enyl, (Z)-hexadec-7-enyl, (E)-hexadec-7-enyl, (Z)-hexadec-9-enyl, (7Z,10Z)-hexadeca-7,10-dienyl, (7Z,10Z,13Z)-hexadeca-7,10,13-trienyl, (Z)-octadec-9-enyl, (9Z,12Z)-octadeca-9,12-dienyl and (11Z,14Z)-icosa-11,14-dienyl, and more preferably include (7Z,10Z)-hexadeca-7,10-dienyl and (9Z,12Z)-octadeca-9,12-dienyl.

Linear or branched C10-C24 alkynyl refer to linear or branched C10-C24 alkynyl having 1 to 3 triple bonds, and examples thereof include dec-9-ynyl, dodec-4-ynyl, dodec-11-ynyl, tetradec-5-ynyl, tetradec-6-ynyl, hexadec-7-ynyl, hexadeca-3,5-diynyl, hexadeca-5,7-diynyl and octadec-9-ynyl, preferably include hexadec-7-ynyl and octadec-9-ynyl, and more preferably include octadec-9-ynyl.

Furthermore, in formula (CL-I), $R^{101}$ and $R^{103}$ preferably are the same linear or branched C10-C24 alkyl, C10-C24 alkenyl or C10-C24 alkynyl, more preferably are the same linear or branched C10-C24 alkyl or C10-C24 alkenyl, and even more preferably are the same linear C10-C24 alkenyl.

Examples of C1-C3 alkylenes include methylene, ethylene and propylene, preferably include methylene and ethylene, and more preferably include methylene.

Examples of C1-C6 alkyl include methyl, ethyl, propyl, isopropyl, cyclopropyl, butyl, isobutyl, sec-butyl, tert-butyl, cyclobutyl, cyclopropylmethyl, pentyl, isopentyl, sec-pentyl, neopentyl, tert-pentyl, cyclopentyl, hexyl and cyclohexyl, preferably include methyl, ethyl, propyl, isopropyl, butyl, isobutyl, sec-butyl, tert-butyl, pentyl, isopentyl, sec-pentyl, tert-pentyl, neopentyl and hexyl, and more preferably include methyl, ethyl and propyl.

Examples of C3-C6 alkenyl include allyl, 1-propenyl, butenyl, pentenyl and hexenyl, and preferably include an allyl.

Monoalkylamino groups and dialkylamino groups respectively refer to amino groups substituted with one, or two of the same or different, C1-C6 alkyl (same as previously defined), or C1-C6 alkyl (same as previously defined) substituted with amino, methylamino, ethylamino, dimethylamino, diethylamino, pyrrolidinyl, piperidyl or morpholinyl, and examples thereof include methylamino, ethylamino, propylamino, butylamino, pentylamino, hexylamino, dimethylamino, diethylamino, ethylmethylamino, methylpropylamino, butylmethylamino, methylpentylamino, hexylmethylamino, aminoethylamino, aminopropylamino, (aminoethylmethylamine and bis(aminoethyl)amino groups, preferably include methylamino, ethylamino, dimethylamino, diethylamino, aminopropylamino and bis(aminoethyl)amino groups, and more preferably include methylamino and dimethylamino groups.

Trialkylammonio groups refer to ammonio groups substituted with three of the same or different C1-C6 alkyl (same as previously defined) or C1-C6 alkyl (same as previously defined) substituted with amino, methylamino, ethylamino, dimethylamino, diethylamino, pyrrolidyl, piperidyl or morpholinyl, and examples thereof include trimethylammonio, ethyldimethylammonio, diethylmethylammonio, triethylammonio, tripropylammonio, tributylammonio, tripentylammonio, trihexylammonio, tris(aminoethyl)ammonio, (aminoethyl)dimethylammonio and bis(aminoethyl)methylammonio groups, preferably include trimethylammonio, triethylammonio, tris(aminoethyl)ammonio, (aminoethyl)dimethylammonio and bis(aminoethyl)methylammonio groups, and more preferably include a trimethylammonio group.

In Compound (CL-I), the trialkylammonio group may also form a salt with a pharmaceutically acceptable anion (same as previously defined).

Alkoxy groups refer to hydroxyl substituted with a C1-C6 alkyl (same as previously defined) or a C1-C6 alkyl (same as previously defined) substituted with an amino, methylamino, ethylamino, dimethylamino, diethylamino, pyrrolidinyl, piperidyl or morpholinyl, and examples thereof include methoxy, ethoxy, propyloxy, butyloxy, pentyloxy, hexyloxy, aminoethoxy and methylaminoethoxy groups, preferably include methoxy, ethoxy, aminoethoxy and methylaminoethoxy groups, and more preferably include a methoxy group.

Monoalkylcarbamoyl and dialkylcarbamoyl respectively refer to carbamoyl substituted with one, or two of the same or different, C1-C6 alkyl (same as previously defined) or C1-C6 alkyl substituted with amino, methylamino, ethylamino, dimethylamino, diethylamino, pyrrolidinyl, piperidyl or morpholinyl, and examples thereof include methylcarbamoyl, ethylcarbamoyl, propylcarbamoyl, butylcarbamoyl, pentylcarbamoyl, hexylcarbamoyl, dimethylcarbamoyl, diethylcarbamoyl, ethylmethylcarbamoyl, methylpropylcarbamoyl, butylmethylcarbamoyl, methylpentylcarbamoyl, hexylmethylcarbamoyl, aminoethylcarbamoyl, aminopropylcarbamoyl, (aminoethyl)methylcarbamoyl and bis(aminoethyl)carbamoyl, preferably include methylcarbamoyl, ethylcarbamoyl and dimethylcarbamoyl, and more preferably include methylcarbamoyl and dimethylcarbamoyl.

$L^{101}$ and $L^{102}$ more preferably are hydrogen atoms. In this case, $R^{101}$ and $R^{102}$ are preferably the same or different and are a dodecyl, tetradecyl, (Z)-dodec-7-enyl, (Z)-tetradec-7-enyl, (Z)-hexadec-4-enyl, (Z)-hexadec-7-enyl, (E)-hexadec-7-enyl, (Z)-hexadec-9-enyl, (7Z,10Z)-hexadeca-7,10-dienyl, (7Z,10Z,13Z)-hexadeca-7,10,13-trienyl, (Z)-octadec-9-enyl or (9Z,12Z)-octadeca-9,12-dienyl, more preferably are a (Z)-tetradec-7-enyl, (Z)-hexadec-7-enyl, (7Z,10Z)-hexadeca-7,10-dienyl or (9Z,12Z)-octadeca-9,12-dienyl, and even more preferably are the same and are (Z)-tetradec-7-enyl, (Z)-hexadec-7-enyl, (7Z,10Z)-hexadeca-7,10-dienyl or (9Z,12Z)-octadeca-9,12-dienyl.

Furthermore, In the case $L^{101}$ and $L^{102}$ are hydrogen atoms, $X^{101}$ preferably is a hydrogen atom, methyl, pyrrolidyn-3-yl, piperidin-3-yl or piperidin-4-yl or a C1-C6 alkyl or C3-C6 alkenyl substituted with 1 to 3 of the same or different amino, monoalkylamino, dialkylamino, trialkylammonio, hydroxyl, alkoxy, carbamoyl, monoalkylcarbamoyl, dialkylcarbamoyl, pyrrolidinyl, piperidyl or morpholinyl, and more preferably is a hydrogen atom or methyl, or a C1-C6 alkyl or C3-C6 alkenyl substituted with 1 to 3 of the same or different amino, hydroxyl or carbamoyl, and even more preferably is a hydrogen atom or methyl.

In the case $L^{101}$ and $L^{102}$ are combined together to form a single bond or C1-C3 alkylene group, $R^{101}$ and $R^{102}$ are preferably the same or different and are a tetradecyl, hexadecyl, (Z)-tetradec-9-enyl, (Z)-hexadec-9-enyl, (Z)-octadec-6-enyl, (Z)-octadec-9-enyl, (E)-octadec-9-enyl, (Z)-octradec-11-enyl, (9Z,12Z)-octadeca-9,12-dienyl, (9Z,12Z,15Z)-octadeca-9,12,15-trienyl, (Z)-icos-11-enyl or (11Z,14Z)-icosa-11,14-dienyl, more preferably are a (Z)-octadec-9-enyl or (9Z,12Z)-octadeca-9,12-dienyl, and even more preferably are the same and are (Z)-octadec-9-enyl or (9Z,12Z)-octadeca-9,12-dienyl.

In the case $L^{101}$ and $L^{102}$ are combined together to form a single bond or C1-C3 alkylene, $X^{101}$ more preferably is a hydrogen atom, methyl, pyrrolidin-3-yl, piperidin-3-yl or piperidin-4-yl or a C1-C6 alkyl or C3-C6 alkenyl substituted with 1 to 3 of the same or different amino, monoalkylamino, dialkylamino, trialkylammonio, hydroxyl, alkoxy, carbamoyl, monoalkylcarbamoyl, dialkylcarbamoyl, pyrrolidinyl, piperidyl or morpholinyl, even more preferably is a hydrogen atom, methyl or C1-C6 alkyl or C3-C6 alkenyl substituted with 1 to 3 of the same or different amino, hydroxyl or carbamoyl, and most preferably is a hydrogen atom or methyl.

In the case $L^{101}$ and $L^{102}$ are combined together to form a single bond, $L^{103}$ representing —CO— or —CO—O—, and preferably representing —CO—, is a more preferred embodiment of the present invention. In this case, $X^{101}$ preferably is an aminomethyl, 1,2-diaminoethyl, 2-aminoethyl, 1,3-diaminopropyl, 1,4-diaminobutyl, 1,5-diaminopentyl, 3-aminopropyl, 4-aminobutyl or 5-aminopentyl, and more preferably is a 1,2-diaminoethyl, 1,3-diaminopropyl, 1,4-diaminobutyl or 1,5-diaminopentyl. $R^{101}$ and $R^{102}$ are preferably the same or different and are a tetradecyl, hexadecyl, (Z)-tetradec-9-enyl, (Z)-hexadec-9-enyl, (Z)-octadec-6-enyl, (Z)-octadec-9-enyl, (E)-octadec-9-enyl, (Z)-octadec-11-enyl, (9Z,12Z)-octadeca-9,12-dienyl, (9Z,12Z,15Z)-octadeca-9,12,15-trienyl or (Z)-icos-11-enyl or (11Z,14Z)- icosa-11,14-dienyl, more preferably are a (Z)-octadec-9-enyl or (9Z,12Z)-octadeca-9,12-dienyl, and even more preferably are the same and are (Z)-octadec-9-enyl or (9Z,12Z)-octadeca-9,12-dienyl.

$L^{103}$ more preferably is a single bond.

In the case $L^{103}$ is a single bond, $X^{101}$ more preferably is a hydrogen atom, methyl, pyrrolidin-3-yl, piperidin-3-yl or piperidin-4-yl, or a C1-C6 alkyl or C3-C6 alkenyl substituted with 1 to 3 of the same or different amino, monoalkylamino, dialkylamino, trialkylammonio, hydroxyl, alkoxy, carbamoyl, monoalkylcarbamoyl, dialkylcarbamoyl, pyrrolidinyl, piperidyl or morpholinyl, even more preferably is a hydrogen atom, methyl, hydroxymethyl, 2-hydroxyethyl, 2,3-dihydroxypropyl, 2-hydroxypropyl, 3-hydroxypropyl, 2-hydroxy-3-methoxypropyl, aminomethyl, 2-aminoethyl, 3-aminopropyl, 4-aminobutyl, 5-aminopentyl, 2-(N,N-dimethylamino)ethyl, 3-(N,N-dimethylamino)propyl, 2-carbamoylethyl, 2-dimethylcarbamoylethyl or 1-methylpiperidin-4-yl, and most preferably is a hydrogen atom or methyl.

In the case $L^{103}$ is —CO— or —CO—O—, $X^{101}$ more preferably is a pyrrolidin-3-yl, piperidin-3-yl or piperidin-4-yl, or a C1-C6 alkyl or C3-C6 alkenyl substituted with 1 to 3 of the same or different amino, monoalkylamino, dialkylamino, trialkylammonio, hydroxyl, alkoxy, carbamoyl, monoalkylcarbamoyl, dialkylcarbamoyl, pyrrolidinyl, piperidyl or morpholinyl, and at least one of the substituents is an amino, monoalkylamino, dialkylamino, trialkylammonio, pyrrolidinyl, piperidyl or morpholinyl, and $R^3$ even more preferably is an aminomethyl, 1,2-diaminoethyl, 2-aminoethyl, 3-diaminopropyl, 3-aminopropyl, 1,4-diaminobutyl, 4-aminobutyl, 1,5-diaminopentyl, 5-aminopentyl, (N,N-dimethylamino)methyl, 2-(N,N-dimethylamino)ethyl, 3-(N,N-dimethylamino)propyl, 1-hydroxy-2-aminoethyl or 1-amino-2-hydroxyethyl, and most preferably is a 1,2-diaminoethyl, 2-aminoethyl, 1,3-diaminopropyl, 3-aminopropyl, 1,4-diaminobutyl, 4-aminobutyl, 1,5-diaminopentyl or 5-aminopentyl.

$L^{103}$ representing a single bond and $X^{101}$ representing a hydrogen atom is also a more preferred embodiment of the present invention. In this case, $R^{101}$ and $R^{102}$ are preferably the same or different and are a dodecyl, tetradecyl, (Z)-dodec-7-enyl, (Z)-tetradec-7-enyl, (Z)-hexadec-4-enyl, (Z)-hexadec-7-enyl, (E)-hexadec-7-enyl, (Z)-hexadec-9-enyl, (7Z,10Z)-hexadeca-7,10-dienyl, (7Z,10Z,13Z)-hexadeca-7,10,13-trienyl, (Z)-octadec-9-enyl or (9Z,12Z)-octadeca-9,12-dienyl, are more preferably the same or different and are a (Z)-tetradec-7-enyl or (7Z,10Z)-hexadeca-7,10-dienyl, and even more preferably are the same and are (Z)-tetradec-7-enyl, (Z)-hexadec-7-enyl or (7Z,10Z)-hexadeca-7,10-dienyl.

$L^{103}$ representing a single bond and $X^{101}$ representing a methyl is also a more preferred embodiment of the present invention. In this case, $R^{101}$ and $R^{102}$ are preferably the same or different and are a dodecyl, tetradecyl, (Z)-dodec-7-enyl, (Z)-tetradec-7-enyl, (Z)-hexadec-4-enyl, (Z)-hexadec-7-enyl, (E)-hexadec-7-enyl, (Z)-hexadec-9-enyl, (7Z,10Z)-hexadeca-7,10-dienyl, (7Z,10Z,13Z)-hexadeca-7,10,13-trienyl, (Z)-octadec-9-enyl or (9Z,12Z)-octadeca-9,12-dienyl, more preferably are the same or different and are a (Z)-tetradec-7-enyl, (7Z,10Z)-hexadeca-7,10-dienyl or (9Z,12Z)-octadeca-9,12-dienyl, and even more preferably are the same and are (Z)-tetradec-7-enyl, (7Z,10Z)-hexadeca-7,10-dienyl or (9Z,12Z)-octadeca-9,12-dienyl.

In the definitions of each group in formula (CL-II), examples of linear or branched C12-C24 alkyl include dodecyl, tridecyl, tetradecyl, 2,6,10-trimethylundecyl, pentadecyl, 3,7,11-trimethyldodecyl, hexadecyl, heptadecyl, octadecyl, 6,10,14-trimethylpentadcan-2-yl, nonadecyl, 2,6,10,14-tetramethylpentadecyl, icosyl, 3,7,11,15-tetramethylhexadecyl, henicosyl, docosyl, tricosyl and tetracosyl, preferably include dodecyl, tridecyl, tetradecyl, pentadecyl, hexadecyl, heptadecyl and octadecyl, nonadecyl and icosyl, and more preferably include dodecyl, tridecyl, tetradecyl, pentadecyl, hexadecyl, heptadecyl and octadecyl.

Linear or branched C12-C24 alkenyl refer to linear or branched C12-C24 alkenyl containing 1 to 3 double bonds, and examples thereof include (Z)-tridec-8-enyl, (Z)-tetradec-9-enyl, (Z)-pentadec-8-enyl, (Z)-hexadec-9-enyl, (Z)-heptadec-5-enyl, (Z)-octadec-6-enyl, (Z)-heptadec-8-enyl, (Z)-octadec-9-enyl, (E)-heptadec-8-enyl, (E)-octadec-9-enyl, (Z)-heptadec-10-enyl, (Z)-octadec-11-enyl, (8Z,11Z)-heptadeca-8,11-dienyl, (9Z,12Z)-octadeca-9,12-dienyl, (8Z,11Z,14Z)-octadeca-8,11,14-trienyl, (9Z,12Z,15Z)-octadeca-9,12,15-trienyl, (Z)-nonadec-10-enyl, (Z)-icos-11-enyl, (10Z,13Z)-nonadeca-10,13-dienyl, (11Z,14Z)-icosa-11,14-dienyl, 2,6,10-trimethylundeca-1,5,9-trienyl, 3,7,11-trimethyldodeca-2,6,10-trienyl, 2,6,10,14-tetramethylpentadec-1-enyl and 3,7,11,15-tetramethylhexadec-2-enyl, preferably include (Z)-pentadec-8-enyl, (Z)-hexadec-9-enyl, (Z)-heptadec-5-enyl, (Z)-octadec-6-enyl, (Z)-heptadec-8-enyl, (Z)-octadec-9-enyl, (8Z,11Z)-heptadeca-8,11-dienyl and (9Z,12Z)-octadeca-9,12-dienyl, and more preferably include (Z)-heptadec-8-enyl, (Z)-octadec-9-enyl, (8Z,11Z)-heptadeca-8,11-dienyl and (9Z,12Z)-octadeca-9,12-dienyl.

Linear or branched C12-C24 alkynyl refer to linear or branched C12-C24 alkynyl having 1 to 3 triple bonds, and examples thereof include dodec-11-ynyl, tridec-12-ynyl, pentadec-6-ynyl, hexadec-7-ynyl, pentadeca-4,6-diynyl, hexadeca-5,7-diynyl, heptadec-8-ynyl and octadec-9-ynyl, preferably include pentadec-6-ynyl, hexadec-7-ynyl, pentadeca-4,6-diynyl, hexadeca-5,7-diynyl, heptadec-8-ynyl and octadec-9-ynyl, and more preferably include heptadec-8-ynyl and octadec-9-ynyl.

C1-C3 alkylenes, C1-C6 alkyl and C3-C6 alkenyl in the definitions of each group in formula (CL-II) respectively have the same meanings as those in the above-mentioned formula (CL-I).

Monoalkylamino, dialkylamino, trialkylammonio, alkoxy, monoalkylcarbamoyl, dialkylcarbamoyl respectively have the same meanings as those in the above-mentioned formula (CL-I).

$R^{103}$ and $R^{104}$ are preferably the same and are linear or branched C12-C24 alkyl, C12-C24 alkenyl or C12-C24 alkynyl, and are more preferably the same and are linear or branched C12-C24 alkyl or C12-C24 alkenyl.

$L^{104}$ and $L^{105}$ are preferably the same and are —O—, —CO—O— or —O—CO—.

In the case at least one of $L^{104}$ and $L^{105}$ is —O— or —O—CO—, $R^{103}$ and $R^{104}$ are more preferably the same or different and are a dodecyl, tetradecyl, hexadecyl, octadecyl, icosyl, docosyl, tetracosyl, (Z)-tetradec-9-enyl, (Z)-hexadec-9-enyl, (Z)-octadec-6-enyl, (Z)-octadec-9-enyl, (E)-octadec-9-enyl, (Z)-octadec-11-enyl, (9Z,12Z)-octadeca-9,12-dienyl, (9Z,12Z,15Z)-octadeca-9,12,15-trienyl, (Z)-icos-11-enyl, (11Z,14Z)-icosa-11,14-dienyl, 3,7,11-trimethyldodeca-2,6,10-trienyl or 3,7,11,15-tetramethylhexadec-2-enyl, and even more preferably are a tetradecyl, hexadecyl, octadecyl, (Z)-hexadec-9-enyl, (Z)-octadec-6-enyl, (Z)-octadec-9-enyl or (9Z,12Z)-octadeca-9,12-dienyl.

In the case at least one of $L^{104}$ and $L^{105}$ is —CO—O—, $R^{103}$ and $R^{104}$ more preferably respectively are a tridecyl, pentadecyl, heptadecyl, nonadecyl, henicosyl, tricosyl, (Z)- tridec-8-enyl, (Z)-pentadec-8-enyl, (Z)-heptadec-5-enyl, (Z)-heptadec-8-enyl, (E)-heptadec-8-enyl, (Z)-heptadec-10-enyl, (8Z,11Z)-heptadeca-8,11-dienyl, (8Z,11Z,14Z)-octadeca-8,11,14-trienyl, (Z)-nonadec-10-enyl, (10Z,13Z)-nonadeca-10,13-dienyl, (11Z,14Z)-icosa-11,14-dienyl, 2,6,10-trimethylundeca-1,5,9-trienyl or 2,6,10,14-tetramethylpentadec-1-enyl, and even more preferably are a tridecyl, pentadecyl, heptadecyl, (Z)-pentadec-8-enyl, (Z)-heptadec-5-enyl, (Z)-heptadec-8-enyl or (8Z,11Z)-heptadeca-8,11-dienyl.

$p^{101}$ and $p^{102}$ are more preferably simultaneously 0 or 1.

$L^{106}$ and $L^{107}$ more preferably are combined together to form a single bond or C1-C3 alkylene. In the case $L^{106}$ and $L^{107}$ are combined together to form a single bond or C1-C3 alkylene, $X^{102}$ more preferably is a hydrogen atom, methyl, pyrrolidin-2-yl, pyrrolidin-3-yl, piperidin-3-yl, piperidin-4-yl, morpholin-2-yl or morpholin-3-yl, or a C1-C6 alkyl or C3-C6 alkenyl substituted with 1 to 3 of the same or different amino, monoalkylamino, dialkylamino, trialkylammonio, hydroxyl, alkoxy, carbamoyl, monoalkylcarbamoyl, dialkylcarbamoyl, pyrrolidinyl, piperidyl or morpholinyl, even more preferably is a hydrogen atom or methyl, or a C1-C6 alkyl or C3-C6 alkenyl substituted with 1 to 3 of the same or different amino, trialkylammonio, hydroxyl or carbamoyl, and most preferably is a hydrogen atom, methyl, 2,3-dihydroxypropyl, 3-hydroxypropyl, aminomethyl, 1,2-diaminoethyl, 2-aminoethyl, 1,3-diaminopropyl, 1,4-diaminobutyl, 1,5-diaminopentyl, 3-aminopropyl, 4-aminobutyl, 5-aminopentyl or 2-carbamoylethyl. Among these substituents, the alkyl moiety in the monoalkylamino, dialkylamino, trialkylammonio, alkoxy, monoalkylcarbamoyl and dialkylcarbamoyl has the same meaning as the above-mentioned C1-C4 alkyl. Two or three alkyl in the dialkylamino, trialkylammonio and dialkylcarbamoyl may respectively be the same or different.

In the case $L^{106}$ and $L^{107}$ are combined together to form a single bond, $p^{101}$ and $p^{102}$ are preferably the same or different and are an integer of 1 to 3.

In the case $L^{106}$ and $L^{107}$ are combined together to form a single bond, $L^{108}$ is —CO— or —CO—O— and preferably is —CO—.

In the case $L^{106}$ and $L^{107}$ are hydrogen atoms, $X^{102}$ preferably is a hydrogen atom, methyl, pyrrolidin-2-yl, pyrrolidin-3-yl, piperidin-2-yl, piperidin-3-yl, piperidin-4-yl, morpholin-2-yl or morpholin-3-yl, or a C1-C6 alkyl or C3-C6 alkenyl substituted with 1 to 3 of the same or different amino, monoalkylamino, dialkylamino, trialkylammonio, hydroxyl, alkoxy, carbamoyl, monoalkylcarbamoyl, dialkylcarbamoyl, pyrrolidinyl, piperidyl or morpholinyl, more preferably is a hydrogen atom or methyl, or a C1-C6 alkyl or C3-C6 alkenyl substituted with 1 to 3 of the same or different amino, trialkylammonio, hydroxyl or carbamoyl, and even more preferably is a hydrogen atom, methyl, 2,3-dihydroxypropyl, 3-hydroxypropyl, aminomethyl, 1,2-diaminoethyl, 2-aminoethyl, 1,3-diaminopropyl, 1,4-diaminobutyl, 1,5-diaminopentyl, 3-aminopropyl, 4-aminobutyl, 5-aminopentyl or 2-carbamoylethyl. Among these substituents, the alkyl moiety in the monoalkylamino, dialkylamino, trialkylammonio, alkoxy, monoalkylcarbamoyl and dialkylcarbamoyl has the same meaning as the above-mentioned C1-C4 alkyl. Two or three alkyl in the dialkylamino, trialkylammonio and dialkylcarbamoyl may respectively be the same or different.

$L^{108}$ preferably is a single bond. Furthermore, in the case $L^{108}$ is a single bond, $L^{104}$ and $L^{105}$ preferably are —O—.

In the case $L^{108}$ is a single bond, $X^{102}$ preferably is a hydrogen atom, methyl, pyrrolidin-3-yl, piperidin-3-yl or piperidin-4-yl, or a C1-C6 alkyl or C3-C6 alkenyl substituted with 1 to 3 of the same or different amino, monoalkylamino, dialkylamino, trialkylammonio, hydroxyl, alkoxy, carbamoyl, monoalkylcarbamoyl, dialkylcarbamoyl, pyrrolidinyl, piperidyl or morpholinyl, more preferably is a hydrogen atom, methyl, hydroxymethyl, 2-hydroxyethyl, 2,3-dihydroxypropyl, 2-hydroxypropyl, 3-hydroxypropyl, 2-hydroxy-3-methoxypropyl, aminomethyl, 2-aminoethyl, 3-aminopropyl, 4-aminobutyl, 5-aminopentyl, 2-(N,N-dimethylamino)ethyl, 3-(N,N-dimethylamino)propyl, 2-carbamoylethyl, 2-dimethylcarbamoylethyl or 1-methylpiperidin-4-yl, and even more preferably is a hydrogen atom, methyl, 2,3-dihydroxypropyl, 3-hydroxypropyl, 2-aminoethyl, 3-aminopropyl, 4-aminobutyl, 5-aminopentyl or 2-carbamoylethyl. Among these substituents, the alkyl moiety in the monoalkylamino, dialkylamino, trialkylammonio, alkoxy, monoalkylcarbamoyl and dialkylcarbamoyl has the same meaning as the above-mentioned C1-C4 alkyl. Two or three alkyl in the dialkylamino, trialkylammonio and dialkylcarbamoyl may respectively be the same or different.

$L^{104}$ and $L^{105}$ preferably are —O—. However, in the case $L^{108}$ is a single bond and $X^{102}$ is a hydrogen atom, $L^{104}$ and $L^{105}$ are preferably the same and are —CO—O— or —O—CO—, and more preferably are —CO—O—.

In the case $L^{108}$ is —CO— or —CO—O—, $L^{104}$ and $L^{105}$ are preferably the same and are —CO—O— or —O—CO—, and more preferably are —CO—O—.

In the case $L^{108}$ is —CO— or —CO—O—, $X^{102}$ preferably is a pyrrolidin-3-yl, piperidin-3-yl or piperidin-4-yl, or a C1-C6 alkyl or C3-C6 alkenyl substituted with 1 to 3 of the same or different amino, monoalkylamino, dialkylamino, trialkylammonio, hydroxyl, alkoxy, carbamoyl, monoalkylcarbamoyl, dialkylcarbamoyl, pyrrolidinyl, piperidyl or morpholinyl, and at least one of the substituents is an amino, monoalkylamino, dialkylamino, trialkylammonio, pyrrolidinyl, piperidyl or morpholinyl, $X^{102}$ more preferably is an aminomethyl, 1,2-diaminoethyl, 2-aminoethyl, 1,3-diaminopropyl, 3-aminopropyl, 1,4-diaminobutyl, 4-aminobutyl, 1,5-diaminopentyl, 5-aminopentyl, (N,N-dimethylamino)methyl, 2-(N,N-dimethylamino)ethyl, 3-(N,N-dimethylamino)propyl or 1-amino-2-hydroxyethyl, and even more preferably is an aminomethyl, 1,2-diaminoethyl, 2-aminoethyl, 1,3-diaminopropyl, 3-aminopropyl, 1,4-diaminobutyl, 4-aminobutyl, 1,5-diaminopentyl or 5-aminopentyl. Among these substituents, the alkyl moiety in the monoalkylamino, dialkylamino, trialkylammonio, alkoxy, monoalkylcarbamoyl and dialkylcarbamoyl has the same meaning as the above-mentioned C1-C4 alkyl. Two or three alkyl in the dialkylamino, trialkylammonio and dialkylcarbamoyl may respectively be the same or different.

$L^{104}$ and $L^{105}$ are preferably the same and are —CO—O— or —O—CO—, and more preferably are —CO—O—.

In the definitions of each group in formulas (CL-III), (CL-IV) and (CL-V), the linear or branched C8-C24 alkyl, C8-C24 alkenyl and C8-C24 alkynyl respectively have the same meanings as those in the above-mentioned formulas (I) to (IV), and preferably similar groups.

In the definitions of each group in formulas (CL-III), (CL-IV) and (CL-V), examples of the alkyl moiety in C8-C24 alkoxyethyl and C8-C24 alkoxypropyl include those indicated as examples of the above-mentioned linear or branched C8-C24 alkyl.

Examples of the alkynyl moiety in alkynyloxyethyl and alkynyloxypropyl include those indicated as examples of the above-mentioned linear or branched C8-C24 alkynyl.

$R^{105}$ and $R^{106}$ are preferably the same or different and are linear or branched C8-C24 alkyl or C8-C24 alkenyl, are more preferably the same or different and are linear or branched C8-C24 alkenyl, and are even more preferably the same or different and are linear C8-C24 alkenyl. In addition, $R^{105}$ and $R^{106}$ are more preferably the same, and in that case, preferably are linear or branched C12-C24 alkyl, C12-C24 alkenyl or C12-C24 alkynyl, and more preferably are linear C12-C24 alkenyl. Linear or branched C12-C24 alkyl, C12-C24 alkenyl and C12-C24 alkynyl respectively have the same meaning as in the above-mentioned formula (CL-II).

$R^{105}$ and $R^{106}$ are preferably the same or different and are linear or branched C8-C24 alkyl or C8-C24 alkenyl, are more preferably the same or different and are linear or branched C8-C24 alkenyl, and even more preferably are the same or different and are linear C8-C24 alkenyl. In addition, $R^{105}$ and $R^{106}$ are preferably the same and in that case, preferably are linear or branched C15-C20 alkyl, C15-C20 alkenyl or C15-C20 alkynyl, and more preferably are linear C15-C20 alkenyl. Linear or branched C15-C20 alkyl, C15-C20 alkenyl and C15-C20 alkynyl respectively have the same meaning as in the above-mentioned formulas (I) to (IV), and similar groups are preferable.

In the case $R^{105}$ and $R^{106}$ are different, $R^{105}$ preferably is a linear or branched C15-C20 alkyl, C15-C20 alkenyl or C15-C20 alkynyl, and $R^{106}$ preferably is a linear or branched C8-C12 alkyl. Here, examples of linear or branched C8-C12 alkyl include octyl, nonyl, decyl, undecyl and dodecyl, and preferably include octyl, decyl and dodecyl.

$R^{105}$ more preferably is a linear C15-C20 alkenyl and $R^{106}$ more preferably is a linear C8-C12 alkyl, and $R^{105}$ even more preferably is a (Z)-octadec-9-enyl or (9Z,12Z)-octadeca-9,12-dienyl, while $R^{106}$ even more preferably is an octyl, decyl or dodecyl.

In the case $R^{105}$ and $R^{106}$ are different, $R^{105}$ preferably is a linear or branched C8-C24 alkyl, C8-C24 alkenyl or C8-C24 alkynyl, and $R^{106}$ preferably is a C8-C24 alkoxyethyl, C8-C24 alkoxypropyl, C8-C24 alkenyloxyethyl, C8-C24 alkenyloxypropyl, C8-C24 alkynyloxyethyl or C8-C24 alkynyloxypropyl. In this case, $R^{105}$ more preferably is a linear C8-C24 alkenyl and $R^{106}$ more preferably is a C8-C24 alkenyloxyethyl, $R^{105}$ even more preferably is a (Z)-octadec-9-enyl, (9Z,12Z)-octadeca-9,12-dienyl or (11Z,14Z)-icosa-11,14-dienyl and $R^{106}$ even more preferably is a (Z)-octadec-9-enyloxyethyl, (9Z,12Z)-octadeca-9,12-dienyloxyethyl or (11Z,14Z)-icosa-11,14-dienyloxyethyl, and $R^{105}$ most preferably is a (9Z,12Z)-octadeca-9,12-dienyl and $R^{106}$ most preferably is a (9Z,12Z)-octadeca-9,12dienyloxyethyl.

In the case $R^{105}$ and/or $R^{106}$ are the same or different and are a linear or branched C8-C24 alkyl or C8-C24 alkenyl, $R^{105}$ and $R^{106}$ are preferably the same or different and are a tetradecyl, hexadecyl, (Z)-tetradec-9-enyl, (Z)-hexadec-9-enyl, (Z)-octadec-6-enyl, (Z)-octadec-9-enyl, (E)-octadec-9-enyl, (Z)-octadec-11-enyl, (9Z,12Z)-octadeca-9,12-dienyl, (9Z,12Z,15Z)-octadeca-9,12,15-trienyl, (Z)-icos-11-enyl, (11Z,14Z)-icosa-11,14-dienyl or (Z)-docos-13-enyl, are more preferably the same or different and are a hexadecyl, (Z)-hexadec-9-enyl, (Z)-octadec-6-enyl, (Z)-octadec-9-enyl, (9Z,12Z)-octadeca-9,12-dienyl, (Z)-icos-11-enyl or (11Z,14Z)-icosa-11,14-dienyl, are even more preferably the same or different and are a (Z)-octadec-9-enyl, (9Z,12Z)-octadeca-9,12-dienyl or (11Z,14Z)-icosa-11,14-dienyl, and are most preferably the same and are (9Z,12Z)-octadeca-9,12-dienyl.

$R^{107}$ and $R^{108}$ have the same meanings as the above-mentioned $R^{105}$ and $R^{106}$, respectively, and groups similar to the above-mentioned $R^{107}$ and $R^{108}$ are preferable. However, in the case $R^{107}$ is a linear or branched C8-C24 alkyl, C8-C24 alkenyl or C8-C24 alkynyl, $R^{107}$ and $R^{108}$ are preferably the same and are (9Z,12Z)-octadeca-9-dienyl.

$R^{109}$ and $R^{110}$ have the same meanings as the above-mentioned $R^{105}$ and $R^{106}$, respectively, and groups similar to the above-mentioned $R^{109}$ and $R^{110}$ are preferable. However, $R^{109}$ and $R^{110}$ are preferably the same and are C15-C20 alkyl, C15-C20 alkenyl or C15-C20 alkynyl, and more preferably are the same and are (9Z,12Z)-octadeca-9-dienyl.

Examples of C1-C3 alkyl represented by $X^{103}$ and $X^{104}$ include methyl, ethyl, propyl, isopropyl and cyclopropyl, preferably include methyl and ethyl, and even more preferably include methyl.

Examples of C2-C8 alkylenes jointly formed by $X^{103}$ and $X^{104}$ include ethylene, propylene, butylene, pentylene, hexylene, heptylene and octylene, preferably include butylene, pentylene and hexylene, and more preferably include hexylene.

Examples of C2-C8 alkylenes formed by $X^{103}$ with $L^{111}$ include ethylene, propylene, butylene, pentylene, hexylene, heptylene and octylene, preferably include propylene, butylene and pentylene, more preferably include propylene and butylene, and even more preferably include propylene.

$X^{103}$ and $X^{104}$ are preferably the same or different and are a methyl or ethyl, are combined together to form butylene, pentylene or hexylene, or $X^{103}$ forms ethylene, propylene or butylene together with $L^{111}$. In addition, $X^{103}$ and $X^{104}$ are preferably the same or different and are a methyl or ethyl or are combined together to form butylene, pentylene or hexylene, and preferably $X^{103}$ forms ethylene, propylene or butylene together with $L^{111}$ while $X^{104}$ is a methyl or ethyl. More preferably, $X^{103}$ and $X^{104}$ are the same and are methyl or are combined together to form hexylene, and even more preferably $X^{103}$ forms propylene or butylene together with $L^{111}$ while $X^{104}$ is a methyl.

C1-C6 alkyl, C3-C6 alkenyl, monoalkylamino, alkoxy, monoalkylcarbamoyl and dialkylcarbamoyl represented by $L^{111}$ respectively have the same meanings as those in the above-mentioned formula (CL-I).

$L^{111}$ preferably is a hydrogen atom, C1-C6 alkyl, amino, monoalkylamino, hydroxyl or alkoxy group, or a C1-C6 alkyl substituted with 1 to 3 of the same or different amino, monoalkylamino, hydroxyl or alkoxy groups or forms a C2-C6 alkylene together with $X^{103}$, more preferably is a hydrogen atom, methyl, amino, methylamino, hydroxyl or methoxy group or a methyl substituted with 1 to 3 of the same or different amino or hydroxyl, or forms ethylene, propylene or butylene together with $X^{103}$, even more preferably is a hydrogen atom, C1-C3 alkyl or hydroxyl or forms propylene or butylene together with $X^{103}$, and most preferably is a hydrogen atom or forms propylene together with $X^{103}$.

Examples of C1-C6 alkylenes represented by $L^{109}$ and $L^{110}$ include methylene, ethylene, propylene, butylene, pentylene and hexylene, and preferably include methylene and ethylene.

$L^{109}$ preferably is methylene, ethylene or propylene and more preferably is methylene or ethylene, and $L^{110}$ preferably is a single bond, methylene or ethylene and more preferably is a single bond or methylene. The sum of the number of carbon atoms of $L^{109}$ and $L^{110}$ is preferably 1 to 3 and more preferably 2. In either case, preferably $X^{103}$ and $X^{104}$ are the same or different and are a methyl or ethyl and $L^{111}$ is a hydrogen atom, methyl, amino, methylamino, hydroxyl or methoxy group or a methyl substituted with 1 to 3 of the same or different amino or hydroxyl, $X^{103}$ and $X^{104}$ are combined together to form pentylene, hexylene or heptylene and $L^{111}$ preferably is a hydrogen atom, methyl, amino, methylamino, hydroxyl or methoxy group or a methyl substituted with 1 to 3 of the same or different amino or hydroxyl, or $X^{103}$ and $L^{111}$ are combined together to form propylene, butylene or pentylene and $X^{104}$ is a methyl or ethyl, and preferably $X^{103}$ and $X^{104}$ are a methyl and $L^{111}$ is a hydrogen atom, $X^{103}$ and $X^{104}$ are combined together to form pentylene or hexylene and $L^{111}$ is a hydrogen atom, or $X^{103}$ and $L^{111}$ are combined together to form propylene and $X^{104}$ is a methyl.

In the definitions of each group in formula (CL-V), examples of C1-C3 alkyl represented by $X^{105}$ include methyl, ethyl, propyl, isopropyl and cyclopropyl, preferably include methyl, ethyl and isopropyl, and more preferably include methyl and ethyl. Furthermore, $X^{105}$ preferably is a hydrogen atom or methyl and most preferably is a hydrogen atom.

Examples of C1-C3 alkylenes represented by $L^{112}$ include methylene, ethylene and propylene and preferably include methylene and ethylene.

In the definitions of each group in formula (CL-VI) and formula (CL-VII), linear or branched, optionally substituted C8-C24 alkyl, C8-C24 alkenyl and C8-C24 alkynyl have the same meaning as those in the above-mentioned formulas (I) to (V''').

Optionally substituted C1-C4 alkyl, optionally substituted C1-C4 alkoxy groups and optionally substituted C1-C4 acyloxy groups represented by $X^{108}$ in formula (CL-VII) have the same meanings as those in the above-mentioned formulas (I) to (IV).

$R^{111}$ and $R^{112}$ in formula (CL-VI) are preferably the same and are linear or branched C8-C24 alkyl, C8-C24 alkenyl or C8-C24 alkynyl, and are more preferably the same and are linear or branched C8-C24 alkyl or C8-C24 alkenyl.

$R^{111}$ and $R^{112}$ are preferably the same or different and are an octyl, decyl, dodecyl, tetradecyl, hexadecyl, octadecyl, icosyl, docosyl, tetracosyl, (Z)-tetradec-9-enyl, (Z)-hexadec-9-enyl, (Z)-octadec-6-enyl, (Z)-octadec-9-enyl, (E)-octadec-9-enyl, (Z)-octadec-11-enyl, (9Z,12Z)-octadeca-9,12-dienyl, (9Z,12Z,15Z)-octadeca-9,12,15-trienyl, (Z)-icos-11-enyl, (11Z,14Z)-icosa-11,14-dienyl, 3,7,11-trimethyldodeca-2,6,10-trienyl or 3,7,11,15-tetramethylhexadec-2-enyl, are more preferably the same or different and are a dodecyl, tetradecyl, (Z)-hexadec-9-enyl, (Z)-octadec-6-enyl, (Z)-octadec-9-enyl or (9Z,12Z)-octadeca-9,12-dienyl, and even more preferably are the same and are a (Z)-hexadec-9-enyl, (Z)-octadec-6-enyl, (Z)-octadec-9-enyl or (9Z,12Z)-octadeca-9,12-dienyl.

$X^{106}$ and $X^{107}$ are preferably the same or different and are a methyl or ethyl and are more preferably the same and are methyl.

Examples of C2-C8 alkylenes jointly formed by $X^{106}$ and $X^{107}$ include ethylene, propylene, butylene, pentylene, hexylene, heptylene and octylene, preferably include butylene, pentylene and hexylene, and more preferably include butylene and pentylene.

$X^{106}$ and $X^{107}$ are preferably the same and are methyl or are combined together to form butylene, pentylene or hexylene.

$p^{103}$ and $p^{104}$ are preferably simultaneously 0 and $p^{105}$ is preferably 1.

$L^{113}$ and $L^{114}$ are preferably simultaneously 0.

$R^{113}$ and $R^{114}$ are preferably the same and are linear or branched C8-C24 alkyl, C8-C24 alkenyl or C8-C24 alkynyl, and are more preferably the same and are linear or branched C8-C24 alkyl or C8-C24 alkenyl.

C1-C3 alkyl and C2-C8 alkylenes represented by $X^{109}$ and $X^{110}$ respectively have the same meanings as those in the above-mentioned formula (CL-VI).

$X^{108}$ preferably is a hydrogen atom, hydroxyl, methyl or methoxy group, more preferably is a hydrogen atom or hydroxyl, and even more preferably is a hydrogen atom.

$L^{115}$ preferably is —O—CO—. In this case, $p^{106}$ is preferably 0 or 1 and $p^{107}$ is an integer of 2 to 4, and more preferably $p^{106}$ is 0 or 1 and $p^{107}$ is 3.

In the case $L^{115}$ is —CO—O—, $p^{106}$ is preferably 0 and $p^{107}$ preferably is an integer of 2 to 4, and more preferably $p^{106}$ is 0 and $p^{107}$ is 3.

Although specific examples of lipid B used in the present invention are listed in the following Tables 1 to 27, lipid B of the present invention is not limited thereto.

TABLE 1

| Compound No. | Structural Formula |
|---|---|
| CL-1 | |
| CL-2 | |
| CL-3 | |
| CL-4 | |

TABLE 1-continued
| Compound No. | Structural Formula |
|---|---|
| CL-5 | 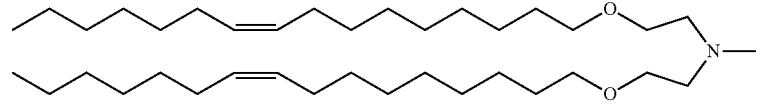 [SMILES: CCCCCC/C=C\CCCCCCCCOCCN(C)CCOCCCCCCCC/C=C\CCCCCC] |
| CL-6 | 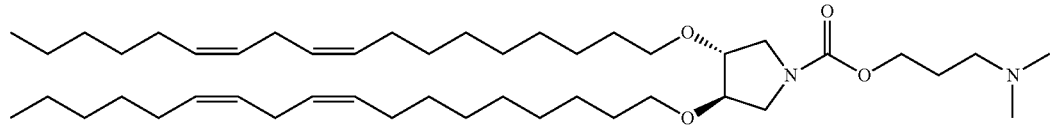 [SMILES: CCCCC/C=C\C/C=C\CCCCCCCCO[C@@H]1CN(C(=O)OCCCN(C)C)C[C@H]1OCCCCCCCC/C=C\C/C=C\CCCCC] |
TABLE 2
| Compound No. | Structural Formula |
|---|---|
| CL-7 | 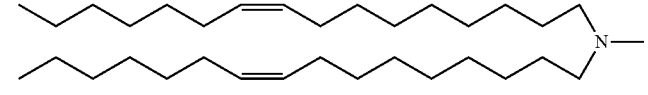 [SMILES: CCCCCC/C=C\CCCCCCCCN(C)CCCCCCCC/C=C\CCCCCC] |
| CL-8 | 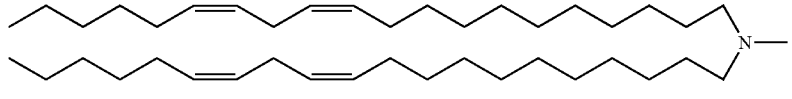 |
| CL-9 | 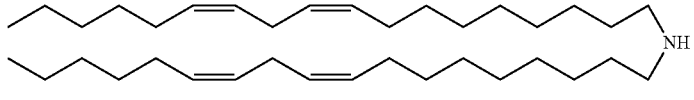 [SMILES: CCCCC/C=C\C/C=C\CCCCCCCCNCCCCCCCC/C=C\C/C=C\CCCCC] |
| CL-10 | 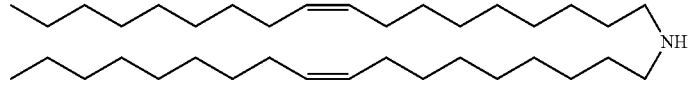 [SMILES: CCCCCCCC/C=C\CCCCCCCCNCCCCCCCC/C=C\CCCCCCCC] |
| CL-11 | 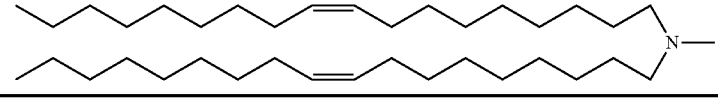 |
TABLE 3
| Compound No. | Structural Formula |
|---|---|
| CL-12 | 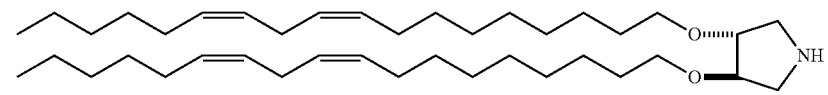 [SMILES: CCCCC/C=C\C/C=C\CCCCCCCCO[C@@H]1CNC[C@H]1OCCCCCCCC/C=C\C/C=C\CCCCC] |
| CL-13 | 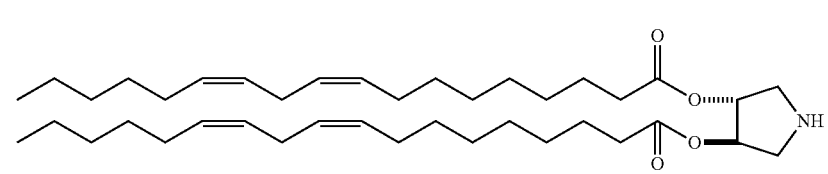 [SMILES: CCCCC/C=C\C/C=C\CCCCCCCC(=O)O[C@@H]1CNC[C@H]1OC(=O)CCCCCCC/C=C\C/C=C\CCCCC] |
| CL-14 | 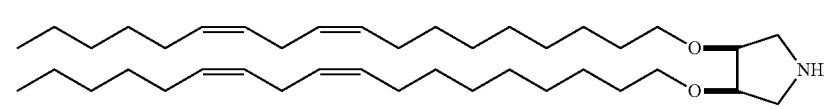 [SMILES: CCCCC/C=C\C/C=C\CCCCCCCCO[C@H]1CNC[C@H]1OCCCCCCCC/C=C\C/C=C\CCCCC] |

TABLE 3-continued

| Compound No. | Structural Formula |
|---|---|
| CL-15 | |
| CL-16 | |
| CL-17 | |
| CL-18 | |
| CL-19 | |
| CL-20 | |
| CL-21 | |

TABLE 4

| Compound No. | Structural Formula |
|---|---|
| CL-22 | |
| CL-23 | |
| CL-24 | |

TABLE 5

| CL-25 | |
|---|---|

TABLE 5-continued
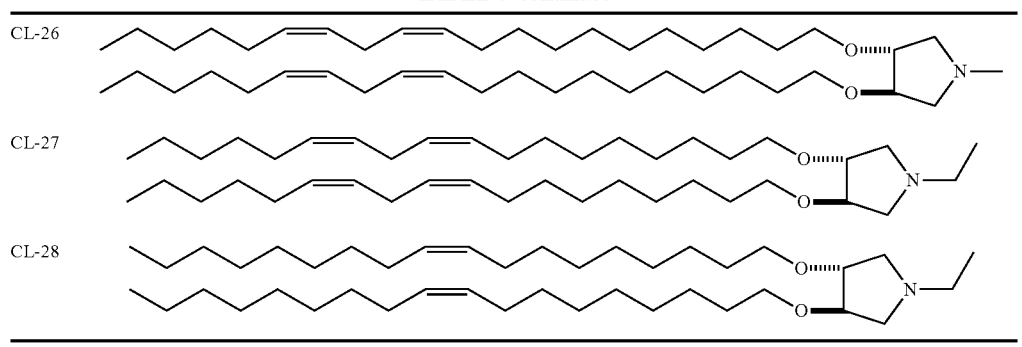
TABLE 6
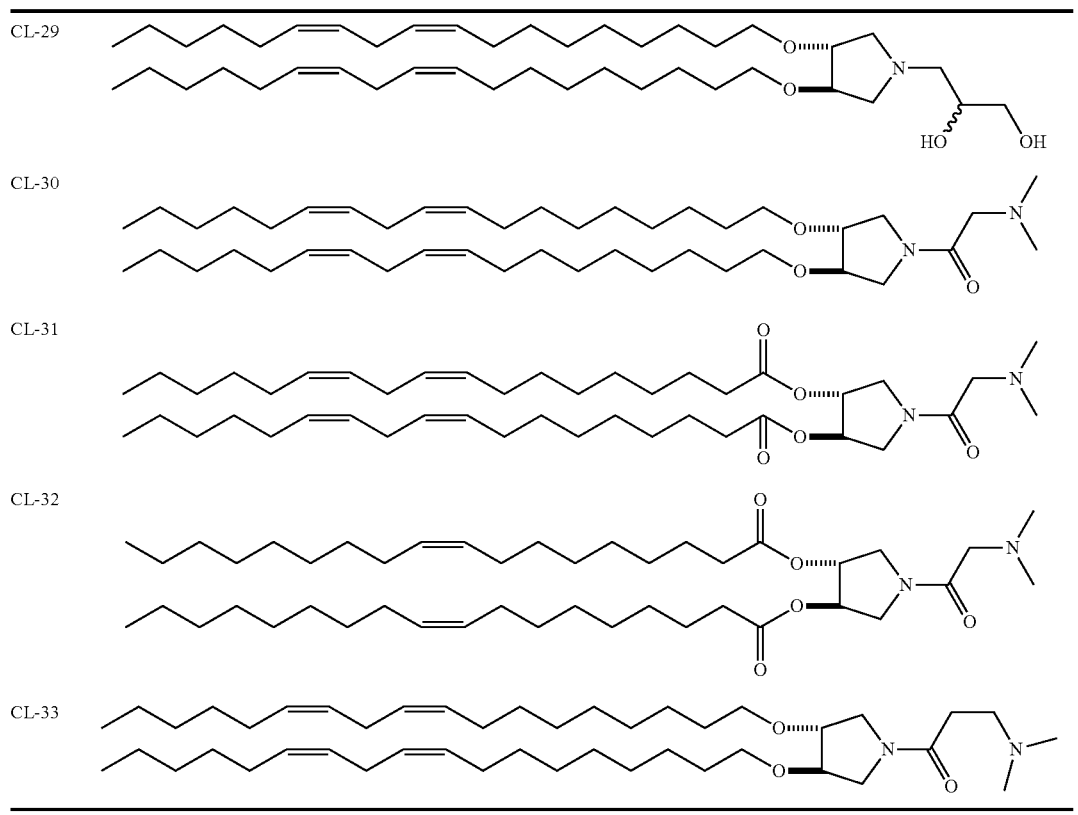
TABLE 7
| Compound No. | Structural Formula |
| --- | --- |
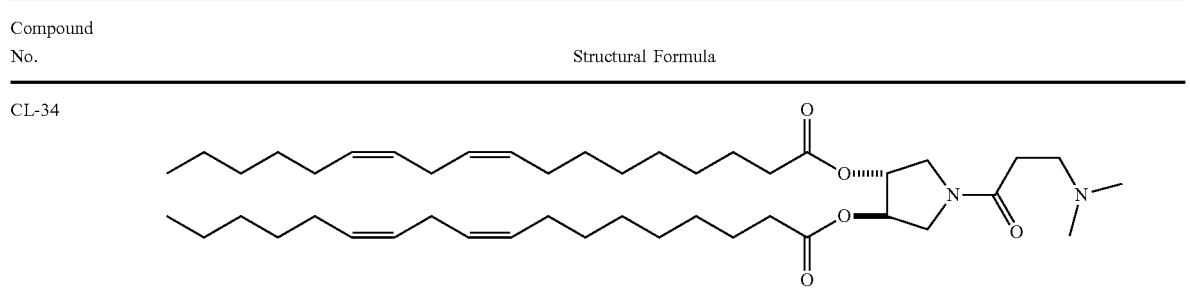

TABLE 7-continued

| Compound No. | Structural Formula |
|---|---|
| CL-35 | |
| CL-36 | |
| CL-37 | |

TABLE 8

| | |
|---|---|
| CL-38 | |
| CL-39 | |
| CL-40 | |
| CL-41 | |

TABLE 9

| | |
|---|---|
| CL-42 | |
| CL-43 | |
| CL-44 | |
| CL-45 | |

TABLE 9-continued
| Compound No. | Structural Formula |
|---|---|
| CL-46 | 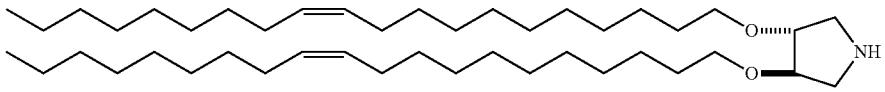 [SMILES: CCCCCCCC/C=C\CCCCCCCCCCO[C@@H]1CNC[C@H]1OCCCCCCCCCC/C=C\CCCCCCCC] |
| CL-47 | 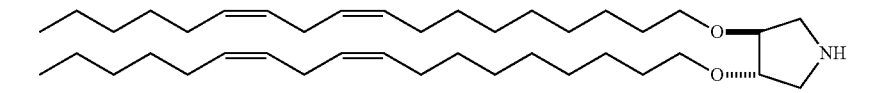 |
| CL-48 | 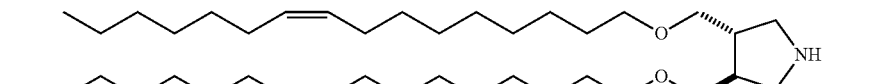 |
| CL-49 | 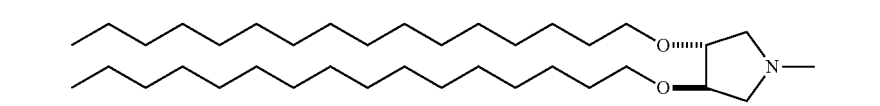 [SMILES: CCCCCCCCCCCCCCCCO[C@@H]1CN(C)C[C@H]1OCCCCCCCCCCCCCCCC] |
| CL-50 | 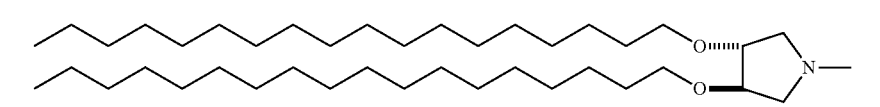 [SMILES: CCCCCCCCCCCCCCCCCCO[C@@H]1CN(C)C[C@H]1OCCCCCCCCCCCCCCCCCC] |
| CL-51 | 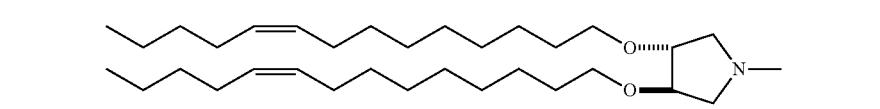 [SMILES: CCCC/C=C\CCCCCCCCO[C@@H]1CN(C)C[C@H]1OCCCCCCCC/C=C\CCCC] |
TABLE 10
| Compound No. | Structural Formula |
|---|---|
| CL-52 | 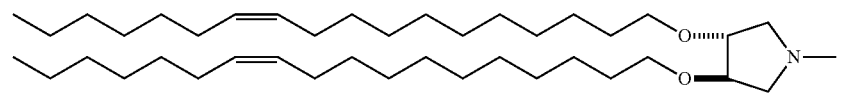 [SMILES: CCCCCC/C=C\CCCCCCCCCCO[C@@H]1CN(C)C[C@H]1OCCCCCCCCCC/C=C\CCCCCC] |
| CL-53 | 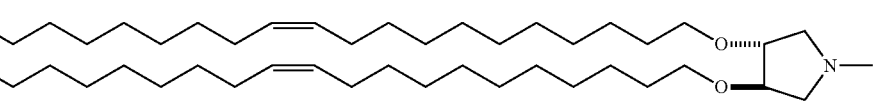 |
| CL-54 | 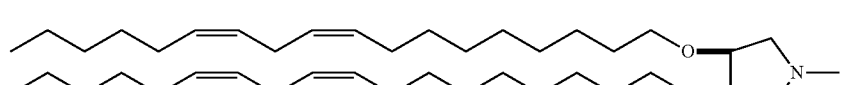 |
| CL-55 | 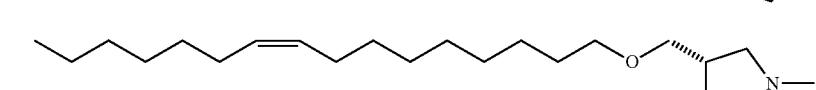 |
| CL-56 | 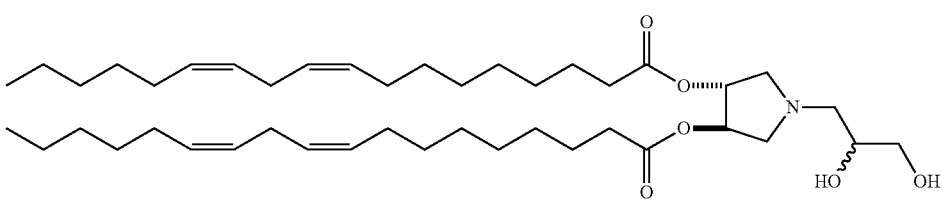 [SMILES: CCCCC/C=C\C/C=C\CCCCCCCC(=O)O[C@@H]1CN(CC(O)CO)C[C@H]1OC(=O)CCCCCCC/C=C\C/C=C\CCCCC] |
| CL-57 | 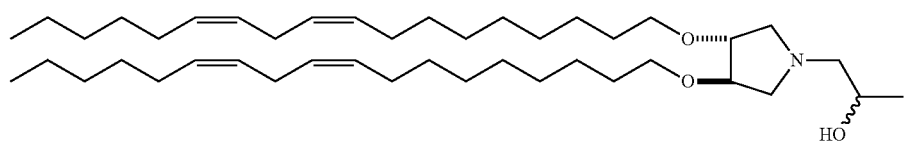 [SMILES: CCCCC/C=C\C/C=C\CCCCCCCCO[C@@H]1CN(CC(C)O)C[C@H]1OCCCCCCCC/C=C\C/C=C\CCCCC] |

TABLE 10-continued

| Compound No. | Structural Formula |
|---|---|
| CL-58 | |
| CL-59 | |

TABLE 11

| Compound No. | Structural Formula |
|---|---|
| CL-60 | |
| CL-61 | |

TABLE 12

| CL-62 | |
|---|---|
| CL-63 | |
| CL-64 | |
| CL-65 | |

TABLE 12-continued
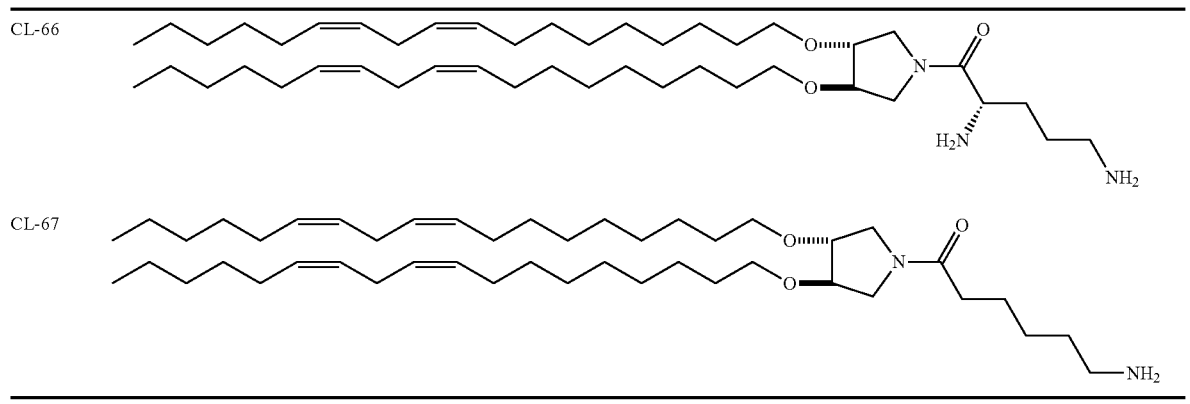
TABLE 13
| Compound No. | Structural Formula |
|---|---|
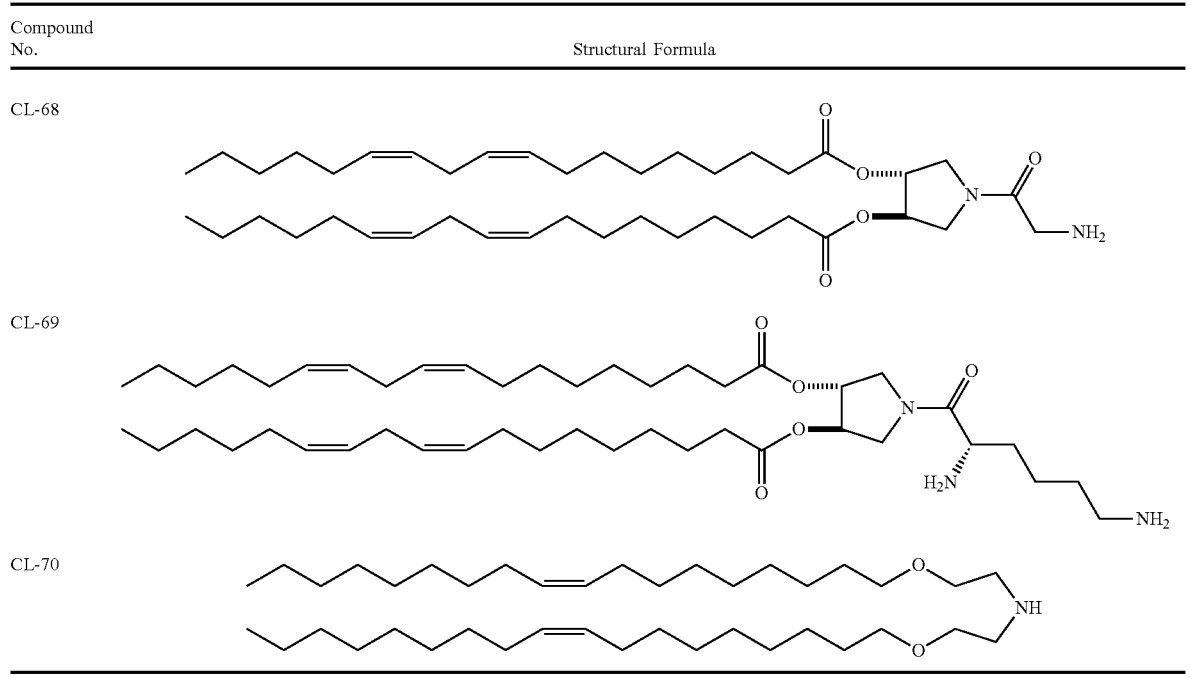
TABLE 14
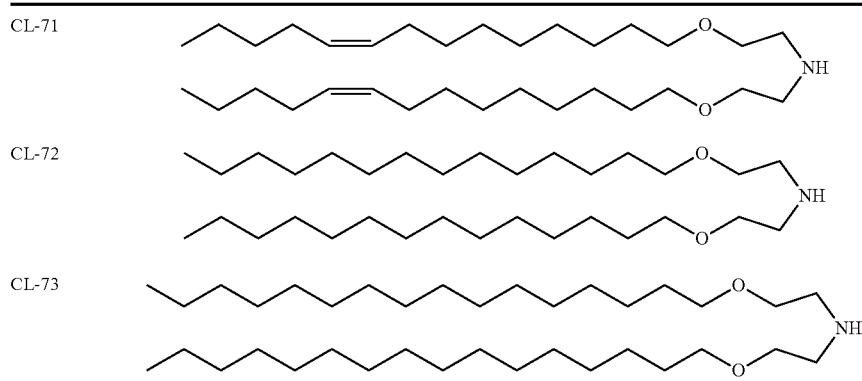

TABLE 14-continued
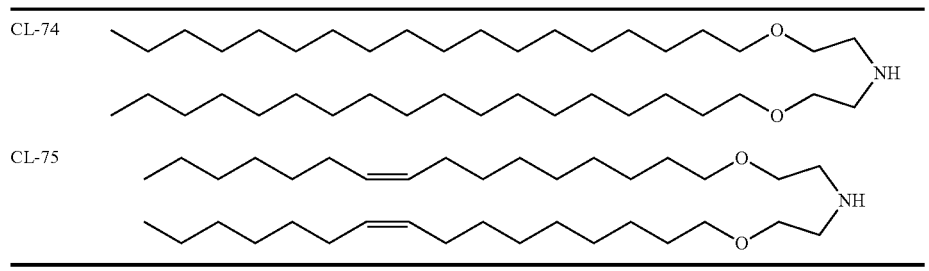
TABLE 15
| Compound No. | Structural Formula |
|---|---|
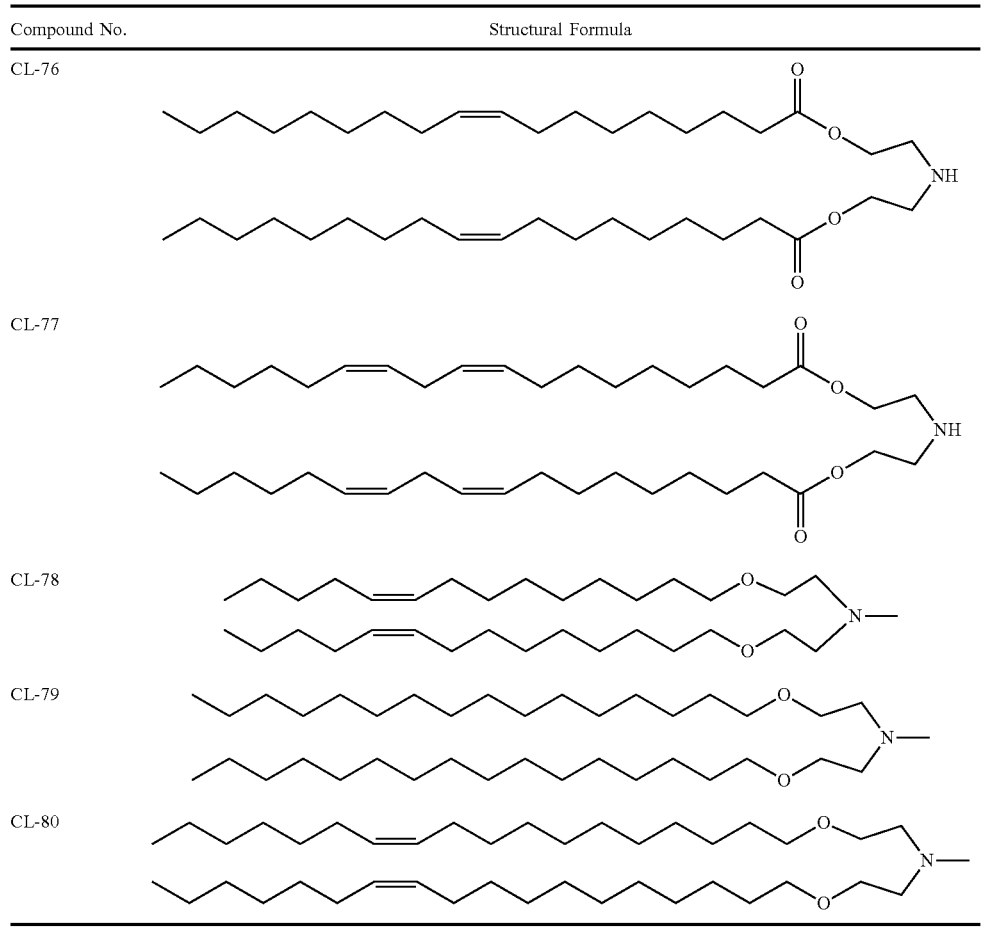
TABLE 16
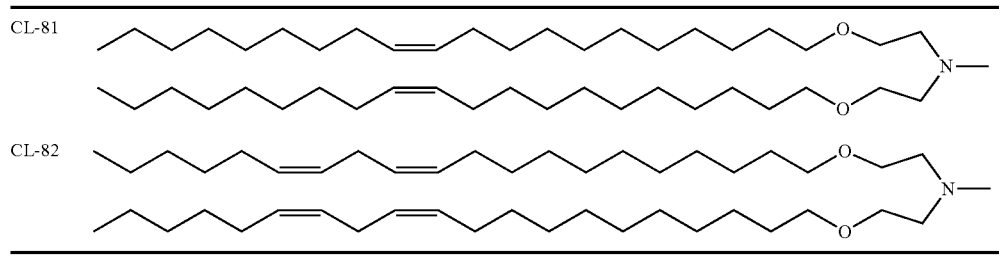

TABLE 17
| Compound No. | Structural Formula |
|---|---|
| CL-83 | 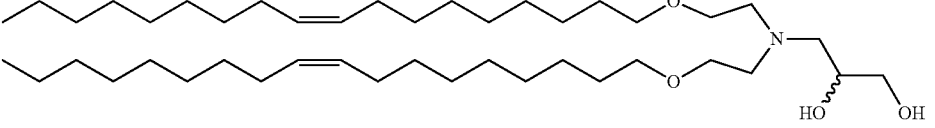 |
| CL-84 | 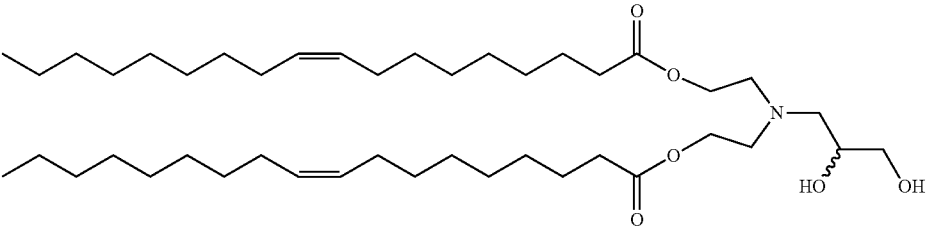 [SMILES: CCCCCCCC/C=C\CCCCCCCC(=O)OCCN(CCOC(=O)CCCCCCC/C=C\CCCCCCCC)CC(O)CO] |
| CL-85 | 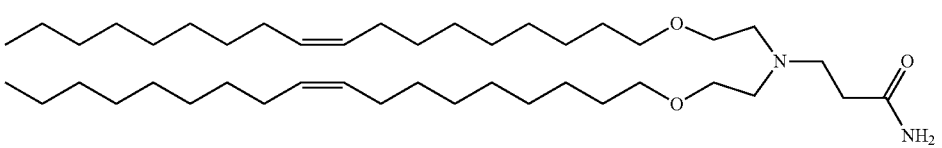 [SMILES: CCCCCCCC/C=C\CCCCCCCCOCCN(CCOCCCCCCCC/C=C\CCCCCCCC)CCC(N)=O] |
| CL-86 | 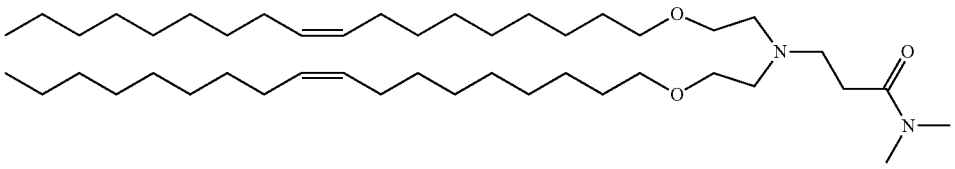 [SMILES: CCCCCCCC/C=C\CCCCCCCCOCCN(CCOCCCCCCCC/C=C\CCCCCCCC)CCC(=O)N(C)C] |
| CL-87 | 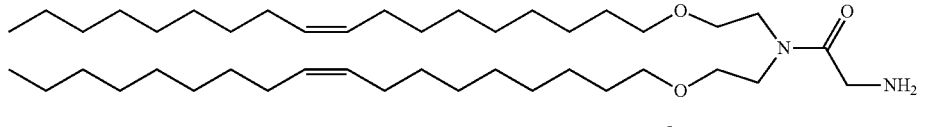 |
| CL-88 | 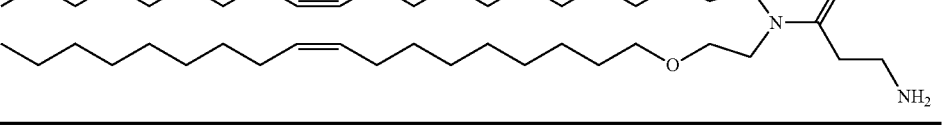 |
TABLE 18
| Compound No. | Structural Formula |
|---|---|
| CL-89 | 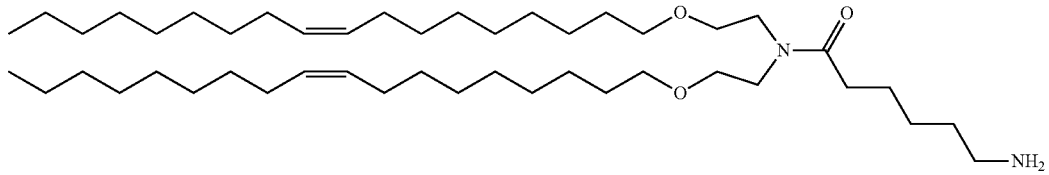 [SMILES: CCCCCCCC/C=C\CCCCCCCCOCCN(CCOCCCCCCCC/C=C\CCCCCCCC)C(=O)CCCCCN] |
| CL-90 | 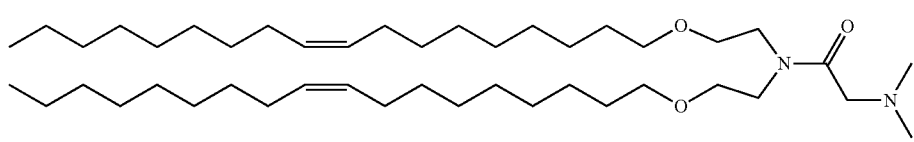 [SMILES: CCCCCCCC/C=C\CCCCCCCCOCCN(CCOCCCCCCCC/C=C\CCCCCCCC)C(=O)CN(C)C] |

TABLE 18-continued

| Compound No. | Structural Formula |
| --- | --- |
| CL-91 | |
| CL-92 | |
| CL-93 | |
| CL-94 | |
| CL-95 | |

TABLE 19

| Compound No. | Structural Formula |
| --- | --- |
| CL-96 | |
| CL-97 | |

TABLE 19-continued

| Compound No. | Structural Formula |
| --- | --- |
| CL-98 | |
| CL-99 | |
| CL-100 | |
| CL-101 | |

TABLE 20

| Compound No. | Structural Formula |
| --- | --- |
| CL-102 | |
| CL-103 | |
| CL-104 | |

TABLE 20-continued
| Compound No. | Structural Formula |
|---|---|
| CL-105 | 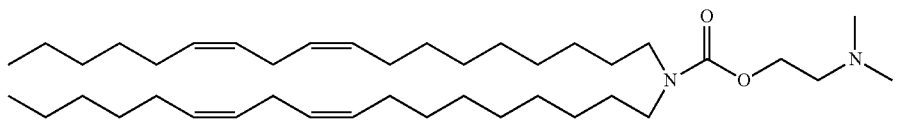 [SMILES: CCCCC/C=C\C/C=C\CCCCCCCCN(CCCCCCCC/C=C\C/C=C\CCCCC)C(=O)OCCN(C)C] |
| CL-106 | 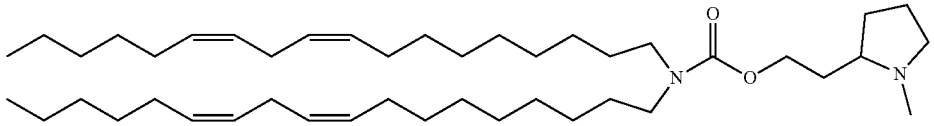 [SMILES: CCCCC/C=C\C/C=C\CCCCCCCCN(CCCCCCCC/C=C\C/C=C\CCCCC)C(=O)OCCC1CCCN1C] |
| CL-107 | 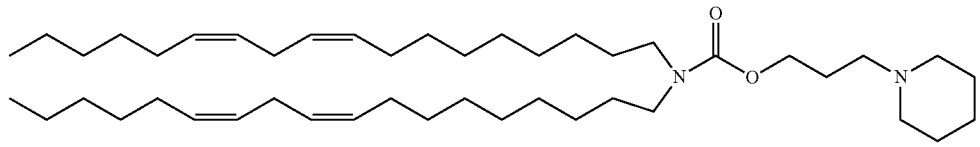 [SMILES: CCCCC/C=C\C/C=C\CCCCCCCCN(CCCCCCCC/C=C\C/C=C\CCCCC)C(=O)OCCCN1CCCCC1] |
| CL-108 | 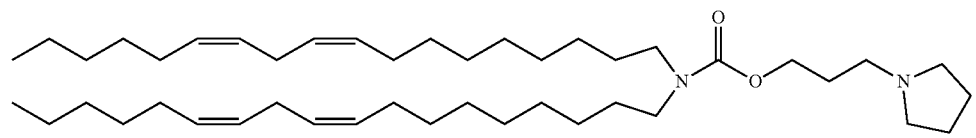 [SMILES: CCCCC/C=C\C/C=C\CCCCCCCCN(CCCCCCCC/C=C\C/C=C\CCCCC)C(=O)OCCCN1CCCC1] |
TABLE 21
| Compound No. | Structural Formula |
|---|---|
| CL-109 | 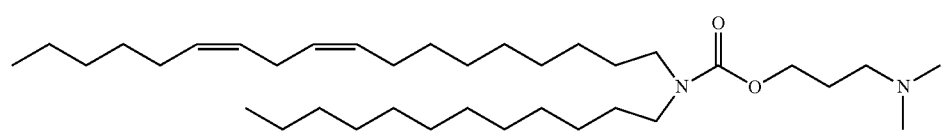 [SMILES: CCCCC/C=C\C/C=C\CCCCCCCCN(CCCCCCCCCCCC)C(=O)OCCCN(C)C] |
| CL-110 | 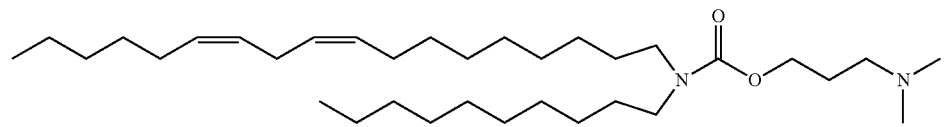 [SMILES: CCCCC/C=C\C/C=C\CCCCCCCCN(CCCCCCCCCC)C(=O)OCCCN(C)C] |
| CL-111 | 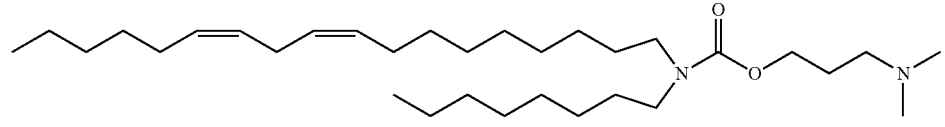 [SMILES: CCCCC/C=C\C/C=C\CCCCCCCCN(CCCCCCCC)C(=O)OCCCN(C)C] |
| CL-112 | 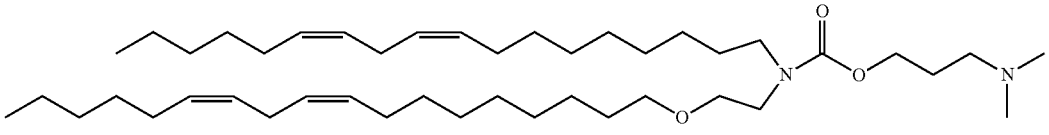 [SMILES: CCCCC/C=C\C/C=C\CCCCCCCCOCCN(CCCCCCCC/C=C\C/C=C\CCCCC)C(=O)OCCCN(C)C] |
| CL-113 | 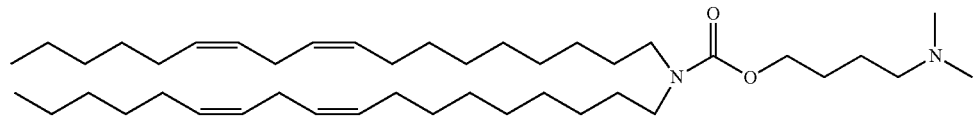 [SMILES: CCCCC/C=C\C/C=C\CCCCCCCCN(CCCCCCCC/C=C\C/C=C\CCCCC)C(=O)OCCCCN(C)C] |

TABLE 22

| Compound No. | Structural Formula |
|---|---|
| CL-114 | |
| CL-115 | |
| CL-116 | |
| CL-117 | |
| CL-118 | |
| CL-119 | |
| CL-120 | |
| CL-121 | |
| CL-122 | |
| CL-123 | |

TABLE 22-continued
| Compound No. | Structural Formula |
|---|---|
| CL-124 | 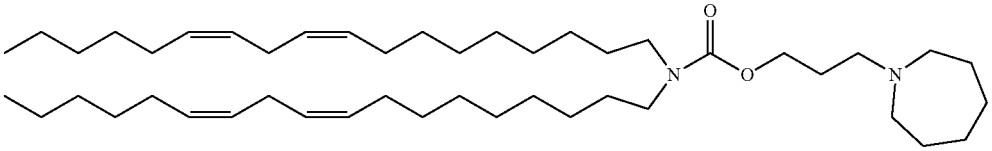 [SMILES: CCCCC/C=C\C/C=C\CCCCCCCCN(CCCCCCCC/C=C\C/C=C\CCCCC)C(=O)OCCCN1CCCCCC1] |
| CL-125 | 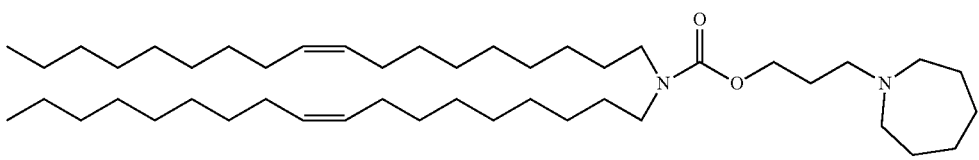 [SMILES: CCCCCCCC/C=C\CCCCCCCCN(CCCCCCCC/C=C\CCCCCCCC)C(=O)OCCCN1CCCCCC1] |
TABLE 23
| CL-126 | 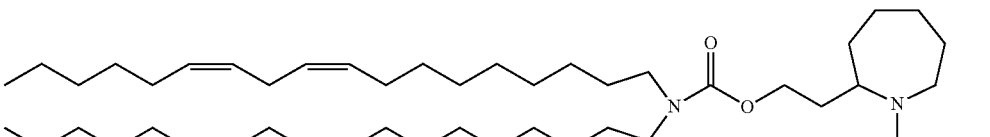 |
|---|---|
| CL-127 | 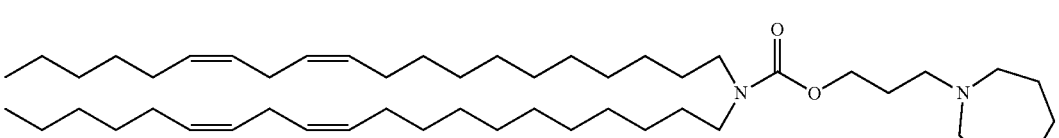 |
| CL-128 | 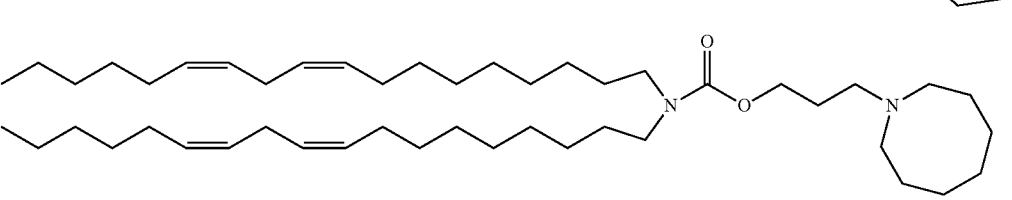 |
TABLE 24
| Compound No. | Structural Formula |
|---|---|
| CL-129 | 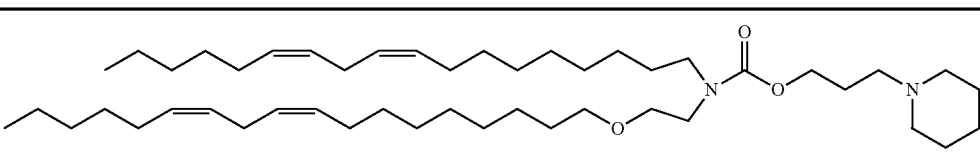 |
| CL-130 | 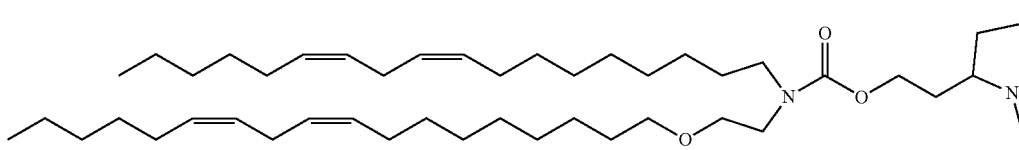 |
| CL-131 | 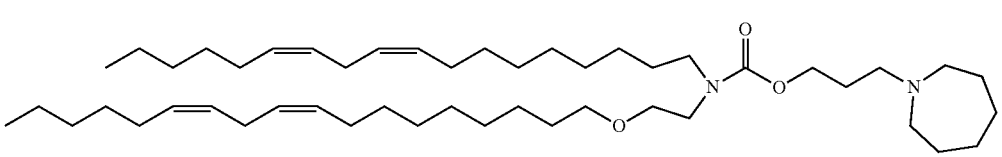 [SMILES: CCCCC/C=C\C/C=C\CCCCCCCCOCCN(CCCCCCCC/C=C\C/C=C\CCCCC)C(=O)OCCCN1CCCCCC1] |

TABLE 24-continued

| Compound No. | Structural Formula |
|---|---|
| CL-132 | |
| CL-133 | |
| CL-134 | |
| CL-135 | |
| CL-136 | |
| CL-137 | |
| CL-138 | |

TABLE 25

| Compound No. | Structural Formula |
|---|---|
| CL-139 | |
| CL-140 | |
| CL-141 | |

TABLE 25-continued
| Compound No. | Structural Formula |
|---|---|
| CL-142 | 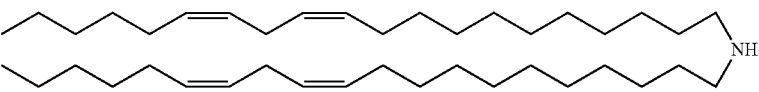 |
| CL-143 | 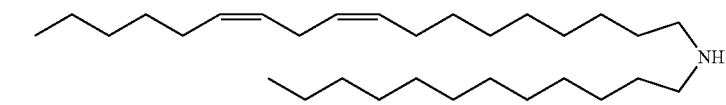 [SMILES: CCCCC/C=C\C/C=C\CCCCCCCCNCCCCCCCCCCCC] |
| CL-144 | 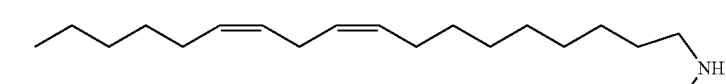 |
| CL-145 | 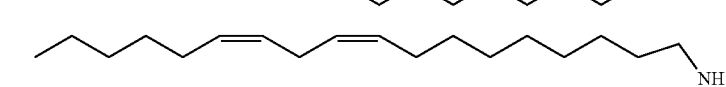 |
| CL-146 | 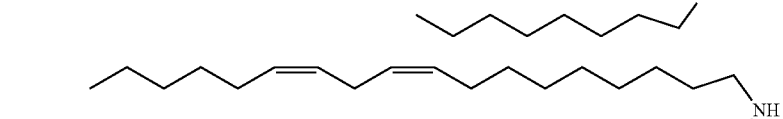 |
| CL-147 | 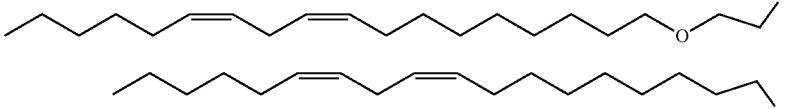 |
| CL-148 | 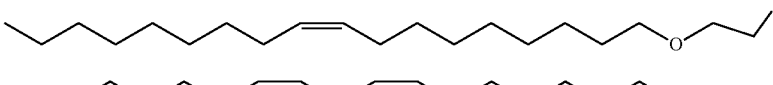 |
TABLE 26
| Compound No. | Structural Formula |
|---|---|
| CL-149 | 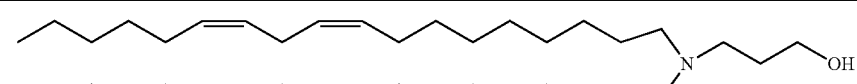 |
| CL-150 | 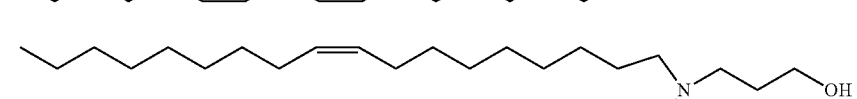 |
| CL-151 | 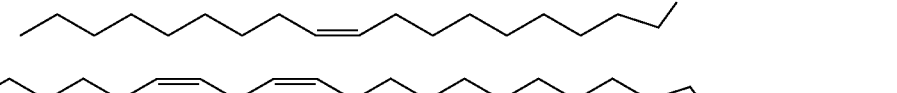 |
| CL-152 | 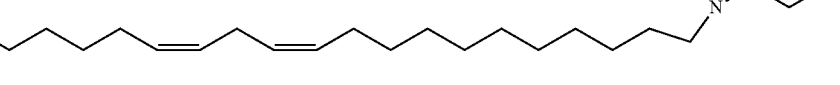 |
| CL-153 | 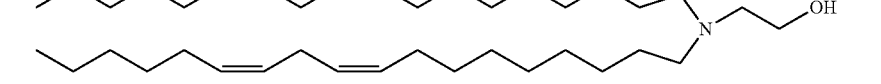 |

TABLE 27

| Compound No. | Structural Formula |
| --- | --- |
| CL-154 | (structure) |
| CL-155 | (structure) |

A lipid having a quaternary ammonium group as a hydrophilic unit and two independent optionally substituted hydrocarbon groups as a hydrophobic unit can be used as a lipid B other than that previously described in the nucleic acid-containing lipid nanoparticles of the present invention. Specific examples of such lipids are listed in Table 28.

TABLE 28

| Compound No. | Structural Formula |
| --- | --- |
| CL-156 | (structure) |
| CL-157 | (structure) |
| CL-158 | (structure) |
| CL-159 | (structure) |
| CL-160 | (structure) |
| CL-161 | (structure) |
| CL-162 | (structure) |

TABLE 28-continued

| Compound No. | Structural Formula |
|---|---|
| CL-163 | ![structure] |
| CL-164 | ![structure] |

Next, an explanation is provided of the method for producing lipid A of the present invention. Furthermore, in the production methods indicated below, in the case a defined group changes under the conditions of the production method or is unsuitable for carrying out the production method, the target compound can be obtained by using a method for introducing and removing protective groups normally used in the field of organic synthesis chemistry (such as "Protective Groups in Organic Synthesis, Third Edition", T. W. Greene, ed., John Wiley & Sons Inc. (1999)). In addition, the order of the reaction steps, such as the introduction of substituents, can also be altered as necessary.

In addition, ordinary unit reactions such as etherification ("Fourth Series of Experimental Chemistry 20: Synthesis of Organic Compounds II", Fourth edition, p. 187, Maruzen Co., Ltd. (1992)), amination ("Fourth Series of Experimental Chemistry 20: Synthesis of Organic Compounds II", Fourth edition, p. 279, Maruzen Co., Ltd. (1992)), esterification ("Fourth Series of Experimental Chemistry 22: Synthesis of Organic Compounds IV", Fourth edition, p. 43, Maruzen Co., Ltd. (1992)) or amidation ("Fourth Series of Experimental Chemistry 22: Synthesis of Organic Compounds IV", Fourth edition, p. 137, Maruzen Co., Ltd. (1992)) described in the production methods indicated below can each be carried out using ordinary reaction conditions described in the existing literature.

Compound (I) can be obtained as described below according to the method of either Synthesis Pathway 1 or 2 or a method that complies with these methods.

Compound (I) can be obtained from ammonia in accordance with Synthesis Pathway 1.

Synthesis Pathway 1

[C90]

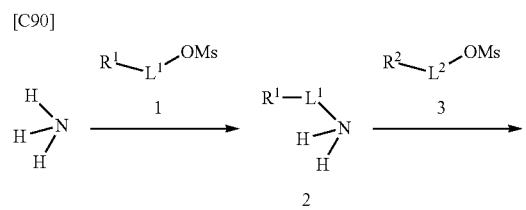

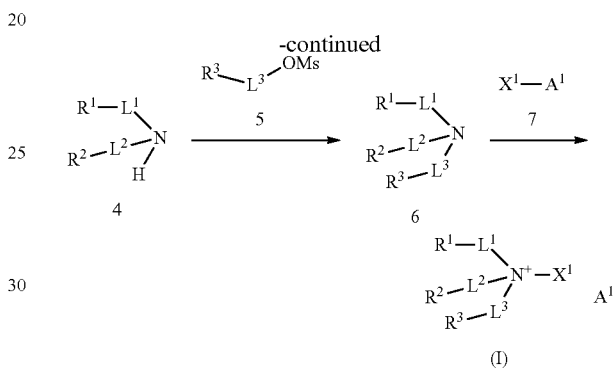

(In the formula, Ms represents a methanesulfonyl group and other groups are the same as previously defined.)

Compound 2 can be obtained by reacting ammonia and Compound 1 in a solvent (polar solvent such as tetrahydrofuran or methanol) at a high temperature (such as 80° C. or higher).

Compound 4 is obtained by reacting Compound 2 and Compound 3 in the presence of base (e.g. inorganic base such as sodium hydroxide) at a high temperature (such as 100° C. or higher). Although a solvent is not necessarily required, a solvent having a high boiling point (e.g. polar solvent such as ethylene glycol) can be used depending on the case.

Compound 6 is obtained by reacting Compound 4 and Compound 5 in the presence of base (e.g. inorganic base such as sodium hydroxide) at a high temperature (such as 100° C. or higher). Although a solvent is not necessarily required, a solvent having a high boiling point (e.g. polar solvent such as ethylene glycol) can be used depending on the case.

A microwave reactor can be preferably used in each of the three heating reactions described above. In addition, halides such as bromides or iodides corresponding to Compounds 1, 3 and 5 can be used instead of these compounds.

Compound 4, in which $R^1$—$L^1$ and $R^2$—$L^2$ are the same, is also obtained from ammonia by using an excess of Compound 1. In addition, Compound 6, in which $R^2$—$L^2$ and $R^3$—$L^3$ are the same, is also obtained from Compound 2 by using an excess of Compound 3. Moreover, Compound 6, in which $R^1$—$L^2$, $R^2$—$L^2$ and $R^3$—$L^3$ are the same, is also obtained from ammonia by further using an excess of Compound 1.

Compound (I) is obtained by reacting Compound 6 and Compound 7 in the presence or absence of solvent (halogen-based solvent such as chloroform) at room temperature or high temperature (such as 100° C. or higher). Furthermore, anion $A^1$ of Compound (I) can be converted to a different anion by, for example, treating Compound (I) with a suitable anion exchange resin.

Compounds such as Compound 1, Compound 3, Compound 5 and Compound 7 used in the reactions can be acquired as commercially available products, by methods described in the examples or methods equivalent thereto, or by known methods described in the literature (such as methods described in "Fifth Series of Experimental Chemistry 13: Synthesis of Organic Compounds I", Fifth edition, p. 374, Maruzen Co., Ltd. (2005)) or methods equivalent thereto.

In addition, Compound 1 can also be obtained by treating the corresponding $R^1$—$L^1$-OH with anhydrous mesylic acid or mesylate chloride.

Moreover, compounds in which $L^1$ of $R^1$—$L^1$-OH is —$Z^1$—$(CY^1Y^2)_{p1}$— (each group has the same meaning as previously described) can be obtained by de-protecting after having reacted any one of $R^1$—OMs, $R^1$—OH, $R^1$—$NY^{7A}$—H ($Y^{7A}$ has the same meaning as previously described) or $R^1$—$CO_2H$ with any one of HO—$(CY^1Y^2)_{p1}$—O—$PRO^1$, MsO—$(CY^1Y^2)_{p1}$—O—$PRO^1$, $HO_2C$—$(CY^1Y^2)_{p1}$—O—$PRO^1$ or H—$NY^{7A}$—$(CY^1Y^2)_{p1}$—O—$PRO^1$ (wherein, $PRO^1$ represents a silyl-based protective group (such as a triethylsilyl group (TES), tert-butyldimethylsilyl group (TBS) or tert-butyldiphenylsilyl group (TBDPS)) by etherification (by using, for example, a strong base such as sodium hydride), amination (such as a substitution reaction), esterification (by using, for example, a condensing agent such as 1-ethyl-3-(3-dimethylaminopropyl)carbodiimide) or amidation (by using, for example, a similar condensing agent).

In addition, compounds in which $L^1$ of $R^1$—$L^1$-OH is —$Z^2$—$(CY^3Y^4)_{p2}$—$Z^3$—$(CY^5Y^6)_{p3}$-(each group has the same meaning as previously described) can also be similarly obtained by applying known reactions one to a plurality of times using reaction substrates corresponding to the target compound.

Compound 3 and Compound 5 can be prepared using the same technique as Compound 1.

Compound (Ia) can be obtained from Compound 8 in accordance with Synthesis Pathway 2.

Synthesis Pathway 2

[C91]

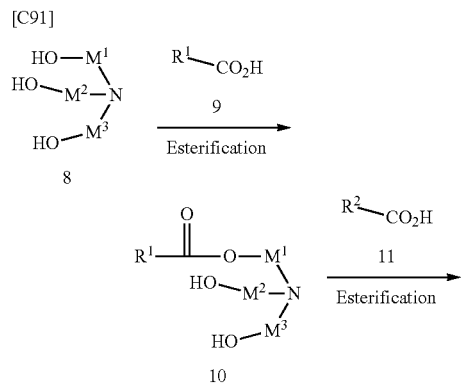

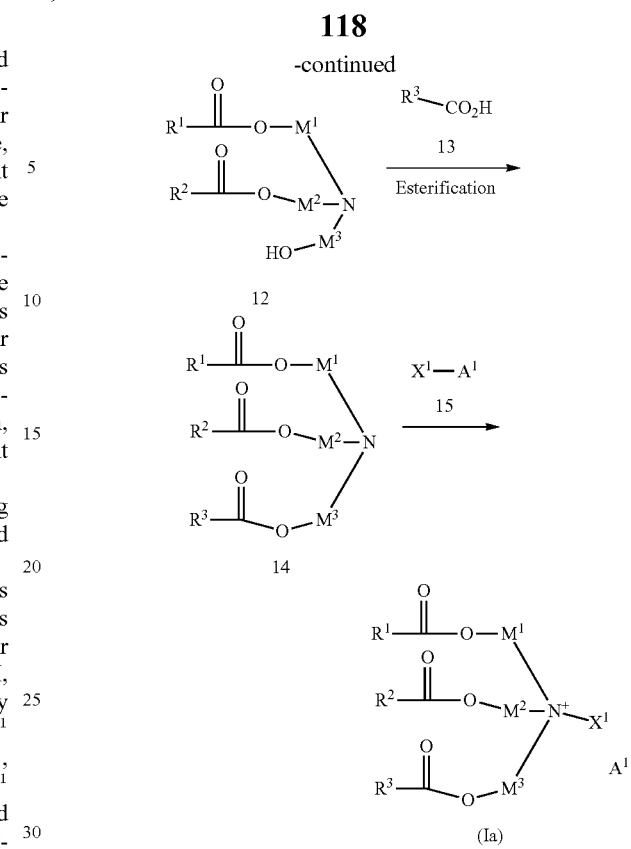

(In the formulas, $M^1$ to $M^3$ may be the same or different and represent —$(CY^1Y^2)_{p1}$— or —$(CY^3Y^4)$—$Z^3$—$(CY^5Y^6)_{p3}$— (each group has the same meaning as previously described), and other groups respectively have the same meanings as previously described.)

Compound 10 is obtained by treating Compound 8 and Compound 9 with a base (e.g. organic base such as triethylamine), a condensing agent (such as 1-ethyl-3-(3-dimethylaminopropyl)carbodiimide hydrochloride or O-(7-aza-1H-benzotriazol-1-yl)-N,N,N',N'-tetramethyluronium hexafluorophosphate) and an activator (activator such as N,N-dimethylaminopyridine) in a solvent (e.g. halogen-based solvent such as chloroform).

Compound 12 is obtained by esterifying Compound 10 and Compound 11 using the same method as described above.

Moreover, Compound 14 is obtained by esterifying Compound 12 and Compound 13 using the same method as described above.

Compound 12, in which $R^1$ and $R^2$ are the same, is also obtained from Compound 8 by using an excess of Compound 9. In addition, Compound 14, in which $R^2$ and $R^3$ are the same, is also obtained from Compound 10 by using an excess of Compound 11. Moreover, Compound 14, in which $R^1$, $R^2$ and $R^3$ are the same, is also obtained from Compound 8 by further using an excess of Compound 9.

Compound (Ia) is obtained by reacting Compound 14 and Compound 15 in the presence or absence of solvent (e.g. halogen-based solvent such as chloroform) at room temperature or high temperature (such as 100° C. or higher). Furthermore, anion $A^1$ of Compound (Ia) can be converted to a different anion by, for example, treating Compound (Ia) with a suitable anion exchange resin.

Compounds such as Compound 8, Compound 9, Compound 11, Compound 14 and Compound 15 used in the reactions can be acquired as commercially available products, by methods described in the examples or methods equivalent thereto, or by known methods described in the literature (such as methods described in "Fifth Series of Experimental Chemistry 14: Synthesis of Organic Compounds II", Fifth edition, p. 1, Maruzen Co., Ltd. (2005), "Fourth Series of Experimental Chemistry 22: Synthesis of Organic Compounds IV", Fourth edition, p. 1, Maruzen Co., Ltd. (1992)) or methods equivalent thereto.

Compound (II) can be obtained in the manner described below using any of the methods of Synthesis Pathways 3 to 17 or methods equivalent thereto.

Compound (IIa) can be obtained from Compound 16 in accordance with Synthesis Pathway 3.

Synthesis Pathway 3

[C92]

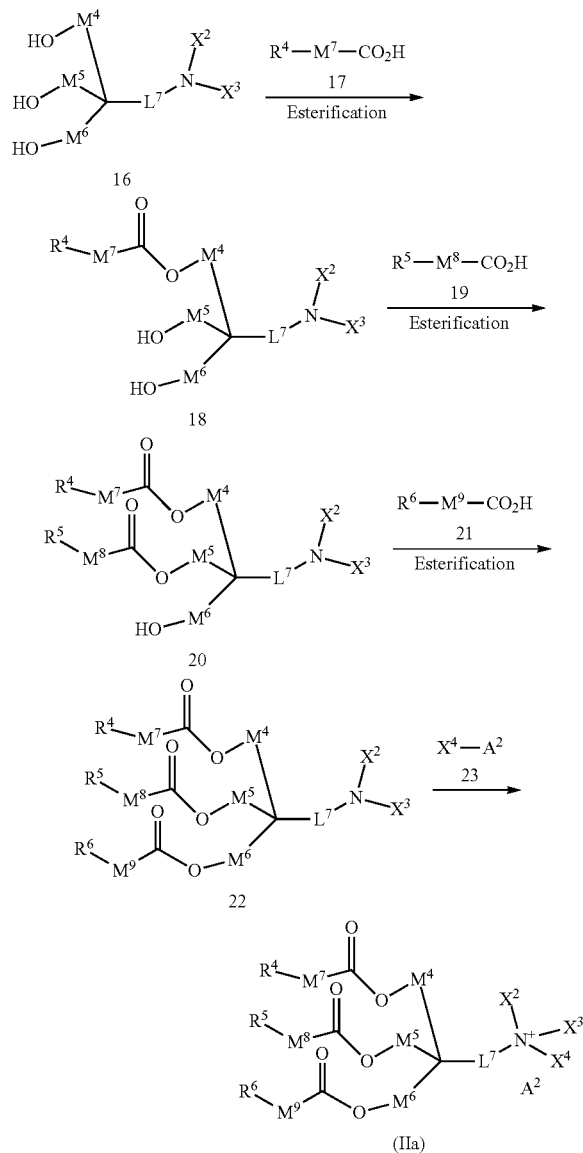

(In the formulas, $M^7$ is not present and $M^4$ represents —$(CY^8Y^9)_{p4}$—, $M^7$ is not present and $M^4$ represents —$(CY^{10}Y^{11})_{p5}$—$Z^6$—$(CY^{12}Y^{13})_{p6}$—, or $M^7$ represents —$Z^5$—$(CY^{10}Y^{11})_{p5}$— and $M^4$ represents —$(CY^{12}Y^{13})_{p6}$— (each group has the same meaning as previously described). In addition, $M^8$ is not present and $M^5$ represents —$(CY^8Y^9)_{p4}$—, $M^8$ is not present and $M^5$ represents —$(CY^{10}Y^{11})_{p5}$—$Z^6$—$(CY^{12}Y^{13})_{p6}$—, or $M^8$ represents —$Z^5$—$(CY^{10}Y^{11})_{p5}$— and $M^5$ represents —$(CY^{12}Y^{13})_{p6}$—. Moreover, $M^9$ is not present and $M^6$ represents —$(CY^8Y^9)_{p4}$—, $M^9$ is not present and $M^6$ represents —$(CY^{10}Y^{11})_{p5}$—$Z^6$—$(CY^{12}Y^{13})_{p6}$—, or $M^9$ represents —$Z^5$—$(CY^{10}Y^{11})_{p5}$— and $M^6$ represents —$(CY^{12}Y^{13})_{p6}$—. Each of the other groups has the same meaning as previously described.)

Compound 22 is obtained by reacting Compound 16, Compound 17, Compound 19 and Compound 21 in order by applying the same reaction conditions as the esterification reaction between Compound 8 and Compound 9 in Synthesis Pathway 2.

Compound (IIa) is obtained from Compound 22 and Compound 23 by reacting by applying the same conditions as the reaction conditions when synthesizing Compound (Ia) by reacting Compound 14 and Compound 15 in Synthesis Pathway 2. Furthermore, anion $A^2$ of Compound (IIa) can be converted to a different anion by, for example, treating Compound (IIa) with a suitable anion exchange resin.

Compounds such as Compound 16, Compound 17, Compound 19, Compound 21 and Compound 23 used in the reactions can be acquired as commercially available products, by methods described in the examples or methods equivalent thereto, or by known methods described in the literature (such as methods described in "Fifth Series of Experimental Chemistry 14: Synthesis of Organic Compounds II", Fifth edition, p. 1, Maruzen Co., Ltd. (2005), "Fourth Series of Experimental Chemistry 22: Synthesis of Organic Compounds IV", Fourth edition, p. 1, Maruzen Co., Ltd. (1992)) or methods equivalent thereto.

Compound 16 can be obtained according to the methods of Synthesis Pathways 12 to 16 to be subsequently described.

Compound 17 in which $M^7$ represents —$Z^5$—$(CY^{10}Y^{11})_{p5}$— can be obtained by de-protecting after having reacted any one of $R^4$—OMs, $R^4$—OH, $R^4$—$NY^{14A}$—H ($Y^{14A}$ has the same meaning as previously described) or $R^4$—$CO_2H$ with any one of HO—$(CY^{10}Y^{11})_{p5}$—CO—O—$PRO^2$, MsO—$(CY^{10}Y^{11})_{p5}$—CO—O—$PRO^2$, $HO_2C$—$(CY^{10}Y^{11})_{p5}$—CO—O—$PRO^2$ or H—$NY^{14A}$—$(CY^{10}Y^{11})_{p5}$—CO—O—$PRO^2$ (wherein, $PRO^2$ represents a carboxylic acid protective group (such as a methyl, tert-butyl or benzyl group) by etherification (by using, for example, a strong base such as sodium hydride), amination (such as a substitution reaction), esterification (using, for example, a condensing agent such as 1-ethyl-3-(3-dimethylaminopropyl)carbodiimide hydrochloride) or amidation (using, for example, a similar condensing agent).

Compound 19 and Compound 21 can be prepared using the same technique as Compound 17.

Introduction of $X^4$ can be carried out first in Synthesis Pathway 3. Namely, Compound (IIa) can be obtained by esterifying Compound 17, Compound 19 and Compound 21 in that order after having first allowed Compound 23 to act on Compound 16.

Compound (IIb) can be obtained from Compound 16 in accordance with Synthesis Pathway 4.

Synthesis Pathway 4

[C93]

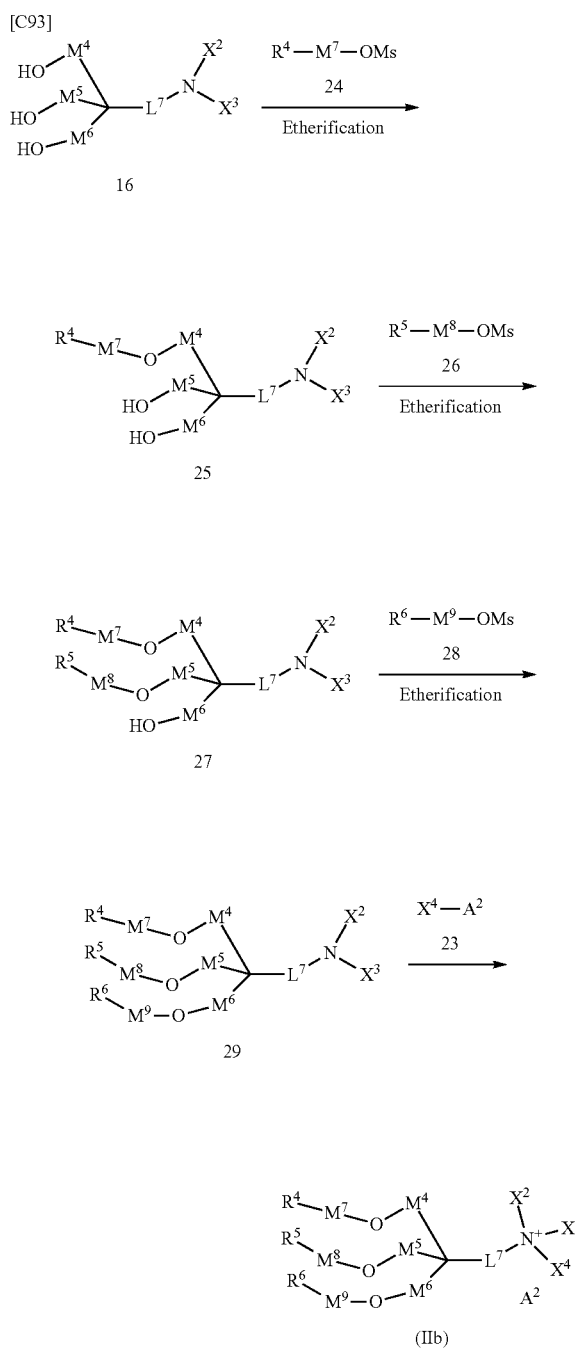

(In the formulas, each group has the same meaning as previously described.)

Compound 25 can be obtained by reacting Compound 16 and Compound 24 in a solvent (e.g. aprotic solvent such as tetrahydrofuran or toluene) and in the presence of base (e.g. inorganic base such as sodium hydride) at a high temperature (such as 100° C. or higher).

Compound 27 is obtained by etherifying Compound 25 and Compound 26 using the same method as previously described.

Compound 29 is obtained by etherifying Compound 27 and Compound 28 using the same method as previously described.

A microwave reactor can be preferably used in each of the three heating reactions described above. In addition, bromides or iodides and the like corresponding to Compounds 24, 26 and 28 can be used instead of these compounds.

Compound 27, in which $R^4$-$M^7$ and $R^5$-$M^8$ are the same, is also obtained from Compound 16 by using an excess of Compound 24. In addition, Compound 29, in which $R^5$-$M^8$ and $R^6$-$M^9$ are the same, is also obtained from Compound 25 by using an excess of Compound 26. Moreover, Compound 29, in which $R^4$-$M^7$, $R^5$-$M^8$ and $R^6$-$M^9$ are the same, is also obtained from Compound 16 by further using an excess of Compound 24.

Compound (IIb) is obtained by reacting Compound 29 and Compound 23 in the presence or absence of solvent (halogen-based solvent such as chloroform) at room temperature or high temperature (such as 100° C. or higher). Furthermore, anion $A^2$ of Compound (IIb) can be converted to a different anion by, for example, treating Compound (IIb) with a suitable anion exchange resin.

Compounds such as Compound 16, Compound 24, Compound 26, Compound 28 and Compound 23 used in the reactions can be acquired as commercially available products, by methods described in the examples or methods equivalent thereto, or by known methods described in the literature (such as methods described in "Fifth Series of Experimental Chemistry 14: Synthesis of Organic Compounds II", Fifth edition, p. 1, Maruzen Co., Ltd. (2005) or "Fifth Series of Experimental Chemistry 13: Synthesis of Organic Compounds I", Fifth edition, p. 374, Maruzen Co., Ltd. (2005)) or methods equivalent thereto.

In addition, Compound 24 can also be obtained by treating the corresponding $R^4$-$M^7$-OH with anhydrous mesylic acid or mesylate chloride.

Moreover, compounds in which $M^7$ of $R^4$-$M^7$-OH is —$Z^5$—$(CY^{10}Y^{11})_{p5}$— (each group has the same meaning as previously described) can be obtained by de-protecting after having reacted any one of $R^4$—OMs, $R^4$—OH, $R^4$—$NY^{14A}$—H ($Y^{14A}$ has the same meaning as previously described) or $R^4$—$CO_2$H with any one of HO—$(CY^{10}Y^{11})_{p1}$—O—$PRO^1$, MsO—$(CY^{10}Y^{11})_{p5}$—O—$PRO^1$, $HO_2C$—$(CY^{10}Y^{11})_{p5}$—O—$PRO^1$ or H—$NY^{14A}$—$(CY^{10}Y^{11})_{p5}$—O—$PRO^1$ (wherein, each group has the same meaning as previously described) by etherification, amination, esterification or amidation.

Compound 26 and Compound 28 can be prepared using the same technique as Compound 24.

As shown in Synthesis Pathway 5, Compound (IIe) can be obtained from Compound 25 obtained in Synthesis Pathway 4 by suitably combining each of the reactions such as esterification used in Synthesis Pathway 3. Moreover, as shown in Synthesis Pathway 5, Compound (IId) can be obtained from Compound 27 obtained in Synthesis Pathway 4 by suitably combining each of the reactions such as esterification used in Synthesis Pathway 3.

Synthesis Pathway 5

[C94]

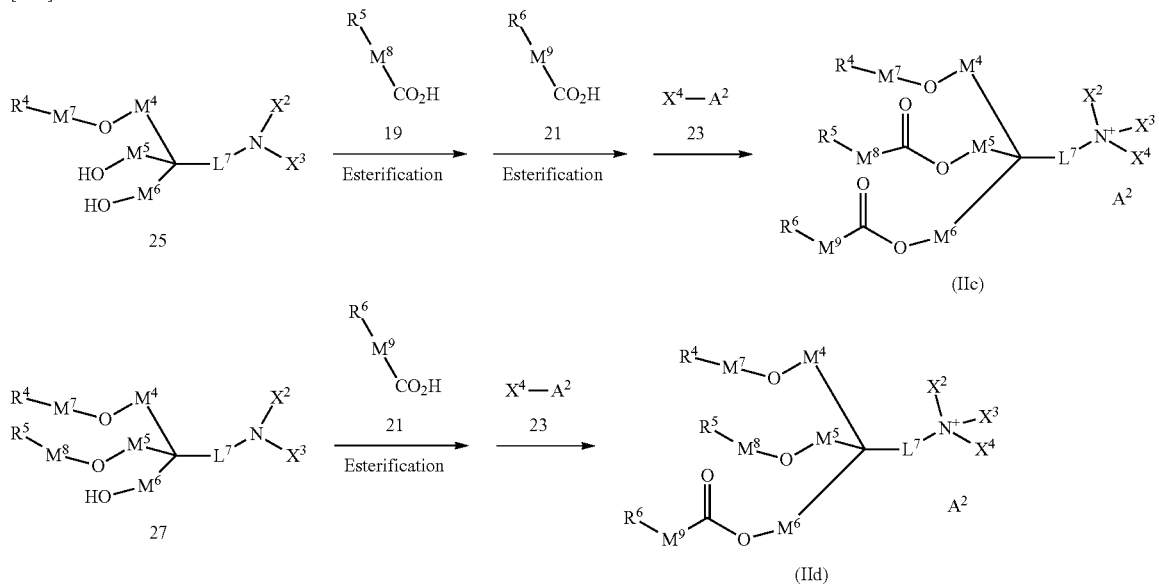

(In the formulas, each group has the same meaning as previously described.)

Compound (IIe) can be obtained from Compound 30 in accordance with Synthesis Pathway 6.

Synthesis Pathway 6

[C95]

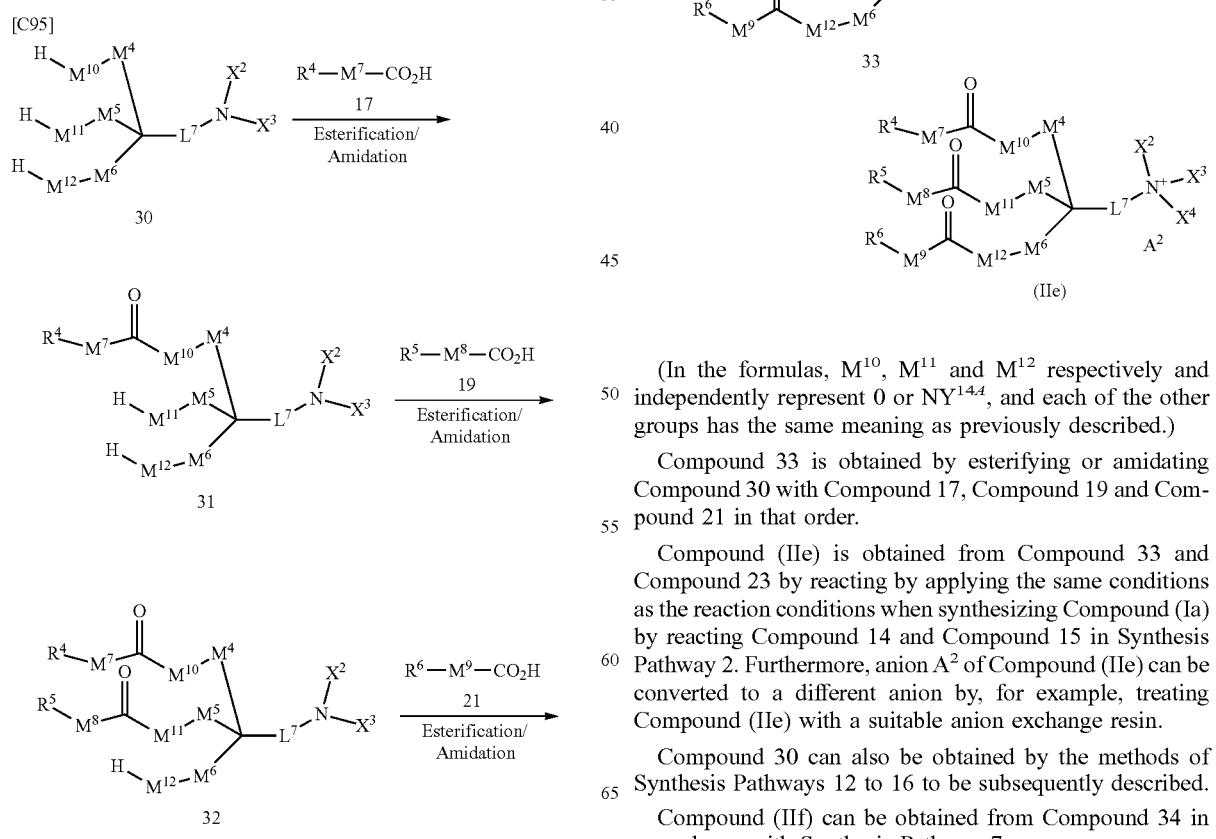

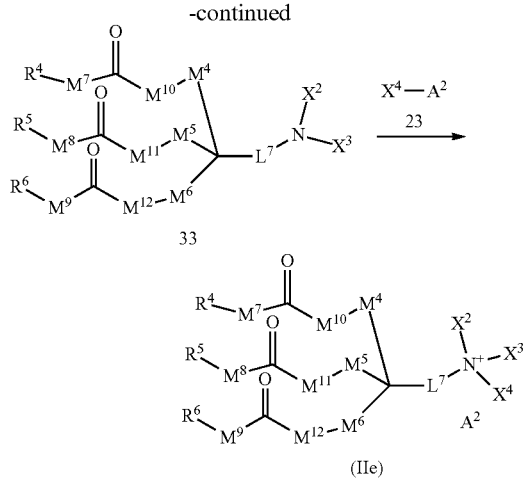

(In the formulas, $M^{10}$, $M^{11}$ and $M^{12}$ respectively and independently represent O or $NY^{14A}$, and each of the other groups has the same meaning as previously described.)

Compound 33 is obtained by esterifying or amidating Compound 30 with Compound 17, Compound 19 and Compound 21 in that order.

Compound (IIe) is obtained from Compound 33 and Compound 23 by reacting by applying the same conditions as the reaction conditions when synthesizing Compound (Ia) by reacting Compound 14 and Compound 15 in Synthesis Pathway 2. Furthermore, anion $A^2$ of Compound (IIe) can be converted to a different anion by, for example, treating Compound (IIe) with a suitable anion exchange resin.

Compound 30 can also be obtained by the methods of Synthesis Pathways 12 to 16 to be subsequently described.

Compound (IIf) can be obtained from Compound 34 in accordance with Synthesis Pathway 7.

Synthesis Pathway 7

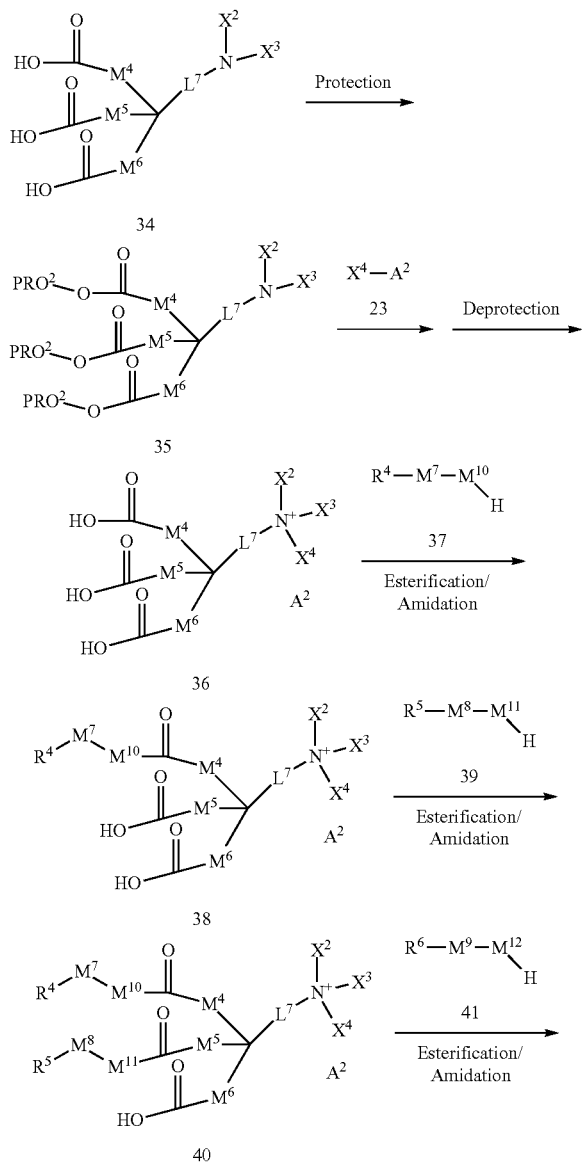

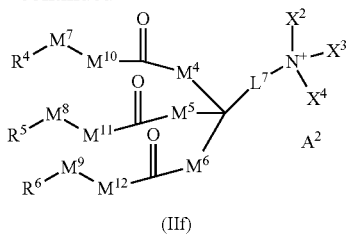

(IIf)

(In the formulas, each group has the same meaning as previously described.)

Compound 35 is obtained by protecting Compound 34 with a suitable protective group.

Compound 36 is obtained by de-protecting under suitable conditions after having reacted Compound 35 and Compound 23 by applying the same conditions as the reaction conditions when synthesizing Compound (Ia) by reacting Compound 14 and Compound 15 in Synthesis Pathway 2.

Compound (IIf) is obtained by esterifying or amidating Compound 36 with Compound 37, Compound 39 and Compound 41 in that order. Furthermore, anion $A^2$ of Compound (IIf) can be converted to a different anion by, for example, treating Compound (IIf) with a suitable anion exchange resin.

Compounds 34, 35 and 36 can be acquired as commercially available products or by methods described in the examples or methods equivalent thereto. In addition, Compounds 34, 35 and 36 can also be obtained by oxidizing the triol compound obtained in Synthesis Pathway 12 or 17 to be subsequently described with an oxidizing agent.

Compound 37 in which $M^{10}$ is $NY^{14.4}$ can also be obtained by reacting $R^4$—$M^7$—OMS (Compound 24) with $Y^{14.4}NH_2$.

Compounds 37 and 39 can be prepared according to the same procedure as Compound 35.

Furthermore, Compound (IIf) can also be obtained by esterifying or amidating Compound 24 with Compound 37, Compound 39 and Compound 41 in that order and finally allowing to act on Compound 23 to introduce $X^4$ as described in Synthesis Pathway 8.

Synthesis Pathway 8

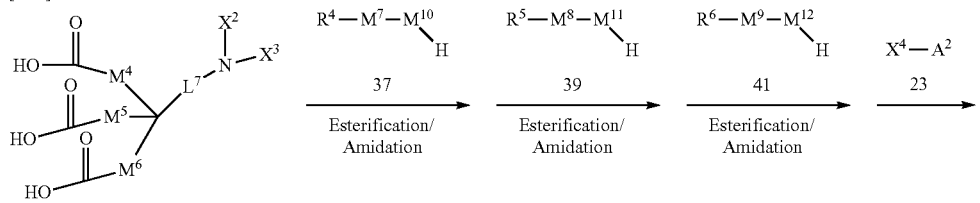

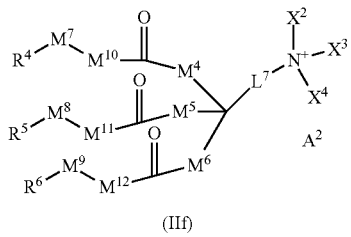

(IIf)

(In the formulas, each group has the same meaning as previously described.)

Compound (IIg) can be obtained from ethyl cyanoacetate in accordance with Synthesis Pathway 9.

Synthesis Pathway 9

[C98]

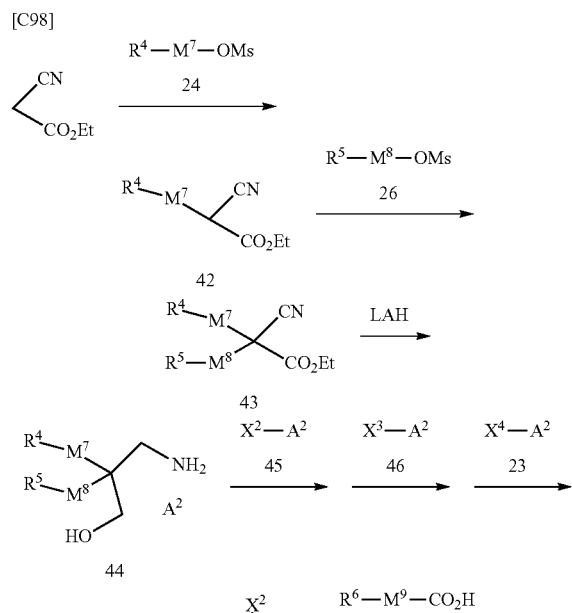

(IIg)

(In the formulas, Et represents an ethyl group, LAH represents lithium aluminum hydride, and each of the other groups has the same meaning as previously described.)

Compound 42 can be obtained by reacting ethyl cyanoacetate and Compound 24 in a solvent (e.g. aprotic solvent such as tetrahydrofuran) and in the presence of base (e.g. inorganic base such as sodium hydride), and an additive (additive such as tetrabutylammonium iodide) depending on the case, at a high temperature (such as 60° C. or higher).

Compound 43 can be obtained by reacting Compound 42 and Compound 26 in a solvent (e.g. aprotic solvent such as tetrahydrofuran) and in the presence of base (e.g. inorganic base such as sodium hydride), and an additive (additive such as tetrabutylammonium iodide) depending on the case, at a high temperature (such as 60° C. or higher).

Compound 43, in which $R^4$ and $R^5$ are the same, can be obtained from cyanoethyl acetate by using an excess of Compound 24.

Compound 44 can be obtained by reducing Compound 43 in a solvent (e.g. aprotic solvent such as tetrahydrofuran) with an excess of lithium aluminum hydride (LAH).

Compound 47 can be obtained by allowing Compound 45, Compound 46 and Compound 23 to act on Compound 44 in that order in the presence or absence of solvent (e.g. halogen-based solvent such as chloroform). Compound 47, in which $X^2$, $X^3$ and $X^4$ are the same, can also be obtained from Compound 44 by using an excess of Compound 45.

Compound (IIg) is obtained from Compound 47 and Compound 21 by reacting by applying the same reaction conditions as the esterification reaction between Compound 8 and Compound 9 in Synthesis Pathway 2. Furthermore, anion $A^2$ of Compound (IIg) can be converted to a different anion by, for example, treating Compound (IIg) with a suitable anion exchange resin.

Compound 45 and Compound 46 are similar to Compound 23.

Compound (IIh) can be obtained from dimethyl malonate in accordance with Synthesis Pathway 10.

Synthesis Pathway 10

[C99]

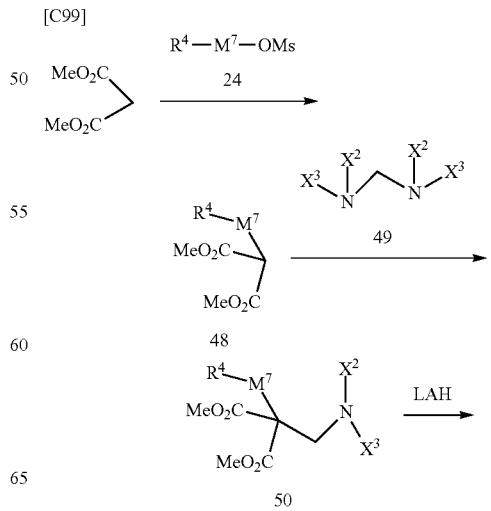

-continued

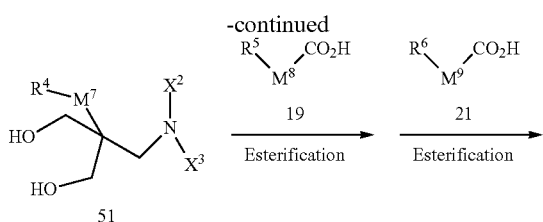

Compound 52 can be obtained by reacting Compound 51 with Compound 19 and Compound 21 by applying the same reaction conditions as the esterification of Compound 8 and Compound 9 in Synthesis Pathway 2.

Compound (IIh) is obtained by reacting Compound 52 and Compound 53 in the presence or absence of solvent (e.g. halogen-based solvent such as chloroform) at room temperature or high temperature (such as 100° C. or higher). Furthermore, anion $A^2$ of Compound (IIh) can be converted to a different anion by treating Compound (IIh) with a suitable anion exchange resin.

Compound 49 can be acquired as a commercially available product, by methods described in the examples or methods equivalent thereto, or by known methods described in the literature (such as methods described in "Helvetica Chimica Acta", Vol. 92, No. 8, pp. 1644-1656, 2009) or methods equivalent thereto.

Compounds 54 and 56 can be obtained in accordance with Synthesis Pathway 12.

Synthesis Pathway 12

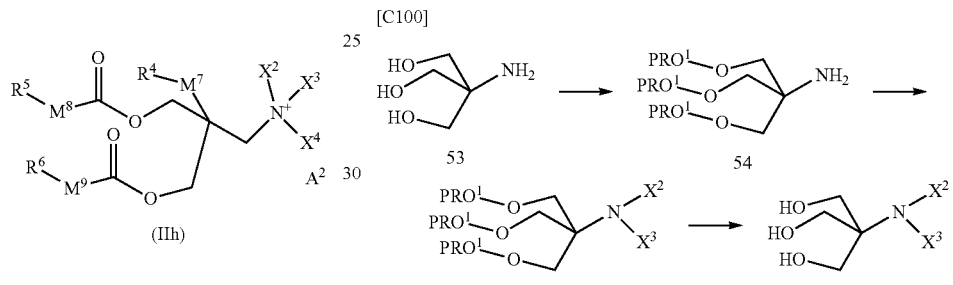

(In the formulas, Me represents a methyl group, LAH represents lithium aluminum hydride, and each of the other groups has the same meaning as previously described.)

Compound 48 can be obtained by reacting dimethyl malonate and Compound 24 in a solvent (e.g. aprotic solvent such as acetonitrile) in the presence of base (e.g. inorganic base such as cesium carbonate), and an additive (additive such as tetrabutylammonium iodide) depending on the case, at a high temperature (such as 50° C.).

Compound 50 can be obtained by reacting Compound 48 and Compound 49 in a solvent (e.g. aprotic solvent such as acetonitrile) in the presence of acetic anhydride and base (e.g. inorganic base such as sodium hydride).

Compound 51 can be obtained by reducing Compound 50 in a solvent (e.g. aprotic solvent such as tetrahydrofuran) with excess lithium aluminum hydride (LAH).

(In the formulas, each group has the same meaning as previously described.)

Compound 54 can be obtained by protecting the hydroxyl groups of Compound 53.

In addition, Compound 53 can be obtained as a commercially available product.

Compound 55 can be obtained by allowing Compound 45 and Compound 46 to act on Compound 54.

Compound 56 can be obtained by de-protecting Compound 55.

Compounds 58 to 65 can be obtained in accordance with Synthesis Pathway 13.

Synthesis Pathway 13

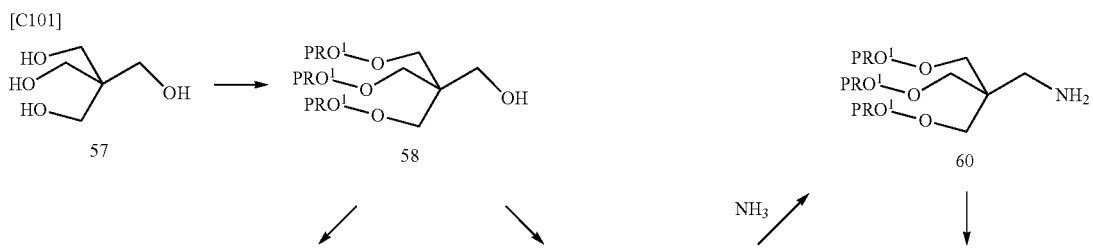

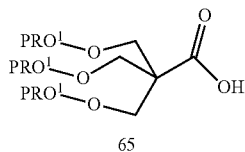
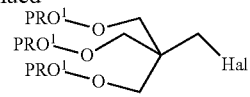
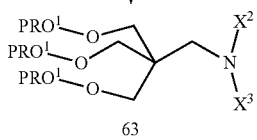
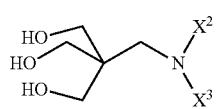

(In the formulas, Hal represents a halogen atom such as chlorine, bromine or iodine, and each of the other groups has the same meaning as previously described.)

Compound 58 can be obtained by protecting the hydroxyl of Compound 57.

In addition, Compound 57 can also be obtained as a commercially available product.

Compound 59 can be obtained by allowing a halogenating reagent (such as chlorine, bromine, iodine or iodine chloride) to act on Compound 58.

Compound 60 is obtained by reacting Compound 59 with ammonia. In addition, Compound 61 is obtained by allowing Compound 45 to act on Compound 60. Moreover, Compound 63 is obtained by allowing Compound 46 to act on Compound 61.

In addition, Compound 63 is also obtained by reacting Compound 59 and Compound 62.

Compound 63 is obtained by de-protecting Compound 62.

Compound 64 is obtained by oxidizing Compound 58 with a suitable oxidizing agent (such as potassium permanganate or Jones reagent).

Compounds 67 to 73 can be obtained in accordance with Synthesis Pathway 14.

Synthesis Pathway 14

[C102]

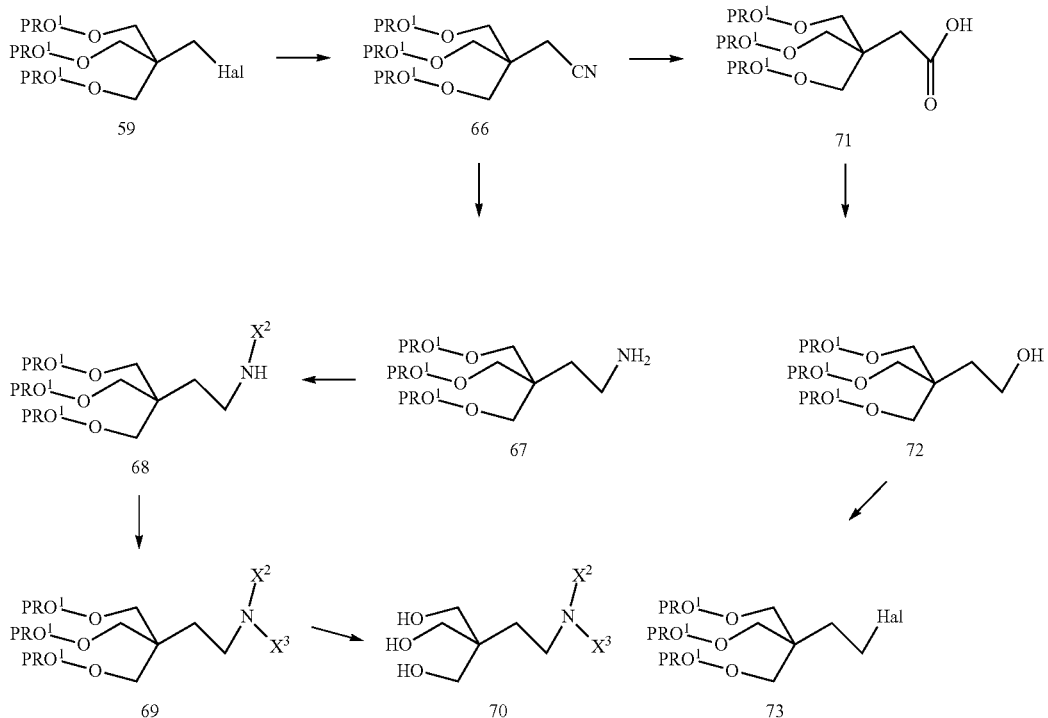

(In the formulas, each group has the same meaning as previously described.)

Compound 66 is obtained by allowing a cyanide (such as sodium cyanide, potassium cyanide or lithium cyanide) to act on Compound 59.

Compound 67 is obtained by reducing Compound 66 with lithium aluminum hydride and the like.

Compound 68 is obtained by allowing Compound 45 to act on Compound 67. In addition, Compound 69 is obtained by allowing Compound 46 to act on Compound 68.

Compound 70 is obtained by de-protecting Compound 69.

Compound 71 is obtained by hydrolyzing Compound 66 with a base (such as sodium hydroxide).

Compound 72 is obtained by reducing Compound 71 with a reducing agent (such as borane).

Compound 73 can be obtained by allowing a halogenating reagent (such as chlorine, bromine, iodine or iodine chloride) to act on Compound 72.

Compounds in which the alkylene chain between each functional group of Compounds 67, 68, 69, 71, 72 and 73 (amino group, monoalkylamino group, dialkylamino group, carboxylic acid group, hydroxyl and halogen atom) and the quaternary carbon has been elongated can be obtained by sequentially carrying out each of the reactions of Synthesis Pathway 14 starting from Compound 59 on Compound 73. In addition, the alkylene chain between each functional group and the quaternary carbon can be elongated as desired by repeating these reactions.

Compound 76 can be synthesized in accordance with Synthesis Pathway 15.

Synthesis Pathway 15

[C103]

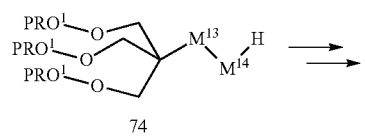

74

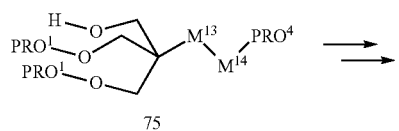

75

-continued

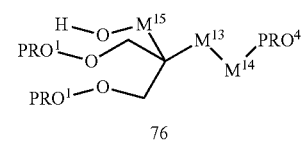

76

(In the formulas, $M^{13}$ is $-(CH_2)_{p201}-$, $M^{15}$ is $-(CH_2)_{p202}-$ (wherein, $p^{201}$ and $p^{202}$ are an integer of 1 to 5), $M^{14}$ is $-O-$, $-CO-O-$ or $-NY^{274}-$, and $PRO^4$ is any of a protective group $PRO^1$ for protecting hydroxyl groups, protective group $PRO^2$ for protecting carboxylic acid groups or protective group $PRO^3$ for protecting amines (such as a carbamate-based protective group such as a tert-butoxycarbonyl, or a benzyl) in accordance with $M^{14}$.)

Compound 74 is obtained by the methods described in Synthesis Pathways 12 to 14 or a method equivalent thereto.

Compound 75 is obtained by suitably protecting or de-protecting Compound 74.

Compound 76 is obtained by the methods described in Synthesis Pathways 12 to 14, or a method equivalent thereto, using Compound 75 for the starting material.

Compounds 77 to 79 can be obtained by sequentially carrying out protection, de-protection and the method described in Synthesis Pathway 15 using Compound 76 for the starting material.

Synthesis Pathway 16

[C104]

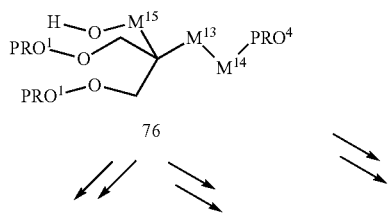

76

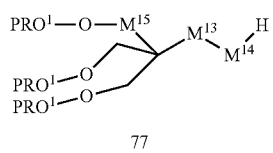

77

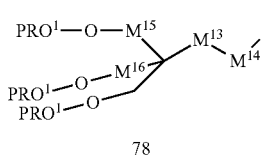

78

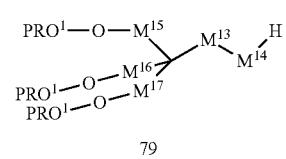

79

(In the formulas, $M^{16}$ and $M^{17}$ respectively are $-(CH_2)_{p203}-$ and $-(CH_2)_{p204}-$ (wherein, $p^{203}$ and $p^{204}$ are integers of 1 to 5), and each of the other groups has the same meanings as previously described.)

Compounds 82, 84, 87, 89, 92 and 95 can be synthesized in accordance with Synthesis Pathway 17.

Synthesis Pathway 17

[C105]

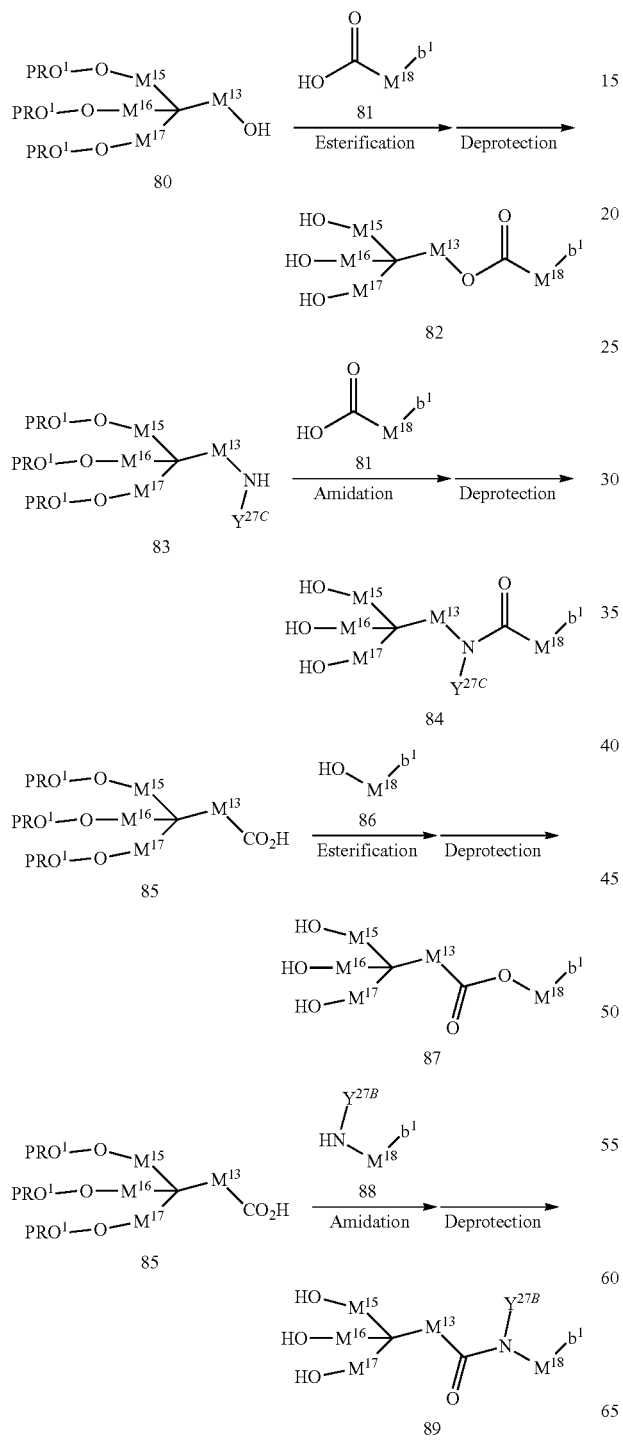

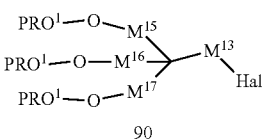

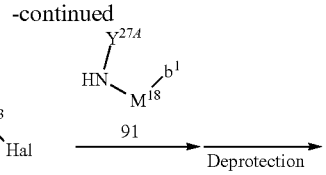

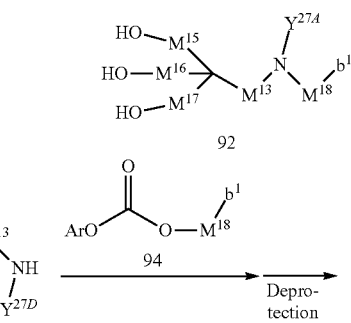

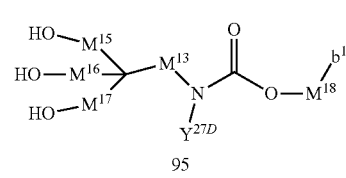

(In the formulas, $M^{18}$ is $-(CY^{19}Y^{20})_{p9}-$ or $-(CY^{23}Y^{24})_{p11}-Z^9-(CY^{25}Y^{26})_{p12}-$. In addition, $b^1$ is

[C106]

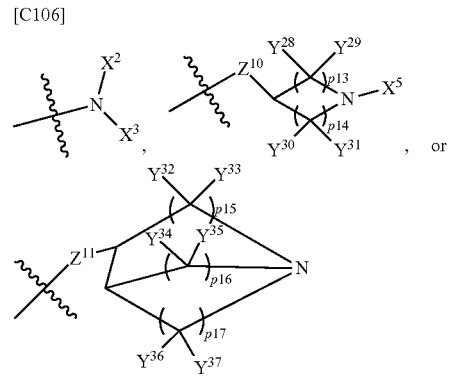

Ar is a p-nitrophenyl, Hal is a halogen atom such as chlorine, bromine or iodine, and each of the other groups has the same meaning as previously described. Furthermore, in the case $p^{13}$ is 0, N bonds directly to the carbon atom adjacent to $Z^{10}$.)

Compound 82 is obtained by condensing Compound 80 and Compound 81 by esterification and then de-protecting.

Compound 84 is obtained by condensing Compound 83 and Compound 81 by amidation and then de-protecting.

Compound 87 is obtained by condensing Compound 85 and Compound 86 by esterification and then de-protecting.

Compound 89 is obtained by condensing Compound 85 and Compound 88 and then de-protecting.

Compound 92 is obtained by subjecting Compound 90 and Compound 91 to a nucleophilic substitution reaction and then de-protecting.

Compound 95 is obtained by subjecting Compound 93 and Compound 94 to a transesterification reaction and then de-protecting.

Compounds 80, 83, 85, 90 and 93 can be obtained according to the methods of Synthesis Pathways 13 to 16 or methods equivalent thereto.

Compounds 81, 86, 88, 91 and 94 in which $M^{18}$ is $-(CY^{19}Y^{20})_{p9}-$ can be obtained as commercially available products, by methods described in the examples or methods equivalent thereto, or by converting functional groups of commercially available products in accordance with established methods.

In this case, compounds in which $b^1$ is

[C107]

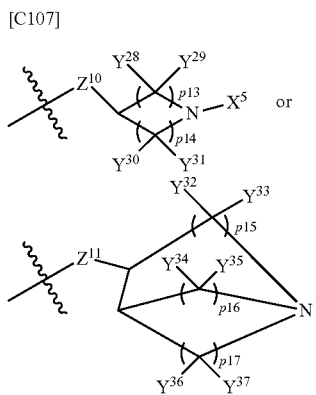

can be obtained by respectively condensing suitable fragments respectively corresponding thereto to each of the following

[C108]

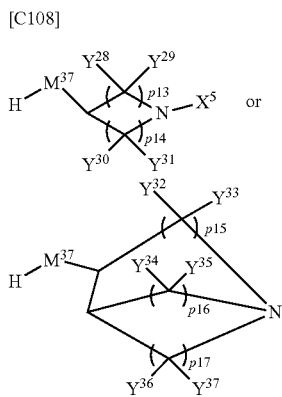

(wherein, $M^{37}$ is $-OH$, $-CO_2H$ or $NY^{38}$ (provided that $Y^{38}$ is a hydrogen atom or optionally substituted C1-C4 alkyl) by amination, esterification or amidation and the like.

In addition, Compounds 81, 86, 88, 91 and 94 in which $M^{18}$ is $-(CY^{23}Y^{24})_{p11}-Z^9-(CY^{25}Y^{26})_{p12}-$ can be obtained by condensing suitable fragments respectively corresponding thereto to compounds similar to Compounds 81, 86, 88, 91 and 94 in which $M^{18}$ is $-(CY^{19}Y^{20})_{p9}-$ by etherification, amination, esterification or amidation and the like.

Compound (III) can be obtained by the methods of Synthesis Pathways 18 to 22, or by methods equivalent thereto, as described below.

Compound (IIIa) can be obtained from Compound 96 in accordance with Synthesis Pathway 18.

Synthesis Pathway 18

[C109]

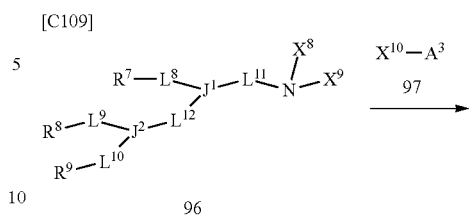

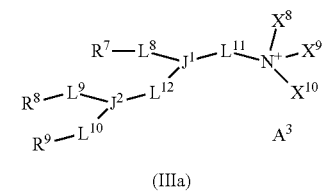

(IIIa)

(In the formulas, each group has the same meaning as previously described.)

Compound (IIIa) is obtained by reacting Compound 96 and Compound 97 in the presence or absence of solvent (halogen-based solvent such as chloroform) at room temperature or high temperature (such as 100° C. or higher). Furthermore, anion $A^3$ of Compound (IIIa) can be converted to a different anion by treating Compound (IIIa) with a suitable anion exchange resin.

Compound 96 can be acquired by methods described in the examples or methods equivalent thereto, or by methods described in the literature (such as U.S. Patent Application Publication No. 2012/0172411) or methods equivalent thereto.

Compounds such as Compound 97 used in the reactions can be acquired as commercially available products, by methods described in the examples or methods equivalent thereto, or by known methods described in the literature or methods equivalent thereto.

Compound (IIIb) can be obtained from ethyl glyoxylate in accordance with Synthesis Pathway 19.

Synthesis Pathway 19

[C110]

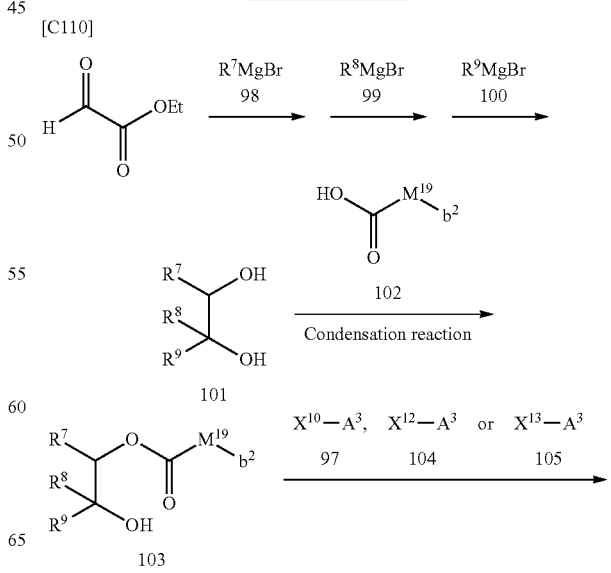

-continued

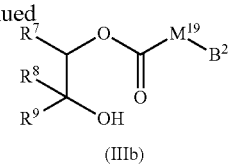

(IIIb)

(In the formulas, $M^{19}$ is $-(CY^{50}Y^{51})_{p23}-$ or $-(CY^{54}Y^{55})_{p25}-Z^{17}-(CY^{56}Y^{57})_{p26}-$ (wherein, each group has the same meaning as previously described), $b^2$ is

[C111]

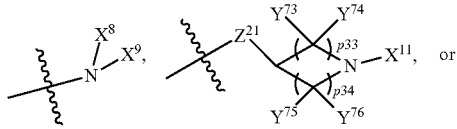

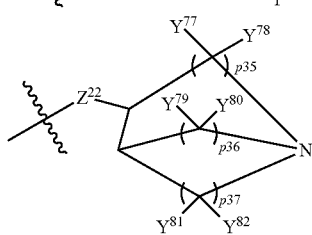

and each of the other groups has the same meaning as previously described. Furthermore, in the case $p^{33}$ is 0, N bonds directly to the carbon atom adjacent to $Z^{21}$.)

Compound 101 is obtained by sequentially reacting ethyl glyoxylate with Grignard reagents 98, 99 and 100 in a solvent (ether-based solvent such as tetrahydrofuran). Furthermore, Compound 101 in which $R^7$, $R^8$ and $R^9$ are the same is obtained by allowing an excess of Compound 98 to act on ethyl glyoxylate.

Compound 103 is obtained by treating Compound 101 and Compound 102 with a base (e.g. organic base such as triethylamine), condensing agent (condensing agent such as 1-ethyl-3-(3-methylaminopropyl)carbodiimide hydrochloride) and activator (activator such as N,N-dimethylaminopyridine) in a solvent (e.g. halogen-based solvent such as chloroform).

Compound (IIIb) is obtained by reacting Compound 103 with Compound 97, Compound 104 or Compound 105 in the presence or absence of solvent (e.g. halogen-based solvent such as chloroform) at room temperature or high temperature (such as 100° C. or higher). Furthermore, anion $A^3$ of Compound (IIIb) can be converted to a different anion by treating Compound (IIIb) with a suitable anion exchange resin.

Compound 98 can be obtained by sequentially allowing a mesylating reagent (such as mesylic anhydride or mesylic chloride), bromide (such as magnesium bromide or lithium bromide) and magnesium metal to act on $R^7$—OH (obtained as a commercially available product or by methods described in the examples or methods equivalent thereto). Compounds 99 and 100 are similar to Compound 98.

Compounds 104 and 105 are similar to Compound 23. Compound 102 is similar to Compound 54.

Compounds 108, 109 and 112 can be respectively obtained from ammonia, ethyl formate and Compound 99 in accordance with Synthesis Pathway 20.

Synthesis Pathway 20

[C112]

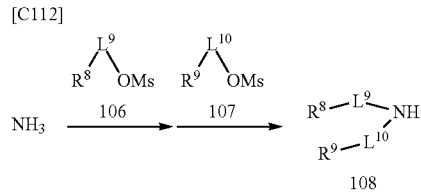

(In the formulas, $M^{21}$ is —OH, $M^{22}$ is HO—CO— and $M^{25}$ is —O—CO—, $M^{21}$ is —NY$^{45C}$—H, $M^{22}$ is HO—CO— and $M^{25}$ is —NY$^{45C}$—CO—, or $M^{21}$ is —CO—OH, $M^{22}$ is H—NY$^{14B}$— and $M^{25}$ is —CO—NY$^{14B}$—. In addition, $M^{20}$ is absent and $M^{23}$ is $-(CY^{39}Y^{40})_{p18}-$, $M^{20}$ is absent and $M^{23}$ is $-(CY^{41}Y^{42})_{p19}-Z^{14}-(CY^{43}Y^{44})_{p20}-$, or $M^{20}$ is $-Z^{13}-(CY^{41}Y^{42})_{p19}-$ and $M^{23}$ is $-(CY^{43}Y^{44})_{p20}-$. Moreover, $M^{24}$ is $-(CY^{63}Y^{64})_{p29}-$ or $-(CY^{67}Y^{68})_{p31}-Z^{20}-(CY^{69}Y^{70})_{p32}-$, and each of the other groups has the same meaning as previously described.)

Compound 108 is obtained by reacting ammonia, Compound 106 and Compound 107 by applying the same reaction conditions as those used to synthesize Compound 4 from ammonia in Synthesis Pathway 1.

Compound 109 is obtained by reacting ethyl formate, Compound 99 and Compound 100 by applying the same reaction conditions as those used to synthesize Compound 101 from ethyl glyoxylate in Synthesis Pathway 19.

Compound 112 can be obtained by condensing Compound 110 and Compound 111 by esterification or amidation and then de-protecting.

Compound 106 and Compound 107 are similar to Compound 1.

Compound 110 in which $M^{21}$ is —OH is similar to $R^1$—$L^1$-OH described in Synthesis Pathway 1. In addition, Compound 110 in which $M^{21}$ is —NY$^{45C}$—H is similar to Compound 37. Moreover, Compound 110 in which $M^{21}$ is —CO—OH is similar to Compound 17.

Compound 111 can be acquired as a commercially available product, by methods described in the examples or methods equivalent thereto, or by known methods described in the literature (such as methods described in "Fourth Series of Experimental Chemistry 20: Synthesis of Organic Compounds II", Fourth edition, p. 187, Maruzen Co., Ltd. (1992)), or methods equivalent thereto.

Compounds (IIIe) and (IIId) can be respectively obtained from Compounds 108 and Compounds 112 and Compounds 109 and 112 in accordance with Synthesis Pathway 21.

Synthesis Pathway 21

[C113]

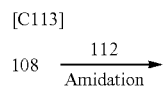

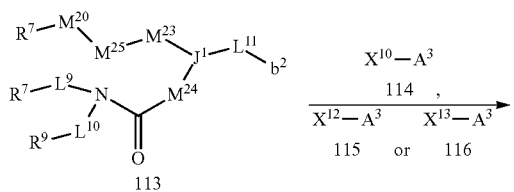

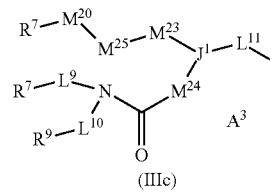

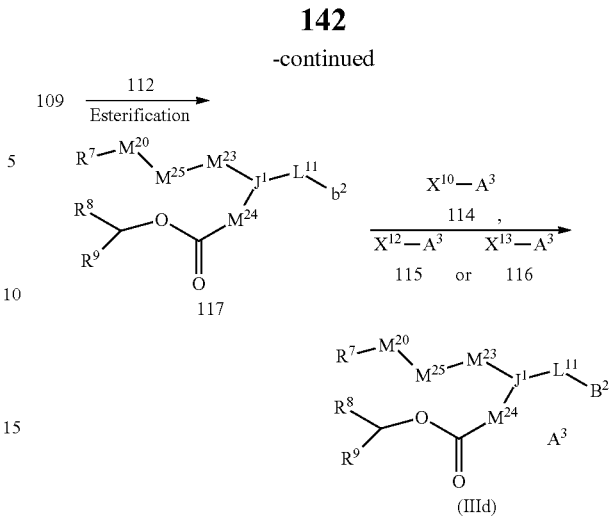

(In the formulas, each group has the same meaning as previously described.)

Compound (IIIc) is obtained by condensing Compounds 108 and 112 by amidation followed by allowing Compound 114, 115 or 116 to act thereon.

Compound (IIId) is obtained by condensing Compounds 109 and 112 by esterification followed by allowing Compound 114, 115 or 116 to act thereon.

Furthermore, anion $A^3$ of Compound (IIIc) or (IIId) can be converted to a different anion by treating Compound (IIIc) or (IIId) with a suitable anion exchange resin.

Each compound used in the reactions is as previously described.

Compound (IV) can be obtained by the methods described in Synthesis Pathways 12 and 13 or methods equivalent thereto as described below.

Compound 127 can be obtained in accordance with Synthesis Pathway 22.

Synthesis Pathway 22

[C114]

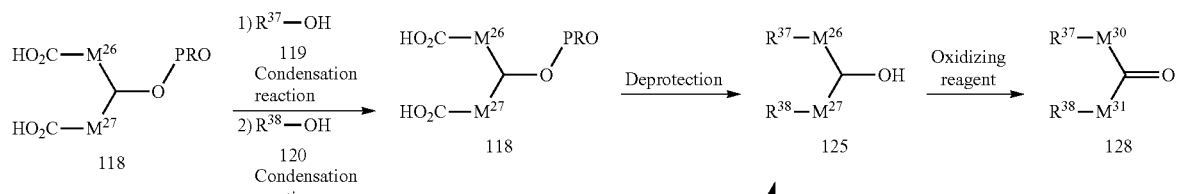

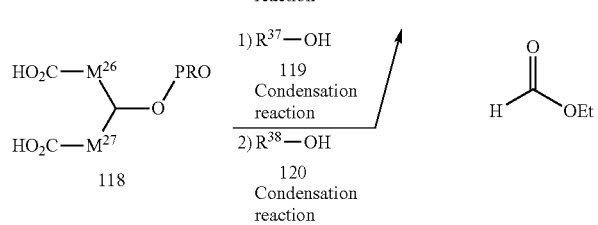

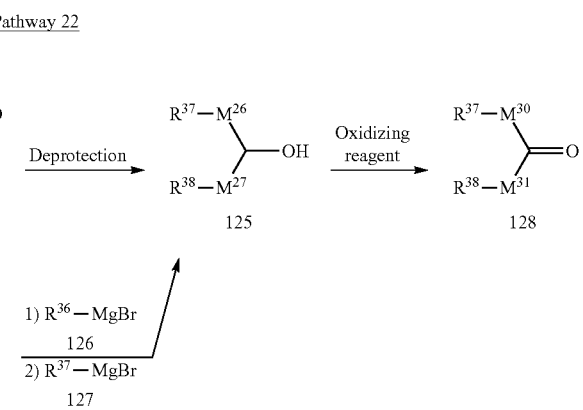

(In the formulas, $M^{26}$ and $M^{27}$, the same or different, are $—(CY^{90}Y^{91})_{p41}—$, $M^{28}$ and $M^{29}$, the same or different, are $—O—CO—(CY^{90}Y^{91})_{p41}—$ or $—CO—O—(CY^{90}Y^{91})_{p41}—$, $M^{30}$ and $M^{31}$, the same or different, are absent or are $—O—CO—(CY^{90}Y^{91})_{p41}—$ or $—CO—O—(CY^{90}Y^{91})_{p41}—$, and each of the other groups has the same meaning as previously described.)

Compound 121 can be obtained by sequentially condensing Compound 118, Compound 119 and Compound 120 by an esterification reaction, or by sequentially condensing Compound 122, Compound 123 and Compound 124 by an esterification reaction.

Compound 125 can be obtained by allowing a de-protecting reagent (de-protecting reagent such as tetra-n-butylammonium fluoride) to act on Compound 121 in a solvent (e.g. ether-based solvent such as tetrahydrofuran), or by sequentially adding Compound 126 and Compound 127 to ethyl formate in a solvent (e.g. ether-based solvent such as tetrahydrofuran).

Compound 128 can be obtained by allowing an oxidizing agent (e.g. organic oxidizing agent such as Dess-Martin reagent or inorganic oxidizing agent such as pyridinium chlorochromate) to act on Compound 125 in a solvent (e.g. aprotic solvent such as chloroform).

Compounds such as Compound 118, Compound 119, Compound 120, Compound 122, Compound 123, Compound 124, Compound 126 and Compound 127 used in the reactions can be acquired as commercially available products, by methods described in the examples or methods equivalent thereto, or by known methods described in the literature (such as methods described in "Fourth Series of Experimental Chemistry 22: Synthesis of Organic Compounds IV", Fourth edition, p. 1, Maruzen Co., Ltd. (1992), "Fourth Series of Experimental Chemistry 20: Synthesis of Organic Compounds II", Fourth edition, p. 1, Maruzen Co., Ltd. (1992), or "Fourth Series of Experimental Chemistry 25: Synthesis of Organic Compounds VII", Fourth edition, p. 59, Maruzen Co., Ltd. (1991)) or methods equivalent thereto.

Compound (IVa) can be obtained from Compound 128 in accordance with Synthesis Pathway 23.

(In the formulas, each group has the same meaning as previously described.)

Compound 130 can be obtained by reacting Compound 128 and Compound 129 in the presence of a reducing agent (e.g. hydride compound such as sodium borohydride or triacetoxyhydride), and an additive (acid such as acetic acid) depending on the case, in a solvent (e.g. halogen-based solvent such as 1,2-dichloroethane).

Compound 132 is obtained by reacting Compound 130 and Compound 131 in the presence of base (e.g. inorganic base such as sodium hydroxide) at a high temperature (such as 100° C. or higher). Although a solvent is not necessarily required, a solvent such as ethylene glycol can be used depending on the case.

Compound (IVa) is obtained by reacting Compound 132 and Compound 133 in the presence or absence of solvent (e.g. halogen-based solvent such as chloroform) at room temperature or high temperature (such as 100° C. or higher). Furthermore, anion $A^4$ of Compound (IVa) can be converted to a different anion by treating Compound (IVa) with a suitable anion exchange resin.

Compounds such as Compound 129, Compound 131 and Compound 133 used in the reactions can be acquired as commercially available products, by methods described in the examples or methods equivalent thereto, or by known methods described in the literature (such as WO 2010/042877, WO 2010/054401, or "Fifth Series of Experimental Chemistry 13: Synthesis of Organic Compounds I", Fifth edition, p. 374, Maruzen Co., Ltd. (2005)) or methods equivalent thereto.

Compound (IVb) can be obtained in accordance with Synthesis Pathway 24.

Synthesis Pathway 23

[C115]

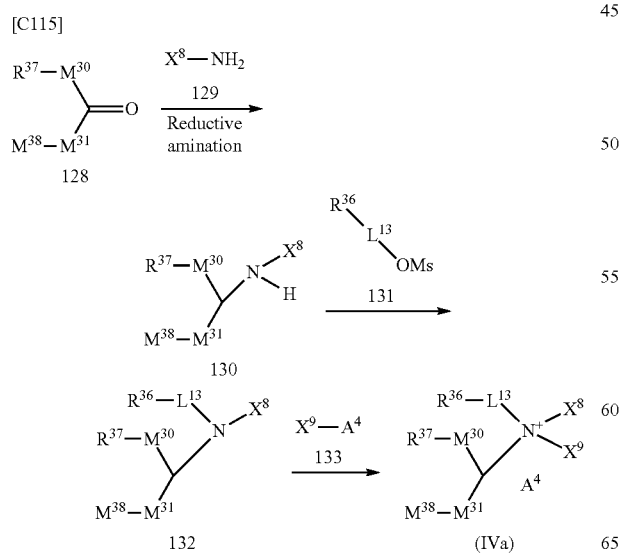

Synthesis Pathway 24

[C116]

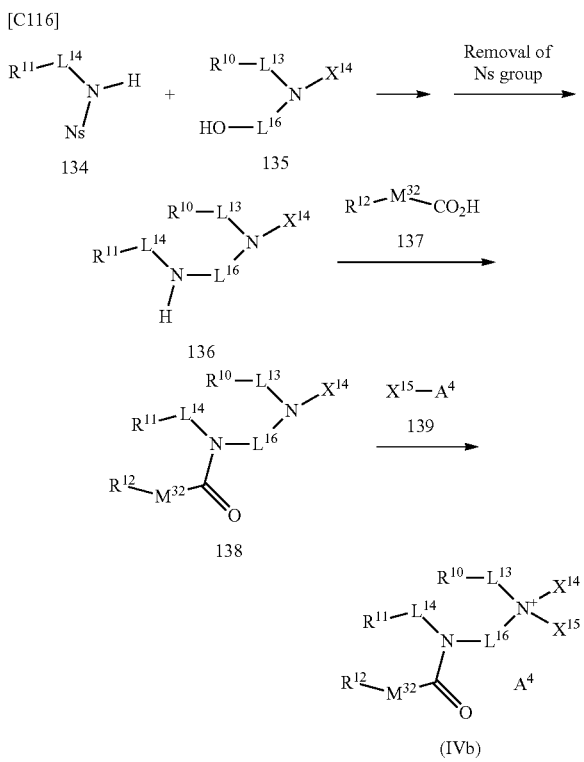

(In the formulas, $M^{32}$ is absent or is —$Z^{27}$—($CY^{92}$ $Y^{93}$)$_{p42}$—, Ns is an o-nitrobenzenesulfonyl, and each of the other groups has the same meaning as previously described.)

Compound 136 is obtained by removing the Ns group by allowing a thiol (dodecane-1-thiol or thiophenol) to act on the resulting condensate after reacting Compound 134, Compound 135, triphenylphosphine and diethyl azodicarboxylate.

Compound 138 is obtained by amidating Compound 136 and Compound 137.

Compound (IVb) is obtained by allowing Compound 139 to act on Compound 138. Furthermore, anion $A^4$ of Compound (IVb) can be converted to a different anion by treating Compound (IVb) with a suitable anion exchange resin.

Compound 134 is obtained by allowing an o-nitrobenzenesulfonyl chloride to act on $R^{11}$-$L^{14}$-$NH_2$. $R^{11}$-$L^{14}$-$NH_2$ can be acquired as a commercially available product, by methods described in the examples or methods equivalent thereto, or by known methods described in the literature (such as "Fourth Series of Experimental Chemistry 20: Synthesis of Organic Compounds II", Fourth edition, p. 279, Maruzen Co., Ltd. (1992)) or methods equivalent thereto.

Compounds such as Compounds 135, 137 and 139 used in the reactions are obtained by any of the previously described methods.

Compound (V'a) can be obtained in accordance with Synthesis Pathway 25.

Synthesis Pathway 25

[C117]

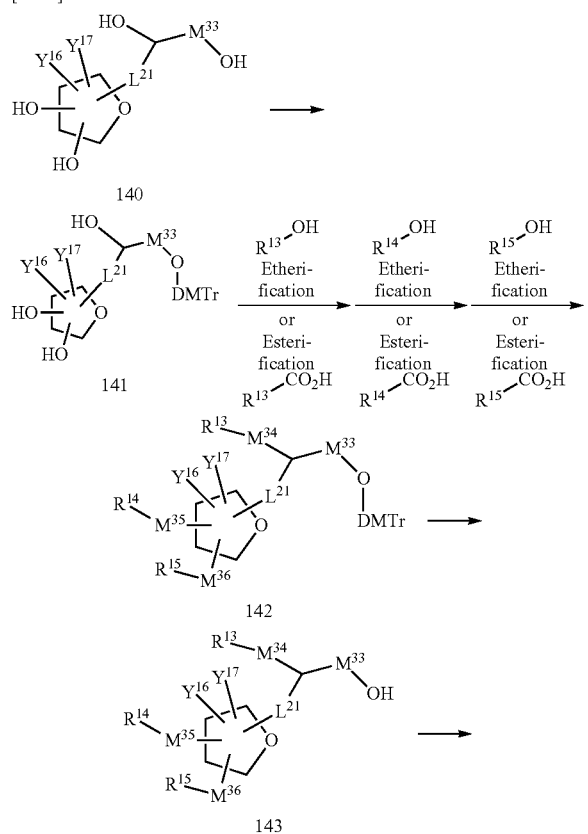

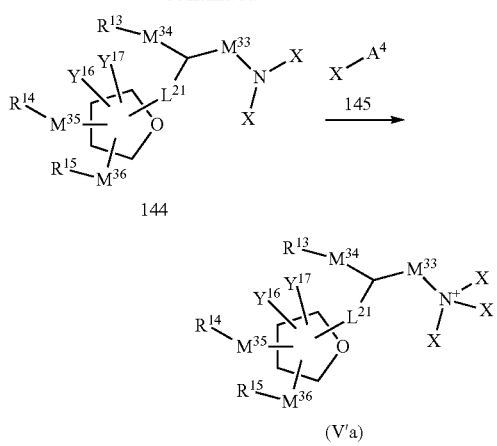

(In the formulas, DMTr is a 2',2''-dimethoxytrityl, $M^{33}$ is —($CY^{122}R^{123}$)$_{p54}$—, —($CY^{124}Y^{125}$)$_{p55}$—$Z^{35}$—($CR^{126}R^{127}$)$_{p56}$— or —($CY^{128}R^{129}$)$_{p57}$—$Z^{36}$—($CY^{130}Y^{131}$)$_{p58}$—$Z^{37}$—($CY^{132}Y^{133}$)$_{p59}$—, $M^{34}$, $M^{35}$ and $M^{36}$ respectively and independently are —O— or —CO—O—, and each of the other groups has the same meaning as previously described.)

Compound 141 is obtained by allowing 2',2''-dimethoxytrityl chloride to act on Compound 140.

Compound 142 is obtained by carrying out three stages of etherification or esterification on Compound 141.

Compound 143 is obtained by treating Compound 142 with acid.

Compound 144 is obtained by activating Compound 143 with a halogenating reagent followed by treating with the corresponding amine compound.

Compound (V'a) is obtained by allowing Compound 145 to act on Compound 144. Furthermore, anion $A^5$ of Compound (V'a) can be converted to a different anion by treating Compound (V'a) with a suitable anion exchange resin.

Compound 140 can be acquired as a commercially available product, natural substance, by methods described in the examples or methods equivalent thereto, or by known methods described in the literature (such as "The Organic Chemistry of Sugars", Daniel E. Levy, ed., Taylor & Francis Group, 2005) or methods equivalent thereto.

Compound (V''a) can be obtained by the similar method as Synthesis Pathway 25 using Compound 146 for the starting material.

Synthesis Pathway 26

[C118]

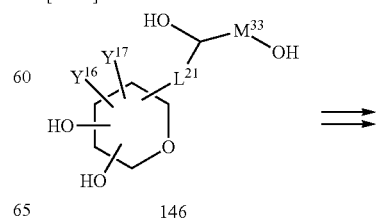

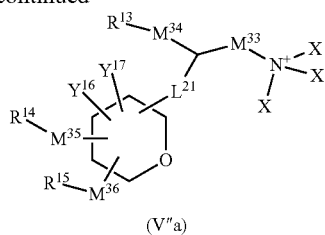

(V″a)

(In the formulas, each group has the same meaning as previously described.)

Compound 146 can be acquired as a commercially available product, natural substance, by methods described in the examples or methods equivalent thereto, or by known methods described in the literature (such as "The Organic Chemistry of Sugars", Daniel E. Levy, ed., Taylor & Francis Group, 2005) or methods equivalent thereto.

Compounds (I) to (V‴) can be obtained by suitably combining any of the methods of the above-mentioned Synthesis Pathways 1 to 26 or equivalent methods thereto.

Compound (CL-I) can be obtained by the method described in WO 2013/089151 or a method equivalent thereto.

Compound (CL-II) can be obtained by the method described in WO 2011/136368 or a method equivalent thereto.

Compound (CL-III), Compound (CL-IV) and Compound (CL-V) can be obtained by the method described in WO 2014/007398 or a method equivalent thereto.

Compound (CL-VI) can be obtained by the method described in WO 2010/042877 or a method equivalent thereto.

Compound (CL-VII) can be obtained by the method described in WO 2010/054401 or a method equivalent thereto.

Although specific examples of lipid A of the present invention are listed in Tables 29 to 44, lipid A is not limited thereto.

TABLE 29

| Compound No. | Structural Formula |
|---|---|
| 1-1 | |
| 1-2 | |
| 1-3 | |
| 1-4 | |
| 1-5 | |

TABLE 29-continued

| Compound No. | Structural Formula |
|---|---|
| 1-6 | (trialkyl ammonium with three unsaturated C18 chains, N+ bonded to propanol group, Cl−) |
| 1-7 | (trialkyl ammonium with three unsaturated C18 chains, N+ bonded to ethanol group, Cl−) |

TABLE 30

| Compound No. | Structural Formula |
|---|---|
| II-1 | (pentaerythritol-based trimester of linoleic acid with trimethylammonium head group, Cl−) |
| II-2 | (pentaerythritol-based trimester of oleic acid with trimethylammonium head group, Cl−) |
| II-3 | (pentaerythritol-based trimester of oleic acid with trimethylammonium head group, Cl−) |
| II-4 | (pentaerythritol-based trimester of saturated fatty acid with trimethylammonium head group, Cl−) |

TABLE 30-continued
| Compound No. | Structural Formula |
| --- | --- |
| II-5 | 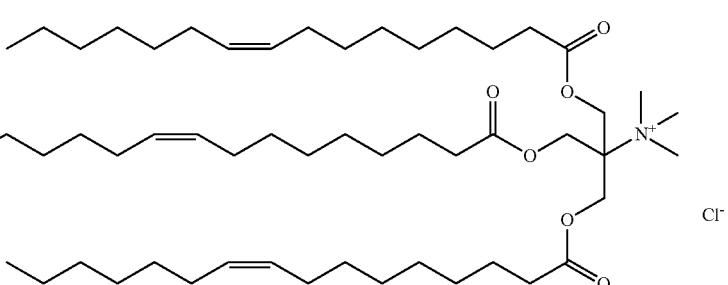 |
| II-6 |  |
TABLE 31
| | |
| --- | --- |
| II-7 | 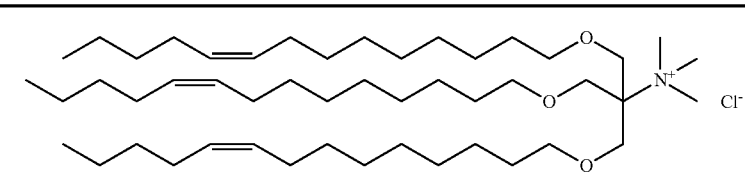 |
| II-8 | 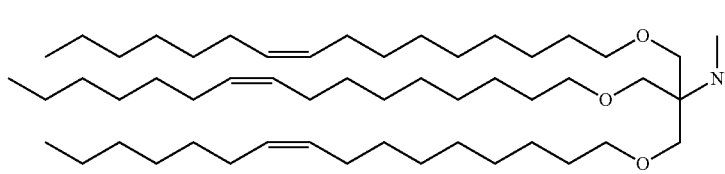 |
| II-9 | 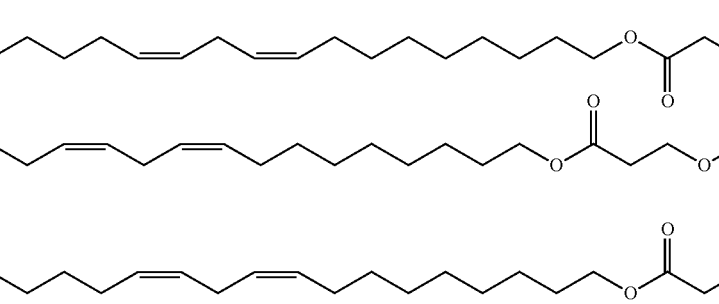 |
| II-10 | 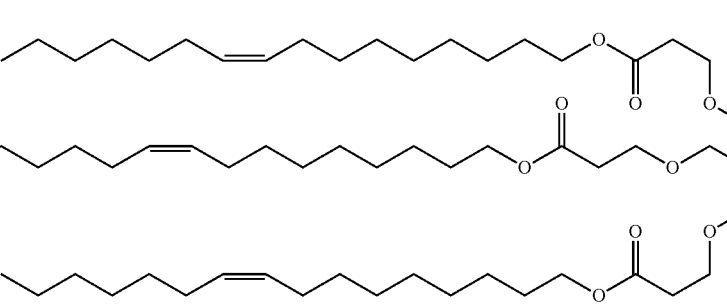 |

TABLE 31-continued
II-11 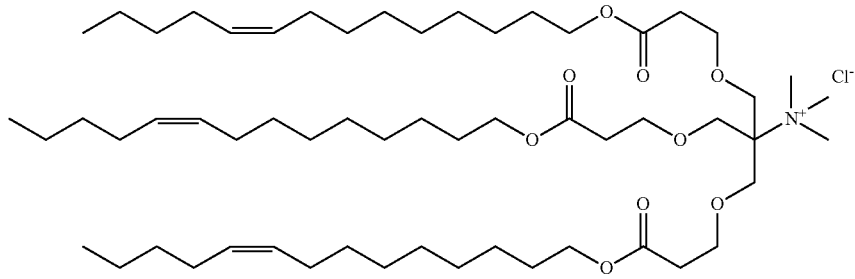 [SMILES: CCCC/C=C\CCCCCCCCOC(=O)CCOCC(COCCC(=O)OCCCCCCCC/C=C\CCCC)(COCCC(=O)OCCCCCCCC/C=C\CCCC)[N+](C)(C)C ; [Cl-]]
II-12 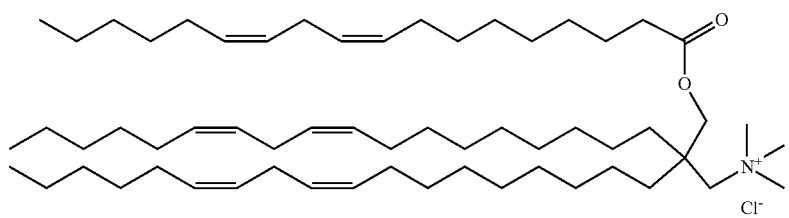 [SMILES: CCCCC/C=C\C/C=C\CCCCCCCCC(CCCCCCCC/C=C\C/C=C\CCCCC)(COC(=O)CCCCCCC/C=C\C/C=C\CCCCC)C[N+](C)(C)C ; [Cl-]]
II-13 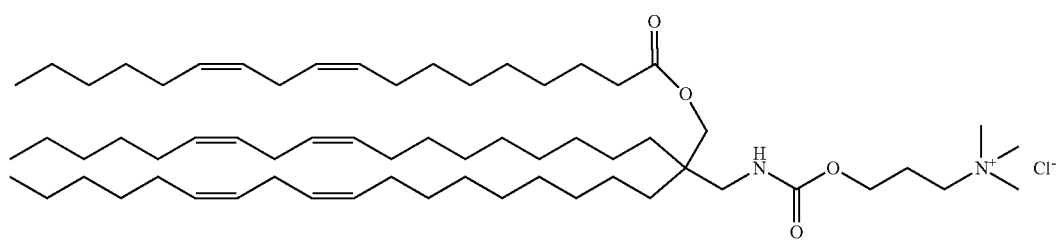 [SMILES: CCCCC/C=C\C/C=C\CCCCCCCCC(CCCCCCCC/C=C\C/C=C\CCCCC)(CNC(=O)OCCC[N+](C)(C)C)COC(=O)CCCCCCC/C=C\C/C=C\CCCCC ; [Cl-]]
TABLE 32
II-14 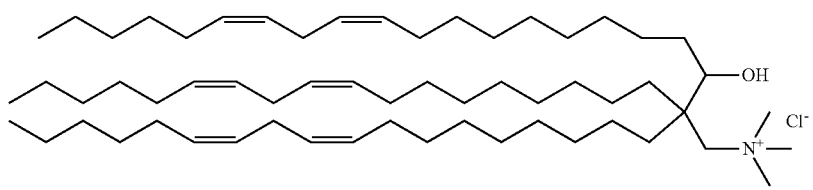 [SMILES: CCCCC/C=C\C/C=C\CCCCCCCCC(O)C(CCCCCCCC/C=C\C/C=C\CCCCC)(CCCCCCCC/C=C\C/C=C\CCCCC)C[N+](C)(C)C ; [Cl-]]
II-15 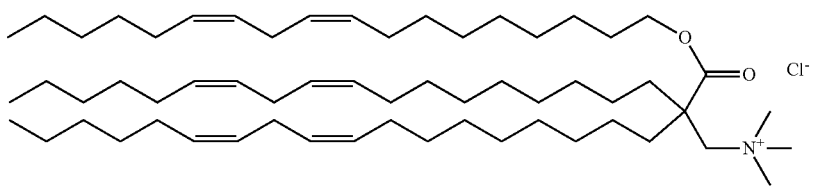 [SMILES: CCCCC/C=C\C/C=C\CCCCCCCCOC(=O)C(CCCCCCCC/C=C\C/C=C\CCCCC)(CCCCCCCC/C=C\C/C=C\CCCCC)C[N+](C)(C)C ; [Cl-]]
II-16 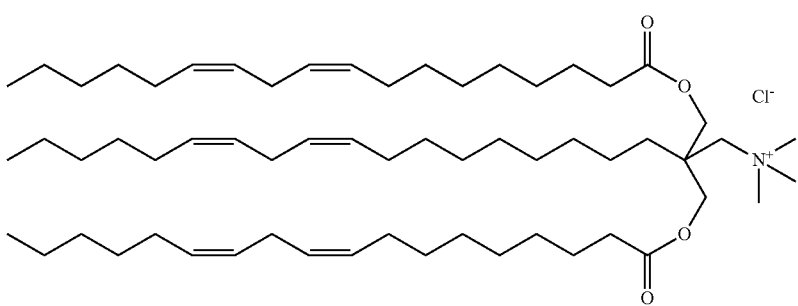 [SMILES: CCCCC/C=C\C/C=C\CCCCCCCCC(COC(=O)CCCCCCC/C=C\C/C=C\CCCCC)(COC(=O)CCCCCCC/C=C\C/C=C\CCCCC)C[N+](C)(C)C ; [Cl-]]

TABLE 32-continued
II-17
II-18
II-19
II-20
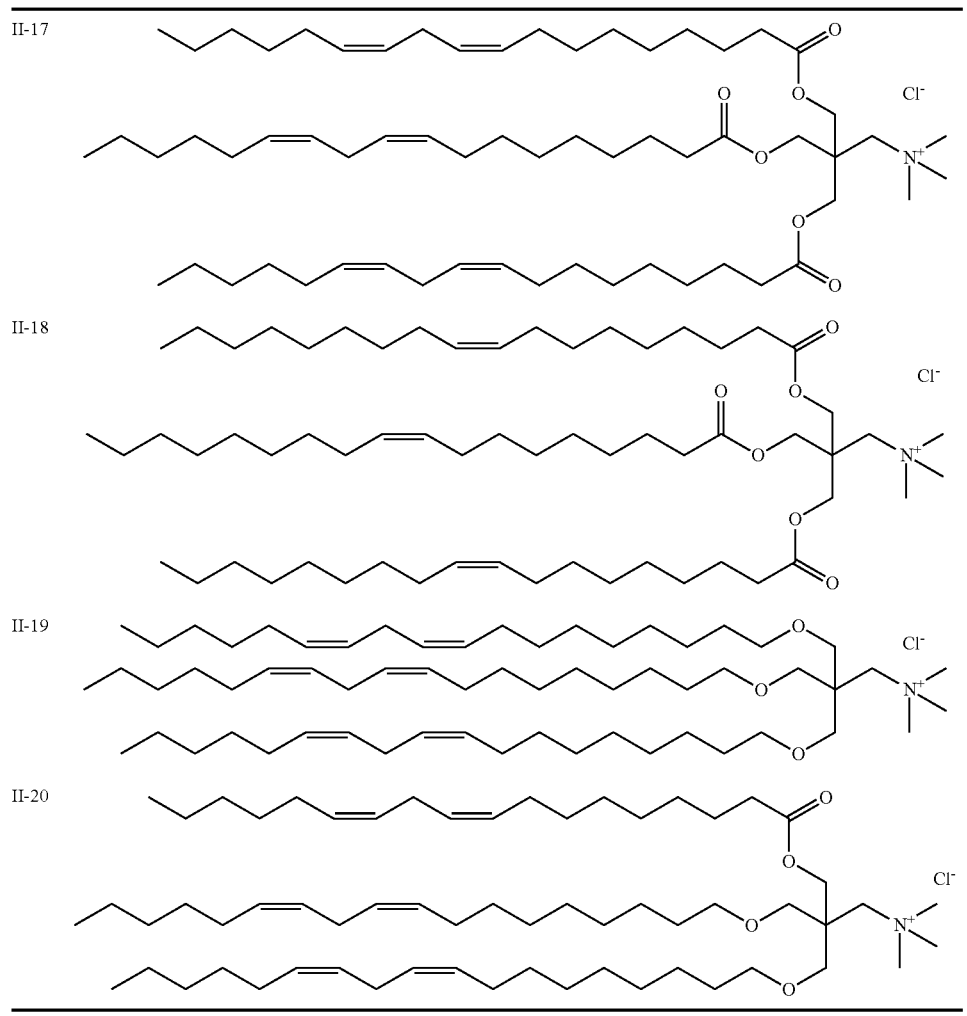
TABLE 33
II-21
II-22
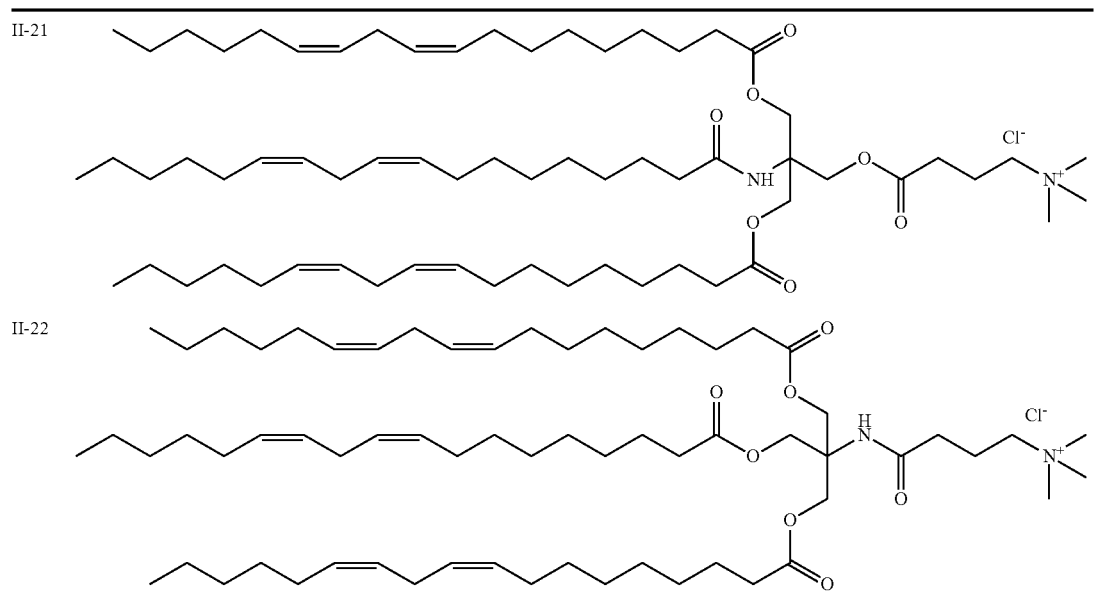

TABLE 33-continued
| Compound No. | Structural Formula |
|---|---|
| II-23 | 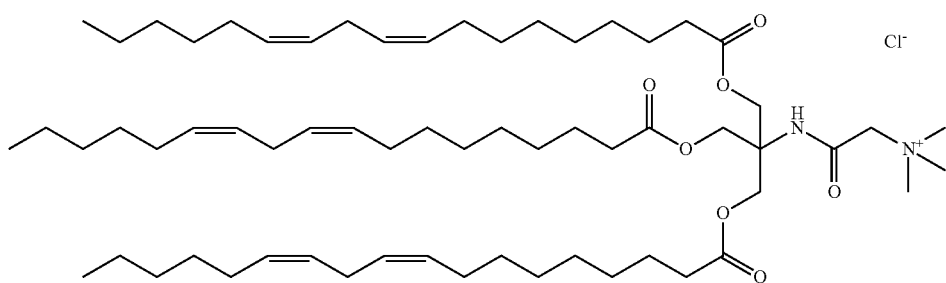 [SMILES: CCCCC/C=C\C/C=C\CCCCCCCC(=O)OCC(COC(=O)CCCCCCC/C=C\C/C=C\CCCCC)(COC(=O)CCCCCCC/C=C\C/C=C\CCCCC)NC(=O)C[N+](C)(C)C ; [Cl-]] |
TABLE 34
| Compound No. | Structural Formula |
|---|---|
| III-1 | 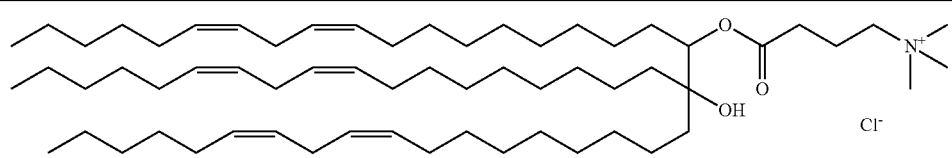 |
TABLE 35
| Compound No. | Structural Formula |
|---|---|
| IV-1 | 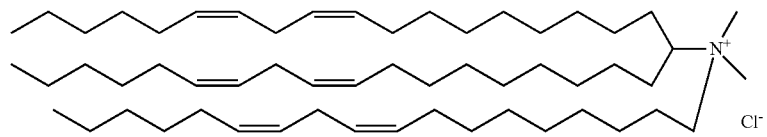 [SMILES: CCCCC/C=C\C/C=C\CCCCCCCCC[N+](C)(C)C(CCCCCCCC/C=C\C/C=C\CCCCC)CCCCCCCC/C=C\C/C=C\CCCCC ; [Cl-]] |
TABLE 36
| Compound No. | Structural Formula |
|---|---|
| II-24 | 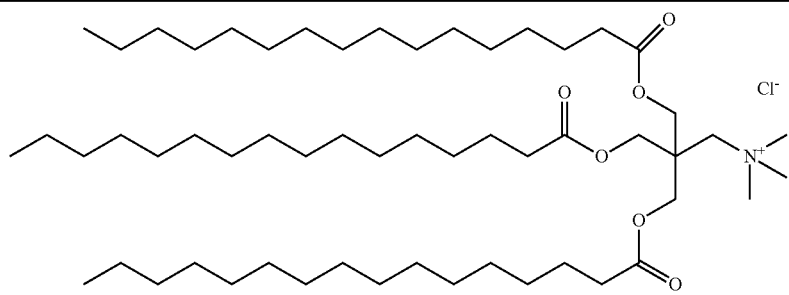 |
| II-25 | 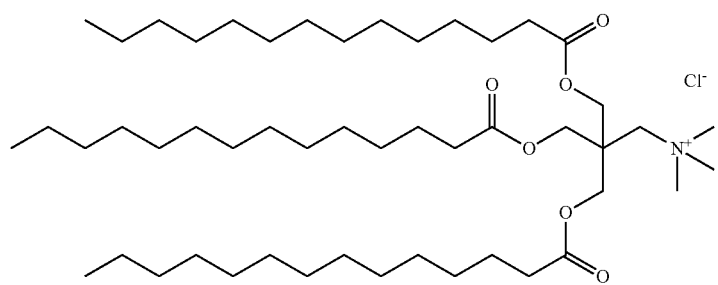 |

TABLE 36-continued

| Compound No. | Structural Formula |
| --- | --- |
| II-26 | |
| II-27 | |
| II-28 | |
| II-29 | |
| II-30 | |

TABLE 37
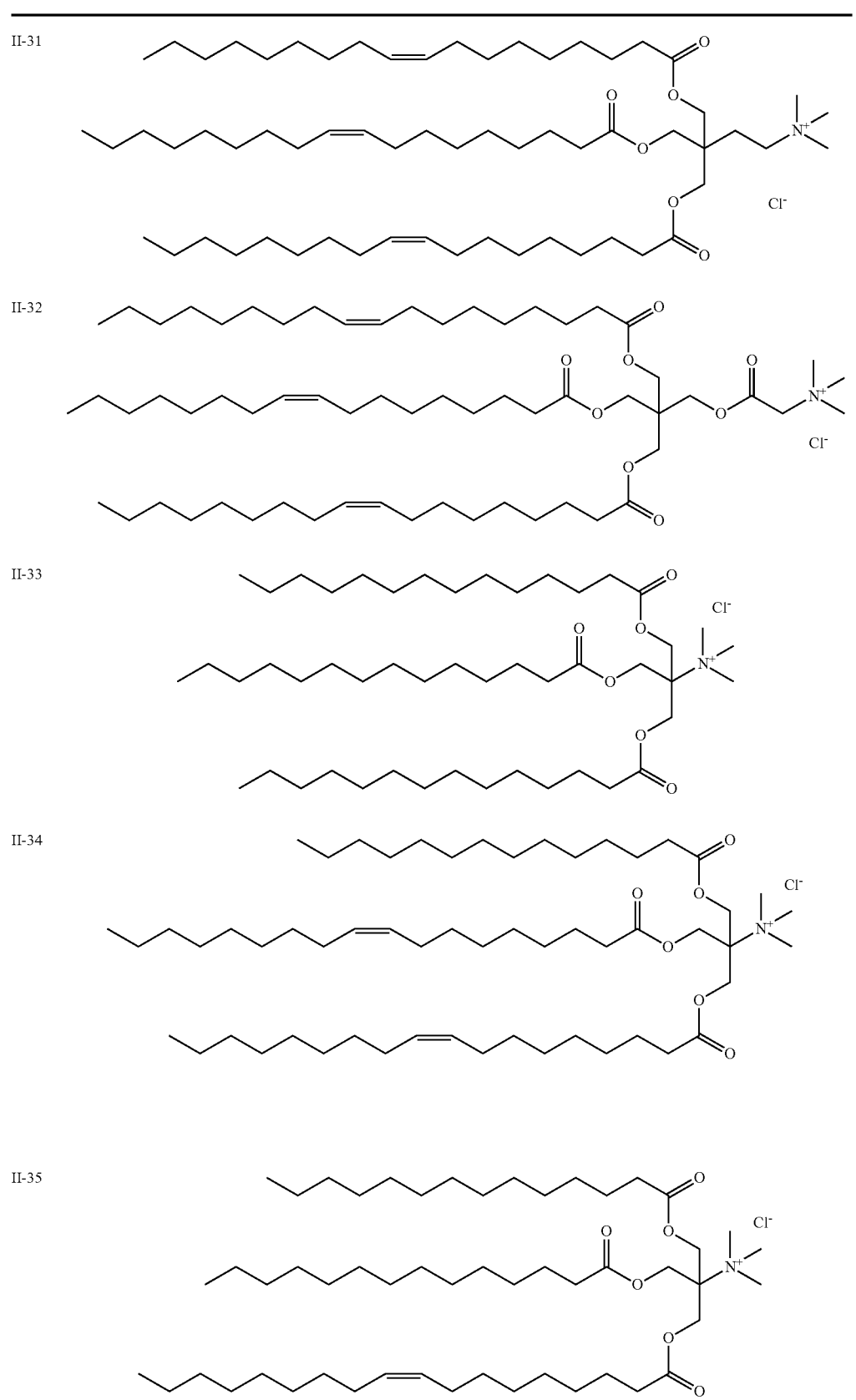

TABLE 37-continued
II-36
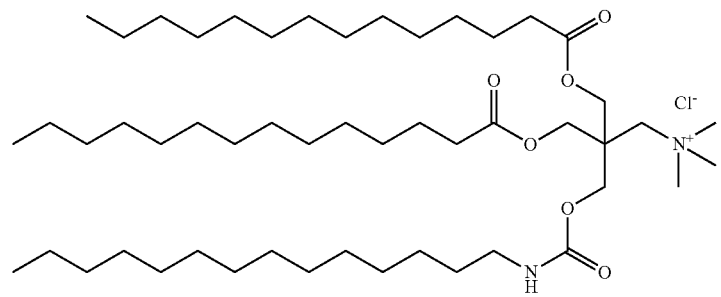 [SMILES: CCCCCCCCCCCCCCNC(=O)OCC(COC(=O)CCCCCCCCCCCCC)(COC(=O)CCCCCCCCCCCCC)C[N+](C)(C)C ; [Cl-]]
II-37
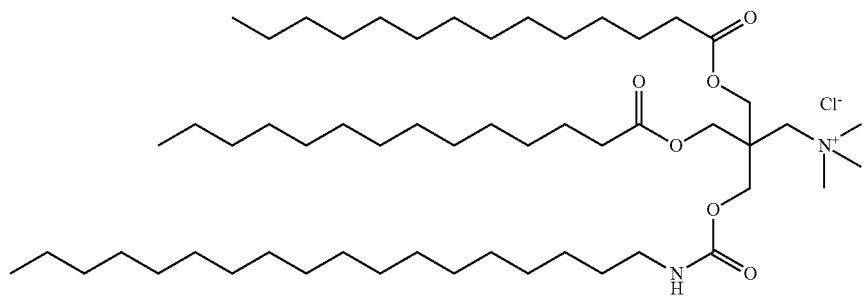 [SMILES: CCCCCCCCCCCCCCCCCCNC(=O)OCC(COC(=O)CCCCCCCCCCCCC)(COC(=O)CCCCCCCCCCCCC)C[N+](C)(C)C ; [Cl-]]
TABLE 38
II-38
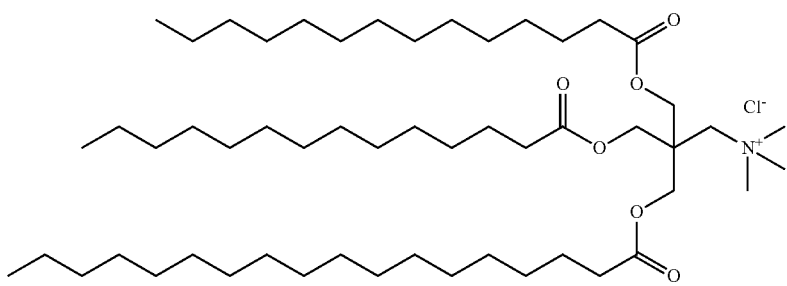 [SMILES: CCCCCCCCCCCCCCCCCC(=O)OCC(COC(=O)CCCCCCCCCCCCC)(COC(=O)CCCCCCCCCCCCC)C[N+](C)(C)C ; [Cl-]]
II-39
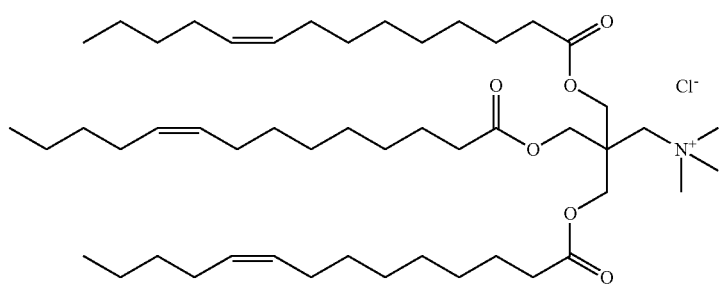 [SMILES: CCCC/C=C\CCCCCCCC(=O)OCC(COC(=O)CCCCCCC/C=C\CCCC)(COC(=O)CCCCCCC/C=C\CCCC)C[N+](C)(C)C ; [Cl-]]
II-40
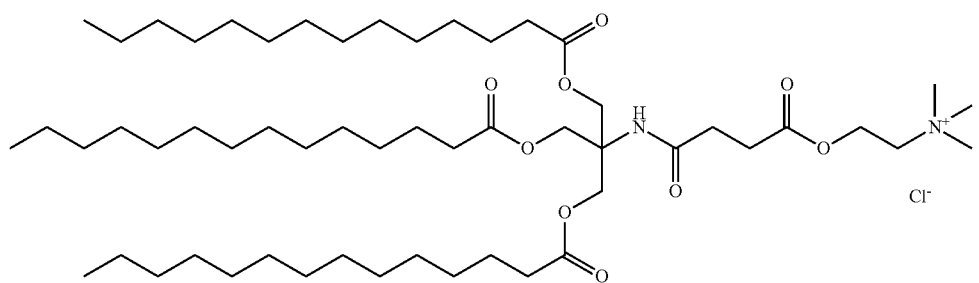 [SMILES: CCCCCCCCCCCCCC(=O)OCC(COC(=O)CCCCCCCCCCCCC)(COC(=O)CCCCCCCCCCCCC)NC(=O)CCC(=O)OCC[N+](C)(C)C ; [Cl-]]

TABLE 38-continued
II-41
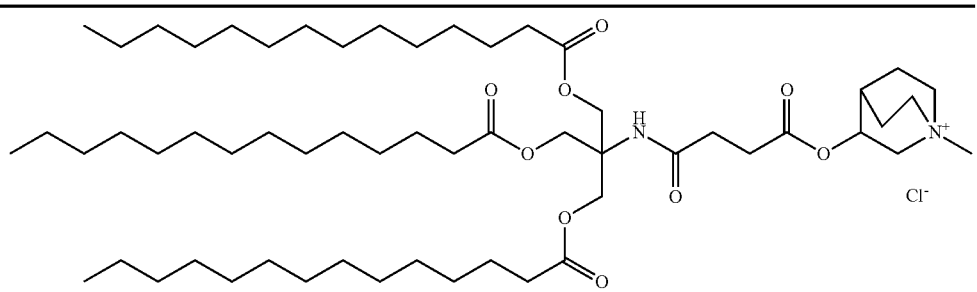
II-42
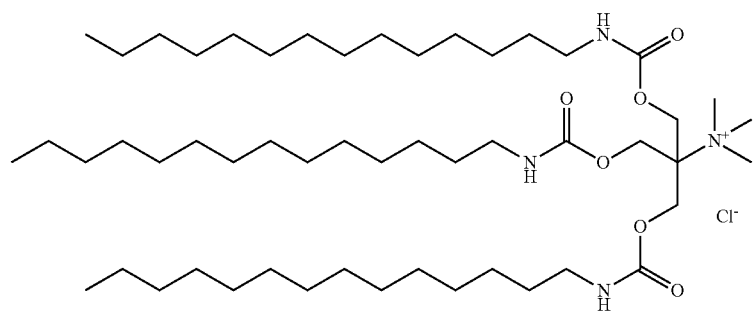 [SMILES: CCCCCCCCCCCCCCNC(=O)OCC(COC(=O)NCCCCCCCCCCCCCC)(COC(=O)NCCCCCCCCCCCCCC)[N+](C)(C)C ; [Cl-]]
II-43
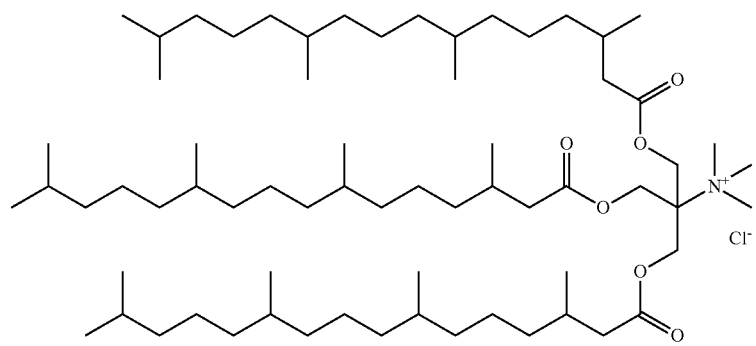 [SMILES: CC(C)CCCC(C)CCCC(C)CCCC(C)CC(=O)OCC(COC(=O)CC(C)CCCC(C)CCCC(C)CCCC(C)C)(COC(=O)CC(C)CCCC(C)CCCC(C)CCCC(C)C)[N+](C)(C)C ; [Cl-]]
II-44
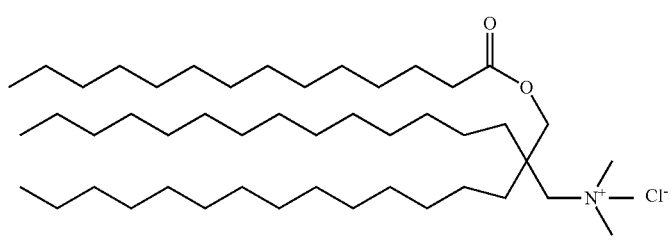 [SMILES: CCCCCCCCCCCCCCC(CCCCCCCCCCCCCC)(COC(=O)CCCCCCCCCCCCC)C[N+](C)(C)C ; [Cl-]]
TABLE 39
II-45
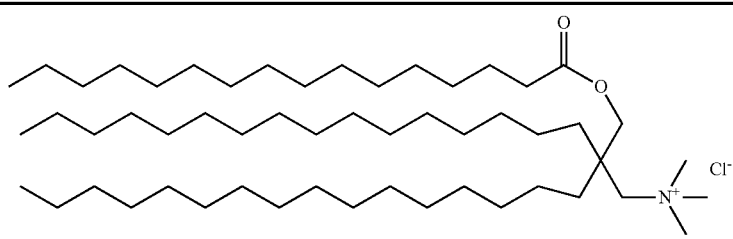

TABLE 39-continued
II-46
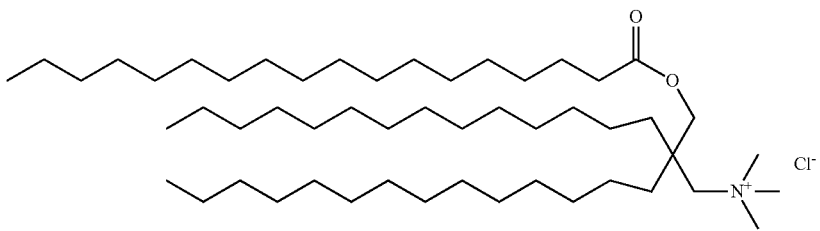 [SMILES: CCCCCCCCCCCCCCCCCC(=O)OCC(CCCCCCCCCCCCCC)(CCCCCCCCCCCCCC)C[N+](C)(C)C ; [Cl-]]
II-47
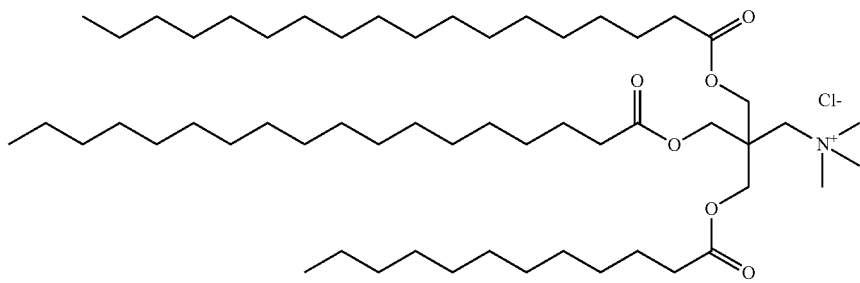 [SMILES: CCCCCCCCCCCCCCCCCC(=O)OCC(COC(=O)CCCCCCCCCCC)(COC(=O)CCCCCCCCCCCCCCCCC)C[N+](C)(C)C ; [Cl-]]
II-48
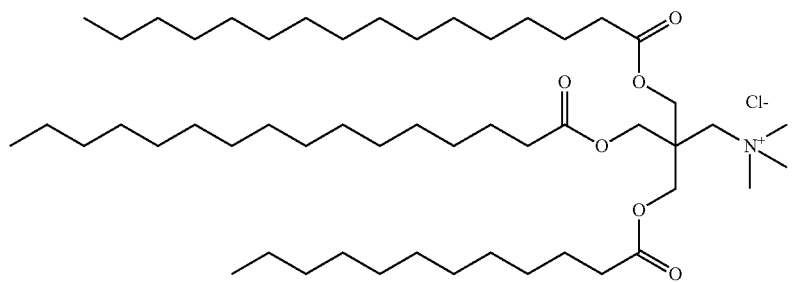 [SMILES: CCCCCCCCCCCCCCCC(=O)OCC(COC(=O)CCCCCCCCCCC)(COC(=O)CCCCCCCCCCCCCCC)C[N+](C)(C)C ; [Cl-]]
II-49
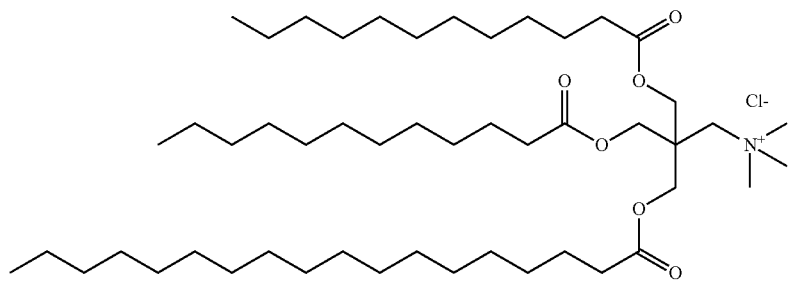 [SMILES: CCCCCCCCCCCCCCCCCC(=O)OCC(COC(=O)CCCCCCCCCCC)(COC(=O)CCCCCCCCCCC)C[N+](C)(C)C ; [Cl-]]
II-50
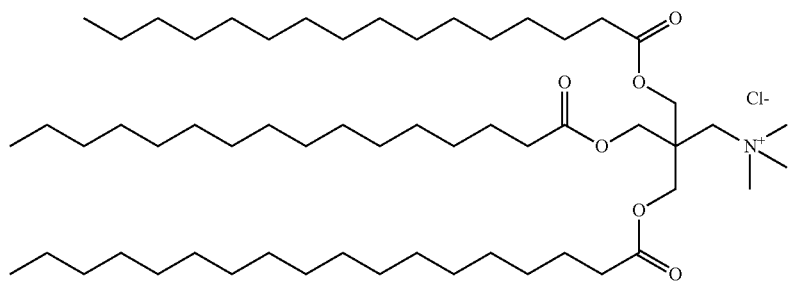 [SMILES: CCCCCCCCCCCCCCCCCC(=O)OCC(COC(=O)CCCCCCCCCCCCCCC)(COC(=O)CCCCCCCCCCCCCCC)C[N+](C)(C)C ; [Cl-]]

TABLE 39-continued
II-51
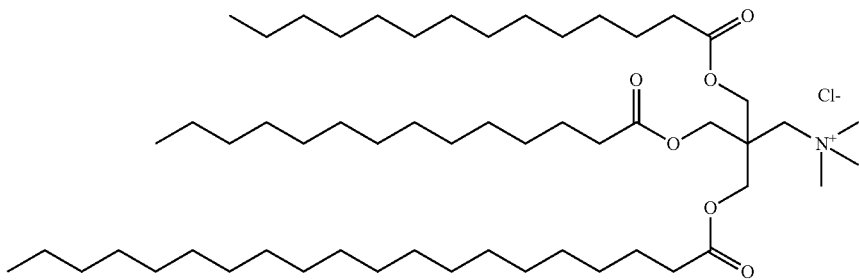 [SMILES: CCCCCCCCCCCCCCCCCCCC(=O)OCC(COC(=O)CCCCCCCCCCCCC)(COC(=O)CCCCCCCCCCCCC)C[N+](C)(C)C ; [Cl-]]
TABLE 40
II-52
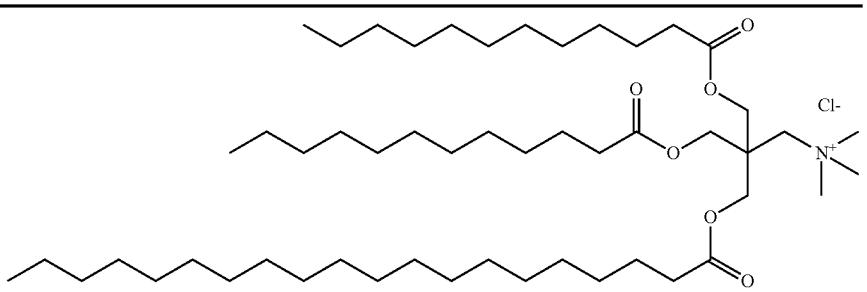
II-53
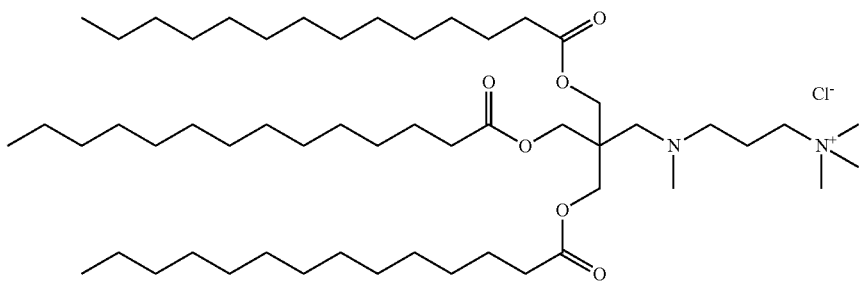 [SMILES: CCCCCCCCCCCCCC(=O)OCC(COC(=O)CCCCCCCCCCCCC)(COC(=O)CCCCCCCCCCCCC)CN(C)CCC[N+](C)(C)C ; [Cl-]]
TABLE 41
| Compound No. | Structural Formula |
| --- | --- |
| III-2 | 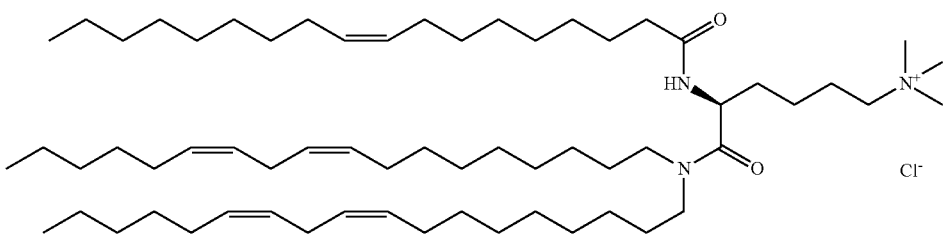 [SMILES: CCCCC/C=C\C/C=C\CCCCCCCCN(CCCCCCCC/C=C\C/C=C\CCCCC)C(=O)[C@H](CCCC[N+](C)(C)C)NC(=O)CCCCCCC/C=C\CCCCCCCC ; [Cl-]] |
| III-3 | 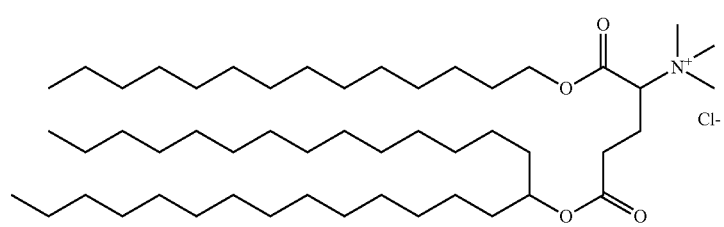 [SMILES: CCCCCCCCCCCCCCOC(=O)C(CCC(=O)OC(CCCCCCCCCCCCCC)CCCCCCCCCCCCCC)[N+](C)(C)C ; [Cl-]] |

TABLE 41-continued

| Compound No. | Structural Formula |
|---|---|
| III-4 | |
| III-5 | |
| III-6 | |
| III-7 | |

TABLE 42

| Compound No. | Structural Formula |
|---|---|
| IV-2 | |
| IV-3 | |

TABLE 43

| Compound No. | Structural Formula |
|---|---|
| V'-1 | 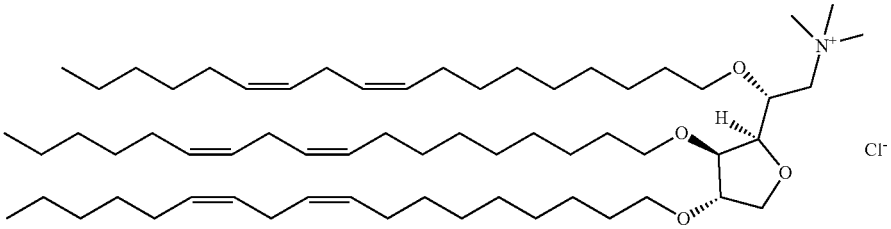 [SMILES: CCCCC/C=C\C/C=C\CCCCCCCCO[C@H]1[C@@H]([C@@H](C[N+](C)(C)C)OCCCCCCCC/C=C\C/C=C\CCCCC)OC[C@@H]1OCCCCCCCC/C=C\C/C=C\CCCCC ; [Cl-]] |

TABLE 44

| Compound No. | Structural Formula |
|---|---|
| V''-1 | 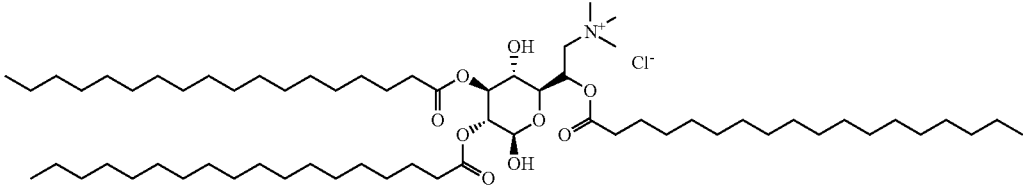 [SMILES: CCCCCCCCCCCCCCCCCC(=O)OC(C[N+](C)(C)C)[C@H]1O[C@@H](O)[C@H](OC(=O)CCCCCCCCCCCCCCCCC)[C@@H](OC(=O)CCCCCCCCCCCCCCCCC)[C@@H]1O ; [Cl-]] |

Any molecule may be used for the nucleic acid used in the present invention provided it is a molecule obtained by polymerizing a nucleotide and/or molecule having the same function as a nucleotide, and examples thereof include polymers of ribonucleotides in the form of ribonucleic acid (RNA), polymers of deoxyribonucleotides in the form of deoxyribonucleic acid (DNA), chimeric nucleic acids of RNA and DNA, and nucleotide polymers in which at least one nucleotide of these nucleic acids is substituted with a molecule having the same function as that nucleotide. In addition, derivatives containing at least partially the structure of a nucleotide and/or molecule obtained by polymerizing molecules having the same function as a nucleotide are also included in the nucleic acid of the present invention. Furthermore, in the present invention, the terms for uracil U and thymine T are interchangeable.

Examples of molecules having the same function as nucleotides include nucleotide derivatives.

Although a nucleotide derivative may be any molecule provided it is a molecule obtained by modifying a nucleotide, molecules obtained by modifying a ribonucleotide or deoxyribonucleotide for the purpose of improving nuclease resistance or stabilizing from other decomposition factors, increasing affinity with complementary strand nucleic acids, increasing cell permeability or more readily visualizing in comparison with RNA or DNA are used preferably.

Examples of nucleotide derivatives include sugar moiety-modified nucleotides, phosphate diester bond-modified nucleotides and base-modified nucleotides.

Although examples of sugar moiety-modified nucleotides include those in which all or a portion of the chemical structure of the sugar of a nucleotide has been modified or substituted with an arbitrary substituent or substituted with an arbitrary atom, 2'-modified nucleotides are used preferably.

Examples of modifying groups of sugar moiety-modified nucleotides include 2'-cyano, 2'-alkyl, 2'-substituted alkyl, 2'-alkenyl, 2'-substituted alkenyl, 2'-halogen, 2'-O-cyano, 2'-O-alkyl, 2'-O-substituted alkyl, 2'-O-alkenyl, 2'-O-substituted alkenyl, 2'-S-alkyl, 2'-S-substituted alkyl, 2'-S-alkenyl, 2'-S-substituted alkenyl, 2'-amino, 2'-NH-alkyl, 2'-NH-substituted alkyl, 2'-NH-alkenyl, 2'-NH-substituted alkenyl, 2'-SO-alkyl, 2'-SO-substituted alkyl, 2'-carboxyl, 2'-CO-alkyl, 2'-CO-substituted alkyl, 2'-Se-alkyl, 2'-Se substituted alkyl, 2'-SiH$_2$-alkyl, 2'-SiH$_2$ substituted alkyl, 2'-ONO$_2$, 2'-NO$_2$, 2'-N$_3$, 2'-amino acid residue (groups in which a hydroxyl has been removed from a carboxylic acid group of an amino acid) and 2'-O-amino acid residue (having the same meaning as the above-mentioned amino acid residue) groups.

Examples of sugar moiety-modified nucleotides include bridged nucleic acids (BNA), having a structure in which a modifying group at the 2'-position is crosslinked to a carbon atom at the 4'-position, and more specifically, locked nucleic acids (LNA), in which an oxygen molecule at the 2'-position and a carbon atom at the 4'-position are crosslinked through methylene, and ethylene-bridged nucleic acids (ENA) (Nucleic Acid Research, 32, e175 (2004)), and these are included in 2'-modified nucleotides.

Examples of sugar moiety-modified nucleotides also include peptide nucleic acids (PNA) (Acc. Chem. Res., 32, 624 (1999)), oxypeptide nucleic acids (OPNA) (J. Am. Chem. Soc., 123, 4653 (2001)), and peptide ribonucleic acids (PRNA) (J. Am. Chem. Soc., 122, 6900 (2000)).

Preferable examples of modifying groups of sugar moiety-modified nucleotides include 2'-cyano, 2'-halogen, 2'-O-cyano, 2'-alkyl, 2'-substituted alkyl, 2'-O-alkyl, 2'-O-substituted alkyl, 2'-O-alkenyl, 2'-O-substituted alkenyl, 2'-Se-alkyl and 2'-Se-substituted alkyl, more preferably include 2'-cyano, 2'-fluoro, 2'-chloro, 2'-bromo, 2'-trifluoromethyl, 2'-O-methyl, 2'-O-ethyl, 2'-O-isopropyl, 2'-O-trifluoromethyl, 2'-O—[2-(methoxy)ethyl], 2'-O—(3-aminopropyl), 2'-O—[2-(N,N-dimethylaminoxy)ethyl], 2'-C-[3-(N,N-dimethylamino)propyl], 2'-O—{2-[2-(N,N-dimethylamino)

ethoxy]ethyl}, 2'-O—[2-(methylamino)-2-oxoethyl] and 2'-Se-methyl, even more preferably include 2'-O-methyl, 2'-O-ethyl and 2'-fluoro groups, and most preferably include 2'-O-methyl and 2'-O-ethyl.

The preferable range of modifying groups in sugar moiety-modified nucleotides can also be defined based on the size thereof, with those equivalent to a size ranging from that of a fluoro group to that of an —O-butyl being preferable, and those equivalent to a size ranging from that of an —O-methyl to that of an —O-ethyl being more preferable.

Examples of alkyl in the modifying groups of sugar moiety-modified nucleotides include C1-C6 alkyl, specific examples of which include C1-C6 alkyl such as a methyl, ethyl, propyl, isopropyl, butyl, isobutyl, sec-butyl, tert-butyl, pentyl, isopentyl, neopentyl or hexyl.

Examples of alkenyl in the modifying groups of sugar moiety-modified nucleotides include C3-C6 alkenyl, specific examples of which include allyl, 1-propenyl, butenyl, pentenyl and hexenyl.

Examples of halogens in the modifying groups of sugar moiety-modified nucleotides include fluorine, chlorine, bromine and iodine atoms.

Examples of amino acids in amino acid residues include aliphatic amino acids (more specifically, glycine, alanine, valine, leucine and isoleucine), hydroxyamino acids (more specifically, serine and threonine), acidic amino acids (more specifically, aspartic acid and glutamic acid), acidic amino acid amides (more specifically, asparagine and glutamine), basic amino acids (more specifically, lysine, hydroxylysine, arginine and ornithine), sulfur-containing amino acids (more specifically, cysteine, cystine and methionine), and imino acids (more specifically, proline and 4-hydroxyproline).

Examples of substituents in substituted alkyl and substituted alkenyl of the modifying groups of sugar moiety-modified nucleotides include halogens (same meaning as previously described), hydroxyl, sulfanyl, amino, oxo and —O-alkyl (wherein the alkyl moiety of the —O-alkyl has the same meaning as C1-C6 alkyl in the above-mentioned modifying groups), —S-alkyl (wherein the alkyl moiety of the —S-alkyl has the same meaning as C1-C6 alkyl in the above-mentioned modifying groups), —NH-alkyl (wherein the alkyl moiety of the —NH-alkyl has the same meaning as C1-C6 alkyl in the above-mentioned modifying groups), dialkylaminoxy groups (wherein the two alkyl moieties in the dialkylaminoxy groups may be the same or different and have the same meaning as C1-C6 alkyl in the above-mentioned modifying groups), dialkylamino groups (wherein the two alkyl moieties in the dialkylamino groups may be the same or different and have the same meaning as C1-C6 alkyl in the above-mentioned modifying groups) and dialkylaminoalkyloxy groups (wherein the two alkyl moieties of the dialkylaminoalkyloxy groups may be the same or different and have the same meaning as C1-C6 alkyl in the above-mentioned modifying groups, and the alkylene moiety refers to an alkylene moiety in which one hydrogen atom has been removed from the C1-C6 alkyl in the above-mentioned modifying groups), and the number of substituents is preferably 1 to 3.

Phosphate diester bond-modified nucleotides refer to those in which all or a portion of the chemical structure of a phosphate diester bond of a nucleotide has been modified or substituted with an arbitrary substituent or substituted with an arbitrary atom, and examples thereof include nucleotides in which a phosphate diester bond has been substituted with a phosphorothioate bond, nucleotides in which a phosphate diester bond has been substituted with a phosphorodithioate bond, nucleotides in which a phosphate diester bond has been substituted with an alkylphosphonate bond, and nucleotides in which a phosphate diester bond has been substituted with a phosphoramidate bond.

Base-modified nucleotides refer to those in which all or a portion of the chemical structure of a base of a nucleotide has been modified or substituted with an arbitrary substituent or substituted with an arbitrary atom, and examples thereof include those in which an oxygen atom in a base has been substituted with a sulfur atom, those in which a hydrogen atom has been substituted with a C1-C6 alkyl, those in which a methyl has been substituted with a hydrogen atom or C2-C6 alkyl, and those in which an amino group has been protected with a protective group such as a C1-C6 alkyl or C1-C6 alkanoyl.

Moreover, examples of nucleotide derivatives include those in which a different chemical substance, such as a lipid, phospholipid, phenazine, folate, phenanthridine, anthraquinone, acridine, fluorescein, rhodamine, coumarin or pigment, has been added to a nucleotide or nucleotide derivative in which at least one sugar moiety, phosphate diester bond or base has been modified, specific examples of which include 5'-polyamine addition nucleotide derivatives, cholesterol addition nucleotide derivatives, steroid addition nucleotide derivatives, bile acid addition nucleotide derivatives, vitamin addition nucleotide derivatives, green fluorescent dye (Cy3) addition nucleotide derivatives, red fluorescent dye (Cy5) addition nucleotide derivatives, fluorescein (6-FAM) addition nucleotide derivatives and biotin addition nucleotide derivatives.

In the nucleic acid used in the present invention, a nucleotide or nucleotide derivative may form a crosslinked structure, such as an alkylene structure, peptide structure, nucleotide structure, ether structure, ester structure or a combination of at least one type thereof, with another nucleotide or nucleotide derivative within that nucleic acid.

The nucleic acid used in the present invention preferably has a molecular weight of 1,000 kDa or less, more preferably 100 kDa or less and even more preferably 30 kDa or less. In addition, examples of the nucleic acid used in the present invention preferably include nucleic acids that inhibit expression of a target gene, and more preferably include nucleic acids having an inhibitory action on the expression of a target gene that uses RNA interference (RNAi).

There are no particular limitations on the target gene in the present invention provided it is a gene that is expressed by producing mRNA and are preferably genes associated with tumors or inflammation, examples of which include genes encoding proteins such as vascular endothelial growth factor (VEGF), vascular endothelial growth factor receptor (VEGFR), fibroblast growth factor, fibroblast growth factor receptor, platelet-derived growth factor, platelet-derived growth factor receptor, hepatocyte growth factor, hepatocyte growth factor receptor, Kruppel-like factor (KLF), expressed sequence tag (Est) transcription factor, nuclear factor, hypoxia-inducible factor, cell cycle-related factors, chromosome replication-related factors, chromosome repair-related factors, microtubule-associated factor, growth signaling pathway-related factors, growth-related transcription factors or apoptosis-related factors, and more specifically, VEGF gene, VEGFR gene, fibroblast growth factor gene, fibroblast growth factor receptor gene, platelet-derived growth factor gene, platelet-derived growth factor receptor gene, hepatocyte growth factor gene, hepatocyte growth factor receptor gene, KLF gene, Est transcription factor gene, nuclear factor gene, hypoxia-inducible factor gene, cell cycle-related factor genes, chromosome replication-related factor genes, chromosome repair-related factor genes, microtubule-associated factor genes (such as CKAP5 gene), growth signaling pathway-related factor genes (such as KRAS gene), growth-related transcription factor genes and apoptosis-related genes (such as BCL-2 gene).

The target gene in the present invention is preferably a gene expressed in, for example, the liver, lungs, kidneys or spleen and more preferably a gene expressed in the liver, examples of which include genes associated with the above-mentioned tumors or inflammation and genes encoding proteins such as the hepatitis B virus genome, hepatitis C virus genome, apolipoprotein (APO), hydroxymethylglutaryl (HMG)-CoA reductase, kexin type 9 serine protease (PCSK9), factor 12, glucagon receptor, glucocorticoid receptor, leukotriene receptor, thromboxane A2 receptor, histamine H1 receptor, carbonic anhydrase, angiotensin convertase, renin, p53, tyrosine phosphatase (PTP), sodium-dependent glucose transporter, tumor necrosis factor, interleukin, hepcidin, transthyretin, antithrombin, protein C or matriptase (such as TMPRSS6 gene).

Although the nucleic acid that inhibits expression of a target gene may be any nucleic acid that contains a base sequence complementary to a portion of the base sequence of mRNA of a gene (target gene) encoding a protein and the like and inhibits expression of a target gene, examples thereof include double-stranded nucleic acids such as siRNA (short interference RNA) or miRNA (micro RNA) and single-stranded nucleic acids such as shRNA (short hairpin RNA), antisense nucleic acids or ribozymes, double-stranded nucleic acids are preferable.

A nucleic acid containing a base sequence complementary to a portion of the base sequence of the mRNA of a target gene is referred to as an antisense strand nucleic acid, while a nucleic acid containing a base sequence complementary to the base sequence of an antisense strand nucleic acid is referred to as a sense strand nucleic acid. Sense strand nucleic acids refer to nucleic acids capable of forming a double-stranded moiety by pairing with an antisense strand nucleic acid, such as nucleic acids per se composed of a portion of a base sequence of a target gene.

A double-stranded nucleic acid refers to a nucleic acid having a portion that forms a double strand as a result of pairing between two strands. The double strand forming portion refers to a portion where a nucleotide or nucleotide derivative that composes a double-stranded nucleic acid forms a double strand by composing base pairs. The number of base pairs that compose the double strand forming portion is normally 15 to 27, preferably 15 to 25, more preferably 15 to 23, even more preferably 15 to 21 and particularly preferably 15 to 19.

The antisense strand nucleic acid of the double strand forming portion preferably uses, for example, a nucleic acid composed of a portion of the sequence of the mRNA of a target gene or a nucleic acid in which 1 to 3 bases, preferably 1 to 2 bases, and more preferably 1 base in the nucleic acid have been substituted, deleted or added, and which has activity that inhibits expression of a target protein. Single-stranded nucleic acids that compose a double-stranded nucleic acid are normally composed of a sequence of 15 to 30 bases (nucleotides), preferably 15 to 29 bases, more preferably 15 to 27 bases, even more preferably 15 to 25 bases, particularly preferably 17 to 23 bases and most preferably 19 to 21 bases.

Either one or both of the antisense strand and sense strand that compose a double-stranded nucleic acid may also have an additional nucleic acid that does not form a double strand on the 3'-side or 5'-side following the double strand forming portion. This portion that does not form a double strand is also referred to as an overhang.

Although a double-stranded nucleic acid having an overhang composed of, for example, 1 to 4 bases, and normally 1 to 3 bases, on the 3'-end or 5'-end of at least one strand is used for the double-stranded nucleic acid having an overhang, that having an overhang composed of 2 bases is used preferably, and that having an overhang composed of dTdT or UU is used more preferably. Although the overhang portion may be possessed by the antisense strand only, sense strand only or both the antisense strand and sense strand, double-stranded nucleic acids having overhangs on both the antisense strand and sense strand are used preferably.

A sequence continuing from the double strand forming portion that partially or completely coincides with the base sequence of the mRNA of a target gene, or a sequence continuing from the double strand forming portion that partially or completely coincides with the base sequence of the complementary strand of the mRNA of a target may be used. Moreover, nucleic acid molecules that form the above-mentioned double-stranded nucleic acid by the action of a ribonuclease such as Dicer (WO 2005/089287) or double-stranded nucleic acids not having an overhang on the 3'-end or 5'-end can also be used as nucleic acids that inhibit expression of a target gene.

In the case the above-mentioned double-stranded nucleic acid is siRNA, the antisense strand is preferably such that the sequence of at least the 1st to 17th base (nucleotide) moving from the 5'-end side towards the 3'-end side is a base sequence complementary to a sequence of 17 contiguous bases of the mRNA of a target gene, and more preferably, the antisense strand is such that the sequence of the 1 st to 19th base moving from the 5'-end side towards the 3'-end side is a base sequence complementary to a sequence of 19 contiguous bases of the mRNA of a target gene, the sequence of the 1st to 21st base is a base sequence complementary to a sequence of 21 contiguous bases of the mRNA of a target gene, or the sequence of the 1st to 25th base is a base sequence complementary to a sequence of 25 contiguous bases of the mRNA of a target gene.

Moreover, in the case the nucleic acid used in the present invention is siRNA, preferably 10% to 70%, more preferably 15% to 60% and even more preferably 20% to 50% of the sugar in the nucleic acid is ribose substituted with a modifying group at the 2'-position. Ribose substituted with a modifying group at the 2'-position in the present invention refers to that in which a hydroxyl at the 2'-position is substituted with a modifying group, and although the configuration with the hydroxyl at the 2'-position of ribose may be the same or different, the configuration is preferably the same as the hydroxyl at the 2'-position of ribose. Examples of modifying groups of ribose substituted with a modifying group at the 2'-position include those exemplified in the definition of modifying groups in 2'-modified nucleotides of sugar moiety-modified nucleotides and hydrogen atoms, preferably include 2'-cyano, 2'-halogen, 2'-C-cyano, 2'-alkyl, 2'-substituted alkyl, 2'-C-alkyl, 2'-C-substituted alkyl, 2'-C-alkenyl, 2'-C-substituted alkenyl, 2'-Se-alkyl and 2'-Se substituted alkyl, more preferably include 2'-cyano, 2'-fluoro, 2'-chloro, 2'-bromo, 2'-trifluoromethyl, 2'-O-methyl, 2'-C-ethyl, 2'-C-isopropyl, 2'-O-trifluoromethyl, 2'-C-[2-(methoxy)ethyl], 2'-C-(3-aminopropyl), 2'-C-[2-(N,N-dimethyl)aminoxy]ethyl, 2'-C-[3-(N,N-dimethylamino) propyl], 2'-O—{2-[2-(N,N-dimethylamino)ethoxy]ethyl}, 2'-C-[2-(methylamino)-2-oxoethyl], 2'-Se-methyl and hydrogen atoms, even more preferably include 2'-O-methyl, 2'-O-ethyl, 2'-fluoro groups and hydrogen atoms, and most preferably include 2'-O-methyl and 2'-O-fluoro groups.

The nucleic acid used in the present invention includes derivatives in which an oxygen atom contained in the phosphate moiety or ester moiety present in the structure of the nucleic acid is substituted with another atom such as a sulfur atom.

Each hydroxyl at the 5'-position of sugars bound to bases on the 5'-ends of the antisense strand and sense strand may be respectively modified by a phosphate group or the above-mentioned modifying groups, or a group converted to a phosphate group or the above-mentioned modifying groups with a nuclease present in the body.

Each hydroxyl at the 3'-position of sugars bound to bases on the 3'-ends of the antisense strand and sense strand may be respectively modified by a phosphate group or the above-mentioned modifying groups, or by a group converted to a phosphate group or the above-mentioned modifying groups with a nuclease present in the body.

Examples of single-stranded nucleic acids include nucleic acids composed of a complementary sequence composed of 15 to 27 contiguous bases (nucleotides), preferably 15 to 25 contiguous bases, more preferably 15 to 23 contiguous bases, even more preferably 15 to 21 contiguous bases, and particularly preferably contiguous 15 to 19 bases of a target gene, or any nucleic acid in which 1 to 3 bases, preferably 1 to 2 bases and more preferably 1 base in the nucleic acid is substituted, deleted or added, and which has activity that inhibits expression of a target protein. The single-stranded nucleic acid preferably uses a single-stranded nucleic acid composed of 10 to 30 contiguous bases (nucleotides), more preferably 10 to 27 contiguous bases, even more preferably 10 to 25 contiguous bases, and particularly preferably 10 to 23 contiguous bases.

A single-stranded nucleic acid in which an antisense strand and sense strand that compose the above-mentioned double-stranded nucleic acid are linked through a spacer sequence (spacer oligonucleotide) may be used as a single-stranded nucleic acid. A single-stranded nucleic acid molecule having 6 to 12 bases is preferable for the spacer oligonucleotide, and the sequence on the 5'-end side thereof preferably consists of 2 U. Examples of spacer oligonucleotides include a nucleic acid composed of the sequence UUCAAGAGA. The order of the antisense strand and sense strand connected by the spacer oligonucleotide is such that either may be on the 5'-side. The single-stranded nucleic acid is preferably a single-stranded nucleic acid such as shRNA in which the double strand forming portion is formed by a stem-loop structure. Single-stranded nucleic acids such as shRNA normally have a length of 50 to 70 bases.

A nucleic acid may be used that has been designed so that the above-mentioned single-stranded nucleic acid or double-stranded nucleic acid is formed due to the action of ribonuclease, and has a length of 70 bases or less, preferably 50 bases or less and more preferably 30 bases or less.

Furthermore, the nucleic acid used in the present invention can be obtained using a known RNA or DNA synthesis method or RNA or DNA modification method.

Although the nucleic acid-containing lipid nanoparticles of the present invention are a complex of lipid A and nucleic acid, the nanoparticles may contain one type or two or more types of lipid A.

The nucleic acid-containing lipid nanoparticles of the present invention may contain one type or two or more types of lipid B, a neutral lipid and/or a lipid derivative or fatty acid derivative of a water-soluble polymer in addition to lipid A and nucleic acid.

The nucleic acid-containing lipid nanoparticles of the present invention may also contain one type or two or more types of lipid B together with lipid A.

Furthermore, the nucleic acid-containing lipid nanoparticles of the present invention can also contain a substance chemically similar to a nucleic acid (in the manner of an anionic polymer such as an anionic peptide) in addition to nucleic acid.

In the present invention, the nucleic acid is dissolved in a water-miscible organic solvent with lipid A together with another lipid as necessary (lipid (lipid B) having a lipid derivative or fatty acid derivative of a water-soluble polymer, a neutral lipid and/or a hydrophilic unit having one optionally substituted amino group, and a hydrophobic unit having two independent optionally substituted hydrocarbon groups) (first lipid solution). In preparing the first lipid solution, the nucleic acid may be dissolved in water or aqueous buffer solution or added to an organic solvent solution of a lipid, or an organic solvent solution of a lipid may be added to an aqueous solution or aqueous buffer solution of the nucleic acid. Moreover, an organic solvent solution of a lipid may be added to a freeze-dried nucleic acid.

After having initially produced an organic solvent solution of a nucleic acid, lipid A and other lipid as necessary (lipid (lipid B) having a lipid derivative or fatty acid derivative of a water-soluble polymer, a neutral lipid and/or a hydrophilic unit having one optionally substituted amino group, and a hydrophobic unit having two independent optionally substituted hydrocarbon groups) (first lipid solution), an organic solvent solution containing a lipid derivative or fatty acid derivative of a water-soluble polymer (second lipid solution) may be added to prepare a third lipid solution.

In the present invention, the first or third lipid solution is mixed with water or an aqueous buffer solution. At this time, lipid nanoparticles having a small size that do not aggregate are obtained by rapidly lowering the organic solvent concentration.

During mixing of the first or third lipid solution with water or aqueous buffer solution, the former may be added to the latter or the latter may be added to the former. In addition, the former and the latter may be simultaneously added to a container while stirring. Moreover, the former and the latter can also be mixed inline. In this case, a T-connector, for example, can be used for the inline mixing device.

Although affected by the nucleic acid used, the lipid which has a hydrophilic unit having one quaternary ammonium group, and three independent optionally substituted hydrocarbon groups (lipid A), and other lipids, the average particle size of the nucleic acid-containing lipid nanoparticles of the present invention can be controlled as desired according to various parameters in the production process. A person with ordinary skill in the art would be able to determine average particle size by preparing a particle sample by suitably altering various parameters in the production process required for controlling the average particle size of the nucleic acid-containing lipid nanoparticles of the present invention and then measuring the average particle size of the resulting sample. Examples of parameters required to control average particle size include nucleic acid concentration in the organic solvent solution, concentration of each lipid, temperature, and composition of organic solvent. In addition, examples of parameters required for controlling average particle size also include temperature, amount of water or aqueous buffer solution and rate of addition of each liquid when diluting the nucleic acid and lipid organic buffer solution with water or aqueous buffer solution.

Although there are no particular limitations thereon, the concentration of the lipid having a hydrophilic unit in the form of one quaternary ammonium group, and three independent optionally substituted hydrocarbon groups (lipid A) in the organic solvent solution prior to mixing with water or aqueous buffer solution in the case of not containing phosphatidylcholine (PC) and cholesterol (Choi) is preferably 1 µM to 2000 µM, more preferably 5 µM to 400 µM, even more preferably 10 µM to 200 µM, and most preferably 20 µM to 100 µM.

Although there are no particular limitations thereon, the concentration of the nucleic acid in the organic solvent solution prior to mixing with water or aqueous buffer solution in the case of not containing PC and Choi is preferably 0.03 µM to 15 µM, more preferably 0.15 µM to 3.0 µM, and even more preferably 0.3 µM to 1.5 µM.

Although there are no particular limitations thereon, the concentration of the lipid derivative or fatty acid derivative of a water-soluble polymer in the organic solvent solution prior to mixing with water or aqueous buffer solution in the case of not containing PC and Choi is preferably 0.5 µM to 200 µM, more preferably 2.5 µM to 40 µM, and even more preferably 5 µM to 20 µM.

Although there are no particular limitations thereon, the concentration of cationic lipid in the organic solvent solution prior to mixing with water or aqueous buffer solution in the case of not containing PC and Choi is preferably 1 µM to 2000 µM, more preferably 5 µM to 400 µM, even more preferably 10 µM to 200 µM, and most preferably 20 µM to 100 µM.

Although there are no particular limitations thereon, the combined concentration of all lipids in the organic solvent solution prior to mixing with water or aqueous buffer solution in the case of not containing PC and Choi is preferably 5 µM to 2000 µM, more preferably 25 µM to 400 µM, and even more preferably 50 µM to 200 µM.

The concentration of the lipid having a hydrophilic unit in the form of one quaternary ammonium group, and three independent optionally substituted hydrocarbon groups (lipid A) in the organic solvent solution prior to mixing with water or aqueous buffer solution in the case of containing PC and Choi is preferably 0.2 µM to 1800 µM, more preferably 1 µM to 360 µM, even more preferably 2 µM to 180 µM, and most preferably 5 µM to 100 µM.

The concentration of the nucleic acid in the organic solvent solution prior to mixing with water or aqueous buffer solution in the case of containing PC and Choi is preferably 0.02 µM to 45 µM, more preferably 0.1 µM to 10 µM, even more preferably 0.2 µM to 5 µM, and most preferably 0.3 µM to 3 µM.

The concentration of the lipid derivative or fatty acid derivative of a water-soluble polymer in the organic solvent solution prior to mixing with water or aqueous buffer solution in the case of containing PC and Choi is preferably 0.3 µM to 1000 µM, more preferably 1.5 µM to 200 µM, even more preferably 3 µM to 100 µM, and most preferably 5 µM to 50 µM.

The concentration of cationic lipid in the organic solvent solution prior to mixing with water or aqueous buffer solution in the case of containing PC and Choi is preferably 2.5 µM to 4200 µM, more preferably 12.5 µM to 840 µM, even more preferably 25 µM to 420 µM, and most preferably 50 µM to 210 µM.

The concentration of neutral lipid in the organic solvent solution prior to mixing with water or aqueous buffer solution in the case of containing PC and Choi is preferably 2.5 µM to 5000 µM, more preferably 12.5 µM to 1000 µM, even more preferably 25 µM to 500 µM, and most preferably 50 µM to 250 µM.

The combined concentration of all lipids in the organic solvent solution prior to mixing with water or aqueous buffer solution in the case of containing PC and Choi is preferably 10 µM to 8000 µM, more preferably 50 µM to 1600 µM, even more preferably 100 µM to 800 µM, and most preferably 150 µM to 400 µM.

Although there are no particular limitations on the temperature during preparation of the organic solvent solution containing nucleic acid and lipid provided the nucleic acid and lipid dissolve, it is preferably 10° C. to 60° C., more preferably 20° C. to 50° C. and even more preferably 20° C. to 30° C. Furthermore, in the case of heating to 30° C. or higher, lipid nanoparticles can be produced using a smaller amount of solvent due to the increase in solubility of the nucleic acid and lipid.

There are no particular limitations on the organic solvent in the organic solvent solution containing nucleic acid and lipid, and a C1-C6 alcohol, such as methanol, ethanol, propanol or butanol, containing water at 0% (v/v) to 50% (v/v), or a mixture thereof is preferable, ethanol or propanol containing water at 0% (v/v) to 50% (v/v) is more preferable, and ethanol containing water at 0% (v/v) to 50% (v/v) is even more preferable. Here, the term "% (v/v)" indicates the percentage of volume occupied by the solute in the entire solution, and is to apply similarly hereinafter.

An inorganic acid such as hydrochloric acid, acetic acid or phosphoric acid, or a salt thereof, can also be added to the solvent in the organic solvent solution containing the nucleic acid and lipid. In this case, the pH of the solvent is preferably 1 to 7, more preferably 1 to 5 and even more preferably 2 to 4.

There are no particular limitations on the volume of water or aqueous buffer solution used in the procedure for adding water or aqueous buffer solution to the organic solvent solution containing the nucleic acid and lipid, and the volume is preferably 0.5 times to 100 times, more preferably 1.5 times to 20 times, and even more preferably 2.0 times to 10 times the volume of organic solvent solution of the nucleic acid and lipid.

In this case, although there are no particular limitations thereon, the organic solvent concentration after having added water or aqueous buffer solution is preferably 50% (v/v) or less, more preferably 40% (v/v) or less, even more preferably 30% (v/v) or less and most preferably 20% (v/v) or less based on the resulting solution. In addition, there are no particular limitations on the aqueous buffer solution provided it has buffering action, and examples thereof include aqueous phosphate buffer solution, aqueous citrate buffer solution and aqueous acetate buffer solution.

Although there are no particular limitations on the temperature when carrying out the above-mentioned addition procedure, the temperature is preferably 10° C. to 60° C., more preferably 20° C. to 50° C., and even more preferably 20° C. to 30° C.

In the above-mentioned addition procedure, it is important to rapidly lower the concentration of the organic solvent solution. More specifically, the organic buffer concentration is changed from 70% (v/v) or more to 50% (v/v) or less preferably within one minute, more preferably within 0.5 minutes, even more preferably within 0.1 minutes, and most preferably within 0.05 minutes.

Although there are no particular limitations on the total number of lipid A molecules in the nucleic acid-containing lipid nanoparticles of the present invention, the number of moles of the quaternary ammonium group in lipid A is preferably 0.01 times or more, more preferably 0.1 to 10 times, even more preferably 0.1 to 4 times, still more preferably 0.1 to 2 times, and most preferably 0.1 to 1 time the number of moles of phosphorous atoms of the nucleic acid that composes the nucleic acid-containing lipid nanoparticles of the present invention. Although there are no particular limitations on the total number of molecules of lipid B in the case the nucleic acid-containing lipid nanoparticles contain lipid B, the number of moles of the quaternary ammonium group in lipid A is preferably 0.1 to 10 times, more preferably 0.5 to 9 times, even more preferably 1 to 8 times, and most preferably 1.5 to 6 times the number of moles of phosphorous atoms of the nucleic acid that composes the nucleic acid-containing lipid nanoparticles of the present invention.

In the case the nucleic acid-containing lipid nanoparticles of the present invention contain lipid B, the ratio of the number of moles of lipid A to the number of moles of lipid B (moles of lipid A/moles of lipid B) is preferably 0.001 or more, more preferably 0.003 to 10, even more preferably 0.005 to 5, still more preferably 0.01 to 3, and most preferably 0.01 to 2.

In the nucleic acid-containing lipid nanoparticles of the present invention, the ratio of the total number of moles of lipid to the number of moles of nucleic acid (total number of moles of lipid/number of moles of nucleic acid) is preferably 50 or more, more preferably 100 to 1000, even more preferably 120 to 800, still more preferably 140 to 600, and most preferably 200 to 500.

In the case the nucleic acid-containing lipid nanoparticles of the present invention contain lipid B, although there are no particular limitations on the total number of molecules of lipid B in the nucleic acid-containing lipid nanoparticles, the total number of molecules of lipid B is preferably 0.1 times or more, more preferably 0.15 times or more, even more preferably 0.2 times or more, and still more preferably 0.25 times or more the total number of moles of lipid. In addition, although there are no particular limitations on the total number of molecules of lipid B in the nucleic acid-containing lipid nanoparticles, the total number of molecules of lipid B is preferably 0.7 times or less, more preferably 0.65 times or less, and even more preferably 0.6 times or less the total number of moles of lipid.

Within the combinations of preferable ranges of upper and lower limits as described above, the total number of molecules of lipid B in the nucleic acid-containing lipid nanoparticles is more preferably 0.10 to 0.70 times, even more preferably 0.15 to 0.65 times, still more preferably 0.20 to 0.65 times, and most preferably 0.25 to 0.60 times the total number of moles of lipid.

The neutral lipid may be any of a simple lipid, complex lipid or derived lipid, and examples thereof include, but are not limited to, phospholipids, glyceroglycolipids, sphingoglycolipids, sphingoids and sterols. In addition, one type of neutral lipid may be used or two or more types may be used in combination.

In the case the nucleic acid-containing lipid nanoparticles of the present invention contain a neutral lipid, although there are no particular limitations on the total number of molecules of neutral lipid, the total number of molecules of neutral lipid is preferably 0.10 to 0.75 times, more preferably 0.20 to 0.70 times, even more preferably 0.20 to 0.65 times, and most preferably 0.30 to 0.60 times the total number of moles of lipid.

Examples of phospholipids in the neutral lipid include, but are not limited to, natural or synthetic phospholipids such as phosphatidylcholines (PC) (more specifically, soybean phosphatidylcholine, egg-yolk phosphatidylcholine (EPC), distearoyl phosphatidylcholine, 1,2-distearoyl-sn-glycero-3-phosphocholine (DSPC), dipalmitoyl phosphatidylcholine, 1,2-dipalmitoyl-sn-glycero-3-phosphocholine (DPPC), palmitoyl-oleoylphosphatidylcholine (POPC), dimyristoyl phosphatidylcholine (DMPC) or dioleyl phosphatidylcholine (DOPC)), phosphatidylethanolamines (more specifically, distearoyl phosphatidylethanolamine (DSPE), dipalmitoyl phosphatidylethanolamine (DPPE), dioleyl phosphatidylethanolamine (DOPE), dimyristoyl phosphatidylethanolamine (DMPE), 16-O-monomethyl PE, 16-O-dimethyl PE, 18-1-trans PE, palmitoyl-oleyl phosphatidylethanolamine (POPE) or 1-stearoyl-2-oleyl-phosphatidylethanolamine (SOPE)), glycerophospholipids (more specifically, phosphatidylserine, phosphatidic acid, phosphatidylglycerol, phosphatidylinositol, palmitoyl-oleyl phosphatidylglycerol (POPG) or lysophosphatidylcholine), sphingophospholipids (more specifically, sphingomyelin or ceramide phosphoethanolamine, ceramide phosphoglycerol, ceramide phosphoglycerophosphoric acid), glycerophosphonolipids, sphingophosphonolipids, natural lecithin (more specifically, egg yolk lecithin or soybean lecithin), or hydrogenated phospholipids (more specifically, hydrogenated soybean phosphatidylcholine).

Examples of glyceroglycolipids in the neutral lipid include, but are not limited to, sulfoxyribosyl glycerides, diglycosyl diglycerides, digalactosyl diglycerides, galactosyl diglycerides and glycosyl diglycerides.

Examples of sphingoglycolipids in the neutral lipid include, but are not limited to, galactosyl cerebrosides, lactosyl cerebrosides and gangliosides.

Examples of sphingoids in the neutral lipid include, but are not limited to, sphingan, icosasphingan, sphingosine and derivatives thereof. Examples of derivatives include those in which the —NH$_2$ of sphingan, icosasphingan or sphingosine and the like has been converted to —NHCO(CH$_2$)$_x$CH$_3$ (wherein, x is an integer of 0 to 18 and preferably 6, 12 or 18).

Examples of sterols in the neutral lipid include, but are not limited to, cholesterol (Choi), dihydrocholesterol, lanosterol, β-sitosterol, campesterol, stigmasterol, brassicasterol, ergosterol, fucosterol and 3β-[N—(N',N'-dimethylaminoethyl)carbamoyl]cholesterol (DC-Chol).

Examples of polymers include, but are not limited to, protein, albumin, dextran, polyfect, chitosan, dextran sulfate, polymers such as poly-L-lysine, polyethyleneimine, polyaspartic acid, styrene-maleic acid copolymer, isopropyl acrylamide-acrylic pyrrolidone copolymer, polyethylene glycol-modified dendrimer, polylactic acid, polylactic acid-polyglycolic acid or polyethylene glycolated polylactic acid, and micelles composed of one or more salts thereof.

Here, polymer salts include metal salts, ammonium salts, acid addition salts, organic amine addition salts and amino acid addition salts. Examples of metal salts include, but are not limited to, alkaline metal salts such as lithium salts, sodium salts or potassium salts, alkaline earth metal salts such as magnesium salts or calcium salts, aluminum salts and zinc salts. Examples of ammonium salts include, but are not limited to, salts of an ammonium group or tetramethylammonium group. Examples of acid addition salts include, but are not limited to, inorganic acid salts such as hydrochlorides, sulfates, nitrates or phosphates, and organic acid salts such as acetates, maleates, fumarates or citrates. Examples of organic amine addition salts include, but are not limited to, addition salts of morpholine or piperidine. Examples of amino acid addition salts include, but are not limited to, addition salts of glycine, phenylalanine, aspartic acid, glutamic acid or lysine.

Any of the nucleic acid-containing lipid nanoparticles of the present invention may also contain a surfactant or a lipid derivative or fatty acid derivative of one or more substances selected from sugars, peptides, nucleic acids and water-soluble polymers.

Examples of surfactants and lipid derivatives or fatty acid derivatives of one or more substances selected from sugars, peptides, nucleic acids and water-soluble polymers preferably include lipid derivatives and fatty acid derivatives of glycolipids or water-soluble polymers, and more preferably include lipid derivatives and fatty acid derivatives of water-soluble polymers. The surfactant, or lipid derivative or fatty acid derivative of one or more substances selected from sugars, peptides, nucleic acids and water-soluble polymers, is preferably a dual-natured substance having a property by which a portion of a molecule thereof bonds with another constituent of a composition by, for example, hydrophobic affinity or electrostatic interaction, and by which the other portion bonds with a solvent during production of the composition by, for example, hydrophilic affinity or electrostatic interaction.

Examples of lipid derivatives or fatty acid derivatives of sugars, peptides or nucleic acids include those obtained by bonding between a sugar such as sucrose, sorbitol or lactose, a peptide such as casein-derived peptide, egg white-derived peptide, soybean-derived peptide or glutathione, or a nucleic acid such as DNA, RNA, plasmid, siRNA or ODN, and a neutral lipid, as exemplified in the definition of the above-mentioned composition, or a fatty acid such as stearic acid, palmitic acid, myristic acid or lauric acid.

Examples of lipid derivatives or fatty acid derivatives of sugars include the glyceroglycolipids and sphingoglycolipids exemplified in the definition of the above-mentioned composition.

Examples of lipid derivatives or fatty acid derivatives of water-soluble polymers include those obtained by bonding between polyethylene glycol, polyglycerin, polyethyleneimine, polyvinyl alcohol, polyacrylic acid, polyacrylamide, oligosaccharides, dextrin, water-soluble cellulose, dextran, chondroitin sulfate, polyglycerin, chitosan, polyvinylpyrrolidone, polyaspartic acid amide, poly-L-lysine, mannan, pullulan, oligoglycerol or a derivative thereof, and a neutral lipid exemplified in the definition of the above-mentioned composition or a fatty acid such as stearic acid, palmitic acid, myristic acid or lauric acid, and salts thereof, more preferably include lipid derivatives or fatty acid derivatives of polyethylene glycol or polyglycerin and salts thereof, and even more preferably include lipid derivatives or fatty acid derivatives of polyethylene glycol and salts thereof.

Examples of lipid derivatives or fatty acid derivatives of polyethylene glycol include polyethylene glycolated lipids [more specifically, polyethylene glycol-phosphatidylethanolamine (more specifically, 1,2-distearoyl-sn-glycero-3-phosphoethanolamine-N-[methoxy(polyethylene glycol)-2000] (PEG-DSPE), 1,2-dipalmitoyl-sn-glycero-3-phosphoethanolamine-N-[methoxy(polyethylene glycol)-2000] (PEG-DPPE) or 1,2-dimyristoyl-sn-glycero-3-phosphoethanolamine-N-[methoxy(polyethylene glycol)-2000] (PEG-DMPE)), polyoxyethylene hydrogenated castor oil 60 or Cremophor EL], polyethylene glycol sorbitan fatty acid esters (more specifically, polyoxyethylene sorbitan monooleate), and polyethylene glycol fatty acid esters, and more preferably include polyethylene glycolated lipids.

Examples of lipid derivatives or fatty acid derivatives of polyglycerin include polyglycerinated lipids (more specifically, polyglycerin-phosphatidylethanolamine) and polyglycerin fatty acid esters, and more preferably include polyglycerinated lipids.

Examples of surfactants include polyoxyethylene sorbitan monooleates (more specifically, Polysorbate 80), polyoxyethylene-polyoxypropylene glycols (more specifically, Pluronic F68), sorbitan fatty acid esters (more specifically, sorbitan monolaurate or sorbitan monooleate), polyoxyethylene derivatives (more specifically, polyoxyethylene hydrogenated castor oil 60 or polyoxyethylene lauryl alcohol), glycerin fatty acid esters and polyethylene glycol alkyl ethers, and preferably include polyoxyethylene-polyoxypropylene glycols, glycerin fatty acid esters and polyethylene glycol alkyl ethers.

Although there are no particular limitations on the total number of molecules of lipid derivatives and fatty acid derivatives of water-soluble polymer in the nucleic acid-containing lipid nanoparticles, the total number of molecules is preferably 0.005 times or more, more preferably 0.01 to 0.30 times, even more preferably 0.02 to 0.25 times, still more preferably 0.03 to 0.20 times, even more preferably still 0.04 to 0.15 times and most preferably 0.04 to 0.12 times the total number of moles of lipid.

In the present invention, the total number of moles of lipid includes the number of moles of lipid A, along with the number of moles of lipid derivatives and fatty acid derivatives of the water-soluble polymer, and, depending on the case, also includes the number of moles of lipid B and neutral lipid. Namely, the number of moles of lipid A is the number of moles obtained by subtracting the total number of moles of lipid derivatives and fatty acid derivatives of the water-soluble polymer, and depending on the case, the total of the number of moles of lipid B and the number of moles of neutral lipid, from 1 based on a value of 1 for the total number of moles of lipid.

In addition, surface modification with a water-soluble polymer, for example, can be arbitrarily carried out on the nucleic acid-containing lipid nanoparticles of the present invention (see "Stealth Liposomes", D. D. Lasic and F. Martin, ed., CRC Press Inc., U.S.A., 1995, pp. 93-102). Examples of water-soluble polymers able to be used in surface modification include, but are not limited to, polyethylene glycol, polyglycerin, polyethyleneimine, polyvinyl alcohol, polyacrylic acid, polyacrylamide, oligosaccharide, dextrin, water-soluble cellulose, dextran, chondroitin sulfate, polyglycerin, chitosan, polyvinylpyrrolidone, polyaspartic acid amide, poly-L-lysine, mannan, pullulan and oligoglycerol, preferably include polyethylene glycol, polyglycerin, polyethyleneimine, polyvinyl alcohol, polyacrylic acid and polyacrylamide, and even more preferably include polyethylene glycol and polyglycerin. In addition, a surfactant or a lipid derivative or fatty acid derivative of one or more substances selected from sugars, peptides, nucleic acids and water-soluble polymers (same meaning as previously described) can be used for surface modification. This surface modification constitutes one method for containing a surfactant, or a lipid derivative or fatty acid derivative of one or more substances selected from sugars, peptides, nucleic acids and water-soluble polymers, in the nucleic acid-containing lipid nanoparticles of the present invention.

A target ligand can be arbitrarily directly bound to the surface of the nucleic acid-containing lipid nanoparticles of the present invention by covalently bonding to a polar head radical of the lipid component of the nucleic acid-containing lipid nanoparticles of the present invention (see WO 2006/116107).

The average particle size of the nucleic acid-containing lipid nanoparticles of the present invention can be further adjusted after preparing the lipid nanoparticles. Examples of methods used to adjust average particle size include extrusion and mechanical crushing of large multi-lamellar liposomes (MLV) (more specifically, using a Manton-Gaulin homogenizer or microfluidizer) (see "Emulsion and Nanosuspensions for the Formulation of Poorly Soluble Drugs", R. H. Muller, S. Benita and B. Bohm, ed., Scientific Publishers Stuttgart, Germany, 1998, pp. 267-294).

The size of the nucleic acid-containing lipid nanoparticles of the present invention is such that the average particle size is preferably 20 nm to 65 nm and more preferably 30 nm to 60 nm.

The size of the nucleic acid-containing lipid nanoparticles of the present invention can be measured by, for example, dynamic light scattering.

Nucleic acid present in the nucleic acid-containing lipid nanoparticles of the present invention can be introduced into cells by introducing the nucleic acid-containing lipid nanoparticles of the present invention into mammalian cells.

Introduction of the nucleic acid-containing lipid nanoparticles of the present invention into mammalian cells in vivo may be carried out in accordance with a known transfection procedure capable of being carried out in vivo. For example, nucleic acid present in the nucleic acid-containing lipid nanoparticles of the present invention can be introduced into the cells at a delivery organ or site by intravenously administering the nucleic acid-containing lipid nanoparticles of the present invention to a mammal, including a human, and delivering to an organ or site where, for example, tumors or inflammation has occurred. Although there are no particular limitations thereon, examples of organs or sites where tumors or inflammation has occurred include the stomach, large intestine, liver, lungs, spleen, pancreas, kidneys, urinary bladder, skin, blood vessel and eye. In addition, nucleic acid present in the nucleic acid-containing lipid nanoparticles of the present invention can be introduced into cells at a delivery organ or site by intravenously administering the nucleic acid-containing lipid nanoparticles of the present invention to a mammal, including a human, and delivering to, for example, the liver, stomach, lungs, kidneys, pancreas and/or spleen. Cells of the liver, lungs, spleen and/or kidneys may be any of normal cells, cells associated with tumors or inflammation, or cells associated with other diseases.

If the nucleic acid present in the nucleic acid-containing lipid nanoparticles of the present invention is a nucleic acid having an action that inhibits expression of a target gene using RNA interference (RNAi), the nucleic acid that inhibits expression of the target gene can be introduced into the cells of a mammal in vivo to inhibit expression of the target gene. The administration target is preferably a human.

If the target gene in the nucleic acid-containing lipid nanoparticles of the present invention is a gene that is expressed in, for example, the liver, stomach, lungs, kidneys, pancreas and/or spleen, and preferably a gene expressed in the liver, the nucleic acid-containing lipid nanoparticles of the present invention can be used as a therapeutic agent or preventive agent of a disease associated with the liver, stomach, lungs, kidneys, pancreas or spleen, and can preferably be used as a therapeutic agent or preventive agent of a disease associated with the liver. Namely, the present invention also provides a method for the treatment of a disease and the like associated with the liver, stomach, lungs, kidneys, pancreas or spleen in which the nucleic acid-containing lipid nanoparticles of the present invention as previously explained are administered to a mammal. The administration target is preferably a human, and more preferably a human afflicted with a disease associated with the liver, stomach, lungs, kidneys, pancreas or spleen.

The nucleic acid-containing lipid nanoparticles of the present invention can also be used as a tool for verifying the efficacy of inhibition of a target gene in an in vivo efficacy evaluation model relating to a therapeutic agent or preventive agent of a disease associated with the liver, stomach, lungs, kidneys, pancreas or spleen.

The nucleic acid-containing lipid nanoparticles of the present invention can also be used as a preparation for the purpose of stabilizing the nucleic acid in a biological component such as a blood component (such as in the blood or gastrointestinal tract), reducing adverse side effects, or increasing accumulation of a drug in a tissue or organ containing the expression site of a target gene.

In the case of using nucleic acid-containing lipid nanoparticles of the present invention as a therapeutic agent or preventive agent of a pharmaceutical for a disease associated with the liver, lungs, pancreas or spleen, the administration route that is most effective at the time of treatment is preferably used for the administration route, and examples thereof include parenteral and oral administration such as oral, intratracheal, intrarectal, subcutaneous, intramuscular or intravenous administration, preferably intravenous administration, subcutaneous administration or intramuscular administration, and more preferably intravenous administration.

Although dosage varies according to such factors as the symptoms and age of the administration target and the administration route, the daily dosage may be, for example, about 0.1 µg to 1000 mg as nucleic acid.

An example of a suitable preparation for intravenous administration or intramuscular administration is an injection preparation, and although a dispersion of a composition prepared according to the above-mentioned method can be used directly in the form of an injection preparation and the like, it can also be used by removing the solvent from the dispersion by, for example, filtration or centrifugation, by freeze-drying the dispersion, and/or freeze-drying the dispersion after adding an excipient such as mannitol, lactose, trehalose, maltose or glycine.

In the case of an injection preparation, the injection preparation is preferably prepared by mixing, for example, water, acid, base, various buffers, physiological saline or amino acid infusion into a dispersion of the above-mentioned composition or composition from which the above-mentioned solvent has been removed or freeze-dried. In addition, an injection preparation can also be prepared by adding an antioxidant such as citric acid, ascorbic acid, cysteine or EDTA, or an isotonic agent such as glycerin, glucose or sodium chloride. In addition, the injection preparation can also be placed in frozen storage by adding an anti-freezing agent such as glycerin.

EXAMPLES

The following provides a detailed explanation of the present invention using examples, reference examples, comparative examples and test examples. However, the present invention is not limited to these examples, reference examples, comparative examples and test examples.

Furthermore, the proton nuclear magnetic spectra ($^1$H-NMR) indicated in the examples and reference examples were measured at 270 MHz, 300 MHz or 400 MHz, and exchangeable protons were not always distinctly observed depending on the compound and measurement conditions. Furthermore, although conventional nomenclature is used to signal multiplicity, br is an apparently broad signal.

Example 1

N-methyl-2-(oleoyloxy)-N,N-bis(2-(oleoyloxy) ethyl)ethanaminium Chloride (Compound I-1)

Step 1:

1-ethyl-3-(3-dimethylaminopropyl)carbodiimide hydrochloride (Tokyo Chemical Industry Co., Ltd., 0.591 g, 3.08 mmol), triethylamine (0.430 mL, 3.08 mmol) and N,N-dimethylaminopyridine (Nacalai Tesque Inc., 0.024 g, 0.19 mmol) were added to a chloroform solution (5 mL) of triethanolamine (Sigma-Aldrich Corp., 0.115 g, 0.771 mmol) and stirred overnight at room temperature. Water was added to the reaction solution followed by extraction with chloroform. The organic layer was washed with saturated aqueous sodium bicarbonate solution and then saturated salt solution followed by drying with anhydrous magnesium sulfate, filtering and concentrating under reduced pressure. The resulting residue was purified by silica gel column chromatography (chloroform/hexane=50/50 to 100/0) to obtain 2,2',2''-nitrilotris(ethane-2,1-diyl)trioleate (0.439 g, 0.466 mmol, yield: 60%).

ESI-MS m/z: 943 (M+H)$^+$; $^1$H-NMR (CDCl$_3$) δ: 0.88 (t, J=6.9 Hz, 9H), 1.23-1.36 (m, 60H), 1.58-1.63 (m, 6H), 1.98-2.04 (m, 12H), 2.29 (t, J=7.6 Hz, 6H), 2.83 (t, J=6.1 Hz, 6H), 4.11 (t, J=6.1 Hz, 6H), 5.31-5.38 (m, 6H).

Step 2:

Methyl iodide (Tokyo Chemical Industry Co., Ltd., 3 mL) was added to the 2,2',2''-nitrilotris(ethane-2,1-diyl)trioleate obtained in Step 1 (0.439 g, 0.466 mmol) and stirred overnight at room temperature. The reaction solution was concentrated under reduced pressure. The residue was dissolved in a small amount of methanol-chloroform (1:1), loaded onto an ion exchange resin (Dow Chemical Co., Dowex™ 1×-2 100 mesh, type CL, about 20 times volume, prewashed with water and methanol), and eluted with methanol-chloroform (1:1). The eluate was concentrated under reduced pressure and the resulting residue was purified by silica gel column chromatography (chloroform/methanol=100/0 to 88/12) to obtain the title compound (0.342 g, 0.344 mmol, yield: 74%).

ESI-MS m/z: 957 (M)$^+$; $^1$H-NMR (CDCl$_3$) δ: 0.88 (t, J=6.9 Hz, 9H), 1.25-1.35 (m, 60H), 1.59-1.63 (m, 6H), 1.99-2.03 (m, 12H), 2.35 (t, J=7.6 Hz, 6H), 3.56 (s, 3H), 4.21 (t, J=4.9 Hz, 6H), 4.61 (t, J=4.9 Hz, 6H), 5.30-5.38 (m, 6H).

Example 2

N-methyl-2-((9Z,12Z)-octadeca-9,12-dienoyloxy)-N,N-bis(2-((9Z,12Z)-octadeca-9,12-dienoyloxy) ethyl)ethanaminium Chloride (Compound I-2)

The title compound (0.100 g, overall yield: 22%) was obtained in the similar manner as Example 1 using (9Z,12Z)-octadec-9,12-dienoic acid (Sigma-Aldrich Corp., 0.704 g, 2.51 mmol) instead of oleic acid.

ESI-MS m/z: 957 (M)$^+$; $^1$H-NMR (CDCl$_3$): 0.89 (t, J=7.0 Hz, 9H), 1.25-1.40 (m, 42H), 1.55-1.66 (m, 6H), 2.05 (q, J=6.9 Hz, 12H), 2.35 (t, J=7.6 Hz, 6H), 2.77 (t, J=6.3 Hz, 6H), 3.54 (s, 3H), 4.21 (t, J=5.1 Hz, 6H), 4.59 (brs, 6H), 5.28-5.43 (m, 12H).

Example 3

(9Z,12Z)—N-methyl-N,N-di((9Z,12Z)-octadeca-9-dienyl)octadeca-9,12-diene-1-aminium Chloride (Compound I-3)

Step 1:

(9Z,12Z)-octadeca-9,12-dienyl methanesulfonate (Nu-Chek Prep, Inc., 3.55 g, 10.1 mmol) was added to ammonia (Tokyo Chemical Industry Co., Ltd., approx. 7 mol/L methanol solution, 8.00 mL, 56.0 mmol) followed by stirring for 3 hours at 130° C. using a microwave reactor. Saturated aqueous sodium bicarbonate solution was added to the reaction solution followed by extracting 5 times with chloroform. The organic layers were combined and washed with saturated salt solution followed by drying with anhydrous magnesium sulfate, filtering and concentrating under reduced pressure to obtain a crude product of (9Z,12Z)-octadeca-9,12-diene-1-amine.

(9Z,12Z)-octadeca-9,12-dienyl methanesulfonate (2.78 g, 8.07 mmol) and a 50% aqueous sodium hydroxide solution (2.00 mL, 50.0 mmol) were added to the resulting crude product followed by stirring in an oil bath for 60 minutes at 110° C. After allowing to cool to room temperature, the reaction solution was diluted with ethyl acetate and washed with water and then saturated salt solution followed by drying with anhydrous magnesium sulfate, filtering and concentrating under reduced pressure. The resulting residue was purified by silica gel column chromatography (hexane/ethyl acetate=100/0 to 90/10) to obtain (9Z,12Z)-tri(9Z,12Z)-octadeca-9,12-dienylamine (1.09 g, 1.43 mmol, yield: 18%).

ESI-MS m/z: 763 (M+H)$^+$.

Step 2:

The title compound (1.06 g, 1.30 mol, yield: 94%) was obtained in the similar manner as Step 2 of Example 1 using (9Z,12Z)-tri(9Z,12Z)-octadeca-9,12-dienylamine (1.05 g, 1.38 mol) obtained in Step 1 instead of 2,2',2''-nitrilotris (ethane-2,1-diyl)trioleate.

ESI-MS m/z: 777 (M)$^+$; $^1$H-NMR (CDCl$_3$) δ: 0.89 (t, J=7.1 Hz, 9H), 1.22-1.45 (m, 48H), 1.61-1.69 (m, 6H), 2.05 (q, J=6.8 Hz, 12H), 2.77 (t, J=6.5 Hz, 6H), 3.55 (s, 3H), 3.44-3.50 (m, 6H), 5.29-5.42 (m, 12H).

Example 4

(Z)—N-methyl-N,N-di((Z)-octadec-9-enyl)octadec-9-ene-1-aminium Chloride (Compound I-4)

The title compound (0.410 g, 0.501 mmol, overall yield: 24%) was obtained in the similar manner as Example 3 using (Z)-octadec-9-enyl methanesulfonate (Nu-Chek Prep, Inc.) instead of (9Z,12Z)-octadeca-9,12-dienyl methanesulfonate.

ESI-MS m/z: 783 (M)$^+$; $^1$H-NMR (CDCl$_3$) δ: 0.88 (t, J=6.9 Hz, 9H), 1.22-1.44 (m, 66H), 1.62-1.69 (m, 6H), 1.98-2.04 (m, 12H), 3.35 (s, 3H), 3.45-3.51 (m, 6H), 5.30-5.39 (m, 6H).

Example 5

(11Z,14Z)—N,N-di((11Z,14Z)-icosa-11,14-dienyl)-N-methylicosa-11,14-diene-1-aminium Chloride (Compound I-5)

The title compound (0.323 g, 0.360 mmol, overall yield: 25%) was obtained in the similar manner as Example 3 using (11Z,14Z)-icosa-11,14-dienyl methanesulfonate (Nu-Chek Prep, Inc.) instead of (9Z,12Z)-octadeca-9,12-dienyl methanesulfonate.

$^1$H-NMR (CDCl$_3$) δ: 0.89 (t, J=6.9 Hz, 9H), 1.24-1.43 (m, 63H), 1.61-1.69 (m, 6H), 2.05 (q, J=6.8 Hz, 12H), 2.77 (t, J=6.6 Hz, 6H), 3.35 (s, 3H), 3.45-3.50 (m, 6H), 5.30-5.42 (m, 12H).

Example 6

(9Z,12Z)—N-(3-hydroxypropyl)-N,N-di((9Z,12Z)-octadeca-9,12-dienyl)octadeca-9,12-dien-1-aminium Chloride (Compound I-6)

3-iodopropan-1-ol (Wako Pure Chemical Industries, Ltd., 0.194 g, 1.04 mmol) was added to a chloroform solution (0.3 mL) of the tri((9Z,12Z)-octadeca-9,12-dienyl)amine (0.199 g, 0.261 mmol) obtained in Step 1 of Example 3 followed by reacting for 40 minutes at 130° C. in a microwave reactor. The reaction solution was dissolved in a small amount of ethanol, loaded onto an ion exchange resin (Sigma-Aldrich Corp., Amberlite® IRA-400, type CL, about 20 times volume, prewashed with water and ethanol) and eluted with ethanol. The eluate was concentrated under reduced pressure and the resulting residue was purified by silica gel column chromatography (chloroform/methanol=100/0 to 88/12) to obtain the title compound (0.146 g, 0.170 mmol, yield: 65%).

ESI-MS m/z: 821 (M)$^+$; $^1$H-NMR (CDCl$_3$) δ: 0.89 (t, J=7.0 Hz, 9H), 1.27-1.39 (m, 49H), 1.67-1.74 (m, 6H), 1.93-1.99 (m, 2H), 2.05 (q, J=6.9 Hz, 12H), 2.77 (t, J=6.2 Hz, 6H), 3.14-3.19 (m, 6H), 3.70-3.74 (m, 2H), 3.79 (t, J=5.1 Hz, 2H), 5.29-5.42 (m, 12H).

Example 7

(9Z,12Z)—N-(2-hydroxyethyl)-N,N-di((9Z,12Z)-octadeca-9,12-dienyl)octadeca-9, 12-dien-1-aminium Chloride (Compound I-7)

The title compound (0.211 g, 0.250 mmol, yield: 85%) was obtained in the similar manner as Example 6 using 2-iodoethan-1-ol (Tokyo Chemical Industries Co., Ltd.) instead of 3-iodopropan-1-ol.

ESI-MS m/z: 807 (M)$^+$; $^1$H-NMR (CDCl$_3$) δ: 0.89 (t, J=7.0 Hz, 9H), 1.27-1.40 (m, 49H), 1.64-1.71 (m, 6H), 2.05 (q, J=6.8 Hz, 12H), 2.77 (t, J=6.3 Hz, 6H), 3.36-3.41 (m, 6H), 3.53-3.56 (m, 2H), 4.08-4.12 (m, 2H), 5.29-5.42 (m, 12H).

Example 8

N,N,N-trimethyl-1,3-bis((9Z,12Z)-octadeca-9,12-dienoyloxy)-2-(((9Z,12Z)-octadeca-9,12-dienoyloxy)methyl)propan-2-aminium Chloride (Compound II-1)

Step 1:

(9Z,12Z)-octadeca-9,12-dienoic acid (2.37 g, 8.45 mmol), 1-ethyl-3-(3-dimethylaminopropyl)carbodiimide hydrochloride (1.62 g, 8.45 mmol) and N,N-dimethylaminopyridine (0.206 g, 1.69 mmol) were added to a chloroform solution (10 mL) of 2-(dimethylamino)-2-(hydroxymethyl)propane-1,3-diol (Zylexa Pharma Ltd., 0.252 g, 1.69 mmol) and stirred overnight at 60° C. After allowing to cool to room temperature, the reaction solution was concentrated under reduced pressure. The resulting residue was purified by silica gel column chromatography (chloroform/methanol=100/0) to obtain (9Z,9'Z,12Z,12'Z)-2-(dimethylamino)-2-(((9Z,12Z)-octadeca-9,12-dienoyloxy)methyl) propane-1,3-diyl dioctadeca-9,12-dienoate (0.334 g, 0.356 mmol, yield: 21%).

ESI-MS m/z: 937 (M+H)$^+$.

Step 2:

Methyl iodide (0.216 mL) was added to a chloroform solution (3 mL) of the (9Z,9'Z,12Z,12'Z)-2-(dimethylamino)-2-(((9Z,12Z)-octadeca-9,12-dienoyloxy)methyl) propane-1,3-diyl dioctadeca-9,12-dienoate obtained in Step 1 followed by stirring overnight at room temperature. Methyl iodide (0.216 mL) was added to the reaction solution followed by stirring overnight at room temperature. The reaction solution was concentrated under reduced pressure. The residue was dissolved in a small amount of methanol-chloroform (1:1), loaded onto an ion exchange resin (Dow Chemical Co., Dowex™ 1×-2 100 mesh, type CL, about 20 times volume, prewashed with water and methanol), and eluted with methanol-chloroform (1:1). The eluate was concentrated under reduced pressure and the resulting residue was purified by silica gel column chromatography (chloroform/methanol=100/0 to 90/10) to obtain the title compound (0.161 g, 0.164 mmol, yield: 47%).

ESI-MS m/z: 951 (M)$^+$; $^1$H-NMR (CDCl$_3$) δ: 0.86 (t, J=6.9 Hz, 9H), 1.22-1.36 (m, 42H), 1.54-1.61 (m, 6H), 2.02 (q, J=6.8 Hz, 12H), 2.34 (t, J=7.7 Hz, 6H), 2.74 (t, J=6.8 Hz, 6H), 3.69 (s, 9H), 4.57 (s, 6H), 5.26-5.39 (m, 2H).

Example 9

N,N,N-trimethyl-1,3-bis((Z)-tetradec-9-enoyloxy)-2-(((Z)-tetradec-9-enoyloxy)methyl)propan-2-aminium Chloride (Compound II-2)

The title compound (0.0854 g, 0.104 mmol, overall yield: 16%) was obtained in the similar manner as Example 8 using cis-9-tetradecenoic acid (Nu-Chek Prep, Inc.) instead of (9Z,12Z)-octadeca-9-dienoic acid.

ESI-MS m/z: 789 (M)$^+$; $^1$H-NMR (CDCl$_3$) δ: 0.89 (t, J=7.1 Hz, 9H), 1.27-1.36 (m, 36H), 1.58-1.64 (m, 6H), 2.02 (q, J=6.5 Hz, 12H), 2.37 (t, J=7.6 Hz, 6H), 3.72 (s, 9H), 4.55 (s, 6H), 5.30-5.38 (m, 6H).

Example 10

N,N,N-trimethyl-1,3-bis(oleoyloxy)-2-(oleoyloxymethyl)propan-2-aminium Chloride (Compound II-3)

The title compound (1.14 g, 1.15 mmol, overall yield: 34%) was obtained in the similar manner as Example 8 using oleic acid instead of (9Z,12Z)-octadeca-9,12-dienoic acid.

ESI-MS m/z: 957 (M)$^+$; $^1$H-NMR (CDCl$_3$) δ: 0.83 (t, J=6.9 Hz, 9H), 1.17-1.32 (m, 60H), 1.51-1.59 (m, 6H), 1.96 (t, J=5.5 Hz, 12H), 2.32 (t, J=7.6 Hz, 6H), 3.70 (s, 9H), 4.56 (s, 6H), 5.25-5.34 (m, 6H).

Example 11

N,N,N-trimethyl-1,3-bis(stearoyloxy)-2-(stearoyloxymethyl)propan-2-aminium Chloride (Compound II-4)

Step 1:
Toluene (10 mL), stearic acid (Tokyo Chemical Industry Co., Ltd., 0.763 g, 2.68 mmol) and p-toluenesulfonic acid monohydrate (0.191 g, 1.01 mmol) were added in order to 2-(dimethylamino)-2-(hydroxymethyl)propane-1,3-diol (0.100 g, 0.670 mmol) followed by stirring overnight under refluxing conditions. The reaction solution was concentrated under reduced pressure and the resulting residue was purified by aminosilica gel column chromatography (chloroform) to obtain 2-(dimethylamino)-2-((stearoyloxy)methyl) propane-1,3-diol distearate (0.120 g, 0.127 mmol, yield: 19%).

ESI-MS m/z: 948 (M+H)$^+$

Step 2:
The title compound (0.0260 g, 0.0260 mmol, yield: 21%) was obtained in the similar manner as Step 2 of Example 1 using 2-(dimethylamino)-2-((stearoyloxy)methyl)propane-1,3-diyl distearate (0.120 g, 0.127 mmol) obtained in Step 1.

ESI-MS m/z: 963 (M)$^+$; $^1$H-NMR (CDCl$_3$) δ: 0.88 (t, J=7.0 Hz, 9H), 1.22-1.36 (m, 84H), 1.56-1.65 (m, 6H), 2.37 (t, J=7.6 Hz, 6H), 3.72 (s, 9H), 4.56 (s, 6H).

Example 12

1,3-bis((Z)-hexadec-9-enoyloxy)-2-(((Z)-hexadec-9-enoyloxy)methyl)-N,N,N-trimethylpropan-2-aminium Chloride (Compound II-5)

The title compound (0.680 g, 0.748 mmol, overall yield: 63%) was obtained in the similar manner as Example 8 using cis-9-hexadecenoic acid instead of (9Z,12Z)-octadeca-9,12-dienoic acid.

ESI-MS m/z: 873 (M)$^+$; $^1$H-NMR (CDCl$_3$) δ: 0.88 (t, J=7.0 Hz, 9H), 1.24-1.36 (m, 48H), 1.56-1.67 (m, 13H), 1.98-2.05 (m, 12H), 2.37 (t, J=7.6 Hz, 6H), 3.75 (s, 9H), 4.53 (s, 6H), 5.29-5.40 (m, 6H).

Example 13

N,N,N-trimethyl-1,3-bis((9Z,12Z)-octadeca-9,12-dienyloxy)-2-(((9Z,12Z)-octadeca-9,12-dienyloxy)methyl)propan-2-aminium Chloride (Compound II-6)

Step 1:
Sodium hydride (Nacalai Tesque Inc., oily, 60%, 0.154 g, 3.84 mmol) and (9Z,12Z)-octadeca-9,12-dienyl methanesulfonate (1.32 g, 3.84 mmol) were added to a toluene solution (5 mL) of 2-dimethylamino-2-hydroxymethylpropane-1,3-diol (Zylexa Pharma Ltd., 0.115 g, 0.768 mmol) followed by stirring overnight under refluxing conditions. After allowing to cool to room temperature, saturated aqueous sodium bicarbonate solution was added to the reaction solution followed by extracting with hexane. The organic layer was dried with anhydrous magnesium sulfate, filtered and concentrated under reduced pressure. The resulting residue was purified by aminosilica gel column chromatography (hexane/ethyl acetate=100/0 to 95/5) to obtain N,N-dimethyl-1,3-bis((9Z,12Z)-octadeca-9,12-dienyloxy)-2-(((9Z,12Z)-octadeca-9,12-dienyloxy)methyl)propan-2-amine (0.195 g, 0.217 mmol, yield: 28%).

ESI-MS m/z: 895 (M+H)$^+$.

Step 2:
Methyl iodide (0.119 mL) was added to a chloroform solution (1 mL) of the N,N-dimethyl-1,3-bis((9Z,12Z)-octadeca-9,12-dienyloxy)-2-(((9Z,12Z)-octadeca-9,12-dienyloxy)methyl)propan-2-amine (0.0849 g, 0.0949 mmol) obtained in Step 1 followed by stirring overnight at room temperature. The reaction solution was concentrated under reduced pressure. The residue was dissolved in a small amount of methanol-chloroform (1:1), loaded onto an ion exchange resin (Dow Chemical Co., Dowex™ 1×-2 100 mesh, type CL, about 20 times volume, prewashed with water and methanol), and eluted with methanol-chloroform (1:1). The eluate was concentrated under reduced pressure and the resulting residue was purified by silica gel column chromatography (chloroform/methanol=100/0 to 90/10) to obtain the title compound (0.0646 g, 0.0684 mmol, yield: 72%).

ESI-MS m/z: 909 (M)$^+$; $^1$H-NMR (CDCl$_3$) δ: 0.89 (t, J=6.9 Hz, 9H), 1.25-1.40 (m, 48H), 1.55-1.63 (m, 6H), 2.02-2.09 (m, 12H), 2.77 (t, J=6.8 Hz, 6H), 3.44 (t, J=6.6 Hz, 6H), 3.62 (s, 9H), 3.82 (s, 6H), 5.29-5.42 (m, 12H).

Example 14

N,N,N-trimethyl-1,3-bis((Z)-tetradec-9-enyloxy)-2-(((Z)-tetradec-9-enyloxy)meth yl)propan-2-aminium Chloride (Compound II-7)

The title compound (0.0729 g, 0.0931 mmol, overall yield: 12%) was obtained in the similar manner as Example 13 using myristoleyl methanesulfonate (Nu-Chek Prep, Inc.) instead of (9Z,12Z)-octadeca-9,12-dienyl methanesulfonate.

ESI-MS m/z: 747 (M)$^+$; $^1$H-NMR (CDCl$_3$) δ: 0.90 (t, J=7.1 Hz, 9H), 1.27-1.37 (m, 42H), 1.54-1.61 (m, 6H), 2.02 (q, J=6.5 Hz, 12H), 3.43 (t, J=6.6 Hz, 6H), 3.64 (s, 8H), 3.81 (s, 6H), 5.31-5.39 (m, 6H).

Example 15

1,3-bis((Z)-hexadec-9-enyloxy)-2-(((Z)-hexadec-9-enyloxy)methyl)-N,N,N-trimethylpropan-2-aminium Chloride (Compound II-8)

The title compound (0.466 g, 0.538 mmol, overall yield: 71%) was obtained in the similar manner as Example 13 using palmitoleyl methanesulfonate (Nu-Chek Prep, Inc.) instead of (9Z,12Z)-octadeca-9,12-dienyl methanesulfonate.

ESI-MS m/z: 831 (M)$^+$; $^1$H-NMR (CDCl$_3$) δ: 0.88 (t, J=6.8 Hz, 9H), 1.23-1.37 (m, 54H), 1.53-1.61 (m, 14H), 2.02 (q, J=5.8 Hz, 12H), 3.43 (t, J=6.5 Hz, 6H), 3.65 (s, 9H), 3.81 (s, 6H), 5.30-5.40 (m, 6H).

Example 16

(6Z,9Z,40Z,43Z)—N,N,N-trimethyl-25-((3-((9Z,12Z)-octadeca-9,12-dienyloxy)-3-oxopropoxy) methyl)-20,30-dioxo-19,23,27,31-tetraoxanonatetraconta-6,9,40,43-tetraen-25-aminium Chloride (Compound II-9)

Step 1:
Di-tert-butyl 3,3'-((2-amino-2-((3-(tert-butoxy)-3-oxopropoxy)methyl)propane-1,3-diyl)bis(oxy))dipropanoate (0.500 g, 0.989 mmol), synthesized using a method complying with the method described in the Journal of Organic Chemistry (J. Org. Chem.), 2002, Vol. 67, pp. 1411-1413, was dissolved in dichloromethane (5 mL) followed by the addition of methyl iodide (1.40 g, 9.89 mmol) and stirring overnight at room temperature. The reaction solution was concentrated under reduced pressure. The residue was dissolved in a small amount of methanol-chloroform (1:1), loaded onto an ion exchange resin (Dowex™ 1×-2 100 mesh, type CL, about 20 times volume, prewashed with water and methanol), and eluted with methanol. The eluate was concentrated under reduced pressure and the resulting residue was purified by silica gel column chromatography (chloroform/methanol=97/3 to 80/20) to obtain 9-((3-(tert-butoxy)-3-oxopropoxy)methyl)-N,N,N,2,2,16,16-heptamethyl-4,14-dioxo-3, 7,11,15-tetraoxaheptadecan-9-aminium chloride (0.144 g, 0.246 mmol, yield: 25%).

ESI-MS m/z: 548 (M+H)$^+$.

Step 2:

The 9-((3-(tert-butoxy)-3-oxopropoxy)methyl)-N,N,N,2,2,16,16-heptamethyl-4,14-dioxo-3, 7,11,15-tetraoxaheptadecan-9-aminium chloride (0.350 g, 0.246 mmol) obtained in Step 1 was dissolved in dichloromethane (2 mL) followed by the addition of trifluoroacetic acid (0.380 mL, 4.92 mmol) and stirring for 3 hours at room temperature. Toluene was added to the reaction solution followed by concentrating under reduced pressure to obtain a crude product of 1,3-bis (2-carboxyethoxy)-2-((2-carboxyethoxy)methyl)-N,N,N-trimethylpropan-2-aminium chloride trifluoroacetate (0.102 g, 0.246 mmol, crude yield: 100%).

ESI-MS m/z: 422 (M+H)$^+$

Step 3:

The crude product of 1,3-bis(2-carboxyethoxy)-2-((2-carboxyethoxy)methyl)-N,N,N-trimethylpropan-2-aminium chloride trifluoroacetate obtained in Step 2 was dissolved in dichloromethane (2 mL) followed by the addition of C-(7-aza-1H-benzotriazol-1-yl)-N,N,N',N'-tetramethyluronium hexafluorophosphate (Wako Pure Chemical Industries, Ltd., 0.20 g, 0.53 mmol), N,N-diisopropylethylamine (0.23 mL, 1.3 mmol) and (9Z,12Z)-octadeca-9,12-dien-1-ol (Tokyo Chemical Industries Co., Ltd., 0.141 g, 0.53 mmol) and stirring overnight at room temperature. Water was added to the reaction solution followed by extraction with chloroform. The organic layer was washed with saturated salt solution, dried with anhydrous magnesium sulfate, filtered and concentrated under reduced pressure. The resulting residue was purified by silica gel column chromatography (chloroform/methanol=90/10 to 80/20) to obtain the title compound (8.0 mg, 6.9 mmol, yield: 5%).

ESI-MS m/z: 1125 (MH)$^+$; $^1$H-NMR (CDCl$_3$) δ: 0.89 (t, J=7.0 Hz, 9H), 1.25-1.39 (m, 48H), 1.58-1.66 (m, 6H), 2.05 (q, J=6.9 Hz, 12H), 2.59 (t, J=5.7 Hz, 6H), 2.77 (t, J=6.7 Hz, 6H), 3.42 (s, 9H), 3.74 (t, J=5.7 Hz, 6H), 4.00 (s, 6H), 4.07 (t, J=6.8 Hz, 6H), 5.29-5.40 (m, 12H).

Example 17

(7Z,38Z)-23-((3-((Z)-hexadec-9-enyloxy)-3-oxopropoxy)methyl)-N,N,N-trimethyl-18,28-dioxo-17, 21,25,29-tetraoxapentatetraconta-7,38-dien-23-aminium Chloride (Compound II-10)

The title compound (0.145 g, 0.134 mmol, overall yield: 17%) was obtained in the similar manner as Example 16 using (Z)-hexadec-9-en-1-ol (Nu-Chek Prep, Inc.) instead of (9Z,12Z)-octadeca-9,12-dien-1-ol.

ESI-MS m/z: 1047 (M)$^+$; $^1$H-NMR (CDCl$_3$) δ: 0.88 (t, J=7.0 Hz, 9H), 1.24-1.38 (m, 54H), 1.58-1.66 (m, 6H), 1.98-2.05 (m, 12H), 2.58 (t, J=5.7 Hz, 6H), 3.47 (s, 9H), 3.74 (t, J=5.7 Hz, 6H), 4.02 (s, 6H), 4.07 (t, J=6.8 Hz, 6H), 5.30-5.40 (m, 6H).

Example 18

(5Z,36Z)—N,N,N-trimethyl-16,26-dioxo-21-((3-oxo-3-((Z)-tetradec-9-enyloxy)propoxy)methyl)-15, 19,23,27-tetraoxahentetraconta-5,36-dien-21-aminium Chloride (Compound II-11)

The title compound (0.189 g, 0.189 mmol, overall yield: 24%) was obtained in the similar manner as Example 16 using (Z)-tetradec-9-en-1-ol (Nu-Chek Prep, Inc.) instead of (9Z,12Z)-octadeca-9,12-dien-1-ol.

ESI-MS m/z: 963 (M)$^+$; $^1$H-NMR (CDCl$_3$) δ: 0.87-0.92 (m, 9H), 1.25-1.38 (m, 42H), 1.55-1.66 (m, 6H), 1.98-2.05 (m, 12H), 2.58 (t, J=5.7 Hz, 6H), 3.47 (s, 9H), 3.75 (t, J=5.7 Hz, 6H), 4.01 (s, 6H), 4.07 (t, J=6.8 Hz, 6H), 5.30-5.41 (m, 6H).

Example 19

(11Z,14Z)—N,N,N-trimethyl-2-(((9Z,12Z)-octadeca-9,12-dienoyloxy)methyl)-2-((9 Z,12Z)-octadeca-9,12-dienyl)icosa-11,14-dien-1-aminium Chloride (Compound II-12)

Step 1:

Ethyl cyanoacetate (Tokyo Chemical Industries Co., Ltd., 1.00 g, 8.84 mmol) and (9Z,12Z)-octadeca-9,12-dienyl methanesulfonate (7.62 g, 22.1 mmol) were dissolved in tetrahydrofuran (30 mL) followed by the addition of sodium hydride (oily, 60%, 1.06 g, 26.5 mmol) and tetra-n-butylammonium iodide (Nacalai Tesque Inc., 3.27 g, 8.84 mmol) while cooling with ice. After foaming had subsided, the reaction solution was stirred for 3 hours at 60° C. Water was added to the reaction solution followed by extraction with hexane. The organic layer was washed with saturated salt solution followed by drying with anhydrous magnesium sulfate and filtering. The resulting solution was concentrated under reduced pressure to obtain a crude product of (11Z, 14Z)-ethyl-2-cyano-2-((9Z,12Z)-octadeca-9,12-dien-1-yl) icosa-11,14-dienoate (3.50 g, 5.74 mmol, crude yield: 65%).

Step 2:

The crude product of (11Z,14Z)-ethyl-2-cyano-2-((9Z, 12Z)-octadeca-9,12-dien-1-yl)icosa-11,14-dienoate (1.50 g, 2.46 mmol) obtained in Step 1 was dissolved in tetrahydrofuran (10 mL) followed by the addition of lithium aluminum hydride (Junsei Chemical Co., Ltd., 0.467 g, 12.3 mmol) while cooling with ice and stirring for 30 minutes. Water (0.5 mL), 15% aqueous sodium hydroxide solution (0.5 mL), water (1.5 mL) and magnesium sulfate were added to the reaction solution in that order followed by briefly stirring and then filtering. After concentrating under reduced pressure, the resulting residue was purified by silica gel column chromatography (chloroform/methanol=99/1 to 85/15) to obtain (11Z,14Z)-2-(aminoethyl)-2-((9Z,12Z)-octadeca-9, 12-dien-1-yl)icosa-11,14-dien-1-ol (1.00 g, 2.46 mmol, yield: 71%).

ESI-MS m/z: 573 (M+H)$^+$.

Step 3:

The (11Z,14Z)-2-(aminoethyl)-2-((9Z,12Z)-octadeca-9, 12-dien-1-yl)icosa-11,14-dien-1-ol (0.350 g, 0.612 mmol) obtained in Step 2 was dissolved in acetonitrile (2 mL) and tetrahydrofuran (2 mL) followed by the addition of 38% aqueous formaldehyde solution (Wako Pure Chemical Industries, Ltd., 0.145 mL, 1.84 mmol), acetic acid (0.035 mL, 0.612 mmol) and sodium triacetoxyborohydride (Acres Organics Co., 0.389 g, 1.84 mmol) and stirring overnight at room temperature. Water was added to the reaction solution followed by extraction with chloroform. The organic layer was washed with saturated salt solution followed by drying with anhydrous magnesium sulfate and filtering. The resulting residue was purified by silica gel column chromatography (chloroform/methanol=99/1 to 85/15) to obtain (11Z,14Z)-2-((dimethylamino)methyl)-2-((9Z,12Z)-octadeca-9,12-dien-1-yl)icosa-11,14-dien-1-ol (0.252 g, 0.420 mmol, yield: 69%).

ESI-MS m/z: 600 (M+H)$^+$

Step 4:

(9Z,12Z)-octadeca-9,12-dienoic acid (0.141 g, 0.504 mmol), O-(7-aza-1H-benzotriazol-1-yl)-N,N,N',N'-tetramethyluronium hexafluorophosphate (0192 g, 0.504 mmol) and N,N-diisopropylethylamine (0.147 mL, 0.840 mmol) were added in that order to a dichloromethane solution (4 mL) of the (11Z,14Z)-2-((dimethylamino)methyl)-2-((9Z,12Z)-octadeca-9,12-dien-1-yl)icosa-11,14-dien-1-ol (0.252 g, 0.420 mmol) obtained in Step 3 followed by stirring for 4 hours at room temperature. Water was added to the reaction solution followed by extraction with hexane. The organic layer was washed with water followed by drying with anhydrous magnesium sulfate, filtering and concentrating under reduced pressure. The resulting residue was purified by silica gel column chromatography (chloroform/methanol=99/1 to 85/15) to obtain (9Z,12Z)-(11Z,14Z)-2-((dimethylamino)methyl)-2-((9Z,12Z)-octadeca-9,12-dien-1-yl)icosa-11,14-dien-1-yl octadeca-9,12-dienoate (0.307 g, 0.356 mmol, yield: 85%).

ESI-MS m/z: 863 (M+H)$^+$

Step 5:

The title compound (0.260 g, 0.285 mmol, yield: 80%) was obtained in the similar manner as Step 2 of Example 1 using (9Z,12Z)-(11Z,14Z)-2-((dimethylamino)methyl)-2-((9Z,12Z)-octadeca-9,12-dien-1-yl)icosa-11,14-dien-1-yl octadeca-9,12-dienoate (0.307 g, 0.356 mmol) obtained in Step 4.

ESI-MS m/z: 877 (M)$^+$; $^1$H-NMR (CDCl$_3$) δ: 0.89 (t, J=7.0 Hz, 9H), 1.22-1.48 (m, 54H), 1.60-1.66 (m, 2H), 2.05 (q, J=6.8 Hz, 12H), 2.38 (t, J=7.6 Hz, 2H), 2.77 (t, J=6.3 Hz, 6H), 3.50 (s, 2H), 3.60 (s, 9H), 4.13 (s, 2H), 5.27-5.44 (m, 12H).

Example 20

N,N,N-trimethyl-3-((11 Z,14Z)-2-(((9Z,12Z)-octadeca-9,12-dienoyloxy)methyl)-2-((9Z,12Z)-octadeca-9,12-dienyl)icosa-11,14-dienylcarbamoyloxy)propan-1-aminium Chloride (Compound II-13)

Step 1:

The (11Z,14Z)-2-(aminoethyl)-2-((9Z,12Z)-octadeca-9,12-dien-1-yl)icosa-11,14-dien-1-ol (0.918 g, 1.61 mmol) obtained in Step 2 of Example 19 was dissolved in tetrahydrofuran (20 mL) followed by the addition of triethylamine (0.671 mL, 4.81 mmol) and di-tert-butyl dicarbonate (Kokusan Chemical Co., Ltd., 0.373 mL, 1.61 mmol) and stirring overnight at room temperature. The reaction solution was concentrated under reduced pressure and the resulting residue was purified by silica gel column chromatography (hexane/ethyl acetate=95/5 to 50/50) to obtain tert-butyl ((11Z,14Z)-2-(hydroxymethyl)-2-((9Z,12Z)-octadeca-9,12-dien-1-yl)icosa-11,14-dien-1-ylcarbamate (0.918 g, 1.37 mmol, yield: 85%).

ESI-MS m/z: 672 (M+H)$^+$.

Step 2:

The tert-butyl ((11Z,14Z)-2-(hydroxymethyl)-2-((9Z,12Z)-octadeca-9,12-dien-1-yl)icosa-11,14-dien-1-ylcarbamate (0.357 g, 0.531 mmol) obtained in Step 1 was dissolved in dichloromethane (5 mL) followed by the addition of (9Z,12Z)-octadeca-9,12-dienoic acid (0.223 g, 0.797 mmol), O-(7-aza-1H-benzotriazol-1-yl)-N,N,N',N'-tetramethyluronium hexafluorophosphate (0.303 mmol, 0.797 mmol), N,N-diisopropylethylamine (0.186 mL, 1.06 mmol) and N,N-dimethylaminopyridine (0.0650 g, 0.531 mmol) and stirring overnight at room temperature. Water was added to the reaction solution followed by extraction with chloroform. The organic layer was washed with saturated salt solution followed by drying with anhydrous magnesium sulfate, filtering and concentrating under reduced pressure. The resulting residue was purified by silica gel column chromatography (hexane/ethyl acetate=99/1 to 90/10) to obtain (9Z,12Z)-(11Z,14Z)-2-(((tert-butoxycarbonylamino)methyl)-2-((9Z,12Z)-octadeca-9,12-dien-1-yl)icosa-11,14-dien-1-yl octadeca-9,12-dienoate (0.395 g, 0.423 mmol, yield: 80%).

ESI-MS m/z: 935 (M+H)$^+$.

Step 3:

The (9Z,12Z)-(11Z,14Z)-2-(((tert-butoxycarbonylamino)methyl)-2-((9Z,12Z)-octadeca-9,12-dien-1-yl)icosa-11,14-dien-1-yl octadeca-9,12-dienoate (0.395 g, 0.423 mmol) obtained in Step 2 was dissolved in dichloromethane (3 mL) followed by the addition of trifluoroacetic acid (1.00 mL, 4.92 mmol) while cooling with ice and stirring for 2 hours at 0° C. 1,2-dichloroethane was added to the reaction solution followed by concentrating under reduced pressure to obtain a crude product of (9Z,12Z)-(11Z,14Z)-2-(aminoethyl)-2-((9Z,12Z)-octadeca-9,12-dien-1-yl)icosa-11,14-dien-1-yl octadeca-9,12-dienoate trifluoroacetate (0.394 g, 0.423 mmol, crude yield: 100%).

ESI-MS m/z: 834 (M+H)$^+$.

Step 4:

The crude product of (9Z,12Z)-(11Z,14Z)-2-(aminoethyl)-2-((9Z,12Z)-octadeca-9,12-dien-1-yl)icosa-11,14-dien-1-yl octadeca-9,12-dienoate trifluoroacetate (0.200 g, 0.215 mmol) obtained in Step 3 was dissolved in acetonitrile (2 mL) followed by the addition of 3-(dimethylamino)propyl-4-nitrophenyl carbonate hydrochloride (0.279 g, 1.07 mmol), synthesized using a method complying with the method described in the Journal of the American Chemical Society (J. Am. Chem. Soc.), 1981, Vol. 103, pp. 4194-4199, triethylamine (0.299 mL, 2.15 mmol) and N,N-dimethylaminopyridine (0.0520 g, 0.429 mmol) and stirring for 2 hours at 60° C. Saturated aqueous sodium bicarbonate solution was added to the reaction solution followed by extraction with chloroform. The organic layer was washed with saturated salt solution followed by drying with anhydrous magnesium sulfate, filtering and concentrating under reduced pressure. The resulting residue was purified by silica gel column chromatography (hexane/ethyl acetate=99/1 to 60/40) to obtain (9Z,12Z)-(11Z,14Z)-2-((((3-(dimethylamino)propoxy)carbonyl)amino)methyl)-2-((9Z,12Z)-octadeca-9,12-dien-1-yl)icosa-11,14-dien-1-yl octadeca-9,12-dienoate (0.0800 g, 0.0830 mmol, yield: 39%).

ESI-MS m/z: 964 (M+H)$^+$.

Step 5:

The title compound (0.025 g, 0.025 mmol, yield: 45%) was obtained in the similar manner as Step 2 of Example 1 using (9Z,12Z)-(11Z,14Z)-2-((((3-(dimethylamino)propoxy)carbonyl)amino)methyl)-2-((9Z,12Z)-octadeca-9, 12-dien-1-yl)icosa-11,14-dien-1-yl octadeca-9,12-dienoate (0.053 g, 0.055 mmol) obtained in Step 4.

ESI-MS m/z: 978 (M)$^+$; $^1$H-NMR (CDCl$_3$) δ: 0.89 (t, J=7.0 Hz, 9H), 1.17-1.40 (m, 54H), 1.56-1.66 (m, 2H), 2.05 (q, J=6.8 Hz, 12H), 2.09-2.17 (m, 2H), 2.33 (t, J=7.6 Hz, 2H), 2.77 (t, J=6.2 Hz, 6H), 3.05 (d, J=6.6 Hz, 2H), 3.44 (s, 9H), 3.73-3.79 (m, 2H), 3.85 (s, 2H), 4.16 (t, J=5.7 Hz, 2H), 5.27-5.44 (m, 12H), 5.72 (t, J=6.5 Hz, 1H).

Example 21

(12Z,15Z)-3-hydroxy-N,N,N-trimethyl-2,2-di((9Z,12Z)-octadeca-9,12-dien-1-yl)henicosa-12,15-dien-1-aminium Chloride (Compound II-14)

Step 1:
The (11Z,14Z)-2-(aminoethyl)-2-((9Z,12Z)-octadeca-9,12-dien-1-yl)icosa-11,14-dien-1-ol (1.35 g, 2.36 mmol) obtained in Step 2 of Example 19 was dissolved in tetrahydrofuran (10 mL) followed by the addition of 38% aqueous formaldehyde solution (Wako Pure Chemical Industries, Ltd., 0.559 mL, 7.08 mmol), acetic acid (0.135 mL, 2.36 mmol) and sodium triacetoxyborohydride (1.50 g, 7.08 mmol) and stirring for 1 hour at room temperature. Water was added to the reaction solution followed by extraction with chloroform. The organic layer was washed with saturated salt solution followed by drying with anhydrous magnesium sulfate, filtering and concentrating under reduced pressure. The resulting residue was purified by silica gel column chromatography (chloroform/methanol=99/1 to 85/15) to obtain (11Z,14Z)-2-((dimethylamino)methyl)-2-((9Z,12Z)-octadeca-9,12-dien-1-yl)icosa-11,14-dien-1-ol (0.610 g, 1.02 mmol, yield: 43%).

ESI-MS m/z: 600 (M+H)$^+$.

Step 2:
The (11Z,14Z)-2-((dimethylamino)methyl)-2-((9Z,12Z)-octadeca-9,12-dien-1-yl)icosa-11,14-dien-1-ol (0.300 g, 0.500 mmol) obtained in Step 1 was dissolved in dichloromethane (3 mL) followed by the addition of Dess-Martin reagent (Tokyo Chemical Industry Co., Ltd., 0.233 g, 0.550 mmol) and stirring for 1 hour at room temperature. Water was added to the reaction solution followed by extraction with chloroform. The organic layer was washed with saturated salt solution followed by drying with anhydrous magnesium sulfate, filtering and concentrating under reduced pressure. The resulting residue was purified by silica gel column chromatography (hexane/ethyl acetate=95/5 to 70/30) to obtain (11Z,14Z)-2-((dimethylamino)methyl)-2-((9Z,12Z)-octadeca-9,12-dien-1-yl)icosa-11,14-dienal (0.160 g, 0.268 mmol, yield: 54%).

ESI-MS m/z: 598 (M+H)$^+$.

Step 3:
Diethyl ether (1 mL) and iodine (one fragment) were added to magnesium (Sigma-Aldrich Corp., 0.0140 g, 0.562 mmol) followed by stirring for 5 minutes at room temperature. A diethyl ether solution (1 mL) of (6Z,9Z)-18-bromooctadeca-6,9-diene (0.176 g, 0.535 mmol), synthesized using a method complying with the method described in WO 2010/42877, was added thereto followed by stirring while refluxing. After confirming that the iodine color was no longer present, a diethyl ether solution (1 mL) of the (11Z,14Z)-2-((dimethylamino)methyl)-2-((9Z,12Z)-octadeca-9,12-dien-1-yl)icosa-11,14-dienal (0.160 g, 0.268 mmol) obtained in Step 2 was added followed by stirring for 1 hour at room temperature. Water was added to the reaction solution followed by extraction with hexane. The organic phase was washed with saturated salt solution followed by drying with anhydrous magnesium sulfate, filtering and concentrating under reduced pressure. The resulting residue was purified by silica gel column chromatography (hexane/ethyl acetate=99/1 to 85/15) to obtain (6Z,9Z,29Z,32Z)-20-((dimethylamino)methyl)-20-((9Z,12Z)-octadeca-9,12-dien-1-yl)octatriaconta-6,9,29,32-tetraen-19-ol (0.0470 g, 0.0550 mol, yield: 21%).

ESI-MS m/z: 848 (M+H)$^+$.

Step 4:
The title compound (0.0012 g, 0.0013 mmol, yield: 2%) was obtained in the similar manner as Step 2 of Example 1 using (6Z,9Z,29Z,32Z)-20-((dimethylamino)methyl)-20-((9Z,12Z)-octadeca-9,12-dien-1-yl)octatriaconta-6,9,29,32-tetraen-19-ol (0.047 g, 0.055 mmol) obtained in Step 3.

ESI-MS m/z: 863 (M)$^+$; $^1$H-NMR (CDCl$_3$) δ: 0.89 (t, J=7.0 Hz, 9H), 1.17-1.40 (m, 58H), 1.54-1.65 (m, 2H), 2.05 (q, J=6.8 Hz, 12H), 2.77 (t, J=6.5 Hz, 6H), 3.29 (d, J=14.4 Hz, 1H), 3.51 (s, 9H), 3.56 (d, J=14.2 Hz, 1H), 3.62-3.70 (m, 1H), 5.29-5.42 (m, 12H).

Example 22

(11Z,14Z)—N,N,N-trimethyl-2-((9Z,12Z)-octadeca-9,12-dien-1-yl)-2-(((9Z,12Z)-octadeca-9,12-dienyloxy)carbonyl)icosa-11,14-dien-1-aminium Chloride (Compound II-15)

Step 1:
The tert-butyl ((11Z,14Z)-2-(hydroxymethyl)-2-((9Z,12Z)-octadeca-9,12-dien-1-yl)icosa-11,14-dien-1-ylcarbamate (0.300 g, 0.448 mmol) obtained in Step 1 of Example 20 was dissolved in acetone (2 mL) followed by the addition of Jones reagent (Sigma-Aldrich Corp., 2 mol/L, 0.224 mL, 0.448 mmol) while cooling with ice and stirring for 1 hour at room temperature. Water was added to the reaction solution followed by extraction with ethyl acetate. The organic layer was washed with saturated salt solution followed by drying with anhydrous magnesium sulfate, filtering and concentrating under reduced pressure. The resulting residue was purified by silica gel column chromatography (hexane/ethyl acetate=95/5 to 50/50) to obtain (11Z,14Z)-2-(((tert-butoxycarbonyl)amino)methyl)-2-((9Z,12Z)-octadeca-9,12-dien-1-yl)icosa-11,14-dienoic acid (0.136 g, 0.198 mmol, yield: 44%).

ESI-MS m/z: 684 (M−H)$^-$.

Step 2:
(11Z,14Z)-(9Z,12Z)-octadeca-9,12-dien-1-yl 2-(((tert-butoxycarbonyl)amino)methyl)-2-((9Z,12Z)-octadeca-9,12-dien-1-yl)icosa-11, 14-dienoate (0.123 g, 0.132 mmol, yield: 75%) was obtained in the similar manner as Step 2 of Example 20 using (11Z,14Z)-2-(((tert-butoxycarbonyl)amino)methyl)-2-((9Z,12Z)-octadeca-9,12-dien-1-yl)icosa-11,14-dienoic acid (0.120 g, 0.175 mmol) obtained in Step 1 and (9Z,12Z)-octadeca-9,12-dien-1-ol (Nu-Chek Prep, Inc., 0.0390 g, 0.350 mmol).

ESI-MS m/z: 935 (M+H)$^+$.

Step 3:
The (11Z,14Z)-(9Z,12Z)-octadeca-9,12-dien-1-yl 2-(((tert-butoxycarbonyl)amino)methyl)-2-((9Z,12Z)-octadeca-9,12-dien-1-yl)icosa-11, 14-dienoate (0.123 g, 0.132 mmol) obtained in Step 2 was dissolved in dichloromethane (1 mL) followed by addition of trifluoroacetic acid (0.300 mL, 3.89 mmol) while cooling with ice and stirring for 1 hour. Saturated aqueous sodium bicarbonate solution was added to the reaction solution followed by extraction with hexane. The organic layer was washed with saturated salt solution followed by drying with anhydrous magnesium sulfate, filtering and concentrating under reduced pressure. The resulting residue was purified by silica gel column chromatography (hexane/ethyl acetate=99/1 to 80/20) to obtain (11Z,14Z)-(9Z,12Z)-octadeca-9,12-dien-1-yl 2-(aminomethyl)-2-((9Z,12Z)-octadeca-9,12-dien-1-yl)icosa-11,14-dienoate (0.110 g, 0.132 mmol, yield: 100%).

ESI-MS m/z: 835 (M+H)$^+$.

Step 4:

(11Z,14Z)-(9Z,12Z)-octadeca-9,12-dien-1-yl 2-((dimethylamino)methyl)-2-((9Z,12Z)-octadeca-9,12-dien-1-yl) icosa-11,14-dienoate (0.0720 g, 0.0830 mmol, yield: 63%) was obtained in the similar manner as Step 1 of Example 21 using (11Z,14Z)-(9Z,12Z)-octadeca-9,12-dien-1-yl 2-(aminomethyl)-2-((9Z,12Z)-octadeca-9,12-dien-1-yl)icosa-11,14-dienoate (0.110 g, 0.132 mmol) obtained in Step 3.

ESI-MS m/z: 862 (M+H)$^+$.

Step 5:

The title compound (0.052 g, 0.057 mmol, yield: 68%) was obtained in the similar manner as Step 2 of Example 1 using (11Z,14Z)-(9Z,12Z)-octadeca-9,12-dien-1-yl 2-((dimethylamino)methyl)-2-((9Z,12Z)-octadeca-9,12-dien-1-yl) icosa-11,14-dienoate (0.072 g, 0.083 mmol) obtained in Step 4.

ESI-MS m/z: 877 (M)$^+$; $^1$H-NMR (CDCl$_3$) δ: 0.89 (t, J=7.0 Hz, 9H), 1.09-1.42 (m, 52H), 1.52-1.81 (m, 6H), 2.05 (q, J=6.8 Hz, 12H), 2.77 (t, J=6.6 Hz, 6H), 3.46 (s, 9H), 3.79 (s, 2H), 4.14 (t, J=6.8 Hz, 2H), 5.28-5.43 (m, 12H).

Example 23

(11Z,14Z)—N,N,N-trimethyl-2,2-bis(((9Z,12Z)-octadeca-9,12-dienoyloxy)methyl)icosa-11,14-dien-1-aminium Chloride (Compound II-16)

Step 1:

Dimethyl malonate (Tokyo Chemical Industry Co., Ltd., 1.00 g, 7.57 mmol) was dissolved in acetonitrile (20 mL) followed by the addition of (9Z,12Z)-octadeca-9,12-dienyl methanesulfonate (2.61 g, 7.57 mmol), cesium carbonate (Wako Pure Chemical Industries, Ltd., 4.93 g, 15.1 mmol) and tetra-n-butylammonium iodide (2.80 g, 7.57 mmol) and stirring overnight at 50° C. Water was added to the reaction solution followed by extraction with hexane. The organic layer was washed with saturated salt solution followed by drying with anhydrous magnesium sulfate, filtering and concentrating under reduced pressure. The resulting residue was purified by silica gel chromatography (hexane/ethyl acetate=90/10 to 70/30) to obtain dimethyl-2-((9Z,12Z)-octadeca-9,12-dien-1-yl) malonate (1.22 g, 3.21 mmol, yield: 42%).

ESI-MS m/z: 381 (M+H)$^+$.

Step 2:

The dimethyl-2-((9Z,12Z)-octadeca-9,12-dien-1-yl) malonate (0.200 g, 0.526 mmol) obtained in Step 1 was dissolved in acetonitrile (3 mL) followed by the addition of N,N,N',N'-tetramethylaminomethane (Tokyo Chemical Industry Co., Ltd., 0.0860 mL, 0.631 mmol) and acetic anhydride (0.0600 mL, 0.631 mmol). Subsequently, sodium hydride (oily, 60%, 0.0320 g, 0.788 mmol) was added while cooling with ice followed by stirring for 3 hours at room temperature. Saturated aqueous ammonium chloride solution was added to the reaction solution followed by extraction with ethyl acetate. The organic layer was washed with saturated salt solution followed by drying with anhydrous magnesium sulfate, filtering and concentrating under reduced pressure. The resulting residue was purified by silica gel column chromatography (hexane/ethyl acetate=100/0 to 60/40) to obtain dimethyl 2-((dimethylamino)methyl)-2-((9Z,12Z)-octadeca-9,12-dien-1-yl) malonate (0.0660 g, 0.151 mmol, yield: 29%).

ESI-MS m/z: 438 (M+H)$^+$.

Step 3:

2-((dimethylamino)methyl)-2-((9Z,12Z)-octadeca-9,12-dien-1-yl)propane-1,3-diol (0.013 g, 0.034 mmol, yield: 23%) was obtained in the similar manner as Step 2 of Example 19 using dimethyl 2-((dimethylamino)methyl)-2-((9Z,12Z)-octadeca-9,12-dien-1-yl) malonate (0.066 g, 0.15 mmol) obtained in Step 2.

ESI-MS m/z: 382 (M+H)$^+$.

Step 4:

(9Z,9'Z,12Z,12'Z)-2-((dimethylamino)methyl)-2-((9Z,12Z)-octadeca-9,12-dien-1-yl)propane-1,3-diyl bis(octadeca-9,12-dienoate (0.017 g, 0.019 mmol, yield: 56%) was obtained in the similar manner as Step 2 of Example 20 using 2-((dimethylamino)methyl)-2-((9Z,12Z)-octadeca-9,12-dien-1-yl)propane-1,3-diol (0.013 g, 0.034 mmol) obtained in Step 3.

ESI-MS m/z: 906 (M+H)$^+$.

Step 5:

The title compound (5.5 mg, 0.0058 mmol, yield: 31%) was obtained in the similar manner as Step 2 of Example 1 using (9Z,9'Z,12Z,12'Z)-2-((dimethylamino)methyl)-2-((9Z,12Z)-octadeca-9,12-dien-1-yl)propane-1,3-diyl bis(octadeca-9,12-dienoate) (0.017 g, 0.019 mmol) obtained in Step 4.

ESI-MS m/z: 921 (M)$^+$; $^1$H-NMR (CDCl$_3$) δ: 0.89 (t, J=7.0 Hz, 9H), 1.23-1.40 (m, 48H), 1.53-1.65 (m, 4H), 2.05 (q, J=6.9 Hz, 12H), 2.38 (t, J=7.6 Hz, 4H), 2.77 (t, J=6.6 Hz, 6H), 3.59 (s, 9H), 3.72 (s, 2H), 4.20 (dd, J=22.1, 12.2 Hz, 4H), 5.28-5.44 (m, 12H).

Example 24

N,N,N-trimethyl-3-((9Z,12Z)-octadeca-9,12-dienoyloxy)-2,2-bis(((9Z,12Z)-octadeca-9,12-dienoyloxy) methyl)propan-1-aminium Chloride (Compound II-17)

Step 1:

Dimethylamine (Sigma-Aldrich Corp., 2.0 mol/L tetrahydrofuran solution, 5.02 mL, 10.1 mmol) was added to 2-(bromomethyl)-2-(hydroxymethyl)propane-1,3-diol (0.200 g, 1.01 mmol) followed by stirring for 15 minutes at 120° C. while irradiating with microwaves. Lithium hydroxide monohydrate (0.0290 g, 1.21 mmol) was added to the reaction solution and the resulting precipitate was filtered. The filtrate was concentrated under reduced pressure to obtain a crude product of 2-((dimethylamino)methyl)-2-(hydroxymethyl)propane-1,3-diol (0.200 g, 1.23 mmol, quantitative).

ESI-MS m/z: 164 (M+H)$^+$.

Step 2:

The title compound (0.0470 g, 0.047 mmol, overall yield: 4.4%) was obtained in the similar manner as Example 8 using crude product of 2-((dimethylamino)methyl)-2-(hydroxymethyl)propane-1,3-diol (0.200 g, 1.23 mmol) obtained in Step 1.

ESI-MS m/z: 965 (M)$^+$; $^1$H-NMR (CDCl$_3$) δ: 0.85-0.94 (m, 9H), 1.24-1.40 (m, 42H), 1.53-1.63 (m, 6H), 2.00-2.10 (m, 12H), 2.38 (t, J=6.9 Hz, 6H), 2.77 (t, J=6.5 Hz, 6H), 3.64 (s, 9H), 3.95 (s, 2H), 4.30 (s, 6H), 5.27-5.43 (m, 12H).

Example 25

N,N,N-trimethyl-3-(oleoyloxy)-2,2-bis(oleoyloxymethyl)propan-1-aminium Chloride (Compound II-18)

The title compound (0.663 g, 0.658 mmol, overall yield: 28%) was obtained in the similar manner as Example 8 using oleic acid instead of the (9Z,12Z)-octadeca-9,12-dienoic acid used in Step 1 of Example 8.

ESI-MS m/z: 971 (M)$^+$; $^1$H-NMR (CDCl$_3$) δ: 0.88 (t, J=6.8 Hz, 9H), 1.22-1.38 (m, 60H), 1.55-1.65 (m, 6H), 2.01 (q, J=5.9 Hz, 12H), 2.38 (t, J=7.6 Hz, 6H), 3.64 (s, 9H), 3.98 (s, 2H), 4.29 (s, 6H), 5.29-5.39 (m, 6H).

Example 26

N,N,N-trimethyl-3-((9Z,12Z)-octadeca-9,12-dienyloxy)-2,2-bis(((9Z,12Z)-octadeca-9,12-dienyloxy)methyl)propan-1-aminium Chloride (Compound II-19)

Step 1:

2-(bromomethyl)-2-(hydroxymethyl)propane-1,3-diol (1.52 g, 7.56 mmol) was added to dimethylamine (approx. 2 mol/L tetrahydrofuran solution, 15.0 mL, 30.0 mmol) followed by stirring for 15 hours at 120° C. using a microwave reactor. After allowing to cool to room temperature, lithium hydroxide (0.217 g, 9.07 mmol) was added to the reaction solution followed by filtering and concentrating under reduced pressure to obtain a crude product of 2-((dimethylamino)methyl)-2-(hydroxymethyl)propane-1,3-diol.

Toluene (30 mL), (9Z,12Z)-octadeca-9,12-dienyl methanesulfonate (6.51 g, 18.9 mmol) and sodium hydride (oily, 60%, 0.756 g, 18.9 mmol) were added to the resulting crude product followed by stirring overnight while refluxing. After allowing to cool to room temperature, saturated aqueous sodium bicarbonate solution was added to the reaction solution followed by extraction with hexane. The organic layer was dried with anhydrous magnesium sulfate, filtered and concentrated under reduced pressure. The resulting residue was purified by aminosilica gel column chromatography (hexane/ethyl acetate=100/0 to 90/10) to obtain N,N-dimethyl-3-((9Z,12Z)-octadeca-9,12-dienyloxy)-2,2-bis(((9Z,12Z)-octadeca-9,12-dienyloxy)methyl)propan-1-amine (0.196 g, 0.216 mmol, yield: 3%) and 3-(dimethylamino)-2,2-bis(((9Z,12Z)-octadeca-9,12-dienyloxy)methyl)propan-1-ol (1.80 g, 2.73 mmol, yield: 36%).

N,N-dimethyl-3-((9Z,12Z)-octadeca-9,12-dienyloxy)-2,2-bis(((9Z,12Z)-octadeca-9,12-dienyloxy)methyl)propan-1-amine ESI-MS m/z: 909 (M+H)$^+$.

3-(dimethylamino)-2,2-bis(((9Z,12Z)-octadeca-9,12-dienyloxy)methyl)propan-1-ol

ESI-MS m/z: 661 (M+H)$^+$.

Step 2:

Methyl iodide (0.500 mL) was added to a chloroform solution (1 mL) of the N,N-dimethyl-3-((9Z,12Z)-octadeca-9,12-dienyloxy)-2,2-bis(((9Z,12Z)-octadeca-9,12-dienyloxy)methyl)propan-1-amine (0.120 g, 0.132 mmol) followed by stirring for 3 hours at room temperature. The reaction solution was concentrated under reduced pressure. The residue was dissolved in a small amount of methanol, loaded onto an ion exchange resin (Amberlite® IRA-400, type CL, about 20 times volume, prewashed with water and ethanol) and eluted with methanol-chloroform (1:1). The eluate was concentrated under reduced pressure and the resulting residue was purified by silica gel column chromatography (chloroform/methanol=100/0 to 90/10) to obtain the title compound (0.0654 g, 0.0682 mmol, yield: 57%).

ESI-MS m/z: 923 (M)$^+$; $^1$H-NMR (CDCl$_3$) δ: 0.89 (t, J=6.8 Hz, 9H), 1.22-1.40 (m, 1H), 1.49-1.59 (m, 6H), 2.05 (q, J=6.9 Hz, 12H), 2.77 (t, J=6.7 Hz, 6H), 3.37 (t, J=6.6 Hz, 6H), 3.45 (s, 6H), 3.55 (s, 9H), 3.58 (s, 2H), 5.28-5.42 (m, 12H).

Example 27

N,N,N-trimethyl-3-((9Z,12Z)-octadeca-9,12-dienoyloxy)-2,2bis(((9Z,12Z)-octadeca-9,12-dienyloxy)methyl)propan-1-aminium Chloride (Compound II-20)

(9Z,12Z)-octadeca-9,12-dienoic acid (0.169 g, 0.602 mmol), 1-ethyl-3-(3-dimethylaminopropyl)carbodiimide hydrochloride (0.154 g, 0.802 mmol) and N,N-dimethylaminopyridine (0.0250 g, 0.201 mmol) were added to a 1,2-dichloroethane solution (4 mL) of the 3-(dimethylamino)-2,2-bis(((9Z,12Z)-octadeca-9,12-dienyloxy)methyl)propan-1-ol (0.265 g, 0.401 mmol) obtained in Step 1 of Example 26 followed by stirring overnight at room temperature. The reaction solution was concentrated under reduced pressure. The resulting residue was purified by silica gel column chromatography (hexane/ethyl acetate=95/5 to 90/10) to obtain a crude product of (9Z,12Z)-3-(dimethylamino)-2,2-(((9Z,12Z)-octadeca-9,12-dienyloxy)methyl)propyl octadeca-9,12-dienoate.

Chloroform (2 mL) and methyl iodide (Tokyo Chemical Industry Co., Ltd., 1.00 mL) were added to the resulting crude product followed by stirring for 5 hours at room temperature. The reaction solution was concentrated under reduced pressure. The residue was dissolved in a small amount of methanol-chloroform (1:1), loaded onto an ion exchange resin (Sigma-Aldrich Corp., Amberlite® IRA-400, type CL, about 20 times volume, prewashed with water and ethanol) and eluted with methanol-chloroform (1:1). The eluate was concentrated under reduced pressure and the resulting residue was purified by silica gel column chromatography (chloroform/methanol=100/0 to 90/10) to obtain the title compound (0.220 g, 0.226 mmol, yield: 56%).

ESI-MS m/z: 937 (M)$^+$; $^1$H-NMR (CDCl$_3$) δ: 0.89 (t, J=7.0 Hz, 9H), 1.22-1.41 (m, 51H), 1.50-1.66 (m, 6H), 2.05 (q, J=6.9 Hz, 12H), 2.38 (t, J=7.5 Hz, 2H), 2.77 (t, J=6.1 Hz, 6H), 3.39 (t, J=6.6 Hz, 4H), 3.44-3.48 (m, 2H), 3.54-3.58 (m, 11H), 3.73 (s, 2H), 4.18 (s, 2H), 5.28-5.43 (m, 11H).

Example 28

N,N,N-trimethyl-4-(2-(9Z,12Z)-octadeca-9,12-dieneamido-3-((9Z,12Z)-octadeca-9,12-dienoyloxy)-2-(((9Z,12Z)-octadeca-9,12-dienoyloxy)methyl)propoxy)-4-oxybutan-1-aminium Chloride (Compound II-21)

Step 1:

(9Z,12Z)-octadeca-9,12-dienoic acid (3.23 g, 11.4 mmol), 1-ethyl-3-(3-dimethylaminopropyl)carbodiimide hydrochloride (2.19 g, 11.4 mmol) and N,N-dimethylaminopyridine (0.279 g, 2.28 mmol) were added to a dichloromethane solution (15 mL) of tert-butyl(1,3-hydroxy-2-(hydroxymethyl)propan-2-yl) carbamate (Key Organics Ltd., 0.505 g, 2.28 mmol) followed by stirring for 1 hour at room temperature. Saturated aqueous sodium bicarbonate solution was added to the reaction solution followed by extraction with chloroform. The organic layer was dried with anhydrous magnesium sulfate, filtered and concentrated under reduced pressure. The resulting residue was purified by silica gel column chromatography (hexane/chloroform=100/0 to 95/5) to obtain (9Z,9'Z,12Z,12'Z)-2-(tert-butoxycarbonylamino-2-(((9Z,12Z)-octadeca-9,12-dienoyloxy)methyl)propane-1,3-diyl dioctadeca-9,12-dienoate (2.08 g, 2.06 mmol, yield: 90%).

$^1$H-NMR (CDCl$_3$) δ: 0.89 (t, J=6.7 Hz, 9H), 1.23-1.40 (m, 9H), 1.43 (s, 9H), 1.57-1.66 (m, 14H), 2.05 (q, J=6.8 Hz, 12H), 2.32 (t, J=7.6 Hz, 6H), 2.77 (t, J=6.5 Hz, 6H), 4.34 (s, 6H), 4.81 (brs, 1H), 5.28-5.43 (m, 12H).

Step 2:

Trifluoroacetic acid (2 mL, 26.0 mmol) was added to a dichloromethane solution (10 mL) of the (9Z,9'Z,12Z,12'Z)-2-(tert-butoxycarbonylamino-2-(((9Z,12Z)-octadeca-9,12-dienoyloxy)methyl)propane-1,3-diyl dioctadeca-9,12-dienoate (2.05 g, 2.03 mmol, 90%) obtained in Step 1 followed by stirring for 1 hour at room temperature. Saturated aqueous sodium bicarbonate solution was added to the reaction solution followed by extraction with chloroform. The organic layer was dried with anhydrous magnesium sulfate, filtered and concentrated under reduced pressure. The resulting residue was purified by aminosilica gel column chromatography (hexane/ethyl acetate=100/0 to 95/5) to obtain (9Z,9'Z,12Z,12'Z)-2-(hydroxymethyl)-2-(9Z,12Z)-octadeca-9,12-dieneamidopropane-1,3-diyl dioctadeca-9,12-dienoate (1.70 g, 1.84 mmol, yield: 91%).

ESI-MS m/z: 909 (M+H)$^+$.

Step 3:

(9Z,12Z)-octadeca-9,12-dienoic acid (Sigma-Aldrich Corp., 2.37 g, 8.45 mmol), 1-ethyl-3-(3-dimethylaminopropyl)carbodiimide hydrochloride (1.62 g, 8.45 mmol) and N,N-dimethylaminopyridine (0.206 g, 1.69 mmol) were added to a dichloromethane solution (9 mL) of the (9Z,9'Z, 12Z,12'Z)-2-(hydroxymethyl)-2-(9Z,12Z)-octadeca-9,12-dieneamidopropane-1,3-diyl dioctadeca-9,12-dienoate (0.8933 g, 0.983 mmol) obtained in Step 2 followed by stirring for 2 hours at room temperature. The reaction solution was concentrated under reduced pressure. The resulting residue was purified by aminosilica gel column chromatography (hexane/ethyl acetate=90/10 to 75/25) to obtain (9Z,9'Z, 12Z,12'Z)-2-((4-(dimethylamino)butanoyloxy)methyl)-2-(9Z,12Z)-octadeca-9,12-dieneamidopropane-1,3-diyl dioctadeca-9,12-dienoate (0.900 g, 0.881 mmol, yield: 90%).

ESI-MS m/z: 1022 (M+H)$^+$.

Step 4:

Methyl iodide (0.493 mL) was added to a chloroform solution (4 mL) of the (9Z,9'Z, 12Z,12'Z)-2-((4-(dimethylamino)butanoyloxy)methyl)-2-(9Z,12Z)-octadeca-9,12-dieneamidopropane-1,3-diyl dioctadeca-9,12-dienoate (0.805 g, 0.788 mmol) obtained in Step 3 followed by stirring overnight at room temperature. The reaction solution was concentrated under reduced pressure. The residue was dissolved in a small amount of methanol-chloroform (1:1), loaded onto an ion exchange resin (Dowex™ 1×-2 100 mesh, type CL, about 20 times volume, prewashed with water and methanol) and eluted with methanol-chloroform (1:1). The eluate was concentrated under reduced pressure and the resulting residue was purified by silica gel column chromatography (chloroform/methanol=90/10 to 80/20) to obtain the title compound (0.740 g, 0.690 mmol, yield: 88%).

ESI-MS m/z: 1036 (M)$^+$; $^1$H-NMR (CDCl$_3$) δ: 0.88 (t, J=6.4 Hz, 9H), 1.21-1.40 (m, 45H), 1.54-1.65 (m, 6H), 2.01-2.08 (m, 12H), 2.09-2.19 (m, 2H), 2.24 (t, J=7.4 Hz, 2H), 2.32 (t, J=7.5 Hz, 4H), 2.57 (t, J=6.2 Hz, 2H), 2.77 (t, J=6.3 Hz, 6H), 3.41 (s, 9H), 3.84 (t, J=8.3 Hz, 6H), 4.37-4.50 (m, 6H), 5.28-5.43 (m, 12H), 6.72 (brs, 1H).

Example 29

4-(1,3-bis((9Z,12Z)-octadeca-9,12-dienoyloxy)-2-(((9Z,12Z)-octadeca-9,12-dienoyloxy)methyl)propan-2-ylamino)-N,N,N-trimethyl-4-oxobutan-1-aminium Chloride (Compound II-22)

Step 1:

Tert-butyldimethylsilyl chloride (Sigma-Aldrich Corp., 9.43 g, 60.7 mmol) and imidazole (Nacalai Tesque Inc., 5.51 g, 80.9 mmol) were added to dichloromethane solution (60 mL) of 2-amino-2-(hydroxymethyl)-1,3-propanediol (Wako Pure Chemical Industries, Ltd., 7.41 g, 61.2 mmol) followed by stirring overnight at room temperature. Saturated salt solution was added to the reaction solution followed by extraction with chloroform. The organic layer was dried with anhydrous magnesium sulfate, filtered and concentrated under reduced pressure. The resulting residue was purified by aminosilica gel column chromatography (hexane/ethyl acetate=100/0 to 95/5) to obtain 6-((tert-butyldimethylsilyloxy)methyl)-2,2,3,3,9,9,10,10-octamethyl-4,8-dioxa-3,9-disilaundecan-6-amine (3.80 g, 8.19 mmol, yield: 40%).

ESI-MS m/z: 464 (M+H)$^+$.

Step 2:

4-(dimethylamino)butyric acid hydrochloride (Sigma-Aldrich Corp., 0.708 g, 4.14 mmol), 1-ethyl-3-(3-dimethylaminopropyl)carbodiimide hydrochloride (0.810 g, 4.14 mmol), N,N-dimethylaminopyridine (0.0170 g, 0.138 mmol) and N,N-diisopropylethylamine (1.45 mL, 8.31 mmol) were added to a dichloromethane solution (10 mL) of the 6-((tert-butyldimethylsilyloxy)methyl)-2,2,3,3,9,9,10,10-octamethyl-4,8-dioxa-3,9-disilaundecan-6-amine (1.28 g, 2.76 mmol) obtained in Step 1 followed by stirring overnight at room temperature. The reaction solution was concentrated under reduced pressure. The resulting residue was purified by aminosilica gel column chromatography (hexane/ethyl acetate=95/5 to 90/10) to obtain N-(6-((tert-butyldimethylsilyloxy)methyl)-2,2,3,3,9,9,10,10-octamethyl-4,8-dioxa-3,9-disilaundecan-6-yl)-4-(dimethylamino)butanamide (1.22 g, 2.11 mmol, yield: 76%).

ESI-MS m/z: 578 (M+H)$^+$.

Step 3:

Tetrabutylammonium fluoride (Tokyo Chemical Industry Co., Ltd., approx. 1 mol/L tetrahydrofuran solution, 7.49 mL, 7.49 mmol) was added to a tetrahydrofuran solution (10 mL) of the N-(6-((tert-butyldimethylsilyloxy)methyl)-2,2,3,3,9,9,10,10-octamethyl-4,8-dioxa-3,9-disilaundecan-6-yl)-4-(dimethylamino)butanamide (1.08 g, 1.87 mmol) obtained in Step 2 followed by stirring for 2 hours at room temperature. (9Z,12Z)-octadeca-9,12-dienoic acid (2.05 g, 7.31 mmol), 1-ethyl-3-(3-dimethylaminopropyl)carbodiimide hydrochloride (1.44 g, 7.51 mmol) and N,N-dimethylaminopyridine (0.0340 g, 0.278 mmol) were added to the reaction solution followed by stirring overnight at room temperature. The reaction solution was concentrated under reduced pressure. The resulting residue was purified by aminosilica gel column chromatography (hexane/ethyl acetate=60/40 to 50/50) to obtain (9Z,9'Z,12Z,12'Z)-2-(4-(dimethylamino)butanamido)-2-(((9Z,12Z)-octadeca-9,12-dienoyloxy)methyl)propane-1,3-diyl dioctadeca-9,12-dienoate (0.405 g, 0.396 mmol, yield: 21%).

ESI-MS m/z: 1022 (M+H)$^+$.

Step 4:

Methyl iodide (Tokyo Chemical Industry Co., Ltd., 0.200 mL) was added to a chloroform solution (3 mL) of the (9Z,9'Z,12Z,12'Z)-2-(4-(dimethylamino)butanamido)-2-(((9Z,12Z)-octadeca-9,12-dienoyloxy)methyl)propane-1,3-diyl dioctadeca-9,12-dienoate (0.335 g, 0.328 mmol) obtained in Step 3 followed by stirring for 2 hours at room temperature. The reaction solution was concentrated under reduced pressure. The residue was dissolved in a small amount of methanol-chloroform (1:1), loaded onto an ion exchange resin (Dowex™ 1×-2 100 mesh, type CL, about 20 times volume, prewashed with water and methanol) and eluted with methanol-chloroform (1:1). The eluate was concentrated under reduced pressure and the resulting residue was purified by silica gel column chromatography (chloroform/methanol=90/10 to 80/20) to obtain the title compound (0.324 g, 0.302 mol, yield: 92%).

ESI-MS m/z: 1036 (M)$^+$; $^1$H-NMR (CDCl$_3$) δ: 0.89 (t, J=7.0 Hz, 9H), 1.23-1.40 (m, 45H), 1.55-1.64 (m, 6H), 2.01-2.12 (m, 14H), 2.34 (t, J=7.6 Hz, 6H), 2.43 (t, J=6.3 Hz, 2H), 2.77 (t, J=6.6 Hz, 6H), 3.37 (s, 9H), 3.77-3.83 (m, 2H), 4.43 (s, 6H), 5.28-5.42 (m, 12H), 6.62 (br s, 1H).

Example 30

2-(1,3-bis((9Z,12Z)-octadeca-9,12-dienoyloxy)-2-(((9Z,12Z)-octadeca-9,12-dienoyloxy)methyl)propan-2-ylamino)-N,N,N-trimethyl-2-oxoethanaminium Chloride (Compound II-23)

The title compound (0.356 g, 0.341 mmol, yield: 17%) was obtained in the similar manner as Example 29 using N,N-dimethylglycine instead of 4-(dimethylamino)butyric acid hydrochloride.

ESI-MS m/z: 1008 (M)$^+$; $^1$H-NMR (CDCl$_3$) δ: 0.89 (t, J=7.0 Hz, 9H), 1.23-1.40 (m, 44H), 1.55-1.64 (m, 26H), 2.01-2.08 (m, 12H), 2.35 (t, J=7.6 Hz, 6H), 2.77 (t, J=6.8 Hz, 6H), 3.40 (s, 9H), 4.46 (s, 6H), 4.70 (s, 2H), 5.28-5.42 (m, 12H), 9.54 (brs, 1H).

Example 31

4-((6Z,9Z,29Z,32Z)-20-hydroxy-20-((9Z,12Z)-octadeca-9,12-dienyl)octatriaconta-6,9,29,32-tetraen-19-yloxy)-N,N,N-trimethyl-4-oxobutan-1-aminium Chloride (Compound III-1)

The title compound (0.146 g, 0.150 mmol, yield: 96%) was obtained in the similar manner as Step 2 of Example 1 using (6Z,9Z,29Z,32Z)-20-hydroxy-20-((9Z,12Z)-octadeca-9,12-dienyl)octatriaconta-6,9,29, 32-tetraen-19-yl 4-(dimethylamino)butanoate (0.144 g, 0.156 mmol) obtained using a method complying with the method described in U.S. Patent Application Publication No. 2012/0172411 (Specification).

ESI-MS m/z: 935 (M)$^+$; $^1$H-NMR (CDCl$_3$) δ: 0.89 (t, J=6.9 Hz, 9H), 1.16-1.79 (m, 60H), 1.98-2.17 (m, 15H), 2.52-2.59 (m, 2H), 2.77 (t, J=6.6 Hz, 6H), 3.44 (s, 9H), 3.69-3.81 (m, 2H), 4.94-4.98 (m, 1H), 5.29-5.42 (m, 12H).

Example 32

(6Z,9Z,28Z,31Z)—N,N-dimethyl-N-((9Z,12Z)-octadeca-9,12-dienyl)heptatriaconta-6,9,28,31-tetraen-19-aminium Chloride (Compound IV-1)

Step 1:

Methylamine (Tokyo Chemical Industry Co., Ltd., approx. 40% methanol solution, 0.110 mL, 1.1 mmol) and acetic acid (0.063 mL, 1.1 mmol) were added to a 1,2-dichloroethane solution (2 mL) of (6Z,9Z,28Z,31Z)-heptatriaconta-6,9,28,31-tetraen-19-one (0.194 g, 0.368 mmol) obtained using a method complying with the method described in WO 2010/042877. Sodium triacetoxyborohydride (0.117 g, 0.552 mmol) was further added followed by stirring for 2 hours at room temperature. Methylamine (approx. 40% methanol solution, 0.110 mL, 1.1 mmol), acetic acid (0.063 mL, 1.1 mmol) and sodium triacetoxyborohydride (0.117 g, 0.552 mmol) were added to the reaction solution followed by stirring for 2 hours. Saturated aqueous sodium bicarbonate solution was added to the reaction solution followed by extracting twice with hexane. The organic layers were combined, dried with anhydrous magnesium sulfate, filtered and concentrated under reduced pressure. The resulting residue was purified by column chromatography (chloroform/methanol=100/0 to 90/10) to obtain (6Z,9Z,28Z,31Z)—N-methylheptatriaconta-6,9,28, 31-tetraen-19-amine (0.121 g, 0.223 mmol, yield: 61%).

ESI-MS m/z: 543 (M+H)$^+$.

Step 2:

(9Z,12Z)-octadeca-9,12-dienyl methanesulfonate (0.154 g, 0.446 mmol) and 50% aqueous sodium hydroxide solution (0.107 g, 1.34 mmol) were added to the (6Z,9Z,28Z, 31Z)—N-methylheptatriaconta-6,9,28,31-tetraen-19-amine (0.121 g, 0.223 mmol) obtained in Step 1 followed by stirring for 2 hours at 135° C. in an oil bath. After allowing the reaction solution to cool to room temperature, saturated salt solution was added followed by washing with hexane. The organic layer was dried with anhydrous magnesium sulfate, filtered and concentrated under reduced pressure. The resulting residue was purified by silica gel column chromatography (hexane/ethyl acetate=100/0 to 85/15) to obtain (6Z,9Z,28Z,31Z)—N-methyl-N-((9Z,12Z)-octadeca-9,12-dienyl)heptatriaconta-6,9,28,31-tetraen-19-amine (0.139 g, 0.175 mmol, yield: 79%).

ESI-MS m/z: 792 (M+H)$^+$.

Step 3:

The title compound (0.114 g, 0.135 mmol, yield: 77%) was obtained in the similar manner as Step 2 of Example 1 using (6Z,9Z,28Z,31Z)—N-methyl-N-((9Z,12Z)-octadeca-9,12-dienyl)heptatriaconta-6,9,28,31-tetraen-19-amine (0.139 g, 0.175 mmol) obtained in Step 2.

ESI-MS m/z: 806 (M)$^+$; $^1$H-NMR (CDCl$_3$) δ: 0.89 (t, J=7.0 Hz, 9H), 1.26-1.56 (m, 54H), 1.65-1.73 (m, 2H), 1.80-1.88 (m, 2H), 2.05 (q, J=7.0 Hz, 12H), 2.77 (t, J=6.3 Hz, 6H), 3.22-3.27 (m, 1H), 3.31 (s, 6H), 3.58-3.62 (m, 2H), 5.29-5.42 (m, 12H).

Example 33

N,N,N-trimethyl-3-(palmitoyloxy)-2,2-bis((palmitoyloxy)methyl)propan-1-aminium Chloride (Compound II-24)

Step 1:

Pyridine (3.12 mL, 38.6 mmol) was added to a 1,2-dichloroethane solution (5 mL) of the 2-((dimethylamino)

methyl)-2-(hydroxymethyl)propane-1,3-diol (0.420 g, 2.57 mmol) obtained in Step 1 of Example 24 followed by adding palmitoyl chloride (Tokyo Chemical Industry Co., Ltd., 6.22 mL, 20.6 mmol) at room temperature and then stirring for 2 hours at 70° C. After allowing the reaction solution to cool to room temperature, water was added followed by extraction with ethyl acetate. The organic phase was washed with saturated salt solution, dried with anhydrous magnesium sulfate and filtered. After concentrating under reduced pressure, the resulting residue was purified by silica gel column chromatography (chloroform) to obtain 2-((dimethylamino)methyl)-2-((palmitoyloxy)methyl)propane-1,3-diyl dipalmitate (0.650 g, 0.740 mmol, yield: 29%).

ESI-MS m/z: 879 (M+H)$^+$.

Step 2:

The title compound (0.056 g, 0.060 mmol, yield: 8%) was obtained in the similar manner as Step 2 of Example 1 using 2-((dimethylamino)methyl)-2-((palmitoyloxy)methyl)propane-1,3-diyl dipalmitate (0.65 g, 0.74 mmol) obtained in Step 1.

ESI-MS m/z: 893 (M)$^+$; $^1$H-NMR (CDCl$_3$) δ: 0.88 (t, J=7.0 Hz, 9H), 1.21-1.34 (m, 72H), 1.54-1.64 (m, 6H), 2.38 (t, J=7.6 Hz, 6H), 3.62 (s, 9H), 3.95 (s, 2H), 4.29 (s, 6H).

Example 34

N,N,N-trimethyl-3-(tetradecanoyloxy)-2,2-bis((tetradecanoyloxy)methyl)propan-1-aminium Chloride (Compound II-25)

The title compound (0.045 g, 0.053 mmol, overall yield: 4%) was obtained in the similar manner as Example 33 using myristoyl chloride (Wake Pure Chemical Industries, Ltd.) instead of palmitoyl chloride.

ESI-MS m/z: 809 (M)$^+$; $^1$H-NMR (CDCl$_3$) δ: 0.88 (t, J=6.8 Hz, 9H), 1.21-1.34 (m, 60H), 1.54-1.64 (m, 6H), 2.38 (t, J=7.6 Hz, 6H), 3.64 (s, 9H), 3.96 (s, 2H), 4.29 (s, 6H).

Example 35

3-(dodecanoyloxy)-2,2-bis((dodecanoyloxy)methyl)-N,N,N-trimethylpropan-1-aminium Chloride (Compound II-26)

The title compound (0.085 g, 0.112 mmol, overall yield: 9%) was obtained in the similar manner as Example 33 using lauroyl chloride (Tokyo Chemical Industry Co., Ltd.) instead of palmitoyl chloride.

ESI-MS m/z: 725 (M)$^+$; $^1$H-NMR (CDCl$_3$) δ: 0.88 (t, J=6.8 Hz, 9H), 1.19-1.34 (m, 48H), 1.54-1.64 (m, 6H), 2.38 (t, J=7.6 Hz, 6H), 3.66 (s, 9H), 3.97 (s, 2H), 4.30 (s, 6H).

Example 36

(Z)—N,N,N-trimethyl-3,3-bis((oleoyloxy)methyl) henicos-12-en-1-aminium Chloride (Compound II-27)

Step 1:

Dimethyl malonate (1.00 g, 7.57 mmol) was dissolved in acetonitrile (25 mL) followed by the addition of (Z)-oct-9-en-1-yl methanesulfonate (3.15 g, 9.08 mmol), cesium carbonate (4.93 g, 15.1 mmol) and tetrabutylammonium iodide (3.35 g, 9.08 mmol) and stirring for 1 hour at 60° C. Water was added to the reaction solution followed by extraction with hexane. The organic layer was washed with saturated salt solution, dried with anhydrous magnesium sulfate, filtered and concentrated under reduced pressure. The resulting residue was purified by silica gel column chromatography (hexane/ethyl acetate=90/10 to 70/30) to obtain (Z)-dimethyl-2-(octadec-9-en-1-yl) malonate (2.54 g, 6.64 mmol, yield: 88%).

ESI-MS m/z: 383 (M+H)$^+$.

Step 2:

The (Z)-dimethyl-2-(octadec-9-en-1-yl) malonate (0.500 g, 1.31 mmol) obtained in Step 1 was dissolved in toluene (6 mL) followed by the addition of sodium hydride (oily, 60%, 0.209 g, 5.23 mmol) while cooling with ice and stirring until foaming subsided. Next, 2-chloro-N,N-dimethylethanamine hydrochloride (Tokyo Chemical Industry, Co., Ltd., 0.377 g, 2.61 mmol) was added followed by stirring for 2 hours at 100° C. Water was added to the reaction solution while cooling with ice followed by extraction with chloroform. The organic layer was washed with saturated salt solution, dried with anhydrous magnesium sulfate, filtered and concentrated under reduced pressure. The resulting residue was purified by silica gel column chromatography (chloroform/methanol=99/1 to 90/10) to obtain (Z)-dimethyl 2-(2-(dimethylamino)ethyl)-2-(octadec-9-en-1-yl) malonate (0.258 g, 0.569 mmol, yield: 44%).

ESI-MS m/z: 454 (M+H)$^+$.

Step 3:

(Z)-2-(2-(dimethylamino)ethyl)-2-(octadec-9-en-1-yl) propane-1,3-diol (0.220 g, 0.553 mmol, quantitative) was obtained in the similar manner as Step 2 of Example 19 using (Z)-dimethyl 2-(2-(dimethylamino)ethyl)-2-(octadec-9-en-1-yl) malonate (0.250 g, 0.551 mmol) obtained in Step 2.

ESI-MS m/z: 398 (M+H)$^+$.

Step 4:

The (Z)-2-(2-(dimethylamino)ethyl)-2-(octadec-9-en-1-yl)propane-1,3-diol (0.220 g, 0.553 mmol) obtained in Step 3 was dissolved in dichloromethane (2 mL) followed by the addition of N,N-diisopropylethylamine (0.386 mL, 2.21 mmol) and then oleoyl chloride (Sigma-Aldrich Corp., 0.457 mL, 1.38 mmol) while cooling with ice and stirring for 10 minutes at room temperature. Water was added to the reaction solution followed by extraction with hexane. The organic phase was washed with saturated salt solution, dried with anhydrous magnesium sulfate, filtered and concentrated under reduced pressure. The resulting residue was purified by silica gel column chromatography (hexane/ethyl acetate=90/10 to 50/50) to obtain (Z)-2-(2-(dimethylamino) ethyl)-2-((Z)-octadec-9-en-1-yl)propane-1,3-diyl dioleate (0.280 g, 0.302 mmol, yield: 55%).

ESI-MS m/z: 927 (M+H)$^+$.

Step 5:

The title compound (0.199 g, 0.204 mmol, yield: 67%) was obtained in the similar manner as Step 2 of Example 1 using (Z)-2-(2-(dimethylamino)ethyl)-2-((Z)-octadec-9-en-1-yl)propane-1,3-diyl dioleate (0.280 g, 0.302 mmol) obtained in Step 4.

ESI-MS m/z: 941 (M)$^+$; $^1$H-NMR (CDCl$_3$) δ: 0.88 (t, J=7.0 Hz, 9H), 1.22-1.39 (m, 66H), 1.55-1.65 (m, 4H), 1.70-1.78 (m, 2H), 1.98-2.06 (m, 12H), 2.33 (t, J=7.6 Hz, 4H), 3.46 (s, 9H), 3.58-3.65 (m, 2H), 3.93-4.03 (m, 4H), 5.29-5.39 (m, 6H).

Example 37

(Z)—N,N,N-trimethyl-4,4-bis((oleoyloxy)methyl) docos-13-en-1-aminium Chloride (Compound II-28)

Step 1:

(Z)-dimethyl 2-(3-(dimethylamino)propyl)-2-(octadec-9-en-1-yl) malonate (0.210 g, 0.449 mmol, yield: 34%) was obtained in the similar manner as Step 2 of Example 36 using 3-chloro-N,N-dimethylpropan-1-amine hydrochloride (Tokyo Chemical Industry Co., Ltd.) instead of 2-chloro-N,N-dimethylethanamine hydrochloride.

ESI-MS m/z: 468 (M+H)$^+$.

Step 2:

The title compound (0.042 g, 0.042 mmol, overall yield: 9%) was obtained in the similar manner as Steps 3, 4 and 5 of Example 36 using (Z)-dimethyl 2-(3-(dimethylamino)propyl)-2-(octadec-9-en-1-yl) malonate (0.210 g, 0.449 mmol) obtained in Step 1 instead of (Z)-dimethyl 2-(2-(dimethylamino)ethyl)-2-(octadec-9-en-1-yl) malonate.

ESI-MS m/z: 955 (M)$^+$; $^1$H-NMR (CDCl$_3$) δ: 0.88 (t, J=6.8 Hz, 9H), 1.22-1.36 (m, 68H), 1.56-1.64 (m, 4H), 1.72-1.82 (m, 2H), 1.96-2.07 (m, 12H), 2.32 (t, J=7.5 Hz, 4H), 3.38 (s, 9H), 3.39-3.46 (m, 2H), 3.93 (d, J=11.2 Hz, 2H), 3.99 (d, J=11.2 Hz, 2H), 5.28-5.40 (m, 6H).

Example 38

N,N,N-trimethyl-3-(stearoyloxy)-2,2-bis((stearoyloxy)methyl)propan-1-aminium Chloride (Compound II-29)

The title compound (0.085 g, 0.112 mmol, overall yield: 6%) was obtained in the similar manner as Example 33 using stearoyl chloride (Tokyo Chemical Industry Co., Ltd.) instead of palmitoyl chloride.

ESI-MS m/z: 977 (M)$^+$; $^1$H-NMR (CDCl$_3$) δ: 0.88 (t, J=6.8 Hz, 9H), 1.21-1.37 (m, 84H), 1.54-1.64 (m, 6H), 2.38 (t, J=7.6 Hz, 6H), 3.65 (s, 9H), 3.96 (s, 2H), 4.30 (s, 6H).

Example 39

N,N,N-trimethyl-3-oleamido-2,2-bis((oleoyloxy) methyl)propan-1-aminium Chloride (Compound II-30)

Step 1:

The 2-((dimethylamino)methyl)-2-(hydroxymethyl)propane-1,3-diol (0.410 g, 2.51 mmol) obtained in Step 1 of Example 24 was dissolved in a mixed solvent of dichloromethane (5 mL) and pyridine (5.08 mL, 62.8 mmol). Oleoyl chloride (1.25 mL, 3.77 mmol) was added while cooling with ice. Water was added to the reaction solution followed by extraction with chloroform. The organic layer was washed with saturated salt solution, dried with anhydrous magnesium sulfate and filtered. After concentrating under reduced pressure, the resulting filtrate was purified by silica gel column chromatography (chloroform/methanol=99/1 to 90/10) to obtain (Z)-2-((dimethylamino)methyl)-2-(hydroxymethyl)propane-1,3-diyl dioleate (0.190 g, 0.275 mmol, yield: 11%).

ESI-MS m/z: 693 (M+H)$^+$.

Step 2:

The (Z)-2-((dimethylamino)methyl)-2-(hydroxymethyl)propane-1,3-diyl dioleate (0.190 g, 2.51 mmol) obtained in Step 1 was dissolved in toluene (2 mL) followed by the addition of diphenylphosphoryl azide (Tokyo Chemical Industry Co., Ltd., 0.118 mL, 0.549 mmol) and 1,8-diazabicyclo[5.4.0]-7-undecene (0.0830 mL, 0.549 mmol) at room temperature and stirring for 1 hour. Since the reaction did not proceed adequately, diphenylphosphoryl azide (0.118 mL, 0.549 mmol) was added followed by stirring for 3 hours while heating at 80° C. After allowing the reaction solution to cool to room temperature, water was added followed by extraction with ethyl acetate. The organic layer was washed with saturated salt solution, dried with anhydrous magnesium sulfate and filtered. After concentrating under reduced pressure, the resulting residue was purified by silica gel column chromatography (hexane/ethyl acetate=95/5 to 60/40) to obtain (Z)-2-(azidomethyl)-2-((dimethylamino)methyl)propane-1,3-diyl dioleate (0.135 g, 0.188 mmol, yield: 69%).

ESI-MS m/z: 718 (M+H)$^+$.

Step 3:

The (Z)-2-(azidomethyl)-2-((dimethylamino)methyl)propane-1,3-diyl dioleate (0.135 g, 2.51 mmol) obtained in Step 2 was dissolved in a mixed solvent of tetrahydrofuran (1 mL) and water (0.1 mL) followed by the addition of triphenylphosphine (Junsei Chemical Co., Ltd., 0.0740 g, 0.282 mmol) and stirring for 3 hours. Water was added to the reaction solution followed by extraction with ethyl acetate. The organic layer was washed with saturated salt solution, dried with anhydrous magnesium sulfate and filtered. As a result of concentrating under reduced pressure, a crude product was obtained in the form of (Z)-2-(aminoethyl)-2-((dimethylamino)methyl)propane-1,3-diyl dioleate (0.130 g, 0.188 mmol, yield: 100%).

ESI-MS m/z: 691 (M+H)$^+$.

Step 4:

N,N-diisopropylethylamine (0.0990 mL, 0.564 mmol) was added to a dichloromethane solution (2 mL) of the (Z)-2-(aminoethyl)-2-((dimethylamino)methyl)propane-1,3-diyl dioleate (0.130 g, 0.188 mmol) obtained in Step 3 followed by the addition of oleoyl chloride while cooling with ice and stirring for 1 hour at room temperature. Water was added to the reaction solution followed by extraction with hexane. The organic layer was washed with saturated salt solution, dried with anhydrous magnesium sulfate and filtered. After concentrating under reduced pressure, and the resulting residue was purified by silica gel column chromatography (hexane/ethyl acetate=97/3 to 60/40) to obtain (Z)-2-((dimethylamino)methyl)-2-(oleamidomethyl)propane-1,3-diyl dioleate (0.105 g, 0.110 mmol, yield: 58%).

ESI-MS m/z: 956 (M+H)$^+$.

Step 5:

The title compound (0.0480 g, 0.0480 mmol, yield: 43%) was obtained in the similar manner as Step 2 of Example 1 using (Z)-2-((dimethylamino)methyl)-2-(oleamidomethyl) propane-1,3-diyl dioleate (0.105 g, 0.110 mmol) obtained in Step 4.

ESI-MS m/z: 970 (M)$^+$; $^1$H-NMR (CDCl$_3$) δ: 0.88 (t, J=6.8 Hz, 9H), 1.21-1.37 (m, 60H), 1.56-1.65 (m, 6H), 1.96-2.05 (m, 12H), 2.36 (t, J=7.6 Hz, 6H), 3.51 (s, 9H), 3.51-3.56 (m, 2H), 4.02 (s, 2H), 4.20 (d, J=12.2 Hz, 2H), 4.30 (d, J=12.2 Hz, 2H), 5.27-5.40 (m, 6H), 8.11-8.20 (m, 1H).

Example 40

N,N,N-trimethyl-4-(oleoyloxy)-3,3-bis(oleoyloxymethyl)butan-1-aminium Chloride (Compound II-31)

Step 1:

Tert-butyldimethylchlorosilane (Tokyo Chemical Industry Co., Ltd., 3.79 g, 25.1 mmol), imidazole (Nacalai Tesque Inc., 3.42 g, 50.2 mmol) and N,N-dimethylaminopyridine (0.061 g, 0.502 mmol) were added to a tetrahydrofuran solution (10 mL) of 2-(bromomethyl)-2-(hydroxymethyl)propane-1,3-diol (Tokyo Chemical Industry Co., Ltd., 1.00 g, 5.02 mmol) followed by stirring overnight at room temperature. Saturated aqueous sodium bicarbonate solution was added to the reaction solution followed by extracting twice with hexane. The organic layers were dried with anhydrous magnesium sulfate followed by concentrating under reduced pressure. The resulting residue was purified by silica gel column chromatography (hexane) to obtain 6-(bromomethyl)-6-((tert-butyldimethylsilyloxy)methyl)-2,2,3,3,9,9,10,10-octamethyl-4,8-dioxa-3,9-disilaundecane (2.50 g, 4.61 mmol, yield: 92%).

$^1$H-NMR (CDCl$_3$) δ: 0.04 (s, 18H), 0.89 (s, 27H), 3.41 (s, 2H), 3.49 (s, 6H).

Step 2:

Sodium cyanide (Nacalai Tesque Inc., 0.529 g, 10.8 mmol) was added to a dimethylsulfoxide solution (10 mL) of the 6-(bromomethyl)-6-((tert-butyldimethylsilyloxy)methyl)-2,2,3,3,9,9,10,10-octamethyl-4,8-dioxa-3,9-disilaundecane (1.849 g, 3.41 mmol) obtained in Step 1 followed by stirring for 3 days at 85° C. After allowing to cool to room temperature, the reaction solution was diluted with hexane, washed with water and then saturated salt solution, dried with anhydrous magnesium sulfate, filtered and concentrated under reduced pressure. The resulting residue was purified by silica gel column chromatography (hexane/ethyl acetate=90/10) to obtain 4-(tert-butyldimethylsilyloxy)-3,3-bis((tert-butyldimethylsilyloxy)methyl)butanenitrile (1.35 g, 2.77 mmol, yield: 81%).

ESI-MS m/z: 489 (M+H)$^+$; $^1$H-NMR (CDCl$_3$) δ: 0.05 (s, 18H), 0.89 (s, 27H), 2.34 (s, 2H), 3.51 (s, 6H).

Step 3:

Lithium aluminum hydride (0.104 g, 2.75 mmol) was added to a tetrahydrofuran solution (10 mL) of the 4-(tert-butyldimethylsilyloxy)-3,3-bis((tert-butyldimethylsilyloxy)methyl)butanenitrile (1.34 g, 2.75 mmol) obtained in Step 2 while cooling with ice followed by stirring for 2 hours at room temperature. Water (0.495 mL, 27.5 mmol) and sodium fluoride (3.46 g, 82.0 mmol) were added to the reaction solution followed by stirring overnight at room temperature. Impurities were removed by celite filtration followed by concentrating the filtrate. The resulting residue was purified by aminosilica gel column chromatography (ethyl acetate) to obtain 4-(tert-butyldimethylsilyloxy)-3,3-bis((tert-butyldimethylsilyloxy)methyl)butan-1-amine (0.435 g, 0.884 mmol, yield: 32%).

ESI-MS m/z: 493 (M+H)$^+$; $^1$H-NMR (CDCl$_3$) δ: 0.02 (s, 18H), 0.88 (s, 27H), 1.38-1.43 (m, 2H), 2.71-2.75 (m, 2H), 3.40 (s, 6H).

Step 4:

38% aqueous formaldehyde solution (0.295 mL) and sodium triacetoxyborohydride (0.431 g, 2.03 mmol) were added to a 1,2-dichloroethane solution (3 mL) of the 4-(tert-butyldimethylsilyloxy)-3,3-bis((tert-butyldimethylsilyloxy)methyl)butan-1-amine (0.200 g, 0.407 mmol) obtained in Step 3 followed by stirring overnight at room temperature. Saturated aqueous sodium bicarbonate solution was added to the reaction solution followed by extracting twice with chloroform. The organic layers were dried with anhydrous magnesium sulfate followed by concentrating under reduced pressure. The residue was purified by silica gel column chromatography (chloroform/methanol=90/10) to obtain a crude product of 4-(tert-butyldimethylsilyloxy)-3,3-bis(tert-butyldimethylsilyloxy)methyl)-N,N-dimethylbutan-1-amine.

Tetrahydrofuran (2 mL) and tetrabutylammonium fluoride (Tokyo Chemical Industry Co., Ltd., approx. 1 mol/L tetrahydrofuran solution, 2.06 mL, 2.06 mmol) were added to the resulting crude product and stirred for 5 hours at room temperature followed by stirring overnight at 60° C. Saturated aqueous sodium bicarbonate solution was added to the reaction solution followed by extracting twice with chloroform. The aqueous layer was concentrated under reduced pressure. Acetone (2 mL), sodium hydroxide (Wake Pure Chemical Industries, Ltd., 2 mol/L aqueous solution, 3 mL, 6 mmol) and oleoyl chloride (0.681 mL, 2.06 mmol) were added to the resulting residue followed by stirring for 3 hours at room temperature. Oleoyl chloride (0.681 mL, 2.06 mmol) was added to the reaction solution followed by stirring overnight at 60° C. After allowing to cool to room temperature, water was added to the reaction solution followed by extracting twice with chloroform. The organic layers were dried with anhydrous magnesium sulfate followed by filtering and concentrating under reduced pressure. The resulting residue was purified by silica gel column chromatography (chloroform/methanol=90/10) to obtain a crude product of (Z)-2-(2-(dimethylamino)ethyl)-2-(oleyloxymethyl)propane-1,3-diyl dioleate. A small amount of the resulting crude product was dissolved in methanol-chloroform (9:1), loaded onto an ion exchange resin (Waters Corp., PoraPack Rxn CX, prewashed with methanol) and eluted with ammonia (Sigma-Aldrich Corp., 2 mol/L methanol solution). The eluate was concentrated under reduced pressure to obtain (Z)-2-(2-(dimethylamino)ethyl)-2-(oleyloxymethyl)propane-1,3-diyl oleate (0.387 g, 0.399 mmol, yield: 98%).

ESI-MS m/z: 971 (M+H)$^+$; $^1$H-NMR (CDCl$_3$) δ: 0.88 (t, J=7.0 Hz, 9H), 1.21-1.38 (m, 62H), 1.54-1.65 (m, 6H), 1.97-2.04 (m, 12H), 2.20 (s, 6H), 2.25-2.32 (m, 8H), 4.04 (s, 6H), 5.29-5.39 (m, 6H).

Step 5:

The title compound (0.0642 g, 0.0630 mmol, yield: 56%) was obtained in the similar manner as Step 2 of Example 1 using (Z)-2-(2-(dimethylamino)ethyl)-2-(oleyloxymethyl)propane-1,3-diyl oleate (0.109 g, 0.112 mmol) obtained in Step 4 instead of 2,2',2''-nitrilotris(ethane-2,1-diyl)trioleate.

ESI-MS m/z: 986 (M)$^+$; $^1$H-NMR (CDCl$_3$) δ: 0.88 (t, J=6.8 Hz, 9H), 1.23-1.37 (m, 74H), 1.55-1.64 (m, 65H), 1.78-1.84 (m, 2H), 1.95-2.06 (m, 13H), 2.35 (t, J=7.6 Hz, 6H), 3.42 (s, 8H), 3.70-3.77 (m, 2H), 4.08 (s, 6H), 5.29-5.39 (m, 6H).

Example 41

N,N,N-trimethyl-2-(3-(oleoyloxy)-2,2-bis((oleoyloxy)methyl)propoxy)-2-oxyethan-1-aminium Chloride (Compound II-32)

Step 1:

Triethylamine (0.475 mL, 3.40 mmol) was added to a tetrahydrofuran solution (5 mL) of 2,2-(dimethyl-1,3-dioxane-5,5-diyl)dimethanol (0.200 g, 1.14 mmol) synthesized according to the method described in U.S. Pat. No. 8,816,099 (Specification) followed by the addition of oleoyl chloride (0.854 g, 2.84 mmol) while cooling with ice and then stirring for 1 hour while still cooling with ice. Water was added to the reaction solution followed by extraction with hexane. The organic layer was washed with saturated salt solution, dried with anhydrous magnesium sulfate and filtered. After concentrating under reduced pressure, the resulting residue was purified by silica gel column chromatography (hexane/ethyl acetate=95/5) to obtain (2,2-dimethyl-1,3-dioxane-5,5-diyl)bis(methylene) dioleate (0.500 g, 0.709 mmol, yield: 63%).

ESI-MS m/z: 705 (M+H)$^+$.

Step 2:

Trifluoroacetic acid (2.00 mL, 26.0 mmol) was added in two parts to a dichloromethane solution (5 mL) of the (2,2-dimethyl-1,3-dioxane-5,5-diyl)bis(methylene) dioleate (0.500 g, 0.709 mmol) obtained in Step 1 while cooling with ice followed by stirring for 1 hour while still cooling with ice. Saturated aqueous sodium bicarbonate solution was added to the reaction solution followed by extraction with ethyl acetate. The organic layer was washed with saturated salt solution, dried with anhydrous magnesium sulfate and filtered. The resulting residue was purified by silica gel column chromatography (hexane/ethyl acetate=90/10 to 50/50) to obtain 2,2-bis(hydroxymethyl)propane-1,3-diyl dioleate (0.207 g, 0.311 mmol, yield: 44%).

ESI-MS m/z: 665 (M+H)$^+$.

Step 3:

Thionyl chloride (1 mL, 13.7 mmol) was added to N,N-dimethylglycine (Tokyo Chemical Industry Co., Ltd., 0.049 g, 0.474 mmol) followed by stirring for 30 minutes at 70° C. After allowing the reaction solution to cool to room temperature, the reaction solution was concentrated under reduced pressure to obtain a crude product of N,N-dimethylglycinoyl chloride. N,N-diisopropylethylamine (0.110 mL, 0.632 mmol) and the above-mentioned crude product in the form of N,N-dimethylglycinoyl chloride were added to a dichloromethane solution (5 mL) of the 2,2-bis(hydroxymethyl)propane-1,3-diyl dioleate (0.207 g, 0.311 mmol) obtained in Step 2 while cooling with ice followed by stirring for 1 hour at room temperature. Water was added to the reaction solution followed by extraction with ethyl acetate. The organic layer was washed with saturated salt solution, washed with anhydrous magnesium sulfate and filtered. The resulting residue was purified by silica gel column chromatography (hexane/ethyl acetate=90/10 to 40/60) to obtain 2-(((dimethylglycyl)oxy)methyl)-2-(hydroxymethyl)propane-1,3-diyl dioleate (0.077 g, 0.103 mmol, yield: 33%).

ESI-MS m/z: 751 (M+H)$^+$.

Step 4:

After adding pyridine (0.0330 mL, 0.411 mmol) to a dichloromethane solution (3 mL) of the 2-(((dimethylglycyl)oxy)methyl)-2-(hydroxymethyl)propane-1,3-diyl dioleate (0.0770 g, 0.103 mmol) obtained in Step 3, oleoyl chloride (0.0620 g, 0.205 mmol) was added while cooling with ice followed by stirring for 30 minutes at room temperature. Water was added to the reaction solution followed by extraction with a mixed solvent of hexane and ethyl acetate (1/1). The organic layer was washed with saturated salt solution, dried with anhydrous magnesium sulfate and filtered. The resulting residue was purified by silica gel column chromatography (hexane/ethyl acetate=95/5) to obtain 2-(((dimethylglycyl)oxy)methyl)-2-((oleoyl)methyl)propane-1,3-diyl dioleate (0.122 g, 0.0600 mmol, yield: 59%).

ESI-MS m/z: 1015 (M+H)$^+$.

Step 5:

The title compound (0.017 g, 0.016 mmol, yield: 27%) was obtained in the similar manner as Step 2 of Example 1 using 2-(((dimethylglycyl)oxy)methyl)-2-((oleoyl)methyl)propane-1,3-diyl dioleate (0.122 g, 0.060 mmol) obtained in Step 4.

ESI-MS m/z: 1029 (M)$^+$; $^1$H-NMR (CDCl$_3$) δ: 0.88 (t, J=6.8 Hz, 9H), 1.19-1.38 (m, 58H), 1.54-1.66 (m, 6H), 1.98-2.04 (m, 12H), 2.28-2.35 (m, 6H), 3.60 (s, 9H), 4.11 (d, J=1.8 Hz, 6H), 4.20 (s, 2H), 5.08 (s, 2H), 5.29-5.41 (m, 6H).

Example 42

N,N,N-trimethy-1,3-bis(tetradecanoyloxy)-2-((tetradecanoyloxy)methyl)propan-2-aminium Chloride (Compound II-33)

Step 1:

Pyridine (4.07 mL, 50.3 mmol) and then tetradecanoyl chloride (4.09 mL, 15.1 mmol) were added to a tetrahydrofuran solution (10 mL) of 2-(dimethylamino)-2-(hydroxymethyl)propane-1,3-diol (1.50 g, 10.1 mmol) followed by stirring for 2 hours while heating at 60° C. Water was added to the reaction solution followed by extraction with ethyl acetate. The organic layer was washed with saturated salt solution, dried with anhydrous magnesium sulfate and filtered. After concentrating under reduced pressure, the resulting residue was purified by silica gel column chromatography (chloroform/methanol=99/1 to 90/10) to obtain 2-(dimethylamino)-2-((tetradecanoyloxy)methyl)propane-1,3-diyl ditetradecanoate (1.50 g, 1.92 mmol, yield: 19%), 2-(dimethylamino)-2-(hydroxymethyl)propane-1,3-diyl ditetradecanoate (0.750 g, 1.32 mmol, yield: 13%) and 2-(dimethylamino)-3-hydroxy-2-(hydroxymethyl)propyl tetradecanoate (0.220 g, 0.612 mmol, yield: 6%).

ESI-MS m/z: 781 (M+H)$^+$
ESI-MS m/z: 570 (M+H)$^+$
ESI-MS m/z: 360 (M+H)$^+$

Step 2:

The title compound (0.530 g, 0.638 mmol, yield: 33%) was obtained in the similar manner as Step 2 of Example 1 using 2-(dimethylamino)-2-((tetradecanoyloxy)methyl)propane-1,3-diyl ditetradecanoate (1.50 g, 1.92 mmol) obtained in Step 1.

ESI-MS m/z: 795 (M)$^+$; $^1$H-NMR (CDCl$_3$) δ: 0.88 (t, J=6.8 Hz, 9H), 1.21-1.33 (m, 60H), 1.55-1.65 (m, 6H), 2.37 (t, J=7.6 Hz, 6H), 3.71 (s, 9H), 4.59 (s, 6H).

Example 43

N,N,N-trimethyl-1,3-bis(oleoyloxy)-2-((tetradecanoyloxy)methyl)propan-2-aminium Chloride (Compound II-34)

Step 1:

Pyridine (0.297 mL, 3.67 mmol) and then oleoyl chloride (0.552 g, 1.84 mmol) were added to a 1,2-dichloroethane solution (3 mL) of the 2-(dimethylamino)-3-hydroxy-2-(hydroxymethyl)propyl tetradecanoate (0.220 g, 0.612 mmol) obtained in Step 1 of Example 42 followed by stirring for 1 hour while heating at 60° C. Water was added to the reaction solution followed by extraction with ethyl acetate. The organic layer was washed with saturated salt solution, dried with anhydrous magnesium sulfate and filtered. The resulting residue was purified by silica gel column chromatography (hexane/ethyl acetate=98/2 to 85/15) to obtain 2-(dimethylamino)-2-((tetradecanoyloxy)methyl)propane-1,3-diyl dioleate (0.250 g, 0.281 mmol, yield: 46%).

ESI-MS m/z: 889 (M+H)+.

Step 2:

The title compound (0.065 g, 0.069 mmol, yield: 25%) was obtained in the similar manner as Step 2 of Example 1 using 2-(dimethylamino)-2-((tetradecanoyloxy)methyl)propane-1,3-diyl dioleate (0.250 g, 0.281 mmol) obtained in Step 1.

ESI-MS m/z: 903 (M)+; $^1$H-NMR (CDCl$_3$) δ: 0.88 (t, J=7.0 Hz, 9H), 1.22-1.38 (m, 60H), 1.56-1.66 (m, 6H), 1.97-2.05 (m, 8H), 2.39 (t, J=7.6 Hz, 6H), 3.72 (s, 9H), 4.58 (s, 6H), 5.28-5.40 (m, 4H).

Example 44

N,N,N-trimethyl-1-(oleyloxy)-3-(tetradecanoyloxy)-2-((tetradecanoyloxy)methyl) propan-2-aminium Chloride (Compound II-35)

Step 1:

Pyridine (0.532 mL, 6.58 mmol) and then oleoyl chloride (0.792 g, 1.84 mmol) were added to a 1,2-dichloroethane solution (3 mL) of the 2-(dimethylamino)-2-(hydroxymethyl)propane-1,3-diyl ditetradecanoate (0.750 g, 1.32 mmol) obtained in Step 1 of Example 42 followed by stirring for 1 hour while heating at 60° C. Water was added to the reaction solution followed by extraction with ethyl acetate. The organic layer was washed with saturated salt solution, dried with anhydrous magnesium sulfate and filtered. The resulting residue was purified by silica gel column chromatography (hexane/ethyl acetate=95/5) to obtain 2-(dimethylamino)-2((oleyloxy)methyl)propane-1,3-diyl ditetradecanoate (0.750 g, 0.899 mmol, yield: 68%).

ESI-MS m/z: 835 (M+H)+.

Step 2:

The title compound (0.092 g, 0.104 mmol, yield: 12%) was obtained in the similar manner as Step 2 of Example 1 using 2-(dimethylamino)-2((oleyloxy)methyl)propane-1,3-diyl ditetradecanoate (0.750 g, 0.899 mmol) obtained in Step 1.

ESI-MS m/z: 849 (M)+; $^1$H-NMR (CDCl$_3$) δ: 0.88 (t, J=6.8 Hz, 9H), 1.19-1.38 (m, 60H), 1.56-1.65 (m, 6H), 1.98-2.06 (m, 4H), 2.39 (t, J=7.6 Hz, 6H), 3.72 (s, 9H), 4.59 (s, 6H), 5.30-5.39 (m, 2H).

Example 45

N,N,N-trimethyl-3-(tetradecanoyloxy)-2-((tetradecanoyloxy)methyl)-2-(((tetradecylcarbamoyl)oxy) methyl)propan-1-aminium Chloride (Compound II-36)

Step 1:

Pyridine (2.03 mL, 38.6 mmol) was added to a tetrahydrofuran solution (7 mL) of the 2-((dimethylamino)methyl)-2-(hydroxymethyl)propane-1,3-diol (0.820 g, 5.02 mmol) obtained in Step 1 of Example 24 followed by the addition of tetradecanoyl chloride (0.930 mL, 3.77 mmol) while cooling with ice and stirring for 2 hours at 60° C. After allowing the reaction solution to cool to room temperature, water was added followed by extraction with ethyl acetate. The organic layer was washed with saturated salt solution, dried with anhydrous magnesium sulfate and filtered. After concentrating under reduced pressure, the resulting residue was purified by silica gel column chromatography (hexane/ethyl acetate=95/5 to 70/30) to obtain 2-((dimethylamino) methyl)-2-(hydroxymethyl)propane-1,3-diyl ditetradecanoate (0.150 g, 0.257 mmol, yield: 5%).

ESI-MS m/z: 584 (M+H)+.

Step 2:

Triethylamine (0.017 mL, 0.123 mmol) was added to a dichloromethane solution (3 mL) of the 2-((dimethylamino) methyl)-2-(hydroxymethyl)propane-1,3-diyl ditetradecanoate (0.060 g, 0.103 mmol) obtained in Step 1 followed by the addition of 4-nitrophenylchloroformate (Tokyo Chemical Industry Co., Ltd., 0.025 g, 0.123 mmol) and then tetradecylamine (Tokyo Chemical Industry Co., Ltd., 0.022 g, 0.103 mmol) while cooling with ice and stirring overnight at room temperature. Water was added to the reaction solution followed by extraction with ethyl acetate. The organic layer was washed with saturated salt solution, dried with anhydrous magnesium sulfate and filtered. The resulting residue was purified by silica gel column chromatography (hexane/ethyl acetate=95/5 to 70/30) to obtain 2-((dimethylamino) methyl)-2-((((tetradecylcarbamoyl)oxy)methyl)propane-1,3-diyl ditetradecanoate (0.052 g, 0.063 mmol, yield: 62%).

ESI-MS m/z: 824 (M+H)+.

Step 3:

The title compound (0.012 g, 0.014 mmol, yield: 21%) was obtained in the similar manner as Step 2 of Example 1 using 2-((dimethylamino)methyl)-2-(((tetradecylcarbamoyl)oxy)methyl)propane-1,3-diyl ditetradecanoate (0.052 g, 0.063 mmol) obtained in Step 2.

ESI-MS m/z: 838 (M)+; $^1$H-NMR (CDCl$_3$) δ: 0.88 (t, J=7.0 Hz, 9H), 1.22-1.33 (m, 62H), 1.51-1.61 (m, 6H), 2.38 (t, J=7.6 Hz, 4H), 3.13 (dd, J=14.2, 5.8 Hz, 2H), 3.59 (s, 9H), 4.12 (s, 2H), 4.19 (s, 2H), 4.21 (d, J=12.0 Hz, 2H), 4.25 (d, J=12.0 Hz, 2H), 6.72 (t, J=5.8 Hz, 1H).

Example 46

N,N,N-trimethyl-3-((octadecylcarbamoyl)oxy)-2,2-bis((tetradecanoyloxy)methyl) propan-1-aminium Chloride (Compound II-37)

Step 1:

The title compound (0.015 g, 0.016 mmol, overall yield: 0.5%) was obtained in the similar manner as Example 45 using stearylamine (Tokyo Chemical Industry Co., Ltd.) instead of tetradecylamine.

ESI-MS m/z: 894 (M)+; $^1$H-NMR (CDCl$_3$) δ: 0.88 (t, J=6.8 Hz, 9H), 1.21-1.34 (m, 70H), 1.51-1.62 (m, 6H), 2.38 (t, J=7.6 Hz, 4H), 3.13 (dd, J=14.3, 5.8 Hz, 2H), 3.60 (s, 9H), 4.12 (s, 2H), 4.19 (s, 2H), 4.21 (d, J=12.2 Hz, 2H), 4.25 (d, J=12.2 Hz, 2H), 6.69 (t, J=5.8 Hz, 1H).

Example 47

N,N,N-trimethyl-3-(stearoyloxy)-2,2-bis((tetradecanoyloxy)methyl)propan-1-aminium Chloride (Compound II-37)

Step 1:

Stearoyl chloride (2.53 g, 8.36 mmol) was added to a pyridine solution (10 mL) of (5-(bromomethyl)-2,2-dimethyl-1,3-dioxan-5-yl) methanol (1.00 g, 4.18 mmol), synthesized according to the method described in Angewandte Chemie International Edition, 2009, Vol. 48, pp. 2126-2130, followed by stirring for 30 minutes at room temperature. Water was added to the reaction solution followed by extraction with ethyl acetate. The organic layer was washed with saturated salt solution, dried with anhydrous magnesium sulfate and filtered. The resulting residue was purified by silica gel column chromatography (hexane/ethyl acetate=90/10) to obtain (5-(bromomethyl)-2,2-dimethyl-1,3-dioxan-5-yl)methyl stearate (0.95 g, 1.879 mmol, yield: 45%).

$^1$H-NMR (CDCl$_3$) δ: 0.89 (t, J=7.0 Hz, 9H), 1.23-1.40 (m, 44H), 1.54-1.64 (m, 26H), 2.01-2.08 (m, 12H), 2.35 (t, J=7.6 Hz, 6H), 2.77 (t, J=6.8 Hz, 6H), 3.40 (s, 9H), 4.46 (s, 6H), 4.70 (s, 2H), 5.28-5.42 (m, 12H), 9.54 (br s, 1H).

Step 2:

Dimethylamine (2.0 mol/L tetrahydrofuran solution, 5.64 mL, 11.3 mmol) was added to an N,N-dimethylformamide solution (10 mL) of the (5-(bromomethyl)-2,2-dimethyl-1,3-dioxan-5-yl)methyl stearate (0.95 g, 1.879 mmol) obtained in Step 1 followed by stirring for 13 hours at 120° C. while irradiating with microwaves. Water was added to the reaction solution followed by extraction with ethyl acetate. The organic layer was washed with saturated salt solution, dried with anhydrous magnesium sulfate and filtered. The resulting residue was purified by silica gel column chromatography (chloroform/methanol=99/1 to 90/10) to obtain (5-((dimethylamino)methyl)-2,2-dimethyl-1,3-dioxan-5-yl)methyl stearate (0.14 g, 0.298 mmol, yield: 16%).

ESI-MS m/z: 470 (M+H)$^+$

Step 3:

3-(dimethylamino)-2,2-bis(hydroxymethyl)propyl stearate (0.12 g, 0.279 mmol, yield: 94%) was obtained in the similar manner as Step 2 of Example 41 using (5-((dimethylamino)methyl)-2,2-dimethyl-1,3-dioxan-5-yl)methyl stearate (0.140 g, 0.298 mmol) obtained in Step 1.

ESI-MS m/z: 430 (M+H)$^+$

Step 4:

Pyridine (0.122 mL, 1.51 mmol) was added to a dichloromethane solution (2 mL) of the 3-(dimethylamino)-2,2-bis(hydroxymethyl)propyl stearate (0.12 g, 0.279 mmol) obtained in Step 3 followed by the addition of tetradecanoyl chloride (0.224 g, 0.98 mmol) while cooling with ice and stirring for 1 hour at room temperature. Water was added to the reaction solution followed by extraction with ethyl acetate. The organic layer was washed with saturated salt solution, dried with anhydrous magnesium sulfate and filtered. After concentrating under reduced pressure, the resulting residue was purified by silica gel column chromatography (hexane/ethyl acetate=95/5) to obtain 2-((dimethylamino)methyl)-2-((stearoyloxy)methyl)propane-1,3-diyl ditetradecanoate (0.150 g, 0.176 mmol, yield: 63%).

ESI-MS m/z: 851 (M+H)$^+$

Step 5:

The title compound (0.032 g, 0.056 mmol, yield: 32%) was obtained in the similar manner as Step 2 of Example 1 using 2-((dimethylamino)methyl)-2-((stearoyloxy)methyl)propane-1,3-diyl ditetradecanoate (0.150 g, 0.176 mmol) obtained in Step 4.

ESI-MS m/z: 865 (M)$^+$; $^1$H-NMR (CDCl$_3$) δ: 0.88 (t, J=6.8 Hz, 9H), 1.19-1.33 (m, 68H), 1.54-1.65 (m, 6H), 2.38 (t, J=7.6 Hz, 6H), 3.63 (s, 9H), 3.95 (s, 2H), 4.29 (s, 6H).

Example 48

N,N,N-trimethyl-3-(((Z)-tetradec-9-enoyl)oxy)-2,2-bis((((Z)-tetradec-9-enoyl)oxy)methyl)propan-1-aminium Chloride (Compound II-39)

Step 1:

Thionyl chloride (1.61 mL, 22.1 mmol) and N,N-dimethylformamide (8.55 mL, 0.110 mmol) were added to a dichloromethane solution (20 mL) of myristoleic acid (Nu-Chek Prep, Inc., 2.50 g, 11.0 mmol) followed by stirring for 1 hour at room temperature. The reaction solution was concentrated under reduced pressure to obtain a crude product of myristoleyl chloride (2.70 g, 11.04 mmol, yield: 100%).

Step 2:

The title compound (0.350 g, 0.417 mmol, overall yield: 27%) was obtained in the similar manner as Example 33 using myristoleyl chloride (1.88 g, 7.66 mmol) obtained in Step 1 instead of palmitoyl chloride.

ESI-MS m/z: 803 (M)$^+$; $^1$H-NMR (CDCl$_3$) δ: 0.86-0.94 (m, 9H), 1.26-1.39 (m, 36H), 1.53-1.64 (m, 6H), 1.97-2.07 (m, 12H), 2.38 (t, J=7.6 Hz, 6H), 3.67 (s, 9H), 3.99 (s, 2H), 4.30 (s, 6H), 5.29-5.39 (m, 6H).

Example 49

2-((4-((1,3-bis(tetradecanoyloxy)-2-((tetradecanoyloxy)methyl)propan-2-yl)amino)-4-oxobutanoyl)oxy)-N,N,N-trimethylethan-1-aminium Chloride (Compound II-40)

Step 1:

1-ethyl-3-(3-dimethylaminopropyl)carbodiimide (0.084 g, 0.440 mmol), 2-(dimethylamino)ethan-1-ol (Tokyo Chemical Industry Co., Ltd., 0.039 g, 0.440 mmol) and 4-dimethylaminopyridine (0.036 g, 0.293 mmol) were added in that order to a dichloromethane solution (3 mL) of 4-((1,3-bis(tetradecanoyloxy)-2-((tetradecanoyloxy)methyl)propan-2-yl)amino)-4-oxo butanoic acid (0.250 g, 0.293 mmol), synthesized using a method complying with the method described in the Australian Journal of Chemistry, 2013, Vol. 66, pp. 23-29, followed by stirring overnight at room temperature. Water was added to the reaction solution followed by extraction with ethyl acetate. The organic layer was washed with saturated salt solution, dried with anhydrous magnesium sulfate and filtered. After concentrating under reduced pressure, the resulting residue was purified by silica gel column chromatography (chloroform/methanol=99/1 to 90/10) to obtain 2-(4-(2-(dimethylamino)ethoxy)-4-oxobutanamido)-2-((tetradecanoyloxy)methy)propane-1,3-diyl ditetradecanoate (0.200 g, 0.217 mmol, yield: 74%).

ESI-MS m/z: 924 (M+H)$^+$

Step 2:

The title compound (0.150 g, 0.154 mmol, yield: 71%) was obtained in the similar manner as Step 2 of Example 1 using 2-(4-(2-(dimethylamino)ethoxy)-4-oxobutanamido)-2-((tetradecanoyloxy)methy)propa ne-1,3-diyl ditetradecanoate (0.200 g, 0.217 mmol) obtained in Step 1.

ESI-MS m/z: 938 (M)$^+$; $^1$H-NMR (CDCl$_3$) δ: 0.88 (t, J=6.8 Hz, 9H), 1.20-1.34 (m, 60H), 1.56-1.65 (m, 6H), 2.34 (t, J=7.6 Hz, 6H), 2.54 (br s, 4H), 3.48 (s, 9H), 4.13-4.21 (m, 2H), 4.40 (s, 6H), 4.57-4.65 (m, 2H), 6.22 (s, 1H).

Example 50

3-((4-((1,3-bis(tetradecanoyloxy)-2-((tetradecanoyloxy)methyl)propan-2-yl)amino)-4-oxobutanoyl)oxy)-1-methylquinuclidin-1-ium Chloride (Compound II-41)

The title compound (0.350 g, 0.417 mmol, overall yield: 46%) was obtained in the similar manner as Example 49 using quinuclidin-3-ol (Tokyo Chemical Industry Co., Ltd.) instead of 2-(dimethylamino)ethan-1-ol.

ESI-MS m/z: 976 (M)$^+$; $^1$H-NMR (CDCl$_3$) δ: 0.88 (t, J=7.0 Hz, 9H), 1.18-1.35 (m, 66H), 1.55-1.66 (m, 6H), 1.97-2.10 (m, 1H), 2.14-2.26 (m, 2H), 2.45-2.70 (m, 6H), 3.34 (s, 3H), 3.61-4.07 (m, 6H), 4.41 (s, 6H), 5.03-5.10 (m, 1H), 6.50 (s, 1H).

Example 51

N,N,N-trimethyl-16,22-dioxo-19-(((tetradecylcarbamoyl)oxy)methyl)-17,21-dioxa-15,23-diazaheptatriacontan-19-aminium Chloride (Compound II-42)

Step 1:
Toluene (4 mL), triethylamine (0.280 mL, 2.01 mmol) and 1-tetradecane isocyanate (1.66 mL, 6.03 mmol) were added in that order to 2-(dimethylamino)-2-(hydroxymethyl)propane-1,3-diol (0.15 g, 1.01 mmol) followed by reacting for 4 hours at 100° C. in a microwave reactor. Water was added to the reaction solution followed by extraction with chloroform. The organic layer was washed with saturated salt solution, dried with anhydrous magnesium sulfate and filtered. After concentrating under reduced pressure, the resulting residue was purified by silica gel column chromatography (chloroform/methanol=99/1 to 90/10) to obtain 2-(dimethylamino)-2-(((tetradecylcarbamoyl)oxy)methyl) propane-1,3-diyl bis(tetradecylcarbamate) (0.872 g, 1.01 mmol, yield: 100%).
ESI-MS m/z: 868 (M+H)$^+$
Step 2:
The title compound (0.761 g, 0.829 mmol, yield: 82%) was obtained in the similar manner as Step 2 of Example 1 using 2-(dimethylamino)-2-(((tetradecylcarbamoyl)oxy) methyl)propane-1,3-diyl bis(tetradecylcarbamate) (0.872 g, 1.01 mmol) obtained in Step 1.
ESI-MS m/z: 882 (M)$^+$; $^1$H-NMR (CDCl$_3$) δ: 0.88 (t, J=7.0 Hz, 9H), 1.22-1.32 (m, 66H), 1.47-1.56 (m, 6H), 3.13 (td, J=14.3, 6.0 Hz, 6H), 3.58 (s, 9H), 4.52 (s, 6H), 6.69 (t, J=6.0 Hz, 3H).

Example 52

N,N,N-trimethyl-1,3-bis(3,7,11,15-tetramethylhexadecanoyloxy)-2-((3,7,11,15-tetramethylhexadecanoyl)methyl)propan-2-aminium Chloride (Compound II-43)

3,7,11,15-tetramethylhexadecanoic acid (0.1826 g, 0.561 mmol), ((((1-cyano-2-ethoxy-2-oxoethyliden)amino)oxy)-4-morpholinomethylene)dimethyl ammonium hexafluorophosphate (Sigma-Aldrich Corp., 0.240 g, 0.561 mmol) and N,N-diisopropylethylamine (0.098 mL, 0.561 mmol) were added to a 1,2-dichloroethane solution (1 mL) of 2-dimethylamino-2-hydroxymethylpropane-1,3-diol (0.0170 g, 0.112 mmol) followed by stirring overnight at 60° C. After allowing to cool to room temperature, the reaction solution was concentrated under reduced pressure. The resulting residue was purified by aminosilica gel column chromatography (hexane/ethyl acetate=95/5) to obtain a crude product of 2-(dimethylamino)-2-((3,7,11,15-tetramethylhexadecanoyloxy)methyl)propane-1,3-di yl bis(3,7,11,15)-tetramethylhexadecanoate). Methyl iodide (1.00 mL, 16.0 mmol) was added to the resulting crude product followed by stirring overnight at room temperature. The reaction solution was concentrated under reduced pressure. The residue was dissolved in a small amount of methanol-chloroform (1:1), loaded onto an ion exchange resin (Dow Chemical Co., Dowex™ 1×-2 100 mesh, type CL, about 20 times volume, prewashed with water and methanol), and eluted with methanol-chloroform (1:1). The eluate was concentrated under reduced pressure and the resulting residue was purified by silica gel column chromatography (chloroform/methanol=90/10) to obtain the title compound (0.0766 g, 0.071 mmol, yield: 63%).
ESI-MS m/z: 1043 (M)$^+$; $^1$H-NMR (CDCl$_3$) δ: 0.81-0.87 (m, 36H), 0.92 (d, J=6.7 Hz, 9H), 0.97-1.42 (m, 60H), 1.51 (tt, J=19.8, 6.7 Hz, 3H), 1.84-1.97 (m, 3H), 2.16 (ddd, J=15.5, 8.4, 2.3 Hz, 3H), 2.38 (ddd, J=15.5, 5.6, 1.6 Hz, 3H), 3.72 (s, 9H), 4.55 (s, 6H).

Example 53

N,N,N-trimethyl-2-((tetradecanoyloxy)methyl)-2-tetradecylhexadecan-1-aminium Chloride (Compound II-44)

The title compound (0.292 g, 0.39 mmol, overall yield: 22%) was obtained in the similar manner as Example 19 using 1-bromotetradecane (Tokyo Chemical Industry Co., Ltd.) and myristic acid (Tokyo Chemical Industry Co., Ltd.) instead of the (9Z,12Z)-octadeca-9,12-dienyl methanesulfonate used in Step 1 of Example 19 and the (9Z,12Z)-octadeca-9,12-dienoic acid used in Step 4, respectively.
ESI-MS m/z: 721 (M)$^+$; $^1$H-NMR (CD$_3$OD) δ: 0.90 (t, J=6.8 Hz, 9H), 1.28-1.32 (m, 70H), 1.49 (br s, 2H), 1.63-1.66 (m, 2H), 2.42 (t, J=7.2 Hz, 2H), 3.26 (s, 9H), 3.43 (s, 2H), 4.18 (s, 2H).

Example 54

2-hexadecyl-N,N,N-trimethyl-2-((palmitoyloxy) methyl)octadeca-1-aminium Chloride (Compound II-45)

The title compound (0.195 g, 0.23 mmol, overall yield: 5%) was obtained in the similar manner as Example 19 using 1-bromohexadecane (Tokyo Chemical Industry Co., Ltd.) and palmitic acid (Tokyo Chemical Industry Co., Ltd.) instead of the (9Z,12Z)-octadeca-9,12-dienyl methanesulfonate used in Step 1 of Example 19 and the (9Z,12Z)-octadeca-9,12-dienoic acid used in Step 4, respectively.
ESI-MS m/z: 805 (M)$^+$; $^1$H-NMR (CD$_3$OD) δ: 0.90 (t, J=6.8 Hz, 9H), 1.28-1.33 (m, 82H), 1.49 (br s, 2H), 1.63-1.67 (m, 2H), 2.43 (t, J=7.2 Hz, 2H), 3.26 (s, 9H), 3.43 (s, 2H), 4.18 (s, 2H).

Example 55

N,N,N-trimethyl-2-((stearoyloxy)methyl)-2-tetradecylhexadecan-1-aminium Chloride (Compound II-46)

The title compound (0.421 g, 0.52 mmol, overall yield: 20%) was obtained in the similar manner as Example 19 using 1-bromohexadecane (Tokyo Chemical Industry Co., Ltd.) and stearic acid (Tokyo Chemical Industry Co., Ltd.) instead of the (9Z,12Z)-octadeca-9,12-dienyl methanesulfonate used in Step 1 of Example 19 and the (9Z,12Z)-octadeca-9,12-dienoic acid used in Step 4, respectively.
ESI-MS m/z: 777 (M)$^+$; $^1$H-NMR (CD$_3$OD) δ: 0.90 (t, J=6.8 Hz, 9H), 1.29-1.33 (m, 78H), 1.49 (br s, 2H), 1.63-1.67 (m, 2H), 2.43 (t, J=7.2 Hz, 2H), 3.27 (s, 9H), 3.44 (s, 2H), 4.18 (s, 2H).

Example 56

3-(dodecanoyloxy)-N,N,N-trimethyl-2-bis((stearoyloxy)methyl)propan-1-aminium Chloride (Compound II-47)

The title compound (0.200 g, 0.417 mmol, overall yield: 0.3%) was obtained in the similar manner as Example 46 using lauroyl chloride (Tokyo Chemical Industry Co., Ltd.) and stearoyl chloride (Tokyo Chemical Industry Co., Ltd.) instead of the stearoyl chloride used in Step 1 of Example 46 and the tetradecanoyl chloride used in Step 4, respectively.

ESI-MS m/z: 893 (M)$^+$; $^1$H-NMR (CDCl$_3$) δ: 0.88 (t, J=6.9 Hz, 9H), 1.21-1.32 (m, 72H), 1.57-1.64 (m, 6H), 2.38 (t, J=7.6 Hz, 6H), 3.63 (s, 9H), 3.99 (s, 2H), 4.29 (s, 6H).

Example 57

3-(dodecanoyloxy)-N,N,N-trimethyl-2,2-bis((palmitoyloxy)methyl)propan-1-aminium Chloride (Compound II-48)

The title compound (0.350 g, 0.40 mmol, overall yield: 0.6%) was obtained in the similar manner as Example 47 using lauroyl chloride (Tokyo Chemical Industry Co., Ltd.) and palmitoyl chloride (Wake Pure Chemical Industries, Ltd.) instead of the stearoyl chloride used in Step 1 of Example 47 and the tetradecanoyl chloride used in Step 4, respectively.

ESI-MS m/z: 837 (M)$^+$; $^1$H-NMR (CDCl$_3$) δ: 0.88 (t, J=6.9 Hz, 9H), 1.21-1.33 (m, 64H), 1.56-1.64 (m, 6H), 2.38 (t, J=7.6 Hz, 6H), 3.66 (s, 9H), 3.98 (s, 2H), 4.29 (s, 6H).

Example 58

3-(dodecanoyloxy)-2-((dodecanoyloxy)methyl)-N,N,N-trimethyl-2-((stearoyloxy) methyl)propan-1-aminium Chloride (Compound No. 11-49)

The title compound (0.210 g, 0.249 mmol, overall yield: 0.3%) was obtained in the similar manner as Example 47 using lauroyl chloride (Tokyo Chemical Industry Co., Ltd.) instead of the tetradecanoyl chloride used in Step 4 of Example 47.

ESI-MS m/z: 809 (M)$^+$; $^1$H-NMR (CDCl$_3$) δ: 0.88 (t, J=6.9 Hz, 9H), 1.23-1.34 (m, 60H), 1.53-1.65 (m, 6H), 2.38 (t, J=7.6 Hz, 6H), 3.63 (s, 9H), 3.97 (s, 2H), 4.29 (s, 6H).

Example 59

N,N,N-trimethyl-3-(palmitoyloxy)-2-((palmitoyloxy)methyl)-2-((stearoyloxy)meth yl)propan-1-aminium Chloride (Compound II-50)

The title compound (0.420 g, 0.44 mmol, overall yield: 0.5%) was obtained in the similar manner as Example 47 using palmitoyl chloride (Tokyo Chemical Industry Co., Ltd.) instead of the tetradecanoyl chloride used in Step 4 of Example 47.

ESI-MS m/z: 921 (M)$^+$; $^1$H-NMR (CDCl$_3$) δ: 0.88 (t, J=6.9 Hz, 9H), 1.21-1.32 (m, 76H), 1.55-1.64 (m, 6H), 2.38 (t, J=7.6 Hz, 6H), 3.67 (s, 9H), 3.99 (s, 2H), 4.29 (s, 6H).

Example 60

3-(icosanoyloxy)-N,N,N-trimethyl-2,2-bis((tetradecanoyloxy)methyl)propan-1-aminium Chloride (Compound II-51)

The title compound was obtained in the similar manner as Example 47 using eicosanoyl chloride (Nu-Chek Prep, Inc.) instead of the stearoyl chloride used in Step 1 of Example 47.

Example 61

3-((dodecanoyloxy)-2-((dodecanoyloxy)methyl)-2-((icosanoyloxy)methyl)-N,N,N-trimethylpropan-1-aminium Chloride (Compound II-52)

The title compound was obtained in the similar manner as Example 47 using eicosanoyl chloride (Nu-Chek Prep, Inc.) and lauroyl chloride (Wake Pure Chemical Industries, Ltd.) instead of the stearoyl chloride used in Step 1 of Example 47 and the tetradecanoyl chloride used in Step 4.

Example 62

N,N,N-trimethyl-3-(methyl(3-(tetradecanoyloxy)-2,2-bis((tetradecanoyloxy)meth yl)propyl)amino)propan-1-aminium Chloride (Compound II-53)

Step 1:

N,N,N'-trimethylpropane-1,3-diamine (0.263 g, 2.26 mmol) was added to an N,N-dimethylacetoamide solution (1 mL) of 2-(bromomethyl)-2-(hydroxymethyl)propane-1,3-diol (0.15 g, 0.754 mmol) followed by reacting for 2 hours at 100° C. in a microwave reactor. Subsequently, N,N-diisopropylethylamine (0.395 mL, 2.26 mmol) and then tetradecanoyl chloride (1.12 g, 4.52 mmol) were added while cooling with ice followed by stirring for 2 hours at room temperature. Water was added to the reaction solution followed by extraction with ethyl acetate. The organic layer was washed with saturated aqueous sodium bicarbonate solution and saturated salt solution, dried with anhydrous magnesium sulfate and filtered. After concentrating under reduced pressure, the resulting residue was purified by silica gel column chromatography (chloroform/methanol=99/1 to 90/10) to obtain 2-(((3-(dimethylamino)propyl)(methyl)amino)methyl)-2-((tetradecanoyloxy)methyl)propane-1,3-diyl ditetradecanoate (0.040 g, 0.046 mmol, yield: 6%).

ESI-MS m/z: 866 (M+H)$^+$

Step 2:

The title compound (0.015 g, 0.016 mmol, yield: 35%) was obtained in the similar manner as Step 2 of Example 1 using 2-(((3-(dimethylamino)propyl)(methyl)amino)methyl)-2-((tetradecanoyloxy)methyl)propane-1,3-diyl ditetradecanoate (0.040 g, 0.046 mmol) obtained in Step 1.

ESI-MS m/z: 880 (M)$^+$; $^1$H-NMR (CDCl$_3$) δ: 0.88 (t, J=6.8 Hz, 9H), 1.20-1.35 (m, 62H), 1.54-1.65 (m, 6H), 1.87-2.03 (m, 2H), 2.21-2.31 (m, 2H), 2.31 (t, J=7.6 Hz, 6H), 2.49 (br s, 3H), 3.40 (s, 9H), 3.52-3.63 (m, 2H), 4.05 (s, 6H).

Example 63

(S)-6-(di(9Z,12Z)-octadeca-9,12-dienylamino)-N,N,N-trimethyl-5-oleamido-6-oxyhexan-1-aminium Chloride (Compound III-2)

Step 1:

(9Z,12Z)-octadeca-9,12-dienyl methanesulfonate (1.55 g, 4.50 mmol) was added to ammonia (approx. 2 mol/L methanol solution, 18.0 mL, 36.0 mmol) followed by stirring for 3 hours at 130° C. using a microwave reactor. Saturated aqueous sodium bicarbonate solution was added to the reaction solution followed by extracting five times with chloroform. The organic layers were combined, washed with saturated salt solution and dried with anhydrous magnesium sulfate followed by filtering and concentrating under reduced pressure to obtain a crude product of (Z)-octadec-9-enylamine.

(9Z,12Z)-octadeca-9,12-dienyl methanesulfonate (1.24 g, 3.60 mmol) and 50% aqueous sodium hydroxide solution (1.44 g, 18.0 mmol) were added to the resulting crude product followed by stirring for 60 minutes at 110° C. in an oil bath. After allowing to cool to room temperature, the reaction solution was diluted with ethyl acetate, washed with water and then saturated salt solution and dried with anhydrous magnesium sulfate followed by filtering and concentrating under reduced pressure. The resulting residue was purified by silica gel column chromatography (chloroform/methanol=100/0 to 95/5) to obtain (9Z,12Z)-di(9Z,12Z)-octadeca-9,12-dienylamine (0.838 g, 1.631 mmol, yield: 36%).

ESI-MS m/z: 515 (M+H)$^+$; $^1$H-NMR (CDCl$_3$) δ: 0.89 (t, J=6.8 Hz, 6H), 1.26-1.38 (m, 32H), 1.45-1.54 (m, 4H), 2.05 (q, J=6.6 Hz, 8H), 2.60 (t, J=7.1 Hz, 4H), 2.77 (t, J=5.9 Hz, 4H), 5.29-5.43 (m, 8H).

Step 2:

Sodium hydroxide (2 mol/L aqueous solution, 5 mL) and oleyl chloride (2.09 g, 6.89 mmol) were added to an acetone solution (5 mL) of (S)-2-amino-6-(tert-butoxycarbonylamino)hexanoic acid (1.94 g, 7.88 mmol) followed by stirring overnight at room temperature. Aqueous hydrochloric acid solution (6 mol/L) was added to the reaction solution followed by extracting twice with chloroform. The organic layer was dried with anhydrous magnesium sulfate followed by filtering and concentrating under reduced pressure. The residue was purified by silica gel column chromatography (chloroform/methanol=90/10 to 80/20) to obtain (S)-6-(tert-butoxycarbonylamino)-2-oleamidohexanoic acid (2.50 g, 4.89 mmol, yield: 71%).

ESI-MS m/z: 510 (M−H)$^-$; $^1$H-NMR (CDCl$_3$) δ: 0.87 (t, J=7.0 Hz, 3H), 1.20-1.54 (m, 33H), 1.57-1.68 (m, 2H), 1.71-1.93 (m, 2H), 1.96-2.05 (m, 4H), 2.18-2.29 (m, 2H), 3.07-3.16 (m, 2H), 4.50-4.60 (m, 1H), 4.63-4.76 (m, 1H), 5.28-5.39 (m, 2H), 6.49-6.57 (m, 1H).

Step 3:

O-(7-aza-1H-benzotriazol-1-yl)-N,N,N',N'-tetramethyluronium hexafluorophosphate (0.433 g, 1.14 mmol), N,N-diisopropylethylamine (0.498 mL, 2.85 mmol) and the (9Z,12Z)-di(9Z,12Z)-octadeca-9,12-dienylamine (0.293 g, 0.570 mmol) obtained in Step 1 were added to a 1,2-dichloroethane solution (4 mL) of the (S)-6-(tert-butoxycarbonylamino)-2-oleamidohexanoic acid (0.291 g, 0.570 mmol) obtained in Step 2 followed by stirring for 4 hours at room temperature. Saturated aqueous sodium bicarbonate solution was added to the reaction solution followed by extracting twice with chloroform. The organic layer was dried with anhydrous magnesium sulfate followed by filtering and concentrating under reduced pressure. The residue was purified by silica gel column chromatography (hexane/ethyl acetate=80/20) to obtain tert-butyl(S)-6-(di(9Z,12Z)-octadeca-9,12-dienylamino)-5-oleamido-6-oxyhexylcarbamate (0.489 g, 0.486 mmol, yield: 85%).

ESI-MS m/z: 1008 (M+H)$^+$; $^1$H-NMR (CDCl$_3$) δ: 0.85-0.92 (m, 9H), 1.20-1.72 (m, 73H), 1.97-2.08 (m, 12H), 2.18 (t, J=7.6 Hz, 2H), 2.74-2.80 (m, 4H), 3.02-3.34 (m, 5H), 3.44-3.53 (m, 1H), 4.55-4.63 (m, 1H), 4.88 (td, J=8.2, 4.6 Hz, 1H), 5.28-5.43 (m, 10H), 6.30 (d, J=8.4 Hz, 1H).

Step 4:

Trifluoroacetic acid (0.500 mL, 6.49 mmol) was added to a 1,2-dichloroethane solution (2 mL) of the tert-butyl(S)-6-(di(9Z,12Z)-octadeca-9,12-dienylamino)-5-oleamido-6-oxyhexylcarbamate (0.459 g, 0.456 mmol) obtained in Step 3 followed by stirring for 1 hour at room temperature. After concentrating the reaction solution under reduced pressure, chloroform and saturated aqueous sodium bicarbonate solution were added to the residue followed by extracting twice with chloroform. The organic layers were dried with anhydrous magnesium sulfate followed by filtering and concentrating under reduced pressure. The residue was purified by silica gel column chromatography (hexane/ethyl acetate=90/10 to 80/20) to obtain N—((S)-6-amino-1-(di((9Z,12Z)-octadeca-9,12-dien-1-yl)amino)-1-oxohexan-2-yl)oleamide (0.259 g, 0.286 mmol, yield: 63%).

ESI-MS m/z: 907 (M+H)$^+$; $^1$H-NMR (CDCl$_3$) δ: 0.86-0.91 (m, 9H), 1.20-1.71 (m, 64H), 1.96-2.09 (m, 12H), 2.21 (t, J=7.5 Hz, 2H), 2.73-2.88 (m, 6H), 3.08-3.47 (m, 4H), 4.81-4.88 (m, 1H), 5.28-5.43 (m, 10H), 6.67 (br s, 1H).

Step 5:

38% aqueous formaldehyde solution (0.300 mL) and sodium triacetoxyborohydride (0.096 g, 0.453 mmol) were added to a 1,2-dichloroethane solution (1 mL) of the N—((S)-6-amino-1-(di((9Z,12Z)-octadeca-9,12-dien-1-yl)amino)-1-oxohexan-2-yl)oleamide (0.137 g, 0.151 mmol) obtained in Step 4 followed by stirring overnight at room temperature. Saturated aqueous sodium bicarbonate solution was added to the reaction solution followed by extracting twice with chloroform. The organic layers were dried with anhydrous magnesium sulfate followed by concentrating under reduced pressure. The residue was purified by aminosilica gel column chromatography (hexane/ethyl acetate=50/50) to obtain N—((S)-1-(di(9Z,12Z)-octadeca-9,12-dienylamino)-6-(dimethylamino)-1-oxohexan-2-yl)oleamide (0.122 g, 0.130 mmol, yield: 86%).

ESI-MS m/z: 936 (M+H)$^+$; $^1$H-NMR (CDCl$_3$) δ: 0.83-0.93 (m, 9H), 1.12-1.77 (m, 64H), 1.95-2.25 (m, 22H), 2.73-2.80 (m, 4H), 3.04-3.15 (m, 1H), 3.20-3.34 (m, 2H), 3.44-3.54 (m, 1H), 4.85-4.91 (m, 1H), 5.28-5.43 (m, 10H), 6.28 (d, J=8.6 Hz, 1H).

Step 6:

The title compound (0.0707 g, 0.0718 mol, yield: 65%) was obtained in the similar manner as Step 2 of Example 8 using N—((S)-1-(di(9Z,12Z)-octadeca-9,12-dienylamino)-6-(dimethylamino)-1-oxohexan-2-yl)oleamide (0.104 g, 0.111 mmol) obtained in Step 5 instead of (9Z,9'Z,12Z,12'Z)-2-(dimethylamino)-2-(((9Z,12Z)-octadeca-9,12-dienoyloxy)methyl) propane-1,3-diyl dioctadeca-9,12-dienoate.

ESI-MS m/z: 950 (M)$^+$; $^1$H-NMR (CDCl$_3$) δ: 0.85-0.91 (m, 9H), 1.12-1.83 (m, 64H), 1.97-2.08 (m, 12H), 2.19 (t, J=7.7 Hz, 2H), 2.74-2.80 (m, 4H), 3.05-3.84 (m, 15H), 4.82-4.90 (m, 1H), 5.28-5.43 (m, 10H), 6.41-6.46 (m, 1H).

Example 64

(S)—N,N,N-trimethyl-5-(nonacosan-15-yloxy)-1,5-dioxo-1-(tetradecyloxy)pentan-2-aminium Chloride (Compound III-3)

Step 1:

Tetradecylmagnesium chloride (Sigma-Aldrich Corp., 1.0 mol/L tetrahydrofuran solution, 59.4 mL, 59.4 mmol) was added to a tetrahydrofuran solution (9 mL) of ethyl formate (Nacalai Tesque Inc., 2.4 mL, 29.7 mmol) followed by stirring for 2 hours at 60° C. The reaction solution was cooled with ice followed by the addition of water and sulfuric acid (Nacalai Tesque Inc., 2.0 mol/L aqueous solution). The precipitate was filtered out to obtain nonacosan-15-ol (6.90 g, 16.2 mmol, yield: 55%).

$^1$H-NMR (CDCl$_3$) δ: 0.88 (t, J=6.8 Hz, 6H), 1.22-1.34 (m, 48H), 1.37-1.49 (m, 2H), 3.54-3.64 (m, 1H).

Step 2:

Para-formaldehyde (Sigma-Aldrich Corp., 5.50 g, 183 mmol) and sodium cyanoborohydride (5.70 g, 90.7 mmol) were added to an ethanol solution (150 mL) of 1-tert-butyl-2-aminopentanedioate hydrochloride (Watanabe Chemical Industries, Ltd., 10.0 g, 30.0 mmol) followed by stirring overnight at room temperature. Saturated aqueous sodium bicarbonate solution was added to the reaction solution followed by extracting twice with chloroform. The organic layers were washed with saturated salt solution, dried with anhydrous magnesium sulfate, filtered and concentrated under reduced pressure. The residue was purified by silica gel column chromatography (hexane/ethyl acetate=35/65) to obtain (S)-5-benzyl-1-tert-butyl-2-(dimethylamino)pentanedioate (8.20 g, 25.5 mmol, yield: 84%).

$^1$H-NMR (CDCl$_3$) δ: 1.48 (s, 9H), 1.95-2.00 (m, 2H), 2.32 (s, 6H), 2.43 (t, J=7.8 Hz, 2H), 3.04 (t, J=7.5 Hz, 1H), 5.12 (s, 6H), 7.29-7.40 (m, 5H).

Step 3:

Palladium-carbon (Tokyo Chemical Industry Co., Ltd., 10% palladium, wetted with approx. 55% water, 820 mg) was added to an ethanol solution (200 mL) of (S)-5-benzyl-1-tert-butyl-2-(dimethylamino)pentanedioate (8.20 g, 25.5 mmol) followed by stirring for 7 hours at room temperature in a hydrogen atmosphere. Impurities were removed by celite filtration followed by concentrating the filtrate. The resulting residue was purified by silica gel column chromatography (dichloromethane/methanol=85/15) to obtain a crude product of (S)-5-tert-butoxy-4-(dimethylamino)-5-oxopentanoic acid (4.83 g, 20.9 mmol, crude yield: 82%).

1,2-dichloroethane (200 mL), the nonacosan-15-ol (9.75 g, 23.0 mmol) obtained in Step 1, 1-ethyl-3-(3-dimethylaminopropyl)carbodiimide hydrochloride (8.01 g, 41.8 mmol) and N,N-dimethylaminopyridine (255 mg, 2.09 mmol) were added to the resulting crude product of (S)-5-tert-butoxy-4-(dimethylamino)-5-oxopentanoic acid (4.83 g, 20.9 mmol) followed by stirring for 3 hours at 50° C. Water was added to the reaction solution followed by extracting twice with dichloromethane. The organic layers were washed with aqueous salt solution and dried with anhydrous magnesium sulfate followed by filtering and concentrating under reduced pressure. The resulting residue was purified by silica gel column chromatography (hexane/ethyl acetate=85/15) to obtain (S)-1-tert-butyl-5-nonacosan-15-yl-2-(dimethylamino)pentanedioate (8.13 g, 12.7 mmol, yield: 61%).

$^1$H-NMR (CDCl$_3$) δ: 0.88 (t, J=6.8 Hz, 6H), 1.20-1.38 (m, 48H), 1.46-1.57 (m, 4H), 1.91-2.00 (m, 2H), 2.33-2.41 (m, 8H), 3.05 (t, J=7.6 Hz, 1H), 4.82-4.93 (m, 1H).

Step 4:

Trifluoroacetic acid (20 mL) was added to a dichloromethane solution (40 mL) of the (S)-1-tert-butyl-5-nonacosan-15-yl-2-(dimethylamino)pentanedioate (8.13 g, 12.7 mmol) obtained in Step 3 followed by stirring overnight at 40° C. The reaction solution was concentrated under reduced pressure. The resulting residue was purified by silica gel column chromatography (dichloromethane/methanol=85/15) to obtain (S)-2-(dimethylamino)-5-(nonacosan-15-yloxy)-5-oxopentanoic acid (6.70 g, 11.5 mmol, yield: 90%).

$^1$H-NMR (CDCl$_3$) δ: 0.89 (t, J=7.0 Hz, 6H), 1.18-1.37 (m, 48H), 1.44-1.60 (m, 4H), 2.00-2.13 (m, 2H), 2.52-2.74 (m, 2H), 2.87 (s, 6H), 3.62-3.73 (m, 1H), 4.80-4.89 (m, 1H).

Step 5:

(1-cyano-2-ethoxy-2-oxoethylidenaminooxy)dimethylamino-morpholino-carbenium hexafluorophosphate (96.0 mL, 0.224 mmol), N,N-diisopropylethylamine (0.060 mL, 0.344 mmol) and tetradecan-1-ol ( ) were added to a 1,2-dichloroethane solution (2.0 mL) of the (S)-2-(dimethylamino)-5-(nonacosan-15-yloxy)-5-oxopentanoic acid (100 mg, 0.172 mmol) obtained in Step 4 followed by stirring overnight at room temperature. Water was added to the reaction solution followed by extraction with dichloromethane. The organic layer was washed with water, dried with anhydrous magnesium sulfate, filtered and concentrated under reduced pressure. The resulting residue was purified by silica gel column chromatography (hexane/ethyl acetate=95/5 to 85/15) to obtain (S)-5-nonacosan-15-yl 1-tetradecyl 2-(dimethylamino)pentanedioate (64.0 mg, 0.0822 mmol, yield: 48%).

$^1$H-NMR (CDCl$_3$) δ: 0.88 (t, J=6.8 Hz, 9H), 1.12-1.39 (m, 70H), 1.45-1.69 (m, 6H), 1.93-2.03 (m, 2H), 2.29-2.38 (m, 8H), 3.16 (t, J=7.4 Hz, 1H), 4.03-4.17 (m, 2H), 4.80-4.91 (m, 1H).

Step 6:

The title compound was obtained in the similar manner as Step 2 of Example 8 using (S)-5-nonacosan-15-yl 1-tetradecyl 2-(dimethylamino)pentanedioate obtained in Step 5 instead of (9Z,9'Z,12Z,12'Z)-2-(dimethylamino)-2-(((9Z,12Z)-octadeca-9,12-dienoyloxy)methyl) propane-1,3-diyl dioctadeca-9,12-dienoate.

Example 65

(S)-1-(dodecyloxy)-N,N,N-trimethyl-5-(nonacosan-15-yloxy)-1,5-dioxopentan-2-aminium Chloride (Compound III-4)

The title compound was obtained in the similar manner as Example 64 using dodecan-1-ol instead of the tetradecan-1-ol used in Step 5 of Example 64.

Example 66

(S)-1-(hexadecyloxy)-N,N,N-trimethyl-5-(nonacosan-15-yloxy)-1,5-dioxopentan-2-aminium Chloride (Compound III-5)

The title compound was obtained in the similar manner as Example 64 using hexadecan-1-ol instead of the tetradecan-1-ol used in Step 5 of Example 64.

Example 67

(S)—N,N,N-trimethyl-5-(nonacosan-15-yloxy)-1-(octadecyloxy)-1,5-dioxopentan-2-aminium Chloride (Compound III-6)

The title compound was obtained in the similar manner as Example 64 using octadecan-1-ol instead of the tetradecan-1-ol used in Step 5 of Example 64.

Example 68

(S,Z)—N,N,N-triethyl-5-(nonacosan-15-yloxy)-1-(octadec-9-enyloxy)-1,5-dioxopentan-2-aminium Chloride (Compound III-7)

The title compound was obtained in the similar manner as Example 64 using (Z)-octadec-9-en-1-ol instead of the tetradecan-1-ol used in Step 5 of Example 64.

Example 69

(6Z,9Z,28Z,31Z)—N,N-dimethyl-N-(2-(N-methyl-stearylamido)ethyl)heptatriaconta-6,9,28,31-tetraen-19-aminium Chloride (Compound IV-2)

Step 1:
Methanol (2 mL), N1,N2-dimethylethane-1,2-diamine (Tokyo Chemical Industry Co., Ltd., 0.085 mL, 0767 mmol) and sodium triacetoxyborohydride (0.325 g, 1.53 mmol) were added to a 1,2-dichloroethane solution (2 mL) of (6Z,9Z,28Z,31Z)-heptatriaconta-6,9,28,31-tetraen-19-one (0.50 g, 0.256 mmol), obtained using a method complying with the method described in WO 2010/042877, followed by stirring for 5 hours at 50° C. Saturated aqueous sodium bicarbonate solution was added to the reaction solution followed by extracting twice with chloroform. The organic layers were dried with anhydrous magnesium sulfate, filtered and concentrated under reduced pressure. The resulting residue was purified by aminosilica gel column chromatography (hexane/ethyl acetate=90/10 to 80/20) to obtain N1-((6Z,9Z,28Z,31Z)-heptatriaconta-6,9,28,31-tetraen-19-yl)-N1,N2-dimethylethane-1,2-diamine (0.0303 g, 0.0506 mmol, yield: 20%).

ESI-MS m/z: 600 (M+H)$^+$; $^1$H-NMR (CDCl$_3$) δ: 0.89 (t, J=6.8 Hz, 6H), 1.13-1.45 (m, 40H), 2.01-2.09 (m, 8H), 2.14 (s, 3H), 2.28-2.40 (m, 1H), 2.43 (s, 3H), 2.52-2.60 (m, 4H), 2.75-2.80 (m, 4H), 5.29-5.42 (m, 8H).

Step 2:
Stearoyl chloride (0.0390 g, 0.129 mmol) and N,N-diisopropylethylamine (0.038 mL, 0.215 mmol) were added to a 1,2-dichloroethane solution (1 mL) of the N1-((6Z,9Z,28Z,31Z)-heptatriaconta-6,9,28,31-tetraen-19-yl)-N1,N2-dimethylethane-1,2-diamine (0.0258 g, 0.0431 mmol) obtained in Step 1 followed by stirring for 1 hour at room temperature. Saturated aqueous sodium bicarbonate solution was added to the reaction solution followed by extracting twice with chloroform. The organic layers were dried with anhydrous magnesium sulfate, filtered and concentrated under reduced pressure. The resulting residue was purified by aminosilica gel column chromatography (hexane/ethyl acetate=90/10) to obtain a crude product of N-(2-((6Z,9Z,28Z,31Z)-heptatriaconta-6,9,28,31-tetraen-19-yl(methyl)amino)ethyl)-N-methylstearylamide.

Methyl iodide (1.00 mL, 16.0 mmol) was added to the resulting crude product followed by stirring for 1 hour at 50° C. The reaction solution was concentrated under reduced pressure. The residue was dissolved in a small amount of methanol-chloroform (1:1), loaded onto an ion exchange resin (Dow Chemical Co., Dowex™ 1x-2 100 mesh, type CL, about 20 times volume, prewashed with water and methanol), and eluted with methanol-chloroform (1:1). The eluate was concentrated under reduced pressure and the resulting residue was purified by silica gel column chromatography (chloroform/methanol=80/20) to obtain the title compound (0.0149 g, 0.0163 mmol, yield: 38%).

ESI-MS m/z: 881 (M)$^+$; $^1$H-NMR (CDCl$_3$) δ: 0.84-0.92 (m, 9H), 1.20-2.09 (m, 78H), 2.27-2.38 (m, 2H), 2.74-2.80 (m, 4H), 3.14-3.45 (m, 9H), 3.77-4.09 (m, 5H), 5.28-5.43 (m, 8H).

Example 70

(9Z,12Z)—N,N-dimethyl-N-(3-((9Z,12Z)—N-((9Z,12Z)-octadeca-9,12-dienyl)octadeca-9,12-dienamido)propyl)octadeca-9,12-dien-1-aminium Chloride (Compound IV-3)

Step 1:
3-aminopropan-1-ol (1.66 g, 21.9 mmol) was added to (9Z,12Z)-octadeca-9,12-dienyl methanesulfonate (0.838 g, 2.43 mmol) followed by stirring for 3 hours at 90° C. The reaction solution was concentrated under reduced pressure and the resulting residue was purified by aminosilica gel column chromatography (hexane/ethyl acetate) to obtain 3-((9Z,12Z)-octadeca-9,12-dienylamino)propan-1-ol (0.722 g, 2.23 mmol, yield: 92%).

ESI-MS m/z: 325 (M+H)$^+$; $^1$H-NMR (CDCl$_3$) δ: 0.89 (t, J=6.9 Hz, 3H), 1.26-1.39 (m, 17H), 1.46 (tt, J=7.1, 6.9 Hz, 3H), 1.69 (tt, J=5.7, 5.4 Hz, 2H), 2.02-2.08 (m, 4H), 2.60 (t, J=7.1 Hz, 2H), 2.75-2.80 (m, 2H), 2.88 (t, J=5.7 Hz, 2H), 3.81 (t, J=5.4 Hz, 2H), 5.30-5.42 (m, 4H).

Step 2:
3-(methyl((9Z,12Z)-octadeca-9,12-dienyl)amino)propan-1-ol (0.220 g, 0.652 mol, yield: 90%) was obtained in the similar manner as Step 5 of Example 63 using 3-((9Z,12Z)-octadeca-9,12-dienylamino)propan-1-ol (0.233 g, 0.722 mol) obtained in Step 1 instead of N—((S)-6-amino-1-(di((9Z,12Z)-octadeca-9,12-dien-1-yl)amino)-1-oxohexan-2-yl)oleamide.

ESI-MS m/z: 338 (M+H)$^+$; $^1$H-NMR (CDCl$_3$) δ: $^1$H-NMR (CDCl$_3$) δ: 0.89 (t, J=7.0 Hz, 3H), 1.24-1.40 (m, 16H), 1.47 (tt, J=7.6, 7.0 Hz, 2H), 1.69 (tt, J=5.7, 5.2 Hz, 2H), 2.01-2.08 (m, 4H), 2.23 (s, 3H), 2.34 (t, J=7.6 Hz, 2H), 2.59 (t, J=5.7 Hz, 2H), 2.75-2.80 (m, 2H), 3.80 (t, J=5.2 Hz, 2H), 5.29-5.42 (m, 4H).

Step 3:
Cesium carbonate (6.74 g, 20.7 mmol), tetra-n-butylammonium iodide (3.05 g, 8.27 mmol) and N-(tert-butoxycarbonyl)-2-nitrobenzenesulfonamide (2.50 g, 8.27 mmol) were added to an acetonitrile solution (30 mL) of (9Z,12Z)-octadeca-9,12-dienyl methanesulfonate (2.85 g, 8.27 mmol) followed by stirring for 3 hours while refluxing. The reaction solution was allowed to cool to room temperature followed by extraction with ethyl acetate. The organic layer was dried with anhydrous magnesium sulfate, filtered and concentrated under reduced pressure. The resulting residue was purified by silica gel column chromatography (hexane/ethyl acetate=70/30) to obtain tert-butyl 2-nitrophenylsulfonyl ((9Z,12Z)-octadeca-9,12-dienyl)carbamate (3.21 g, 5.83 mmol).

Trifluoroacetic acid (9.63 mL, 126 mmol) was added to a dichloromethane solution (23 mL) of the resulting tert-butyl 2-nitrophenylsulfonyl ((9Z,12Z)-octadeca-9,12-dienyl)carbamate (3.21 g, 5.83 mmol) followed by stirring for 0.5 hours at room temperature. The reaction solution was diluted with dichloromethane followed by the addition of aqueous sodium hydroxide solution (1 mol/L) and saturated aqueous sodium bicarbonate solution. The organic layer was washed with saturated salt solution, dried with anhydrous magnesium sulfate, filtered and concentrated under reduced pressure. The resulting residue was purified by silica gel column chromatography (hexane/ethyl acetate=95/5) to obtain 2-nitro-N-((9Z,12Z)-octadeca-9,12-dienyl)benzenesulfonamide (2.48 g, 5.50 mmol, yield: 67%).

ESI-MS m/z: 338 (M+H)$^+$; $^1$H-NMR (CDCl$_3$) δ: 0.89 (t, J=7.0 Hz, 3H), 1.22-1.39 (m, 16H), 1.52 (m, 2H), 2.01-2.05 (m, 4H), 2.77 (t, J=6.6 Hz, 2H), 3.09 (q, J=6.7 Hz, 2H), 5.23 (m, 1H), 5.31-5.42 (m, 4H), 7.71-7.76 (m, 2H), 7.78-7.87 (1H), 813-8.15 (m, 1H).

Step 4:

The 2-nitro-N-((9Z,12Z)-octadeca-9,12-dienyl)benzenesulfonamide (0.441 g, 0.978 mmol) obtained in Step 3, triphenylphosphine (0.257 g, 0.978 mmol) and diethyl azodicarboxylate (Nacalai Tesque Inc., 40% toluene solution, 0.387 mL, 0.851 mmol) were added to a tetrahydrofuran solution (4 mL) of the 3-(methyl((9Z,12Z)-octadeca-9,12-dienyl)amino)propan-1-ol (0.220 g, 0.652 mol) obtained in Step 2 followed by stirring for 2 hours at 50° C. The reaction solution was allowed to cool to room temperature followed by the addition of saturated salt solution and extracting twice with hexane. The organic layers were dried with anhydrous magnesium sulfate, filtered and concentrated under reduced pressure. The resulting residue was purified by aminosilica gel column chromatography (hexane/ethyl acetate=80/20) to obtain a crude product of N-(3-(methyl((9Z,12Z)-octadeca-9,12-dienyl)amino)propyl)-2-nitro-N-((9Z,12Z)-octadeca-9,12-dienyl)benzenesulfonamide.

Dodecane-1-thiol (0.409 mL, 1.63 mmol) and 1,8-diazabicyclo[5.4.0]-7-undecene (0.246 mL, 1.630 mmol) were added to an acetonitrile solution (5 mL) of the resulting crude product of N-(3-(methyl((9Z,12Z)-octadeca-9,12-dienyl)amino)propyl)-2-nitro-N-((9Z,12Z)-octadeca-9,12-dienyl)benzenesulfonamide followed by stirring for 2 hours at 60° C. Water was added to the reaction solution followed by extracting twice with hexane. The organic layers were washed with saturated salt solution, dried with anhydrous magnesium sulfate, filtered and concentrated under reduced pressure. The resulting residue was purified by aminosilica gel column chromatography (hexane/ethyl acetate=75/25) to obtain N1-methyl-N1,N3-di((9Z,12Z)-octadeca-9,12-dienyl)propane-1,3-diamine (0.212 g, 0.363 mmol, yield: 56%).

ESI-MS m/z: 586 (M+H)$^+$; $^1$H-NMR (CDCl$_3$) δ: 0.89 (t, J=7.0 Hz, 6H), 1.22-1.51 (m, 36H), 1.66 (tt, J=7.2, 7.1 Hz, 2H), 2.01-2.08 (m, 8H), 2.20 (s, 3H), 2.29 (t, J=7.6 Hz, 2H), 2.36 (t, J=7.2 Hz, 2H), 2.58 (t, J=7.4 Hz, 2H), 2.62 (t, J=7.1 Hz, 2H), 2.75-2.80 (m, 4H), 5.29-5.43 (m, 8H).

Step 5:

(9Z,12Z)-octadeca-9,12-dienoic acid (0.104 g, 0.370 mmol), 1-ethyl-3-(3-dimethylaminopropyl)carbodiimide hydrochloride (0.106 g, 0.555 mmol) and N,N-dimethylaminopyridine (0.0023 g, 0.0188 mmol) were added to a 1,2-dichloroethane solution (1 mL) of the N1-methyl-N1,N3-di((9Z,12Z)-octadeca-9,12-dienyl)propane-1,3-diamine (0.108 g, 0.185 mmol) obtained in Step 4 followed by stirring for 1 hour at room temperature. The reaction solution was concentrated under reduced pressure. The resulting residue was purified by aminosilica gel column chromatography (hexane/ethyl acetate=85/15) to obtain (9Z,12Z)—N-(3-(methyl((9Z,12Z)-octadeca-9,12-dienyl)amino)propyl)-N-((9Z,12Z)-octadeca-9,12-dienamide (0.146 g, 0.172 mmol, yield: 93%).

ESI-MS m/z: 848 (M+H)$^+$; $^1$H-NMR (CDCl$_3$) δ: 0.89 (t, J=7.0 Hz, 9H), 1.21-1.74 (m, 54H), 2.01-2.08 (m, 12H), 2.18 (s, 3H), 2.24-2.33 (m, 6H), 2.74-2.80 (m, 6H), 3.18-3.5 (m, 5H), 5.29-5.42 (m, 12H).

Step 6:

The title compound (0.0804 g, 0.0895 mmol, yield: 76%) was obtained in the similar manner as Step 2 of Example 8 using (9Z,12Z)—N-(3-(methyl((9Z,12Z)-octadeca-9,12-dienyl)amino)propyl)-N-((9Z,12Z)-octadeca-9,12-dienyl)octadeca-9,12-dienamide (0.100 g, 0.118 mmol) obtained in Step 5 instead of (9Z,9′Z,12Z,12′Z)-2-(dimethylamino)-2-(((9Z,12Z)-octadeca-9,12-dienoyloxy)methyl) propane-1,3-diyl dioctadeca-9,12-dienoate.

ESI-MS m/z: 862 (M)$^+$; $^1$H-NMR (CDCl$_3$) δ: $^1$H-NMR (CDCl$_3$) δ: 0.88 (t, J=7.0 Hz, 9H), 1.22-1.41 (m, 46H), 1.49-1.78 (m, 6H), 1.93-2.10 (m, 14H), 2.30 (t, J=7.6 Hz, 2H), 2.74-2.79 (m, 6H), 3.24-3.35 (m, 8H), 3.36-3.47 (m, 4H), 3.59-3.67 (m, 2H), 5.28-5.42 (m, 12H).

Example 71

(R)-2-((2R,3R,4S)-3,4-bis((9Z,12Z)-octadeca-9,12-dienyloxy)tetrahydrofuran-2-yl)-N,N,N-trimethyl-2-((9Z,12Z)-octadeca-9,12-dienyloxy)ethanaminium Chloride (Compound V'-1)

Step 1:

4,4′-dimethoxytrityl chloride (0.704 g, 2.02 mmol) and N,N-dimethylaminopyridine (0.047 g, 0.383 mmol) were added to a pyridine solution (Wako Pure Chemical Industries, Ltd., 10 mL) of (2R,3R,4S)-2-((R)-1,2-dihydroxyethyl)tetrahydrofuran-3,4-diol (Sigma-Aldrich Corp., 0.135 g, 1.92 mmol) followed by stirring overnight at 50° C. After allowing to cool to room temperature, the reaction solution was concentrated under reduced pressure. The resulting residue was purified by aminosilica gel column chromatography (chloroform/methanol=90/10) to obtain (2R,3R,4S)-2-((R)-2-(bis(4-methoxyphenyl)phenyl)methoxy)-1-hydroxyethyl)tetrahydrofuran-3,4-diol (0.465 g, 0.997 mmol, yield: 52%).

$^1$H-NMR (CDCl$_3$) δ: 1.67-1.74 (m, 1H), 2.73-2.77 (m, 1H), 3.31 (dd, J=9.8, 6.2 Hz, 1H), 3.41-3.50 (m, 2H), 3.70 (dd, J=9.6, 1.3 Hz, 1H), 3.79 (s, 6H), 3.94 (dd, J=6.2, 3.5 Hz, 1H), 4.10-4.24 (m, 3H), 4.26-4.30 (m, 1H), 6.81-6.86 (m, 4H), 7.20-7.36 (m, 7H), 7.41-7.45 (m, 2H).

Step 2:

(9Z,12Z)-octadeca-9,12-dienyl methanesulfonate (0.247 g, 0.717 mmol) and sodium hydride (oily, 60%, 0.0459 g, 1.15 mmol) were added to a tetrahydrofuran solution (1 mL) of the (2R,3R,4S)-2-((R)-2-(bis(4-methoxyphenyl)phenyl)methoxy)-1-hydroxyethyl)tetrahydrofuran-3,4-diol (0.0669 g, 0.143 mmol) obtained in Step 1 followed by stirring overnight while refluxing. After allowing to cool to room temperature, saturated salt solution was added to the reaction solution followed by extraction with hexane. The organic layer was washed with saturated salt solution, dried with anhydrous magnesium sulfate, filtered and concentrated under reduced pressure. The resulting residue was purified by aminosilica gel column chromatography (hexane/ethyl acetate=90/10) to obtain a crude product of (2R,3R,4S)-2-((R)-2-(bis(4-methoxyphenyl)(phenyl)methoxy)-1-((9Z,12Z)-octadeca-9,12-dienyloxy)ethyl)-3,4-bis((9Z,12Z)-octadeca-9,12-dienyloxy)tetrahydrofuran.

Dichloromethane (1 mL) and trifluoroacetic acid (0.0500 mL, 0.649 mmol) were added to the resulting crude product of (2R,3R,4S)-2-((R)-2-(bis(4-methoxyphenyl)(phenyl)methoxy)-1-((9Z,12Z)-octadeca-9,12-dienyloxy)ethyl)-3,4-bis((9Z,12Z)-octadeca-9,12-dienyloxy)tetrahydrofuran followed by stirring for 5 minutes at room temperature. The reaction solution was concentrated under reduced pressure and the resulting residue was purified by silica gel column chromatography (hexane/ethyl acetate=70/30) to obtain (R)-2-((2R,3R,4S)-3,4-bis((9Z,12Z)-octadeca-9,12-dienyloxy)tetrahydrofuran-2-yl)-2-((9Z,12Z)-octadeca-9,12-dienyloxy)ethanol (0.0531 g, 0.0584 mmol, yield: 41%).

$^1$H-NMR (CDCl$_3$) δ: 0.89 (t, J=7.0 Hz, 9H), 1.23-1.43 (m, 48H), 1.50-1.62 (m, 6H), 2.01-2.09 (m, 12H), 2.32 (dd, J=8.2, 4.2 Hz, 1H), 2.74-2.80 (m, 6H), 3.37-3.50 (m, 4H), 3.54-3.69 (m, 3H), 3.69-3.77 (m, 2H), 3.80-3.87 (m, 2H), 3.88-3.95 (m, 2H), 4.06 (dd, J=9.8, 4.7 Hz, 1H), 5.28-5.42 (m, 12H).

Step 3:

Methanesulfonyl chloride (Junsei Chemical Co., Ltd., 0.0500 mL, 0.642 mmol) and triethylamine (0.150 mL, 1.08 mmol) were added to a dichloromethane solution (1 mL) of the (R)-2-((2R,3R,4S)-3,4-bis((9Z,12Z)-octadeca-9,12-dienyloxy)tetrahydrofuran-2-yl)-2-((9Z,12Z)-octadeca-9,12-dienyloxy)ethanol (0.0491 g, 0.0540 mmol) obtained in Step 2 followed by stirring for 1 hour at room temperature. Methanesulfonyl chloride (0.0500 mL, 0.642 mmol) and triethylamine (0.150 mL, 1.08 mmol) were added to the reaction solution followed by stirring for 1 hour at room temperature. Chloroform (1 mL) was added to the reaction solution followed by stirring for 1 hour at room temperature. Methanesulfonyl chloride (0.0500 mL, 0.642 mmol) and triethylamine (0.150 mL, 1.08 mmol) were added to the reaction solution followed by stirring for 2 hours at 40° C. and then stirring for 2 hours while refluxing. Saturated salt solution was added to the reaction solution followed by extraction with chloroform. The organic layer was dried with anhydrous magnesium sulfate, filtered and concentrated under reduced pressure. Tetrahydrofuran (1 mL) and dimethylamine (2.0 mol/L tetrahydrofuran solution, 2 mL, 2.00 mmol) were added to the resulting residue followed by stirring for 5 hours at 130° C. using a microwave reactor. The reaction solution was concentrated under reduced pressure. The resulting residue was purified by aminosilica gel column chromatography (hexane/ethyl acetate=95/5) to obtain a crude product of (R)-2-((2R,3R,4S)-3,4-bis((9Z,12Z)-octadeca-9,12-dienyloxy)tetrahydrofuran-2-yl)-N,N-dimethyl-2-((9Z,12Z)-octadeca-9,12-dienyloxy)ethanamine. Chloroform (0.5 mL) and methyl iodide (1.00 mL, 16.0 mmol) were added to the resulting crude product of (R)-2-((2R,3R,4S)-3,4-bis((9Z,12Z)-octadeca-9,12-dienyloxy)tetrahydrofuran-2-yl)-N, N-dimethyl-2-((9Z,12Z)-octadeca-9,12-dienyloxy)ethanamine followed by stirring for 2 hours at room temperature. The reaction solution was concentrated under reduced pressure. The residue was dissolved in a small amount of methanol-chloroform (1:1), loaded onto an ion exchange resin (Dow Chemical Co., Dowex™ 1×-2 100 mesh, type CL, about 20 times volume, prewashed with water and methanol), and eluted with methanol-chloroform (1:1). The eluate was concentrated under reduced pressure and the resulting residue was purified by silica gel column chromatography (chloroform/methanol=90/10) to obtain the title compound (0.0130 g, 0.0132 mmol, yield: 24%).

ESI-MS m/z: 951 (M)$^+$; $^1$H-NMR (CDCl$_3$) δ: 0.89 (t, J=7.0 Hz, 9H), 1.23-1.40 (m, 48H), 1.51-1.61 (m, 6H), 2.01-2.09 (m, 12H), 2.74-2.80 (m, 6H), 3.34-3.68 (m, 17H), 3.70-3.74 (m, 1H), 3.81-3.84 (m, 1H), 3.93-4.02 (m, 3H), 4.07-4.12 (m, 1H), 5.28-5.43 (m, 12H).

Reference Example 1

Methyldi((9Z,12Z)-octadeca-9,12-dienyl)amine (Compound CL-1)

(9Z,12Z)-octadeca-9,12-dienyl methanesulfonate (1.03 g, 3.00 mmol) was added to methylamine (Sigma-Aldrich Corp., approx. 2 mol/L tetrahydrofuran solution, 10.5 mL, 21.0 mmol) followed by stirring for 90 minutes while heating at 150° C. using a microwave reactor. The reaction solution was diluted with ethyl acetate, washed with 2 mol/L sodium hydroxide solution and then saturated salt water and dried with anhydrous magnesium sulfate followed by filtering and concentrating under reduced pressure to obtain a crude product of methyl((9Z,12Z)-octadeca-9,12-dienyl)amine.

(9Z,12Z)-octadeca-9,12-dienyl methanesulfonate (0.93 g, 2.70 mmol) and 50% aqueous sodium hydroxide solution (0.960 g, 12.0 mmol) were added to the resulting crude product followed by stirring for 60 minutes at 135° C. in an oil bath. After allowing to cool to room temperature, the reaction solution was diluted with ethyl acetate, washed with water and then saturated salt solution, and dried with anhydrous magnesium sulfate followed by filtering and concentrating under reduced pressure. The resulting residue was purified by silica gel column chromatography (chloroform/methanol=100/0 to 97/3) to obtain the title compound (1.07 g, 2.03 mmol, overall yield: 67%).

ESI-MS m/z: 529 (M+H)$^+$; $^1$H-NMR (CDCl$_3$) δ: 0.89 (t, J=6.7 Hz, 6H), 1.29, (br s, 32H), 1.40-1.51 (m, 4H), 1.97-2.06 (m, 8H), 2.20 (s, 3H), 2.30 (t, J=7.6 Hz, 4H), 2.77 (t, J=5.8 Hz, 4H), 5.28-5.43 (m, 8H).

Reference Example 2

2,2-dilinoleyl-4-(2-dimethylaminoethyl)-[1,3]-dioxolane (Compound CL-2)

CL-2 was synthesized using a method complying with the method described in WO 2010/042877.

Reference Example 3

(3R,4R)-3,4-bis((Z)-hexadec-9-enyloxy)-1-methylpyrrolidine (Compound CL-3)

Step 1:

(3R,4R)-1-benzylpyrrolidine-3,4-diol (Diverchim S. A., 146 mg, 0.753 mmol) was dissolved in tetrahydrofuran (5 mL) followed by addition of sodium hydride (oily, 60%, 241 mg, 6.03 mmol) while cooling with ice and then stirring for 30 minutes while refluxing. A tetrahydrofuran solution (5 mL) of (Z)-hexadec-9-enyl methanesulfonate (Nu-Chek Prep, Inc., 600 mg, 1.88 mmol) was dropped into the reaction mixture followed by stirring for 4 hours while refluxing. After allowing to cool to room temperature, the reaction was stopped with water. Saturated salt solution was added to the resulting reaction mixture followed by extracting twice with ethyl acetate. The organic layers were combined and dried with anhydrous magnesium sulfate followed by concentrating under reduced pressure. The residue was purified by silica gel column chromatography (chloroform/ methanol=100/0 to 98/2) to obtain (3R,4R)-1-benzyl-3,4-bis((Z)-hexadec-9-enyloxy)pyrrolidine (231 mg, 0.362 mmol, yield: 48%).

ESI-MS m/z: 639 (M+H)$^+$; $^1$H-NMR (CDCl$_3$) δ: 0.88 (t, J=6.8 Hz, 6H), 1.28-1.37 (m, 36H), 1.50-1.60 (m, 4H), 2.01 (q, J=5.9 Hz, 8H), 2.50 (dd, J=9.8, 4.6 Hz, 2H), 2.85 (dd, J=9.8, 5.9 Hz, 2H), 3.34-3.47 (m, 4H), 3.59 (q, J=12.6 Hz, 2H), 3.83 (t, J=4.6 Hz, 2H), 5.29-5.40 (m, 4H), 7.20-7.34 (m, 5H).

Step 2:

The (3R,4R)-1-benzyl-3,4-bis((Z)-hexadec-9-enyloxy)pyrrolidine (208 mg, 0.326 mmol) obtained in Step 1 was dissolved in 1,2-dichloroethane (4 mL) followed by the addition of 1-chloroethyl chloroformate (Tokyo Chemical Industry Co., Ltd., 0.107 mL, 0.978 mmol) and stirring for 1 hour at 130° C. Methanol (4 mL) was added to the reaction solution followed by additionally stirring for 1 hour at 130° C. After allowing to cool to room temperature, the reaction solution was concentrated under reduced pressure and the resulting residue was purified by silica gel column chromatography (chloroform/methanol=100/0 to 92/8). The resulting organic layer was washed with saturated aqueous sodium bicarbonate solution and then saturated salt solution and dried with anhydrous magnesium sulfate followed by filtering and concentrating under reduced pressure to obtain (3R,4R)-3,4-bis((Z)-hexadec-9-enyloxy)pyrrolidine (160 mg, 0.292 mmol, yield: 89%).

ESI-MS m/z: 549 (M+H)$^+$; $^1$H-NMR (CDCl$_3$) δ: 0.88 (t, J=6.6 Hz, 6H), 1.27-1.36 (m, 34H), 1.50-1.59 (m, 4H), 1.82 (brs, 3H), 2.01 (q, J=6.2 Hz, 8H), 2.84 (dd, J=12.5, 3.0 Hz, 2H), 3.10 (dd, J=12.5, 5.0 Hz, 2H), 3.43 (t, J=6.8 Hz, 4H), 3.77 (dd, J=5.0, 3.0 Hz, 2H), 5.29-5.40 (m, 4H).

Step 3:

The (3R,4R)-3,4-bis((Z)-hexadec-9-enyloxy)pyrrolidine (107 mg, 0.195 mmol) obtained in Step 2 was dissolved in 1,2-dichloroethane (1.5 mL) and methanol (1.5 mL) followed by the addition of formaldehyde (0.145 mL, 1.95 mmol) and sodium triacetoxyborohydride (207 mg, 0.976 mmol) and stirring for 1 hour at room temperature. Saturated aqueous sodium bicarbonate solution was added to the reaction solution followed by extraction of the aqueous layer with ethyl acetate. The organic layer was washed with saturated salt solution and dried with anhydrous magnesium sulfate followed by filtering and concentrating under reduced pressure. The resulting residue was purified by silica gel column chromatography (chloroform/methanol=100/0 to 96/4) to obtain the title compound (107 mg, 0.190 mmol, yield: 97%).

ESI-MS m/z: 563 (M+H)$^+$; $^1$H-NMR (CDCl$_3$) δ: 0.88 (t, J=6.8 Hz, 6H), 1.27-1.38 (m, 34H), 1.52-1.62 (m, 4H), 1.67 (br s, 2H), 2.01 (q, J=6.1 Hz, 8H), 2.32 (s, 3H), 2.47 (dd, J=9.8, 4.4 Hz, 2H), 2.83 (dd, J=9.8, 5.8 Hz, 2H), 3.36-3.49 (m, 4H), 3.81 (t, J=4.4 Hz, 2H), 5.29-5.41 (m, 4H).

Reference Example 4

3-(dimethylamino)propyl di((Z)-octadec-9-enyl) carbamate (Compound CL-4)

Step 1:

(Z)-octadec-9-enyl methanesulfonate (1.04 g, 3.00 mmol) was added to ammonia (Tokyo Chemical Industry Co., Ltd., approx. 2 mol/L methanol solution, 12.0 mL, 24.0 mmol) followed by stirring for 3 hours at 130° C. using a microwave reactor. Saturated aqueous sodium bicarbonate solution was added to the reaction solution followed by extracting five times with chloroform. The organic layers were combined, washed with saturated salt solution and dried with anhydrous magnesium sulfate followed by filtering and concentrating under reduced pressure to obtain a crude product of (Z)-octadec-9-enylamine.

(Z)-octadec-9-enyl methanesulfonate (0.832 g, 2.40 mmol) and 50% aqueous sodium hydroxide solution (0.960 g, 12.0 mmol) were added to the resulting crude product followed by stirring for 60 minutes at 110° C. in an oil bath. After allowing to cool to room temperature, the reaction solution was diluted with ethyl acetate, washed with water and then saturated salt solution, and dried with anhydrous magnesium sulfate followed by filtering and concentrating under reduced pressure. The resulting residue was purified by silica gel column chromatography (chloroform/methanol=100/0 to 95/5) to obtain di((Z)-octadec-9-enyl)amine (0.562 g, 1.085 mmol, yield: 36%).

ESI-MS m/z: 519 (M+H)$^+$; $^1$H-NMR (CDCl$_3$) δ: 0.88 (t, J=6.7 Hz, 6H), 1.29 (br s, 45H), 1.41-1.52 (m, 4H), 1.97-2.05 (m, 8H), 2.58 (t, J=7.2 Hz, 4H), 5.28-5.40 (m, 4H).

Step 2:

The di((Z)-octadec-9-enyl)amine (0.156 g, 0.301 mmol) obtained in Step 1 was dissolved in chloroform (3 mL) followed by the addition of 3-(dimethylamino)propyl-4-nitrophenyl carbonate hydrochloride (0.138 g, 0.452 mmol), synthesized using a method complying with the method described in the Journal of the American Chemical Society (J. Am. Chem. Soc.), 1981, Vol. 103, pp. 4194-4199, and triethylamine (0.168 mL, 1.21 mmol) and stirring for 60 minutes at 110° C. using a microwave reactor. 3-(dimethylamino)propyl 4-nitrophenyl carbonate hydrochloride (22.9 mg, 0.0753 mmol) was added to the reaction solution followed by stirring for 20 minutes at 110° C. using a microwave reactor. 3-(dimethylamino)propyl 4-nitrophenyl carbonate hydrochloride (22.9 mg, 0.0753 mmol) was added to the reaction solution followed by stirring for 20 minutes at 110° C. using a microwave reactor. 3-(dimethylamino)propyl 4-nitrophenyl carbonate hydrochloride (22.9 mg, 0.0753 mmol) was added to the reaction solution followed by stirring for 20 minutes at 110° C. using a microwave reactor. The reaction solution was diluted with chloroform, washed with saturated aqueous sodium bicarbonate solution and then washed with saturated salt solution and dried with anhydrous magnesium sulfate followed by filtering and concentrating under reduced pressure. The resulting residue was dissolved in a small amount of n-hexane/ethyl acetate (1/4), adsorbed onto a pad of amino-modified silica gel and eluted with n-hexane/ethyl acetate (1/4) followed by concentration under reduced pressure. The resulting residue was purified by silica gel column chromatography (chloroform/methanol=100/0 to 95/5) to obtain the title compound (0.173 g, 0.267 mmol, yield: 89%).

ESI-MS m/z: 648 (M+H)$^+$; $^1$H-NMR (CDCl$_3$) δ: 0.88 (t, J=6.6 Hz, 6H), 1.28 (br s, 44H), 1.45-1.55 (m, 4H), 1.75-1.85 (m, 2H), 1.97-2.04 (m, 8H), 2.23 (s, 6H), 2.34 (t, J=7.6 Hz, 2H), 3.13-3.24 (m, 4H), 4.10 (t, J=6.4 Hz, 2H), 5.28-5.40 (m, 4H).

Reference Example 5

N-methyl-N,N-bis(2-((Z)-hexadec-9-enyloxy)ethyl) amine (Compound CL-5)

A toluene solution (2 mL) of N-methyldiethanolamine (Tokyo Chemical Industry Co., Ltd., 82.6 mg, 0.693 mmol) was added to a toluene suspension (2 mL) of sodium hydride (oily, 60%, 222 mg, 5.55 mmol) while stirring followed by dropping in a toluene solution (2 mL) of (Z)-hexadec-9-enyl methanesulfonate (530 mg, 1.66 mmol). The resulting mixture was stirred for 2 hours while refluxing. After allowing to cool to room temperature, the reaction was stopped with water. Saturated salt solution was added to the resulting mixture followed by extraction with ethyl acetate. The organic layer was dried with anhydrous magnesium sulfate followed by concentrating under reduced pressure. The residue was purified by silica gel column chromatography (chloroform/methanol=100/0 to 98/2) to obtain the title compound (199 mg, 0.353 mmol, yield: 51%).

ESI-MS m/z: 565 (M+H)$^+$; $^1$H-NMR (CDCl$_3$) δ: 0.88 (t, J=6.8 Hz, 6H), 1.29 (br s, 36H), 1.51-1.56 (m, 4H), 1.97-2.04 (m, 8H), 2.33 (s, 3H), 2.64 (t, J=6.1 Hz, 4H), 3.41 (t, J=6.8 Hz, 4H), 3.52 (t, J=6.1 Hz, 4H), 5.28-5.40 (m, 4H).

Reference Example 6

(3R,4R)-3-(dimethylamino)propyl 3,4-bis((9Z,12Z)-octadeca-9,12-dienyloxy)pyrrolidine-1-carboxylate (Compound CL-6)

Step 1:

A toluene solution (70 mL) of (3R,4R)-1-benzylpyrrolidine-3,4-diol (Diverchim S. A., 3.50 g, 18.1 mmol) was added to a toluene suspension (100 mL) of sodium hydride (oily, 60%, 5.80 g, 145 mmol) while stirring followed by dropping in a toluene solution (30 mL) of (9Z,12Z)-octadeca-9,12-dienyl methanesulfonate (15.6 g, 45.3 mmol). The resulting mixture was stirred overnight while refluxing. After allowing to cool to room temperature, the reaction was stopped with saturated aqueous ammonium chloride solution. Saturated salt solution was added to the resulting mixture followed by extracting twice with ethyl acetate. The organic layers were combined and dried with anhydrous magnesium sulfate followed by concentrating under reduced pressure. The residue was purified by silica gel column chromatography (methanol/chloroform=0/100 to 2/98) to obtain (3R,4R)-1-benzyl-3,4-bis((9Z,12Z)-octadeca-9,12-dienyloxy)pyrrolidine (6.96 g, 10.1 mmol, yield: 56%).

ESI-MS m/z: 691 (M+H)$^+$; $^1$H-NMR (CDCl$_3$) δ: 0.89 (t, J=6.9 Hz, 6H), 1.26-1.38 (m, 30H), 1.52-1.62 (m, 6H), 2.05 (q, J=6.3 Hz, 8H), 2.50 (dd, J=9.9, 4.3 Hz, 2H), 2.77 (t, J=5.8 Hz, 4H), 2.85 (dd, J=9.6, 5.9 Hz, 2H), 3.37-3.45 (m, 4H), 3.52-3.66 (m, 2H), 3.83 (t, J=4.6 Hz, 2H), 5.28-5.43 (m, 8H), 7.23-7.33 (m, 5H).

Step 2:

The (3R,4R)-1-benzyl-3,4-bis((9Z,12Z)-octadeca-9,12-dienyloxy)pyrrolidine (6.96 g, 10.1 mmol) obtained in Step 1 was dissolved in 1,2-dichloroethane (100 mL) followed by the addition of 1-chloroethyl chloroformate (3.30 mL, 30.3 mmol) and stirring for 1 hour at 130° C. Methanol (100 mL) was added to the reaction solution followed by additionally stirring for 1 hour at 130° C. After allowing to cool to room temperature, the reaction solution was concentrated under reduced pressure and the resulting residue was purified by silica gel column chromatography (chloroform/methanol=100/0 to 92/8). The resulting organic layer was washed with saturated aqueous sodium bicarbonate solution and then saturated aqueous sodium chloride solution and dried with anhydrous magnesium sulfate followed by filtering and concentrating under reduced pressure to obtain (3R,4R)-3,4-bis((9Z,12Z)-octadeca-9,12-dienyloxy)pyrrolidine (5.56 g, 9.27 mmol, yield: 92%).

ESI-MS m/z: 601 (M+H)$^+$; $^1$H-NMR (CDCl$_3$) δ: 0.89 (t, J=6.9 Hz, 6H), 1.29-1.41 (m, 30H), 1.49-1.60 (m, 4H), 1.67 (br s, 3H), 2.05 (q, J=6.5 Hz, 8H), 2.75-2.85 (m, 6H), 3.09 (dd, J=12.4, 5.1 Hz, 2H), 3.37-3.49 (m, 4H), 3.76 (dd, J=5.0, 3.3 Hz, 2H), 5.28-5.43 (m, 8H).

Step 3:

The title compound (0.101 g, 0.139 mmol, 75%) was obtained in the similar manner as Step 2 of Reference Example 4 using (3R,4R)-3,4-bis((9Z,12Z)-octadeca-9,12-dienyloxy)pyrrolidine (0.111 g, 0.185 mmol) obtained in Step 2 instead of di((Z)-octadec-9-enyl)amine.

ESI-MS m/z: 730 (M+H)$^+$; $^1$H-NMR (CDCl$_3$) δ: 0.89 (t, J=6.9 Hz, 6H), 1.24-1.40 (m, 32H), 1.50-1.57 (m, 4H), 1.77-1.83 (m, 2H), 2.02-2.08 (m, 8H), 2.23 (s, 6H), 2.34 (t, J=7.4 Hz, 2H), 2.77 (t, J=6.8 Hz, 4H), 3.38-3.56 (m, 8H), 3.83-3.86 (m, 2H), 4.11 (t, J=6.5 Hz, 2H), 5.30-5.42 (m, 8H).

Example 72

Nucleic acid-containing lipid nanoparticles were produced in the following manner using Compound I-1 obtained in Example 1, Compound CL-1 obtained in Reference Example 1 and 1,2-distearoyl-sn-glycero-3-phosphoethanolamine-N-[methoxy(polyethylene glycol)-2000] (PEG-DSPE). The nucleic acid used was siRNA composed of base sequences consisting of a sense strand (5'-CCGUCGUAUUCGUGAGCAAGA-3') and an antisense strand (5'-UUGCUCACGAAUACGACGGUG-3') that inhibits the expression of luciferase (to be referred to as "Luc") gene, and was acquired from GeneDesign Inc. (to be referred to as "Luc siRNA").

Compound I-1 obtained in Example 1 was dissolved in 100% isopropyl alcohol to 10 mg/mL to prepare a lipid stock solution. Compound CL-1 obtained in Reference Example 1 was dissolved in 100% isopropyl alcohol to 50 mg/mL to prepare a lipid stock solution. 1,2-distearoyl-sn-glycero-3-phosphoethanolamine-N-[methoxy(polyethylene glycol)-2000] (PEG-DSPE) (NOF Corp.) was dissolved in 100% isopropyl alcohol to 20 mg/mL to prepare a lipid stock solution. Each lipid stock solution was stored at −20° C. and used after returning to room temperature after dissolving the lipid by warming to 60° C. immediately prior to formulating into a preparation.

Luc siRNA was dissolved in water for injection to 1 mg/mL to prepare an Luc siRNA solution.

The above-mentioned lipid stock solution of Compound I-1 was added to 20 mL of 80% isopropyl alcohol so as to be 0.469 μmol. Continuing, after adding 200 μL of the above-mentioned Luc siRNA solution and stirring for 1 minute, the above-mentioned lipid stock solutions of Compound CL-1 and PEG-DSPE were added to this solution at a ratio of Compound CL-1/PEG-DSPE of 1.41 μmol/0.209 μmol. Subsequently, water for injection was added at the rate of 62 mL/sec or higher to prepare a 20% or less isopropyl alcohol solution and form a crude preparation. The resulting crude preparation was concentrated using Amicon Ultra (Millipore Corp.) followed by replacing the solvent with physiological saline and filtering in a clean bench using a 0.2 μm filter (Toyo Roshi Kaisha, Ltd.). Moreover, the siRNA concentration of the resulting preparation was measured and diluted using physiological saline to an siRNA concentration of 0.1 mg/mL to obtain Preparation 1.

Example 73

The following indicates an example of the production of nucleic acid-containing lipid nanoparticles using Lipid A and Lipid B at various ratios.

Nucleic acid-containing lipid nanoparticles were produced in the following manner using Compound I-1 obtained in Example 1 and Compound CL-1 obtained in Reference Example 1.

The above-mentioned lipid stock solution of Compound I-1 was added to 20 mL of 80% isopropyl alcohol so as to be 0.939 μmol. Continuing, after adding 200 μL of the above-mentioned Luc siRNA solution and stirring for 1 minute, the above-mentioned lipid stock solutions of Compound CL-1 and PEG-DSPE were added to this solution at a ratio of Compound CL-1/PEG-DSPE of 0.939 μmol/0.209 μmol. Subsequently, water for injection was added at the rate of 62 mL/sec or higher to prepare a 20% or less isopropyl alcohol solution and form a crude preparation. The resulting crude preparation was concentrated using Amicon Ultra (Millipore Corp.) followed by replacing the solvent with physiological saline and filtering in a clean bench using a 0.2 μm filter (Toyo Roshi Kaisha, Ltd.). Moreover, the siRNA concentration of the resulting preparation was measured and diluted using physiological saline to an siRNA concentration of 0.1 mg/mL to obtain Preparation 2.

Example 74

Nucleic acid-containing lipid nanoparticles were produced in the following manner using Compound I-1 obtained in Example 1 and Compound CL-1 obtained in Reference Example 1.

The above-mentioned lipid stock solution of Compound I-1 was added to 20 mL of 80% isopropyl alcohol so as to be 1.41 μmol. Continuing, after adding 200 μL of the above-mentioned Luc siRNA solution and stirring for 1 minute, the above-mentioned lipid stock solutions of Compound CL-1 and PEG-DSPE were added to this solution at a ratio of Compound CL-1/PEG-DSPE of 0.469 μmol/0.209 μmol. Subsequently, water for injection was added at the rate of 62 mL/sec or higher to prepare a 20% or less isopropyl alcohol solution and form a crude preparation. The resulting crude preparation was concentrated using Amicon Ultra (Millipore Corp.) followed by replacing the solvent with physiological saline and filtering in a clean bench using a 0.2 μm filter (Toyo Roshi Kaisha, Ltd.). Moreover, the siRNA concentration of the resulting preparation was measured and diluted using physiological saline to an siRNA concentration of 0.1 mg/mL to obtain Preparation 3.

Example 75

Nucleic acid-containing lipid nanoparticles were produced in the manner indicated below using Compound I-1 obtained in Example 1.

The above-mentioned lipid stock solution of Compound I-1 was added to 20 mL of 80% isopropyl alcohol so as to be 1.88 μmol. Continuing, after adding 200 μL of the above-mentioned Luc siRNA solution and stirring for 1 minute, the above-mentioned lipid stock solution of PEG-DSPE was added to this solution so as to be 0.209 μmol. Subsequently, water for injection was added at the rate of 62 mL/sec or higher to prepare a 20% or less isopropyl alcohol solution and form a crude preparation. The resulting crude preparation was concentrated using Amicon Ultra (Millipore Corp.) followed by replacing the solvent with physiological saline and filtering in a clean bench using a 0.2 μm filter (Toyo Roshi Kaisha, Ltd.). Moreover, the siRNA concentration of the resulting preparation was measured and diluted using physiological saline to an siRNA concentration of 0.1 mg/mL to obtain Preparation 4.

Example 76

Nucleic acid-containing lipid nanoparticles were produced in the manner indicated below using Compound I-1 obtained in Example 1 and Compound CL-1 obtained in Reference Example 1.

1,2-dimyristoyl-sn-glycero-3-phosphoethanolamine-N-[methoxy(polyethylene glycol)-2000] (PEG-DMPE) (NOF Corp.) was dissolved in 100% isopropyl alcohol to 20 mg/mL to prepare a lipid stock solution. Preparation 5 was obtained in the similar manner as Example 72 with the exception of changing the PEG-DSPE of Preparation 1 to PEG-DMPE.

Example 77

Preparation 6 was obtained in the similar manner as Example 73 with the exception of changing the PEG-DSPE of Preparation 2 to PEG-DMPE.

Example 78

Preparation 7 was obtained in the similar manner as Example 74 with the exception of changing the PEG-DSPE of Preparation 3 to PEG-DMPE.

Example 79

Preparation 8 was obtained in the similar manner as Example 75 with the exception of changing the PEG-DSPE of Preparation 4 to PEG-DMPE.

Example 80

Nucleic acid-containing lipid nanoparticles were produced in the following manner using Compound I-1 obtained in Example 1 and Compound CL-2 obtained in Reference Example 2.

Compound CL-2 obtained in Reference Example 2 was dissolved in 100% isopropyl alcohol to 10 mg/mL to prepare a lipid stock solution. The lipid stock solution was stored at −20° C. and used after returning to room temperature after dissolving the lipid by warming to 60° C. immediately prior to formulating into a preparation.

Preparation 9 was obtained in the similar manner as Example 77 with the exception of changing Compound CL-1 of Preparation 6 to Compound CL-2.

Comparative Example 1

0.2 mL of the above-mentioned Luc siRNA solution was added to 20 mL of 80% isopropyl alcohol. Continuing, the above-mentioned lipid stock solutions of Compound CL-1 and PEG-DSPE were added at a ratio of Compound CL-1/PEG-DSPE of 1.88 μmol/0.209 μmol. Subsequently, water for injection was added at the rate of about 62 mL/sec or higher to prepare a 20% or less isopropyl alcohol solution and form a crude preparation. The resulting crude preparation was concentrated using Amicon Ultra (Millipore Corp.) followed by replacing the solvent with physiological saline and filtering in a clean bench using a 0.2 μm filter (Toyo Roshi Kaisha, Ltd.). Moreover, the siRNA concentration of the resulting preparation was measured and diluted using physiological saline to an siRNA concentration of 0.1 mg/mL to obtain Preparation 10.

Comparative Example 2

Preparation 11 was obtained in the similar manner as Comparative Example 1 with the exception of changing the PEG-DSPE of Preparation 10 to PEG-DMPE.

Comparative Example 3

Preparation 12 was obtained in the similar manner as Comparative Example 1 with the exception of changing Compound CL-1 of Preparation 11 to Compound CL-2 obtained in Reference Example 2.

Test Example 1

Measurement of Average Particle Size of Nucleic Acid-Containing Lipid Nanoparticles in a Preparation The average particle size of nucleic acid-containing lipid nanoparticles in a preparation was measured with a particle size measurement device (Zetasizer Nano ZS, Malvern Instruments Ltd.), and the result is shown in Table 45. Furthermore, PDI in the table indicates the polydispersity index.

TABLE 45

| Preparation No. | Size (nm) | PDI |
|---|---|---|
| 1 | 41.1 | 0.077 |
| 2 | 40.56 | 0.112 |
| 3 | 51.62 | 0.064 |
| 4 | 45.37 | 0.122 |
| 5 | 40.05 | 0.131 |
| 6 | 40.98 | 0.145 |
| 7 | 50.07 | 0.191 |
| 8 | 49.99 | 0.122 |
| 9 | 47.32 | 0.172 |
| 10 | 25.99 | 0.166 |
| 11 | 31.16 | 0.275 |
| 12 | 47.41 | 0.125 |

As a result, by dispersing lipid B (Compound CL-1 or CL-2), PEG lipid (PEG-DSPE or PEG-DMPE) and nucleic acid in isopropyl alcohol, adding water to the dispersion at a rate of 62 mL/sec or higher, and lowering the isopropyl alcohol concentration to 20% (v/v %) based on the resulting solution, the resulting Preparations 1 to 12 as described in Examples 72 to 80 and Comparative Examples 1 to 3 demonstrated a small average particle size of 52 nm or less regardless of whether or not they contained lipid A (Compound I-1).

Test Example 2

Evaluation of Serum Stability of siRNA Present in Nucleic Acid-Containing Lipid Nanoparticles The stability of siRNA contained in each of the preparations obtained in Examples 72 to 75 and 80 and Comparative Examples 1 and 3 (Preparations 1 to 4, 9, 10 and 12) was confirmed using method described below. After diluting each preparation with physiological saline to a final nucleic acid concentration of 0.05 mg/mL, fetal bovine serum (FBS, Gibco, 5891746D) was added to a concentration of 10% (v/v %) followed by incubating for 120 minutes at 37° C. The resulting solution was placed on ice followed by the addition of 150 μL of Trizol reagent (Trizol LS Reagent, Invitrogen Corp.) and 40 μL of chloroform, stirring with a vortex stirrer, allowing to stand undisturbed for 15 minutes, and recovering the supernatant containing nucleic acid following centrifugation for use as sample.

One equivalent of loading buffer (Novex TBU-Urea Sample Buffer, Invitrogen Corp.) was added to the sample, after which the sample was subjected to polyacrylamide gel electrophoresis (Novex 15% TBE-Urea Gel, Invitrogen Corp.), electrophoresed with running buffer (Novex TBE Running Buffer), and stained using nucleic acid staining reagent (SYBR Green II RNAGel Stain, Takara Bio Inc.).

As a result, although the siRNA present in Preparations 10 and 12 that did not contain Compound I-1 was degraded, siRNA in the preparations containing Compound I-1 (Preparations 1 to 4 and 9) was not degraded (FIG. 1). Moreover, a higher content of Compound I-1 was observed to result in greater inhibition of nucleic acid degradation by serum. On the basis thereof, Compound I-1 was suggested to contribute to the formation of lipid nanoparticles that improve the stability of siRNA with respect to serum.

Test Example 3

Evaluation Test of In Vitro Activity of Nucleic Acid-Containing Lipid Nanoparticles Each of the preparations of Comparative Examples 2 and 3 and Examples 76 to 80 (Preparations 5 to 9, 11 and 12) were introduced into HeLa cells derived from human cervical cancer in which expression of luciferase had been inhibited (referred to as Luc2CP-HeLa cells) according to the method described below.

After diluting with Opti-MEM (Gibco) to a final nucleic acid concentration of 0.3 nM to 100 nM, 20 μL aliquots of each preparation were dispensed into a 96-well culture plate followed by suspending the Luc2CP-HeLa cells in minimum essential medium (MEM) containing 1.25% fetal bovine serum (FBS, SAFC Biosciences Ltd.), disseminating the cells in the culture plate at 7500 cells/80 μl/well, and culturing under conditions of 37° C. and 5% $CO_2$ to introduce each preparation into the Luc2CP-HeLa cells. In addition, untreated cells were disseminated as a negative control.

The cells introduced with each preparation were cultured for 24 hours in an incubator at 37° C. and 5% $CO_2$ followed by treating the cells using a cell growth test assay (Cell Titer-Fluor Cell Viability Assay, Promega Corp., G6080) and luciferase quantification system (Steady-Glo Luciferase Assay System, Promega Corp., E2520) in accordance with the methods described in the manuals provided with the products, and measuring their respective luminescence intensities with a plate reader. The resulting amount of light emitted by luciferin was corrected with the amount of fluorescent light obtained with the cell growth test assay. The amount of light emitted by each preparation treatment group was calculated as a relative percentage based on a value of 1 for the amount of light emitted by the negative control after correction.

As is clear from FIG. 2, the inhibition rates of expression of Luc after introducing Preparations 5 to 9 containing Compound I-1 into Luc2CP-HeLa cells derived from human cervical cancer cells are higher in comparison with those of Preparations 11 and 12 not containing Compound I-1.

Accordingly, the lipid nanoparticles containing lipid A of the present invention were clearly determined to be preparations that enable nucleic acid to be introduced into cells and the like and facilitate the delivery of drugs into cells in vitro.

Example 81

Nucleic acid-containing lipid nanoparticles containing Compound I-1 obtained in Example 1, PEG-DMPE, 1,2- distearoyl-sn-glycero-3-phosphocholine (DSPC), cholesterol and Compound CL-1 obtained in Reference Example 1 were prepared in the manner indicated below.

The DSPC and cholesterol were acquired from NCR Corp.

The 1 mg/mL Luc siRNA solution described in Example 72 was used for the nucleic acid.

Compound I-1 obtained in Example 1 was dissolved in 100% isopropyl alcohol to 10 mg/mL to prepare a lipid stock solution.

Compound CL-1 obtained in Reference Example 1 was dissolved in 100% isopropyl alcohol to 50 mg/mL to prepare a lipid stock solution. The PEG-DMPE, DSPC and cholesterol were each dissolved in 100% isopropyl alcohol to 20 mg/mL to prepare their respective lipid stock solutions. Each lipid stock solution was stored at −20° C. and used after returning to room temperature after dissolving the lipid by warming to 60° C. immediately prior to formulating into a preparation.

Compound I-1 was added to 20 mL of 80% isopropyl alcohol so as to be 0.156 µmol. Continuing, after adding 200 µL of siRNA solution and stirring for 1 minute, the lipid stock solutions of Compound CL-1, PEG-DMPE, DSPC and cholesterol were added to this solution at a ratio of Compound CL-1/PEG-DMPE/DSPC/cholesterol of 1.88 µmol/0.145 µmol/0.566 µmol/1.17 µmol. Subsequently, water for injection was added at the rate of 62 mL/sec or higher to prepare a 20% or less isopropyl alcohol solution and form a crude preparation. The resulting crude preparation was concentrated using Amicon Ultra (Millipore Corp.) followed by replacing the solvent with physiological saline and filtering in a clean bench using a 0.2 µm filter (Toyo Roshi Kaisha, Ltd.). Moreover, the siRNA concentration of the resulting preparation was measured and diluted using physiological saline to an siRNA concentration of 0.1 mg/mL to obtain Preparation 13.

Example 82

Nucleic acid-containing lipid nanoparticles containing Compound I-1 obtained in Example 1, PEG-DMPE, 1,2-distearoyl-sn-glycero-3-phosphocholine (DSPC), cholesterol and Compound CL-1 obtained in Reference Example 1 were prepared in the manner indicated below.

Compound I-1 was added to 20 mL of 80% isopropyl alcohol so as to be 0.313 µmol. Continuing, after adding 200 µL of siRNA solution and stirring for 1 minute, the lipid stock solutions of Compound CL-1, PEG-DMPE, DSPC and cholesterol were added to this solution at a ratio of Compound CL-1/PEG-DMPE/DSPC/cholesterol of 1.88 µmol/0.145 µmol/0.515 µmol/1.07 µmol. Subsequently, water for injection was added at the rate of 62 mL/sec or higher to prepare a 20% or less isopropyl alcohol solution and form a crude preparation. The resulting crude preparation was concentrated using Amicon Ultra (Millipore Corp.) followed by replacing the solvent with physiological saline and filtering in a clean bench using a 0.2 µm filter (Toyo Roshi Kaisha, Ltd.). Moreover, the siRNA concentration of the resulting preparation was measured and diluted using physiological saline to an siRNA concentration of 0.1 mg/mL to obtain Preparation 14.

Example 83

Nucleic acid-containing lipid nanoparticles containing Compound I-1 obtained in Example 1, PEG-DMPE, 1,2-distearoyl-sn-glycero-3-phosphocholine (DSPC), cholesterol and Compound CL-1 obtained in Reference Example 1 were prepared in the manner indicated below.

Compound I-1 was added to 20 mL of 80% isopropyl alcohol so as to be 0.469 µmol. Continuing, after adding 200 µL of siRNA solution and stirring for 1 minute, the lipid stock solutions of Compound CL-1, PEG-DMPE, DSPC and cholesterol were added to this solution at a ratio of Compound CL-1/PEG-DMPE/DSPC/cholesterol of 1.88 µmol/0.145 µmol/0.464 µmol/0.963 µmol. Subsequently, water for injection was added at the rate of 62 mL/sec or higher to prepare a 20% or less isopropyl alcohol solution and form a crude preparation. The resulting crude preparation was concentrated using Amicon Ultra (Millipore Corp.) followed by replacing the solvent with physiological saline and filtering in a clean bench using a 0.2 µm filter (Toyo Roshi Kaisha, Ltd.). Moreover, the siRNA concentration of the resulting preparation was measured and diluted using physiological saline to an siRNA concentration of 0.1 mg/mL to obtain Preparation 15.

Example 84

Nucleic acid-containing lipid nanoparticles containing Compound I-1 obtained in Example 1, PEG-DMPE, 1,2-distearoyl-sn-glycero-3-phosphocholine (DSPC), cholesterol and Compound CL-1 obtained in Reference Example 1 were prepared in the manner indicated below.

Compound I-1 was added to 20 mL of 80% isopropyl alcohol so as to be 0.626 µmol. Continuing, after adding 200 µL of siRNA solution and stirring for 1 minute, the lipid stock solutions of Compound CL-1, PEG-DMPE, DSPC and cholesterol were added to this solution at a ratio of Compound CL-1/PEG-DMPE/DSPC/cholesterol of 1.88 µmol/0.145 µmol/0.413 µmol/0.858 µmol. Subsequently, water for injection was added at the rate of 62 mL/sec or higher to prepare a 20% or less isopropyl alcohol solution and form a crude preparation. The resulting crude preparation was concentrated using Amicon Ultra (Millipore Corp.) followed by replacing the solvent with physiological saline and filtering in a clean bench using a 0.2 µm filter (Toyo Roshi Kaisha, Ltd.). Moreover, the siRNA concentration of the resulting preparation was measured and diluted using physiological saline to an siRNA concentration of 0.1 mg/mL to obtain Preparation 16.

Example 85

Preparation 17 was obtained in the similar manner as Example 81 with the exception of changing Compound CL-1 of Preparation 13 to Compound CL-2.

Example 86

Preparation 18 was obtained in the similar manner as Example 82 with the exception of changing Compound CL-1 of Preparation 14 to Compound CL-2.

Example 87

Preparation 19 was obtained in the similar manner as Example 83 with the exception of changing Compound CL-1 of Preparation 15 to Compound CL-2.

Example 88

Preparation 20 was obtained in the similar manner as Example 84 with the exception of changing Compound CL-1 of Preparation 16 to Compound CL-2.

Comparative Example 4

Nucleic acid-containing lipid nanoparticles containing PEG-DMPE, DSPC, cholesterol and Compound CL-1 were produced in the manner indicated below.

0.2 mL of Luc siRNA solution was added to 20 mL of 80% isopropyl alcohol. Continuing, Compound CL-1, PEG-DMPE, DSPC and cholesterol were added to this solution at a ratio of Compound CL-1/PEG-DMPE/DSPC/cholesterol of 1.88 µmol/O. 145 µmol/0.617 µmol/1.28 µmol. Subsequently, water for injection was added at the rate of 62 mL/sec or higher to prepare a 20% or less isopropyl alcohol solution and form a crude preparation. The resulting crude preparation was concentrated using Amicon Ultra (Millipore Corp.) followed by replacing the solvent with physiological saline and filtering in a clean bench using a 0.2 µm filter (Toyo Roshi Kaisha, Ltd.). Moreover, the siRNA concentration of the resulting preparation was measured and diluted using physiological saline to an siRNA concentration of 0.1 mg/mL to obtain Preparation 21.

Comparative Example 5

Preparation 22 was obtained in the similar manner as Comparative Example 4 with the exception of changing Compound CL-1 of Preparation 21 to Compound CL-2.

Test Example 4

Measurement of Average Particle Size of Nucleic Acid-Containing Lipid Nanoparticles The average particle size of nucleic acid-containing lipid nanoparticles in a preparation was measured with a particle size measurement device (Zetasizer Nano ZS, Malvern Instruments Ltd.) (Table 46). Furthermore, PDI in the table indicates the polydispersity index.

TABLE 46

| Preparation No. | Size (nm) | PDI |
|---|---|---|
| 13 | 38.29 | 0.146 |
| 14 | 45.23 | 0.163 |
| 15 | 45.74 | 0.116 |
| 16 | 45.46 | 0.161 |
| 17 | 50.18 | 0.135 |
| 18 | 55.92 | 0.164 |
| 19 | 55.81 | 0.199 |
| 20 | 53.36 | 0.192 |
| 21 | 33.44 | 0.326 |
| 22 | 47.73 | 0.165 |

As a result, Preparations 13 to 22 (13-22) described in Examples 81 to 88 and Comparative Examples 4 and 5, formed by dispersing a complex of lipid B (Compound CL-1 or CL-2), DSPC, cholesterol, PEG-DMPE and nucleic acid in isopropyl alcohol and rapidly adding water to the dispersion, demonstrated a small average particle size of 56 nm or less regardless of whether or not they contained lipid A (Compound I-1).

Test Example 5

Evaluation Test of In Vitro Activity of Nucleic Acid-Containing Lipid Nanoparticles Each of Preparations 13 to 22 obtained in Examples 81 to 88 and Comparative Examples 4 and 5 were introduced into HeLa cells derived from human cervical cancer in which expression of luciferase had been inhibited (Luc2CP-HeLa cells) according to the method described below.

After diluting with Opti-MEM (Gibco) to a final nucleic acid concentration of 0.3 nM to 100 nM, 20 µL aliquots of each preparation were dispensed into a 96-well culture plate followed by suspending the Luc2CP-HeLa cells in minimum essential medium (MEM) containing 1.25% fetal bovine serum (FBS, SAFC Biosciences Ltd.), disseminating the cells in the culture plate at 7500 cells/80 µl/well, and culturing under conditions of 37° C. and 5% $CO_2$ to introduce each preparation into the Luc2CP-HeLa cells. In addition, untreated cells were disseminated as a negative control.

The cells introduced with each preparation were cultured for 24 hours in an incubator at 37° C. and 5% $CO_2$ followed by treating the cells using a luciferase quantification system (Steady-Glo Luciferase Assay System, Promega Corp., E2520) in accordance with the method described in the manual provided with the product, and measuring their respective luminescence intensities with a plate reader. The amount of light emitted by each preparation treatment group was calculated as a relative percentage based on a value of 1 for the amount of light emitted by the negative control.

As is clear from FIG. 3, the inhibition rates of expression of Luc after introducing those preparations containing lipid B in the form of Compound CL-1 and containing Compound I-1 (Preparations 13 to 16) into Luc2CP-HeLa cells derived from human cervical cancer cells are higher in comparison with that of the preparation not containing Compound I-1 (Preparation 21). In addition, similar results were obtained for those preparations containing lipid B in the form of Compound CL-2 and containing Compound I-1 (Preparations 17 to 20) in a comparison with the preparation not containing Compound I-1 (Preparation 22).

Accordingly, the lipid nanoparticles containing lipid A of the present invention were clearly determined to be preparations that enable nucleic acid to be introduced into cells and the like and facilitate the delivery of drugs into cells in vitro.

Example 89

Nucleic acid-containing lipid nanoparticles containing Compound I-1, PEG-DMPE, DSPC, cholesterol and various types of lipid B were prepared in the manner indicated below.

The 1 mg/mL Luc siRNA solution described in Example 72 was used for the nucleic acid.

Lipid B, PEG-DMPE, DSPC and cholesterol were each dissolved in 100% isopropyl alcohol to 20 mg/mL to prepare lipid stock solutions. Lipid A was dissolved in 100% isopropyl alcohol to 5 mg/mL to 10 mg/mL to prepare lipid stock solutions. Each lipid stock solution was stored at −20° C. and used after returning to room temperature after dissolving the lipid by warming to 60° C. immediately prior to formulating into a preparation.

Compound I-1 obtained in Example 1 was dissolved in 100% isopropyl alcohol to 10 mg/mL to prepare a lipid stock solution. The stock solution was stored at −20° C. and used after returning to room temperature after dissolving the lipid by warming to 60° C. immediately prior to formulating into a preparation.

Compound I-1 was added to 20 mL of 80% isopropyl alcohol so as to be 0.626 µmol. Continuing, after adding 200 µL of siRNA solution and stirring for 1 minute, the lipid stock solutions of Compound CL-5, PEG-DMPE, DSPC and cholesterol were added to this solution at a ratio of Compound CL-5/PEG-DMPE/DSPC/cholesterol of 1.88 µmol/

0.145 µmol/0.413 µmol/0.858 µmol. Subsequently, water for injection was added at the rate of 62 mL/sec or higher to prepare a 20% or less isopropyl alcohol solution and form a crude preparation. The resulting crude preparation was concentrated using Amicon Ultra (Millipore Corp.) followed by replacing the solvent with physiological saline and filtering in a clean bench using a 0.2 µm filter (Toyo Roshi Kaisha, Ltd.). Moreover, the siRNA concentration of the resulting preparation was measured and diluted using physiological saline to an siRNA concentration of 0.1 mg/mL to obtain Preparation 23.

Example 90

Preparation 24 was obtained in the similar manner as Example 89 with the exception of changing Compound CL-5 of Preparation 23 to Compound CL-3 obtained in Reference Example 3.

Example 91

Preparation 25 was obtained in the similar manner as Example 89 with the exception of changing Compound CL-5 of Preparation 23 to Compound CL-4 obtained in Reference Example 4.

Comparative Example 6

0.2 mL of Luc siRNA solution was added to 20 mL of 80% isopropyl alcohol. Continuing, the above-mentioned lipid stock solutions of Compound CL-5, PEG-DMPE, DSPC and cholesterol were added at a ratio of Compound CL-5/PEG-DMPE/DSPC/cholesterol of 1.88 µmol/0.145 µmol/0.617 µmol/1.28 µmol. Subsequently, water for injection was added at the rate of 62 mL/sec or higher to prepare a 20% or less isopropyl alcohol solution and form a crude preparation. The resulting crude preparation was concentrated using Amicon Ultra (Millipore Corp.) followed by replacing the solvent with physiological saline and filtering in a clean bench using a 0.2 µm filter (Toyo Roshi Kaisha, Ltd.). Moreover, the siRNA concentration of the resulting preparation was measured and diluted using physiological saline to an siRNA concentration of 0.1 mg/mL to obtain Preparation 26.

Comparative Example 7

Preparation 27 was obtained in the similar manner as Comparative Example 6 with the exception of changing Compound CL-5 of Preparation 26 to Compound CL-3 obtained in Reference Example 3.

Comparative Example 8

Preparation 28 was obtained in the similar manner as Comparative Example 6 with the exception of changing Compound CL-5 of Preparation 26 to Compound CL-6 obtained in Reference Example 6.

Comparative Example 9

Preparation 29 was obtained in the similar manner as Comparative Example 6 with the exception of changing Compound CL-5 of Preparation 26 to Compound CL-4 obtained in Reference Example 4.

Test Example 6

Measurement of Average Particle Size of Nucleic Acid-Containing Lipid Nanoparticles The average particle size of nucleic acid-containing lipid nanoparticles in a preparation was measured with a particle size measurement device (Zetasizer Nano ZS, Malvern Instruments Ltd.) (Table 47). Furthermore, PDI in the table indicates the polydispersity index.

TABLE 47

| Preparation No. | Lipid A | Lipid B | Size (nm) | PDI |
|---|---|---|---|---|
| 23 | I-1 | CL-5 | 47.96 | 0.081 |
| 24 | I-1 | CL-3 | 45.23 | 0.102 |
| 25 | I-1 | CL-4 | 45.28 | 0.162 |
| 26 | — | CL-5 | 42.42 | 0.186 |
| 27 | — | CL-3 | 36.77 | 0.168 |
| 28 | — | CL-6 | 37.83 | 0.190 |
| 29 | — | CL-4 | 35.42 | 0.255 |

As a result, Preparations 23 to 29 described in Examples 89 to 91 and Comparative Examples 6 to 9, formed by dispersing a complex of lipid B (Compounds CL-3 to CL-6), DSPC, cholesterol, PEG-DMPE and nucleic acid in isopropyl alcohol and rapidly adding water to the dispersion, demonstrated a small average particle size of 50 nm or less regardless of whether or not they contained lipid A (Compound I-1).

Test Example 7

Evaluation Test of In Vitro Activity of Nucleic Acid-Containing Lipid Nanoparticles Each of the preparations obtained in Examples 89 to 91 and Comparative Examples 6 to 9 (Preparations 23 to 29) were introduced into HeLa cells derived from human cervical cancer in which expression of luciferase had been inhibited (Luc2CP-HeLa cells) according to the method described below.

After diluting with Opti-MEM (Gibco) to a final nucleic acid concentration of 10 nM, 20 µL aliquots of each preparation were dispensed into a 96-well culture plate followed by suspending the Luc2CP-HeLa cells in minimum essential medium (MEM) containing 1.25% fetal bovine serum (FBS, SAFC Biosciences Ltd.), disseminating the cells in the culture plate at 7500 cells/80 µl/well, and culturing under conditions of 37° C. and 5% $CO_2$ to introduce each preparation into the Luc2CP-HeLa cells. In addition, untreated cells were disseminated as a negative control.

The cells introduced with each preparation were cultured for 24 hours in an incubator at 37° C. and 5% $CO_2$ followed by treating the cells using a luciferase quantification system (Steady-Glo Luciferase Assay System, Promega Corp., E2520) in accordance with the method described in the manual provided with the product, and measuring their respective luminescence intensities with a plate reader. The amount of light emitted by each preparation treatment group was calculated as a relative percentage based on a value of 1 for the amount of light emitted by the negative control.

As is clear from FIG. 4, the inhibition rates of expression of Luc after introducing those preparations containing Compound I-1 (Preparations 23 to 25) into Luc2CP-HeLa cells were higher in comparison with those of the preparations not containing Compound I-1 (Preparations 26 to 29).

Accordingly, the lipid nanoparticles containing lipid A of the present invention enable nucleic acid to be introduced into cells and the like, and based on the results of in vitro testing, are assumed to be preparations that facilitate the delivery of drugs into cells in vivo as well.

Nucleic acid-containing lipid nanoparticles containing various types of lipid A, various types of lipid B, PEG-DMPE, DSPC and cholesterol were prepared in the manner indicated below.

The 1 mg/mL Luc siRNA solution described in Example 72 was used for the nucleic acid used in Examples 92 to 216, lipid A was dissolved in 100% isopropyl alcohol to 5 mg/mL to 10 mg/mL to prepare lipid stock solutions, PEG-DMPE, DSPC and cholesterol were each dissolved in 100% isopropyl alcohol to 20 mg/mL to respectively prepare lipid stock solutions, and lipid B was dissolved in 100% isopropyl alcohol to 10 mg/mL to 20 mg/mL to prepare lipid stock solutions. Each stock solution was stored at −20° C. and used after returning to room temperature after dissolving the lipid by warming to 60° C. immediately prior to formulating into a preparation.

Example 92

Preparation 30 was obtained in the similar manner as Example 84 with the exception of changing Compound I-1 of Preparation 16 to Compound I-4 obtained in Example 4.

Example 93

Preparation 31 was obtained in the similar manner as Example 90 with the exception of changing Compound I-1 of Preparation 24 to Compound I-4 obtained in Example 4.

Example 94

Preparation 32 was obtained in the similar manner as Example 91 with the exception of changing Compound I-1 of Preparation 25 to Compound I-4 obtained in Example 4.

Example 95

Preparation 33 was obtained in the similar manner as Example 84 with the exception of changing Compound I-1 of Preparation 16 to Compound I-5 obtained in Example 5.

Example 96

Preparation 34 was obtained in the similar manner as Example 90 with the exception of changing Compound I-1 of Preparation 24 to Compound I-5 obtained in Example 5.

Example 97

Preparation 35 was obtained in the similar manner as Example 89 with the exception of changing Compound CL-5 of Preparation 23 to Compound CL-6 obtained in Reference Example 6, and changing Compound I-1 to Compound I-5 obtained in Example 5.

Example 98

Preparation 36 was obtained in the similar manner as Example 91 with the exception of changing Compound I-1 of Preparation 25 to Compound I-5 obtained in Example 5.

Example 99

Preparation 37 was obtained in the similar manner as Example 84 with the exception of changing Compound I-1 of Preparation 16 to Compound II-6 obtained in Example 13.

Example 100

Preparation 38 was obtained in the similar manner as Example 89 with the exception of changing Compound I-1 of Preparation 23 to Compound II-6 obtained in Example 13.

Example 101

Preparation 39 was obtained in the similar manner as Example 90 with the exception of changing Compound I-1 of Preparation 24 to Compound II-6 obtained in Example 13.

Example 102

Preparation 40 was obtained in the similar manner as Example 97 with the exception of changing Compound I-5 of Preparation 35 to Compound II-6 obtained in Example 13.

Example 103

Preparation 41 was obtained in the similar manner as Example 91 with the exception of changing Compound I-1 of Preparation 25 to Compound II-6 obtained in Example 13.

Example 104

Preparation 42 was obtained in the similar manner as Example 84 with the exception of changing Compound I-1 of Preparation 16 to Compound II-2 obtained in Example 9.

Example 105

Preparation 43 was obtained in the similar manner as Example 89 with the exception of changing Compound I-1 of Preparation 23 to Compound II-2 obtained in Example 9.

Example 106

Preparation 44 was obtained in the similar manner as Example 90 with the exception of changing Compound I-1 of Preparation 24 to Compound II-2 obtained in Example 9.

Example 107

Preparation 45 was obtained in the similar manner as Example 91 with the exception of changing Compound I-1 of Preparation 25 to Compound II-2 obtained in Example 9.

Example 108

Preparation 46 was obtained in the similar manner as Example 90 with the exception of changing Compound I-1 of Preparation 24 to Compound I-3 obtained in Example 3.

Example 109

Preparation 47 was obtained in the similar manner as Example 90 with the exception of changing Compound I-1 of Preparation 24 to Compound II-7 obtained in Example 14.

Example 110

Preparation 48 was obtained in the similar manner as Example 82 with the exception of changing Compound I-1 of Preparation 14 to Compound II-1 obtained in Example 8.

Example 111

Preparation 49 was obtained in the similar manner as Example 110 with the exception of changing Compound CL-1 of Preparation 48 to Compound CL-5 obtained in Reference Example 5.

Example 112

Preparation 50 was obtained in the similar manner as Example 110 with the exception of changing Compound CL-1 of Preparation 48 to Compound CL-3 obtained in Reference Example 3.

Example 113

Preparation 51 was obtained in the similar manner as Example 110 with the exception of changing Compound CL-1 of Preparation 48 to Compound CL-4 obtained in Reference Example 4.

Example 114

Preparation 52 was obtained in the similar manner as Example 82 with the exception of changing Compound I-1 of Preparation 14 to Compound II-3 obtained in Example 10.

Example 115

Preparation 53 was obtained in the similar manner as Example 111 with the exception of changing Compound II-1 of Preparation 49 to Compound II-3 obtained in Example 10.

Example 116

Preparation 54 was obtained in the similar manner as Example 113 with the exception of changing Compound II-1 of Preparation 51 to Compound II-3 obtained in Example 10.

Example 117

Preparation 55 was obtained in the similar manner as Example 82 with the exception of changing Compound I-1 of Preparation 14 to Compound II-12 obtained in Example 19.

Example 118

Preparation 56 was obtained in the similar manner as Example 111 with the exception of changing Compound II-1 of Preparation 49 to Compound II-12 obtained in Example 19.

Example 119

Preparation 57 was obtained in the similar manner as Example 113 with the exception of changing Compound II-1 of Preparation 51 to Compound II-12 obtained in Example 19.

Example 120

Preparation 58 was obtained in the similar manner as Example 82 with the exception of changing Compound CL-1 of Preparation 14 to Compound CL-6 obtained in Reference Example 6, and changing Compound I-1 to Compound II-12 obtained in Example 19.

Example 121

Preparation 59 was obtained in the similar manner as Example 82 with the exception of changing Compound I-1 of Preparation 14 to Compound II-21 obtained in Example 28.

Example 122

Preparation 60 was obtained in the similar manner as Example 111 with the exception of changing Compound II-1 of Preparation 49 to Compound II-21 obtained in Example 28.

Example 123

Preparation 61 was obtained in the similar manner as Example 113 with the exception of changing Compound II-1 of Preparation 51 to Compound II-21 obtained in Example 28.

Example 124

Preparation 62 was obtained in the similar manner as Example 81 with the exception of changing Compound I-1 of Preparation 13 to Compound II-17 obtained in Example 24.

Example 125

Preparation 63 was obtained in the similar manner as Example 124 with the exception of changing Compound CL-1 of Preparation 62 to Compound CL-4 obtained in Reference Example 4.

Example 126

Preparation 64 was obtained in the similar manner as Example 82 with the exception of changing Compound I-1 of Preparation 14 to Compound IV-3 obtained in Example 70.

Example 127

Preparation 65 was obtained in the similar manner as Example 82 with the exception of changing Compound I-1 of Preparation 14 to Compound III-2 obtained in Example 63.

Example 128

Preparation 66 was obtained in the similar manner as Example 82 with the exception of changing Compound I-1 of Preparation 14 to Compound II-23 obtained in Example 30.

Example 129

Preparation 67 was obtained in the similar manner as Example 111 with the exception of changing Compound II-1 of Preparation 49 to Compound II-23 obtained in Example 30.

Example 130

Preparation 68 was obtained in the similar manner as Example 82 with the exception of changing Compound I-1 of Preparation 14 to Compound II-28 obtained in Example 37.

Example 131

Preparation 69 was obtained in the similar manner as Example 111 with the exception of changing Compound II-1 of Preparation 49 to Compound II-28 obtained in Example 37.

Example 132

Preparation 70 was obtained in the similar manner as Example 82 with the exception of changing Compound I-1 of Preparation 14 to Compound II-22 obtained in Example 29.

Example 133

Preparation 71 was obtained in the similar manner as Example 111 with the exception of changing Compound II-1 of Preparation 49 to Compound II-22 obtained in Example 29.

Example 134

Preparation 72 was obtained in the similar manner as Example 82 with the exception of changing Compound I-1 of Preparation 14 to Compound II-10 obtained in Example 17.

Example 135

Preparation 73 was obtained in the similar manner as Example 111 with the exception of changing Compound II-1 of Preparation 49 to Compound II-10 obtained in Example 17.

Example 136

Preparation 74 was obtained in the similar manner as Example 82 with the exception of changing Compound I-1 of Preparation 14 to Compound II-30 obtained in Example 39.

Example 137

Preparation 75 was obtained in the similar manner as Example 111 with the exception of changing Compound II-1 of Preparation 49 to Compound II-30 obtained in Example 39.

Example 138

Preparation 76 was obtained in the similar manner as Example 82 with the exception of changing Compound I-1 of Preparation 14 to Compound II-31 obtained in Example 40.

Example 139

Preparation 77 was obtained in the similar manner as Example 111 with the exception of changing Compound II-1 of Preparation 49 to Compound II-31 obtained in Example 40.

Example 140

Preparation 78 was obtained in the similar manner as Example 82 with the exception of changing Compound I-1 of Preparation 14 to Compound II-34 obtained in Example 43.

Example 141

Preparation 79 was obtained in the similar manner as Example 111 with the exception of changing Compound II-1 of Preparation 49 to Compound II-34 obtained in Example 43.

Example 142

Preparation 80 was obtained in the similar manner as Example 82 with the exception of changing Compound I-1 of Preparation 14 to Compound II-16 obtained in Example 23.

Example 143

Preparation 81 was obtained in the similar manner as Example 111 with the exception of changing Compound II-1 of Preparation 49 to Compound II-16 obtained in Example 23.

Example 144

Preparation 82 was obtained in the similar manner as Example 111 with the exception of changing Compound II-1 of Preparation 49 to Compound I-2 obtained in Example 2.

Example 145

Preparation 83 was obtained in the similar manner as Example 111 with the exception of changing Compound II-1 of Preparation 49 to Compound II-5 obtained in Example 12.

Example 146

Preparation 84 was obtained in the similar manner as Example 111 with the exception of changing Compound II-1 of Preparation 49 to Compound II-18 obtained in Example 25.

Example 147

Preparation 85 was obtained in the similar manner as Example 111 with the exception of changing Compound II-1 of Preparation 49 to Compound II-27 obtained in Example 36.

Example 148

Preparation 86 was obtained in the similar manner as Example 111 with the exception of changing Compound II-1 of Preparation 49 to Compound II-20 obtained in Example 27.

Example 149

Preparation 87 was obtained in the similar manner as Example 111 with the exception of changing Compound II-1 of Preparation 49 to Compound II-15 obtained in Example 22.

Example 150

Preparation 88 was obtained in the similar manner as Example 111 with the exception of changing Compound II-1 of Preparation 49 to Compound III-1 obtained in Example 31.

Example 151

Preparation 89 was obtained in the similar manner as Example 82 with the exception of changing Compound I-1 of Preparation 14 to Compound II-35 obtained in Example 44.

Example 152

Preparation 90 was obtained in the similar manner as Example 111 with the exception of changing Compound II-1 of Preparation 49 to Compound II-35 obtained in Example 44.

Example 153

Preparation 91 was obtained in the similar manner as Example 82 with the exception of changing Compound I-1 of Preparation 14 to Compound II-41 obtained in Example 50.

Example 154

Preparation 92 was obtained in the similar manner as Example 111 with the exception of changing Compound II-1 of Preparation 49 to Compound II-41 obtained in Example 50.

Example 155

Preparation 93 was obtained in the similar manner as Example 82 with the exception of changing Compound I-1 of Preparation 14 to Compound II-24 obtained in Example 33.

Example 156

Preparation 94 was obtained in the similar manner as Example 111 with the exception of changing Compound II-1 of Preparation 49 to Compound II-24 obtained in Example 33.

Example 157

Preparation 95 was obtained in the similar manner as Example 82 with the exception of changing Compound I-1 of Preparation 14 to Compound II-25 obtained in Example 34.

Example 158

Preparation 96 was obtained in the similar manner as Example 111 with the exception of changing Compound II-1 of Preparation 49 to Compound II-25 obtained in Example 34.

Example 159

Preparation 97 was obtained in the similar manner as Example 82 with the exception of changing Compound I-1 of Preparation 14 to Compound II-26 obtained in Example 35.

Example 160

Preparation 98 was obtained in the similar manner as Example 111 with the exception of changing Compound II-1 of Preparation 49 to Compound II-26 obtained in Example 35.

Example 161

Preparation 99 was obtained in the similar manner as Example 82 with the exception of changing Compound I-1 of Preparation 14 to Compound II-42 obtained in Example 51.

Example 162

Preparation 100 was obtained in the similar manner as Example 111 with the exception of changing Compound II-1 of Preparation 49 to Compound II-42 obtained in Example 51.

Example 163

Preparation 101 was obtained in the similar manner as Example 82 with the exception of changing Compound I-1 of Preparation 14 to Compound II-43 obtained in Example 52.

Example 164

Preparation 102 was obtained in the similar manner as Example 111 with the exception of changing Compound II-1 of Preparation 49 to Compound II-43 obtained in Example 52.

Example 165

Preparation 103 was obtained in the similar manner as Example 82 with the exception of changing Compound I-1 of Preparation 14 to Compound II-36 obtained in Example 45.

Example 166

Preparation 104 was obtained in the similar manner as Example 111 with the exception of changing Compound II-1 of Preparation 49 to Compound II-36 obtained in Example 45.

Example 167

Preparation 105 was obtained in the similar manner as Example 111 with the exception of changing Compound II-1 of Preparation 49 to Compound II-17 obtained in Example 24.

Example 168

Preparation 106 was obtained in the similar manner as Example 81 with the exception of changing Compound I-1 of Preparation 13 to Compound II-4 obtained in Example 11.

Example 169

Preparation 107 was obtained in the similar manner as Example 168 with the exception of changing Compound CL-1 of Preparation 106 to Compound CL-5 obtained in Reference Example 5.

Example 170

Preparation 108 was obtained in the similar manner as Example 82 with the exception of changing Compound I-1 of Preparation 14 to Compound II-33 obtained in Example 42.

Example 171

Preparation 109 was obtained in the similar manner as Example 111 with the exception of changing Compound II-1 of Preparation 49 to Compound II-33 obtained in Example 42.

Example 172

Preparation 110 was obtained in the similar manner as Example 82 with the exception of changing Compound I-1 of Preparation 14 to Compound II-37 obtained in Example 46.

Example 173

Preparation 111 was obtained in the similar manner as Example 111 with the exception of changing Compound II-1 of Preparation 49 to Compound II-37 obtained in Example 46.

Example 174

Preparation 112 was obtained in the similar manner as Example 81 with the exception of changing Compound I-1 of Preparation 13 to Compound II-29 obtained in Example 38.

Example 175

Preparation 113 was obtained in the similar manner as Example 169 with the exception of changing Compound II-4 of Preparation 107 to Compound II-29 obtained in Example 38.

Example 176

Preparation 114 was obtained in the similar manner as Example 111 with the exception of changing Compound II-1 of Preparation 49 to Compound II-38 obtained in Example 47.

Example 177

Preparation 115 was obtained in the similar manner as Example 111 with the exception of changing Compound II-1 of Preparation 49 to Compound II-8 obtained in Example 15.

Example 178

Preparation 116 was obtained in the similar manner as Example 111 with the exception of changing Compound II-1 of Preparation 49 to Compound II-11 obtained in Example 18.

Example 179

Preparation 117 was obtained in the similar manner as Example 111 with the exception of changing Compound II-1 of Preparation 49 to Compound II-39 obtained in Example 48.

Example 180

Preparation 118 was obtained in the similar manner as Example 81 with the exception of changing Compound I-1 of Preparation 13 to Compound IV-3 obtained in Example 70.

Example 181

Preparation 119 was obtained in the similar manner as Example 169 with the exception of changing Compound II-4 of Preparation 107 to Compound IV-3 obtained in Example 70.

Example 182

Preparation 120 was obtained in the similar manner as Example 81 with the exception of changing Compound I-1 of Preparation 13 to Compound III-2 obtained in Example 63.

Example 183

Preparation 121 was obtained in the similar manner as Example 169 with the exception of changing Compound II-4 of Preparation 107 to Compound III-2 obtained in Example 63.

Example 184

Preparation 122 was obtained in the similar manner as Example 81 with the exception of changing Compound I-1 of Preparation 13 to Compound IV-2 obtained in Example 69.

Example 185

Preparation 123 was obtained in the similar manner as Example 169 with the exception of changing Compound II-4 of Preparation 107 to Compound IV-2 obtained in Example 69.

Example 186

Preparation 124 was obtained in the similar manner as Example 81 with the exception of changing Compound I-1 of Preparation 13 to Compound II-13 obtained in Example 20.

Example 187

Preparation 125 was obtained in the similar manner as Example 169 with the exception of changing Compound II-4 of Preparation 107 to Compound II-13 obtained in Example 20.

Example 188

Compound II-17 obtained in Example 24 was added to 20 mL of 80% isopropyl alcohol so as to be 0.0782 µmol. Continuing, after adding 200 µL of siRNA solution and stirring for 1 minute, Compound CL-1, PEG-DMPE, DSPC and cholesterol were added at a ratio of Compound CL-1/PEG-DMPE/DSPC/cholesterol of 1.88 µmol/0.145 µmol/0.591 µmol/1.23 µmol. Subsequently, water for injection was added at the rate of 62 mL/sec or higher to prepare a 20% or less isopropyl alcohol solution and form a crude preparation. The resulting crude preparation was concentrated using Amicon Ultra (Millipore Corp.) followed by replacing the solvent with physiological saline and filtering in a clean bench using a 0.2 µm filter (Toyo Roshi Kaisha, Ltd.). Moreover, the siRNA concentration of the resulting preparation was measured and diluted using physiological saline to an siRNA concentration of 0.1 mg/mL to obtain Preparation 126.

Example 189

Preparation 127 was obtained in the similar manner as Example 81 with the exception of changing Compound I-1 of Preparation 13 to Compound I-6 obtained in Example 6.

Example 190

Preparation 128 was obtained in the similar manner as Example 81 with the exception of changing Compound I-1 of Preparation 13 to Compound IV-1 obtained in Example 32.

Example 191

Preparation 129 was obtained in the similar manner as Example 169 with the exception of changing Compound II-4 of Preparation 107 to Compound IV-1 obtained in Example 32.

Example 192

Compound IV-1 obtained in Example 32 was added to 20 mL of 80% isopropyl alcohol so as to be 0.156 µmol. Continuing, after adding 200 µL of siRNA solution and stirring for 1 minute, Compound CL-5, PEG-DMPE, DSPC and cholesterol were added at a ratio of Compound CL-5/PEG-DMPE/DSPC/cholesterol of 1.88 µmol/0.784 µmol/0.358 µmol/0.743 µmol. Subsequently, water for injection was added at the rate of 62 mL/sec or higher to prepare a 20% or less isopropyl alcohol solution and form a crude preparation. The resulting crude preparation was concentrated using Amicon Ultra (Millipore Corp.) followed by replacing the solvent with physiological saline and filtering in a clean bench using a 0.2 µm filter (Toyo Roshi Kaisha, Ltd.). Moreover, the siRNA concentration of the resulting preparation was measured and diluted using physiological saline to an siRNA concentration of 0.1 mg/mL to obtain Preparation 130.

Test Example 8

Measurement of Average Particle Size of Nucleic Acid-Containing Lipid Nanoparticles The average particle size of nucleic acid-containing lipid nanoparticles in a preparation was measured with a particle size measurement device (Zetasizer Nano ZS, Malvern Instruments Ltd.) (Table 48). Furthermore, PDI in the table indicates the polydispersity index.

TABLE 48

| Preparation No. | Lipid A | Lipid B | Size (nm) | PDI |
|---|---|---|---|---|
| 30 | I-4 | CL-1 | 41.06 | 0.104 |
| 31 | I-4 | CL-3 | 46.62 | 0.097 |
| 32 | I-4 | CL-4 | 53.82 | 0.115 |
| 33 | I-5 | CL-1 | 44.43 | 0.090 |
| 34 | I-5 | CL-3 | 53.73 | 0.073 |
| 35 | I-5 | CL-6 | 52.91 | 0.137 |
| 36 | I-5 | CL-4 | 51.74 | 0.149 |
| 37 | II-6 | CL-1 | 52.34 | 0.122 |
| 38 | II-6 | CL-5 | 52.00 | 0.126 |
| 39 | II-6 | CL-3 | 54.43 | 0.147 |
| 40 | II-6 | CL-6 | 52.85 | 0.238 |
| 41 | II-6 | CL-4 | 57.72 | 0.155 |
| 42 | II-2 | CL-1 | 45.40 | 0.147 |
| 43 | II-2 | CL-5 | 48.83 | 0.129 |
| 44 | II-2 | CL-3 | 48.35 | 0.118 |
| 45 | II-2 | CL-4 | 50.65 | 0.212 |
| 46 | I-3 | CL-3 | 55.88 | 0.076 |
| 47 | II-7 | CL-3 | 55.27 | 0.076 |
| 48 | II-1 | CL-1 | 47.40 | 0.132 |
| 49 | II-1 | CL-5 | 47.15 | 0.130 |
| 50 | II-1 | CL-3 | 58.84 | 0.125 |
| 51 | II-1 | CL-4 | 49.65 | 0.152 |
| 52 | II-3 | CL-1 | 44.86 | 0.096 |
| 53 | II-3 | CL-5 | 47.27 | 0.084 |
| 54 | II-3 | CL-4 | 49.53 | 0.163 |
| 55 | II-12 | CL-1 | 45.42 | 0.120 |
| 56 | II-12 | CL-5 | 44.45 | 0.159 |
| 57 | II-12 | CL-4 | 44.55 | 0.196 |
| 58 | II-17 | CL-6 | 44.00 | 0.127 |
| 59 | II-21 | CL-1 | 43.36 | 0.110 |
| 60 | II-21 | CL-5 | 44.79 | 0.107 |
| 61 | II-21 | CL-4 | 42.91 | 0.135 |
| 62 | II-17 | CL-1 | 47.49 | 0.119 |
| 63 | II-17 | CL-4 | 46.42 | 0.133 |
| 64 | IV-3 | CL-1 | 37.40 | 0.379 |
| 65 | III-2 | CL-1 | 38.46 | 0.481 |
| 66 | II-23 | CL-1 | 41.72 | 0.086 |
| 67 | II-23 | CL-5 | 43.22 | 0.148 |
| 68 | II-28 | CL-1 | 45.44 | 0.063 |
| 69 | II-28 | CL-5 | 40.14 | 0.299 |
| 70 | II-22 | CL-1 | 39.24 | 0.196 |
| 71 | II-22 | CL-5 | 44.95 | 0.111 |
| 72 | II-10 | CL-1 | 40.94 | 0.142 |
| 73 | II-10 | CL-5 | 46.66 | 0.172 |
| 74 | II-30 | CL-1 | 41.21 | 0.138 |
| 75 | II-30 | CL-5 | 43.16 | 0.155 |
| 76 | II-31 | CL-1 | 39.81 | 0.161 |
| 77 | II-31 | CL-5 | 39.35 | 0.158 |

TABLE 48-continued

| Preparation No. | Lipid A | Lipid B | Size (nm) | PDI |
|---|---|---|---|---|
| 78 | II-34 | CL-1 | 36.20 | 0.231 |
| 79 | II-34 | CL-5 | 35.44 | 0.248 |
| 80 | II-16 | CL-1 | 49.24 | 0.026 |
| 81 | II-16 | CL-5 | 49.48 | 0.092 |
| 82 | I-2 | CL-5 | 45.51 | 0.153 |
| 83 | II-5 | CL-5 | 46.18 | 0.198 |
| 84 | II-18 | CL-5 | 45.68 | 0.199 |
| 85 | II-27 | CL-5 | 46.30 | 0.151 |
| 86 | II-20 | CL-5 | 46.37 | 0.110 |
| 87 | II-15 | CL-5 | 43.42 | 0.135 |
| 88 | II-1 | CL-5 | 36.83 | 0.270 |
| 89 | II-35 | CL-1 | 35.62 | 0.218 |
| 90 | II-35 | CL-5 | 43.46 | 0.166 |
| 91 | II-41 | CL-1 | 38.04 | 0.128 |
| 92 | II-41 | CL-5 | 45.00 | 0.093 |
| 93 | II-24 | CL-1 | 41.58 | 0.077 |
| 94 | II-24 | CL-5 | 33.76 | 0.228 |
| 95 | II-25 | CL-1 | 39.30 | 0.117 |
| 96 | II-25 | CL-5 | 43.56 | 0.127 |
| 97 | II-26 | CL-1 | 37.38 | 0.162 |
| 98 | II-26 | CL-5 | 42.13 | 0.107 |
| 99 | II-42 | CL-1 | 40.80 | 0.100 |
| 100 | II-42 | CL-5 | 44.30 | 0.121 |
| 101 | II-43 | CL-1 | 45.21 | 0.078 |
| 102 | II-43 | CL-5 | 48.76 | 0.062 |
| 103 | II-36 | CL-1 | 39.66 | 0.121 |
| 104 | II-36 | CL-5 | 46.25 | 0.072 |
| 105 | II-17 | CL-5 | 48.35 | 0.163 |
| 106 | II-4 | CL-1 | 41.31 | 0.124 |
| 107 | II-4 | CL-5 | 45.13 | 0.104 |
| 108 | II-33 | CL-1 | 37.60 | 0.137 |
| 109 | II-33 | CL-5 | 44.60 | 0.092 |
| 110 | II-37 | CL-1 | 44.77 | 0.055 |
| 111 | II-37 | CL-5 | 48.45 | 0.112 |
| 112 | II-29 | CL-1 | 42.69 | 0.126 |
| 113 | II-29 | CL-5 | 47.35 | 0.136 |
| 114 | II-38 | CL-5 | 43.54 | 0.124 |
| 115 | II-8 | CL-5 | 38.46 | 0.182 |
| 116 | II-11 | CL-5 | 43.49 | 0.178 |
| 117 | II-39 | CL-5 | 40.70 | 0.183 |
| 118 | IV-3 | CL-1 | 39.23 | 0.186 |
| 119 | IV-3 | CL-5 | 46.95 | 0.164 |
| 120 | III-2 | CL-1 | 38.99 | 0.197 |
| 121 | III-2 | CL-5 | 44.14 | 0.154 |
| 122 | IV-2 | CL-1 | 43.59 | 0.134 |
| 123 | IV-2 | CL-5 | 48.43 | 0.116 |
| 124 | II-13 | CL-1 | 43.16 | 0.141 |
| 125 | II-13 | CL-5 | 43.25 | 0.195 |
| 126 | II-17 | CL-1 | 38.51 | 0.181 |
| 127 | I-6 | CL-1 | 41.89 | 0.129 |
| 128 | IV-1 | CL-1 | 31.92 | 0.303 |
| 129 | IV-1 | CL-5 | 39.04 | 0.284 |
| 130 | IV-1 | CL-5 | 23.13 | 0.434 |

As a result, Preparations 30 to 130 described in Examples 92 to 192 demonstrated a small average particles size of 60 nm or less.

Test Example 9

Evaluation Test of In Vitro Activity of Nucleic Acid-Containing Lipid Nanoparticles Each of the preparations obtained in Examples 92 to 192 (Preparations 30 to 130) were introduced into HeLa cells derived from human cervical cancer forcibly expressing luciferase (Luc2CP-HeLa cells) according to the method described below.

After diluting with Opti-MEM (Gibco) to a final nucleic acid concentration of 10 nM, 20 μL aliquots of each preparation were dispensed into a 96-well culture plate followed by suspending the Luc2CP-HeLa cells in minimum essential medium (MEM) containing 1.25% fetal bovine serum (FBS, SAFC Biosciences Ltd.), disseminating the cells in the culture plate at 7500 cells/80 μl/well, and culturing under conditions of 37° C. and 5% $CO_2$ to introduce each preparation into the Luc2CP-HeLa cells. In addition, untreated cells were disseminated as a negative control group.

The cells introduced with each preparation were cultured for 24 hours in an incubator at 37° C. and 5% $CO_2$ followed by treating the cells using a luciferase quantification system (Steady-Glo Luciferase Assay System, Promega Corp., E2520) in accordance with the method described in the manual provided with the product, and measuring their respective luminescence intensities with a plate reader. The amount of light emitted by each preparation treatment group was calculated as a relative percentage based on a value of 1 for the amount of light emitted by the negative control group. Table 49 indicates the Luc inhibition rates of Preparation 21 described in Comparative Example 4 and Preparations 26 to 29 described in Comparative Examples 6 to 9, which do not contain lipid A, that were set in each round of testing.

As is clear from Table 49, the preparations containing lipid A (Preparations 30 to 130) inhibited expression of Luc when introduced into Luc2CP-HeLa cells.

Accordingly, the lipid nanoparticles containing lipid A of the present invention were clearly determined to be preparations that enable nucleic acid to be introduced into cells and the like and facilitate the delivery of drugs into cells in vitro.

TABLE 49

| Testing Round | Preparation No. | Lipid A | Lipid B | KD (%) |
|---|---|---|---|---|
| 1 | 30 | I-4 | CL-1 | 35.5 |
| 1 | 31 | I-4 | CL-3 | 53.5 |
| 1 | 32 | I-4 | CL-4 | 84.9 |
| 1 | 33 | I-5 | CL-1 | 28.1 |
| 1 | 34 | I-5 | CL-3 | 58.4 |
| 1 | 35 | I-5 | CL-6 | 81.2 |
| 1 | 36 | I-5 | CL-4 | 90.6 |
| 1 | 21 | — | CL-1 | 19.1 |
| 1 | 27 | — | CL-3 | 21.6 |
| 1 | 28 | — | CL-6 | 73.3 |
| 1 | 29 | — | CL-4 | 63.7 |
| 2 | 37 | II-6 | CL-1 | 74.5 |
| 2 | 38 | II-6 | CL-5 | 79.6 |
| 2 | 39 | II-6 | CL-3 | 87.7 |
| 2 | 40 | II-6 | CL-6 | 82.1 |
| 2 | 41 | II-6 | CL-4 | 97.1 |
| 2 | 42 | II-2 | CL-1 | 63.6 |
| 2 | 43 | II-2 | CL-5 | 46.9 |
| 2 | 44 | II-2 | CL-3 | 60.8 |
| 2 | 45 | II-2 | CL-4 | 96.9 |
| 2 | 21 | — | CL-1 | 45.4 |
| 2 | 26 | — | CL-5 | 33.4 |
| 2 | 27 | — | CL-3 | 26.6 |
| 2 | 28 | — | CL-6 | 81.1 |
| 2 | 29 | — | CL-4 | 49.9 |
| 3 | 46 | I-3 | CL-3 | 46.5 |
| 3 | 47 | II-7 | CL-3 | 62.2 |
| 3 | 27 | — | CL-3 | 31.2 |
| 4 | 48 | II-1 | CL-1 | 94.7 |
| 4 | 49 | II-1 | CL-5 | 89.3 |
| 4 | 50 | II-1 | CL-3 | 94.5 |
| 4 | 51 | II-1 | CL-4 | 97.7 |
| 4 | 52 | II-3 | CL-1 | 85.9 |
| 4 | 53 | II-3 | CL-5 | 95.5 |
| 4 | 54 | II-3 | CL-4 | 97.8 |
| 4 | 21 | — | CL-1 | 22.0 |
| 4 | 26 | — | CL-5 | 31.6 |
| 4 | 27 | — | CL-3 | 18.6 |
| 4 | 29 | — | CL-4 | 61.1 |
| 5 | 55 | II-12 | CL-1 | 92.1 |
| 5 | 56 | II-12 | CL-5 | 76.3 |
| 5 | 57 | II-12 | CL-4 | 86.6 |
| 5 | 58 | II-17 | CL-6 | 87.1 |

TABLE 49-continued

| Testing Round | Preparation No. | Lipid A | Lipid B | KD (%) |
|---|---|---|---|---|
| 5 | 21 | — | CL-1 | 55.7 |
| 5 | 26 | — | CL-5 | 55.9 |
| 5 | 28 | — | CL-6 | 70.8 |
| 5 | 29 | — | CL-4 | 62.7 |
| 6 | 59 | II-21 | CL-1 | 84.6 |
| 6 | 60 | II-21 | CL-5 | 40.3 |
| 6 | 61 | II-21 | CL-4 | 81.0 |
| 6 | 62 | II-17 | CL-1 | 94.7 |
| 6 | 63 | II-17 | CL-4 | 96.3 |
| 6 | 21 | — | CL-1 | 54.9 |
| 6 | 26 | — | CL-5 | 39.6 |
| 6 | 29 | — | CL-4 | 46.9 |
| 7 | 64 | IV-3 | CL-1 | 93.7 |
| 7 | 65 | III-2 | CL-1 | 37.1 |
| 7 | 66 | II-23 | CL-1 | 87.4 |
| 7 | 67 | II-23 | CL-5 | 83.1 |
| 7 | 68 | II-28 | CL-1 | 64.3 |
| 7 | 69 | II-28 | CL-5 | 72.8 |
| 7 | 70 | II-22 | CL-1 | 92.2 |
| 7 | 71 | II-22 | CL-5 | 76.7 |
| 7 | 72 | II-10 | CL-1 | 86.6 |
| 7 | 73 | II-10 | CL-5 | 87.6 |
| 7 | 74 | II-30 | CL-1 | 74.0 |
| 7 | 75 | II-30 | CL-5 | 92.1 |
| 7 | 76 | II-31 | CL-1 | 59.8 |
| 7 | 77 | II-31 | CL-5 | 86.4 |
| 7 | 78 | II-34 | CL-1 | 70.1 |
| 7 | 79 | II-34 | CL-5 | 87.4 |
| 7 | 80 | II-16 | CL-1 | 81.9 |
| 7 | 81 | II-16 | CL-5 | 79.4 |
| 7 | 82 | I-2 | CL-5 | 55.7 |
| 7 | 83 | II-5 | CL-5 | 89.0 |
| 7 | 84 | II-18 | CL-5 | 94.5 |
| 7 | 85 | II-27 | CL-5 | 89.6 |
| 7 | 86 | II-20 | CL-5 | 93.3 |
| 7 | 87 | II-15 | CL-5 | 94.0 |
| 7 | 88 | II-1 | CL-5 | 92.3 |
| 7 | 89 | II-35 | CL-1 | 28.8 |
| 7 | 90 | II-35 | CL-5 | 66.1 |
| 7 | 21 | — | CL-1 | 1.5 |
| 7 | 26 | — | CL-5 | 36.7 |
| 8 | 91 | II-41 | CL-1 | 16.5 |
| 8 | 92 | II-41 | CL-5 | 16.3 |
| 8 | 93 | II-24 | CL-1 | 23.2 |
| 8 | 94 | II-24 | CL-5 | 25.9 |
| 8 | 95 | II-25 | CL-1 | 17.4 |
| 8 | 96 | II-25 | CL-5 | 38.0 |
| 8 | 97 | II-26 | CL-1 | 50.7 |
| 8 | 98 | II-26 | CL-5 | 81.7 |
| 8 | 99 | II-42 | CL-1 | 21.1 |
| 8 | 100 | II-42 | CL-5 | 30.8 |
| 8 | 101 | II-43 | CL-1 | 50.0 |
| 8 | 102 | II-43 | CL-5 | 44.5 |
| 8 | 103 | II-36 | CL-1 | 14.3 |
| 8 | 104 | II-36 | CL-5 | 32.4 |
| 8 | 105 | II-17 | CL-5 | 97.3 |
| 8 | 106 | II-4 | CL-1 | 17.9 |
| 8 | 107 | II-4 | CL-5 | 36.4 |
| 8 | 108 | II-33 | CL-1 | 12.5 |
| 8 | 109 | II-33 | CL-5 | 47.6 |
| 8 | 110 | II-37 | CL-1 | 29.2 |
| 8 | 111 | II-37 | CL-5 | 75.9 |
| 8 | 112 | II-29 | CL-1 | 14.1 |
| 8 | 113 | II-29 | CL-5 | 43.1 |
| 8 | 114 | II-38 | CL-5 | 34.3 |
| 8 | 115 | II-8 | CL-5 | 37.4 |
| 8 | 116 | II-11 | CL-5 | 48.7 |
| 8 | 117 | II-39 | CL-5 | 66.7 |
| 8 | 118 | IV-3 | CL-1 | 36.6 |
| 8 | 119 | IV-3 | CL-5 | 55.3 |
| 8 | 120 | III-2 | CL-1 | 41.5 |
| 8 | 121 | III-2 | CL-5 | 45.1 |
| 8 | 21 | — | CL-1 | −20.9 |
| 8 | 26 | — | CL-5 | 14.4 |
| 9 | 122 | IV-2 | CL-1 | 66.5 |
| 9 | 123 | IV-2 | CL-5 | 83.3 |
| 9 | 124 | II-13 | CL-1 | 5.3 |
| 9 | 125 | II-13 | CL-5 | 48.3 |
| 9 | 126 | II-17 | CL-1 | 5.0 |
| 9 | 127 | I-6 | CL-1 | 34.7 |
| 9 | 128 | IV-1 | CL-1 | 62.1 |
| 9 | 129 | IV-1 | CL-5 | 82.3 |
| 9 | 130 | IV-1 | CL-5 | 74.3 |
| 9 | 21 | — | CL-1 | −24.8 |
| 9 | 26 | — | CL-5 | 44.3 |

Nucleic acid-containing lipid nanoparticles were prepared in the manner indicated below while changing the ratios of each of the components of Compound II-3, Compound CL-1, PEG-DMPE, DSPC and cholesterol.

Example 193

Nucleic acid-containing lipid nanoparticles containing Compound II-3 obtained in Example 10, PEG-DMPE, DSPC, cholesterol and Compound CL-1 obtained in Reference Example 1 were prepared in the manner indicated below.

Compound II-3 was added to 20 mL of 80% isopropyl alcohol so as to be 0.313 µmol. Continuing, after adding 200 µL of siRNA solution and stirring for 1 minute, Compound CL-1, PEG-DMPE, DSPC and cholesterol were added to this solution at a ratio of Compound CL-1/PEG-DMPE/DSPC/cholesterol of 1.04 µmol/0.145 µmol/0.761 µmol/1.66 µmol. Subsequently, water for injection was added at the rate of 62 mL/sec or higher to prepare a 20% or less isopropyl alcohol solution and form a crude preparation. The resulting crude preparation was concentrated using Amicon Ultra (Millipore Corp.) followed by replacing the solvent with physiological saline and filtering in a clean bench using a 0.2 µm filter (Toyo Roshi Kaisha, Ltd.). Moreover, the siRNA concentration of the resulting preparation was measured and diluted using physiological saline to an siRNA concentration of 0.1 mg/mL to obtain Preparation 131.

Example 194

Nucleic acid-containing lipid nanoparticles containing Compound II-3 obtained in Example 10, PEG-DMPE, DSPC, cholesterol and Compound CL-1 obtained in Reference Example 1 were prepared in the manner indicated below.

Compound II-3 was added to 20 mL of 80% isopropyl alcohol so as to be 0.313 µmol. Continuing, after adding 200 µL of siRNA solution and stirring for 1 minute, Compound CL-1, PEG-DMPE, DSPC and cholesterol were added to this solution at a ratio of Compound CL-1/PEG-DMPE/DSPC/cholesterol of 1.04 µmol/0.145 µmol/O. 104 µmol/2.32 µmol. Subsequently, water for injection was added at the rate of 62 mL/sec or higher to prepare a 20% or less isopropyl alcohol solution and form a crude preparation. The resulting crude preparation was concentrated using Amicon Ultra (Millipore Corp.) followed by replacing the solvent with physiological saline and filtering in a clean bench using a 0.2 µm filter (Toyo Roshi Kaisha, Ltd.). Moreover, the siRNA concentration of the resulting preparation was measured and diluted using physiological saline to an siRNA concentration of 0.1 mg/mL to obtain Preparation 132.

Example 195

Nucleic acid-containing lipid nanoparticles containing Compound II-3 obtained in Example 10, PEG-DMPE, DSPC, cholesterol and Compound CL-1 obtained in Reference Example 1 were prepared in the manner indicated below.

Compound II-3 was added to 20 mL of 80% isopropyl alcohol so as to be 0.313 µmol. Continuing, after adding 200 µL of siRNA solution and stirring for 1 minute, Compound CL-1, PEG-DMPE, DSPC and cholesterol were added to this solution at a ratio of Compound CL-1/PEG-DMPE/DSPC/cholesterol of 3.21 µmol/0.217 µmol/1.61 µmol/0.53 µmol. Subsequently, water for injection was added at the rate of 62 mL/sec or higher to prepare a 20% or less isopropyl alcohol solution and form a crude preparation. The resulting crude preparation was concentrated using Amicon Ultra (Millipore Corp.) followed by replacing the solvent with physiological saline and filtering in a clean bench using a 0.2 µm filter (Toyo Roshi Kaisha, Ltd.). Moreover, the siRNA concentration of the resulting preparation was measured and diluted using physiological saline to an siRNA concentration of 0.1 mg/mL to obtain Preparation 133.

Example 196

Nucleic acid-containing lipid nanoparticles containing Compound II-3 obtained in Example 10, PEG-DMPE, DSPC, cholesterol and Compound CL-1 obtained in Reference Example 1 were prepared in the manner indicated below.

Compound II-3 was added to 20 mL of 80% isopropyl alcohol so as to be 0.313 µmol. Continuing, after adding 200 µL of siRNA solution and stirring for 1 minute, Compound CL-1, PEG-DMPE, DSPC and cholesterol were added to this solution at a ratio of Compound CL-1/PEG-DMPE/DSPC/cholesterol of 3.48 µmol/0.217 µmol/0.374 µmol/1.50 µmol. Subsequently, water for injection was added at the rate of 62 mL/sec or higher to prepare a 20% or less isopropyl alcohol solution and form a crude preparation. The resulting crude preparation was concentrated using Amicon Ultra (Millipore Corp.) followed by replacing the solvent with physiological saline and filtering in a clean bench using a 0.2 µm filter (Toyo Roshi Kaisha, Ltd.). Moreover, the siRNA concentration of the resulting preparation was measured and diluted using physiological saline to an siRNA concentration of 0.1 mg/mL to obtain Preparation 134.

Example 197

Nucleic acid-containing lipid nanoparticles containing Compound II-3 obtained in Example 10, PEG-DMPE, DSPC, cholesterol and Compound CL-1 obtained in Reference Example 1 were prepared in the manner indicated below.

Compound II-3 was added to 20 mL of 80% isopropyl alcohol so as to be 0.313 µmol. Continuing, after adding 200 µL of siRNA solution and stirring for 1 minute, Compound CL-1, PEG-DMPE, DSPC and cholesterol were added to this solution at a ratio of Compound CL-1/PEG-DMPE/DSPC/cholesterol of 2.63 µmol/1.18 µmol/1.32 µmol/0.44 µmol. Subsequently, water for injection was added at the rate of 62 mL/sec or higher to prepare a 20% or less isopropyl alcohol solution and form a crude preparation. The resulting crude preparation was concentrated using Amicon Ultra (Millipore Corp.) followed by replacing the solvent with physiological saline and filtering in a clean bench using a 0.2 µm filter (Toyo Roshi Kaisha, Ltd.). Moreover, the siRNA concentration of the resulting preparation was measured and diluted using physiological saline to an siRNA concentration of 0.1 mg/mL to obtain Preparation 135.

Comparative Example 10

Nucleic acid-containing lipid nanoparticles not containing lipid A were prepared in the manner indicated below while changing the ratios of each of the components of Compound CL-1, PEG-DMPE, DSPC and cholesterol.

The 1 mg/mL Luc siRNA solution described in Example 72 was used for the nucleic acid.

Compound CL-1 obtained in Reference Example 1, PEG-DMPE, DSPC and cholesterol were each dissolved in 100% isopropyl alcohol to 20 mg/mL to prepare lipid stock solutions. The lipid stock solutions were stored at −20° C. and used after returning to room temperature after dissolving the lipid by warming to 60° C. immediately prior to formulating into a preparation.

0.2 mL of the Luc siRNA solution was added to 20 mL of 80% isopropyl alcohol. Continuing, each of the lipids was added at a ratio of Compound CL-1/PEG-DMPE/DSPC/cholesterol of 1.04 µmol/0.145 µmol/0.860 µmol/1.88 µmol. Subsequently, water for injection was added at the rate of 62 mL/sec or higher to prepare a 20% or less isopropyl alcohol solution and form a crude preparation. The resulting crude preparation was concentrated using Amicon Ultra (Millipore Corp.) followed by replacing the solvent with physiological saline and filtering in a clean bench using a 0.2 µm filter (Toyo Roshi Kaisha, Ltd.). Moreover, the siRNA concentration of the resulting preparation was measured and diluted using physiological saline to an siRNA concentration of 0.1 mg/mL to obtain Preparation 136.

Comparative Example 11

Nucleic acid-containing lipid nanoparticles not containing lipid A were prepared in the manner indicated below while changing the ratios of each of the components of Compound CL-1, PEG-DMPE, DSPC and cholesterol.

0.2 mL of the Luc siRNA solution was added to 20 mL of 80% isopropyl alcohol. Continuing, each of the lipids was added at a ratio of Compound CL-1/PEG-DMPE/DSPC/cholesterol of 1.04 µmol/0.145 µmol/0.117 µmol/2.62 µmol. Subsequently, water for injection was added at the rate of 62 mL/sec or higher to prepare a 20% or less isopropyl alcohol solution and form a crude preparation. The resulting crude preparation was concentrated using Amicon Ultra (Millipore Corp.) followed by replacing the solvent with physiological saline and filtering in a clean bench using a 0.2 µm filter (Toyo Roshi Kaisha, Ltd.). Moreover, the siRNA concentration of the resulting preparation was measured and diluted using physiological saline to an siRNA concentration of 0.1 mg/mL to obtain Preparation 137.

Comparative Example 12

Nucleic acid-containing lipid nanoparticles not containing lipid A were prepared in the manner indicated below while changing the ratios of each of the components of Compound CL-1, PEG-DMPE, DSPC and cholesterol.

0.2 mL of the Luc siRNA solution was added to 20 mL of 80% isopropyl alcohol. Continuing, each of the lipids was added at a ratio of Compound CL-1/PEG-DMPE/DSPC/cholesterol of 3.21 µmol/0.217 µmol/1.84 µmol/0.61 µmol. Subsequently, water for injection was added at the rate of 62 mL/sec or higher to prepare a 20% or less isopropyl alcohol solution and form a crude preparation. The resulting crude preparation was concentrated using Amicon Ultra (Millipore Corp.) followed by replacing the solvent with physiological saline and filtering in a clean bench using a 0.2 µm filter (Toyo Roshi Kaisha, Ltd.). Moreover, the siRNA concentration of the resulting preparation was measured and diluted using physiological saline to an siRNA concentration of 0.1 mg/mL to obtain Preparation 138.

Comparative Example 13

Nucleic acid-containing lipid nanoparticles not containing lipid A were prepared in the manner indicated below while changing the ratios of each of the components of Compound CL-1, PEG-DMPE, DSPC and cholesterol.

0.2 mL of the Luc siRNA solution was added to 20 mL of 80% isopropyl alcohol. Continuing, each of the lipids was added at a ratio of Compound CL-1/PEG-DMPE/DSPC/cholesterol of 3.48 µmol/0.217 µmol/0.437 µmol/1.75 µmol. Subsequently, water for injection was added at the rate of 62 mL/sec or higher to prepare a 20% or less isopropyl alcohol solution and form a crude preparation. The resulting crude preparation was concentrated using Amicon Ultra (Millipore Corp.) followed by replacing the solvent with physiological saline and filtering in a clean bench using a 0.2 µm filter (Toyo Roshi Kaisha, Ltd.). Moreover, the siRNA concentration of the resulting preparation was measured and diluted using physiological saline to an siRNA concentration of 0.1 mg/mL to obtain Preparation 139.

Test Example 10

Measurement of Average Particle Size of Nucleic Acid-Containing Lipid Nanoparticles The average particle size of nucleic acid-containing lipid nanoparticles in a preparation was measured with a particle size measurement device (Zetasizer Nano ZS, Malvern Instruments Ltd.) (Table 50). Furthermore, PDI in the table indicates the polydispersity index.

TABLE 50

| Preparation No. | Lipid A | Lipid B | Size (nm) | PDI |
|---|---|---|---|---|
| 131 | II-3 | CL-1 | 38.68 | 0.147 |
| 132 | II-3 | CL-1 | 41.71 | 0.097 |
| 133 | II-3 | CL-1 | 44.32 | 0.160 |
| 134 | II-3 | CL-1 | 47.18 | 0.111 |
| 135 | II-3 | CL-1 | 37.25 | 0.123 |
| 136 |  | CL-1 | 36.92 | 0.199 |
| 137 |  | CL-1 | 33.71 | 0.102 |
| 138 |  | CL-1 | 34.00 | 0.206 |
| 139 |  | CL-1 | 37.32 | 0.157 |

As a result, Preparations 131 to 135 described in Examples 193 to 197 and Preparations 136 to 139 described in Comparative Examples 10 to 13 demonstrated a small average particles size of 60 nm or less regardless of whether or not they contained lipid A (Compound II-3).

Test Example 11

Evaluation Test of In Vitro Activity of Nucleic Acid-Containing Lipid Nanoparticles Each of the preparations obtained in Examples 193 to 197 (Preparations 131 to 135) and each of the preparations obtained in Comparative Examples 10 to 13 (Preparations 136 to 139) were introduced into HeLa cells derived from human cervical cancer forcibly expressing luciferase (Luc2CP-HeLa cells) according to the method described below.

After diluting with Opti-MEM (Gibco) to a final nucleic acid concentration of 10 nM, 20 µL aliquots of each preparation were dispensed into a 96-well culture plate followed by suspending the Luc2CP-HeLa cells in minimum essential medium (MEM) containing 1.25% fetal bovine serum (FBS, SAFC Biosciences Ltd.), disseminating the cells in the culture plate at 7500 cells/80 µl/well, and culturing under conditions of 37° C. and 5% $CO_2$ to introduce each preparation into the Luc2CP-HeLa cells. In addition, untreated cells were disseminated as a negative control group.

The cells introduced with each preparation were cultured for 24 hours in an incubator at 37° C. and 5% $CO_2$ followed by treating the cells using a luciferase quantification system (Steady-Glo Luciferase Assay System, Promega Corp., E2520) in accordance with the method described in the manual provided with the product, and measuring their respective luminescence intensities with a plate reader. The amount of light emitted by each preparation treatment group was calculated as a relative percentage based on a value of 1 for the amount of light emitted by the negative control group.

As is clear from Table 51, the preparations containing lipid A (Preparations 131 to 135) inhibited expression of Luc regardless of the content of each component.

Accordingly, the lipid nanoparticles containing lipid A of the present invention were clearly determined to be preparations that enable nucleic acid to be introduced into cells and the like and facilitate the delivery of drugs into cells in vitro.

TABLE 51

| Preparation No. | Lipid A | Lipid B | KD (%) |
|---|---|---|---|
| 131 | II-3 | CL-1 | 36.3 |
| 132 | II-3 | CL-1 | 51.8 |
| 133 | II-3 | CL-1 | 30.7 |
| 134 | II-3 | CL-1 | 50.5 |
| 135 | II-3 | CL-1 | 5.9 |
| 136 |  | CL-1 | −25.6 |
| 137 |  | CL-1 | −24.4 |
| 138 |  | CL-1 | −56.7 |
| 139 |  | CL-1 | −46.5 |

Nucleic acid-containing lipid nanoparticles containing lipid A, lipid B, PEG-DMPE, DSPC and cholesterol were prepared in the manner indicated below.

Example 198

Preparation 141 was obtained in the similar manner as Example 89 with the exception of changing Compound I-1 of Preparation 23 to Compound I-4 obtained in Example 4.

Example 199

Preparation 142 was obtained in the similar manner as Example 89 with the exception of changing Compound I-1 of Preparation 23 to Compound I-5 obtained in Example 5.

Example 200

Preparation 143 was obtained in the similar manner as Example 84 with the exception of changing Compound I-1 of Preparation 16 to Compound I-3 obtained in Example 3.

Example 201

Preparation 144 was obtained in the similar manner as Example 169 with the exception of changing Compound II-4 of Preparation 107 to Compound I-6 obtained in Example 6.

Example 202

Preparation 145 was obtained in the similar manner as Example 120 with the exception of changing Compound II-17 of Preparation 58 to Compound II-1 obtained in Example 8.

Example 203

Preparation 146 was obtained in the similar manner as Example 97 with the exception of changing Compound I-5 of Preparation 35 to Compound II-2 obtained in Example 9.

Example 204

Preparation 147 was obtained in the similar manner as Example 84 with the exception of changing Compound I-1 of Preparation 16 to Compound II-7 obtained in Example 14.

Example 205

Preparation 148 was obtained in the similar manner as Example 89 with the exception of changing Compound I-1 of Preparation 23 to Compound II-7 obtained in Example 14.

Example 206

Preparation 149 was obtained in the similar manner as Example 120 with the exception of changing Compound II-17 of Preparation 58 to Compound II-3 obtained in Example 10.

Example 207

Preparation 150 was obtained in the similar manner as Example 120 with the exception of changing Compound II-17 of Preparation 58 to Compound II-12 obtained in Example 19.

Example 208

Preparation 151 was obtained in the similar manner as Example 169 with the exception of changing Compound II-4 of Preparation 107 to Compound II-9 obtained in Example 16.

Example 209

Preparation 152 was obtained in the similar manner as Example 111 with the exception of changing Compound II-1 of Preparation 49 to Compound II-32 obtained in Example 41.

Example 210

Preparation 153 was obtained in the similar manner as Example 111 with the exception of changing Compound II-1 of Preparation 49 to Compound II-40 obtained in Example 49.

Example 211

Compound II-3 obtained in Example 10 was added to 20 mL of 80% isopropyl alcohol so as to be 0.313 µmol. Continuing, after adding 200 µL of siRNA solution and stirring for 1 minute, Compound CL-1, PEG-DMPE, DSPC and cholesterol were added to this solution at a ratio of Compound CL-1/PEG-DMPE/DSPC/cholesterol of 2.85 µmol/1.176 µmol/0.307 µmol/1.23 µmol. Subsequently, water for injection was added at the rate of 62 mL/sec or higher to prepare a 20% or less isopropyl alcohol solution and form a crude preparation. The resulting crude preparation was concentrated using Amicon Ultra (Millipore Corp.) followed by replacing the solvent with physiological saline and filtering in a clean bench using a 0.2 µm filter (Toyo Roshi Kaisha, Ltd.). Moreover, the siRNA concentration of the resulting preparation was measured and diluted using physiological saline to an siRNA concentration of 0.1 mg/mL to obtain Preparation 154.

Example 212

Preparation 155 was obtained in the similar manner as Example 97 with the exception of changing Compound I-5 of Preparation 35 to Compound III-1 obtained in Example 31.

Example 213

Preparation 156 was obtained in the similar manner as Example 192 with the exception of changing Compound CL-5 of Preparation 130 to Compound CL-1 obtained in Reference Example 1.

Example 214

Preparation 157 was obtained in the similar manner as Example 82 with the exception of changing Compound I-1 of Preparation 14 to Compound II-44 obtained in Example 53.

Example 215

Preparation 158 was obtained in the similar manner as Example 82 with the exception of changing Compound I-1 of Preparation 14 to Compound II-45 obtained in Example 54.

Example 216

Preparation 159 was obtained in the similar manner as Example 82 with the exception of changing Compound I-1 of Preparation 14 to Compound II-46 obtained in Example 55.

Test Example 12

Measurement of Average Particle Size of Nucleic Acid-Containing Lipid Nanoparticles The average particle size of nucleic acid-containing lipid nanoparticles in a preparation was measured with a particle size measurement device (Zetasizer Nano ZS, Malvern Instruments Ltd.) (Table 52). Furthermore, PDI in the table indicates the polydispersity index.

TABLE 52

| Preparation No. | Lipid A | Lipid B | Size (nm) | PDI |
|---|---|---|---|---|
| 141 | I-4 | CL-5 | 46.18 | 0.063 |
| 142 | I-5 | CL-5 | 43.77 | 0.117 |

TABLE 52-continued

| Preparation No. | Lipid A | Lipid B | Size (nm) | PDI |
|---|---|---|---|---|
| 143 | I-3 | CL-1 | 47.63 | 0.107 |
| 144 | I-6 | CL-5 | 45.12 | 0.154 |
| 145 | II-1 | CL-6 | 44.75 | 0.169 |
| 146 | II-2 | CL-6 | 49.96 | 0.161 |
| 147 | II-7 | CL-1 | 46.44 | 0.125 |
| 148 | II-7 | CL-5 | 41.65 | 0.172 |
| 149 | II-3 | CL-6 | 48.76 | 0.223 |
| 150 | II-12 | CL-6 | 45.24 | 0.154 |
| 151 | II-9 | CL-5 | 34.37 | 0.294 |
| 152 | II-32 | CL-5 | 45.16 | 0.106 |
| 153 | II-40 | CL-5 | 43.31 | 0.163 |
| 154 | II-3 | CL-1 | 35.14 | 0.098 |
| 155 | II-1 | CL-6 | 48.60 | 0.148 |
| 156 | IV-1 | CL-1 | 20.11 | 0.459 |
| 157 | II-44 | CL-1 | 46.39 | 0.133 |
| 158 | II-45 | CL-1 | 43.46 | 0.09 |
| 159 | II-46 | CL-1 | 43.04 | 0.089 |

As a result, Preparations 141 to 159 described in Examples 198 to 216 demonstrated a small average particles size of 50 nm or less.

Nucleic acid-containing lipid particles were prepared in the manner indicated below while changing the contents of each of the components of Compound II-3 obtained in Example 10 or Compound II-12 obtained in Example 19, Compound CL-1 obtained in Reference Example 1, PEG-DSPE, DSPC and cholesterol.

Furthermore, the 1 mg/mL of Luc siRNA solution described in Example 72 was used for the nucleic acid in Examples 217 to 253. Lipid A was dissolved in 100% ethanol to 10 mg/mL to prepare a lipid stock solution, while Compound CL-1, PEG-DSPE, DSPC and cholesterol were respectively dissolved in 100% ethanol to 20 mg/mL to prepare lipid stock solutions. Each stock solution was stored at −20° C. and used after returning to room temperature after dissolving the lipid by warming to 60° C. immediately prior to formulating into a preparation.

Example 217

Nucleic acid-containing lipid nanoparticles containing Compound II-3 obtained in Example 10, PEG-DSPE, cholesterol and Compound CL-1 obtained in Reference Example 1 were prepared in the manner indicated below.

Compound II-3 was added to 20 mL of 80% ethanol so as to be 0.313 µmol. Continuing, after adding 200 µL of siRNA solution and stirring for 1 minute, Compound CL-1, PEG-DSPE and cholesterol were added to this solution at a ratio of Compound CL-1/PEG-DSPE/cholesterol of 1.88 µmol/0.235 µmol/1.49 µmol. Subsequently, water for injection was added at the rate of 62 mL/sec or higher to prepare a 20% or less ethanol solution and form a crude preparation. The resulting crude preparation was concentrated using Amicon Ultra (Millipore Corp.) followed by replacing the solvent with physiological saline and filtering in a clean bench using a 0.2 µm filter (Toyo Roshi Kaisha, Ltd.). Moreover, the siRNA concentration of the resulting preparation was measured and diluted using physiological saline to an siRNA concentration of 0.1 mg/mL to obtain Preparation 160.

Example 218

Nucleic acid-containing lipid nanoparticles containing Compound II-3 obtained in Example 10, PEG-DSPE, DSPC, cholesterol and Compound CL-1 obtained in Reference Example 1 were prepared in the manner indicated below.

Compound II-3 was added to 20 mL of 80% ethanol so as to be 0.313 µmol. Continuing, after adding 200 µL of siRNA solution and stirring for 1 minute, Compound CL-1, PEG-DSPE, DSPC and cholesterol were added to this solution at a ratio of Compound CL-1/PEG-DSPE/DSPC/cholesterol of 1.88 µmol/0.235 µmol/0.486 µmol/1.01 µmol. Subsequently, water for injection was added at the rate of 62 mL/sec or higher to prepare a 20% or less ethanol solution and form a crude preparation. The resulting crude preparation was concentrated using Amicon Ultra (Millipore Corp.) followed by replacing the solvent with physiological saline and filtering in a clean bench using a 0.2 µm filter (Toyo Roshi Kaisha, Ltd.). Moreover, the siRNA concentration of the resulting preparation was measured and diluted using physiological saline to an siRNA concentration of 0.1 mg/mL to obtain Preparation 167.

Example 219

Nucleic acid-containing lipid nanoparticles containing Compound II-3 obtained in Example 10, PEG-DSPE, DSPC, cholesterol and Compound CL-1 obtained in Reference Example 1 were prepared in the manner indicated below.

Compound II-3 was added to 20 mL of 80% ethanol so as to be 0.313 µmol. Continuing, after adding 200 µL of siRNA solution and stirring for 1 minute, Compound CL-1, PEG-DSPE, DSPC and cholesterol were added to this solution at a ratio of Compound CL-1/PEG-DSPE/DSPC/cholesterol of 2.02 µmol/0.235 µmol/1.01 µmol/0.337 µmol. Subsequently, water for injection was added at the rate of 62 mL/sec or higher to prepare a 20% or less ethanol solution and form a crude preparation. The resulting crude preparation was concentrated using Amicon Ultra (Millipore Corp.) followed by replacing the solvent with physiological saline and filtering in a clean bench using a 0.2 µm filter (Toyo Roshi Kaisha, Ltd.). Moreover, the siRNA concentration of the resulting preparation was measured and diluted using physiological saline to an siRNA concentration of 0.1 mg/mL to obtain Preparation 162.

Example 220

Nucleic acid-containing lipid nanoparticles containing Compound II-3 obtained in Example 10, PEG-DSPE, DSPC, cholesterol and Compound CL-1 obtained in Reference Example 1 were prepared in the manner indicated below.

Compound II-3 was added to 20 mL of 80% ethanol so as to be 0.313 µmol. Continuing, after adding 200 µL of siRNA solution and stirring for 1 minute, Compound CL-1, PEG-DSPE, DSPC and cholesterol were added to this solution at a ratio of Compound CL-1/PEG-DSPE/DSPC/cholesterol of 2.19 µmol/0.235 µmol/0.236 µmol/0.944 µmol. Subsequently, water for injection was added at the rate of 62 mL/sec or higher to prepare a 20% or less ethanol solution and form a crude preparation. The resulting crude preparation was concentrated using Amicon Ultra (Millipore Corp.) followed by replacing the solvent with physiological saline and filtering in a clean bench using a 0.2 µm filter (Toyo Roshi Kaisha, Ltd.). Moreover, the siRNA concentration of the resulting preparation was measured and diluted using physiological saline to an siRNA concentration of 0.1 mg/mL to obtain Preparation 163.

Example 221

Nucleic acid-containing lipid nanoparticles containing Compound II-3 obtained in Example 10, PEG-DSPE, DSPC, cholesterol and Compound CL-1 obtained in Reference Example 1 were prepared in the manner indicated below.
Compound II-3 was added to 20 mL of 80% ethanol so as to be 0.313 μmol. Continuing, after adding 200 μL of siRNA solution and stirring for 1 minute, Compound CL-1, PEG-DSPE, DSPC and cholesterol were added to this solution at a ratio of Compound CL-1/PEG-DSPE/DSPC/cholesterol of 1.52 μmol/0.235 μmol/1.62 μmol/0.236 μmol. Subsequently, water for injection was added at the rate of 62 mL/sec or higher to prepare a 20% or less ethanol solution and form a crude preparation. The resulting crude preparation was concentrated using Amicon Ultra (Millipore Corp.) followed by replacing the solvent with physiological saline and filtering in a clean bench using a 0.2 μm filter (Toyo Roshi Kaisha, Ltd.). Moreover, the siRNA concentration of the resulting preparation was measured and diluted using physiological saline to an siRNA concentration of 0.1 mg/mL to obtain Preparation 164.

Example 222

Nucleic acid-containing lipid nanoparticles containing Compound II-3 obtained in Example 10, PEG-DSPE, DSPC, cholesterol and Compound CL-1 obtained in Reference Example 1 were prepared in the manner indicated below.
Compound II-3 was added to 20 mL of 80% ethanol so as to be 0.313 μmol. Continuing, after adding 200 μL of siRNA solution and stirring for 1 minute, Compound CL-1, PEG-DSPE, DSPC and cholesterol were added to this solution at a ratio of Compound CL-1/PEG-DSPE/DSPC/cholesterol of 1.52 μmol/0.235 μmol/0.944 μmol/0.910 μmol. Subsequently, water for injection was added at the rate of 62 mL/sec or higher to prepare a 20% or less ethanol solution and form a crude preparation. The resulting crude preparation was concentrated using Amicon Ultra (Millipore Corp.) followed by replacing the solvent with physiological saline and filtering in a clean bench using a 0.2 μm filter (Toyo Roshi Kaisha, Ltd.). Moreover, the siRNA concentration of the resulting preparation was measured and diluted using physiological saline to an siRNA concentration of 0.1 mg/mL to obtain Preparation 165.

Example 223

Nucleic acid-containing lipid nanoparticles containing Compound II-3 obtained in Example 10, PEG-DSPE, DSPC, cholesterol and Compound CL-1 obtained in Reference Example 1 were prepared in the manner indicated below.
Compound II-3 was added to 20 mL of 80% ethanol so as to be 0.313 μmol. Continuing, after adding 200 μL of siRNA solution and stirring for 1 minute, Compound CL-1, PEG-DSPE, DSPC and cholesterol were added to this solution at a ratio of Compound CL-1/PEG-DSPE/DSPC/cholesterol of 1.52 μmol/0.235 μmol/0.236 μmol/1.62 μmol. Subsequently, water for injection was added at the rate of 62 mL/sec or higher to prepare a 20% or less ethanol solution and form a crude preparation. The resulting crude preparation was concentrated using Amicon Ultra (Millipore Corp.) followed by replacing the solvent with physiological saline and filtering in a clean bench using a 0.2 μm filter (Toyo Roshi Kaisha, Ltd.). Moreover, the siRNA concentration of the resulting preparation was measured and diluted using physiological saline to an siRNA concentration of 0.1 mg/mL to obtain Preparation 166.

Example 224

Nucleic acid-containing lipid nanoparticles containing Compound II-3 obtained in Example 10, PEG-DSPE, DSPC, cholesterol and Compound CL-1 obtained in Reference Example 1 were prepared in the manner indicated below.
Compound II-3 was added to 20 mL of 80% ethanol so as to be 0.313 μmol. Continuing, after adding 200 μL of siRNA solution and stirring for 1 minute, Compound CL-1, PEG-DSPE, DSPC and cholesterol were added to this solution at a ratio of Compound CL-1/PEG-DSPE/DSPC/cholesterol of 1.01 μmol/0.235 μmol/2.09 μmol/0.270 μmol. Subsequently, water for injection was added at the rate of 62 mL/sec or higher to prepare a 20% or less ethanol solution and form a crude preparation. The resulting crude preparation was concentrated using Amicon Ultra (Millipore Corp.) followed by replacing the solvent with physiological saline and filtering in a clean bench using a 0.2 μm filter (Toyo Roshi Kaisha, Ltd.). Moreover, the siRNA concentration of the resulting preparation was measured and diluted using physiological saline to an siRNA concentration of 0.1 mg/mL to obtain Preparation 167.

Example 225

Nucleic acid-containing lipid nanoparticles containing Compound II-3 obtained in Example 10, PEG-DSPE, DSPC, cholesterol and Compound CL-1 obtained in Reference Example 1 were prepared in the manner indicated below.
Compound II-3 was added to 20 mL of 80% ethanol so as to be 0.313 μmol. Continuing, after adding 200 μL of siRNA solution and stirring for 1 minute, Compound CL-1, PEG-DSPE, DSPC and cholesterol were added to this solution at a ratio of Compound CL-1/PEG-DSPE/DSPC/cholesterol of 1.01 μmol/0.235 μmol/1.42 μmol/0.944 μmol. Subsequently, water for injection was added at the rate of 62 mL/sec or higher to prepare a 20% or less ethanol solution and form a crude preparation. The resulting crude preparation was concentrated using Amicon Ultra (Millipore Corp.) followed by replacing the solvent with physiological saline and filtering in a clean bench using a 0.2 μm filter (Toyo Roshi Kaisha, Ltd.). Moreover, the siRNA concentration of the resulting preparation was measured and diluted using physiological saline to an siRNA concentration of 0.1 mg/mL to obtain Preparation 168.

Example 226

Nucleic acid-containing lipid nanoparticles containing Compound II-3 obtained in Example 10, PEG-DSPE, DSPC, cholesterol and Compound CL-1 obtained in Reference Example 1 were prepared in the manner indicated below.
Compound II-3 was added to 20 mL of 80% ethanol so as to be 0.313 μmol. Continuing, after adding 200 μL of siRNA solution and stirring for 1 minute, Compound CL-1, PEG-DSPE, DSPC and cholesterol were added to this solution at a ratio of Compound CL-1/PEG-DSPE/DSPC/cholesterol of 1.01 μmol/0.235 μmol/0.742 μmol/1.62 μmol. Subsequently, water for injection was added at the rate of 62 mL/sec or higher to prepare a 20% or less ethanol solution and form a crude preparation. The resulting crude preparation was concentrated using Amicon Ultra (Millipore Corp.) followed by replacing the solvent with physiological saline and filtering in a clean bench using a 0.2 μm filter (Toyo Roshi Kaisha, Ltd.). Moreover, the siRNA concentration of the resulting preparation was measured and diluted using physiological saline to an siRNA concentration of 0.1 mg/mL to obtain Preparation 169.

Example 227

Nucleic acid-containing lipid nanoparticles containing Compound II-3 obtained in Example 10, PEG-DSPE, DSPC, cholesterol and Compound CL-1 obtained in Reference Example 1 were prepared in the manner indicated below.

Compound II-3 was added to 20 mL of 80% ethanol so as to be 0.313 μmol. Continuing, after adding 200 μL of siRNA solution and stirring for 1 minute, Compound CL-1, PEG-DSPE, DSPC and cholesterol were added to this solution at a ratio of Compound CL-1/PEG-DSPE/DSPC/cholesterol of 1.01 μmol/0.235 μmol/0.101 μmol/2.26 μmol. Subsequently, water for injection was added at the rate of 62 mL/sec or higher to prepare a 20% or less ethanol solution and form a crude preparation. The resulting crude preparation was concentrated using Amicon Ultra (Millipore Corp.) followed by replacing the solvent with physiological saline and filtering in a clean bench using a 0.2 μm filter (Toyo Roshi Kaisha, Ltd.). Moreover, the siRNA concentration of the resulting preparation was measured and diluted using physiological saline to an siRNA concentration of 0.1 mg/mL to obtain Preparation 170.

Example 228

Nucleic acid-containing lipid nanoparticles containing Compound II-3 obtained in Example 10, PEG-DSPE, DSPC, cholesterol and Compound CL-1 obtained in Reference Example 1 were prepared in the manner indicated below.

Compound II-3 was added to 20 mL of 80% ethanol so as to be 0.313 μmol. Continuing, after adding 200 μL of siRNA solution and stirring for 1 minute, Compound CL-1, PEG-DSPE, DSPC and cholesterol were added to this solution at a ratio of Compound CL-1/PEG-DSPE/DSPC/cholesterol of 2.82 μmol/0.353 μmol/0.779 μmol/1.62 μmol. Subsequently, water for injection was added at the rate of 62 mL/sec or higher to prepare a 20% or less ethanol solution and form a crude preparation. The resulting crude preparation was concentrated using Amicon Ultra (Millipore Corp.) followed by replacing the solvent with physiological saline and filtering in a clean bench using a 0.2 μm filter (Toyo Roshi Kaisha, Ltd.). Moreover, the siRNA concentration of the resulting preparation was measured and diluted using physiological saline to an siRNA concentration of 0.1 mg/mL to obtain Preparation 171.

Example 229

Nucleic acid-containing lipid nanoparticles containing Compound II-3 obtained in Example 10, PEG-DSPE, DSPC, cholesterol and Compound CL-1 obtained in Reference Example 1 were prepared in the manner indicated below.

Compound II-3 was added to 20 mL of 80% ethanol so as to be 0.313 μmol. Continuing, after adding 200 μL of siRNA solution and stirring for 1 minute, Compound CL-1, PEG-DSPE, DSPC and cholesterol were added to this solution at a ratio of Compound CL-1/PEG-DSPE/DSPC/cholesterol of 3.03 μmol/0.353 μmol/1.56 μmol/0.521 μmol. Subsequently, water for injection was added at the rate of 62 mL/sec or higher to prepare a 20% or less ethanol solution and form a crude preparation. The resulting crude preparation was concentrated using Amicon Ultra (Millipore Corp.) followed by replacing the solvent with physiological saline and filtering in a clean bench using a 0.2 μm filter (Toyo Roshi Kaisha, Ltd.). Moreover, the siRNA concentration of the resulting preparation was measured and diluted using physiological saline to an siRNA concentration of 0.1 mg/mL to obtain Preparation 172.

Example 230

Nucleic acid-containing lipid nanoparticles containing Compound II-3 obtained in Example 10, PEG-DSPE, DSPC, cholesterol and Compound CL-1 obtained in Reference Example 1 were prepared in the manner indicated below.

Compound II-3 was added to 20 mL of 80% ethanol so as to be 0.313 μmol. Continuing, after adding 200 μL of siRNA solution and stirring for 1 minute, Compound CL-1, PEG-DSPE, DSPC and cholesterol were added to this solution at a ratio of Compound CL-1/PEG-DSPE/DSPC/cholesterol of 3.39 μmol/0.353 μmol/0.365 μmol/1.46 μmol. Subsequently, water for injection was added at the rate of 62 mL/sec or higher to prepare a 20% or less ethanol solution and form a crude preparation. The resulting crude preparation was concentrated using Amicon Ultra (Millipore Corp.) followed by replacing the solvent with physiological saline and filtering in a clean bench using a 0.2 μm filter (Toyo Roshi Kaisha, Ltd.). Moreover, the siRNA concentration of the resulting preparation was measured and diluted using physiological saline to an siRNA concentration of 0.1 mg/mL to obtain Preparation 173.

Example 231

Nucleic acid-containing lipid nanoparticles containing Compound II-3 obtained in Example 10, PEG-DSPE, DSPC, cholesterol and Compound CL-1 obtained in Reference Example 1 were prepared in the manner indicated below.

Compound II-3 was added to 20 mL of 80% ethanol so as to be 0.313 μmol. Continuing, after adding 200 μL of siRNA solution and stirring for 1 minute, Compound CL-1, PEG-DSPE, DSPC and cholesterol were added to this solution at a ratio of Compound CL-1/PEG-DSPE/DSPC/cholesterol of 2.35 μmol/0.353 μmol/2.50 μmol/0.365 μmol. Subsequently, water for injection was added at the rate of 62 mL/sec or higher to prepare a 20% or less ethanol solution and form a crude preparation. The resulting crude preparation was concentrated using Amicon Ultra (Millipore Corp.) followed by replacing the solvent with physiological saline and filtering in a clean bench using a 0.2 μm filter (Toyo Roshi Kaisha, Ltd.). Moreover, the siRNA concentration of the resulting preparation was measured and diluted using physiological saline to an siRNA concentration of 0.1 mg/mL to obtain Preparation 174.

Example 232

Nucleic acid-containing lipid nanoparticles containing Compound II-3 obtained in Example 10, PEG-DSPE, DSPC, cholesterol and Compound CL-1 obtained in Reference Example 1 were prepared in the manner indicated below.

Compound II-3 was added to 20 mL of 80% ethanol so as to be 0.313 µmol. Continuing, after adding 200 µL of siRNA solution and stirring for 1 minute, Compound CL-1, PEG-DSPE, DSPC and cholesterol were added to this solution at a ratio of Compound CL-1/PEG-DSPE/DSPC/cholesterol of 2.35 µmol/0.353 µmol/1.46 µmol/1.41 µmol. Subsequently, water for injection was added at the rate of 62 mL/sec or higher to prepare a 20% or less ethanol solution and form a crude preparation. The resulting crude preparation was concentrated using Amicon Ultra (Millipore Corp.) followed by replacing the solvent with physiological saline and filtering in a clean bench using a 0.2 µm filter (Toyo Roshi Kaisha, Ltd.). Moreover, the siRNA concentration of the resulting preparation was measured and diluted using physiological saline to an siRNA concentration of 0.1 mg/mL to obtain Preparation 175.

Example 233

Nucleic acid-containing lipid nanoparticles containing Compound II-3 obtained in Example 10, PEG-DSPE, DSPC, cholesterol and Compound CL-1 obtained in Reference Example 1 were prepared in the manner indicated below.

Compound II-3 was added to 20 mL of 80% ethanol so as to be 0.313 µmol. Continuing, after adding 200 µL of siRNA solution and stirring for 1 minute, Compound CL-1, PEG-DSPE, DSPC and cholesterol were added to this solution at a ratio of Compound CL-1/PEG-DSPE/DSPC/cholesterol of 2.35 µmol/0.353 µmol/0.365 µmol/2.50 µmol. Subsequently, water for injection was added at the rate of 62 mL/sec or higher to prepare a 20% or less ethanol solution and form a crude preparation. The resulting crude preparation was concentrated using Amicon Ultra (Millipore Corp.) followed by replacing the solvent with physiological saline and filtering in a clean bench using a 0.2 µm filter (Toyo Roshi Kaisha, Ltd.). Moreover, the siRNA concentration of the resulting preparation was measured and diluted using physiological saline to an siRNA concentration of 0.1 mg/mL to obtain Preparation 176.

Example 234

Nucleic acid-containing lipid nanoparticles containing Compound II-3 obtained in Example 10, PEG-DSPE, DSPC, cholesterol and Compound CL-1 obtained in Reference Example 1 were prepared in the manner indicated below.

Compound II-3 was added to 20 mL of 80% ethanol so as to be 0.313 µmol. Continuing, after adding 200 µL of siRNA solution and stirring for 1 minute, Compound CL-1, PEG-DSPE, DSPC and cholesterol were added to this solution at a ratio of Compound CL-1/PEG-DSPE/DSPC/cholesterol of 1.56 µmol/0.353 µmol/3.23 µmol/0.417 µmol. Subsequently, water for injection was added at the rate of 62 mL/sec or higher to prepare a 20% or less ethanol solution and form a crude preparation. The resulting crude preparation was concentrated using Amicon Ultra (Millipore Corp.) followed by replacing the solvent with physiological saline and filtering in a clean bench using a 0.2 µm filter (Toyo Roshi Kaisha, Ltd.). Moreover, the siRNA concentration of the resulting preparation was measured and diluted using physiological saline to an siRNA concentration of 0.1 mg/mL to obtain Preparation 177.

Example 235

Nucleic acid-containing lipid nanoparticles containing Compound II-3 obtained in Example 10, PEG-DSPE, DSPC, cholesterol and Compound CL-1 obtained in Reference Example 1 were prepared in the manner indicated below.

Compound II-3 was added to 20 mL of 80% ethanol so as to be 0.313 µmol. Continuing, after adding 200 µL of siRNA solution and stirring for 1 minute, Compound CL-1, PEG-DSPE, DSPC and cholesterol were added to this solution at a ratio of Compound CL-1/PEG-DSPE/DSPC/cholesterol of 1.56 µmol/0.353 µmol/1.15 µmol/2.50 µmol. Subsequently, water for injection was added at the rate of 62 mL/sec or higher to prepare a 20% or less ethanol solution and form a crude preparation. The resulting crude preparation was concentrated using Amicon Ultra (Millipore Corp.) followed by replacing the solvent with physiological saline and filtering in a clean bench using a 0.2 µm filter (Toyo Roshi Kaisha, Ltd.). Moreover, the siRNA concentration of the resulting preparation was measured and diluted using physiological saline to an siRNA concentration of 0.1 mg/mL to obtain Preparation 178.

Example 236

Nucleic acid-containing lipid nanoparticles containing Compound II-3 obtained in Example 10, PEG-DSPE, DSPC, cholesterol and Compound CL-1 obtained in Reference Example 1 were prepared in the manner indicated below.

Compound II-3 was added to 20 mL of 80% ethanol so as to be 0.313 µmol. Continuing, after adding 200 µL of siRNA solution and stirring for 1 minute, Compound CL-1, PEG-DSPE, DSPC and cholesterol were added to this solution at a ratio of Compound CL-1/PEG-DSPE/DSPC/cholesterol of 1.56 µmol/0.353 µmol/O. 156 µmol/3.49 µmol. Subsequently, water for injection was added at the rate of 62 mL/sec or higher to prepare a 20% or less ethanol solution and form a crude preparation. The resulting crude preparation was concentrated using Amicon Ultra (Millipore Corp.) followed by replacing the solvent with physiological saline and filtering in a clean bench using a 0.2 µm filter (Toyo Roshi Kaisha, Ltd.). Moreover, the siRNA concentration of the resulting preparation was measured and diluted using physiological saline to an siRNA concentration of 0.1 mg/mL to obtain Preparation 179.

Example 237

Nucleic acid-containing lipid nanoparticles containing Compound II-12 obtained in Example 19, PEG-DSPE, DSPC, cholesterol and Compound CL-1 obtained in Reference Example 1 were prepared in the manner indicated below.

Compound II-12 was added to 20 mL of 80% ethanol so as to be 0.313 µmol. Continuing, after adding 200 µL of siRNA solution and stirring for 1 minute, Compound CL-1, PEG-DSPE, DSPC and cholesterol were added to this solution at a ratio of Compound CL-1/PEG-DSPE/DSPC/cholesterol of 1.88 µmol/0.235 µmol/0.486 µmol/1.01 µmol. Subsequently, water for injection was added at the rate of 62

Example 238

Preparation 181 was obtained in the similar manner as Example 219 with the exception of changing Compound II-3 of Preparation 162 to Compound II-12 obtained in Example 19.

Example 239

Preparation 182 was obtained in the similar manner as Example 221 with the exception of changing Compound II-3 of Preparation 164 to Compound II-12 obtained in Example 19.

Example 240

Preparation 183 was obtained in the similar manner as Example 222 with the exception of changing Compound II-3 of Preparation 165 to Compound II-12 obtained in Example 19.

Example 241

Preparation 184 was obtained in the similar manner as Example 223 with the exception of changing Compound II-3 of Preparation 166 to Compound II-12 obtained in Example 19.

Example 242

Preparation 185 was obtained in the similar manner as Example 224 with the exception of changing Compound II-3 of Preparation 167 to Compound II-12 obtained in Example 19.

Example 243

Preparation 186 was obtained in the similar manner as Example 226 with the exception of changing Compound II-3 of Preparation 169 to Compound II-12 obtained in Example 19.

Example 244

Preparation 187 was obtained in the similar manner as Example 227 with the exception of changing Compound II-3 of Preparation 170 to Compound II-12 obtained in Example 19.

Example 245

Preparation 188 was obtained in the similar manner as Example 228 with the exception of changing Compound II-3 of Preparation 171 to Compound II-12 obtained in Example 19.

Example 246

Preparation 189 was obtained in the similar manner as Example 229 with the exception of changing Compound II-3 of Preparation 172 to Compound II-12 obtained in Example 19.

Example 247

Preparation 190 was obtained in the similar manner as Example 230 with the exception of changing Compound II-3 of Preparation 173 to Compound II-12 obtained in Example 19.

Example 248

Preparation 191 was obtained in the similar manner as Example 231 with the exception of changing Compound II-3 of Preparation 174 to Compound II-12 obtained in Example 19.

Example 249

Preparation 192 was obtained in the similar manner as Example 232 with the exception of changing Compound II-3 of Preparation 175 to Compound II-12 obtained in Example 19.

Example 250

Preparation 193 was obtained in the similar manner as Example 233 with the exception of changing Compound II-3 of Preparation 176 to Compound II-12 obtained in Example 19.

Example 251

Compound II-12 was added to 20 mL of 80% isopropyl alcohol so as to be 0.313 µmol. Continuing, after adding 200 µL of siRNA solution and stirring for 1 minute, Compound CL-1, PEG-DSPE, DSPC and cholesterol were added at a ratio of Compound CL-1/PEG-DSPE/DSPC/cholesterol of 1.56 µmol/0.353 µmol/2.19 µmol/1.46 µmol. Subsequently, water for injection was added at the rate of 62 mL/sec or higher to prepare a 20% or less isopropyl alcohol solution and form a crude preparation. The resulting crude preparation was concentrated using Amicon Ultra (Millipore Corp.) followed by replacing the solvent with physiological saline and filtering in a clean bench using a 0.2 µm filter (Toyo Roshi Kaisha, Ltd.). Moreover, the siRNA concentration of the resulting preparation was measured and diluted using physiological saline to an siRNA concentration of 0.1 mg/mL to obtain Preparation 194.

Example 252

Preparation 195 was obtained in the similar manner as Example 235 with the exception of changing Compound II-3 of Preparation 178 to Compound II-12 obtained in Example 19.

Example 253

Preparation 196 was obtained in the similar manner as Example 236 with the exception of changing Compound II-3 of Preparation 179 to Compound II-12 obtained in Example 19.

Test Example 13

Measurement of Average Particle Size of Nucleic Acid-Containing Lipid Nanoparticles The average particle size of nucleic acid-containing lipid nanoparticles in a preparation was measured with a particle size measurement device (Zetasizer Nano ZS, Malvern Instruments Ltd.) (Table 53). Furthermore, PDI in the table indicates the polydispersity index.

TABLE 53

| Preparation No. | Lipid A | Lipid B | Size (nm) | PDI |
|---|---|---|---|---|
| 160 | CL-1 | II-3 | 47.52 | 0.086 |
| 161 | CL-1 | II-3 | 37.40 | 0.094 |
| 162 | CL-1 | II-3 | 39.35 | 0.095 |
| 163 | CL-1 | II-3 | 41.37 | 0.094 |
| 164 | CL-1 | II-3 | 42.78 | 0.284 |
| 165 | CL-1 | II-3 | 40.27 | 0.150 |
| 166 | CL-1 | II-3 | 38.03 | 0.126 |
| 167 | CL-1 | II-3 | 37.59 | 0.276 |
| 168 | CL-1 | II-3 | 43.68 | 0.209 |
| 169 | CL-1 | II-3 | 34.06 | 0.142 |
| 170 | CL-1 | II-3 | 34.85 | 0.156 |
| 171 | CL-1 | II-3 | 38.01 | 0.089 |
| 172 | CL-1 | II-3 | 44.22 | 0.145 |
| 173 | CL-1 | II-3 | 43.46 | 0.127 |
| 174 | CL-1 | II-3 | 43.77 | 0.279 |
| 175 | CL-1 | II-3 | 41.89 | 0.181 |
| 176 | CL-1 | II-3 | 40.23 | 0.133 |
| 177 | CL-1 | II-3 | 22.06 | 0.185 |
| 178 | CL-1 | II-3 | 38.50 | 0.158 |
| 179 | CL-1 | II-3 | 41.84 | 0.116 |
| 180 | CL-1 | II-12 | 44.92 | 0.073 |
| 181 | CL-1 | II-12 | 42.99 | 0.080 |
| 182 | CL-1 | II-12 | 34.19 | 0.229 |
| 183 | CL-1 | II-12 | 44.16 | 0.168 |
| 184 | CL-1 | II-12 | 43.04 | 0.090 |
| 185 | CL-1 | II-12 | 46.91 | 0.248 |
| 186 | CL-1 | II-12 | 43.46 | 0.168 |
| 187 | CL-1 | II-12 | 39.04 | 0.129 |
| 188 | CL-1 | II-12 | 43.25 | 0.087 |
| 189 | CL-1 | II-12 | 42.50 | 0.158 |
| 190 | CL-1 | II-12 | 44.49 | 0.088 |
| 191 | CL-1 | II-12 | 35.69 | 0.175 |
| 192 | CL-1 | II-12 | 41.35 | 0.136 |
| 193 | CL-1 | II-12 | 44.50 | 0.102 |
| 194 | CL-1 | II-12 | 47.14 | 0.185 |
| 195 | CL-1 | II-12 | 42.33 | 0.154 |
| 196 | CL-1 | II-12 | 41.19 | 0.122 |

As a result, Preparations 160 to 196 described in Examples 217 to 253 demonstrated a small average particles size of 50 nm or less.

Example 254

Preparation of Nucleic Acid-Containing Lipid Nanoparticles used to Evaluate Permeability in Collagen Gel Nucleic acid-containing lipid nanoparticles containing Compound I-1 and having a small particle size were prepared in the manner indicated below.

The nucleic acid used was composed of base sequences consisting of a sense strand [(5'-Y_N(H)_GCCAGACUUU-GUUGGAUUUGAAAtt-3')] and an antisense strand [(5'-AAUUCAAA(M)UC(M)CA(M)AC(M)AA(M)AG(M)UC(M)UG(M)GC(M)U(M)U(M)-3')] (wherein, N(M)=2'-OMe RNA, upper case=RNA, lower case=DNA, Y=Alexa 488 and N(H) indicates an ssH amino linker). This siRNA inhibits expression of HPRT1 gene and was acquired from GeneDesign Inc. (to be referred to as "AF488-HPRT1 siRNA"). AF488-HPRT1 siRNA was dissolved in water for injection to 1 mg/mL to prepare an AF488-HPRT1 siRNA solution. PEG-DSPE, DSPC and cholesterol were acquired from NOF Corp.

Compound I-1 obtained in Example 1 was dissolved in 100% isopropyl alcohol to 10 mg/mL to prepare a lipid stock solution. Compound CL-1 obtained in Reference Example 1, PEG-DSPE, DSPC and cholesterol were dissolved in 100% isopropyl alcohol to 20 mg/mL to prepare lipid stock solutions. The stock solutions were stored at −20° C. and used after returning to room temperature after dissolving the lipid by warming to 60° C. immediately prior to formulating into a preparation.

Compound I-1 was added to 20 mL of 80% isopropyl alcohol so as to be 0.581 μmol. Continuing, after adding 200 μL of siRNA solution and stirring for 1 minute, Compound CL-1, PEG-DSPE, DSPC and cholesterol were added to the solution at a ratio of Compound CL-1/PEG-DSPE/DSPC/cholesterol of 1.88 μmol/0.235 μmol/0.398 μmol/0.827 μmol. Subsequently, water for injection was added at the rate of 62 mL/sec or higher to prepare a 20% or less isopropyl alcohol solution and form a crude preparation. The resulting crude preparation was concentrated using Amicon Ultra (Millipore Corp.) followed by replacing the solvent with physiological saline and filtering in a clean bench using a 0.2 μm filter (Toyo Roshi Kaisha, Ltd.). Moreover, the siRNA concentration of the resulting preparation was measured and diluted using physiological saline to an siRNA concentration of 0.1 mg/mL to obtain Preparation 197.

Comparative Example 14

Nucleic acid-containing lipid nanoparticles not containing Compound I-1 and having a large particle size were prepared in the manner indicated below.

PEG-DSPE, DSPC and cholesterol were acquired from NOF Corp.

Compound CL-1 obtained in Reference Example 1, PEG-DSPE, DSPC and cholesterol were dissolved in 100% isopropyl alcohol to 20 mg/mL to prepare lipid stock solutions. The stock solutions were stored at −20° C. and used after returning to room temperature after dissolving the lipid by warming to 60° C. immediately prior to formulating into a preparation.

AF488-HPRT1 siRNA described in Example 80 was used for the nucleic acid.

0.2 mL of AF488-HPRT1 siRNA solution was added to 20 mL of 80% isopropyl alcohol. Continuing, each lipid was added so that the ratio of Compound CL-1/PEG-DSPE/DSPC/cholesterol was 1.88 μmol/0.235 μmol/0.587 μmol/1.22 μmol. Subsequently, water for injection was added at the rate of about 0.2 mL/sec or lower to prepare a 20% or less isopropyl alcohol solution and form a crude preparation. The resulting crude preparation was concentrated using Amicon Ultra (Millipore Corp.) followed by replacing the solvent with physiological saline and filtering in a clean bench using a 0.2 μm filter (Toyo Roshi Kaisha, Ltd.). Moreover, the siRNA concentration of the resulting preparation was measured and diluted using physiological saline to an siRNA concentration of 0.1 mg/mL to obtain Preparation 198.

Comparative Example 15

Nucleic acid-containing lipid nanoparticles containing Compound I-1 and having a large particle size were prepared in the manner indicated below.

PEG-DSPE, DSPC and cholesterol were acquired from NOF Corp. AF488-HPRT1 siRNA described in Example 254 was used for the nucleic acid.

Compound I-1 obtained in Example 1 was dissolved in 100% isopropyl alcohol to 10 mg/mL to prepare a lipid stock solution. Compound CL-1 obtained in Reference Example 1, PEG-DSPE, DSPC and cholesterol were dissolved in 100% isopropyl alcohol to 20 mg/mL to prepare lipid stock solutions. The stock solutions were stored at −20° C. and used after returning to room temperature after dissolving the lipid by warming to 60° C. immediately prior to formulating into a preparation. Compound I-1 was added to 20 mL of 80% isopropyl alcohol so as to be 0.581 µmol. Continuing, after adding 200 µL of siRNA solution and stirring for 1 minute, Compound CL-1, PEG-DSPE, DSPC and cholesterol were added to the solution at a ratio of Compound CL-1/PEG-DSPE/DSPC/cholesterol of 1.88 µmol/0.235 µmol/0.398 µmol/0.827 µmol. Subsequently, water for injection was added at the rate of 0.22 mL/sec or lower to prepare a 20% or less isopropyl alcohol solution and form a crude preparation. The resulting crude preparation was concentrated using Amicon Ultra (Millipore Corp.) followed by replacing the solvent with physiological saline and filtering in a clean bench using a 0.2 µm filter (Toyo Roshi Kaisha, Ltd.). Moreover, the siRNA concentration of the resulting preparation was measured and diluted using physiological saline to an siRNA concentration of 0.1 mg/mL to obtain Preparation 199.

Test Example 14

Measurement of Average Particle Size of Nucleic Acid-Containing Lipid Nanoparticles The average particle size of nucleic acid-containing lipid nanoparticles in a preparation was measured with a particle size measurement device (Zetasizer Nano ZS, Malvern Instruments Ltd.) (Table 54). Furthermore, PDI in the table indicates the polydispersity index.

TABLE 54

| Preparation No. | Size (nm) | PDI |
|---|---|---|
| 197 | 39.65 | 0.118 |
| 198 | 79.45 | 0.160 |
| 199 | 97.84 | 0.062 |

Test Example 15

Evaluation of Permeability of Nucleic Acid-Containing Lipid Nanoparticles in Collagen Gel Each of the preparations obtained in Example 254 and Comparative Examples 14 and 15 were evaluated for permeability according to the methods indicated below. After adding 13.4 µL of 1 M sodium hydroxide (Wako Pure Chemical Industries, Ltd.) and 68.78 µL of 0.17 M EDTA solution (Nacalai Tesque Inc.) to 500 µL of rat-derived collagen type I (BD Biosciences) and vortexing, the mixture was added to a 500 µL tube (assist tube) and allowed to stand undisturbed for 1 day at room temperature. Preparations 197 to 199 were added thereto and allowed to stand undisturbed for 7 days followed by observing fluorescence with a Lumino Image Analyzer (LAS3000, Fujifilm Corp.).

As is clear from FIG. 5, in contrast to the nucleic acid-containing lipid nanoparticles having a small particle size (Preparation 197) easily permeating the collagen gel by slipping through gaps in the gel, the nucleic acid-containing lipid nanoparticles having a large particle size (Preparations 197 and 199) were confirmed to remain in the upper portion of the collagen gel due to being unable to slip through gaps in the gel.

Test Example 16

Evaluation of Permeability of Nucleic Acid-Containing Lipid Nanoparticles in Collagen Gel Each of AF488-HPRT1 siRNA described in Example 254, Preparation 197 obtained in Example 254 and Preparation 199 obtained in Comparative Example 15 were evaluated for permeability according to the methods indicated below. After adding 13.4 µL of 1 M sodium hydroxide (Wake Pure Chemical Industries, Ltd.) and 68.78 µL of 0.17 M EDTA solution (Nacalai Tesque Inc.) to 500 µL of rat-derived collagen type I (BD Biosciences) and vortexing, the mixture was filled into a 1 mL Terumo syringe and allowed to stand undisturbed for 1 day at room temperature. AF488-HPRT1 siRNA alone, Preparation 197 and Preparation 199 were added thereto and allowed to stand undisturbed for 24 hours followed by recovery of the gel and observing fluorescence with a Lumino Image Analyzer (LAS3000, Fujifilm Corp.).

As is clear from FIG. 6, in contrast to the nucleic acid-containing lipid nanoparticles having a small particle size (Preparation 197) easily permeating the collagen gel by slipping through gaps in the gel, the nucleic acid-containing lipid nanoparticles having a large particle size (Preparation 199) were confirmed to remain in the upper portion of the collagen gel due to being unable to slip through gaps in the gel. As shown in FIG. 7, as a result of measuring the permeated distance through the collagen gel, the nucleic acid-containing lipid nanoparticles having a small particle size (Preparation 197) demonstrated a permeation distance roughly twice that of the nucleic acid-containing lipid nanoparticles having a large particle size (Preparation 199).

INDUSTRIAL APPLICABILITY

According to the present invention, nucleic acid-containing lipid nanoparticles can be produced that are more stable and smaller than conventional particles, and the nucleic acid can be easily introduced into, for example, cells located in deep tumor tissue by administering these stable, small nucleic acid-containing lipid nanoparticles to a mammal and the like.

SEQUENCE LISTING FREE TEXT

SEQ ID NO: 1 indicates the base sequence of the sense strand of Luc siRNA.

SEQ ID NO: 2 indicates the base sequence of the antisense strand of Luc siRNA.

SEQ ID NO: 3 indicates the base sequence of the sense strand of AF488-HPRT1 siRNA.

SEQ ID NO: 4 indicates the base sequence of the antisense strand of AF488-HPRT1 siRNA.

What is claimed is:

1. Nucleic acid-containing lipid nanoparticles, comprising: a lipid (lipid A), which has a hydrophilic unit having a single quaternary ammonium group and three independent, substituted and either unsubstituted or substituted hydrocarbon groups; a lipid derivative or fatty acid derivative of a water-soluble polymer; and a nucleic acid, wherein the number of moles of the quaternary ammonium group in the lipid A is 0.1 to 10 times the number of moles of phosphorous atoms in the nucleic acid, the average particle size is 20 nm to 65 nm, and the lipid A is a lipid represented by:

formula (II)

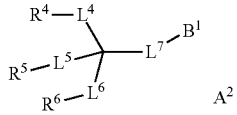

(II)

(wherein, $R^4$ to $R^6$, the same or different, are a linear or branched, and either unsubstituted or substituted C8-C24 alkyl, C8-C24 alkenyl or C8-C24 alkynyl, $L^4$ to $L^6$, the same or different, are absent or are —$Z^4$—$(CY^8Y^9)_{p4}$— or —$Z^5$—$(CY^{10}Y^{11})_{p5}$—$Z^6$—$(CY^{12}Y^{13})_{p6}$— (wherein, $Y^8$ to $Y^{13}$, the same or different, are a hydrogen atom or optionally substituted C1-C4 alkyl, $Z^4$ to $Z^6$, the same or different, are —O—, —$NY^{14A}$—, —CO—O—, —O—CO—, —CO—$NY^{14B}$—, —$NY^{4C}$—CO— or (wherein, $Y^{14A}$ to $Y^{14D}$ the same or different, are a hydrogen atom or optionally substituted C1-C4 alkyl), $p^4$ is an integer of 0 to 5, $p^5$ is an integer of 1 to 5, and $p^6$ is an integer of 0 to 5), $L^7$ is $(CY^{15}Y^{16})_{p7}$—, —$(CY^{17}Y^{18})_{p8}$—$Z^7$—$(CY^{19}Y^{20})_{p9}$— —$(CY^{21}Y^{22})_{p10}$—$Z^8$—$(CY^{23}Y^{24})_{p11}$—$Z^9$—$(CY^{25}Y^{26})_{p12}$— (wherein, $Y^{15}$ to $Y^{26}$, the same or different, are a hydrogen atom or optionally substituted C1-C4 alkyl, $Z^7$ to $Z^9$, the same or different, are —O—, —$NY^{27A}$—, —CO—O—, or —O—CO—, (wherein, $Y^{27A}$, the same or different, is a hydrogen atom or optionally substituted C1-C4 alkyl), $p^7$ is an integer of 1 to 5, $p^8$ is an integer of 0 to 5, $p^9$ is an integer of 1 to 5, $p^{10}$ is an integer of 0 to 5, $p^{11}$ is an integer of 1 to 5, and $p^{12}$ is an integer of 1 to 5), $B^1$ is

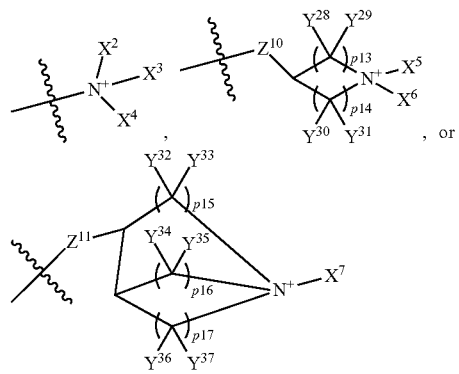

(wherein, $X^2$ and $X^3$, the same or different, are an optionally substituted C1-C4 alkyl or are combined together to form an optionally substituted C4-C6 heterocycle with an adjacent nitrogen atom, $X^4$ is an optionally substituted C1-C4 alkyl, $X^5$ and $X^6$, the same or different, are an optionally substituted C1-C4 alkyl or are combined together to form an optionally substituted C4-C6 heterocycle with an adjacent nitrogen atom, $X^7$ is an optionally substituted C1-C4 alkyl, $Y^{28}$ to $Y^{37}$, the same or different, are a hydrogen atom or optionally substituted C1-C4 alkyl, $Z^{10}$ and $Z^{11}$, the same or different, are —O—, —$NY^{38A}$—, —OO—O—, —O—CO—, —CO—$NY^{38B}$, —$NY^{38C}$—CO— or —$NY^{38D}$—CO—O— (wherein, $Y^{38A}$ to $Y^{38D}$, the same or different, are a hydrogen atom or optionally substituted C1-C4 alkyl), $p^{13}$ is an integer of 0 to 5, and $p^{14}$ to $p^{17}$, the same or different, are an integer of 1 to 5), and $A^2$ is a pharmaceutically acceptable anion);

and a lipid (lipid B), which has a hydrophilic unit having one secondary or tertiary amino group or one substituted secondary or tertiary amino group, and a hydrophobic unit having two independent linear C8-C24 alkyl or alkenyl groups or two independent substituted linear C8-C24 alkyl or alkenyl groups;

wherein the ratio of the number of moles of lipid A to the number of moles of lipid B is 0.01 to 2;

wherein the nucleic acid has a molecular weight of 1,000 kDa or less.

2. The lipid nanoparticles according to claim 1, wherein the lipid A is represented by formula (II), and in formula (II), one of $L^4$ to $L^6$ is —CO—O—$(CY^8Y^9)_{p4}$—, —O—CO—

$(CY^8Y^9)_{p4}$— or —O—CO—$(CY^{10}Y^{11})_{p5}$—O—$(CY^{12}Y^{13})_{p6}$— or two or more of $L^4$ to $L^6$, the same or different, are —CO—O—$(CY^8Y^9)_{p4}$—, —O—CO—$(CY^8Y^9)_{p4}$— or —O—CO—$(CY^{10}Y^{11})_{p5}$—O—$(CY^{12}Y^{13})_{p6}$— and), $R^4$ to $R^6$ are linear or branched C15-C20 alkenyl or C9-C18 alkyl and are the same.

3. The nucleic acid-containing lipid nanoparticles of claim 1, wherein the number of moles of lipid A is smaller than the number of moles of lipid B.

\* \* \* \* \*

SEQUENCE LISTING

<160> NUMBER OF SEQ ID NOS: 4

<210> SEQ ID NO 1
<211> LENGTH: 21
<212> TYPE: RNA
<213> ORGANISM: Artificial Sequence
<220> FEATURE:
<223> OTHER INFORMATION: Luc siRNA sense

<400> SEQUENCE: 1
ccgucguauu cgugagcaag a                                              21

<210> SEQ ID NO 2
<211> LENGTH: 21
<212> TYPE: RNA
<213> ORGANISM: Artificial Sequence
<220> FEATURE:
<223> OTHER INFORMATION: Luc siRNA antisense

<400> SEQUENCE: 2
uugcucacga auacgacggu g                                              21

<210> SEQ ID NO 3
<211> LENGTH: 25
<212> TYPE: DNA
<213> ORGANISM: Artificial Sequence
<220> FEATURE:
<223> OTHER INFORMATION: AF488-HPRT1 siRNA sense
<220> FEATURE:
<221> NAME/KEY: misc_feature
<222> LOCATION: (1)..(23)
<223> OTHER INFORMATION: RNA
<220> FEATURE:
<221> NAME/KEY: misc_feature
<222> LOCATION: (24)..(25)
<223> OTHER INFORMATION: DNA

<400> SEQUENCE: 3
gccagacuuu guuggauuug aaatt                                          25

<210> SEQ ID NO 4
<211> LENGTH: 27
<212> TYPE: RNA
<213> ORGANISM: Artificial Sequence
<220> FEATURE:
<223> OTHER INFORMATION: AF488-HPRT1 siRNA antisense
<220> FEATURE:
<221> NAME/KEY: modified_base
<222> LOCATION: (9)..(9)
<223> OTHER INFORMATION: am
<220> FEATURE:
<221> NAME/KEY: modified_base
<222> LOCATION: (11)..(11)
<223> OTHER INFORMATION: cm
<220> FEATURE:
<221> NAME/KEY: modified_base
<222> LOCATION: (13)..(13)
<223> OTHER INFORMATION: am
<220> FEATURE:
<221> NAME/KEY: modified_base
<222> LOCATION: (15)..(15)
<223> OTHER INFORMATION: cm
<220> FEATURE:
<221> NAME/KEY: modified_base
<222> LOCATION: (17)..(17)
<223> OTHER INFORMATION: am
<220> FEATURE:
<221> NAME/KEY: modified_base
<222> LOCATION: (19)..(19)
<223> OTHER INFORMATION: gm
<220> FEATURE:
<221> NAME/KEY: modified_base

```
<222> LOCATION: (21)..(21)
<223> OTHER INFORMATION: cm
<220> FEATURE:
<221> NAME/KEY: modified_base
<222> LOCATION: (23)..(23)
<223> OTHER INFORMATION: gm
<220> FEATURE:
<221> NAME/KEY: modified_base
<222> LOCATION: (25)..(25)
<223> OTHER INFORMATION: cm
<220> FEATURE:
<221> NAME/KEY: modified_base
<222> LOCATION: (26)..(27)
<223> OTHER INFORMATION: um

<400> SEQUENCE: 4
aauuucaaau ccaacaaagu cuggcuu                                       27
```